United States Patent
Banville et al.

(10) Patent No.: US 10,428,077 B2
(45) Date of Patent: *Oct. 1, 2019

(54) IMIDAZOTHIADIAZOLE AND IMIDAZOPYRAZINE DERIVATIVES AS PROTEASE ACTIVATED RECEPTOR4 (PAR4) INHIBITORS FOR TREATING PLATELET AGGREGATION

(71) Applicants: BRISTOL-MYERS SQUIBB COMPANY, Princeton, NJ (US); UNIVERSITE DE MONTREAL, Montreal (CA)

(72) Inventors: Jacques Banville, Saint-Hubert (CA); Roger Remillard, Napierville (CA); Edward H. Ruediger, Greenfield Park (CA); Daniel H. Deon, Denver, CO (US); Marc Gagnon, Ville Saint-Laurent (CA); Laurence Dube, Laval (CA); Julia Guy, Montreal (CA); Eldon Scott Priestley, Yardley, PA (US); Shoshana L. Posy, Highland Park, NJ (US); Brad D. Maxwell, Doylestown, PA (US); Pancras C. Wong, Plainsboro, NJ (US); R. Michael Lawrence, Yardley, PA (US); Michael M. Miller, Pennington, NJ (US)

(73) Assignees: Bristol-Myers Squibb Company, Princeton, NJ (US); Université de Montréal, Montréal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/020,043

(22) Filed: Jun. 27, 2018

(65) Prior Publication Data
US 2018/0305376 A1 Oct. 25, 2018

Related U.S. Application Data

(60) Continuation of application No. 15/593,534, filed on May 12, 2017, now Pat. No. 10,047,103, which is a
(Continued)

(51) Int. Cl.
*C07D 487/04* (2006.01)
*C07D 513/04* (2006.01)
(Continued)

(52) U.S. Cl.
CPC .......... *C07D 487/04* (2013.01); *A61K 31/433* (2013.01); *A61K 31/435* (2013.01); *A61K 31/4439* (2013.01); *A61K 31/454* (2013.01); *A61K 31/496* (2013.01); *A61K 31/497* (2013.01); *A61K 31/5025* (2013.01); *A61K 31/5377* (2013.01); *A61K 31/5386* (2013.01); *A61K 31/541* (2013.01); *A61K 31/55* (2013.01); *A61K 31/553* (2013.01); *A61K 45/06* (2013.01); *A61K 51/0453* (2013.01);
(Continued)

(58) Field of Classification Search
CPC .................................................... C07D 487/04
See application file for complete search history.

(56) References Cited

U.S. PATENT DOCUMENTS

| 4,444,770 A | 4/1984 | Meyer et al. |
|---|---|---|
| 6,673,815 B2 | 1/2004 | Devasthale et al. |

(Continued)

FOREIGN PATENT DOCUMENTS

| CA | 2584745 A1 | 10/2007 |
|---|---|---|
| CN | 102372701 A | 3/2012 |

(Continued)

OTHER PUBLICATIONS

STN Database Record for RN 1177489-39-2, database entry date Aug. 28, 2009.

(Continued)

*Primary Examiner* — Matthew P Coughlin
(74) *Attorney, Agent, or Firm* — Hoffmann & Baron, LLP

(57) ABSTRACT

The present invention provides thiazole compounds of Formula I wherein W, Y, $R^0$, $R^2$, $R^4$, $R^5$, $R^6$, $R^7$, $X^1$, $X^2$, $X^3$ and $X^4$ are as defined herein, or a stereoisomer, tautomer, pharmaceutically acceptable salt, prodrug ester or solvate form thereof, wherein all of the variables are as defined herein. These compounds are inhibitors of platelet aggregation and thus can be used as medicaments for treating or preventing thromboembolic disorders.

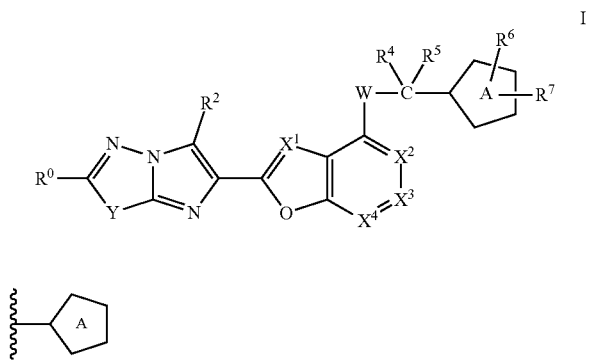

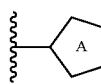

9 Claims, 2 Drawing Sheets

Related U.S. Application Data division of application No. 14/396,771, filed as application No. PCT/US2013/037956 on Apr. 24, 2013, now Pat. No. 9,688,695.

(60) Provisional application No. 61/787,680, filed on Mar. 15, 2013, provisional application No. 61/638,577, filed on Apr. 26, 2012.

(51) Int. Cl.

| | | |
|---|---|---|
| *C07D 519/00* | (2006.01) | |
| *A61K 45/06* | (2006.01) | |
| *A61K 31/433* | (2006.01) | |
| *A61K 31/4439* | (2006.01) | |
| *A61K 31/454* | (2006.01) | |
| *A61K 31/496* | (2006.01) | |
| *A61K 31/497* | (2006.01) | |
| *A61K 31/5025* | (2006.01) | |
| *A61K 31/5377* | (2006.01) | |
| *A61K 31/541* | (2006.01) | |
| *A61K 31/553* | (2006.01) | |
| *A61K 31/435* | (2006.01) | |
| *A61K 31/5386* | (2006.01) | |
| *A61K 31/55* | (2006.01) | |
| *A61K 51/04* | (2006.01) | |
| *C07B 59/00* | (2006.01) | |

(52) U.S. Cl.
CPC .......... *C07B 59/002* (2013.01); *C07D 513/04* (2013.01); *C07D 519/00* (2013.01); *C07B 2200/05* (2013.01)

(56) References Cited

U.S. PATENT DOCUMENTS

| | | | |
|---|---|---|---|
| 8,114,400 B2 | 2/2012 | Schirok et al. | |
| 9,605,024 B2 | 3/2017 | Kornacker et al. | |
| 9,688,695 B2 | 6/2017 | Banville et al. | |
| 10,047,103 B2 * | 8/2018 | Banville | C07D 487/04 |
| 2007/0155779 A1 | 7/2007 | Verhoest | |
| 2015/0119390 A1 | 4/2015 | Martel et al. | |
| 2015/0133446 A1 | 5/2015 | Lawrence et al. | |
| 2017/0247395 A1 | 8/2017 | Banville et al. | |

FOREIGN PATENT DOCUMENTS

| | | |
|---|---|---|
| DE | 2823686 | 12/1979 |
| DE | 102006054757 | 5/2008 |
| EP | 0005783 A1 | 12/1979 |
| EP | 0041215 | 12/1981 |
| EP | 0158012 A1 | 10/1985 |
| EP | 0185345 A1 | 6/1986 |
| EP | 0299209 A2 | 1/1989 |
| EP | 0379979 A1 | 8/1990 |
| EP | 0497258 | 8/1992 |
| EP | 2518066 A1 | 10/2012 |
| IN | 903/MUM/2004 | 6/2007 |
| WO | 99/46232 | 9/1999 |
| WO | 01/27118 | 4/2001 |
| WO | 01/27119 | 4/2001 |
| WO | 2001/27118 | 4/2001 |
| WO | 2001/27119 | 4/2001 |
| WO | 01/81344 | 11/2001 |
| WO | 03/040114 | 5/2003 |
| WO | 03/051890 | 6/2003 |
| WO | 2004/063159 | 7/2004 |
| WO | 2004/111060 | 12/2004 |
| WO | 2004/111061 | 12/2004 |
| WO | 2005/048948 | 6/2005 |
| WO | 2005/048953 | 6/2005 |
| WO | 2005/080355 | 9/2005 |
| WO | 2007/002540 | 1/2007 |
| WO | 2007/039177 | 4/2007 |
| WO | 2007/106469 | 9/2007 |
| WO | 2007/118318 A1 | 10/2007 |
| WO | 2008/083238 | 7/2008 |
| WO | 2008/104279 | 9/2008 |
| WO | 2008/141249 | 11/2008 |
| WO | 2009/017954 | 2/2009 |
| WO | 2009/023179 | 2/2009 |
| WO | 2009/027733 | 3/2009 |
| WO | 2009/040507 | 4/2009 |
| WO | 2009/079683 | 7/2009 |
| WO | 2009/123992 | 10/2009 |
| WO | 2010/036629 | 4/2010 |
| WO | 2010/075376 | 7/2010 |
| WO | 2011/074658 | 6/2011 |
| WO | 2012/021696 | 2/2012 |
| WO | 2013/028670 | 2/2013 |
| WO | 2013/160873 A1 | 10/2013 |
| WO | 2013/163241 | 10/2013 |
| WO | 2013/163244 | 10/2013 |
| WO | 2013/163248 A1 | 10/2013 |
| WO | WO-2013163248 A1 * | 10/2013 ............... C07K 7/06 |
| WO | 2013/171639 A1 | 11/2013 |
| WO | 2013/177188 A1 | 11/2013 |
| WO | 2013/186692 A1 | 12/2013 |
| WO | 2013/192130 A1 | 12/2013 |
| WO | 2014/009447 A1 | 1/2014 |
| WO | 2014/011974 A1 | 1/2014 |
| WO | 2014/015167 | 1/2014 |
| WO | 2014/035860 A1 | 3/2014 |
| WO | 2014/060411 A1 | 4/2014 |
| WO | 2014/097151 A2 | 6/2014 |
| WO | 2014/100323 A1 | 6/2014 |

OTHER PUBLICATIONS

STN Database Record for RN 1177349-45-9, database entry date Aug. 28, 2009.
STN Database Record for RN 1097163-93-3, database entry date Jan. 28, 2009.
STN Database Record for RN 1096958-09-6, database entry date Jan. 28, 2009.
STN Database Record for RN 1096958-08-5, database entry date Jan. 28, 2009.
Japanese Office Action for JP Application No. 2015-509103, dated Aug. 16, 2016.
Abdel-Wahab, B.F. et al., "Synthesis of New 2-Naphthyl Ethers and Their Protective Activities against DNA Damage Induced by Bleomycin-Iron", Chem. Phar. Bull., vol. 57, No. 12, pp. 1348-1351 (2009).
Bailin, G.B. et al., "Imidazo[1,2-b]pyridazanes. XIII. Syntheses and Central Nervous System Activities of Some 2-Benzyl(phenethyl, biphenyl-4'-yl, 6'-methylnaphthalen-2'-yl, t-butyl and cyclohexyl)-3-methoxy(acylaminomethyl and dimethylaminomethyl)-6-variously substituted))imidazo[1,2-b]pyridazines", Aust. J. Chem., vol. 45, pp. 1281-1300 (1992).
Bhovi, V.K. et al., "Synthesis of Some Mannich Bases and Novel Benzofuran Derivatives Containing Imidazo[2,1-b] [1,3,4]thiadiazoles as Biological Agents", Current Chemical Biology, vol. 4, No. 2, pp. 145-150 (2010).
CAS Registry No. 1096958-08-5, Entered STN: Jan. 28, 2009.
CAS Registry No. 1097016-53-9, Entered STN: Jan. 28, 2009.
CAS Registry No. 1097037-01-8, Entered STN: Jan. 28, 2009.
CAS Registry No. 1097163-93-3, Entered STN: Jan. 28, 2009.
Rani, R. et al., "Microwave Assisted Facile Synthesis and Antimicrobial Activity of Some New Imidazo[2,1-b]-1,3,4-thiadiazoles", Indian Journal of Heterocyclic Chemistry, vol. 18, pp. 121-124 (2008).
Tegginamath, G. et al., "Synthesis of novel imidazo[2,1-b][1,3,4]thiadiazoles appended to sydnone as anticancer agents", Medicinal Chemistry Research, vol. 22, pp. 4367-4375 (2013).
Chilean Search Report, PCT 2014-002915, dated Oct. 2, 2015.
Beresneva, Tatjana, et al., "Palladium-catalyzed synthesis of novel tetra- and penta-cyclic biologically active benzopyran-and pyridopyran-containing heterocyclic systems", Arkivoc 2013 (ix) pp. 185-194.

(56) References Cited

OTHER PUBLICATIONS

Terme, Thierry, et al., "Synthesis of 2-Substituted-3-nitroimidazo[1,2-b]pyridazines as Potential Biologically Active Agents", J. Heterocyclic Chem., 39, pp. 173-177, 2002.

Barlin, Gordon B. et al., "Imidazo[1,2-b]pyridazines: Syntheses and Interaction with Central and Peripheral-Type (Mitochondrial) Benzodiazepine Receptors", J. Heterocyclic Chem., 35, pp. 1205-1217, 1998.

Barlin, Gordon B. et al., "Imidazo[1,2-b]pyridazines. XX Syntheses of Some 3-Acylaminomethyl-6-(chloro, fluoro, methoxy, methylthio, phenoxy and phenylthio)-2-(phenyl,4-t-butylphenyl, 4-cyclohexylphenyl,β-naphthyl and styryl) imidazo[1,2-b]pyridazines and Their Interaction with Central and Peripheral-Type Benzodiazepine Receptors", Aust. J. Chem, 1996, 49 pp. 451-461.

Barlin, Gordon B. et al., Imidazo[1,2-b]pyridazines. XIX Syntheses and Central Nervous System Activities of Some 6-Arylthio(aryloxy and alkylthio)-3-(acetamidomethyl, benzamidomethyl, methoxy and unsubstituted)-2-arylimidazo[1,2-b]pyridazines, Aust. J. Chem, 1996, 49 pp. 443-449.

Matyus, Peter, et al., "Ligands for the Central Benzodiazepine Receptor: Structure-Affinity Relationship Studies on Imidazo[1,2-b]pyridazines", Aust. J. Chem, 1996, 49 pp. 435-442.

Davies, Les P., et al., "New Imidazo[1,2-b]Pyridazine Ligands for Peripheral Type Benzodiazepine Receptors on Mitochondna and Monocytes", Life Sciences, vol. 57, No. 25, pp. 381-386, 1995.

Barlin, Gordon B. et al., "Imidazo[1,2-b]pyridazines. XVI Synthesis and Central Nervous System Activities of Some 6-(Chloro, Alkylthio, Phenylthio, Benzylthio or Pyridinylmethylthio)-3-(unsubstituted, benzamidomethyl or methoxy)-2-(styryl or benzoyl)imidazo[1,2-b]pyridazines", Aust. J. Chem, 1994, 47 pp. 1989-1999.

\* cited by examiner

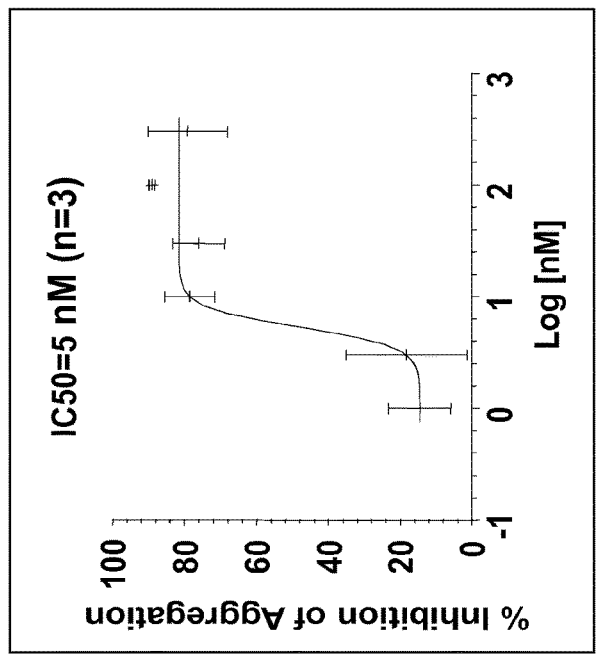
Fig 1B. Inhibition of Platelet Aggregation by Example 3 Dose-Response Curve
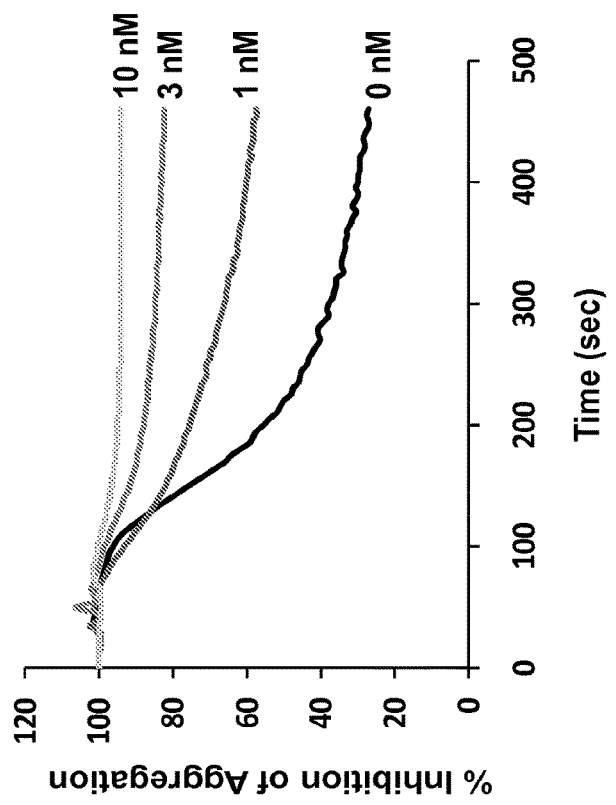
Fig 1A. Inhibition of Human Washed Platelet Aggregation by Example 3 Induced by 1.5 nM Alpha-Thrombin

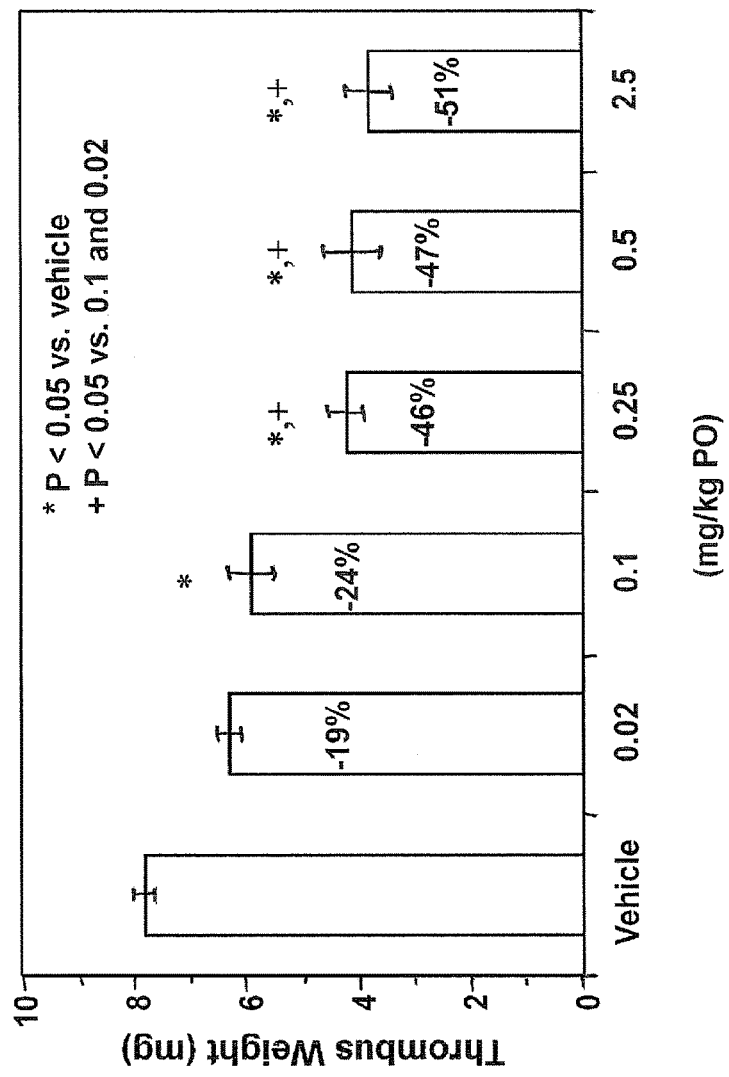
Fig 1C. Antithrombotic Efficacy of Example 3 in a Cynomolgus Monkey Electrolytic Injury-induced Carotid Artery Thrombosis Model

IMIDAZOTHIADIAZOLE AND IMIDAZOPYRAZINE DERIVATIVES AS PROTEASE ACTIVATED RECEPTOR4 (PAR4) INHIBITORS FOR TREATING PLATELET AGGREGATION

CROSS-REFERENCE TO RELATED APPLICATIONS

This application is a continuation of U.S. patent application Ser. No. 15/593,534, filed May 12, 2017, which is a divisional of U.S. patent application Ser. No. 14/396,771, filed Oct. 24, 2014, issued as U.S. Pat. No. 9,688,695 on Jun. 27, 2017, which is a National Stage Entry of PCT/US13/37956, filed Apr. 24, 2013, which claims the benefit of U.S. Provisional Application No. 61/638,577, filed on Apr. 26, 2012, and U.S. Provisional Application No. 61/787,680, filed on Mar. 15, 2013. The contents of each of these aforementioned applications are incorporated herein by reference in entirety.

FIELD OF THE INVENTION

The present invention provides novel imidazothiadiazole and imidazopyridazine inhibitors of platelet aggregation which are useful in preventing or treating thromboembolic disorders. This invention also relates to pharmaceutical compositions containing these compounds and methods of using the same.

BACKGROUND OF THE INVENTION

Thromboembolic diseases remain the leading cause of death in developed countries despite the availability of anticoagulants such as warfarin (COUMADIN®), heparin, low molecular weight heparins (LMWH), synthetic pentasaccharides, and antiplatelet agents such as aspirin and clopidogrel (PLAVIX®).

Current anti-platelet therapies have limitations including increased risk of bleeding as well as partial efficacy (relative cardiovascular risk reduction in the 20 to 30% range). Thus, discovering and developing safe and efficacious oral or parenteral antithrombotics for the prevention and treatment of a wide range of thromboembolic disorders remains an important goal.

Alpha-thrombin is the most potent known activator of platelet aggregation and degranulation. Activation of platelets is causally involved in atherothrombotic vascular occlusions. Thrombin activates platelets by cleaving G-protein coupled receptors termed protease activated receptors (PARs). PARs provide their own cryptic ligand present in the N-terminal extracellular domain that is unmasked by proteolytic cleavage, with subsequent intramolecular binding to the receptor to induce signaling (tethered ligand mechanism; Coughlin, S. R., *Nature*, 407:258-264 (2000)). Synthetic peptides that mimic the sequence of the newly formed N-terminus upon proteolytic activation can induce signaling independent of receptor cleavage. Platelets are a key player in atherothrombotic events. Human platelets express at least two thrombin receptors, commonly referred to as PAR1 and PAR4. Inhibitors of PAR1 have been investigated extensively, and several compounds, including vorapaxar and atopaxar have advanced into late stage clinical trials. Recently, in the TRACER phase III trial in ACS patients, vorapaxar did not significantly reduce cardiovascular events, but significantly increased the risk of major bleeding (Tricoci, P. et al., *N. Eng. J. Med.*, 366(1):20-33 (2012). Thus, there remains a need to discover new antiplatelet agents with increased efficacy and reduced bleeding side effects.

There are several early reports of preclinical studies of PAR4 inhibitors. Lee, F-Y. et al., "Synthesis of 1-Benzyl-3-(5'-hydroxymethyl-2'-furyl)indazole Analogues as Novel Antiplatelet Agents", *J. Med. Chem.*, 44(22):3746-3749 (2001) discloses in the abstract that the compound

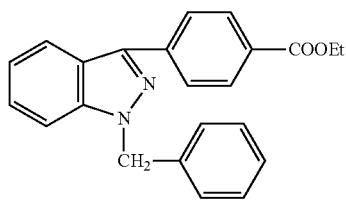

"was found to be a selective and potent inhibitor or protease-activated receptor type 4 (PAR4)-dependent platelet activation."

Compound 58 is also referred to as YD-3 in Wu, C-C. et al., "Selective Inhibition of Protease-activated Receptor 4-dependent Platelet Activation by YD-3", *Thromb. Haemnost.*, 87:1026-1033 (2002). Also, see Chen, H. S. et al., "Synthesis and platelet activity", *J. Bioorg. Med. Chem.*, 16:1262-1278 (2008).

EP1166785 A1 and EP0667345 disclose various pyrazole derivatives which are useful as inhibitors of platelet aggregation.

SUMMARY OF THE INVENTION

It has been found that imidazothiadiazole and imidazopyridazine compounds in accordance with the present invention are PAR4 antagonists which inhibit platelet aggregation in gamma-thrombin induced platelet aggregation assays. Moreover, a compound(s) of the present invention has been shown to inhibit platelet aggregation in an alpha-thrombin induced platelet aggregation assay, and to inhibit thrombus formation in an arterial thrombosis model in cynomolgus monkeys.

Accordingly, the present invention provides novel imidazothiadiazole analogues and imidazopyridazine analogues which are PAR4 antagonists and are useful as selective inhibitors of platelet aggregation, including stereoisomers, tautomers, pharmaceutically acceptable salts, solvates, or prodrug esters thereof.

The present invention also provides processes and intermediates for making the compounds of the present invention or stereoisomers, tautomers, pharmaceutically acceptable salts, solvates, or prodrug esters thereof.

The present invention also provides pharmaceutical compositions comprising a pharmaceutically acceptable carrier and at least one of the compounds of the present invention or stereoisomers, tautomers, pharmaceutically acceptable salts, solvates, or prodrug esters thereof.

The present invention also provides a method for the treatment or prophylaxis of thromboembolic disorders comprising administering to a patient in need of such treatment or prophylaxis a therapeutically effective amount of at least one of the compounds of the present invention or stereoisomers, tautomers, pharmaceutically acceptable salts, solvates, or prodrug esters thereof.

The present invention also provides the compounds of the present invention or stereoisomers, tautomers, pharmaceutically acceptable salts, solvates, or prodrug esters thereof, for use in therapy.

The present invention also provides the use of the compounds of the present invention or stereoisomers, tautomers, pharmaceutically acceptable salts, solvates, or prodrug esters thereof, for the manufacture of a medicament for the treatment or prophylaxis of a thromboembolic disorder.

Other features and advantages of the invention will be apparent from the following detailed description and claims.

BRIEF DESCRIPTION OF THE FIGURES

FIG. 1A is a graph which shows the effectiveness of Example 3 in inhibiting aggregation of human washed platelets stimulated by 1.5 nM alpha-thrombin;

FIG. 1B is a graph which shows the $IC_{50}$ of Example 3 in inhibiting alpha-thrombin-induced platelet aggregation; and FIG. 1C is a graph which shows the antithrombotic efficacy of Example 3 in the cynomolgus monkey electrolytic injury-induced carotid artery thrombosis model.

DETAILED DESCRIPTION

In one embodiment, the present invention provides imidazothiadiazole or imidazopyridazine compounds, stereoisomers, tautomers, salts, solvates or prodrugs thereof, of Formula I having the structure:

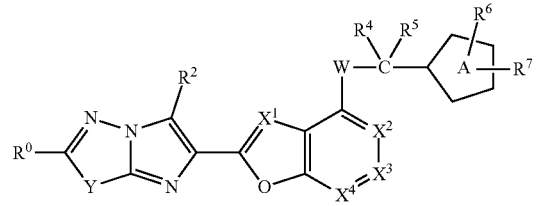

I wherein:
W is O or S;
$R^0$ is $R^1$ or $R^{1a}$;
Y is S or —$CR^8$=$CR^9$—;
$R^1$ is independently selected from the group consisting of:
halo,
$C_1$-$C_4$ alkyl,
$C_2$-$C_3$ alkenyl,
$C_2$-$C_3$ alkynyl,
$C_3$-$C_4$ cycloalkyl,
$C_1$-$C_4$ alkoxy,
$C_1$-$C_2$ alkoxy-$C_1$-$C_2$ alkyl,
tetrahydrofuran-2-yl;
$C_1$-$C_4$ alkylthio,
$C_1$-$C_4$ alkylNH—,
($C_1$-$C_4$ alkyl)$_2$N—,
halo-$C_1$-$C_2$-alkyl, which contains 1 to 5 halogens, where halo is F or Cl,
halo-$C_3$-$C_4$ cycloalkyl,
halo-$C_1$-$C_2$ alkoxy, and
halo-$C_1$-$C_2$ alkylthio;
$R^{1a}$ is independently selected from the group consisting of:
H,
halo,
$C_1$-$C_4$ alkyl,
$C_2$-$C_3$ alkenyl,
$C_2$-$C_3$ alkynyl,
$C_3$-$C_4$ cycloalkyl,
$C_1$-$C_4$ alkoxy,
$C_1$-$C_2$ alkoxy-$C_1$-$C_2$ alkyl,
tetrahydrofuran-2-yl;
$C_1$-$C_4$ alkylthio,
$C_1$-$C_4$ alkylNH—,
($C_1$-$C_4$ alkyl)$_2$N—,
halo-$C_1$-$C_2$-alkyl, which contains 1 to 5 halogens, where halo is F or Cl,
halo-$C_3$-$C_4$ cycloalkyl,
halo-$C_1$-$C_2$ alkoxy, and
halo-$C_1$-$C_2$ alkylthio;
$R^8$ and $R^9$ are independently selected from the group consisting of:
H,
halo,
$C_1$-$C_4$ alkyl,
$C_1$-$C_4$ alkoxy,
halo-$C_1$-$C_2$ alkyl,
halo-$C_1$-$C_2$ alkoxy,
CN, and
OH;
provided that at least one of $R^{1a}$, $R^8$ and $R^9$ is other than H;
$R^2$ is selected from the group consisting of:
H,
halo,
$C_1$-$C_4$ alkyl,
$C_1$-$C_4$ alkoxy, and
cyano;
$X^1$ is selected from the group consisting of CH, N or $CR^{10}$;
$X^2$, $X^3$ and $X^4$ are independently selected from $CR^3$ or N;
$R^3$ is selected from the group consisting of H, $C_1$-$C_4$ alkyl, $C_2$-$C_4$ alkenyl, $C_2$-$C_4$ alkynyl, $C_1$-$C_4$ alkoxy, $C_1$-$C_4$ alkylthio, halo, OH, CN, $OCF_3$, $OCHF_2$, $OCH_2F$, $C_1$-$C_2$-alkoxy-$C_1$-$C_2$-alkoxy, halo-$C_1$-$C_3$-alkyl, which contains 1 to 5 halogens, benzyloxy substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano, and —$(CH_2)_n^1$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano;
$R^4$ and $R^5$ are independently selected from H and $C_1$-$C_6$ alkyl, or $R^4$ and $R^5$ can be taken together with the carbon to which they are attached to form a $C_3$-$C_7$ cycloalkyl ring;

is a 5-membered heteroaryl ring containing at least one O, N or S atom;
$R^6$ is selected from the group consisting of H, halo, $OCF_3$, $OCHF_2$, OH, CN, $NO_2$, $NR^{11}R^{12}$, COOH, $C_1$-$C_4$ alkoxycarbonyl, (C=O)$NR^{11}R^{12}$, $C_1$-$C_4$ alkylsulfonyl, S(=O)$_2NR^{11}R^{12}$, and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$- alkoxy-$C_1$-$C_4$-alkyl)-$C_1$-$C_4$-alkyl, di-$C_1$-$C_4$-alkylamino, $C_3$-$C_6$-cycloalkyl, and $C_1$-$C_4$ alkylthio, or $R^6$ is B-D-, where D is a linker, which is selected from: a single bond,

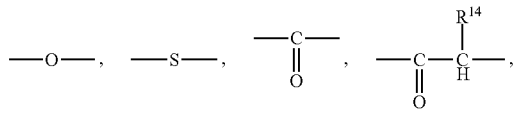

$C_1$-$C_4$ alkylene substituted by 0 to 4 groups independently selected from halo or OH,
$C_1$-$C_4$ alkyleneoxy,
$C_1$-$C_4$ alkylenethio,
$C_1$-$C_4$ alkyleneoxy-$C_1$-$C_4$-alkylene,
$C_1$-$C_4$-alkylenethio-$C_1$-$C_4$-alkylene,
—S—$C_1$-$C_4$-alkylene,
—O—$C_1$-$C_4$-alkylene,
$C_2$-$C_6$ alkenylene, and B is selected from the group consisting of:

$C_6$-$C_{10}$ aryl substituted by 0 to 3 groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{11}R^{12}$, OH, $C_1$-$C_4$-alkylcarbonyloxy-$C_1$-$C_4$-alkyl, hydroxy-$C_1$-$C_4$-alkyl, cyano-$C_1$-$C_4$-alkyl, $COOR^{14}$, $SO_2R^{14}$, $(C=O)NR^{11}R^{12}$, $SO_2NR^{11}R^{12}$, $N(R^{13})(C=O)NR^{11}R^{12}$, $N(R^{13})(C=O)OR^{14}$, $N(R^{13})(C=O)R^{14}$, $NR^{13}S(O)R^{14}$, $NR^{13}SO_2R^{14}$, $O(C=O)NR^{11}R^{12}$, $O(C=O)OR^{14}$, $O(C=O)R^{14}$, $(C=O)OR^{14}$, and 5-6-membered heteroaryl, 5- to 10-membered heteroaryl substituted by 0 to 3 groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{11}R^{12}$, OH, $C_1$-$C_4$-alkylcarbonyloxy-$C_1$-$C_4$-alkyl, hydroxy-$C_1$-$C_4$-alkyl, $COOR^{14}$, $SO_2R^{14}$, $(C=O)NR^{11}R^{12}$, $SO_2NR^{11}R^{12}$, $N(R^{13})(C=O)NR^{11}R^{12}$, $N(R^{13})(C=O)OR^{14}$, $N(R^{13})(C=O)R^{14}$, $NR^{13}S(O)R^{14}$, $NR^{13}SO_2R^{14}$, $O(C=O)NR^{11}R^{12}$, $O(C=O)OR^{14}$, $O(C=O)R^{14}$, $(C=O)OR^{14}$, 5-6-membered heteroaryl, and $(CH_2)$phenyl, 4- to 10-membered heterocyclyl containing carbon atoms and 1 to 2 additional heteroatoms selected from N, O, and S, and substituted by 0 to 3 groups independently selected from the group consisting of halo, oxo, —$(CHR^{13})_n^1$-5- or 6-membered heteroaryl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; $NR^{13}S(O)R^{14}$, $NR^{13}SO_2R^{14}$, —$(CHR^{13})_n^1$-4- to 10-membered-heterocyclyl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; OH, hydroxy-$C_1$-$C_4$-alkyl, $C_1$-$C_4$ alkoxy, halo-$C_1$-$C_4$ alkoxy, di-$C_1$-$C_4$-alkylamino-$C_1$-$C_4$-alkyl, $NR_{11}R_{12}$, cyano, $C_1$-$C_4$ alkyl, halo-$C_1$-$C_4$ alkyl, $C_3$-$C_6$ cycloalkyl, $C_1$-$C_4$-alkoxy-$C_1$-$C_4$-alkyl, $C_3$-$C_6$ cycloalkyl-$C_1$-$C_4$-alkylcarbonyl, $C_6$-$C_{10}$ arylcarbonyl, $C_1$-$C_4$-alkylcarbonyloxy-$C_1$-$C_4$-alkyl, $COOR^{14}$, $SO_2R^{14}$, $(C=O)NR^{11}R^{12}$, $SO_2NR^{11}R^{12}$, $N(R^{13})(C=O)NR^{11}R^{12}$, $N(R^{13})(C=O)OR^{14}$, $N(R^{13})(C=O)R^{14}$, $O(C=O)NR^{11}R^{12}$, $O(C=O)OR^{14}$, $O(C=O)R^{14}$, $(C=O)OR^{14}$, and $C_6$-$C_{10}$ aryl substituted by 0 to 3 groups consisting of halo, $C_1$-$C_4$ alkoxy, $C_1$-$C_4$ alkyl, cyclopropyl, $C_1$-$C_4$-alkoxycarbonyl, $(C=O)NR^{11}R^{12}$, $CF_3$, $OCF_3$, and $CF_2CH_3$;

$C_3$-$C_6$ cycloalkyl which may contain unsaturation, substituted by 0 to 3 groups independently selected from the group consisting of halo, $CF_3$, $OCF_3$, 5- or 6-membered heteroaryl, OH, oxo, hydroxy-$C_1$-$C_4$-alkyl, $C_6$-$C_{10}$ aryl, COOH, oxo, $C_1$-$C_4$-alkoxycarbonyl, $(C=O)NR^{11}R^{12}$, $NR^{11}R^{12}$ and $C_1$-$C_4$ alkyl; and $C_5$-$C_{11}$ spirocycloalkyl which may contain unsaturation and optionally containing 1 to 3 heteroatoms selected from O, N or S and substituted by 0 to 3 groups independently selected from the group consisting of halo, $CF_3$, $OCF_3$, 5- or 6-membered heteroaryl, OH, hydroxy-$C_1$-$C_4$-alkyl, $C_6$-$C_{10}$ aryl, and $C_1$-$C_4$ alkyl;

$R^{11}$ and $R^{12}$ are independently, at each occurrence, selected from the group consisting of:
H,
$C_1$-$C_4$ alkyl,
halo-$C_1$-$C_4$-alkyl,
$C_2$-$C_4$ alkenyl,
$C_2$-$C_4$ alkynyl,
—$(CR^{14}R^{14})_n^1$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano,
—$(CHR^{13})_n^1$—$C_3$-$C_6$-cycloalkyl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl,
—$(CHR^{13})_n^1$-4- to 10-membered-heterocyclyl substituted by 0 to 3 groups independently selected from the group consisting of halo, $CF_3$, $OCF_3$, 5- or 6-membered heteroaryl, OH, oxo, hydroxy-$C_1$-$C_4$-alkyl, and $C_1$-$C_4$ alkyl,
—$(CHR^{13})_n^1$-5- to 10-membered-heteroaryl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl,
di-$C_1$-$C_4$-alkylamino-$C_1$-$C_4$-alkyl,
$C_1$-$C_4$-alkylcarbonylamino-$C_1$-$C_4$-alkyl,
di-$C_1$-$C_4$-alkoxy-$C_1$-$C_4$-alkyl,
di-$C_1$-$C_4$-alkylaminophenyl,
hydroxy-$C_1$-$C_4$-alkyl,
cyano-$C_1$-$C_4$-alkyl,
$C_1$-$C_4$-alkoxy-$C_1$-$C_4$-alkyl,
$C_1$-$C_4$-alkoxycarbonyl-$C_1$-$C_4$-alkyl,
$C_1$-$C_4$-alkoxycarbonyl,
$C_1$-$C_4$-alkylcarbonyl,
phenylcarbonyl;
$C_1$-$C_4$-alkoxycarbonylamino-$C_1$-$C_4$-alkylcarbonyl,
di-$C_1$-$C_4$-alkylamino-$C_1$-$C_4$-alkylcarbonyl,
amino-$C_1$-$C_4$-alkylcarbonyl,
4- to 10-membered-heterocyclyl-carbonyl, and alternatively, $R^{11}$ and $R^{12}$, when attached to the same nitrogen, combine to form a 4- to 8-membered heterocyclic ring containing carbon atoms substituted by 0 to 3 groups independently selected from the group consisting of halo, $CF_3$, $CHF_2$, $OCF_3$, $OCHF_2$, $OCH_2F$, 5- or 6-membered heteroaryl, OH, oxo, hydroxy-$C_1$-$C_4$-alkyl, $C_1$-$C_4$ alkyl and $C_1$-$C_4$ alkoxy, and 0 to 2 additional heteroatoms selected from N, $NR^{13}$, O and $S(O)_p$;

$R^{13}$ is independently, at each occurrence, selected from the group consisting of H, $C_1$-$C_6$ alkyl and —$(CH_2)$phenyl;

$R^{14}$ is independently, at each occurrence, selected from the group consisting of H, $C_1$-$C_6$ alkyl, halo-$C_1$-$C_4$-alkyl, $C_1$-$C_4$-alkoxycarbonylamino, ($C_6$-$C_{10}$ arylcarbonylamino), (a 5- to 10-membered heteroarylcarbonylamino) and —$(CH_2)_{n^1}$phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano, $R^7$ is selected from the group consisting of H, halo, hydroxyl, oxo, $C_1$-$C_4$ alkyl, hydroxy-$C_1$-$C_4$-alkyl, $C_1$-$C_4$-alkoxy-$C_1$-$C_4$-alkyl, halo-$C_1$-$C_4$-alkyl, which contains 1 to 5 halogens, $C_1$-$C_4$-alkoxy, and halo-$C_1$-$C_4$-alkoxy;

or $R^6$ and $R^7$ can be taken together with the carbons to which they attach to form a $C_6$-$C_{10}$ aryl ring;

$R^{10}$ is selected from the group consisting of $C_1$-$C_4$ alkyl, halo, $C_1$-$C_4$ alkoxy, and halo-$C_1$-$C_2$-alkyl, which contains 1 to 5 halogens, where halo is F or Cl;

$n^1$, at each occurrence, is selected from 0, 1, 2, 3, 4 or 5; and p, at each occurrence, is selected from 0, 1 and 2.

In another embodiment, the present invention provides compounds, stereoisomers, tautomers, salts, solvates or prodrugs thereof, wherein W is O.

In another embodiment, the present invention provides compounds, stereoisomers, tautomers, salts, solvates or prodrugs thereof, wherein:

$R^0$ is $R^1$ or $R^{1a}$;

Y is S or —$CR^8$=$CR^9$—;

$R^1$ is independently selected from the group consisting of:
halo,
$C_1$-$C_4$ alkoxy,
halo-$C_1$-$C_2$-alkyl, which contains 1 to 5 halogens, where halo is F or Cl, and $C_1$-$C_4$ alkylthio;

$R^{1a}$ is independently selected from the group consisting of:
H,
halo,
$C_1$-$C_4$ alkyl,
$C_1$-$C_4$ alkoxy,
halo-$C_1$-$C_2$-alkyl, which contains 1 to 5 halogens, and $C_1$-$C_4$ alkylthio;

$R^8$ and $R^9$ are independently selected from the group consisting of:
H,
halo,
$C_1$-$C_4$ alkyl,
$C_1$-$C_4$ alkoxy,
$CF_3$,
$CF_3O$,
$CHF_2$, and
OH;

provided that at least one of $R^{1a}$, $R^8$ and $R^9$ is other than H;

$R^2$ is selected from the group consisting of:
H,
halo,
$C_1$-$C_4$ alkyl,
$C_1$-$C_4$ alkoxy, and
cyano;

$X^1$ is selected from the group consisting of CH, N or $CR^{10}$;

$X^2$, $X^3$ and $X^4$ are independently selected from $CR^3$ or N;

$R^3$ is selected from the group consisting of H, $C_1$-$C_4$ alkoxy, $C_1$-$C_4$ alkylthio, halo, $OCF_3$, $OCHF_2$, $OCH_2F$, and halo-$C_1$-$C_2$-alkyl, which contains 1 to 5 halogens;

$R^4$ and $R^5$ are independently selected from H and $C_1$-$C_6$ alkyl, or $R^4$ and $R^5$ can be taken together with the carbon to which they are attached to form a $C_3$-$C_7$ cycloalkyl ring;

is a 5-membered heteroaryl ring containing at least one O, N or S atom;

$R^6$ is selected from the group consisting of H, halo, $OCF_3$, $OCHF_2$, OH, CN, $NO_2$, $NR^{11}R^{12}$, COOH, $C_1$-$C_4$ alkoxycarbonyl, (C=O)$NR^{11}R^{12}$, $C_1$-$C_4$ alkylsulfonyl, S(=O)$_2NR^{11}R^{12}$, and $C_1$-$C_4$ alkyl substituted by 0 to 3 groups independently selected from halo, $CF_3$, $OCF_3$, OH, hydroxy-$C_1$-$C_4$-alkyl, $C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, and $C_1$-$C_4$ alkylthio, or $R^6$ is B-D-, where D is a linker, which is selected from: a single bond,

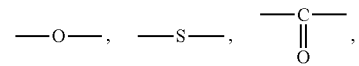

$C_1$-$C_4$ alkylene,
$C_1$-$C_4$ alkyleneoxy,
$C_1$-$C_4$ alkylenethio,
$C_1$-$C_4$ alkyleneoxy-$C_1$-$C_4$-alkylene,
$C_1$-$C_4$-alkylenethio-$C_1$-$C_4$-alkylene,
—S—$C_1$-$C_4$-alkylene, and
—O—$C_1$-$C_4$-alkylene, and B is selected from the group consisting of:

$C_6$-$C_{10}$ aryl substituted by 0 to 3 groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{11}R^{12}$, OH, $C_1$-$C_4$-alkylcarbonyloxy-$C_1$-$C_4$-alkyl, hydroxy-$C_1$-$C_4$-alkyl, $COOR^{14}$, $SO_2R^{14}$, (C=O)$NR^{11}R^{12}$, $SO_2NR^{11}R^{12}$, $N(R^{13})$(C=O)$NR^{11}R^{12}$, $N(R^{13})$(C=O)$OR^{14}$, $N(R^{13})$(C=O)$R^{14}$, $NR^{13}S(O)R^{14}$, $NR^{13}SO_2R^{14}$, O(C=O)$NR^{11}R^{12}$, O(C=O)$OR^{14}$, O(C=O)$R^{14}$, (C=O)$OR^{14}$, and 5-6-membered heteroaryl, 5- to 10-membered heteroaryl substituted by 0 to 3 groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{11}R^{12}$, OH, $C_1$-$C_4$-alkylcarbonyloxy-$C_1$-$C_4$-alkyl, hydroxy-$C_1$-$C_4$-alkyl, $COOR^{14}$, $SO_2R^{14}$, (C=O)$NR^{11}R^{12}$, $SO_2NR^{11}R^{12}$, $N(R^{13})$(C=O)$NR^{11}R^{12}$, $N(R^{13})$(C=O)$OR^{14}$, $N(R^{13})$(C=O)$R^{14}$, $NR^{13}S(O)R^{14}$, $NR^{13}SO_2R^{14}$, O(C=O)$NR^{11}R^{12}$, O(C=O)$OR^{14}$, O(C=O)$R^{14}$, (C=O)$OR^{14}$, 5-6-membered heteroaryl, and ($CH_2$)phenyl, 4- to 10-membered heterocyclyl containing carbon atoms and 1 to 2 additional heteroatoms selected from N, O, and S, and substituted by 0 to 3 groups independently selected from the group consisting of halo, oxo, —$(CHR^{13})_{n^1}$-5- or 6-membered heteroaryl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; $NR^{13}S(O)R^{14}$, $NR^{13}SO_2R^{14}$, —$(CHR^{13})_{n^1}$-4- to 10-membered-heterocyclyl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; OH, hydroxy-$C_1$-$C_4$-alkyl, $C_1$-$C_4$ alkoxy, halo-$C_1$-$C_4$ alkoxy, di-$C_1$-$C_4$-alkylamino-$C_1$-$C_4$-alkyl, $NR_{11}R_{12}$, cyano, $C_1$-$C_4$ alkyl, halo-$C_1$-$C_4$ alkyl, $C_3$-$C_6$ cycloalkyl, $C_1$-$C_4$- alkoxy-$C_1$-$C_4$-alkyl, $C_3$-$C_6$ cycloalkyl-$C_1$-$C_4$-alkylcarbonyl, $C_6$-$C_{10}$ arylcarbonyl, $C_1$-$C_4$-alkylcarbonyloxy-$C_1$-$C_4$-alkyl, COO$R^{14}$, SO$_2R^{14}$, (C=O)N$R^{11}R^{12}$, SO$_2$N$R^{11}R^{12}$, N($R^{13}$)(C=O)N$R^{11}R^{12}$, N($R^{13}$)(C=O)O$R^{14}$, N($R^{13}$)(C=O)$R^{14}$O(C=O)N$R^{11}R^{12}$, O(C=O)O$R^{14}$, O(C=O)$R^{14}$, (C=O)O$R^{14}$, and $C_6$-$C_{10}$ aryl substituted by 0 to 3 groups independently selected from the group consisting of halo, $C_1$-$C_4$ alkoxy, $C_1$-$C_4$ alkyl, cyclopropyl, $C_1$-$C_4$-alkoxycarbonyl, (C=O)N$R^{11}R^{12}$, CF$_3$, OCF$_3$, and CF$_2$CH$_3$;

$C_3$-$C_6$ cycloalkyl which may contain unsaturation, substituted by 0 to 3 groups independently selected from the group consisting of halo, CF$_3$, OCF$_3$, 5- or 6-membered heteroaryl, OH, oxo, hydroxy-$C_1$-$C_4$-alkyl, $C_6$-$C_{10}$ aryl, COOH, oxo, $C_1$-$C_4$-alkoxycarbonyl, (C=O)N$R^{11}R^{12}$, and $C_1$-$C_4$ alkyl; and $C_5$-$C_{11}$ spirocycloalkyl which may contain unsaturation and optionally containing 1 to 3 heteroatoms selected from O, N or S and substituted by 0 to 3 groups independently selected from the group consisting of halo, CF$_3$, OCF$_3$, 5- or 6-membered heteroaryl, OH, hydroxy-$C_1$-$C_4$-alkyl, $C_6$-$C_{10}$ aryl, and $C_1$-$C_4$ alkyl;

$R^{11}$ and $R^{12}$ are independently, at each occurrence, selected from the group consisting of:
H,
$C_1$-$C_4$ alkyl,
halo-$C_1$-$C_4$-alkyl,
$C_2$-$C_4$ alkenyl,
$C_2$-$C_4$ alkynyl,
—(C$R^{14}R^{14}$)$_n^1$-phenyl substituted by 0 to 3 groups independently selected from the group consisting of halo, $C_1$-$C_4$ alkoxy, $C_1$-$C_4$ alkyl, cyclopropyl, CF$_3$, OCF$_3$, 5- or 6-membered heteroaryl, OH, OCHF$_2$, di-$C_1$-$C_4$-alkylamino, and cyano,
—(CH$R^{13}$)$_n^1$—$C_3$-$C_6$-cycloalkyl substituted by 0 to 3 groups independently selected from the group consisting of halo, CF$_3$, OCF$_3$, 5- or 6-membered heteroaryl, OH, hydroxy-$C_1$-$C_4$-alkyl, and $C_1$-$C_4$ alkyl,
—(CH$R^{13}$)$_n^1$-4- to 10-membered-heterocyclyl substituted by 0 to 3 groups independently selected from the group consisting of halo, CF$_3$, OCF$_3$, 5- or 6-membered heteroaryl, OH, oxo, hydroxy-$C_1$-$C_4$-alkyl, and $C_1$-$C_4$ alkyl,
—(CH$R^{13}$)$_n^1$-5- to 10-membered-heteroaryl substituted by 0 to 3 groups independently selected from the group consisting of halo, CF$_3$, OCF$_3$, 5- or 6-membered heteroaryl, OH, hydroxy-$C_1$-$C_4$-alkyl, and $C_1$-$C_4$ alkyl,
di-$C_1$-$C_4$-alkylamino-$C_1$-$C_4$-alkyl,
$C_1$-$C_4$-alkylcarbonylamino-$C_1$-$C_4$-alkyl,
di-$C_1$-$C_4$-alkoxy-$C_1$-$C_4$-alkyl,
di-$C_1$-$C_4$-alkylaminophenyl,
hydroxy-$C_1$-$C_4$-alkyl,
cyano-$C_1$-$C_4$-alkyl,
$C_1$-$C_4$-alkoxy-$C_1$-$C_4$-alkyl,
$C_1$-$C_4$-alkoxycarbonyl-$C_1$-$C_4$-alkyl,
$C_1$-$C_4$-alkoxycarbonyl,
$C_1$-$C_4$-alkylcarbonyl,
phenylcarbonyl;
$C_1$-$C_4$-alkoxycarbonylamino-$C_1$-$C_4$-alkylcarbonyl,
di-$C_1$-$C_4$-alkylamino-$C_1$-$C_4$-alkylcarbonyl,
amino-$C_1$-$C_4$-alkylcarbonyl,
4- to 10-membered-heterocyclyl-carbonyl, and alternatively, $R^{11}$ and $R^{12}$, when attached to the same nitrogen, combine to form a 4- to 6-membered heterocyclic ring containing carbon atoms substituted by 0 to 3 groups independently selected from the group consisting of halo, CF$_3$, CHF$_2$, OCF$_3$, OCHF$_2$, OCH$_2$F, 5- or 6-membered heteroaryl, OH, oxo, hydroxy-$C_1$-$C_4$-alkyl, $C_1$-$C_4$ alkyl and $C_1$-$C_4$ alkoxy, and 0 to 2 additional heteroatoms selected from N, N$R^{13}$, O and S(O)$_p$;

$R^{13}$ is independently, at each occurrence, selected from the group consisting of H, $C_1$-$C_6$ alkyl and —(CH$_2$)phenyl;

$R^7$ is selected from the group consisting of H, halo, $C_1$-$C_3$ alkyl, hydroxy-$C_1$-$C_3$-alkyl, halo-$C_1$-$C_2$-alkyl, which contains 1 to 3 halogens, and halo-$C_1$-$C_2$-alkoxy;

$R^{10}$ is selected from the group consisting of $C_1$-$C_3$ alkyl, halo, $C_1$-$C_2$ alkoxy, and halo-$C_1$-$C_2$-alkyl, which contains 1 to 3 halogens, where halo is F or Cl;

$n^1$ is selected from 0, 1, 2, 3, 4 or 5; and p, at each occurrence, is selected from 0, 1 and 2.

In yet another embodiment, the present invention provides compounds, stereoisomers, tautomers, salts, solvates or prodrugs thereof, wherein:
Y is S or CH=CH—;
$X^1$ is CH or N;
$X^2$, $X^3$ and $X^4$ are each independently C$R^3$;
$R^0$ is $R^1$ or $R^{1a}$;
$R^1$ and $R^{1a}$ are independently selected from the group consisting of:
$C_1$-$C_2$ alkyl,
$C_1$-$C_2$ alkylthio,
$C_1$-$C_2$ alkoxy, and
halo-$C_1$-$C_2$-alkyl which contains 1 to 5 halogens;
$R^2$ is H;
$R_3$ is selected from the group consisting of:
H
$C_1$-$C_2$ alkoxy, and
halo; and
$R^4$ and $R^5$ are each H.

In still yet another embodiment, the present invention provides compounds, stereoisomers, tautomers, salts, solvates or prodrugs thereof, wherein the compounds are compounds of Formula IA and IB:

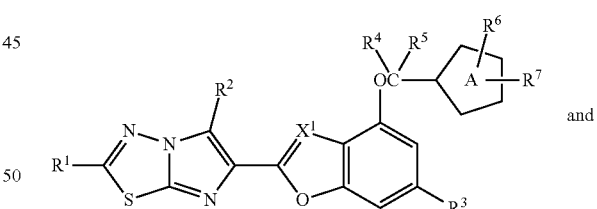

IA and

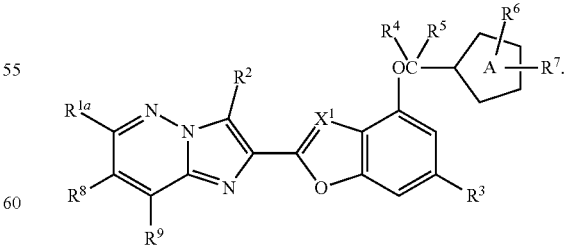

IB

In one embodiment, the present invention provides compounds, stereoisomers, tautomers, salts, solvates or prodrugs thereof, wherein the compounds are compounds of Formula IC, ID, IE and IF:

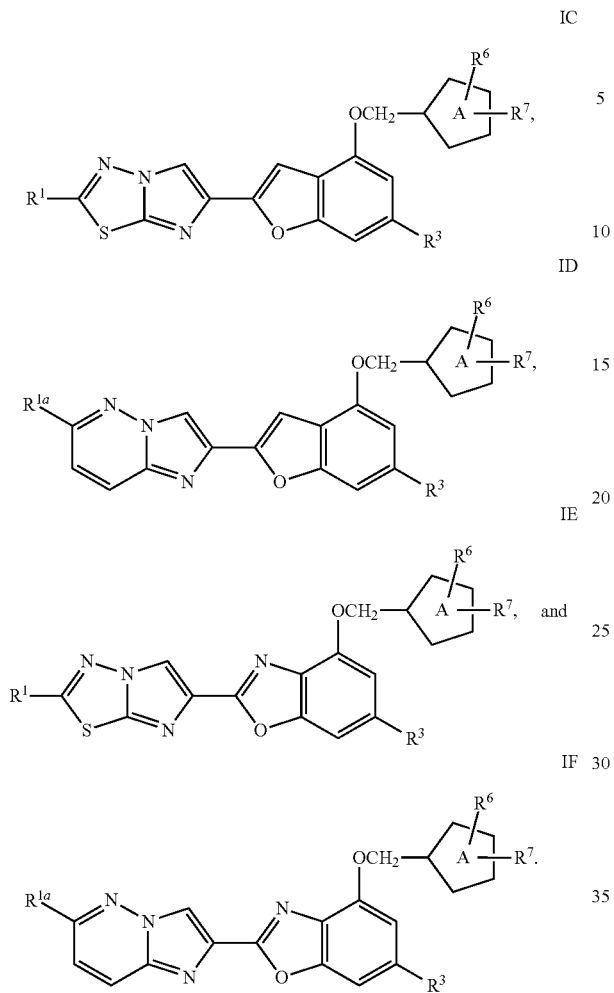

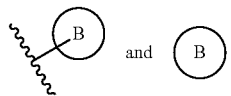

and is selected from the group consisting of:
- $C_6$-$C_{10}$ aryl substituted by 0 to 3 groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{11}R^{12}$, OH, $C_1$-$C_4$-alkylcarbonyloxy-$C_1$-$C_4$-alkyl, hydroxy-$C_1$-$C_4$-alkyl, $COOR^{14}$, $SO_2R^{14}$, $(C=O)NR^{11}R^{12}$, $SO_2NR^{11}R^{12}$, $N(R^{13})(C=O)NR^{11}R^{12}$, $N(R^{13})(C=O)OR^{14}$, $N(R^{13})(C=O)R^{14}$, $NR^{13}S(O)R^{14}$, $NR^{13}SO_2R^{14}$, $O(C=O)NR^{11}R^{12}$, $O(C=O)OR^{14}$, $O(C=O)R^{14}$, $(C=O)OR^{14}$, and 5-6-membered heteroaryl,
- 5- to 10-membered heteroaryl substituted by 0 to 3 groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{11}R^{12}$, OH, $C_1$-$C_4$-alkylcarbonyloxy-$C_1$-$C_4$-alkyl, hydroxy-$C_1$-$C_4$-alkyl, $COOR^{14}$, $SO_2R^{14}$, $(C=O)NR^{11}R^{12}$, $SO_2NR^{11}R^{12}$, $N(R^{13})(C=O)NR^{11}R^{12}$, $N(R^{13})(C=O)OR^{14}$, $N(R^{13})(C=O)R^{14}$, $NR^{13}S(O)R^{14}$, $NR^{13}SO_2R^{14}$, $O(C=O)NR^{11}R^{12}$, $O(C=O)OR^{14}$, $O(C=O)R^{14}$, $(C=O)OR^{14}$, 5-6-membered heteroaryl, and $(CH_2)$phenyl,
- 4- to 10-membered heterocyclyl containing carbon atoms and 1 to 2 additional heteroatoms selected from N, O, and S, and substituted by 0 to 3 groups independently selected from the group consisting of halo, oxo, —$(CHR^{13})_n^1$-5- or 6-membered heteroaryl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; $NR^{13}S(O)R^{14}$, $NR^{13}SO_2R^{14}$, —$(CHR^{13})_n^1$-4- to 10-membered-heterocyclyl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; OH, hydroxy-$C_1$-$C_4$-alkyl, $C_1$-$C_4$ alkoxy, halo-$C_1$-$C_4$ alkoxy, di-$C_1$-$C_4$-alkylamino-$C_1$-$C_4$-alkyl, $NR_{11}R_{12}$, cyano, $C_1$-$C_4$ alkyl, halo-$C_1$-$C_4$ alkyl, $C_3$-$C_6$ cycloalkyl, $C_1$-$C_4$-alkoxy-$C_1$-$C_4$-alkyl, $C_3$-$C_6$ cycloalkyl-$C_1$-$C_4$-alkylcarbonyl, $C_6$-$C_{10}$ arylcarbonyl, $C_1$-$C_4$-alkylcarbonyloxy-$C_1$-$C_4$-alkyl, $COOR^{14}$, $SO_2R^{14}$, $(C=O)NR^{11}R^{12}$, $SO_2NR^{11}R^{12}$, $N(R^{13})(C=O)NR^{11}R^{12}$, $N(R^{13})(C=O)OR^{14}$, $N(R^{13})(C=O)R^{14}$, $O(C=O)NR^{11}R^{12}$, $O(C=O)OR^{14}$, $O(C=O)R^{14}$, $(C=O)OR^{14}$, and $C_6$-$C_{10}$ aryl substituted by 0 to 3 groups independently selected from the group consisting of halo, $C_1$-$C_4$ alkoxy, $C_1$-$C_4$ alkyl, cyclopropyl, $C_1$-$C_4$-alkoxycarbonyl, $(C=O)NR^{11}R^{12}$, $CF_3$, $OCF_3$, and $CF_2CH_3$; and
- $C_3$-$C_6$ cycloalkyl which may contain unsaturation, substituted by 0 to 3 groups independently selected from the group consisting of halo, $CF_3$, $OCF_3$, 5- or 6-membered heteroaryl, OH, oxo, hydroxy-$C_1$-$C_4$-alkyl, $C_6$-$C_{10}$ aryl, COOH, oxo, $C_1$-$C_4$-alkoxycarbonyl, $(C=O)NR^{11}R^{12}$, and $C_1$-$C_4$ alkyl.

In one embodiment, the present invention provides compounds, stereoisomers, tautomers, salts, solvates or prodrugs thereof, wherein the compounds are compounds of Formula IA.

In one embodiment, the present invention provides compounds, stereoisomers, tautomers, salts, solvates or prodrugs thereof, wherein the compounds are compounds of Formula IB.

In one embodiment, the present invention provides compounds, stereoisomers, tautomers, salts, solvates or prodrugs thereof, wherein the compounds are compounds of Formula IC.

In one embodiment, the present invention provides compounds, stereoisomers, tautomers, salts, solvates or prodrugs thereof, wherein the compounds are compounds of Formula ID.

In one embodiment, the present invention provides compounds, stereoisomers, tautomers, salts, solvates or prodrugs thereof, wherein the compounds are compounds of Formula IE.

In one embodiment, the present invention provides compounds, stereoisomers, tautomers, salts, solvates or prodrugs thereof, wherein the compounds are compounds of Formula IF.

In yet another embodiment, the present invention provides compounds, stereoisomers, tautomers, salts, solvates or prodrugs thereof, wherein $R^6$ is In yet another embodiment, the present invention provides compounds, stereoisomers, tautomers, salts, solvates or prodrugs thereof, wherein $R^6$ is selected from the group consisting of H, halo, $OCF_3$, $OCHF_2$, $NR^{11}R^{12}$, $C_1$-$C_4$ alkoxycarbonyl, $(C=O)NR^{11}R^{12}$, $C_1$-$C_4$ alkylsulfonyl, $S(=O)_2NR^{11}R^{12}$, and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, and $C_3$-$C_6$-cycloalkyl.

In yet another embodiment, the present invention provides compounds, stereoisomers, tautomers, salts, solvates or prodrugs thereof, wherein

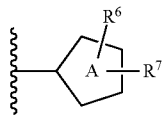

is selected from the group consisting of

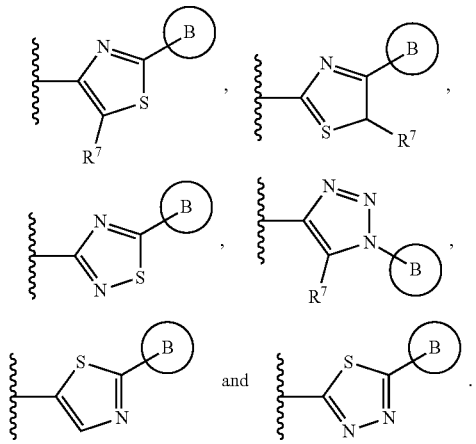

In still yet another embodiment, the present invention provides compounds, stereoisomers, tautomers, salts, solvates or prodrugs thereof, wherein:

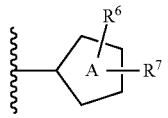

is selected from the group consisting of

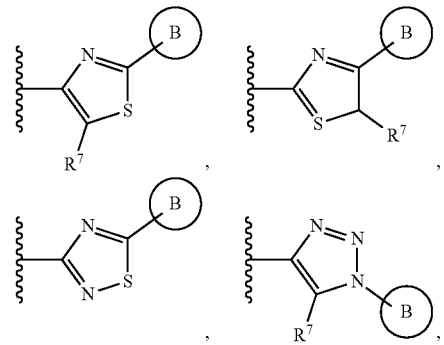

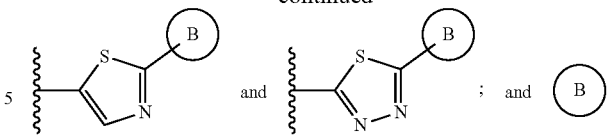

is selected from the group consisting of:

- $C_6$-$C_{10}$ aryl substituted by 0 to 3 groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{11}R^{12}$, OH, $C_1$-$C_4$-alkylcarbonyloxy-$C_1$-$C_4$-alkyl, hydroxy-$C_1$-$C_4$-alkyl, $COOR^{14}$, $SO_2R^{14}$, $(C=O)NR^{11}R^{12}$, $SO_2NR^{11}R^{12}$, $N(R^{13})(C=O)NR_{11}R_{12}$, $N(R^{13})(C=O)OR^{14}$, $N(R^{13})(C=O)R^{14}$, $NR^{13}S(O)R^{14}$, $NR^{13}SO_2R^{14}$, $O(C=O)NR^{11}R^{12}$, $O(C=O)OR^{14}$, $O(C=O)R^{14}$, $(C=O)OR^{14}$, and 5-6-membered heteroaryl,
- 5- to 10-membered heteroaryl substituted by 0 to 3 groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{11}R^{12}$, OH, $C_1$-$C_4$-alkylcarbonyloxy-$C_1$-$C_4$-alkyl, hydroxy-$C_1$-$C_4$-alkyl, $COOR^{14}$, $SO_2R^{14}$, $(C=O)NR^{11}R^{12}$, $SO_2NR^{11}R^{12}$, $N(R^{13})(C=O)NR^{11}R^{12}$, $N(R^{13})(C=O)OR^{14}$, $N(R^{13})(C=O)R^{14}$, $NR^{13}S(O)R^{14}$, $NR^{13}SO_2R^{14}$, $O(C=O)NR^{11}R^{12}$, $O(C=O)OR^{14}$, $O(C=O)R^{14}$, $(C=O)OR^{14}$, 5-6-membered heteroaryl, and $(CH_2)$phenyl,
- 4- to 10-membered heterocyclyl containing carbon atoms and 1 to 2 additional heteroatoms selected from N, O, and S, and substituted by 0 to 3 groups independently selected from the group consisting of halo, oxo, —$(CHR^{13})_n$-1-5- or 6-membered heteroaryl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; $NR^{13}S(O)R^{14}$, $NR^{13}SO_2R^{14}$, —$(CHR^{13})_n$-1-4- to 10-membered-heterocyclyl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; OH, hydroxy-$C_1$-$C_4$-alkyl, $C_1$-$C_4$ alkoxy, halo-$C_1$-$C_4$ alkoxy, di-$C_1$-$C_4$-alkylamino-$C_1$-$C_4$-alkyl, $NR_{11}R_{12}$, cyano, $C_1$-$C_4$ alkyl, halo-$C_1$-$C_4$ alkyl, $C_3$-$C_6$ cycloalkyl, $C_1$-$C_4$-alkoxy-$C_1$-$C_4$-alkyl, $C_3$-$C_6$ cycloalkyl-$C_1$-$C_4$-alkylcarbonyl, $C_6$-$C_{10}$ arylcarbonyl, $C_1$-$C_4$-alkylcarbonyloxy-$C_1$-$C_4$-alkyl, $COOR^{14}$, $SO_2R^{14}$, $(C=O)NR^{11}R^{12}$, $SO_2NR^{11}R^{12}$, $N(R^{13})(C=O)NR^{11}R^{12}$, $N(R^{13})(C=O)OR^4$, $N(R^{13})(C=O)R^{14}$, $O(C=O)NR^{11}R^{12}$, $O(C=O)OR^{14}$, $O(C=O)R^{14}$, $(C=O)OR^{14}$, and $C_6$-$C_{10}$ aryl substituted by 0 to 3 groups independently selected from the group consisting of halo, $C_1$-$C_4$ alkoxy, $C_1$-$C_4$ alkyl, cyclopropyl, $C_1$-$C_4$-alkoxycarbonyl, $(C=O)NR^{11}R^{12}$, $CF_3$, $OCF_3$, and $CF_2CH_3$; and
- $C_3$-$C_6$ cycloalkyl which may contain unsaturation, substituted by 0 to 3 groups independently selected from the group consisting of halo, $CF_3$, $OCF_3$, 5- or 6-membered heteroaryl, OH, oxo, hydroxy-$C_1$-$C_4$-alkyl, $C_6$-$C_{10}$ aryl, COOH, oxo, $C_1$-$C_4$-alkoxycarbonyl, $(C=O)NR^{11}R^{12}$, and $C_1$-$C_4$ alkyl.

In one embodiment, the present invention provides compounds, stereoisomers, tautomers, salts, solvates or prodrugs thereof, wherein:

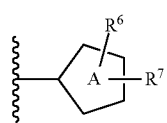

is selected from the group consisting of

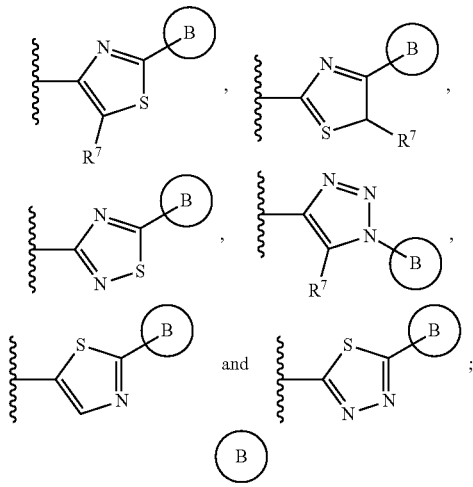

is selected from the group consisting of:
- $C_6$-$C_{10}$ aryl substituted by 0 to 3 groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{11}R^{12}$, OH, $C_1$-$C_4$-alkylcarbonyloxy-$C_1$-$C_4$-alkyl, hydroxy-$C_1$-$C_4$-alkyl, $COOR^{14}$, $SO_2R^{14}$, $(C=O)NR^{11}R^{12}$, $SO_2NR^{11}R^{12}$, $N(R^3)(C=O)NR^{11}R^{12}$, $N(R^{13})(C=O)OR^{14}$, $N(R^{13})(C=O)R^{14}$, $NR^{13}S(O)R^{14}$, $NR^{13}SO_2R^{14}$, $O(C=O)NR^{11}R^{12}$, $O(C=O)OR^{14}$, $O(C=O)R^{14}$, $(C=O)OR^{14}$, and 5-6-membered heteroaryl,
- 5- to 10-membered heteroaryl substituted by 0 to 3 groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{11}R^{12}$, OH, $C_1$-$C_4$-alkylcarbonyloxy-$C_1$-$C_4$-alkyl, hydroxy-$C_1$-$C_4$-alkyl, $COOR^{14}$, $SO_2R^{14}$, $(C=O)NR^{11}R^{12}$, $SO_2NR^{11}R^{12}$, $N(R^{13})(C=O)NR^{11}R^{12}$, $N(R^{13})(C=O)OR^{14}$, $N(R^{13})(C=O)R^{14}$, $NR^{13}S(O)R^{14}$, $NR^{13}SO_2R^{14}$, $O(C=O)NR^{11}R^{12}$, $O(C=O)OR^{14}$, $O(C=O)R^{14}$, $(C=O)OR^{14}$, 5-6-membered heteroaryl, and $(CH_2)$phenyl,
- 4- to 10-membered heterocyclyl containing carbon atoms and 1 to 2 additional heteroatoms selected from N, O, and S, and substituted by 0 to 3 groups independently selected from the group consisting of halo, oxo, $-(CHR^{13})_n^1$-5- or 6-membered heteroaryl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; $NR^{13}S(O)R^{14}$, $NR^{13}SO_2R^{14}$, $-(CHR^{13})_n^1$-4- to 10-membered-heterocyclyl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; OH, hydroxy-$C_1$-$C_4$-alkyl, $C_1$-$C_4$ alkoxy, halo-$C_1$-$C_4$ alkoxy, di-$C_1$-$C_4$-alkylamino-$C_1$-$C_4$-alkyl, $NR_{11}R_{12}$, cyano, $C_1$-$C_4$ alkyl, halo-$C_1$-$C_4$ alkyl, $C_3$-$C_6$ cycloalkyl, $C_1$-$C_4$-alkoxy-$C_1$-$C_4$-alkyl, $C_3$-$C_6$ cycloalkyl-$C_1$-$C_4$-alkylcarbonyl, $C_6$-$C_{10}$ arylcarbonyl, $C_1$-$C_4$-alkylcarbonyloxy-$C_1$-$C_4$-alkyl, $COOR^{14}$, $SO_2R^{14}$, $(C=O)NR^{11}R^{12}$, $SO_2NR^{11}R^{12}$, $N(R^{13})(C=O)NR^{11}R^{12}$, $N(R^{13})(C=O)OR^{14}$, $N(R^{13})(C=O)R^{14}$, $O(C=O)NR^{11}R^{12}$, $O(C=O)OR^{14}$, $O(C=O)R^{14}$, $(C=O)OR^{14}$, and $C_6$-$C_{10}$ aryl substituted by 0 to 3 groups independently selected from the group consisting of halo, $C_1$-$C_4$ alkoxy, $C_1$-$C_4$ alkyl, cyclopropyl, $C_1$-$C_4$-alkoxycarbonyl, $(C=O)NR^{11}R^{12}$, $CF_3$, $OCF_3$, and $CF_2CH_3$; and
- $C_3$-$C_6$ cycloalkyl which may contain unsaturation, substituted by 0 to 3 groups independently selected from the group consisting of halo, $CF_3$, $OCF_3$, 5- or 6-membered heteroaryl, OH, oxo, hydroxy-$C_1$-$C_4$-alkyl, $C_6$-$C_{10}$ aryl, COOH, oxo, $C_1$-$C_4$-alkoxycarbonyl, $(C=O)NR^{11}R^{12}$, and $C_1$-$C_4$ alkyl; and $R^7$ is selected from the group consisting of H, halo, $C_1$-$C_4$ alkyl, and hydroxy-$C_1$-$C_4$-alkyl.

In another embodiment, the present invention provides compounds, stereoisomers, tautomers, salts, solvates or prodrugs thereof, wherein:

W is O or S;
$R^0$ is $R^1$ or $R^{1a}$;
Y is S or $-CR^8=CR^9-$;
$R^1$ is independently selected from the group consisting of:
- halo,
- $C_1$-$C_4$ alkyl,
- $C_2$-$C_3$ alkenyl,
- $C_2$-$C_3$ alkynyl,
- $C_3$-$C_4$ cycloalkyl,
- $C_1$-$C_4$ alkoxy,
- $C_1$-$C_2$ alkoxy-$C_1$-$C_2$ alkyl,
- tetrahydrofuran-2-yl;
- $C_1$-$C_4$ alkylthio,
- halo-$C_1$-$C_2$-alkyl, which contains 1 to 5 halogens, where halo is F or Cl,
- halo-$C_3$-$C_4$ cycloalkyl,
- halo-$C_1$-$C_2$ alkoxy, and
- halo-$C_1$-$C_2$ alkylthio;

$R^{1a}$ is independently selected from the group consisting of:
- H,
- halo,
- $C_1$-$C_4$ alkyl,
- $C_2$-$C_3$ alkenyl,
- $C_2$-$C_3$ alkynyl,
- $C_3$-$C_4$ cycloalkyl,
- $C_1$-$C_4$ alkoxy,
- $C_1$-$C_2$ alkoxy-$C_1$-$C_2$ alkyl,
- tetrahydrofuran-2-yl;
- $C_1$-$C_4$ alkylthio,
- halo-$C_1$-$C_2$-alkyl, which contains 1 to 5 halogens, where halo is F or Cl,
- halo-$C_3$-$C_4$ cycloalkyl,
- halo-$C_1$-$C_2$ alkoxy, and
- halo-$C_1$-$C_2$ alkylthio;

$R^8$ and $R^9$ are independently selected from the group consisting of:
- H,
- halo,
- $C_1$-$C_4$ alkyl,
- $C_1$-$C_4$ alkoxy,
- halo-$C_1$-$C_2$ alkyl,
- halo-$C_1$-$C_2$ alkoxy, and
- OH;

provided that at least one of $R^{1a}$, $R^8$ and $R^9$ is other than H;

$R^2$ is selected from the group consisting of:
H,
halo,
$C_1$-$C_4$ alkyl, and
$C_1$-$C_4$ alkoxy;
$X^1$ is selected from the group consisting of CH, N or $CR^{10}$;
$X^2$, $X^3$ and $X^4$ are independently selected from $CR^3$ or N;
$R^3$ is selected from the group consisting of H, $C_1$-$C_4$ alkyl, $C_2$-$C_4$ alkenyl, $C_2$-$C_4$ alkynyl, $C_1$-$C_4$ alkoxy, $C_1$-$C_4$ alkylthio, halo, OH, CN, $OCF_3$, $C_1$-$C_2$-alkoxy-$C_1$-$C_2$-alkoxy, halo-$C_1$-$C_3$-alkyl, which contains 1 to 5 halogens, benzyloxy substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano, and —$(CH_2)_n{}^1$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano;
$R^4$ and $R^5$ are independently selected from H and $C_1$-$C_6$ alkyl, or $R^4$ and $R^5$ can be taken together with the carbon to which they are attached to form a $C_3$-$C_7$ cycloalkyl ring;

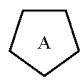

is a 5-membered heteroaryl ring containing at least one O, N or S atom;
$R^6$ is selected from the group consisting of H, halo, $OCF_3$, $OCHF_2$, OH, CN, $NO_2$, $NR^{11}R^{12}$, COOH, $C_1$-$C_4$ alkoxycarbonyl, $(C=O)NR^{11}R^{12}$, $C_1$-$C_4$ alkylsulfonyl, and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, and $C_1$-$C_4$ alkylthio, or
$R^6$ is B-D-, where D is a linker, which is selected from:
a single bond,

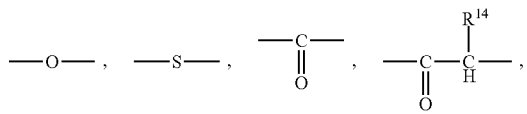

$C_1$-$C_4$ alkylene substituted by 0 to 4 groups independently selected from halo or OH,
$C_1$-$C_4$ alkyleneoxy,
$C_1$-$C_4$ alkylenethio,
$C_1$-$C_4$ alkyleneoxy-$C_1$-$C_4$-alkylene,
$C_1$-$C_4$-alkylenethio-$C_1$-$C_4$-alkylene,
$C_2$-$C_6$ alkenylene, and
B is selected from the group consisting of:
$C_6$-$C_{10}$ aryl substituted by 0 to 3 groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{11}R^{12}$, OH, $C_1$-$C_4$-alkylcarbonyloxy-$C_1$-$C_4$-alkyl, hydroxy-$C_1$-$C_4$-alkyl, $COOR^{14}$, $SO_2R^{14}$, $(C=O)NR^{11}R^{12}$, $SO_2NR^{11}R^{12}$, $N(R^{13})(C=O)NR^{11}R^{12}$, $N(R^{13})(C=O)OR^{14}$, $N(R^{13})(C=O)R^{14}$, $NR^{13}S(O)R^{14}$, $NR^{13}SO_2R^{14}$, $O(C=O)NR^{11}R^{12}$, $O(C=O)OR^{14}$, $O(C=O)R^{14}$, $(C=O)OR^{14}$, and 5-6-membered heteroaryl,
5- to 10-membered heteroaryl substituted by 0 to 3 groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{11}R^{12}$, OH, $C_1$-$C_4$-alkylcarbonyloxy-$C_1$-$C_4$-alkyl, hydroxy-$C_1$-$C_4$-alkyl, $COOR^{14}$, $SO_2R^{14}$, $(C=O)NR^{11}R^{12}$, $SO_2NR^{11}R^{12}$, $N(R^{13})(C=O)NR^{11}R^{12}$, $N(R^{13})(C=O)OR^{14}$, $N(R^{13})(C=O)R^{14}$, $NR^{13}S(O)R^{14}$, $NR^{13}SO_2R^{14}$, $O(C=O)NR^{11}R^{12}$, $O(C=O)OR^{14}$, $O(C=O)R^{14}$, $(C=O)OR^{14}$, 5-6-membered heteroaryl, and $(CH_2)$phenyl,
4- to 10-membered heterocyclyl containing carbon atoms and 1 to 2 additional heteroatoms selected from N, O, and S, and substituted by 0 to 3 groups independently selected from the group consisting of halo, oxo, —$(CHR^{13})_n{}^1$-5- or 6-membered heteroaryl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; $NR^{13}S(O)R^{14}$, $NR^{13}SO_2R^{14}$, —$(CHR^{13})_n{}^1$-4- to 10-membered-heterocyclyl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; OH, hydroxy-$C_1$-$C_4$-alkyl, $C_1$-$C_4$ alkoxy, halo-$C_1$-$C_4$ alkoxy, di-$C_1$-$C_4$-alkylamino-$C_1$-$C_4$-alkyl, $NR_{11}R_{12}$, cyano, $C_1$-$C_4$ alkyl, halo-$C_1$-$C_4$ alkyl, $C_3$-$C_6$ cycloalkyl, $C_1$-$C_4$-alkoxy-$C_1$-$C_4$-alkyl, $C_3$-$C_6$ cycloalkyl-$C_1$-$C_4$-alkylcarbonyl, $C_6$-$C_{10}$ arylcarbonyl, $C_1$-$C_4$-alkylcarbonyloxy-$C_1$-$C_4$-alkyl, $COOR^{14}$, $SO_2R^{14}$, $(C=O)NR^{11}R^{12}$, $SO_2NR^{11}R^{12}$, $N(R^{13})(C=O)NR^{11}R^{12}$, $N(R^{13})(C=O)OR^{14}$, $N(R^{13})(C=O)R^{14}O(C=O)NR^{11}R^{12}$, $O(C=O)OR^{14}$, $O(C=O)R^{14}$, $(C=O)OR^{14}$, and $C_6$-$C_{10}$ aryl substituted by 0 to 3 groups independently selected from the group consisting of halo, $C_1$-$C_4$ alkoxy, $C_1$-$C_4$ alkyl, cyclopropyl, $C_1$-$C_4$-alkoxycarbonyl, $(C=O)NR^{11}R^{12}$, $CF_3$, $OCF_3$, and $CF_2CH_3$;
$C_3$-$C_6$ cycloalkyl which may contain unsaturation, substituted by 0 to 3 groups independently selected from the group consisting of halo, $CF_3$, $OCF_3$, 5- or 6-membered heteroaryl, OH, oxo, hydroxy-$C_1$-$C_4$-alkyl, $C_6$-$C_{10}$ aryl, COOH, oxo, $C_1$-$C_4$-alkoxycarbonyl, $(C=O)NR^{11}R^{12}$, and $C_1$-$C_4$ alkyl; and
$C_5$-$C_{11}$ spirocycloalkyl which may contain unsaturation and optionally containing 1 to 3 heteroatoms selected from O, N or S and substituted by 0 to 3 groups independently selected from the group consisting of halo, $CF_3$, $OCF_3$, 5- or 6-membered heteroaryl, OH, hydroxy-$C_1$-$C_4$-alkyl, $C_6$-$C_{10}$ aryl, and $C_1$-$C_4$ alkyl;
$R^{11}$ and $R^{12}$ are independently, at each occurrence, selected from the group consisting of:
H,
$C_1$-$C_4$ alkyl,
halo-$C_1$-$C_4$-alkyl,
$C_2$-$C_4$ alkenyl,
$C_2$-$C_4$ alkynyl,
—$(CR^{14}R^{14})_n{}^1$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano,
—$(CHR^{13})_n{}^1$—$C_3$-$C_6$-cycloalkyl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl, —(CHR$^{13}$)$_{n^1}$-4- to 10-membered-heterocyclyl substituted by 0 to 3 groups independently selected from the group consisting of halo, CF$_3$, OCF$_3$, 5- or 6-membered heteroaryl, OH, oxo, hydroxy-C$_1$-C$_4$-alkyl, and C$_1$-C$_4$ alkyl, —(CHR$^{13}$)$_{n^1}$-5- to 10-membered-heteroaryl substituted by 0 to 3 groups independently selected from the group consisting of halo, CF$_3$, OCF$_3$, 5- or 6-membered heteroaryl, OH, hydroxy-C$_1$-C$_4$-alkyl, and C$_1$-C$_4$ alkyl, di-C$_1$-C$_4$-alkylamino-C$_1$-C$_4$-alkyl,
di-C$_1$-C$_4$-alkoxy-C$_1$-C$_4$-alkyl,
hydroxy-C$_1$-C$_4$-alkyl,
cyano-C$_1$-C$_4$-alkyl,
C$_1$-C$_4$-alkoxy-C$_1$-C$_4$-alkyl,
C$_1$-C$_4$-alkoxycarbonyl-C$_1$-C$_4$-alkyl,
C$_1$-C$_4$-alkoxycarbonyl,
C$_1$-C$_4$-alkylcarbonyl,
phenylcarbonyl;
C$_1$-C$_4$-alkoxycarbonylamino-C$_1$-C$_4$-alkylcarbonyl,
di-C$_1$-C$_4$-alkylamino-C$_1$-C$_4$-alkylcarbonyl,
amino-C$_1$-C$_4$-alkylcarbonyl, 4- to 10-membered-heterocyclyl-carbonyl, and alternatively, R$^{11}$ and R$^{12}$, when attached to the same nitrogen, combine to form a 4- to 8-membered heterocyclic ring containing carbon atoms substituted by 0 to 3 groups independently selected from the group consisting of halo, CF$_3$, CHF$_2$, OCF$_3$, OCHF$_2$, OCH$_2$F, 5- or 6-membered heteroaryl, OH, oxo, hydroxy-C$_1$-C$_4$-alkyl, C$_1$-C$_4$ alkyl and C$_1$-C$_4$ alkoxy, and 0 to 2 additional heteroatoms selected from N, NR$^{13}$, O and S(O)$_p$;

R$^{13}$ is independently, at each occurrence, selected from the group consisting of H, C$_1$-C$_6$ alkyl and —(CH$_2$)phenyl;

R$^{14}$ is independently, at each occurrence, selected from the group consisting of H, C$_1$-C$_6$ alkyl, halo-C$_1$-C$_4$-alkyl, C$_1$-C$_4$-alkoxycarbonylamino, (C$_6$-C$_{10}$ arylcarbonylamino), (a 5- to 10-membered heteroarylcarbonylamino) and —(CH$_2$)$_{n^1}$phenyl substituted by 0 to 3 groups independently selected from the group consisting of halo, C$_1$-C$_4$ alkoxy, C$_1$-C$_4$ alkyl, cyclopropyl, CF$_3$, OCF$_3$, 5- or 6-membered heteroaryl, OH, OCHF$_2$, di-C$_1$-C$_4$-alkylamino, and cyano;

R$^7$ is selected from the group consisting of H, halo, hydroxyl, oxo, C$_1$-C$_4$ alkyl, hydroxy-C$_1$-C$_4$-alkyl, C$_1$-C$_4$-alkoxy-C$_1$-C$_4$-alkyl, halo-C$_1$-C$_4$-alkyl, which contains 1 to 5 halogens, C$_1$-C$_4$-alkoxy, and halo-C$_1$-C$_4$-alkoxy;

R$^{10}$ is selected from the group consisting of C$_1$-C$_4$ alkyl, halo, C$_1$-C$_4$ alkoxy, and halo-C$_1$-C$_2$-alkyl, which contains 1 to 5 halogens, where halo is F or Cl;

n$^1$, at each occurrence, is selected from 0, 1, 2, 3, 4 or 5; and p, at each occurrence, is selected from 0, 1 and 2.

In yet another embodiment, the present invention provides compounds, stereoisomers, tautomers, salts, solvates or prodrugs thereof, wherein:

W is O or S;
R$^0$ is R$^1$ or R$^{1a}$;
Y is S or —CR$^8$=CR$^9$—;
R$^1$ is independently selected from the group consisting of:
halo,
C$_1$-C$_4$ alkyl,
C$_2$-C$_3$ alkenyl,
C$_2$-C$_3$ alkynyl,
C$_3$-C$_4$ cycloalkyl,
C$_1$-C$_4$ alkoxy,
C$_1$-C$_4$ alkylthio,
halo-C$_1$-C$_2$-alkyl, which contains 1 to 5 halogens, where halo is F or Cl,
halo-C$_3$-C$_4$ cycloalkyl,
halo-C$_1$-C$_2$ alkoxy, and
halo-C$_1$-C$_2$ alkylthio;

R$^{1a}$ is independently selected from the group consisting of:
H,
halo,
C$_1$-C$_4$ alkyl,
C$_2$-C$_3$ alkenyl,
C$_2$-C$_3$ alkynyl,
C$_3$-C$_4$ cycloalkyl,
C$_1$-C$_4$ alkoxy,
C$_1$-C$_4$ alkylthio,
halo-C$_1$-C$_2$-alkyl, which contains 1 to 5 halogens, where halo is F or Cl,
halo-C$_3$-C$_4$ cycloalkyl,
halo-C$_1$-C$_2$ alkoxy, and
halo-C$_1$-C$_2$ alkylthio;

R$^8$ and R$^9$ are independently selected from the group consisting of:
H,
halo,
C$_1$-C$_4$ alkyl,
C$_1$-C$_4$ alkoxy,
halo-C$_1$-C$_2$ alkyl, and
halo-C$_1$-C$_2$ alkoxy;

provided that at least one of R$^{1a}$, R$^8$ and R$^9$ is other than H;

R$^2$ is selected from the group consisting of:
H,
halo, and
C$_1$-C$_4$ alkyl;

X$^1$ is selected from the group consisting of CH, N or CR$^{10}$;

X$^2$, X$^3$ and X$^4$ are independently selected from CR$^3$ or N;

R$^3$ is selected from the group consisting of H, C$_1$-C$_4$ alkyl, C$_2$-C$_4$ alkenyl, C$_2$-C$_4$ alkynyl, C$_1$-C$_4$ alkoxy, C$_1$-C$_4$ alkylthio, halo, OH, CN, OCF$_3$, C$_1$-C$_2$-alkoxy-C$_1$-C$_2$-alkoxy, halo-C$_1$-C$_3$-alkyl, which contains 1 to 5 halogens, and —(CH$_2$)$_{n^1}$-phenyl substituted by 0 to 3 groups independently selected from the group consisting of halo, C$_1$-C$_4$ alkoxy, C$_1$-C$_4$ alkyl, cyclopropyl, CF$_3$, OCF$_3$, 5- or 6-membered heteroaryl, OH, OCHF$_2$, di-C$_1$-C$_4$-alkylamino, and cyano;

R$^4$ and R$^5$ are independently selected from H and C$_1$-C$_6$ alkyl, or R$^4$ and R$^5$ can be taken together with the carbon to which they are attached to form a C$_3$-C$_7$ cycloalkyl ring;

is a 5-membered heteroaryl ring containing at least one O, N or S atom;

R$^6$ is selected from the group consisting of H, halo, OCF$_3$, OCHF$_2$, OH, CN, NO$_2$, NR$^{11}$R$^{12}$, COOH, C$_1$-C$_4$ alkoxycarbonyl, (C=O)NR$^{11}$R$^{12}$ and C$_1$-C$_5$ alkyl substituted by 0 to 7 groups independently selected from halo, CF$_3$, OCF$_3$, OH, hydroxy-C$_1$-C$_4$-alkyl, C$_1$-C$_4$ alkoxy, C$_1$-C$_4$ alkoxy-C$_1$-C$_4$ alkoxy, di-C$_1$-C$_4$-alkylaminophenyl-C$_1$-C$_4$-alkyl, (di-C$_1$-C$_4$-alkoxy-C$_1$-C$_4$-alkyl)-C$_1$-C$_4$-alkyl, di-C$_1$-C$_4$-alkylamino, C$_3$-C$_6$-cycloalkyl, and C$_1$-C$_4$ alkylthio, or $R^6$ is B-D-, where D is a linker, which is selected from: a single bond,

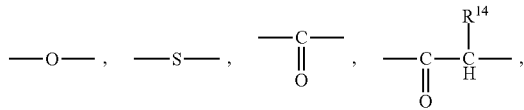

$C_1$-$C_4$ alkylene substituted by 0 to 4 groups independently selected from halo or OH,
$C_1$-$C_4$ alkyleneoxy,
$C_1$-$C_4$ alkylenethio,
$C_2$-$C_6$ alkenylene, and B is selected from the group consisting of:
$C_6$-$C_{10}$ aryl substituted by 0 to 3 groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{11}R^{12}$, OH, $C_1$-$C_4$-alkylcarbonyloxy-$C_1$-$C_4$-alkyl, hydroxy-$C_1$-$C_4$-alkyl, $COOR^{14}$, $SO_2R^{14}$, $(C=O)NR^{11}R^{12}$, $SO_2NR^{11}R^{12}$, $N(R^{13})(C=O)NR^{11}R^{12}$, $N(R^{13})(C=O)OR^{14}$, $N(R^{13})(C=O)R^{14}$, $NR^{13}S(O)R^{14}$, $NR^{13}SO_2R^{14}$, $O(C=O)NR^{11}R^{12}$, $O(C=O)OR^{14}$, $O(C=O)R^{14}$, $(C=O)OR^{14}$, and 5-6-membered heteroaryl, 5- to 10-membered heteroaryl substituted by 0 to 3 groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{11}R^{12}$, OH, $C_1$-$C_4$-alkylcarbonyloxy-$C_1$-$C_4$-alkyl, hydroxy-$C_1$-$C_4$-alkyl, $COOR^{14}$, $SO_2R^{14}$, $(C=O)NR^{11}R^{12}$, $SO_2NR^{11}R^{12}$, $N(R^{13})(C=O)NR^{11}R^{12}$, $N(R^{13})(C=O)OR^{14}$, $N(R^{13})(C=O)R^{14}$, $NR^{13}S(O)R^{14}$, $NR^{13}SO_2R^{14}$, $O(C=O)NR^{11}R^{12}$, $O(C=O)OR^{14}$, $O(C=O)R^{14}$, $(C=O)OR^{14}$, 5-6-membered heteroaryl, and $(CH_2)$phenyl, 4- to 10-membered heterocyclyl containing carbon atoms and 1 to 2 additional heteroatoms selected from N, O, and S, and substituted by 0 to 3 groups independently selected from the group consisting of halo, oxo, $-(CHR^{13})_n^1$-5- or 6-membered heteroaryl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; $NR^{13}S(O)R^{14}$, $NR^{13}SO_2R^{14}$, $-(CHR^{13})_n^1$-4- to 10-membered-heterocyclyl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; OH, hydroxy-$C_1$-$C_4$-alkyl, $C_1$-$C_4$ alkoxy, halo-$C_1$-$C_4$ alkoxy, di-$C_1$-$C_4$-alkylamino-$C_1$-$C_4$-alkyl, $NR_{11}R_{12}$, cyano, $C_1$-$C_4$ alkyl, halo-$C_1$-$C_4$ alkyl, $C_3$-$C_6$ cycloalkyl, $C_1$-$C_4$-alkoxy-$C_1$-$C_4$-alkyl, $C_3$-$C_6$ cycloalkyl-$C_1$-$C_4$-alkylcarbonyl, $C_6$-$C_{10}$ arylcarbonyl, $C_1$-$C_4$-alkylcarbonyloxy-$C_1$-$C_4$-alkyl, $COOR^{14}$, $SO_2R^{14}$, $(C=O)NR^{11}R^{12}$, $SO_2NR^{11}R^{12}$, $N(R^{13})(C=O)NR^{11}R^{12}$, $N(R^{13})(C=O)OR^{14}$, $N(R^3)(C=O)R^{14}$, $O(C=O)NR^{11}R^{12}$, $O(C=O)OR^{14}$, $O(C=O)R^{14}$, $(C=O)OR^{14}$, and $C_6$-$C_{10}$ aryl substituted by 0 to 3 groups independently selected from the group consisting of halo, $C_1$-$C_4$ alkoxy, $C_1$-$C_4$ alkyl, cyclopropyl, $C_1$-$C_4$-alkoxycarbonyl, $(C=O)NR^{11}R^{12}$, $CF_3$, $OCF_3$, and $CF_2CH_3$;

$C_3$-$C_6$ cycloalkyl which may contain unsaturation, substituted by 0 to 3 groups independently selected from the group consisting of halo, $CF_3$, $OCF_3$, 5- or 6-membered heteroaryl, OH, oxo, hydroxy-$C_1$-$C_4$-alkyl, $C_6$-$C_{10}$ aryl, COOH, oxo, $C_1$-$C_4$-alkoxycarbonyl, $(C=O)NR^{11}R^{12}$, and $C_1$-$C_4$ alkyl; and $C_5$-$C_{11}$ spirocycloalkyl which may contain unsaturation and optionally containing 1 to 3 heteroatoms selected from O, N or S and substituted by 0 to 3 groups independently selected from the group consisting of halo, $CF_3$, $OCF_3$, 5- or 6-membered heteroaryl, OH, hydroxy-$C_1$-$C_4$-alkyl, $C_6$-$C_{10}$ aryl, and $C_1$-$C_4$ alkyl;

$R^{11}$ and $R^{12}$ are independently, at each occurrence, selected from the group consisting of:
H,
$C_1$-$C_4$ alkyl,
halo-$C_1$-$C_4$-alkyl,
$C_2$-$C_4$ alkenyl,
$-(CR^{14}R^{14})_n^1$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano,
$-(CHR^{13})_n^1-C_3$-$C_6$-cycloalkyl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl,
$-(CHR^{13})_n^1$-4- to 10-membered-heterocyclyl substituted by 0 to 3 groups independently selected from the group consisting of halo, $CF_3$, $OCF_3$, 5- or 6-membered heteroaryl, OH, oxo, hydroxy-$C_1$-$C_4$-alkyl, and $C_1$-$C_4$ alkyl,
$-(CHR^{13})_n^1$-5- to 10-membered-heteroaryl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl,
di-$C_1$-$C_4$-alkylamino-$C_1$-$C_4$-alkyl,
di-$C_1$-$C_4$-alkoxy-$C_1$-$C_4$-alkyl,
hydroxy-$C_1$-$C_4$-alkyl,
cyano-$C_1$-$C_4$-alkyl,
$C_1$-$C_4$-alkoxy-$C_1$-$C_4$-alkyl,
$C_1$-$C_4$-alkoxycarbonyl-$C_1$-$C_4$-alkyl,
$C_1$-$C_4$-alkoxycarbonyl,
$C_1$-$C_4$-alkylcarbonyl,
phenylcarbonyl;
$C_1$-$C_4$-alkoxycarbonylamino-$C_1$-$C_4$-alkylcarbonyl,
di-$C_1$-$C_4$-alkylamino-$C_1$-$C_4$-alkylcarbonyl,
amino-$C_1$-$C_4$-alkylcarbonyl,
4- to 10-membered-heterocyclyl-carbonyl, and
alternatively, $R^1$ and $R^{12}$, when attached to the same nitrogen, combine to form a 4- to 8-membered heterocyclic ring containing carbon atoms substituted by 0 to 3 groups independently selected from the group consisting of halo, $CF_3$, $CHF_2$, $OCF_3$, $OCHF_2$, $OCH_2F$, 5- or 6-membered heteroaryl, OH, oxo, hydroxy-$C_1$-$C_4$-alkyl, $C_1$-$C_4$ alkyl and $C_1$-$C_4$ alkoxy, and 0 to 2 additional heteroatoms selected from N, $NR^{13}$, O and $S(O)_p$;

$R^{13}$ is independently, at each occurrence, selected from the group consisting of H, $C_1$-$C_6$ alkyl and $-(CH_2)$phenyl;

$R^{14}$ is independently, at each occurrence, selected from the group consisting of H, $C_1$-$C_6$ alkyl, halo-$C_1$-$C_4$-alkyl, $C_1$-$C_4$-alkoxycarbonylamino, $(C_6$-$C_{10}$ arylcarbonylamino) and $-(CH_2)_n^1$phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano, $R^7$ is selected from the group consisting of H, halo, hydroxyl, oxo, $C_1$-$C_4$ alkyl, hydroxy-$C_1$-$C_4$-alkyl, $C_1$-$C_4$-alkoxy-$C_1$-$C_4$-alkyl, halo-$C_1$-$C_4$-alkyl, which contains 1 to 5 halogens, and $C_1$-$C_4$-alkoxy;

$R^{10}$ is selected from the group consisting of $C_1$-$C_4$ alkyl, halo, and halo-$C_1$-$C_2$-alkyl, which contains 1 to 5 halogens, where halo is F or Cl;

$n^1$, at each occurrence, is selected from 0, 1, 2, 3 or 4; and p, at each occurrence, is selected from 0, 1 and 2.

In yet another embodiment, the present invention provides compounds, stereoisomers, tautomers, salts, solvates or prodrugs thereof, wherein:

W is O;
$R^0$ is $R^1$ or $R^{1a}$;
Y is S or —$CR^8$=$CR^9$—;
$R^1$ is independently selected from the group consisting of:
halo,
$C_1$-$C_4$ alkyl,
$C_2$-$C_3$ alkenyl,
$C_2$-$C_3$ alkynyl,
$C_3$-$C_4$ cycloalkyl,
$C_1$-$C_4$ alkoxy,
$C_1$-$C_4$ alkylthio,
halo-$C_1$-$C_2$-alkyl, which contains 1 to 5 halogens, where halo is F or Cl, and
halo-$C_3$-$C_4$ cycloalkyl;
$R^{1a}$ is independently selected from the group consisting of:
H,
halo,
$C_1$-$C_4$ alkyl,
$C_2$-$C_3$ alkenyl,
$C_2$-$C_3$ alkynyl,
$C_3$-$C_4$ cycloalkyl,
$C_1$-$C_4$ alkoxy,
$C_1$-$C_4$ alkylthio,
halo-$C_1$-$C_2$-alkyl, which contains 1 to 5 halogens, where halo is F or Cl, and
halo-$C_3$-$C_4$ cycloalkyl;
$R^8$ and $R^9$ are independently selected from the group consisting of:
H,
halo,
$C_1$-$C_4$ alkyl,
$C_1$-$C_4$ alkoxy, and
halo-$C_1$-$C_2$ alkyl;
provided that at least one of $R^{1a}$, $R^8$ and $R^9$ is other than H;
$R^2$ is selected from the group consisting of:
H,
halo, and
$C_1$-$C_4$ alkyl;
$X^1$ is selected from the group consisting of CH, N or $CR^{10}$;
$X^2$, $X^3$ and $X^4$ are independently selected from $CR^3$;
$R^3$ is selected from the group consisting of H, $C_1$-$C_4$ alkyl, $C_1$-$C_4$ alkoxy, $C_1$-$C_4$ alkylthio, halo, OH, CN, $OCF_3$, $C_1$-$C_2$-alkoxy-$C_1$-$C_2$-alkoxy, halo-$C_1$-$C_3$-alkyl, which contains 1 to 5 halogens, and —$(CH_2)_n^1$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano;
$R^4$ and $R^5$ are independently selected from H and $C_1$-$C_6$ alkyl;

is a 5-membered heteroaryl ring containing at least one O, N or S atom;
$R^6$ is selected from the group consisting of H, halo, $OCF_3$, $OCHF_2$, OH, CN, $NO_2$, $NR^{11}R^{12}$, $C_1$-$C_4$ alkoxycarbonyl, (C=O)$NR^{11}R^{12}$ and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, and $C_1$-$C_4$ alkylthio, or
$R^6$ is B-D-, where D is a linker, which is selected from:
a single bond,

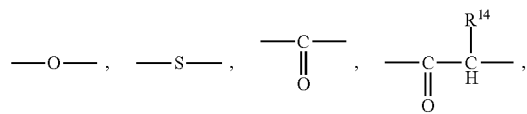

$C_1$-$C_4$ alkylene substituted by 0 to 4 groups independently selected from halo or OH,
$C_1$-$C_4$ alkyleneoxy,
$C_2$-$C_6$ alkenylene, and
B is selected from the group consisting of:
$C_6$-$C_{10}$ aryl substituted by 0 to 3 groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{11}R^{12}$, OH, $C_1$-$C_4$-alkylcarbonyloxy-$C_1$-$C_4$-alkyl, hydroxy-$C_1$-$C_4$-alkyl, $COOR^{14}$, $SO_2R^{14}$, (C=O)$NR^{11}R^{12}$, $SO_2NR^{11}R^{12}$, $N(R^{13})$(C=O)$NR^{11}R^{12}$, $N(R^{13})$(C=O)$OR^{14}$, $N(R^{13})$(C=O)$R^{14}$, $NR^{13}S(O)R^{14}$, $NR^{13}SO_2R^{14}$, O(C=O)$NR^{11}R^{12}$, O(C=O)$OR^{14}$, O(C=O)$R^{14}$, (C=O)$OR^{14}$, and 5-6-membered heteroaryl,
5- to 10-membered heteroaryl substituted by 0 to 3 groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{11}R^{12}$, OH, $C_1$-$C_4$-alkylcarbonyloxy-$C_1$-$C_4$-alkyl, hydroxy-$C_1$-$C_4$-alkyl, $COOR^{14}$, $SO_2R^{14}$, (C=O)$NR^{11}R^{12}$, $SO_2NR^{11}R^{12}$, $N(R^{13})$(C=O)$NR^{11}R^{12}$, $N(R^{13})$(C=O)$OR^{14}$, $N(R^{13})$(C=O)$R^{14}$, $NR^{13}S(O)R^{14}$, $NR^{13}SO_2R^{14}$, O(C=O)$NR^{11}R^{12}$, O(C=O)$OR^{14}$, O(C=O)$R^{14}$, (C=O)$OR^{14}$, 5-6-membered heteroaryl, and $(CH_2)$phenyl,
4- to 10-membered heterocyclyl containing carbon atoms and 1 to 2 additional heteroatoms selected from N, O, and S, and substituted by 0 to 3 groups independently selected from the group consisting of halo, oxo, —$(CHR^{13})_n^1$-5- or 6-membered heteroaryl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; $NR^{13}S(O)R^{14}$, $NR^{13}SO_2R^{14}$, —$(CHR^{13})_n^1$-4- to 10-membered-heterocyclyl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; OH, hydroxy-$C_1$-$C_4$-alkyl, $C_1$-$C_4$ alkoxy, halo-$C_1$-$C_4$ alkoxy, di-$C_1$-$C_4$-alkylamino-$C_1$-$C_4$-alkyl, $NR_{11}R_{12}$, cyano, $C_1$-$C_4$ alkyl, halo-$C_1$-$C_4$ alkyl, $C_3$-$C_6$ cycloalkyl, $C_1$-$C_4$-alkoxy-$C_1$-$C_4$-alkyl, $C_3$-$C_6$ cycloalkyl-$C_1$-$C_4$-alkylcarbonyl, $C_6$-$C_{10}$ arylcarbonyl, $C_1$-$C_4$-alkylcarbonyloxy-$C_1$-$C_4$-alkyl, $COOR^{14}$, $SO_2R^{14}$, (C=O)$NR^{11}R^{12}$, $SO_2NR^{11}R^{12}$, $N(R^{13})$(C=O)$NR^{11}R^{12}$, $N(R^{13})$(C=O)$OR^{14}$, $N(R^{13})$(C=O)$R^{14}$, O(C=O)$NR^{11}R^{12}$, O(C=O)$OR^{14}$, O(C=O)$R^{14}$,

(C=O)OR$^{14}$, and C$_6$-C$_{10}$ aryl substituted by 0 to 3 groups independently selected from the group consisting of halo, C$_1$-C$_4$ alkoxy, C$_1$-C$_4$ alkyl, cyclopropyl, C$_1$-C$_4$-alkoxycarbonyl, (C=O)NR$^{11}$R$^{12}$, CF$_3$, OCF$_3$, and CF$_2$CH$_3$;

C$_3$-C$_6$ cycloalkyl which may contain unsaturation, substituted by 0 to 3 groups independently selected from the group consisting of halo, CF$_3$, OCF$_3$, 5- or 6-membered heteroaryl, OH, oxo, hydroxy-C$_1$-C$_4$-alkyl, C$_6$-C$_{10}$ aryl, COOH, oxo, C$_1$-C$_4$-alkoxycarbonyl, (C=O)NR$^{11}$R$^{12}$, and C$_1$-C$_4$ alkyl; and C$_5$-C$_{11}$ spirocycloalkyl which may contain unsaturation and optionally containing 1 to 3 heteroatoms selected from O, N or S and substituted by 0 to 3 groups independently selected from the group consisting of halo, CF$_3$, OCF$_3$, 5- or 6-membered heteroaryl, OH, hydroxy-C$_1$-C$_4$-alkyl, C$_6$-C$_{10}$ aryl, and C$_1$-C$_4$ alkyl;

R$^{11}$ and R$^{12}$ are independently, at each occurrence, selected from the group consisting of:
H,
C$_1$-C$_4$ alkyl,
halo-C$_1$-C$_4$-alkyl,
C$_2$-C$_4$ alkenyl,
—(CR$^{14}$R$^{14}$)$_n$$^1$-phenyl substituted by 0 to 3 groups independently selected from the group consisting of halo, C$_1$-C$_4$ alkoxy, C$_1$-C$_4$ alkyl, cyclopropyl, CF$_3$, OCF$_3$, 5- or 6-membered heteroaryl, OH, OCHF$_2$, di-C$_1$-C$_4$-alkylamino, and cyano, —(CHR$^{13}$)$_n$$^1$—C$_3$-C$_6$-cycloalkyl substituted by 0 to 3 groups independently selected from the group consisting of halo, CF$_3$, OCF$_3$, 5- or 6-membered heteroaryl, OH, hydroxy-C$_1$-C$_4$-alkyl, and C$_1$-C$_4$ alkyl,
—(CHR$^{13}$)$_n$$^1$-4- to 10-membered-heterocyclyl substituted by 0 to 3 groups independently selected from the group consisting of halo, CF$_3$, OCF$_3$, 5- or 6-membered heteroaryl, OH, oxo, hydroxy-C$_1$-C$_4$-alkyl, and C$_1$-C$_4$ alkyl,
—(CHR$^{13}$)$_n$$^1$-5- to 10-membered-heteroaryl substituted by 0 to 3 groups independently selected from the group consisting of halo, CF$_3$, OCF$_3$, 5- or 6-membered heteroaryl, OH, hydroxy-C$_1$-C$_4$-alkyl, and C$_1$-C$_4$ alkyl,
di-C$_1$-C$_4$-alkylamino-C$_1$-C$_4$-alkyl,
di-C$_1$-C$_4$-alkoxy-C$_1$-C$_4$-alkyl,
hydroxy-C$_1$-C$_4$-alkyl,
cyano-C$_1$-C$_4$-alkyl,
C$_1$-C$_4$-alkoxy-C$_1$-C$_4$-alkyl,
C$_1$-C$_4$-alkoxycarbonyl-C$_1$-C$_4$-alkyl,
C$_1$-C$_4$-alkoxycarbonyl,
C$_1$-C$_4$-alkylcarbonyl,
phenylcarbonyl;
C$_1$-C$_4$-alkoxycarbonylamino-C$_1$-C$_4$-alkylcarbonyl, and di-C$_1$-C$_4$-alkylamino-C$_1$-C$_4$-alkylcarbonyl,
alternatively, R$^{11}$ and R$^{12}$, when attached to the same nitrogen, combine to form a 4- to 8-membered heterocyclic ring containing carbon atoms substituted by 0 to 3 groups independently selected from the group consisting of halo, CF$_3$, CHF$_2$, OCF$_3$, OCHF$_2$, OCH$_2$F, 5- or 6-membered heteroaryl, OH, oxo, hydroxy-C$_1$-C$_4$-alkyl, C$_1$-C$_4$ alkyl and C$_1$-C$_4$ alkoxy, and 0 to 2 additional heteroatoms selected from N, NR$^{13}$, O and S(O)$_p$;

R$^{13}$ is independently, at each occurrence, selected from the group consisting of H, C$_1$-C$_6$ alkyl and —(CH$_2$)phenyl;

R$^{14}$ is independently, at each occurrence, selected from the group consisting of H, C$_1$-C$_6$ alkyl, halo-C$_1$-C$_4$-alkyl, C$_1$-C$_4$-alkoxycarbonylamino and —(CH$_2$)$_n$$^1$phenyl substituted by 0 to 3 groups independently selected from the group consisting of halo, C$_1$-C$_4$ alkoxy, C$_1$-C$_4$ alkyl, cyclopropyl, CF$_3$, OCF$_3$, 5- or 6-membered heteroaryl, OH, OCHF$_2$, di-C$_1$-C$_4$-alkylamino, and cyano, R$^7$ is selected from the group consisting of H, halo, hydroxyl, oxo, C$_1$-C$_4$ alkyl, hydroxy-C$_1$-C$_4$-alkyl, C$_1$-C$_4$-alkoxy-C$_1$-C$_4$-alkyl and halo-C$_1$-C$_4$-alkyl, which contains 1 to 5 halogens;

R$^{10}$ is selected from the group consisting of C$_1$-C$_4$ alkyl, halo, and halo-C$_1$-C$_2$-alkyl, which contains 1 to 5 halogens, where halo is F or Cl;

n$^1$, at each occurrence, is selected from 0, 1, 2 or 3; and
p, at each occurrence, is selected from 0, 1 and 2.

In still yet another embodiment, the present invention provides compounds, stereoisomers, tautomers, salts, solvates or prodrugs thereof, wherein:
W is O;
R$^0$ is R$^1$ or R$^{1a}$;
Y is S or —CR$^8$=CR$^9$—;
R$^1$ is independently selected from the group consisting of:
halo,
C$_1$-C$_4$ alkyl,
C$_2$-C$_3$ alkenyl,
C$_2$-C$_3$ alkynyl,
C$_3$-C$_4$ cycloalkyl,
C$_1$-C$_4$ alkoxy,
C$_1$-C$_4$ alkylthio, and
halo-C$_1$-C$_2$-alkyl, which contains 1 to 5 halogens, where halo is F or Cl;

R$^{1a}$ is independently selected from the group consisting of:
H,
halo,
C$_1$-C$_4$ alkyl,
C$_2$-C$_3$ alkenyl,
C$_2$-C$_3$ alkynyl,
C$_3$-C$_4$ cycloalkyl,
C$_1$-C$_4$ alkoxy,
C$_1$-C$_4$ alkylthio, and
halo-C$_1$-C$_2$-alkyl, which contains 1 to 5 halogens, where halo is F or Cl;

R$^8$ and R$^9$ are independently selected from the group consisting of:
H,
halo,
C$_1$-C$_4$ alkyl, and
halo-C$_1$-C$_2$ alkyl;
provided that at least one of R$^{1a}$, R$^8$ and R$^9$ is other than H;

R$^2$ is selected from the group consisting of:
H,
halo, and
C$_1$-C$_4$ alkyl;

X$^1$ is selected from the group consisting of CH, N or CR$^{10}$;

X$^2$, X$^3$ and X$^4$ are independently selected from CR$^3$;

R$^3$ is selected from the group consisting of H, C$_1$-C$_4$ alkyl, C$_1$-C$_4$ alkoxy, C$_1$-C$_4$ alkylthio, halo, OH, CN, OCF$_3$, halo-C$_1$-C$_3$-alkyl, which contains 1 to 5 halogens, and —(CH$_2$)$_n$$^1$-phenyl substituted by 0 to 3 groups independently selected from the group consisting of halo, C$_1$-C$_4$ alkoxy, C$_1$-C$_4$ alkyl, cyclopropyl, CF$_3$, OCF$_3$, 5- or 6-membered heteroaryl, OH, OCHF$_2$, di-C$_1$-C$_4$-alkylamino, and cyano;

R$^4$ and R$^5$ are independently selected from H and C$_1$-C$_6$ alkyl;

i is a 5-membered heteroaryl ring containing at least one O, N or S atom;

$R^6$ is selected from the group consisting of H, halo, $OCF_3$, $OCHF_2$, OH, $NR^{11}R^{12}$, $C_1$-$C_4$ alkoxycarbonyl, (C=O)$NR^{11}R^{12}$ and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, and $C_1$-$C_4$ alkylthio, or $R^6$ is B-D-, where D is a linker, which is selected from: a single bond,

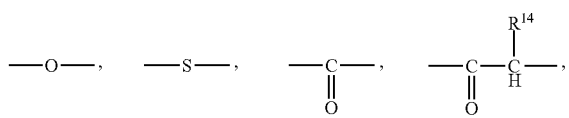

$C_1$-$C_4$ alkylene substituted by 0 to 4 groups independently selected from halo or OH, $C_2$-$C_6$ alkenylene, and B is selected from the group consisting of:
$C_6$-$C_{10}$ aryl substituted by 0 to 3 groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{11}R^{12}$, OH, $C_1$-$C_4$-alkylcarbonyloxy-$C_1$-$C_4$-alkyl, hydroxy-$C_1$-$C_4$-alkyl, $COOR^{14}$, $SO_2R^{14}$, (C=O)$NR^{11}R^{12}$, $SO_2NR^{11}R^{12}$, $N(R^{13})$(C=O)$NR^{11}R^{12}$, $N(R^{13})$(C=O)$OR^{14}$, $N(R^{13})$(C=O)$R^{14}$, $NR^{13}S(O)R^{14}$, $NR^{13}SO_2R^{14}$, O(C=O)$NR^{11}R^{12}$, O(C=O)$OR^{14}$, O(C=O)$R^{14}$, (C=O)$OR^{14}$, and 5-6-membered heteroaryl, 5- to 10-membered heteroaryl substituted by 0 to 3 groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{11}R^{12}$, OH, $C_1$-$C_4$-alkylcarbonyloxy-$C_1$-$C_4$-alkyl, hydroxy-$C_1$-$C_4$-alkyl, $COOR^{14}$, $SO_2R^{14}$, (C=O)$NR^{11}R^{12}$, $SO_2NR^{11}R^{12}$, $N(R^{13})$(C=O)$NR^{11}R^{12}$, $N(R^{13})$(C=O)$OR^{14}$, $N(R^{13})$(C=O)$R^{14}$, $NR^{13}S(O)R^{14}$, $NR^{13}SO_2R^{14}$, O(C=O)$NR^{11}R^{12}$, O(C=O)$OR^{14}$, O(C=O)$R^{14}$, (C=O)$OR^{14}$, 5-6-membered heteroaryl, and ($CH_2$)phenyl, 4- to 10-membered heterocyclyl containing carbon atoms and 1 to 2 additional heteroatoms selected from N, O, and S, and substituted by 0 to 3 groups independently selected from the group consisting of halo, oxo, —(CHR$^{13}$)$_{n^1}$-5- or 6-membered heteroaryl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; $NR^{13}S(O)R^{14}$, $NR^{13}SO_2R^{14}$, —(CHR$^{13}$)$_{n^1}$-4- to 10-membered-heterocyclyl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; OH, hydroxy-$C_1$-$C_4$-alkyl, $C_1$-$C_4$ alkoxy, halo-$C_1$-$C_4$ alkoxy, di-$C_1$-$C_4$-alkylamino-$C_1$-$C_4$-alkyl, $NR_{11}R_{12}$, cyano, $C_1$-$C_4$ alkyl, halo-$C_1$-$C_4$ alkyl, $C_3$-$C_6$ cycloalkyl, $C_1$-$C_4$-alkoxy-$C_1$-$C_4$-alkyl, $C_3$-$C_6$ cycloalkyl-$C_1$-$C_4$-alkylcarbonyl, $C_6$-$C_{10}$ arylcarbonyl, $C_1$-$C_4$-alkylcarbonyloxy-$C_1$-$C_4$-alkyl, $COOR^{14}$, $SO_2R^{14}$, (C=O)$NR^{11}R^{12}$, $SO_2NR^{11}R^{12}$, $N(R^{13})$(C=O)$NR^{11}R^{12}$, $N(R^{13})$(C=O)$OR^{14}$, $N(R^{13})$(C=O)$R^{14}$, O(C=O)$NR^{11}R^{12}$, O(C=O)$OR^{14}$, O(C=O)$R^{14}$, (C=O)$OR^{14}$, and $C_6$-$C_{10}$ aryl substituted by 0 to 3 groups independently selected from the group consisting of halo, $C_1$-$C_4$ alkoxy, $C_1$-$C_4$ alkyl, cyclopropyl, $C_1$-$C_4$-alkoxycarbonyl, (C=O)$NR^{11}R^{12}$, $CF_3$, $OCF_3$, and $CF_2CH_3$; and $C_3$-$C_6$ cycloalkyl which may contain unsaturation, substituted by 0 to 3 groups independently selected from the group consisting of halo, $CF_3$, $OCF_3$, 5- or 6-membered heteroaryl, OH, oxo, hydroxy-$C_1$-$C_4$-alkyl, $C_6$-$C_{10}$ aryl, COOH, oxo, $C_1$-$C_4$-alkoxycarbonyl, (C=O)$NR^{11}R^{12}$, and $C_1$-$C_4$ alkyl;

$R^{11}$ and $R^{12}$ are independently, at each occurrence, selected from the group consisting of:
H,
$C_1$-$C_4$ alkyl,
halo-$C_1$-$C_4$-alkyl,
$C_2$-$C_4$ alkenyl,
—(CR$^{14}$R$^{14}$)$_{n^1}$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano,
—(CHR$^{13}$)$_{n^1}$—$C_3$-$C_6$-cycloalkyl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl,
—(CHR$^{13}$)$_{n^1}$-4- to 10-membered-heterocyclyl substituted by 0 to 3 groups independently selected from the group consisting of halo, $CF_3$, $OCF_3$, 5- or 6-membered heteroaryl, OH, oxo, hydroxy-$C_1$-$C_4$-alkyl, and $C_1$-$C_4$ alkyl,
—(CHR$^{13}$)$_{n^1}$-5- to 10-membered-heteroaryl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl,
di-$C_1$-$C_4$-alkylamino-$C_1$-$C_4$-alkyl,
di-$C_1$-$C_4$-alkoxy-$C_1$-$C_4$-alkyl,
hydroxy-$C_1$-$C_4$-alkyl,
cyano-$C_1$-$C_4$-alkyl,
$C_1$-$C_4$-alkoxy-$C_1$-$C_4$-alkyl,
$C_1$-$C_4$-alkoxycarbonyl-$C_1$-$C_4$-alkyl,
$C_1$-$C_4$-alkoxycarbonyl,
$C_1$-$C_4$-alkylcarbonyl, and
phenylcarbonyl;
alternatively, $R^{11}$ and $R^{12}$, when attached to the same nitrogen, combine to form a 4- to 8-membered heterocyclic ring containing carbon atoms substituted by 0 to 3 groups independently selected from the group consisting of halo, $CF_3$, $CHF_2$, $OCF_3$, $OCHF_2$, $OCH_2F$, 5- or 6-membered heteroaryl, OH, oxo, hydroxy-$C_1$-$C_4$-alkyl, $C_1$-$C_4$ alkyl and $C_1$-$C_4$ alkoxy, and 0 to 2 additional heteroatoms selected from N, $NR^{13}$, O and S(O)$_p$;

$R^{13}$ is independently, at each occurrence, selected from the group consisting of H, $C_1$-$C_6$ alkyl and —($CH_2$)phenyl;

$R^{14}$ is independently, at each occurrence, selected from the group consisting of H, $C_1$-$C_6$ alkyl, halo-$C_1$-$C_4$-alkyl and —($CH_2$)$_{n^1}$phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano, $R^7$ is selected from the group consisting of H, halo, oxo, $C_1$-$C_4$ alkyl, hydroxy-$C_1$-$C_4$-alkyl, $C_1$-$C_4$-alkoxy-$C_1$-$C_4$-alkyl and halo-$C_1$-$C_4$-alkyl, which contains 1 to 5 halogens;

$R^{10}$ is selected from the group consisting of $C_1$-$C_4$ alkyl, halo, and halo-$C_1$-$C_2$-alkyl, which contains 1 to 5 halogens, where halo is F or Cl;

$n^1$, at each occurrence, is selected from 0, 1, 2 or 3; and p, at each occurrence, is selected from 0, 1 and 2.

In one embodiment, the present invention provides compounds, stereoisomers, tautomers, salts, solvates or prodrugs thereof, wherein:

W is O;
$R^0$ is $R^1$ or $R^{1a}$;
Y is S or —$CR^8$=$CR^9$—;
$R^1$ is independently selected from the group consisting of:
halo,
$C_1$-$C_4$ alkyl,
$C_2$-$C_3$ alkenyl,
$C_1$-$C_4$ alkoxy,
$C_1$-$C_4$ alkylthio, and
halo-$C_1$-$C_2$-alkyl, which contains 1 to 5 halogens, where halo is F or Cl;
$R^{1a}$ is independently selected from the group consisting of:
H,
halo,
$C_1$-$C_4$ alkyl,
$C_2$-$C_3$ alkenyl,
$C_1$-$C_4$ alkoxy,
$C_1$-$C_4$ alkylthio, and
halo-$C_1$-$C_2$-alkyl, which contains 1 to 5 halogens, where halo is F or Cl;
$R^8$ and $R^9$ are independently selected from the group consisting of:
H,
halo,
$C_1$-$C_4$ alkyl, and
halo-$C_1$-$C_2$ alkyl;
provided that at least one of $R^{1a}$, $R^8$ and $R^9$ is other than H;
$R^2$ is selected from the group consisting of:
H,
halo, and
$C_1$-$C_4$ alkyl;
$X^1$ is selected from the group consisting of CH or $CR^{10}$;
$X^2$, $X^3$ and $X^4$ are independently selected from $CR^3$;
$R^3$ is selected from the group consisting of H, $C_1$-$C_4$ alkyl, $C_1$-$C_4$ alkoxy, $C_1$-$C_4$ alkylthio, halo, OH, halo-$C_1$-$C_3$-alkyl, which contains 1 to 5 halogens, and —$(CH_2)_n^1$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano;
$R^4$ and $R^5$ are independently selected from H and $C_1$-$C_6$ alkyl;

is a 5-membered heteroaryl ring containing at least one O, N or S atom;
$R^6$ is selected from the group consisting of H, halo, OH, $NR^{11}R^{12}$, $C_1$-$C_4$ alkoxycarbonyl, (C=O)$NR^{11}R^{12}$ and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, and $C_1$-$C_4$ alkylthio, or $R^6$ is B-D-, where D is a linker, which is selected from: a single bond,

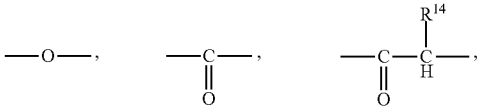

$C_1$-$C_4$ alkylene substituted by 0 to 4 groups independently selected from halo or OH,
$C_2$-$C_6$ alkenylene, and
B is selected from the group consisting of:
$C_6$-$C_{10}$ aryl substituted by 0 to 3 groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{11}R^{12}$, OH, $C_1$-$C_4$-alkylcarbonyloxy-$C_1$-$C_4$-alkyl, hydroxy-$C_1$-$C_4$-alkyl, $COOR^{14}$, $SO_2R^{14}$, (C=O)$NR^{11}R^{12}$, $SO_2NR^{11}R^{12}$, $N(R^{13})$(C=O)$NR^{11}R^{12}$, $N(R^{13})$(C=O)$OR^{14}$, $N(R^{13})$(C=O)$R^{14}$, $NR^{13}S(O)R^{14}$, $NR^{13}SO_2R^{14}$, O(C=O)$NR^{11}R^{12}$, O(C=O)$OR^{14}$, O(C=O)$R^{14}$, (C=O)$OR^{14}$, and 5-6-membered heteroaryl,
5- to 10-membered heteroaryl substituted by 0 to 3 groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{11}R^{12}$, OH, $C_1$-$C_4$-alkylcarbonyloxy-$C_1$-$C_4$-alkyl, hydroxy-$C_1$-$C_4$-alkyl, $COOR^{14}$, $SO_2R^{14}$, (C=O)$NR^{11}R^{12}$, $SO_2NR^{11}R^{12}$, $N(R^{13})$(C=O)$NR^{11}R^{12}$, $N(R^{13})$(C=O)$OR^{14}$, $N(R^{13})$(C=O)$R^{14}$, $NR^{13}S(O)R^{14}$, $NR^{13}SO_2R^{14}$, O(C=O)$NR^{11}R^{12}$, O(C=O)$OR^{14}$, O(C=O)$R^{14}$, (C=O)$OR^{14}$, 5-6-membered heteroaryl, and $(CH_2)$phenyl,
4- to 10-membered heterocyclyl containing carbon atoms and 1 to 2 additional heteroatoms selected from N, O, and S, and substituted by 0 to 3 groups independently selected from the group consisting of halo, oxo, —$(CHR^{13})_n^1$-5- or 6-membered heteroaryl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; $NR^{13}S(O)R^{14}$, $NR^{13}SO_2R^{14}$, —$(CHR^{13})_n^1$-4- to 10-membered-heterocyclyl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; OH, hydroxy-$C_1$-$C_4$-alkyl, $C_1$-$C_4$ alkoxy, halo-$C_1$-$C_4$ alkoxy, di-$C_1$-$C_4$-alkylamino-$C_1$-$C_4$-alkyl, $NR_{11}R_{12}$, cyano, $C_1$-$C_4$ alkyl, halo-$C_1$-$C_4$ alkyl, $C_3$-$C_6$ cycloalkyl, $C_1$-$C_4$-alkoxy-$C_1$-$C_4$-alkyl, $C_3$-$C_6$ cycloalkyl-$C_1$-$C_4$-alkylcarbonyl, $C_6$-$C_{10}$ arylcarbonyl, $C_1$-$C_4$-alkylcarbonyloxy-$C_1$-$C_4$-alkyl, $COOR^{14}$, $SO_2R^{14}$, (C=O)$NR^{11}R^{12}$, $SO_2NR^{11}R^{12}$, $N(R^{13})$(C=O)$NR^{11}R^{12}$, $N(R^{13})$(C=O)$OR^{14}$, $N(R^{13})$(C=O)$R^{14}$, O(C=O)$NR^{11}R^{12}$, O(C=O)$OR^{14}$, O(C=O)$R^{14}$, (C=O)$OR^{14}$, and $C_6$-$C_{10}$ aryl substituted by 0 to 3 groups independently selected from the group consisting of halo, $C_1$-$C_4$ alkoxy, $C_1$-$C_4$ alkyl, cyclopropyl, $C_1$-$C_4$-alkoxycarbonyl, (C=O)$NR^{11}R^{12}$, $CF_3$, $OCF_3$, and $CF_2CH_3$; and
$C_3$-$C_6$ cycloalkyl which may contain unsaturation, substituted by 0 to 3 groups independently selected from the group consisting of halo, $CF_3$, $OCF_3$, 5- or 6-membered heteroaryl, OH, oxo, hydroxy-$C_1$-$C_4$-alkyl, $C_6$-$C_{10}$ aryl, COOH, oxo, $C_1$-$C_4$-alkoxycarbonyl, (C=O)$NR^{11}R^{12}$, and $C_1$-$C_4$ alkyl;

$R^{11}$ and $R^{12}$ are independently, at each occurrence, selected from the group consisting of:
H,
$C_1$-$C_4$ alkyl,
halo-$C_1$-$C_4$-alkyl,
$C_2$-$C_4$ alkenyl,
—$(CR^{14}R^{14})_{n^1}$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano,
—$(CHR^{13})_{n^1}$—$C_3$-$C_6$-cycloalkyl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl,
—$(CHR^{13})_{n^1}$-4- to 10-membered-heterocyclyl substituted by 0 to 3 groups independently selected from the group consisting of halo, $CF_3$, $OCF_3$, 5- or 6-membered heteroaryl, OH, oxo, hydroxy-$C_1$-$C_4$-alkyl, and $C_1$-$C_4$ alkyl,
—$(CHR^{13})_{n^1}$-1-5- to 10-membered-heteroaryl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl,
di-$C_1$-$C_4$-alkylamino-$C_1$-$C_4$-alkyl,
di-$C_1$-$C_4$-alkoxy-$C_1$-$C_4$-alkyl,
hydroxy-$C_1$-$C_4$-alkyl,
cyano-$C_1$-$C_4$-alkyl,
$C_1$-$C_4$-alkoxy-$C_1$-$C_4$-alkyl,
$C_1$-$C_4$-alkoxycarbonyl-$C_1$-$C_4$-alkyl, and
$C_1$-$C_4$-alkoxycarbonyl;
alternatively, $R^{11}$ and $R^{12}$, when attached to the same nitrogen, combine to form a 4- to 8-membered heterocyclic ring containing carbon atoms substituted by 0 to 3 groups independently selected from the group consisting of halo, $CF_3$, $CHF_2$, $OCF_3$, $OCHF_2$, $OCH_2F$, 5- or 6-membered heteroaryl, OH, oxo, hydroxy-$C_1$-$C_4$-alkyl, $C_1$-$C_4$ alkyl and $C_1$-$C_4$ alkoxy, and 0 to 2 additional heteroatoms selected from N, $NR^{13}$, O and $S(O)_p$;
$R^{13}$ is independently, at each occurrence, selected from the group consisting of H, $C_1$-$C_6$ alkyl and —$(CH_2)$phenyl;
$R^{14}$ is independently, at each occurrence, selected from the group consisting of H, $C_1$-$C_6$ alkyl and —$(CH_2)_{n^1}$phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano,
$R^7$ is selected from the group consisting of H, halo, $C_1$-$C_4$ alkyl, hydroxy-$C_1$-$C_4$-alkyl, $C_1$-$C_4$-alkoxy-$C_1$-$C_4$-alkyl and halo-$C_1$-$C_4$-alkyl, which contains 1 to 5 halogens;
$R^{10}$ is selected from the group consisting of $C_1$-$C_4$ alkyl, halo, and halo-$C_1$-$C_2$-alkyl, which contains 1 to 5 halogens, where halo is F or Cl;
$n^1$, at each occurrence, is selected from 0, 1, 2 or 3; and
p, at each occurrence, is selected from 0, 1 and 2.

In another embodiment, the present invention provides compounds, stereoisomers, tautomers, salts, solvates or prodrugs thereof, wherein:
W is O;
$R^0$ is $R^1$ or $R^{1a}$;
Y is S or —$CR^8$=$CR^9$—;
$R^1$ is independently selected from the group consisting of:
halo,
$C_1$-$C_4$ alkyl,
$C_1$-$C_4$ alkoxy,
$C_1$-$C_4$ alkylthio, and
halo-$C_1$-$C_2$-alkyl, which contains 1 to 5 halogens, where halo is F or Cl;
$R^{1a}$ is independently selected from the group consisting of:
H,
halo,
$C_1$-$C_4$ alkyl,
$C_1$-$C_4$ alkoxy,
$C_1$-$C_4$ alkylthio, and
halo-$C_1$-$C_2$-alkyl, which contains 1 to 5 halogens, where halo is F or Cl;
$R^8$ and $R^9$ are independently selected from the group consisting of:
H,
$C_1$-$C_4$ alkyl, and
halo-$C_1$-$C_2$ alkyl;
provided that at least one of $R^{1a}$, $R^8$ and $R^9$ is other than H;
$R^2$ is selected from the group consisting of:
H, and
halo;
$X^1$ is selected from the group consisting of CH or $CR^{10}$;
$X^2$, $X^3$ and $X^4$ are independently selected from $CR^3$;
$R^3$ is selected from the group consisting of H, $C_1$-$C_4$ alkyl, $C_1$-$C_4$ alkoxy, $C_1$-$C_4$ alkylthio, halo, halo-$C_1$-$C_3$-alkyl, which contains 1 to 5 halogens, and —$(CH_2)_{n^1}$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano;
$R^4$ and $R^5$ are independently selected from H and $C_1$-$C_6$ alkyl;

is a 5-membered heteroaryl ring containing at least one O, N or S atom;
$R^6$ is selected from the group consisting of H, halo, $NR^{11}R^{12}$, $C_1$-$C_4$ alkoxycarbonyl, (C=O)$NR^{11}R^{12}$ and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, and $C_1$-$C_4$ alkylthio, or
$R^6$ is B-D-, where D is a linker, which is selected from: a single bond,

$C_1$-$C_4$ alkylene substituted by 0 to 4 groups independently selected from halo or OH,
$C_2$-$C_6$ alkenylene, and
B is selected from the group consisting of:
$C_6$-$C_{10}$ aryl substituted by 0 to 3 groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{11}R^{12}$, OH, $C_1$-$C_4$-alkylcarbonyloxy-$C_1$-$C_4$-alkyl, hydroxy-$C_1$-$C_4$-alkyl, $COOR^{14}$, $SO_2R^{14}$, (C=O)$NR^{11}R^{12}$, $SO_2NR^{11}R^{12}$, $N(R^{13})(C=O)NR^{11}R^{12}$, $N(R^{13})(C=O)$ OR$^{14}$, N(R$^{13}$)(C=O)R$^{14}$, NR$^{13}$S(O)R$^{14}$, NR$^{13}$SO$_2$R$^{14}$, O(C=O)NR$^{11}$R$^{12}$, O(C=O)OR$^{14}$, O(C=O)R$^{14}$, (C=O)OR$^{14}$, and 5-6-membered heteroaryl, 5- to 10-membered heteroaryl substituted by 0 to 3 groups independently selected from the group consisting of halo, C$_1$-C$_4$ alkoxy, halo-C$_1$-C$_4$ alkoxy, C$_1$-C$_4$ alkyl, halo-C$_1$-C$_4$ alkyl, C$_3$-C$_6$ cycloalkyl, cyano, nitro, NR$^{11}$R$^{12}$, OH, C$_1$-C$_4$-alkylcarbonyloxy-C$_1$-C$_4$-alkyl, hydroxy-C$_1$-C$_4$-alkyl, COOR$^{14}$, SO$_2$R$^{14}$, (C=O)NR$^{11}$R$^{12}$, SO$_2$NR$^{11}$R$^{12}$, N(R$^{13}$)(C=O)NR$^{11}$R$^{12}$, N(R$^{13}$)(C=O)OR$^{14}$, N(R$^{13}$)(C=O)R$^{14}$, NR$^{13}$S(O)R$^{14}$, NR$^{13}$SO$_2$R$^{14}$, O(C=O)NR$^{11}$R$^{12}$, O(C=O)OR$^{14}$, O(C=O)R$^{14}$, (C=O)OR$^{14}$, 5-6-membered heteroaryl, and (CH$_2$)phenyl, 4- to 10-membered heterocyclyl containing carbon atoms and 1 to 2 additional heteroatoms selected from N, O, and S, and substituted by 0 to 3 groups independently selected from the group consisting of halo, oxo, —(CHR$^{13}$)$_{n^1}$-5- or 6-membered heteroaryl substituted by 0 to 3 groups independently selected from the group consisting of halo, C$_1$-C$_4$ alkoxy, C$_1$-C$_4$ alkyl, cyclopropyl, CF$_3$, OCF$_3$, and CF$_2$CH$_3$; NR$^{13}$S(O)R$^{14}$, NR$^{13}$SO$_2$R$^{14}$, —(CHR$^{13}$)$_{n^1}$-4- to 10-membered-heterocyclyl substituted by 0 to 3 groups independently selected from the group consisting of halo, C$_1$-C$_4$ alkoxy, C$_1$-C$_4$ alkyl, cyclopropyl, CF$_3$, OCF$_3$, and CF$_2$CH$_3$; OH, hydroxy-C$_1$-C$_4$-alkyl, C$_1$-C$_4$ alkoxy, halo-C$_1$-C$_4$ alkoxy, di-C$_1$-C$_4$-alkylamino-C$_1$-C$_4$-alkyl, NR$_{11}$R$_{12}$, cyano, C$_1$-C$_4$ alkyl, halo-C$_1$-C$_4$ alkyl, C$_3$-C$_6$ cycloalkyl, C$_1$-C$_4$-alkoxy-C$_1$-C$_4$-alkyl, C$_3$-C$_6$ cycloalkyl-C$_1$-C$_4$-alkylcarbonyl, C$_6$-C$_{10}$ arylcarbonyl, C$_1$-C$_4$-alkylcarbonyloxy-C$_1$-C$_4$-alkyl, COOR$^{14}$, SO$_2$R$^{14}$, (C=O)NR$^{11}$R$^{12}$, SO$_2$NR$^{11}$R$^{12}$, N(R$^{13}$)(C=O)NR$^{11}$R$^{12}$, N(R$^{13}$)(C=O)OR$^{14}$, N(R$^{13}$)(C=O)R$^{14}$, O(C=O)NR$^{11}$R$^{12}$, O(C=O)OR$^{14}$, O(C=O)R$^{14}$, (C=O)OR$^{14}$, and C$_6$-C$_{10}$ aryl substituted by 0 to 3 groups independently selected from the group consisting of halo, C$_1$-C$_4$ alkoxy, C$_1$-C$_4$ alkyl, cyclopropyl, C$_1$-C$_4$-alkoxycarbonyl, (C=O)NR$^{11}$R$^{12}$, CF$_3$, OCF$_3$, and CF$_2$CH$_3$; and C$_3$-C$_6$ cycloalkyl which may contain unsaturation, substituted by 0 to 3 groups independently selected from the group consisting of halo, CF$_3$, OCF$_3$, 5- or 6-membered heteroaryl, OH, oxo, hydroxy-C$_1$-C$_4$-alkyl, C$_6$-C$_{10}$ aryl, COOH, oxo, C$_1$-C$_4$-alkoxycarbonyl, (C=O)NR$^{11}$R$^{12}$, and C$_1$-C$_4$ alkyl;

R$^{11}$ and R$^{12}$ are independently, at each occurrence, selected from the group consisting of:
H,
C$_1$-C$_4$ alkyl,
halo-C$_1$-C$_4$-alkyl,
C$_2$-C$_4$ alkenyl,
—(CR$^{14}$R$^{14}$)$_{n^1}$-phenyl substituted by 0 to 3 groups independently selected from the group consisting of halo, C$_1$-C$_4$ alkoxy, C$_1$-C$_4$ alkyl, cyclopropyl, CF$_3$, OCF$_3$, 5- or 6-membered heteroaryl, OH, OCHF$_2$, di-C$_1$-C$_4$-alkylamino, and cyano,
—(CHR$^{13}$)$_{n^1}$—C$_3$-C$_6$-cycloalkyl substituted by 0 to 3 groups independently selected from the group consisting of halo, CF$_3$, OCF$_3$, 5- or 6-membered heteroaryl, OH, hydroxy-C$_1$-C$_4$-alkyl, and C$_1$-C$_4$ alkyl,
—(CHR$^{13}$)$_{n^1}$-4- to 10-membered-heterocyclyl substituted by 0 to 3 groups independently selected from the group consisting of halo, CF$_3$, OCF$_3$, 5- or 6-membered heteroaryl, OH, hydroxy-C$_1$-C$_4$-alkyl, and C$_1$-C$_4$ alkyl,
—(CHR$^{13}$)$_{n^1}$-5- to 10-membered-heteroaryl substituted by 0 to 3 groups independently selected from the group consisting of halo, CF$_3$, OCF$_3$, 5- or 6-membered heteroaryl, OH, hydroxy-C$_1$-C$_4$-alkyl, and C$_1$-C$_4$ alkyl,
di-C$_1$-C$_4$-alkylamino-C$_1$-C$_4$-alkyl,
di-C$_1$-C$_4$-alkoxy-C$_1$-C$_4$-alkyl,
hydroxy-C$_1$-C$_4$-alkyl,
cyano-C$_1$-C$_4$-alkyl, and
C$_1$-C$_4$-alkoxy-C$_1$-C$_4$-alkyl;

alternatively, R$^{11}$ and R$^{12}$, when attached to the same nitrogen, combine to form a 4- to 8-membered heterocyclic ring containing carbon atoms substituted by 0 to 3 groups independently selected from the group consisting of halo, CF$_3$, CHF$_2$, OCF$_3$, OCHF$_2$, OCH$_2$F, 5- or 6-membered heteroaryl, OH, oxo, hydroxy-C$_1$-C$_4$-alkyl, C$_1$-C$_4$ alkyl and C$_1$-C$_4$ alkoxy, and 0 to 2 additional heteroatoms selected from N, NR$^{13}$, O and S(O)$_p$;

R$^{13}$ is independently, at each occurrence, selected from the group consisting of H and C$_1$-C$_6$ alkyl;

R$^{14}$ is independently, at each occurrence, selected from the group consisting of H, C$_1$-C$_6$ alkyl and —(CH$_2$)$_{n^1}$phenyl substituted by 0 to 3 groups independently selected from the group consisting of halo, C$_1$-C$_4$ alkoxy, C$_1$-C$_4$ alkyl, cyclopropyl, CF$_3$, OCF$_3$, 5- or 6-membered heteroaryl, OH, OCHF$_2$, di-C$_1$-C$_4$-alkylamino, and cyano, R$^7$ is selected from the group consisting of H, halo, C$_1$-C$_4$ alkyl, hydroxy-C$_1$-C$_4$-alkyl and halo-C$_1$-C$_4$-alkyl, which contains 1 to 5 halogens;

R$^{10}$ is selected from the group consisting of C$_1$-C$_4$ alkyl, halo, and halo-C$_1$-C$_2$-alkyl, which contains 1 to 5 halogens, where halo is F or Cl;

n$^1$, at each occurrence, is selected from 0, 1, 2 or 3; and p, at each occurrence, is selected from 0, 1 and 2.

In yet another embodiment, the present invention provides compounds, stereoisomers, tautomers, salts, solvates or prodrugs thereof, wherein:
W is O;
R$^0$ is R$^1$ or R$^{1a}$;
Y is S or —CR$^8$=CR$^9$—;
R$^1$ is independently selected from the group consisting of:
C$_1$-C$_4$ alkyl,
C$_1$-C$_4$ alkoxy,
C$_1$-C$_4$ alkylthio, and
halo-C$_1$-C$_2$-alkyl, which contains 1 to 5 halogens, where halo is F or Cl;
R$^{1a}$ is independently selected from the group consisting of:
H,
C$_1$-C$_4$ alkyl,
C$_1$-C$_4$ alkoxy,
C$_1$-C$_4$ alkylthio, and
halo-C$_1$-C$_2$-alkyl, which contains 1 to 5 halogens, where halo is F or Cl;
R$^8$ and R$^9$ are independently selected from the group consisting of:
H,
C$_1$-C$_4$ alkyl, and
halo-C$_1$-C$_2$ alkyl;
provided that at least one of R$^{1a}$, R$^8$ and R$^9$ is other than H;
R$^2$ is H;
X$^1$ is selected from the group consisting of CH;
X$^2$, X$^3$ and X$^4$ are independently selected from CR$^3$;
R$^3$ is selected from the group consisting of H, C$_1$-C$_4$ alkyl, C$_1$-C$_4$ alkoxy, halo, halo-C$_1$-C$_3$-alkyl, which contains 1 to 5 halogens, and —(CH$_2$)$_{n^1}$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano;

$R^4$ and $R^5$ are independently selected from H and $C_1$-$C_6$ alkyl;

is a 5-membered heteroaryl ring containing at least one O, N or S atom;

$R^6$ is selected from the group consisting of H, halo, $NR^{11}R^{12}$, $C_1$-$C_4$ alkoxycarbonyl, (C=O)$NR^{11}R^{12}$ and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, and $C_1$-$C_4$ alkylthio, or $R^6$ is B-D-, where D is a linker, which is selected from: a single bond,

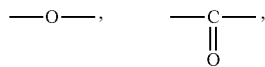

and $C_1$-$C_4$ alkylene substituted by 0 to 4 groups independently selected from halo or OH;

B is selected from the group consisting of:

$C_6$-$C_{10}$ aryl substituted by 0 to 3 groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{11}R^{12}$, OH, $C_1$-$C_4$-alkylcarbonyloxy-$C_1$-$C_4$-alkyl, hydroxy-$C_1$-$C_4$-alkyl, $COOR^{14}$, $SO_2R^{14}$, (C=O)$NR^{11}R^{12}$, $SO_2NR^{11}R^{12}$, $N(R^{13})$(C=O)$NR^{11}R^{12}$, $N(R^{13})$(C=O)$OR^{14}$, $N(R^{13})$(C=O)$R^{14}$, $NR^{13}S(O)R^{14}$, $NR^{13}SO_2R^{14}$, O(C=O)$NR^{11}R^{12}$, O(C=O)$OR^{14}$, O(C=O)$R^{14}$, (C=O)$OR^{14}$, and 5-6-membered heteroaryl, 5- to 10-membered heteroaryl substituted by 0 to 3 groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{11}R^{12}$, OH, $C_1$-$C_4$-alkylcarbonyloxy-$C_1$-$C_4$-alkyl, hydroxy-$C_1$-$C_4$-alkyl, $COOR^{14}$, $SO_2R^{14}$, (C=O)$NR^{11}R^{12}$, $SO_2NR^{11}R^{12}$, $N(R^{13})$(C=O)$NR^{11}R^{12}$, $N(R^{13})$(C=O)$OR^{14}$, $N(R^{13})$(C=O)$R^{14}$, $NR^{13}S(O)R^{14}$, $NR^{13}SO_2R^{14}$, O(C=O)$NR^{11}R^{12}$, O(C=O)$OR^{14}$, O(C=O)$R^{14}$, (C=O)$OR^{14}$, 5-6-membered heteroaryl, and $(CH_2)$phenyl, 4- to 10-membered heterocyclyl containing carbon atoms and 1 to 2 additional heteroatoms selected from N, O, and S, and substituted by 0 to 3 groups independently selected from the group consisting of halo, oxo, —(CHR$^{13}$)$_{n^1}$-5- or 6-membered heteroaryl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; $NR^{13}S(O)R^{14}$, $NR^{13}SO_2R^{14}$, —(CHR$^{13}$)$_{n^1}$-4- to 10-membered-heterocyclyl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; OH, hydroxy-$C_1$-$C_4$-alkyl, $C_1$-$C_4$ alkoxy, halo-$C_1$-$C_4$ alkoxy, di-$C_1$-$C_4$-alkylamino-$C_1$-$C_4$-alkyl, $NR_{11}R_{12}$, cyano, $C_1$-$C_4$ alkyl, halo-$C_1$-$C_4$ alkyl, $C_3$-$C_6$ cycloalkyl, $C_1$-$C_4$-alkoxy-$C_1$-$C_4$-alkyl, $C_3$-$C_6$ cycloalkyl-$C_1$-$C_4$-alkylcarbonyl, $C_6$-$C_{10}$ arylcarbonyl, $C_1$-$C_4$-alkylcarbonyloxy-$C_1$-$C_4$-alkyl, $COOR^{14}$, $SO_2R^{14}$, (C=O)$NR^{11}R^{12}$, $SO_2NR^{11}R^{12}$, $N(R^{13})$(C=O)$NR^{11}R^{12}$, $N(R^{13})$(C=O)$OR^{14}$, $N(R^{13})$(C=O)$R^{14}$, O(C=O)$NR^{11}R^{12}$, O(C=O)$OR^{14}$, O(C=O)$R^{14}$, (C=O)$OR^{14}$, and $C_6$-$C_{10}$ aryl substituted by 0 to 3 groups independently selected from the group consisting of halo, $C_1$-$C_4$ alkoxy, $C_1$-$C_4$ alkyl, cyclopropyl, $C_1$-$C_4$-alkoxycarbonyl, (C=O)$NR^{11}R^{12}$, $CF_3$, $OCF_3$, and $CF_2CH_3$; and $C_3$-$C_6$ cycloalkyl which may contain unsaturation, substituted by 0 to 3 groups independently selected from the group consisting of halo, $CF_3$, $OCF_3$, 5- or 6-membered heteroaryl, OH, oxo, hydroxy-$C_1$-$C_4$-alkyl, $C_6$-$C_{10}$ aryl, COOH, oxo, $C_1$-$C_4$-alkoxycarbonyl, (C=O)$NR^{11}R^{12}$, and $C_1$-$C_4$ alkyl;

$R^{11}$ and $R^{12}$ are independently, at each occurrence, selected from the group consisting of:

H, $C_1$-$C_4$ alkyl, halo-$C_1$-$C_4$-alkyl, $C_2$-$C_4$ alkenyl,

—(CR$^{14}$R$^{14}$)$_{n^1}$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano, —(CHR$^{13}$)$_{n^1}$—$C_3$-$C_6$-cycloalkyl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl, —(CHR$^{13}$)$_{n^1}$-4- to 10-membered-heterocyclyl substituted by 0 to 3 groups independently selected from the group consisting of halo, $CF_3$, $OCF_3$, 5- or 6-membered heteroaryl, OH, oxo, hydroxy-$C_1$-$C_4$-alkyl, and $C_1$-$C_4$ alkyl, —(CHR$^{13}$)$_{n^1}$-5- to 10-membered-heteroaryl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl, di-$C_1$-$C_4$-alkylamino-$C_1$-$C_4$-alkyl, hydroxy-$C_1$-$C_4$-alkyl, and cyano-$C_1$-$C_4$-alkyl;

alternatively, $R^{11}$ and $R^{12}$, when attached to the same nitrogen, combine to form a 4- to 8-membered heterocyclic ring containing carbon atoms substituted by 0 to 3 groups independently selected from the group consisting of halo, $CF_3$, $CHF_2$, $OCF_3$, $OCHF_2$, $OCH_2F$, 5- or 6-membered heteroaryl, OH, oxo, hydroxy-$C_1$-$C_4$-alkyl, $C_1$-$C_4$ alkyl and $C_1$-$C_4$ alkoxy, and 0 to 2 additional heteroatoms selected from N, $NR^{13}$, O and S(O)$_p$;

$R^{13}$ is independently, at each occurrence, selected from the group consisting of H and $C_1$-$C_6$ alkyl;

$R^{14}$ is independently, at each occurrence, selected from the group consisting of H, $C_1$-$C_6$ alkyl and —(CH$_2$)$_{n^1}$phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano, $R^7$ is selected from the group consisting of H, halo, $C_1$-$C_4$ alkyl, hydroxy-$C_1$-$C_4$-alkyl and halo-$C_1$-$C_4$-alkyl, which contains 1 to 5 halogens;

$n^1$, at each occurrence, is selected from 0, 1, 2 or 3; and p, at each occurrence, is selected from 0, 1 and 2.

In yet another embodiment, the present invention provides compounds, stereoisomers, tautomers, salts, solvates or prodrugs thereof, wherein:

W is O;

$R^0$ is $R^1$ or $R^{1a}$;

Y is S or $-CR^8=CR^9-$;

$R^1$ is independently selected from the group consisting of:
- $C_1$-$C_4$ alkoxy,
- $C_1$-$C_4$ alkylthio, and
- halo-$C_1$-$C_2$-alkyl, which contains 1 to 5 halogens, where halo is F or Cl;

$R^{1a}$ is independently selected from the group consisting of:
- H,
- $C_1$-$C_4$ alkyl,
- $C_1$-$C_4$ alkoxy,
- $C_1$-$C_4$ alkylthio, and
- halo-$C_1$-$C_2$-alkyl, which contains 1 to 5 halogens, where halo is F or Cl;

$R^8$ and $R^9$ are independently selected from the group consisting of:
- H,
- $C_1$-$C_4$ alkyl, and
- halo-$C_1$-$C_2$ alkyl;

provided that at least one of $R^{1a}$, $R^8$ and $R^9$ is other than H;

$R^2$ is H;

$X^1$ is selected from the group consisting of CH;

$X^2$, $X^3$ and $X^4$ are independently selected from $CR^3$;

$R^3$ is selected from the group consisting of H, $C_1$-$C_4$ alkyl, $C_1$-$C_4$ alkoxy, halo and halo-$C_1$-$C_3$-alkyl, which contains 1 to 5 halogens;

$R^4$ and $R^5$ are independently selected from H and $C_1$-$C_6$ alkyl;

is a 5-membered heteroaryl ring containing at least one O, N or S atom;

$R^6$ is selected from the group consisting of H, halo, $NR^{11}R^{12}$, $C_1$-$C_4$ alkoxycarbonyl and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, and $C_1$-$C_4$ alkylthio, or $R^6$ is B-D-, where D is a linker, which is selected from:
a single bond,

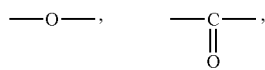

and
$C_1$-$C_4$ alkylene substituted by 0 to 4 groups independently selected from halo or OH;

B is selected from the group consisting of:
$C_6$-$C_{10}$ aryl substituted by 0 to 3 groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{11}R^{12}$, OH, $C_1$-$C_4$-alkylcarbonyloxy-$C_1$-$C_4$-alkyl, hydroxy-$C_1$-$C_4$-alkyl, $COOR^{14}$, $SO_2R^{14}$, $(C=O)NR^{11}R^{12}$, $SO_2NR^{11}R^{12}$, $N(R^{13})(C=O)NR^{11}R^{12}$, $N(R^{13})(C=O)OR^{14}$, $N(R^{13})(C=O)R^{14}$, $NR^{13}S(O)R^{14}$, $NR^{13}SO_2R^{14}$, $O(C=O)NR^{11}R^{12}$, $O(C=O)OR^{14}$, $O(C=O)R^{14}$, $(C=O)OR^{14}$, and 5-6-membered heteroaryl, 5- to 10-membered heteroaryl substituted by 0 to 3 groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{11}R^{12}$, OH, $C_1$-$C_4$-alkylcarbonyloxy-$C_1$-$C_4$-alkyl, hydroxy-$C_1$-$C_4$-alkyl, $COOR^{14}$, $SO_2R^{14}$, $(C=O)NR^{11}R^{12}$, $SO_2NR^{11}R^{12}$, $N(R^{13})(C=O)NR^{11}R^{12}$, $N(R^{13})(C=O)OR^{14}$, $N(R^{13})(C=O)R^{14}$, $NR^{13}S(O)R^{14}$, $NR^{13}SO_2R^{14}$, $O(C=O)NR^{11}R^{12}$, $O(C=O)OR^{14}$, $O(C=O)R^{14}$, $(C=O)OR^{14}$, 5-6-membered heteroaryl, and $(CH_2)$phenyl, 4- to 10-membered heterocyclyl containing carbon atoms and 1 to 2 additional heteroatoms selected from N, O, and S, and substituted by 0 to 3 groups independently selected from the group consisting of halo, oxo, $-(CHR^{13})_n^1$-5- or 6-membered heteroaryl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; $NR^{13}S(O)R^{14}$, $NR^{13}SO_2R^{14}$, $-(CHR^{13})_n^1$-4- to 10-membered-heterocyclyl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; OH, hydroxy-$C_1$-$C_4$-alkyl, $C_1$-$C_4$ alkoxy, halo-$C_1$-$C_4$ alkoxy, di-$C_1$-$C_4$-alkylamino-$C_1$-$C_4$-alkyl, $NR_{11}R_{12}$, cyano, $C_1$-$C_4$ alkyl, halo-$C_1$-$C_4$ alkyl, $C_3$-$C_6$ cycloalkyl, $C_1$-$C_4$-alkoxy-$C_1$-$C_4$-alkyl, $C_3$-$C_6$ cycloalkyl-$C_1$-$C_4$-alkylcarbonyl, $C_6$-$C_{10}$ arylcarbonyl, $C_1$-$C_4$-alkylcarbonyloxy-$C_1$-$C_4$-alkyl, $COOR^{14}$, $SO_2R^{14}$, $(C=O)NR^{11}R^{12}$, $SO_2NR^{11}R^{12}$, $N(R^{13})(C=O)NR^{11}R^{12}$, $N(R^{13})(C=O)OR^{14}$, $N(R^{13})(C=O)R^{14}$, $O(C=O)NR^{11}R^{12}$, $O(C=O)OR^{14}$, $O(C=O)R^{14}$, $(C=O)OR^{14}$, and $C_6$-$C_{10}$ aryl substituted by 0 to 3 groups independently selected from the group consisting of halo, $C_1$-$C_4$ alkoxy, $C_1$-$C_4$ alkyl, cyclopropyl, $C_1$-$C_4$-alkoxycarbonyl, $(C=O)NR^{11}R^{12}$, $CF_3$, $OCF_3$, and $CF_2CH_3$; and $C_3$-$C_6$ cycloalkyl which may contain unsaturation, substituted by 0 to 3 groups independently selected from the group consisting of halo, $CF_3$, $OCF_3$, 5- or 6-membered heteroaryl, OH, oxo, hydroxy-$C_1$-$C_4$-alkyl, $C_6$-$C_{10}$ aryl, COOH, oxo, $C_1$-$C_4$-alkoxycarbonyl, $(C=O)NR^{11}R^{12}$, and $C_1$-$C_4$ alkyl;

$R^{11}$ and $R^{12}$ are independently, at each occurrence, selected from the group consisting of:
H,
$C_1$-$C_4$ alkyl,
halo-$C_1$-$C_4$-alkyl,
$-(CR^{14}R^{14})_n^1$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano,
$-(CHR^{13})_n^1-C_3$-$C_6$-cycloalkyl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl,
$-(CHR^{13})_n^1$-4- to 10-membered-heterocyclyl substituted by 0 to 3 groups independently selected from the group consisting of halo, $CF_3$, $OCF_3$, 5- or 6-membered heteroaryl, OH, oxo, hydroxy-$C_1$-$C_4$-alkyl, and $C_1$-$C_4$ alkyl, —(CHR$^{13}$)$_n$$^1$-5- to 10-membered-heteroaryl substituted by 0 to 3 groups independently selected from the group consisting of halo, CF$_3$, OCF$_3$, 5- or 6-membered heteroaryl, OH, hydroxy-C$_1$-C$_4$-alkyl, and C$_1$-C$_4$ alkyl, hydroxy-C$_1$-C$_4$-alkyl, and cyano-C$_1$-C$_4$-alkyl;

alternatively, R$^{11}$ and R$^{12}$, when attached to the same nitrogen, combine to form a 4- to 8-membered heterocyclic ring containing carbon atoms substituted by 0 to 3 groups independently selected from the group consisting of halo, CF$_3$, CHF$_2$, OCF$_3$, OCHF$_2$, OCH$_2$F, 5- or 6-membered heteroaryl, OH, oxo, hydroxy-C$_1$-C$_4$-alkyl, C$_1$-C$_4$ alkyl and C$_1$-C$_4$ alkoxy;

R$^{13}$ is independently, at each occurrence, selected from the group consisting of H and C$_1$-C$_6$ alkyl;

R$^{14}$ is independently, at each occurrence, selected from the group consisting of H, C$_1$-C$_6$ alkyl and —(CH$_2$)$_n$$^1$phenyl substituted by 0 to 3 groups independently selected from the group consisting of halo, C$_1$-C$_4$ alkoxy, C$_1$-C$_4$ alkyl, cyclopropyl, CF$_3$, OCF$_3$, 5- or 6-membered heteroaryl, OH, OCHF$_2$, di-C$_1$-C$_4$-alkylamino, and cyano, R$^7$ is selected from the group consisting of H, halo, C$_1$-C$_4$ alkyl and halo-C$_1$-C$_4$-alkyl, which contains 1 to 5 halogens; and n$^1$, at each occurrence, is selected from 0, 1 or 2.

In still yet another embodiment, the present invention provides compounds, stereoisomers, tautomers, salts, solvates or prodrugs thereof, wherein:

Y is S or —CH=CH—;

R$^1$ and R$^{1a}$ are selected from the group consisting of:
CH$_3$,
SCH$_3$,
OCH$_3$,
CH(CH$_3$)F,
C(CH$_3$)F$_2$, and
CF$_3$;

X$^1$ is CH or N;

X$^2$ and X$^4$ are each CH; and

X$^3$ is CR$^3$ where R$^3$ is OCH$_3$, F or Cl;

the 5-membered heteroaryl ring

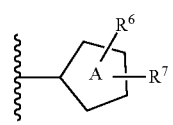

is selected from the group consisting of

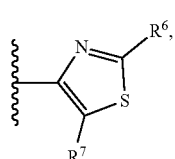 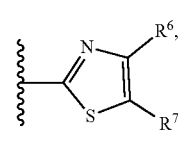

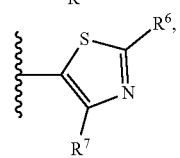 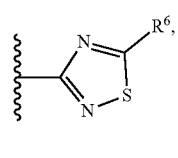

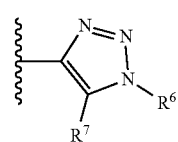 and 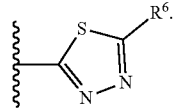

R$^6$ is selected from the group consisting of:

a) phenyl or substituted phenyl, which is selected from the group consisting of

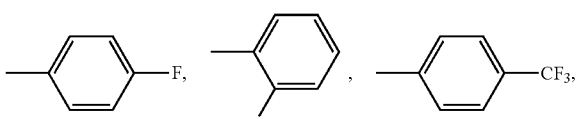

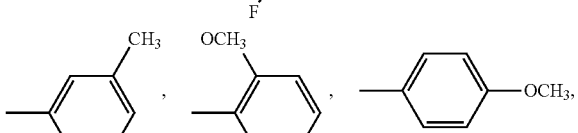

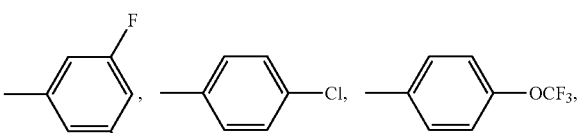

b) heterocyclyl, which is selected from the group consisting of

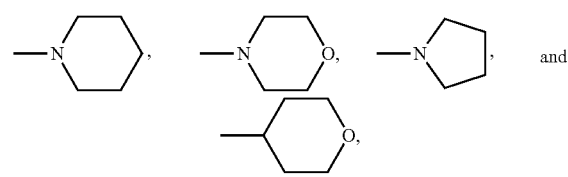

c) substituted heterocyclyl, which is selected from the group consisting of

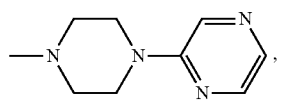

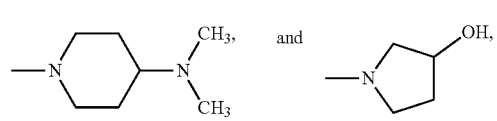

d) cycloalkyl, which is selected from the group consisting of

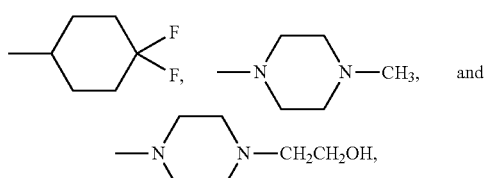

e) heteroaryl-$C_1$-$C_3$-alkyl, which is

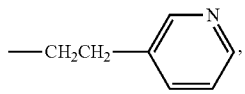

f) heteroaryl, which is selected from the group consisting of

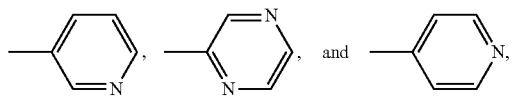

g) substituted heteroaryl, which is selected from the group consisting of

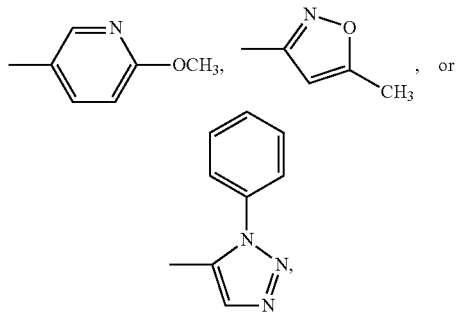

h) haloalkyl, which is —$CF_3$,
i) halo, which is Br,
j) alkoxyalkoxyalkyl, which is —$CH_2OCH_2CH_2OCH_3$,
k) alkyl which is selected from —$CH_2CH_3$ or $CH_3$,
l) aryl-$C_1$-$C_3$-alkyl, which is selected from

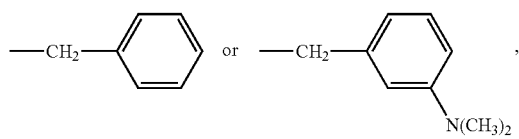

m) H,
n) —$NR^{11}R^{12}$, which is selected from the group consisting of

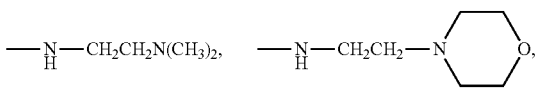

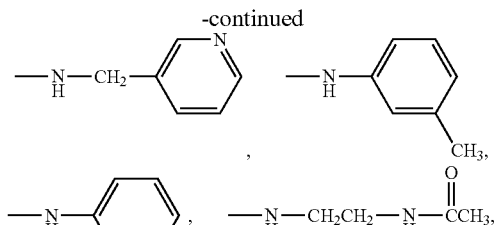

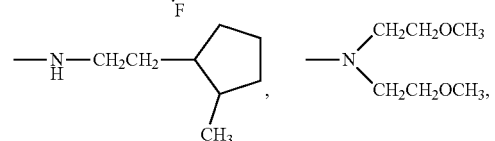

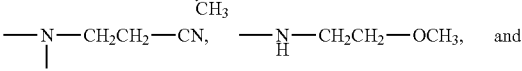

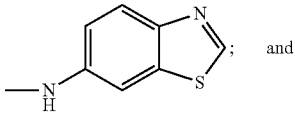

$R^7$ is selected from the group consisting of H and $C_1$-$C_4$ alkyl.

In one embodiment, the present invention provides compounds, stereoisomers, tautomers, salts, solvates or prodrugs thereof, wherein:

is selected from the group consisting of

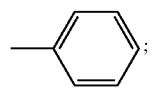

substituted phenyl, which is selected from the group consisting of

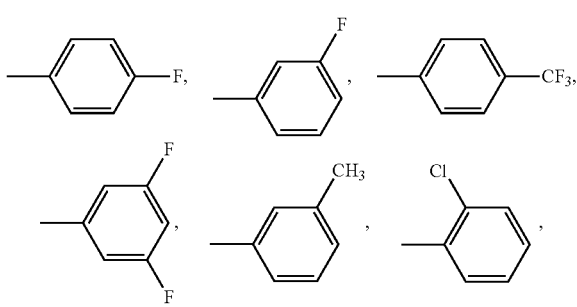

-continued

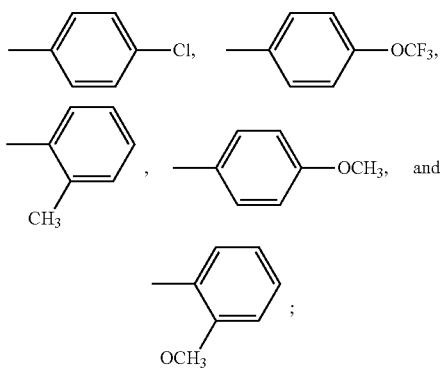

heteroaryl, which is selected from the group consisting of

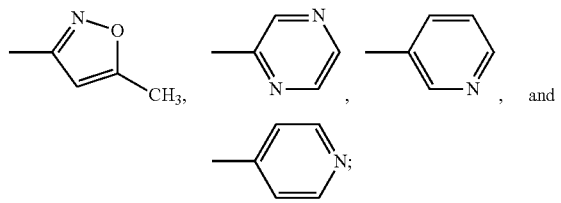

heterocyclyl, which is selected from the group consisting of

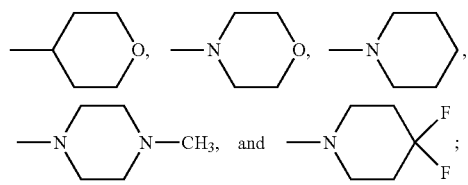

and cycloalkyl, which is

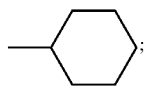

and $R^7$ is selected from H or $C_1$-$C_4$ alkyl.

In yet another embodiment, the present invention provides compounds, stereoisomers, tautomers, salts, solvates or prodrugs thereof, wherein:

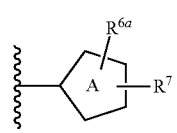

is selected from the group consisting of

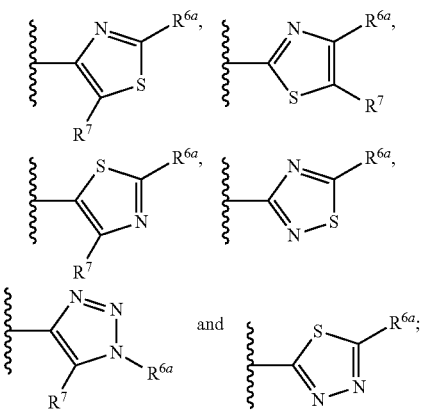

$R^6$ is selected from the group consisting of H, halo, $CF_3$, $OCF_3$, $OCHF_2$, $C_3$-$C_6$ cycloalkyloxy, OH, CN, $NO_2$, $NR^{11}R^{12}$, COOH, $C_1$-$C_4$ alkoxycarbonyl, $C(=O)NR^{11}R^{12}$, $C_1$-$C_4$ alkylsulfonyl, $S(=O)_2NR^{11}R^{12}$, phenyloxy, phenylthio, phenyl-$C_1$-$C_4$-alkoxy, heteroaryl-$C_1$-$C_4$-alkoxy, and phenyl-$C_1$-$C_4$-alkyl; and $R^7$ is H or $CH_3$.

In still yet another embodiment, the present invention provides compounds, stereoisomers, tautomers, salts, solvates or prodrugs thereof, wherein:

Y is S;

$X^1$ is CH;

$R^2$ is H;

$R^4$ and $R^5$ are each H;

$R^1$ is $OCH_3$ or —$CH(CH_3)F$;

$R^3$ is $OCH_3$ or F;

$R^4$ and $R^5$ are each H;

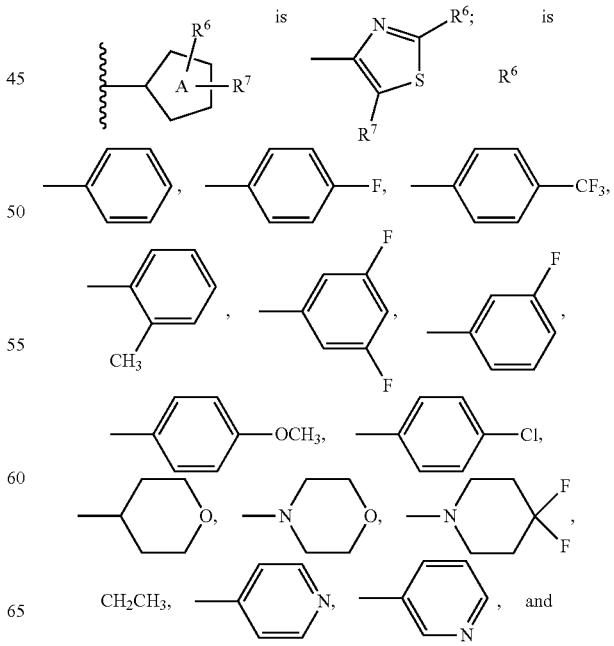

-continued

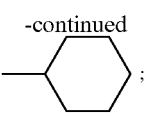

and

R⁷ is H or CH₃.

In one embodiment, the present invention provides compounds, stereoisomers, tautomers, salts, solvates or prodrugs thereof, wherein:

Y is CH=CH;
$X^1$ is CH;
$R^2$ is H;
$R^4$ and $R^5$ are each H;
$R^{1a}$ is CH₃;
$R^3$ is OCH₃ or F;

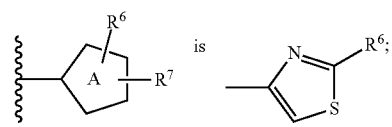

$R^6$ is selected from the group consisting of

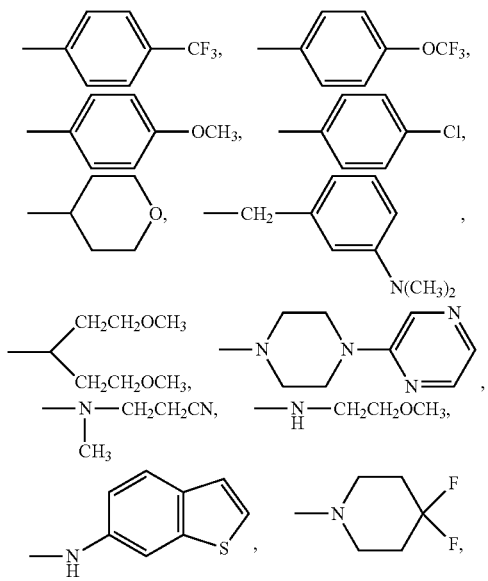

and —CH₂CH₃; and $R^7$ is H.

In another embodiment, the present invention provides compounds, stereoisomers, tautomers, salts, solvates or prodrugs thereof, wherein:

$R^0$ is $C_1$-$C_4$ alkoxy, $C_1$-$C_4$ alkyl, halo-$C_1$-$C_2$-alkyl, which contains 1 to 5 halogens, where halo is F or Cl, or halo;
$R^2$ is H;
$R^3$ is $C_1$-$C_4$ alkoxy or halo;
$R^4$ is H; and
$R^5$ is H.

In yet another embodiment, the present invention provides compounds, stereoisomers, tautomers, salts, solvates or prodrugs thereof, wherein:

$X^1$ is CH;

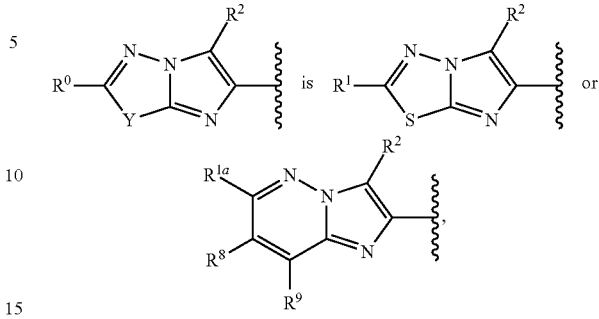

$R^{1a}$ is independently selected from $C_1$-$C_4$ alkyl, halo-$C_1$-$C_2$-alkyl, which contains 1 to 5 halogens, where halo is F or Cl, or $C_1$-$C_3$ alkoxy;
$R^8$ and $R^9$ are each H; and
$R^2$ is H.

In still yet another embodiment, the present invention provides compounds, stereoisomers, tautomers, salts, solvates or prodrugs thereof, wherein:

$X^1$ is CH or N;
$R^3$ is OCH₃ or fluoro; and
$R^6$ is
$C_1$-$C_3$ alkyl,
halo-$C_1$-$C_2$-alkyl,
phenyl,
phenyl substituted with 0 to 3 substituents selected from 1 or 2 halo groups, halo-$C_1$-$C_2$ alkyl which contains 1 to 5 halogens, $C_1$-$C_3$ alkyl and $C_1$-$C_3$ alkoxy, or

In one embodiment, the present invention provides compounds, stereoisomers, tautomers, salts, solvates or prodrugs thereof, wherein

is a 5-membered heteroaryl ring containing one or two N atoms and one S atom or three N atoms.

In another embodiment, the present invention provides compounds, stereoisomers, tautomers, salts, solvates or prodrugs thereof, wherein:

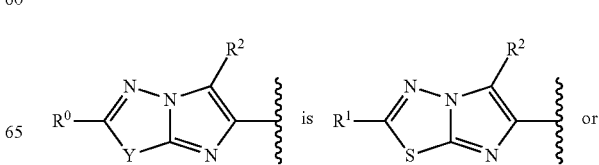

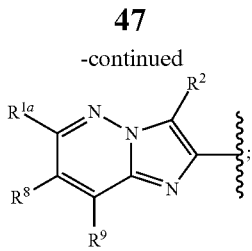

$X^1$ is CH;
$R^1$ is $OCH_3$, $CH_3$, $C_2H_5$ or $i\text{-}C_3H_7$;
$R^{1a}$ is $CH_3$;
$R^2$ is H;
$R^3$ is $OCHF_2$, $OCH_3$ or F;

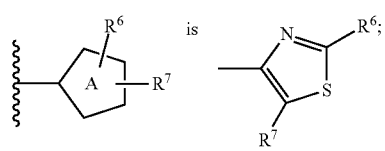

and
$R^8$ and $R^9$ are each H.

In yet another embodiment, the present invention provides compounds, stereoisomers, tautomers, salts, solvates or prodrugs thereof, wherein:

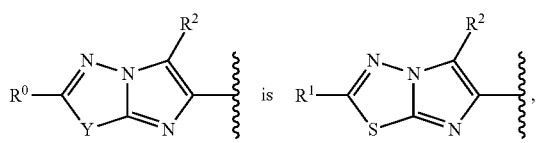

where
$R^1$ is $OCH_3$, —$CHFCH_3$, or —$CF_2CH_3$;
$R^2$ is H;
$X^1$ is CH;
$R^3$ is $OCH_3$ or fluoro;

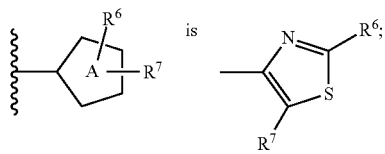

$R^6$ is selected from the group consisting of:
a) phenyl substituted by 0 to 3 groups independently selected from the group consisting of fluoro, chloro, —$CH_3$, —$CF_3$, OH, cyano, —$CH_2CN$, —$OCH_3$, —$OCF_3$, —$CH_2OH$, —$C(CH3)_2OH$, —$SO_2CH_3$ and $(C=O)NR^{11}R^{12}$, wherein $NR^{11}R^{12}$ is selected from:

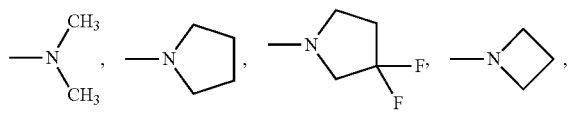

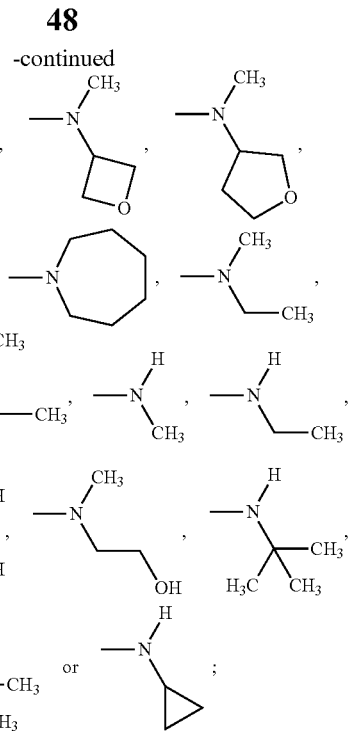

b) pyridinyl or pyrimidinyl substituted by 0 to 3 groups independently selected from the group consisting of fluoro, chloro, —$CH_3$ and —$OCH_3$;
c) tetrahydropyranyl, tetrahydrothiopyranyl, piperidinyl, morpholinyl, thiomorpholinyl or piperazine substituted by 0 to 3 groups independently selected from the group consisting of fluoro, OH, —$CH_3$ and —$NH_2$; and
d) cyclohexyl substituted by 0 to 3 groups independently selected from the group consisting of fluoro, OH and $NH_2$; and $R^7$ is selected from the group consisting of H and —$CH_3$.

In still yet another embodiment, the present invention provides compounds, stereoisomers, tautomers, salts, solvates or prodrugs thereof, wherein:

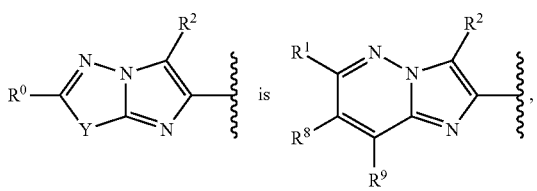

where
$R^1$ is $CH_3$;
$X^1$ is CH;
$R^2$ is H;
$R^3$ is $OCH_3$;

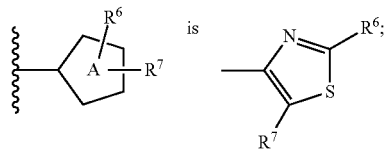

$R^6$ is selected from the group consisting of:
 a) phenyl substituted by 0 to 3 groups independently selected from the group consisting of chloro, —$CF_3$, cyano, —$OCH_3$, —$OCF_3$, —$SO_2CH_3$ and (C=O)N($CH_3$)$_2$;
 b) pyridinyl or pyrimidinyl substituted by 0 to 3 groups independently selected from the group consisting of fluoro, chloro, —$CH_3$ and —$OCH_3$; and
 c) piperidinyl, morpholinyl or thiomorpholinyl substituted by 0 to 3 groups independently selected from the group consisting of fluoro, OH, —$CH_3$ and —$NH_2$;
$R^7$ is selected from the group consisting of H and —$CH_3$; and
$R^8$ and $R^9$ are each H.

In yet another embodiment, the present invention provides compounds, stereoisomers, tautomers, salts, solvates or prodrugs thereof, wherein:
 W is O or S;
 $R^0$ is $R^1$ or $R^{1a}$;
 Y is S or —$CR^8$=$CR^9$—;
 $R^1$ is independently selected from the group consisting of:
  halo,
  $C_1$-$C_4$ alkyl,
  $C_2$-$C_3$ alkenyl,
  $C_2$-$C_3$ alkynyl,
  $C_3$-$C_4$ cycloalkyl,
  $C_1$-$C_4$ alkoxy,
  $C_1$-$C_2$ alkoxy-$C_1$-$C_2$ alkyl,
  tetrahydrofuran-2-yl;
  $C_1$-$C_4$ alkylthio,
  halo-$C_1$-$C_2$-alkyl, which contains 1 to 5 halogens, where halo is F or Cl,
  halo-$C_3$-$C_4$ cycloalkyl,
  halo-$C_1$-$C_2$ alkoxy, and
  halo-$C_1$-$C_2$ alkylthio;
 $R^{1a}$ is independently selected from the group consisting of:
  H,
  halo,
  $C_1$-$C_4$ alkyl,
  $C_2$-$C_3$ alkenyl,
  $C_2$-$C_3$ alkynyl,
  $C_3$-$C_4$ cycloalkyl,
  $C_1$-$C_4$ alkoxy,
  $C_1$-$C_2$ alkoxy-$C_1$-$C_2$ alkyl,
  tetrahydrofuran-2-yl;
  $C_1$-$C_4$ alkylthio,
  halo-$C_1$-$C_2$-alkyl, which contains 1 to 5 halogens, where halo is F or Cl,
  halo-$C_3$-$C_4$ cycloalkyl,
  halo-$C_1$-$C_2$ alkoxy, and
  halo-$C_1$-$C_2$ alkylthio;
 $R^8$ and $R^9$ are independently selected from the group consisting of:
  H,
  halo,
  $C_1$-$C_4$ alkyl,
  $C_1$-$C_4$ alkoxy,
  halo-$C_1$-$C_2$ alkyl, and
  halo-$C_1$-$C_2$ alkoxy;
 provided that at least one of $R^{1a}$, $R^8$ and $R^9$ is other than H;
 $R^2$ is selected from the group consisting of:
  H,
  halo,
  $C_1$-$C_3$ alkyl, and
  $C_1$-$C_2$ alkoxy;

$X^1$ is selected from the group consisting of CH, N or $CR^{10}$;
$X^2$, $X^3$ and $X^4$ are independently selected from $CR^3$ or N;
$R^3$ is selected from the group consisting of H, $C_1$-$C_4$ alkyl, $C_2$-$C_4$ alkenyl, $C_2$-$C_4$ alkynyl, $C_1$-$C_4$ alkoxy, $C_1$-$C_4$ alkylthio, halo, OH, CN, $OCF_3$, $C_1$-$C_2$-alkoxy-$C_1$-$C_2$-alkoxy, halo-$C_1$-$C_3$-alkyl, which contains 1 to 5 halogens, benzyloxy substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano, and —$(CH_2)_n^1$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano;

$R^4$ and $R^5$ are independently selected from H and $C_1$-$C_6$ alkyl, or $R^4$ and $R^5$ can be taken together with the carbon to which they are attached to form a $C_3$-$C_7$ cycloalkyl ring;

is a 5-membered heteroaryl ring containing at least one O, N or S atom;
$R^6$ is selected from the group consisting of H, halo, $OCF_3$, $OCHF_2$, OH, CN, $NO_2$, $NR^{11}R^{12}$, COOH, $C_1$-$C_4$ alkoxycarbonyl, (C=O)$NR^{11}R^{12}$, $C_1$-$C_4$ alkylsulfonyl, and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylamino-phenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, and $C_1$-$C_4$ alkylthio, or
$R^6$ is B-D-, where D is a linker, which is selected from:
 a single bond,

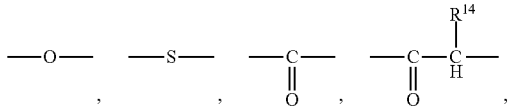

$C_1$-$C_4$ alkylene substituted by 0 to 4 groups independently selected from halo or OH,
 $C_1$-$C_4$ alkyleneoxy,
 $C_1$-$C_4$ alkylenethio,
 $C_1$-$C_4$ alkyleneoxy-$C_1$-$C_4$-alkylene,
 $C_1$-$C_4$-alkylenethio-$C_1$-$C_4$-alkylene,
 $C_2$-$C_6$ alkenylene, and
 B is selected from the group consisting of:
  $C_6$-$C_{10}$ aryl substituted by 0 to 3 groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{11}R^{12}$, OH, $C_1$-$C_4$-alkylcarbonyloxy-$C_1$-$C_4$-alkyl, hydroxy-$C_1$-$C_4$-alkyl, $COOR^{14}$, $SO_2R^{14}$, (C=O)$NR^{11}R^{12}$, $SO_2NR^{11}R^{12}$, $N(R^{13})$(C=O)$NR^{11}R^{12}$, $N(R^{13})$(C=O)$OR^{14}$, $N(R^{13})$(C=O)$R^{14}$, $NR^{13}S(O)R^{14}$, $NR^{13}SO_2R^{14}$, O(C=O)$NR^{11}R^{12}$, O(C=O)$OR^{14}$, O(C=O)$R^{14}$, (C=O)$OR^{14}$, and 5-6-membered heteroaryl,
  5- to 10-membered heteroaryl substituted by 0 to 3 groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{11}R^{12}$, OH, $C_1$-$C_4$-alkylcarbonyloxy-$C_1$-$C_4$-alkyl, hydroxy-$C_1$-$C_4$-alkyl, COOR$^{14}$, SO$_2$R$^{14}$, (C=O)NR$^{11}$R$^{12}$, SO$_2$NR$^{11}$R$^{12}$, N(R$^{13}$)(C=O)NR$^{11}$R$^{12}$, N(R$^{13}$)(C=O)OR$^{14}$, N(R$^{13}$)(C=O)R$^{14}$, NR$^{13}$S(O)R$^{14}$, NR$^{13}$SO$_2$R$^{14}$, O(C=O)NR$^{11}$R$^{12}$, O(C=O)OR$^{14}$, O(C=O)R$^{14}$, (C=O)OR$^{14}$, 5-6-membered heteroaryl, and (CH$_2$)phenyl, 4- to 10-membered heterocyclyl containing carbon atoms and 1 to 2 additional heteroatoms selected from N, O, and S, and substituted by 0 to 3 groups independently selected from the group consisting of halo, oxo, —(CHR$^{13}$)$_n{}^1$-5- or 6-membered heteroaryl substituted by 0 to 3 groups independently selected from the group consisting of halo, $C_1$-$C_4$ alkoxy, $C_1$-$C_4$ alkyl, cyclopropyl, CF$_3$, OCF$_3$, and CF$_2$CH$_3$; NR$^{13}$S(O)R$^{14}$, NR$^{13}$SO$_2$R$^{14}$, —(CHR$^{13}$)$_n{}^1$-4- to 10-membered-heterocyclyl substituted by 0 to 3 groups independently selected from the group consisting of halo, $C_1$-$C_4$ alkoxy, $C_1$-$C_4$ alkyl, cyclopropyl, CF$_3$, OCF$_3$, and CF$_2$CH$_3$; OH, hydroxy-$C_1$-$C_4$-alkyl, $C_1$-$C_4$ alkoxy, halo-$C_1$-$C_4$ alkoxy, di-$C_1$-$C_4$-alkylamino-$C_1$-$C_4$-alkyl, NR$_{11}$R$_{12}$, cyano, $C_1$-$C_4$ alkyl, halo-$C_1$-$C_4$ alkyl, $C_3$-$C_6$ cycloalkyl, $C_1$-$C_4$-alkoxy-$C_1$-$C_4$-alkyl, $C_3$-$C_6$ cycloalkyl-$C_1$-$C_4$-alkylcarbonyl, $C_6$-$C_{10}$ arylcarbonyl, $C_1$-$C_4$-alkylcarbonyloxy-$C_1$-$C_4$-alkyl, COOR$^{14}$, SO$_2$R$^{14}$, (C=O)NR$^{11}$R$^{12}$, SO$_2$NR$^{11}$R$^{12}$, N(R$^{13}$)(C=O)NR$^{11}$R$^{12}$, N(R$^{13}$)(C=O)OR$^{14}$, N(R$^{13}$)(C=O)R$^{14}$, O(C=O)NR$^{11}$R$^{12}$, O(C=O)OR$^{14}$, O(C=O)R$^{14}$, (C=O)OR$^{14}$, and $C_6$-$C_{10}$ aryl substituted by 0 to 3 groups independently selected from the group consisting of halo, $C_1$-$C_4$ alkoxy, $C_1$-$C_4$ alkyl, cyclopropyl, $C_1$-$C_4$-alkoxycarbonyl, (C=O)NR$^{11}$R$^{12}$, CF$_3$, OCF$_3$, and CF$_2$CH$_3$;

$C_3$-$C_6$ cycloalkyl which may contain unsaturation, substituted by 0 to 3 groups independently selected from the group consisting of halo, CF$_3$, OCF$_3$, 5- or 6-membered heteroaryl, OH, oxo, hydroxy-$C_1$-$C_4$-alkyl, $C_6$-$C_{10}$ aryl, COOH, oxo, $C_1$-$C_4$-alkoxycarbonyl, (C=O)NR$^{11}$R$^{12}$, and $C_1$-$C_4$ alkyl; and $C_5$-$C_{11}$ spirocycloalkyl which may contain unsaturation and optionally containing 1 to 3 heteroatoms selected from O, N or S and substituted by 0 to 3 groups independently selected from the group consisting of halo, CF$_3$, OCF$_3$, 5- or 6-membered heteroaryl, OH, hydroxy-$C_1$-$C_4$-alkyl, $C_6$-$C_{10}$ aryl, and $C_1$-$C_4$ alkyl;

R$^{11}$ and R$^{12}$ are independently, at each occurrence, selected from the group consisting of:
H,
$C_1$-$C_4$ alkyl,
halo-$C_1$-$C_4$-alkyl,
$C_2$-$C_4$ alkenyl,
$C_2$-$C_4$ alkynyl,
—(CR$^{14}$R$^{14}$)$_n{}^1$-phenyl substituted by 0 to 3 groups independently selected from the group consisting of halo, $C_1$-$C_4$ alkoxy, $C_1$-$C_4$ alkyl, cyclopropyl, CF$_3$, OCF$_3$, 5- or 6-membered heteroaryl, OH, OCHF$_2$, di-$C_1$-$C_4$-alkylamino, and cyano,
—(CHR$^{13}$)$_n{}^1$—$C_3$-$C_6$-cycloalkyl substituted by 0 to 3 groups independently selected from the group consisting of halo, CF$_3$, OCF$_3$, 5- or 6-membered heteroaryl, OH, hydroxy-$C_1$-$C_4$-alkyl, and $C_1$-$C_4$ alkyl,
—(CHR$^{13}$)$_n{}^1$-4- to 10-membered-heterocyclyl substituted by 0 to 3 groups independently selected from the group consisting of halo, CF$_3$, OCF$_3$, 5- or 6-membered heteroaryl, OH, oxo, hydroxy-$C_1$-$C_4$-alkyl, and $C_1$-$C_4$ alkyl,
—(CHR$^{13}$)$_n{}^1$-5- to 10-membered-heteroaryl substituted by 0 to 3 groups independently selected from the group consisting of halo, CF$_3$, OCF$_3$, 5- or 6-membered heteroaryl, OH, hydroxy-$C_1$-$C_4$-alkyl, and $C_1$-$C_4$ alkyl, di-$C_1$-$C_4$-alkylamino-$C_1$-$C_4$-alkyl,
di-$C_1$-$C_4$-alkoxy-$C_1$-$C_4$-alkyl,
hydroxy-$C_1$-$C_4$-alkyl,
cyano-$C_1$-$C_4$-alkyl,
$C_1$-$C_4$-alkoxy-$C_1$-$C_4$-alkyl,
$C_1$-$C_4$-alkoxycarbonyl-$C_1$-$C_4$-alkyl,
$C_1$-$C_4$-alkoxycarbonyl,
$C_1$-$C_4$-alkylcarbonyl,
phenylcarbonyl;
$C_1$-$C_4$-alkoxycarbonylamino-$C_1$-$C_4$-alkylcarbonyl,
di-$C_1$-$C_4$-alkylamino-$C_1$-$C_4$-alkylcarbonyl,
amino-$C_1$-$C_4$-alkylcarbonyl,
4- to 10-membered-heterocyclyl-carbonyl, and
alternatively, R$^{11}$ and R$^{12}$, when attached to the same nitrogen, combine to form a 4- to 8-membered heterocyclic ring containing carbon atoms substituted by 0 to 3 groups independently selected from the group consisting of halo, CF$_3$, CHF$_2$, OCF$_3$, OCHF$_2$, OCH$_2$F, 5- or 6-membered heteroaryl, OH, oxo, hydroxy-$C_1$-$C_4$-alkyl, $C_1$-$C_4$ alkyl and $C_1$-$C_4$ alkoxy, and 0 to 2 additional heteroatoms selected from N, NR$^{13}$, O and S(O)$_p$;

R$^{13}$ is independently, at each occurrence, selected from the group consisting of H, $C_1$-$C_6$ alkyl and —(CH$_2$)phenyl;

R$^{14}$ is independently, at each occurrence, selected from the group consisting of H, $C_1$-$C_6$ alkyl, halo-$C_1$-$C_4$-alkyl, $C_1$-$C_4$-alkoxycarbonylamino, (C$_6$-$C_{10}$ arylcarbonylamino), (a 5- to 10-membered heteroarylcarbonylamino) and —(CH$_2$)$_n{}^1$phenyl substituted by 0 to 3 groups independently selected from the group consisting of halo, $C_1$-$C_4$ alkoxy, $C_1$-$C_4$ alkyl, cyclopropyl, CF$_3$, OCF$_3$, 5- or 6-membered heteroaryl, OH, OCHF$_2$, di-$C_1$-$C_4$-alkylamino, and cyano, R$^7$ is selected from the group consisting of H, halo, hydroxyl, oxo, $C_1$-$C_4$ alkyl, hydroxy-$C_1$-$C_4$-alkyl, $C_1$-$C_4$-alkoxy-$C_1$-$C_4$-alkyl, halo-$C_1$-$C_4$-alkyl, which contains 1 to 5 halogens, $C_1$-$C_4$-alkoxy, and halo-$C_1$-$C_4$-alkoxy;

R$^{10}$ is selected from the group consisting of $C_1$-$C_4$ alkyl, halo, $C_1$-$C_4$ alkoxy, and halo-$C_1$-$C_2$-alkyl, which contains 1 to 5 halogens, where halo is F or Cl;

n$^1$, at each occurrence, is selected from 0, 1, 2, 3, 4 or 5; and p, at each occurrence, is selected from 0, 1 and 2.

In yet another embodiment, the present invention provides compounds, stereoisomers, tautomers, salts, solvates or prodrugs thereof, wherein:
W is O or S;
R$^0$ is R$^1$ or R$^{1a}$;
Y is S or —CR$^8$=CR$^9$—;
R$^1$ is independently selected from the group consisting of:
halo,
$C_1$-$C_4$ alkyl,
$C_2$-$C_3$ alkenyl,
$C_2$-$C_3$ alkynyl,
$C_3$-$C_4$ cycloalkyl,
$C_1$-$C_4$ alkoxy,
$C_1$-$C_4$ alkylthio,
halo-$C_1$-$C_2$-alkyl, which contains 1 to 5 halogens, where halo is F or Cl,
halo-$C_3$-$C_4$ cycloalkyl,
halo-$C_1$-$C_2$ alkoxy, and
halo-$C_1$-$C_2$ alkylthio;

R$^{1a}$ is independently selected from the group consisting of:
H,
halo,
$C_1$-$C_4$ alkyl,
$C_2$-$C_3$ alkenyl,
$C_2$-$C_3$ alkynyl, $C_3$-$C_4$ cycloalkyl,
$C_1$-$C_4$ alkoxy,
$C_1$-$C_4$ alkylthio,
halo-$C_1$-$C_2$-alkyl, which contains 1 to 5 halogens, where halo is F or Cl,
halo-$C_3$-$C_4$ cycloalkyl,
halo-$C_1$-$C_2$ alkoxy, and
halo-$C_1$-$C_2$ alkylthio;

$R^8$ and $R^9$ are independently selected from the group consisting of:
H,
halo,
$C_1$-$C_4$ alkyl,
$C_1$-$C_4$ alkoxy,
halo-$C_1$-$C_2$ alkyl, and
halo-$C_1$-$C_2$ alkoxy;
provided that at least one of $R^{1a}$, $R^8$ and $R^9$ is other than H;
$R^2$ is selected from the group consisting of:
H,
fluoro,
chloro, and
$CH_3$;
$X^1$ is selected from the group consisting of CH, N or $CR^{10}$;
$X^2$, $X^3$ and $X^4$ are independently selected from $CR^3$ or N;
$R^3$ is selected from the group consisting of H, $C_1$-$C_3$ alkyl, $C_2$-$C_3$ alkenyl, $C_2$-$C_3$ alkynyl, $C_1$-$C_3$ alkoxy, $C_1$-$C_3$ alkylthio, halo, OH, CN, $OCF_3$, and halo-$C_1$-$C_3$-alkyl, which contains 1 to 5 halogens;
$R^4$ and $R^5$ are independently selected from H and $C_1$-$C_3$ alkyl, or $R^4$ and $R^5$ can be taken together with the carbon to which they are attached to form a cyclopropyl ring;

is a 5-membered heteroaryl ring containing at least one O, N or S atom;
$R^6$ is selected from the group consisting of H, halo, $OCF_3$, $OCHF_2$, OH, CN, $NO_2$, $NR^{11}R^{12}$, COOH, $C_1$-$C_4$ alkoxycarbonyl, (C=O)$NR^{11}R^{12}$ and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, and $C_1$-$C_4$ alkylthio, or
$R^6$ is B-D-, where D is a linker, which is selected from:
a single bond,

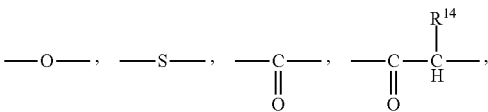

$C_1$-$C_4$ alkylene substituted by 0 to 4 groups independently selected from halo or OH,
$C_1$-$C_4$ alkyleneoxy,
$C_1$-$C_4$ alkylenethio,
$C_2$-$C_6$ alkenylene, and
B is selected from the group consisting of:
$C_6$-$C_{10}$ aryl substituted by 0 to 3 groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{11}R^{12}$, OH, $C_1$-$C_4$-alkylcarbonyloxy-$C_1$-$C_4$-alkyl, hydroxy-$C_1$-$C_4$-alkyl, $COOR^{14}$, $SO_2R^{14}$, (C=O)$NR^{11}R^{12}$, $SO_2NR^{11}R^{12}$, $N(R^{13})$(C=O)$NR^{11}R^{12}$, $N(R^{13})$(C=O)$OR^{14}$, $N(R^{13})$(C=O)$R^{14}$, $NR^{13}S(O)R^{14}$, $NR^{13}SO_2R^{14}$, O(C=O)$NR^{11}R^{12}$, O(C=O)$OR^{14}$, O(C=O)$R^{14}$, (C=O)$OR^{14}$, and 5-6-membered heteroaryl, 5- to 10-membered heteroaryl substituted by 0 to 3 groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{11}R^{12}$, OH, $C_1$-$C_4$-alkylcarbonyloxy-$C_1$-$C_4$-alkyl, hydroxy-$C_1$-$C_4$-alkyl, $COOR^{14}$, $SO_2R^{14}$, (C=O)$NR^{11}R^{12}$, $SO_2NR^{11}R^{12}$, $N(R^{13})$(C=O)$NR^{11}R^{12}$, $N(R^{13})$(C=O)$OR^{14}$, $N(R^{13})$(C=O)$R^{14}$, $NR^{13}S(O)R^{14}$, $NR^{13}SO_2R^{14}$, O(C=O)$NR^{11}R^{12}$, O(C=O)$OR^{14}$, O(C=O)$R^{14}$, (C=O)$OR^{14}$, 5-6-membered heteroaryl, and $(CH_2)$phenyl, 4- to 10-membered heterocyclyl containing carbon atoms and 1 to 2 additional heteroatoms selected from N, O, and S, and substituted by 0 to 3 groups independently selected from the group consisting of halo, oxo, —$(CHR^{13})_n^1$-5- or 6-membered heteroaryl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; $NR^{13}S(O)R^{14}$, $NR^{13}SO_2R^{14}$, —$(CHR^{13})_n^1$-4- to 10-membered-heterocyclyl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; OH, hydroxy-$C_1$-$C_4$-alkyl, $C_1$-$C_4$ alkoxy, halo-$C_1$-$C_4$ alkoxy, di-$C_1$-$C_4$-alkylamino-$C_1$-$C_4$-alkyl, $NR_{11}R_{12}$, cyano, $C_1$-$C_4$ alkyl, halo-$C_1$-$C_4$ alkyl, $C_3$-$C_6$ cycloalkyl, $C_1$-$C_4$-alkoxy-$C_1$-$C_4$-alkyl, $C_3$-$C_6$ cycloalkyl-$C_1$-$C_4$-alkylcarbonyl, $C_6$-$C_{10}$ arylcarbonyl, $C_1$-$C_4$-alkylcarbonyloxy-$C_1$-$C_4$-alkyl, $COOR^{14}$, $SO_2R^{14}$, (C=O)$NR^{11}R^{12}$, $SO_2NR^{11}R^{12}$, $N(R^{13})$(C=O)$NR^{11}R^{12}$, $N(R^{13})$(C=O)$OR^{14}$, $N(R^{13})$(C=O)$R^{14}$, O(C=O)$NR^{11}R^{12}$, O(C=O)$OR^{14}$, O(C=O)$R^{14}$, (C=O)$OR^{14}$, and $C_6$-$C_{10}$ aryl substituted by 0 to 3 groups independently selected from the group consisting of halo, $C_1$-$C_4$ alkoxy, $C_1$-$C_4$ alkyl, cyclopropyl, $C_1$-$C_4$-alkoxycarbonyl, (C=O)$NR^{11}R^{12}$, $CF_3$, $OCF_3$, and $CF_2CH_3$;

$C_3$-$C_6$ cycloalkyl which may contain unsaturation, substituted by 0 to 3 groups independently selected from the group consisting of halo, $CF_3$, $OCF_3$, 5- or 6-membered heteroaryl, OH, oxo, hydroxy-$C_1$-$C_4$-alkyl, $C_6$-$C_{10}$ aryl, COOH, oxo, $C_1$-$C_4$-alkoxycarbonyl, (C=O)$NR^{11}R^{12}$, and $C_1$-$C_4$ alkyl; and $C_5$-$C_{11}$ spirocycloalkyl which may contain unsaturation and optionally containing 1 to 3 heteroatoms selected from O, N or S and substituted by 0 to 3 groups independently selected from the group consisting of halo, $CF_3$, $OCF_3$, 5- or 6-membered heteroaryl, OH, hydroxy-$C_1$-$C_4$-alkyl, $C_6$-$C_{10}$ aryl, and $C_1$-$C_4$ alkyl;

$R^{11}$ and $R^{12}$ are independently, at each occurrence, selected from the group consisting of:
H,
$C_1$-$C_4$ alkyl,
halo-$C_1$-$C_4$-alkyl,
$C_2$-$C_4$ alkenyl,
—$(CR^{14}R^{14})_n^1$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano, —(CHR$^{13}$)$_{n^1}$—C$_3$-C$_6$-cycloalkyl substituted by 0 to 3 groups independently selected from the group consisting of halo, CF$_3$, OCF$_3$, 5- or 6-membered heteroaryl, OH, hydroxy-C$_1$-C$_4$-alkyl, and C$_1$-C$_4$ alkyl, —(CHR$^{13}$)$_{n^1}$-4- to 10-membered-heterocyclyl substituted by 0 to 3 groups independently selected from the group consisting of halo, CF$_3$, OCF$_3$, 5- or 6-membered heteroaryl, OH, oxo, hydroxy-C$_1$-C$_4$-alkyl, and C$_1$-C$_4$ alkyl, —(CHR$^{13}$)$_{n^1}$-5- to 10-membered-heteroaryl substituted by 0 to 3 groups independently selected from the group consisting of halo, CF$_3$, OCF$_3$, 5- or 6-membered heteroaryl, OH, hydroxy-C$_1$-C$_4$-alkyl, and C$_1$-C$_4$ alkyl, di-C$_1$-C$_4$-alkylamino-C$_1$-C$_4$-alkyl,
di-C$_1$-C$_4$-alkoxy-C$_1$-C$_4$-alkyl,
hydroxy-C$_1$-C$_4$-alkyl,
cyano-C$_1$-C$_4$-alkyl,
C$_1$-C$_4$-alkoxy-C$_1$-C$_4$-alkyl,
C$_1$-C$_4$-alkoxycarbonyl-C$_1$-C$_4$-alkyl,
C$_1$-C$_4$-alkoxycarbonyl,
C$_1$-C$_4$-alkylcarbonyl,
phenylcarbonyl;
C$_1$-C$_4$-alkoxycarbonylamino-C$_1$-C$_4$-alkylcarbonyl,
di-C$_1$-C$_4$-alkylamino-C$_1$-C$_4$-alkylcarbonyl,
amino-C$_1$-C$_4$-alkylcarbonyl,
4- to 10-membered-heterocyclyl-carbonyl, and alternatively, R$^{11}$ and R$^{12}$, when attached to the same nitrogen, combine to form a 4- to 8-membered heterocyclic ring containing carbon atoms substituted by 0 to 3 groups independently selected from the group consisting of halo, CF$_3$, CHF$_2$, OCF$_3$, OCHF$_2$, OCH$_2$F, 5- or 6-membered heteroaryl, OH, oxo, hydroxy-C$_1$-C$_4$-alkyl, C$_1$-C$_4$ alkyl and C$_1$-C$_4$ alkoxy, and 0 to 2 additional heteroatoms selected from N, NR$^{13}$, O and S(O)$_p$;

R$^{13}$ is independently, at each occurrence, selected from the group consisting of H, C$_1$-C$_6$ alkyl and —(CH$_2$)phenyl;

R$^{14}$ is independently, at each occurrence, selected from the group consisting of H, C$_1$-C$_6$ alkyl, halo-C$_1$-C$_4$-alkyl, C$_1$-C$_4$-alkoxycarbonylamino, (C$_6$-C$_{10}$ arylcarbonylamino) and —(CH$_2$)$_{n^1}$phenyl substituted by 0 to 3 groups independently selected from the group consisting of halo, C$_1$-C$_4$ alkoxy, C$_1$-C$_4$ alkyl, cyclopropyl, CF$_3$, OCF$_3$, 5- or 6-membered heteroaryl, OH, OCHF$_2$, di-C$_1$-C$_4$-alkylamino, and cyano, R$^7$ is selected from the group consisting of H, halo, hydroxyl, oxo, C$_1$-C$_4$ alkyl, hydroxy-C$_1$-C$_4$-alkyl, C$_1$-C$_4$-alkoxy-C$_1$-C$_4$-alkyl, halo-C$_1$-C$_4$-alkyl, which contains 1 to 5 halogens, and C$_1$-C$_4$-alkoxy;

R$^{10}$ is selected from the group consisting of C$_1$-C$_4$ alkyl, halo, and halo-C$_1$-C$_2$-alkyl, which contains 1 to 5 halogens, where halo is F or Cl;

n$^1$, at each occurrence, is selected from 0, 1, 2, 3 or 4; and
p, at each occurrence, is selected from 0, 1 and 2.

In still yet another embodiment, the present invention provides compounds, stereoisomers, tautomers, salts, solvates or prodrugs thereof, wherein:

W is O;
R$^0$ is R$^1$ or R$^{1a}$;
Y is S or —CR$^8$=CR$^9$—;
R$^1$ is independently selected from the group consisting of:
halo,
C$_1$-C$_2$ alkyl,
cyclopropyl,
C$_1$-C$_2$ alkoxy,
C$_1$-C$_2$ alkylthio, halo-C$_1$-C$_2$-alkyl, which contains 1 to 5 halogens, where halo is F or Cl, and
halo-C$_3$-C$_4$ cycloalkyl;

R$^{1a}$ is independently selected from the group consisting of:
H,
halo,
C$_1$-C$_2$ alkyl,
cyclopropyl,
C$_1$-C$_2$ alkoxy,
C$_1$-C$_2$ alkylthio,
halo-C$_1$-C$_2$-alkyl, which contains 1 to 5 halogens, where halo is F or Cl, and
halo-C$_3$-C$_4$ cycloalkyl;

R$^8$ and R$^9$ are independently selected from the group consisting of:
H,
fluoro,
chloro,
C$_1$-C$_3$ alkyl,
C$_1$-C$_2$ alkoxy, and
halo-C$_1$-C$_2$ alkyl;

provided that at least one of R$^{1a}$, R$^8$ and R$^9$ is other than H;
R$^2$ is H;
X$^1$ is selected from the group consisting of CH or N;
X$^2$, X$^3$ and X$^4$ are independently selected from CR$^3$;
R$^3$ is selected from the group consisting of H, C$_1$-C$_3$ alkyl, C$_1$-C$_3$ alkoxy, fluoro, chloro, OCF$_3$, and halo-C$_1$-C$_2$-alkyl, which contains 1 to 5 halogens;
R$^4$ and R$^5$ are independently selected from H and methyl;

is a 5-membered heteroaryl ring selected from thiazole, thiadiazole, oxazole, oxadiazole, and triazole;

R$^6$ is selected from the group consisting of H, halo, OCF$_3$, OCHF$_2$, OH, CN, NO$_2$, NR$^{11}$R$^{12}$, C$_1$-C$_4$ alkoxycarbonyl, (C=O)NR$^{11}$R$^{12}$ and C$_1$-C$_5$ alkyl substituted by 0 to 7 groups independently selected from halo, CF$_3$, OCF$_3$, OH, hydroxy-C$_1$-C$_4$-alkyl, C$_1$-C$_4$ alkoxy, C$_1$-C$_4$ alkoxy-C$_1$-C$_4$ alkoxy, di-C$_1$-C$_4$-alkylaminophenyl-C$_1$-C$_4$-alkyl, (di-C$_1$-C$_4$-alkoxy-C$_1$-C$_4$-alkyl)-C$_1$-C$_4$-alkyl, di-C$_1$-C$_4$-alkylamino, C$_3$-C$_6$-cycloalkyl, and C$_1$-C$_4$ alkylthio, or R$^6$ is B-D-, where D is a linker, which is selected from:
a single bond,

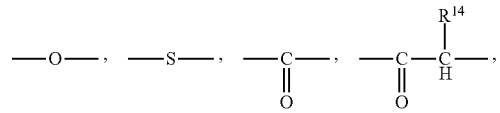

C$_1$-C$_4$ alkylene substituted by 0 to 4 groups independently selected from halo or OH,
C$_1$-C$_4$ alkyleneoxy,
C$_2$-C$_6$ alkenylene, and
B is selected from the group consisting of:
C$_6$-C$_{10}$ aryl substituted by 0 to 3 groups independently selected from the group consisting of halo, C$_1$-C$_4$ alkoxy, halo-C$_1$-C$_4$ alkoxy, C$_1$-C$_4$ alkyl, halo-C$_1$-C$_4$ alkyl, C$_3$-C$_6$ cycloalkyl, cyano, nitro, NR$^{11}$R$^{12}$, OH, C$_1$-C$_4$-alkylcarbonyloxy-C$_1$-C$_4$-alkyl, hydroxy-C$_1$-C$_4$-alkyl, COOR$^{14}$, SO$_2$R$^{14}$, (C=O)NR$^{11}$R$^{12}$, SO$_2$NR$^{11}$R$^{12}$, N(R$^{13}$)(C=O)NR$^{11}$R$^{12}$, N(R$^{13}$)(C=O)OR$^{14}$, N(R$^{13}$)(C=O)R$^{14}$, NR$^{13}$S(O)R$^{14}$, NR$^{13}$SO$_2$R$^{14}$, $O(C=O)NR^{11}R^{12}$, $O(C=O)OR^{14}$, $O(C=O)R^{14}$, $(C=O)OR^{14}$, and 5-6-membered heteroaryl, 5- to 10-membered heteroaryl substituted by 0 to 3 groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{11}R^{12}$, OH, $C_1$-$C_4$-alkylcarbonyloxy-$C_1$-$C_4$-alkyl, hydroxy-$C_1$-$C_4$-alkyl, $COOR^{14}$, $SO_2R^{14}$, $(C=O)NR^{11}R^{12}$, $SO_2NR^{11}R^{12}$, $N(R^{13})(C=O)NR^{11}R^{12}$, $N(R^{13})(C=O)OR^{14}$, $N(R^{13})(C=O)R^{14}$, $NR^{13}S(O)R^{14}$, $NR^{13}SO_2R^{14}$, $O(C=O)NR^{11}R^{12}$, $O(C=O)OR^{14}$, $O(C=O)R^{14}$, $(C=O)OR^{14}$, 5-6-membered heteroaryl, and $(CH_2)$phenyl, 4- to 10-membered heterocyclyl containing carbon atoms and 1 to 2 additional heteroatoms selected from N, O, and S, and substituted by 0 to 3 groups independently selected from the group consisting of halo, oxo, —$(CHR^{13})_n{}^1$-5- or 6-membered heteroaryl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; $NR^{13}S(O)R^{14}$, $NR^{13}SO_2R^{14}$, —$(CHR^{13})_n{}^1$-4- to 10-membered-heterocyclyl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; OH, hydroxy-$C_1$-$C_4$-alkyl, $C_1$-$C_4$ alkoxy, halo-$C_1$-$C_4$ alkoxy, di-$C_1$-$C_4$-alkylamino-$C_1$-$C_4$-alkyl, $NR_{11}R_{12}$, cyano, $C_1$-$C_4$ alkyl, halo-$C_1$-$C_4$ alkyl, $C_3$-$C_6$ cycloalkyl, $C_1$-$C_4$-alkoxy-$C_1$-$C_4$-alkyl, $C_3$-$C_6$ cycloalkyl-$C_1$-$C_4$-alkylcarbonyl, $C_6$-$C_{10}$ arylcarbonyl, $C_1$-$C_4$-alkylcarbonyloxy-$C_1$-$C_4$-alkyl, $COOR^{14}$, $SO_2R^{14}$, $(C=O)NR^{11}R^{12}$, $SO_2NR^{11}R^{12}$, $N(R^{13})(C=O)NR^{11}R^{12}$, $N(R^{13})(C=O)OR^4$, $N(R^{13})(C=O)R^{14}O(C=O)NR^{11}R^{12}$, $O(C=O)OR^{14}$, $O(C=O)R^{14}$, $(C=O)OR^{14}$, and $C_6$-$C_{10}$ aryl substituted by 0 to 3 groups independently selected from the group consisting of halo, $C_1$-$C_4$ alkoxy, $C_1$-$C_4$ alkyl, cyclopropyl, $C_1$-$C_4$-alkoxycarbonyl, $(C=O)NR^{11}R^{12}$, $CF_3$, $OCF_3$, and $CF_2CH_3$;

$C_3$-$C_6$ cycloalkyl which may contain unsaturation, substituted by 0 to 3 groups independently selected from the group consisting of halo, $CF_3$, $OCF_3$, 5- or 6-membered heteroaryl, OH, oxo, hydroxy-$C_1$-$C_4$-alkyl, $C_6$-$C_{10}$ aryl, COOH, oxo, $C_1$-$C_4$-alkoxycarbonyl, $(C=O)NR^{11}R^{12}$, and $C_1$-$C_4$ alkyl; and $C_5$-$C_{11}$ spirocycloalkyl which may contain unsaturation and optionally containing 1 to 3 heteroatoms selected from O, N or S and substituted by 0 to 3 groups independently selected from the group consisting of halo, $CF_3$, $OCF_3$, 5- or 6-membered heteroaryl, OH, hydroxy-$C_1$-$C_4$-alkyl, $C_6$-$C_{10}$ aryl, and $C_1$-$C_4$ alkyl;

$R^{11}$ and $R^{12}$ are independently, at each occurrence, selected from the group consisting of:
H,
$C_1$-$C_4$ alkyl,
halo-$C_1$-$C_4$-alkyl,
$C_2$-$C_4$ alkenyl,
—$(CR^{14}R^{14})_n{}^1$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano,
—$(CHR^{13})_n{}^1$—$C_3$-$C_6$-cycloalkyl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl,
—$(CHR^{13})_n{}^1$-4- to 10-membered-heterocyclyl substituted by 0 to 3 groups independently selected from the group consisting of halo, $CF_3$, $OCF_3$, 5- or 6-membered heteroaryl, OH, oxo, hydroxy-$C_1$-$C_4$-alkyl, and $C_1$-$C_4$ alkyl,
—$(CHR^{13})_n{}^1$-5- to 10-membered-heteroaryl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl,
di-$C_1$-$C_4$-alkylamino-$C_1$-$C_4$-alkyl,
di-$C_1$-$C_4$-alkoxy-$C_1$-$C_4$-alkyl,
hydroxy-$C_1$-$C_4$-alkyl,
cyano-$C_1$-$C_4$-alkyl,
$C_1$-$C_4$-alkoxy-$C_1$-$C_4$-alkyl,
$C_1$-$C_4$-alkoxycarbonyl-$C_1$-$C_4$-alkyl,
$C_1$-$C_4$-alkoxycarbonyl,
$C_1$-$C_4$-alkylcarbonyl,
phenylcarbonyl;
$C_1$-$C_4$-alkoxycarbonylamino-$C_1$-$C_4$-alkylcarbonyl, and
di-$C_1$-$C_4$-alkylamino-$C_1$-$C_4$-alkylcarbonyl, alternatively, $R^{11}$ and $R^{12}$, when attached to the same nitrogen, combine to form a 4- to 8-membered heterocyclic ring containing carbon atoms substituted by 0 to 3 groups independently selected from the group consisting of halo, $CF_3$, $CHF_2$, $OCF_3$, $OCHF_2$, $OCH_2F$, 5- or 6-membered heteroaryl, OH, oxo, hydroxy-$C_1$-$C_4$-alkyl, $C_1$-$C_4$ alkyl and $C_1$-$C_4$ alkoxy, and 0 to 2 additional heteroatoms selected from N, $NR^{13}$, O and $S(O)_p$;

$R^{13}$ is independently, at each occurrence, selected from the group consisting of H, $C_1$-$C_6$ alkyl and —$(CH_2)$phenyl;

$R^{14}$ is independently, at each occurrence, selected from the group consisting of H, $C_1$-$C_6$ alkyl, halo-$C_1$-$C_4$-alkyl, $C_1$-$C_4$-alkoxycarbonylamino and —$(CH_2)_n{}^1$phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano, $R^7$ is selected from the group consisting of H, halo, hydroxyl, oxo, $C_1$-$C_3$ alkyl, hydroxy-$C_1$-$C_3$-alkyl, and halo-$C_1$-$C_2$-alkyl, which contains 1 to 5 halogens;

$n^1$, at each occurrence, is selected from 0, 1, 2 or 3; and p, at each occurrence, is selected from 0, 1 and 2.

In one embodiment, the present invention provides compounds, stereoisomers, tautomers, salts, solvates or prodrugs thereof, wherein:

W is O;
$R^0$ is $R^1$ or $R^{1a}$;
Y is S or —$CR^8=CR^9$—;
$R^1$ is independently selected from the group consisting of:
$C_1$-$C_2$ alkyl,
$C_1$-$C_2$ alkoxy,
$C_1$-$C_2$ alkylthio, and
halo-$C_1$-$C_2$-alkyl, which contains 1 to 5 halogens, where halo is F or Cl;

$R^{1a}$ is independently selected from the group consisting of:
H,
fluoro,
chloro,
$C_1$-$C_2$ alkyl,
$C_1$-$C_2$ alkoxy,
$C_1$-$C_2$ alkylthio, and
halo-$C_1$-$C_2$-alkyl, which contains 1 to 5 halogens, where halo is F or Cl;

$R^8$ and $R^9$ are independently selected from the group consisting of:
H,
fluoro,
chloro,
$CH_3$,
$OCH_3$,
$CF_3$, and
$CHF_2$;
provided that at least one of $R^{1a}$, $R^8$ and $R^9$ is other than H;
$R^2$ is H;
$X^1$ is selected from the group consisting of CH or N;
$X^2$ and $X^4$ are CH;
$X^3$ is $CR^3$;
$R^3$ is selected from the group consisting of H, $C_1$-$C_3$ alkyl, $C_1$-$C_3$ alkoxy, fluoro, chloro, $OCF_3$, and halo-$C_1$-$C_2$-alkyl, which contains 1 to 5 halogens;
$R^4$ and $R^5$ are independently selected from H and $C_1$-$C_6$ alkyl;

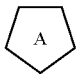

is a 5-membered heteroaryl ring selected from thiazole, thiadiazole, oxazole, oxadiazole, and triazole;
$R^6$ is selected from the group consisting of H, halo, $OCF_3$, $OCHF_2$, OH, $NR^{11}R^{12}$, $C_1$-$C_4$ alkoxycarbonyl, (C=O)$NR^{11}R^{12}$ and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, and $C_1$-$C_4$ alkylthio, or
$R^6$ is B-D-, where D is a linker, which is selected from: a single bond,

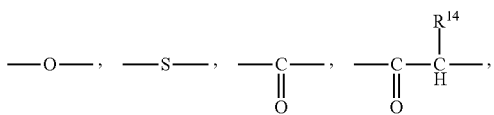

$C_1$-$C_4$ alkylene substituted by 0 to 4 groups independently selected from halo or OH, and
$C_2$-$C_6$ alkenylene, and
B is selected from the group consisting of:
$C_6$-$C_{10}$ aryl substituted by 0 to 3 groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{11}R^{12}$, OH, $C_1$-$C_4$-alkylcarbonyloxy-$C_1$-$C_4$-alkyl, hydroxy-$C_1$-$C_4$-alkyl, $COOR^{14}$, $SO_2R^{14}$, (C=O)$NR^{11}R^{12}$, $SO_2NR^{11}R^{12}$, $N(R^{13})$(C=O)$NR^{11}R^{12}$, $N(R^{13})$(C=O)$OR^{14}$, $N(R^{13})$(C=O)$R^{14}$, $NR^{13}S(O)R^{14}$, $NR^{13}SO_2R^{14}$, O(C=O)$NR^{11}R^{12}$, O(C=O)$OR^{14}$, O(C=O)$R^{14}$, (C=O)$OR^{14}$, and 5-6-membered heteroaryl,
5- to 10-membered heteroaryl substituted by 0 to 3 groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{11}R^{12}$, OH, $C_1$-$C_4$-alkylcarbonyloxy-$C_1$-$C_4$-alkyl, hydroxy-$C_1$-$C_4$-alkyl, $COOR^{14}$, $SO_2R^{14}$, (C=O)$NR^{11}R^{12}$, $SO_2NR^{11}R^{12}$, $N(R^{13})$(C=O)$NR^{11}R^{12}$, $N(R^{13})$(C=O)$OR^{14}$, $N(R^{13})$(C=O)$R^{14}$, $NR^{13}S(O)R^{14}$, $NR^{13}SO_2R^{14}$, O(C=O)$NR^{11}R^{12}$, O(C=O)$OR^{14}$, O(C=O)$R^{14}$, (C=O)$OR^{14}$, 5-6-membered heteroaryl, and (CH$_2$)phenyl,
4- to 10-membered heterocyclyl containing carbon atoms and 1 to 2 additional heteroatoms selected from N, O, and S, and substituted by 0 to 3 groups independently selected from the group consisting of halo, oxo, —(CHR$^{13}$)$_n^1$-5- or 6-membered heteroaryl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; $NR^{13}S(O)R^{14}$, $NR^{13}SO_2R^{14}$, —(CHR$^{13}$)$_n^1$-4- to 10-membered-heterocyclyl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; OH, hydroxy-$C_1$-$C_4$-alkyl, $C_1$-$C_4$ alkoxy, halo-$C_1$-$C_4$ alkoxy, di-$C_1$-$C_4$-alkylamino-$C_1$-$C_4$-alkyl, $NR_{11}R_{12}$, cyano, $C_1$-$C_4$ alkyl, halo-$C_1$-$C_4$ alkyl, $C_3$-$C_6$ cycloalkyl, $C_1$-$C_4$-alkoxy-$C_1$-$C_4$-alkyl, $C_3$-$C_6$ cycloalkyl-$C_1$-$C_4$-alkylcarbonyl, $C_6$-$C_{10}$ arylcarbonyl, $C_1$-$C_4$-alkylcarbonyloxy-$C_1$-$C_4$-alkyl, $COOR^{14}$, $SO_2R^{14}$, (C=O)$NR^{11}R^{12}$, $SO_2NR^{11}R^{12}$, $N(R^{13})$(C=O)$NR^{11}R^{12}$, $N(R^{13})$(C=O)$OR^{14}$, $N(R^{13})$(C=O)$R^{14}$, O(C=O)$NR^{11}R^{12}$, O(C=O)$OR^{14}$, O(C=O)$R^{14}$, (C=O)$OR^{14}$, and $C_6$-$C_{10}$ aryl substituted by 0 to 3 groups independently selected from the group consisting of halo, $C_1$-$C_4$ alkoxy, $C_1$-$C_4$ alkyl, cyclopropyl, $C_1$-$C_4$-alkoxycarbonyl, (C=O)$NR^{11}R^{12}$, $CF_3$, $OCF_3$, and $CF_2CH_3$; and
$C_3$-$C_6$ cycloalkyl which may contain unsaturation, substituted by 0 to 3 groups independently selected from the group consisting of halo, $CF_3$, $OCF_3$, 5- or 6-membered heteroaryl, OH, oxo, hydroxy-$C_1$-$C_4$-alkyl, $C_6$-$C_{10}$ aryl, COOH, oxo, $C_1$-$C_4$-alkoxycarbonyl, (C=O)$NR^{11}R^{12}$, and $C_1$-$C_4$ alkyl;
$R^{11}$ and $R^{12}$ are independently, at each occurrence, selected from the group consisting of:
H,
$C_1$-$C_4$ alkyl,
halo-$C_1$-$C_4$-alkyl,
$C_2$-$C_4$ alkenyl,
—(CR$^{14}$R$^{14}$)$_n^1$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano,
—(CHR$^{13}$)$_n^1$—$C_3$-$C_6$-cycloalkyl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl,
—(CHR$^{13}$)$_n^1$-4- to 10-membered-heterocyclyl substituted by 0 to 3 groups independently selected from the group consisting of halo, $CF_3$, $OCF_3$, 5- or 6-membered heteroaryl, OH, oxo, hydroxy-$C_1$-$C_4$-alkyl, and $C_1$-$C_4$ alkyl,
—(CHR$^{13}$)$_n^1$-5- to 10-membered-heteroaryl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl,
di-$C_1$-$C_4$-alkylamino-$C_1$-$C_4$-alkyl,
di-$C_1$-$C_4$-alkoxy-$C_1$-$C_4$-alkyl,
hydroxy-$C_1$-$C_4$-alkyl,
cyano-$C_1$-$C_4$-alkyl,
$C_1$-$C_4$-alkoxy-$C_1$-$C_4$-alkyl,
$C_1$-$C_4$-alkoxycarbonyl-$C_1$-$C_4$-alkyl,
$C_1$-$C_4$-alkoxycarbonyl,
$C_1$-$C_4$-alkylcarbonyl, and
phenylcarbonyl;

alternatively, $R^{11}$ and $R^{12}$, when attached to the same nitrogen, combine to form a 4- to 8-membered heterocyclic ring containing carbon atoms substituted by 0 to 3 groups independently selected from the group consisting of halo, $CF_3$, $CHF_2$, $OCF_3$, $OCHF_2$, $OCH_2F$, 5- or 6-membered heteroaryl, OH, oxo, hydroxy-$C_1$-$C_4$-alkyl, $C_1$-$C_4$ alkyl and $C_1$-$C_4$ alkoxy, and 0 to 2 additional heteroatoms selected from N, $NR^{13}$, O and $S(O)_p$;

$R^{13}$ is independently, at each occurrence, selected from the group consisting of H, and $C_1$-$C_3$ alkyl;

$R^{14}$ is independently, at each occurrence, selected from the group consisting of H, $C_1$-$C_3$ alkyl, and halo-$C_1$-$C_2$-alkyl;

$R^7$ is selected from the group consisting of H, fluoro, chloro, oxo, $C_1$-$C_3$ alkyl, hydroxy-$C_1$-$C_3$-alkyl, and halo-$C_1$-$C_2$-alkyl, which contains 1 to 5 halogens;

$n^1$, at each occurrence, is selected from 0, 1, 2 or 3; and p, at each occurrence, is selected from 0, 1 and 2.

In another embodiment, the present invention provides compounds, stereoisomers, tautomers, salts, solvates or prodrugs thereof, wherein:

W is O;

$R^0$ is $R^1$ or $R^{1a}$;

Y is S or —CH=CH—;

$R^1$ is independently selected from the group consisting of:
$CH_3$,
$OCH_3$,
$SCH_3$,
$CHFCH_3$, and
$CF_2CH_3$;

$R^{1a}$ is independently selected from the group consisting of:
chloro,
$CH_3$, and
$OCH_3$;

$R^2$ is H;

$X^1$ is CH;

$X^2$ and $X^4$ are CH;

$X^3$ is $CR^3$;

$R^3$ is selected from the group consisting of $OCH_3$, fluoro, and chloro;

$R^4$ and $R^5$ are independently selected from H and $CH_3$;

is a 5-membered heteroaryl ring selected from thiazole and oxazole;

$R^6$ is selected from the group consisting of, $NR^{11}R^{12}$, and $C_1$-$C_5$ alkyl substituted by 0 to 3 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, and $C_1$-$C_4$ alkylthio, or $R^6$ is B-D-, where D is a single bond;

B is selected from the group consisting of:
$C_6$-$C_{10}$ aryl substituted by 0 to 3 groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{11}R^{12}$, OH, $C_1$-$C_4$-alkylcarbonyloxy-$C_1$-$C_4$-alkyl, hydroxy-$C_1$-$C_4$-alkyl, $COOR^{14}$, $SO_2R^{14}$, (C=O)$NR^{11}R^{12}$, $SO_2NR^{11}R^{12}$, $N(R^{13})(C=O)NR^{11}R^{12}$, $N(R^{13})(C=O)OR^{14}$, $N(R^{13})(C=O)R^{14}$, $NR^{13}S(O)R^{14}$, $NR^{13}SO_2R^{14}$, $O(C=O)NR^{11}R^{12}$, $O(C=O)OR^{14}$, $O(C=O)R^{14}$, (C=O)$OR^{14}$, and 5-6-membered heteroaryl, 5- to 10-membered heteroaryl substituted by 0 to 3 groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{11}R^{12}$, OH, $C_1$-$C_4$-alkylcarbonyloxy-$C_1$-$C_4$-alkyl, hydroxy-$C_1$-$C_4$-alkyl, $COOR^{14}$, $SO_2R^{14}$, (C=O)$NR^{11}R^{12}$, $SO_2NR^{11}R^{12}$, $N(R^{13})(C=O)NR^{11}R^{12}$, $N(R^{13})(C=O)OR^{14}$, $N(R^{13})(C=O)R^{14}$, $NR^{13}S(O)R^{14}$, $NR^{13}SO_2R^{14}$, $O(C=O)NR^{11}R^{12}$, $O(C=O)OR^{14}$, $O(C=O)R^{14}$, (C=O)$OR^{14}$, 5-6-membered heteroaryl, and $(CH_2)$phenyl, 4- to 10-membered heterocyclyl containing carbon atoms and 1 to 2 additional heteroatoms selected from N, O, and S, and substituted by 0 to 3 groups independently selected from the group consisting of halo, oxo, —(CHR$^{13}$)$_{n^1}$-5- or 6-membered heteroaryl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; $NR^{13}S(O)R^{14}$, $NR^{13}SO_2R^{14}$, —(CHR$^{13}$)$_{n^1}$-4- to 10-membered-heterocyclyl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; OH, hydroxy-$C_1$-$C_4$-alkyl, $C_1$-$C_4$ alkoxy, halo-$C_1$-$C_4$ alkoxy, di-$C_1$-$C_4$-alkylamino-$C_1$-$C_4$-alkyl, $NR_{11}R_{12}$, cyano, $C_1$-$C_4$ alkyl, halo-$C_1$-$C_4$ alkyl, $C_3$-$C_6$ cycloalkyl, $C_1$-$C_4$-alkoxy-$C_1$-$C_4$-alkyl, $C_3$-$C_6$ cycloalkyl-$C_1$-$C_4$-alkylcarbonyl, $C_6$-$C_{10}$ arylcarbonyl, $C_1$-$C_4$-alkylcarbonyloxy-$C_1$-$C_4$-alkyl, $COOR^{14}$, $SO_2R^{14}$, (C=O)$NR^{11}R^{12}$, $SO_2NR^{11}R^{12}$, $N(R^{13})(C=O)NR^{11}R^{12}$, $N(R^{13})(C=O)OR^{14}$, $N(R^{13})(C=O)R^{14}$, $O(C=O)NR^{11}R^{12}$, $O(C=O)OR^{14}$, $O(C=O)R^{14}$, (C=O)$OR^{14}$, and $C_6$-$C_{10}$ aryl substituted by 0 to 3 groups independently selected from the group consisting of halo, $C_1$-$C_4$ alkoxy, $C_1$-$C_4$ alkyl, cyclopropyl, $C_1$-$C_4$-alkoxycarbonyl, (C=O)$NR^{11}R^{12}$, $CF_3$, $OCF_3$, and $CF_2CH_3$; and $C_3$-$C_6$ cycloalkyl which may contain unsaturation, substituted by 0 to 3 groups independently selected from the group consisting of halo, $CF_3$, $OCF_3$, 5- or 6-membered heteroaryl, OH, oxo, hydroxy-$C_1$-$C_4$-alkyl, $C_6$-$C_{10}$ aryl, COOH, oxo, $C_1$-$C_4$-alkoxycarbonyl, (C=O)$NR^{11}R^{12}$, and $C_1$-$C_4$ alkyl;

$R^{11}$ and $R^{12}$ are independently, at each occurrence, selected from the group consisting of:
H,
$C_1$-$C_4$ alkyl,
halo-$C_1$-$C_4$-alkyl,
di-$C_1$-$C_4$-alkylamino-$C_1$-$C_4$-alkyl,
di-$C_1$-$C_4$-alkoxy-$C_1$-$C_4$-alkyl,
hydroxy-$C_1$-$C_4$-alkyl,
cyano-$C_1$-$C_4$-alkyl,
$C_1$-$C_4$-alkoxy-$C_1$-$C_4$-alkyl,
$C_1$-$C_4$-alkoxycarbonyl-$C_1$-$C_4$-alkyl, and
$C_1$-$C_4$-alkoxycarbonyl;

alternatively, $R^{11}$ and $R^{12}$, when attached to the same nitrogen, combine to form a 4- to 7-membered heterocyclic ring containing carbon atoms substituted by 0 to 2 groups independently selected from the group consisting of halo, $CF_3$, $CHF_2$, $OCF_3$, $OCHF_2$, $OCH_2F$, OH, oxo, hydroxy-$C_1$-$C_2$-alkyl, $C_1$-$C_3$ alkyl and $C_1$-$C_3$ alkoxy, and 0 to 2 additional heteroatoms selected from N, $NR^{13}$, O and $S(O)_p$;

$R^{13}$ is independently, at each occurrence, selected from the group consisting of H, and $C_1$-$C_3$ alkyl;

$R^{14}$ is independently, at each occurrence, selected from the group consisting of H, and $C_1$-$C_3$ alkyl $R^7$ is selected from the group consisting of H, fluoro, chloro, $C_1$-$C_3$ alkyl, hydroxy-$C_1$-$C_3$-alkyl, and halo-$C_1$-$C_2$-alkyl, which contains 1 to 5 halogens;

$n^1$, at each occurrence, is selected from 0, 1, 2 or 3; and p, at each occurrence, is selected from 0, 1 and 2.

In yet another embodiment, the present invention provides compounds, stereoisomers, tautomers, salts, solvates or prodrugs thereof, wherein the compounds are selected from the examples, preferably Examples 3 to 318.

In still yet another embodiment, the present invention provides compounds, stereoisomers, tautomers, salts, solvates or prodrugs thereof, wherein the compounds are selected from:

Chiral

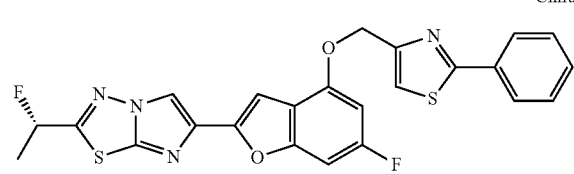

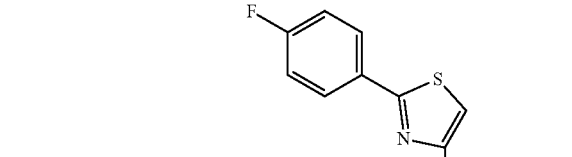

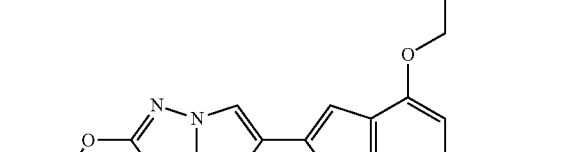


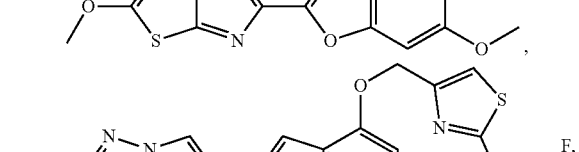

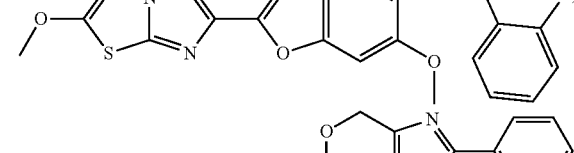

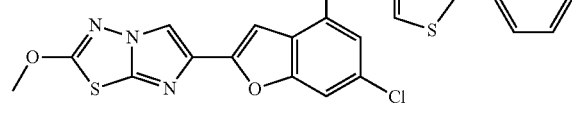

-continued

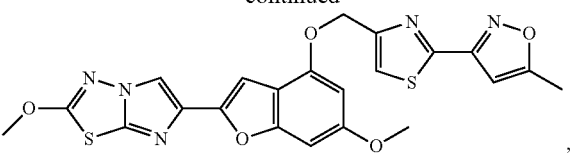

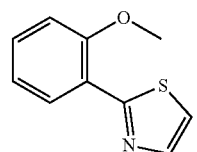

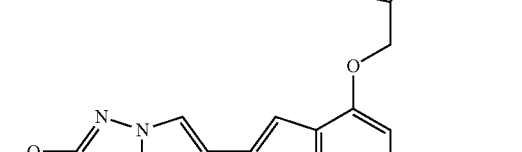

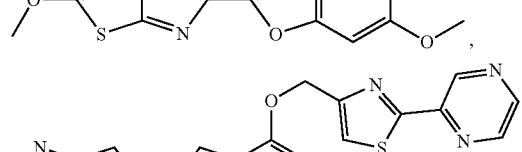

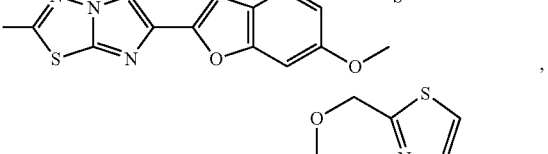

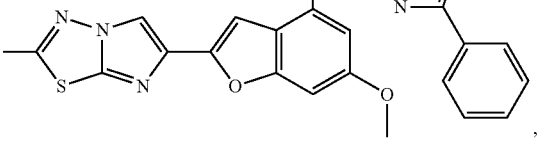

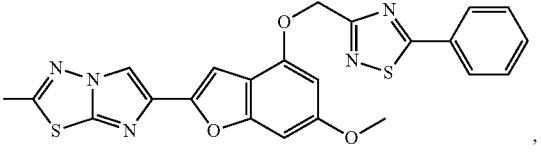

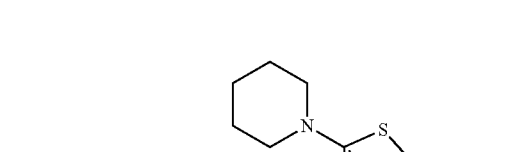

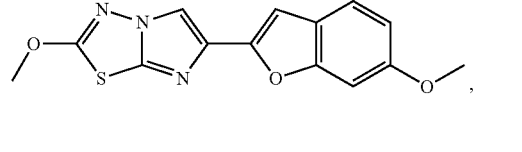

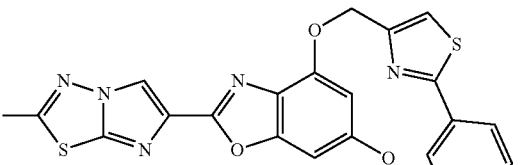

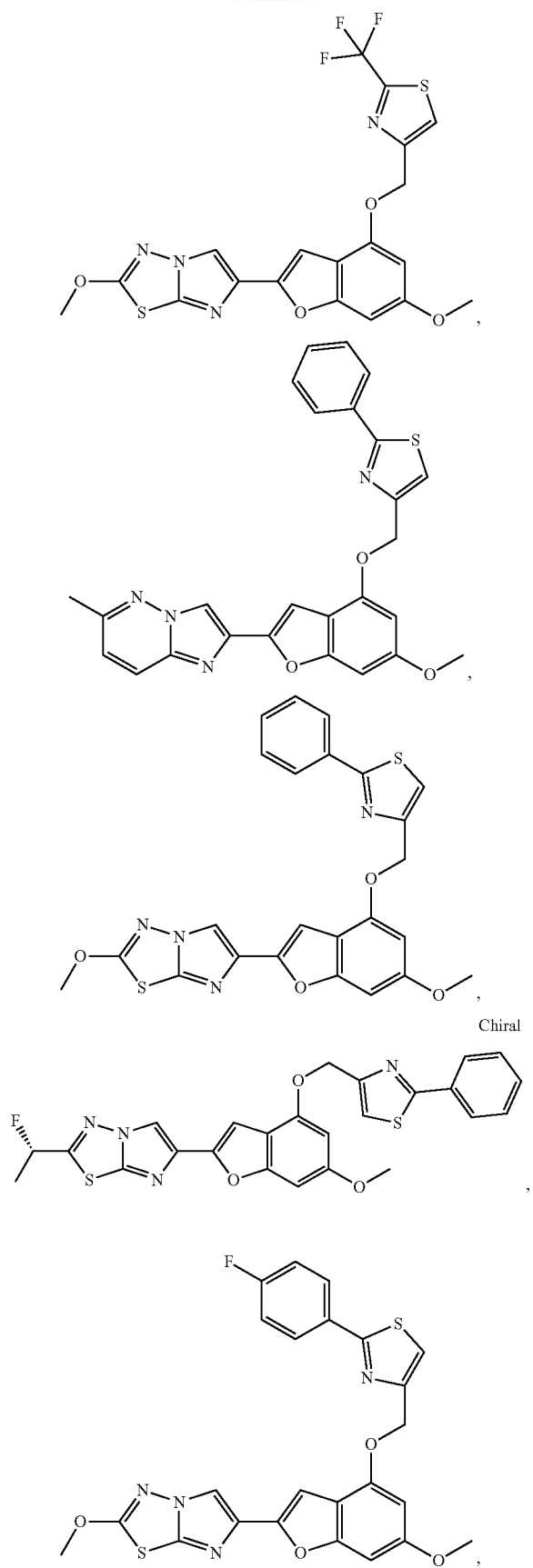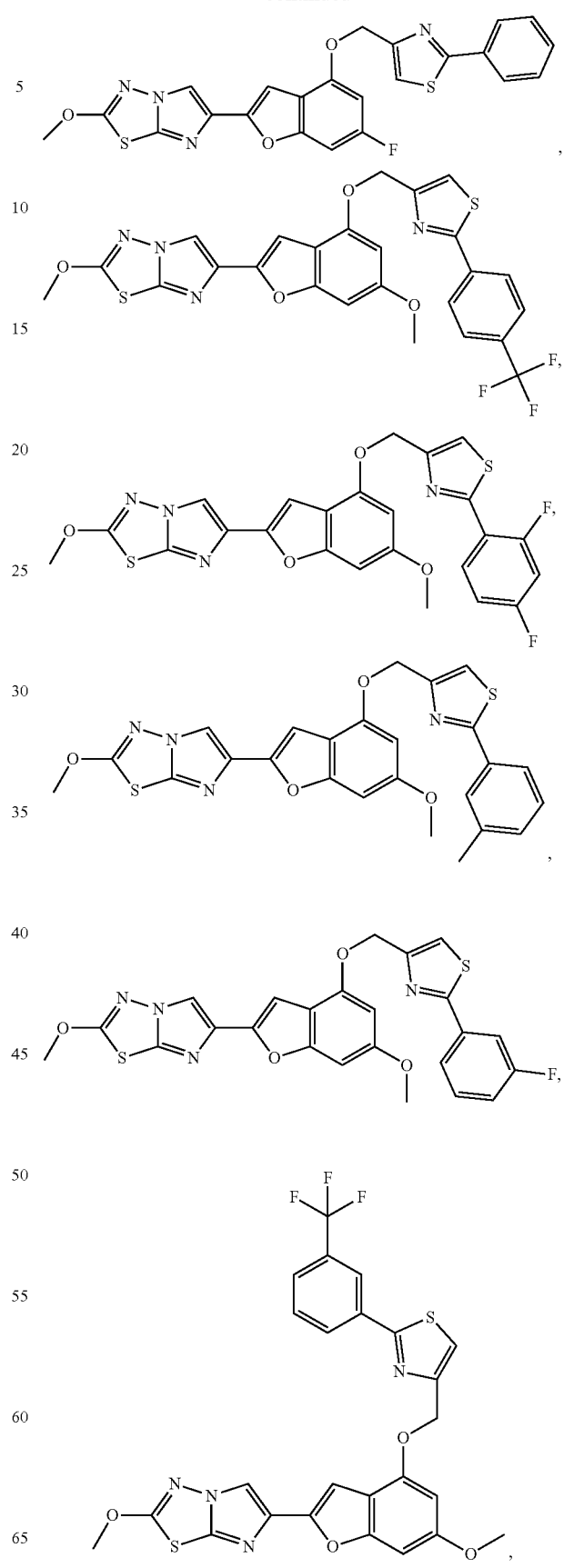

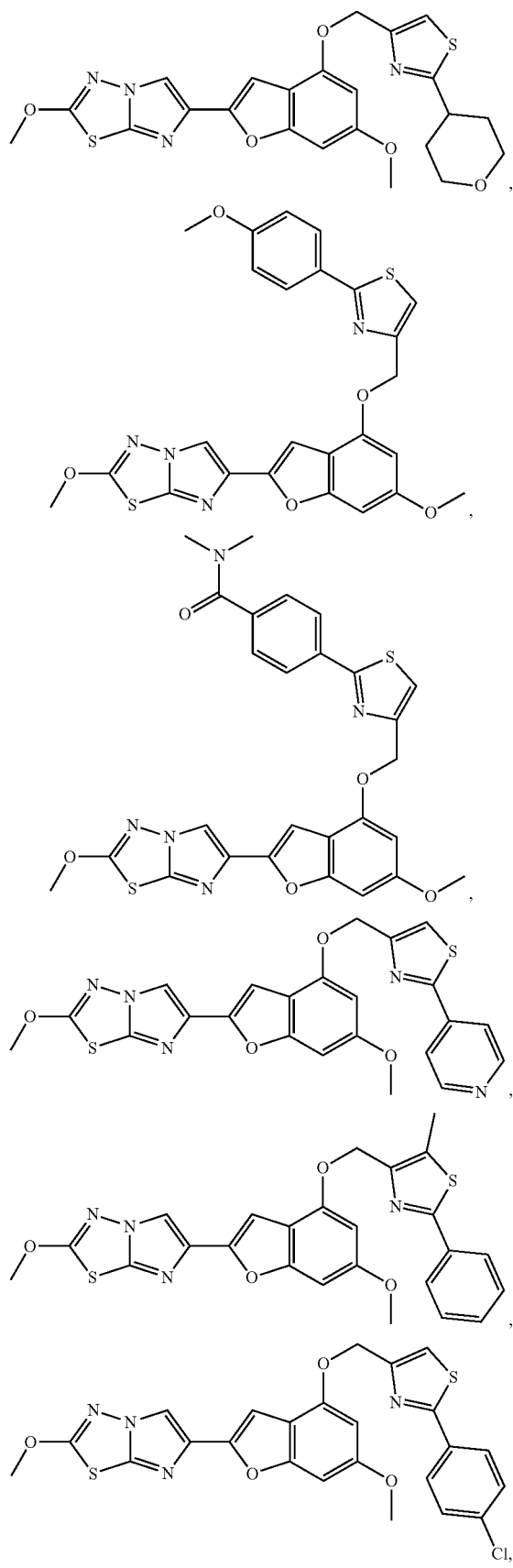
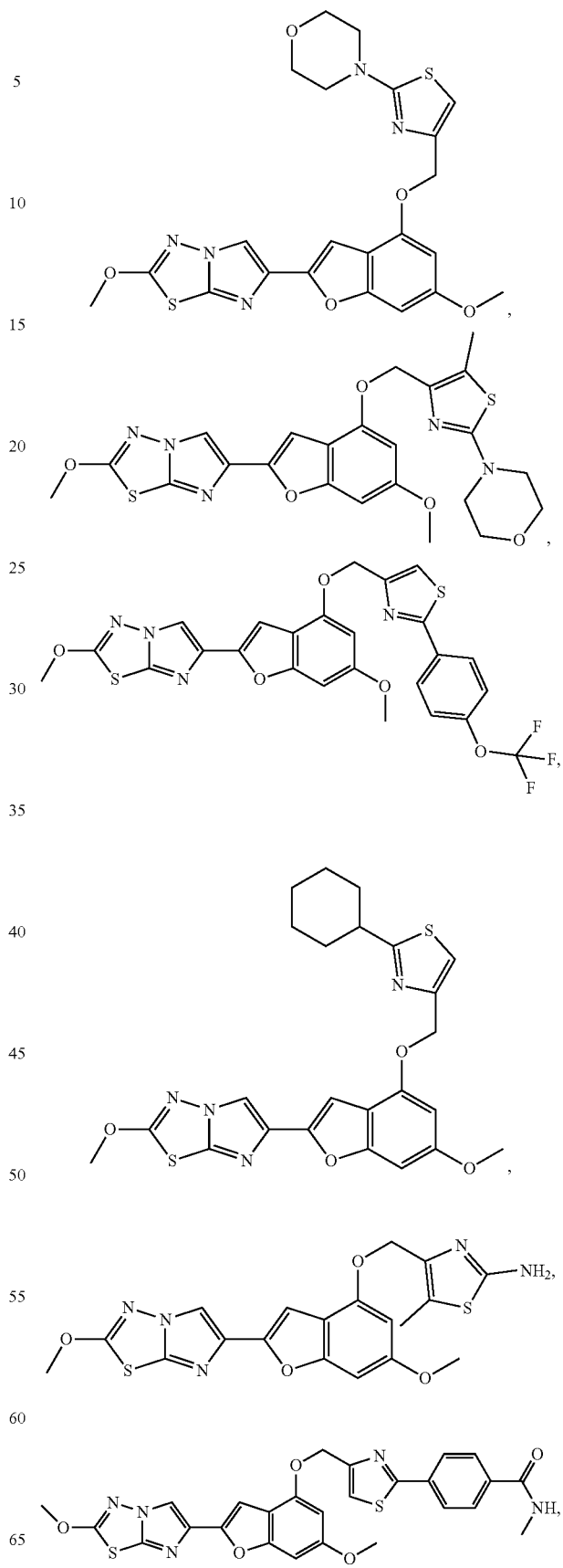

-continued

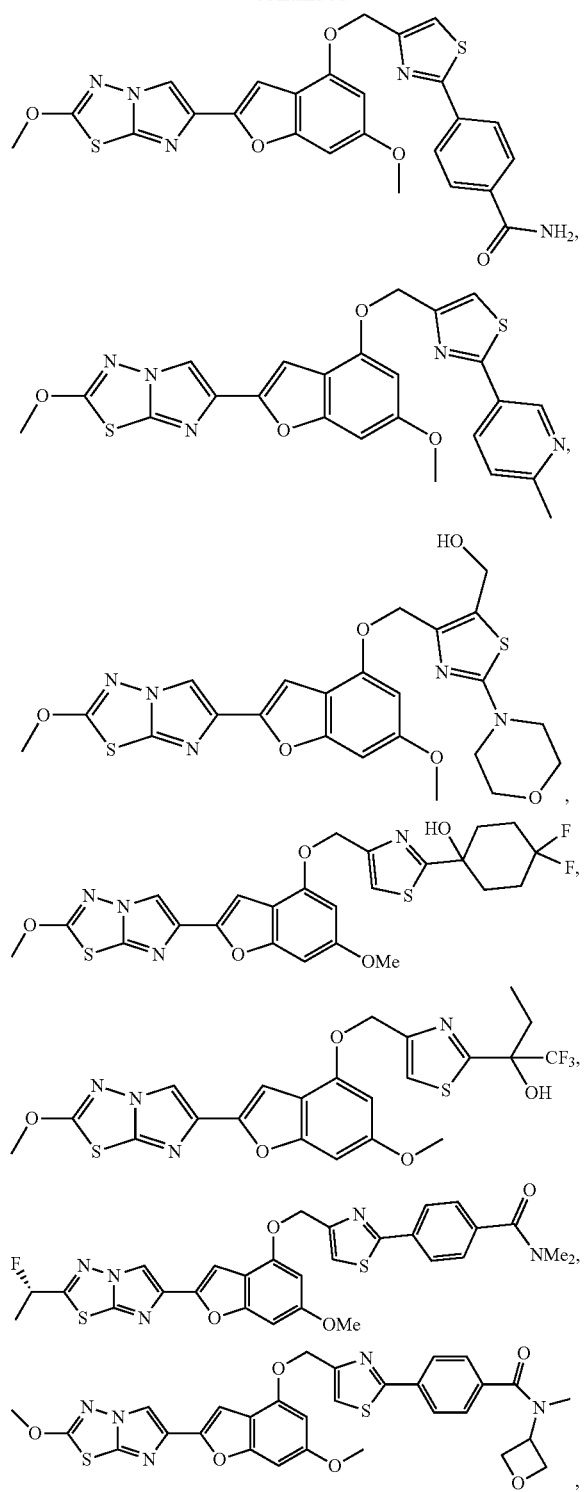

-continued

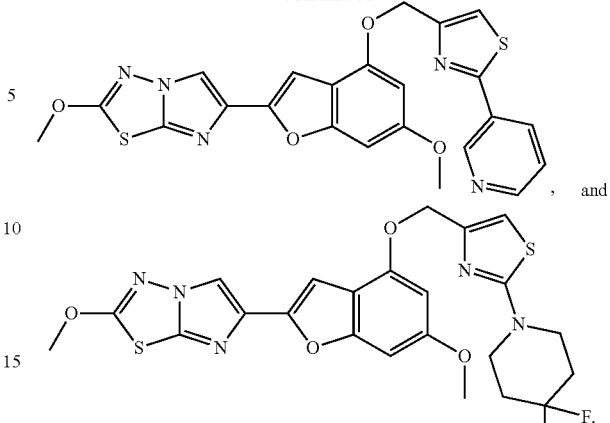

, and

Preferably, PAR4 compounds of the invention have $IC_{50}s$ in the FLIPR Assay (described hereinafter) of about 10 μM, preferably 5 μM or less, more preferably 500 nM or less, and even more preferably 10 nM or less. Activity data for compounds of the present invention is presented in the tables of Example F.

In some embodiments, the present invention provides at least one compound of the present invention or a stereoisomer, tautomer, pharmaceutically acceptable salt, solvate, or prodrug ester thereof.

In some embodiments, the present invention provides a pharmaceutical composition, which includes a pharmaceutically acceptable carrier and a therapeutically effective amount of a compound of Formula I, IA, IB, IC, ID, IE, or IF, preferably, a compound selected from one of the examples, more preferably, Examples 3 to 318, or stereoisomers, tautomers, pharmaceutically acceptable salts, prodrug esters, or solvates thereof, alone or in combination with another therapeutic agent.

In some embodiments, the present invention provides a pharmaceutical composition which further includes another therapeutic agent(s). In a preferred embodiment, the present invention provides a pharmaceutical composition, wherein the additional therapeutic agent(s) are an anti-platelet agent or a combination thereof. Preferably, the anti-platelet agent(s) are P2Y12 antagonists and/or aspirin. Preferably, the P2Y12 antagonists are clopidogrel, ticagrelor, or prasugrel. In another preferred embodiment, the present invention provides a pharmaceutical composition, wherein the additional therapeutic agent(s) are an anticoagulant or a combination thereof. Preferably, the anticoagulant agent(s) are FXa inhibitors or thrombin inhibitors. Preferably, the FXa inhibitors are apixaban or rivaroxaban. Preferably, the thrombin inhibitor is dabigatran.

In some embodiments, the present invention provides a method for the treatment or prophylaxis of a thromboembolic disorder which includes the step of administering to a subject (for example, a human) in need of such treatment or prophylaxis a therapeutically effective amount of at least one of the compounds of the present invention or stereoisomers, tautomers, pharmaceutically acceptable salts, solvates, or prodrug esters thereof.

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of a compound of Formula I, IA, IB, IC, ID, IE, or IF, preferably, a compound selected from one of the examples, more preferably, Examples 3 to 318, or stereoisomers, tautomers, pharmaceutically acceptable salts, prodrug esters, or solvates thereof, wherein the thromboembolic disorder is selected from the group consisting of arterial cardiovascular thromboembolic disorders, venous cardiovascular thromboembolic disorders, cerebrovascular thromboembolic disorders, and thromboembolic disorders in the chambers of the heart or in the peripheral circulation.

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of a compound of Formula I, IA, IB, IC, ID, IE, or IF, preferably, a compound selected from one of the examples, more preferably, Examples 3 to 318, or stereoisomers, tautomers, pharmaceutically acceptable salts, prodrug esters, or solvates thereof, wherein the thromboembolic disorder is selected from the group consisting of acute coronary syndrome, unstable angina, stable angina, ST-elevated myocardial infarction, non-ST-elevated myocardial infarction, atrial fibrillation, myocardial infarction, transient ischemic attack, stroke, atherosclerosis, peripheral arterial disease, venous thrombosis, deep vein thrombosis, thrombophlebitis, arterial embolism, coronary arterial thrombosis, cerebral arterial thrombosis, cerebral embolism, kidney embolism, pulmonary embolism, cancer-related thrombosis, and thrombosis resulting from medical implants, devices, and procedures in which blood is exposed to an artificial surface that promotes thrombosis.

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of a compound of Formula I, IA, IB, IC, ID, IE, or IF, preferably, a compound selected from one of the examples, more preferably, Examples 3 to 318, or stereoisomers, tautomers, pharmaceutically acceptable salts, prodrug esters, or solvates thereof, wherein the thromboembolic disorder is selected from the group consisting of acute coronary syndrome, unstable angina, stable angina, ST-elevated myocardial infarction, and non-ST-elevated myocardial infarction.

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of a compound of Formula I, IA, IB, IC, ID, IE, or IF, preferably, a compound selected from one of the examples, more preferably, Examples 3 to 318, or stereoisomers, tautomers, pharmaceutically acceptable salts, prodrug esters, or solvates thereof, wherein the thromboembolic disorder is selected from the group consisting of transient ischemic attack and stroke.

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of a compound of Formula I, IA, IB, IC, ID, IE, or IF, preferably, a compound selected from one of the examples, more preferably, Examples 3 to 318, or stereoisomers, tautomers, pharmaceutically acceptable salts, prodrug esters, or solvates thereof, wherein the thromboembolic disorder is peripheral arterial disease.

In some embodiments, the present invention includes a method as described above wherein the thromboembolic disorder is selected from unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In some embodiments, the present invention includes a method of inhibiting or preventing platelet aggregation, which includes the step of administering to a subject (such as a human) in need thereof a therapeutically effective amount of a PAR4 antagonist, which is a compound of Formula I, IA, IB, IC, ID, IE, or IF, preferably, a compound selected from one of the examples, more preferably, Examples 3 to 318, of the invention.

OTHER EMBODIMENTS OF THE INVENTION

In some embodiments, the present invention provides a process for making a compound of the present invention or a stereoisomer, tautomer, pharmaceutically acceptable salt, solvate or prodrug ester thereof.

In some embodiments, the present invention provides an intermediate for making a compound of the present invention or a stereoisomer, tautomer, pharmaceutically acceptable salt, solvate or prodrug ester thereof.

In some embodiments, the invention provides a method of treatment or prophylaxis of a thromboembolic disorder involving administering to a subject in need thereof (e.g., a human) a therapeutically effective amount of a compound that binds to PAR4 (such as a compound of Formula I of the invention) and inhibits PAR4 cleavage and/or signaling, wherein said subject has a dual PAR1/PAR4 platelet receptor repertoire.

In some embodiments, the present invention provides a compound of the present invention or stereoisomers, tautomers, pharmaceutically acceptable salts, solvates, or prodrug esters thereof, for use in therapy for the treatment or prophylaxis of a thromboembolic disorder.

In some embodiments, the present invention also provides the use of a compound of the present invention or stereoisomers, tautomers, pharmaceutically acceptable salts, solvates, or prodrug esters thereof, for the manufacture of a medicament for the treatment or prophylaxis of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

Chemistry

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis- and trans-geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated. When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. All processes used to prepare compounds of the present invention and intermediates made therein are considered to be part of the present invention. When enantiomeric or diastereomeric products are prepared, they can be separated by conventional methods, for example, by chromatography or fractional crystallization. Compounds of the present invention, and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The molecular weight of compounds of the present invention is preferably less than about 800 grams per mole.

As used herein, the term "alkyl" or "alkylene", alone or as part of another group, is intended to include both branched and straight-chain saturated aliphatic hydrocarbon groups having from 1 to 10 carbons or the specified number of carbon atoms. For example, "$C_{1-10}$ alkyl" (or alkylene), is intended to include $C_1$, $C_2$, $C_3$, $C_4$, $C_5$, $C_6$, $C_7$, $C_5$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl), as well as chain isomers thereof, and the like as well as such groups which may optionally include 1 to 4 substituents such as halo, for example F, Br, Cl, or I, or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl, and/or alkylthio as well as (=O), $OR_a$, $SR_a$, (=S), —$NR_aR_b$, —N(alkyl)$_3^+$, —$NR_aSO_2$, —$NR_aSO_2R_c$, —$SO_2R$—$SO_2NR_aR_b$, —$SO_2NR_aC(=O)R_b$, $SO_3H$, —$PO(OH)_2$, —$C(=O)R_a$, —$CO_2R_a$, —$C(=O)NR_aR_b$, —$C(=O)(C_1$-$C_4$ alkylene)N-$R_aR_b$, —$C(=O)NR_a(SO_2)R_b$, —$CO_2(C_1$-$C_4$ alkylene)$NR_aR_b$, —$NR_aC(=O)R_b$, —$NR_aCO_2R_b$, —$NR_a(C_1$-$C_4$ alkylene)$CO_2R_b$, =N—OH, =N—O-alkyl, wherein $R_a$ and $R_b$ are the same or different and are independently selected from hydrogen, alkyl, alkenyl, $CO_2H$, $CO_2$(alkyl), $C_3$-$C_7$cycloalkyl, phenyl, benzyl, phenylethyl, naphthyl, a 4- to 7-membered heterocyclo, or a 5- to 6-membered heteroaryl, or when attached to the same nitrogen atom may join to form a heterocyclo or heteroaryl, and R, is selected from same groups as $R_a$ and $R_b$ but is not hydrogen. Each group $R_a$ and $R_b$ when other than hydrogen, and each R, group optionally has up to three further substituents attached at any available carbon or nitrogen atom of $R_a$, $R_b$, and/or $R_c$, said substituent(s) being the same or different and are independently selected from the group consisting of ($C_1$-$C_6$)alkyl, ($C_2$-$C_6$)alkenyl, hydroxy, halogen, cyano, nitro, $CF_3$, O($C_1$-$C_6$ alkyl), $OCF_3$, C(=O)H, C(=O)($C_1$-$C_6$ alkyl), $CO_2H$, $CO_2$($C_1$-$C_6$ alkyl), $NHCO_2$($C_1$-$C_6$ alkyl), —S($C_1$-$C_6$ alkyl), —$NH_2$, NH($C_1$-$C_6$ alkyl), N($C_1$-$C_6$ alkyl)$_2$, N($CH_3$)$_3^+$, $SO_2$($C_1$-$C_6$ alkyl), C(=O)($C_1$-$C_4$ alkylene)$NH_2$, C(=O)($C_1$-$C_4$ alkylene)NH(alkyl), C(=O)($C_1$-$C_4$ alkylene)N($C_1$-$C_4$ alkyl)$_2$, $C_3$-$C_7$ cycloalkyl, phenyl, benzyl, phenylethyl, phenyloxy, benzyloxy, naphthyl, a 4- to 7-membered heterocyclo, or a 5- to 6-membered heteroaryl. When a substituted alkyl is substituted with an aryl, heterocyclo, cycloalkyl, or heteroaryl group, said ringed systems are as defined below and thus may have zero, one, two, or three substituents, also as defined below.

"Alkenyl" or "alkenylene", alone or as part of another group, is intended to include hydrocarbon chains of either straight or branched configuration and having one or more carbon-carbon double bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonyl-amino, nitro, cyano, thiol, and/or alkylthio.

"Alkynyl" or "alkynylene", alone or as part of another group, is intended to include hydrocarbon chains of either straight or branched configuration and having one or more carbon-carbon triple bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio.

The term "alkoxy" or "alkyloxy", alone or as part of another group, refers to an —O-alkyl group, where alkyl is as defined above. "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy", alone or as part of another group, represents an alkyl group or alkoxy group as defined above with the indicated number of carbon atoms attached through a sulphur bridge; for example methyl-S— and ethyl-S—.

"Halo" or "halogen", alone or as part of another group, includes fluoro, chloro, bromo, and iodo.

"Haloalkyl" is intended to include both branched and straight-chain saturated aliphatic hydrocarbon groups having the specified number of carbon atoms, substituted with 1 to 7 halogens, preferably 1 to 4 halogens, preferably F and/or Cl. Examples of haloalkyl include, but are not limited to, fluoromethyl, difluoromethyl, trifluoromethyl, trichloromethyl, pentafluoroethyl, pentachloroethyl, 1,1-difluoroethyl, 1-fluoroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 to 7 fluorine atoms, preferably 1 to 4 fluorine atoms.

"Halo-$C_1$-$C_2$-alkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl), and tricyclic alkyl, containing a total of 3 to 10 carbons forming the ring ($C_3$-$C_{10}$ cycloalkyl), and which may be fused to 1 or 2 aromatic rings as described for aryl, which includes cyclopropyl, cyclobutyl, cyclopentyl, cyclohexyl, cycloheptyl, cyclooctyl, cyclodecyl, cyclododecyl, cyclohexenyl, norbornyl,

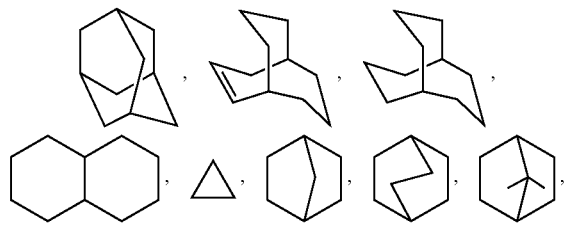

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents for alkyl, as well as such groups including 2 free bonds and thus are linking groups.

As used herein, "carbocycle" or "carbocyclic residue" is intended to mean any stable 3-, 4-, 5-, 6-, or 7-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, John Wiley & Sons, Inc., New York (1997). "$C_{6-10}$ aryl" refers to phenyl and naphthyl. Unless otherwise specified, "aryl", "$C_{6-10}$ aryl" or "aromatic residue" may be unsubstituted or substituted with 1 to 3 groups selected from OH, $OC_1$-$C_3$ alkoxy, Cl, F, Br, I, CN, $NO_2$, $NH_2$, $N(CH_3)H$, $N(CH_3)_2$, $CF_3$, $OCF_3$, $OCHF_2$, $C(=O)CH_3$, $SCH_3$, $S(=O)CH_3$, $S(=O)_2CH_3$, $C_1$-$C_3$ alkyl, $CO_2H$, and $CO_2CH_3$.

As used herein, the term "heterocycle", "heterocyclo" or "heterocyclic" group is intended to mean a stable 4- to 14-membered monocyclic, bicyclic or tricyclic heterocyclic ring which is saturated or partially unsaturated and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized (i.e., N O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may optionally be substituted on carbon or on a nitrogen atom if the resulting compound is stable, with 1 to 3 groups selected from OH, $OC_1$-$C_3$ alkoxy, Cl, F, Br, I, CN, $NO_2$, $NH_2$, $N(CH_3)H$, $N(CH_3)_2$, $CF_3$, $OCF_3$, $OCHF_2$, =O, $C(=O)CH_3$, $SCH_3$, $S(=O)CH_3$, $S(=O)_2CH_3$, $C_1$-$C_3$ alkyl, $CO_2H$ and $CO_2CH_3$. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. Spiro and bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge. When the term "heterocycle" is used, it is not intended to include heteroaryl.

Exemplary monocyclic heterocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane, and tetrahydro-1,1-dioxothienyl, and the like.

Exemplary bicyclic heterocyclo groups include quinuclidinyl.

Preferred heterocyclo groups include

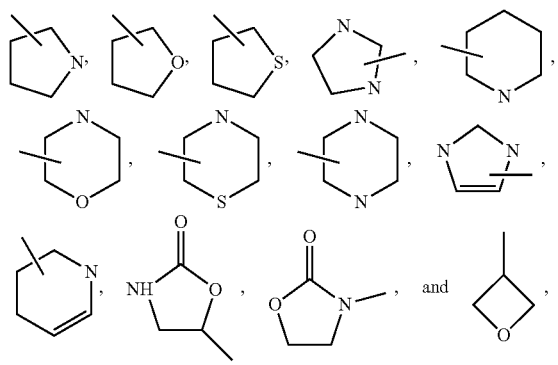

and which optionally may be substituted.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are unsubstituted or substituted with 1 to 3 groups selected from OH, $OC_1$-$C_3$ alkoxy, Cl, F, Br, I, CN, $NO_2$, $NH_2$, $N(CH_3)H$, $N(CH_3)_2$, $CF_3$, $OCF_3$, $OCHF_2$, =O, $C(=O)CH_3$, $SCH_3$, $S(=O)CH_3$, $S(=O)_2CH_3$, $C_1$-$C_3$ alkyl, $CO_2H$ and $CO_2CH_3$. The nitrogen atom is substituted or unsubstituted (i.e., N or NR wherein R is H or another substituent, if defined). The nitrogen and sulfur heteroatoms may optionally be oxidized (i.e., N—O and $S(O)_p$, wherein p is 0, 1 or 2). Bridged rings are also included in the definition of heteroaryl. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

Preferred heteroaryl groups include

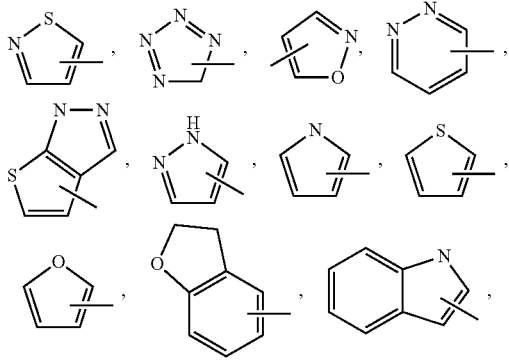

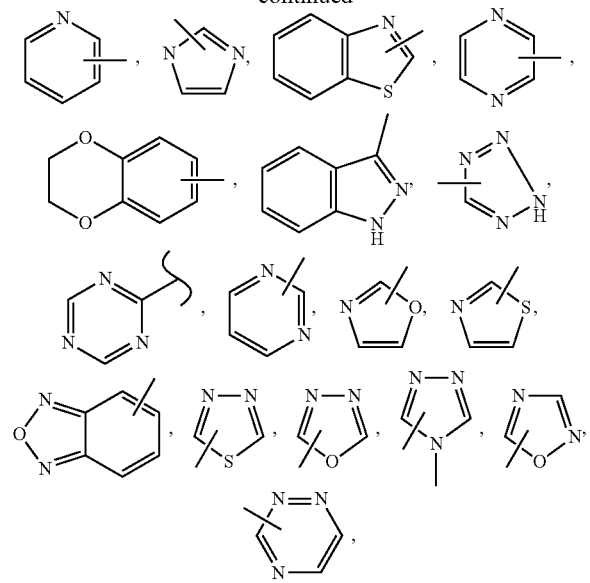

and the like.

When the term "unsaturated" is used herein to refer to a ring or group, which group may be fully unsaturated or partially unsaturated.

The term "acyl" alone or as part of another group refers to a carbonyl group linked to an organic radical, more particularly, the group $C(=O)R_e$, as well as the bivalent groups —C(=O)— or —$C(=O)R_e$—, which are linked to organic radicals. The group $R_e$ can be selected from alkyl, alkenyl, alkynyl, aminoalkyl, substituted alkyl, substituted alkenyl, or substituted alkynyl, as defined herein, or when appropriate, the corresponding bivalent group, e.g., alkylene, alkenylene, and the like.

The designation "⌇⌇" or "⎯ξ⎯" or "⎯ξ⎯" attached to a ring or other group refers to a free bond or linking group.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The term "counterion" is used to represent a negatively charged species such as chloride, bromide, hydroxide, acetate, and sulfate.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative. In cases in which there are quaternary carbon atoms in compounds of the present invention, these can be replaced by silicon atoms, provided they do not form Si—N or Si—O bonds.

When any variable occurs more than one time in any constituent or formula for a compound, its definition at each occurrence is independent of its definition at every other occurrence. Thus, for example, if a group is shown to be substituted with 0 to 3 $R^{3a}$, then said group may optionally be substituted with up to three $R^{3a}$ groups, and at each occurrence $R^{3a}$ is selected independently from the definition of $R^{3a}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, L. V., Jr., ed., *Remington: The Science and Practice of Pharmacy*, 22nd Edition, Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);
b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);
c) Bundgaard, H., *Adv. Drug Deliv. Rev.*, 8:1-38 (1992);
d) Bundgaard, H. et al., *J. Pharm. Sci.*, 77:285 (1988);
e) Kakeya, N. et al., *Chem. Pharm. Bull.*, 32:692 (1984); and
f) Rautio, J (Editor). *Prodrugs and Targeted Delivery (Methods and Principles in Medicinal Chemistry)*, Vol 47, Wiley-VCH, 2011.

Preparation of prodrugs is well known in the art and described in, for example, King, F. D., ed., *Medicinal Chemistry: Principles and Practice*, The Royal Society of Chemistry, Cambridge, UK (2nd Edition, reproduced (2006)); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, 3rd Edition, Academic Press, San Diego, Calif. (2008).

Isotopically labeled compounds of the present invention, i.e., wherein one or more of the atoms described are replaced by an isotope of that atom (e.g., $^{12}C$ replaced by $^{13}C$ or by $^{14}C$; and isotopes of hydrogen including tritium and deuterium), are also provided herein. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

Compounds of the present invention are, subsequent to their preparation, preferably isolated and purified to obtain a composition containing an amount by weight equal to or greater than 98%, preferably 99%, compound of the present invention ("substantially pure"), which is then used or formulated as described herein. Such "substantially pure" compounds are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and insoluble solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" for thin layer chromatography, "SM" for starting material, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "tlc" for thin layer chromatography. "α", "β", "R", "S", "E", and "Z" are stereochemical designations familiar to one skilled in the art.

| | |
|---|---|
| Me | methyl |
| Et | ethyl |
| Pr | propyl |
| i-Pr | isopropyl |
| Bu | butyl |
| i-Bu | isobutyl |
| t-Bu | tert-butyl |
| Ph | phenyl |
| Bn | benzyl |
| AcOH | acetic acid |
| MeOH | methanol |
| EtOH | ethanol |
| EtOAc | ethyl acetate |
| Et$_2$O | diethyl ether |
| i-PrOH or IPA | isopropanol |
| HOAc | acetic acid |
| BOP reagent | benzotriazol-1-yloxytris(dimethylamino)phosphonium hexafluorophosphate |
| BBr$_3$ | boron tribromide |
| Boc | tert-butyloxycarbonyl |
| cDNA | complimentary DNA |
| CDCl$_3$ | deuterated chloroform |
| CH$_2$Cl$_2$ | dichloromethane |
| CH$_3$CN | acetonitrile |
| ACN | acetonitrile |
| DABCO | 1,4-diazabicyclo[2.2.2]octane |
| DCE | 1,2 dichloroethane |
| DCM | dichloromethane |
| DCC | dicyclohexylcarbodiimide |
| DIAD | diisopropyl azodicarboxylate |
| DIEA or DIPEA | N,N-diisopropylethylamine |
| DME | 1,2-dimethoxyethane |
| DMF | dimethyl formamide |
| DMAP | N,N-dimethylaminopyridine |
| DMSO | dimethyl sulfoxide |
| DPPA | diphenyl phosphoryl azide |
| EDC (or EDC•HCl) or EDCI (or EDCI•HCl) or EDAC | 3-ethyl-3'-(dimethylamino)propyl-carbodiimide hydrochloride or 1-(3-dimethylaminopropyl)-3-ethylcarbodiimide hydrochloride |
| EDTA | ethylenediaminetetraacetic acid |
| HATU | O-(7-azabenzotriazol-1-yl)-N,N,N',N'-tetramethyluronium hexafluorophosphate |
| HCl | hydrochloric acid |
| HEPES | 4-(2-hydroxyethyl)piperaxine-1-ethanesulfonic acid |
| Hex | hexane |
| HOBt or HOBT | 1-hydroxybenzotriazole monohydrate |
| Hunig's base | N,N-diisopropylethyl amine |
| LAH | lithium aluminum hydride |
| LDA | Lithium diisopropylamide |
| LiHMDS | Lithium bis(trimethylsilyl) amide |
| mCPBA or m-CPBA | meta-chloroperbenzoic acid |
| NMM | N-methylmorpholine |
| Pd/C | palladium on carbon |
| PPA | polyphosphoric acid |
| PS | polystyrene |
| PXPd2 | bis[di-tert-butyl phosphinous chloride-kP]di-m-chlorodichloro dipalladium |
| PyBOP | (benzotriazol-1-yloxy)tripyrrolidinophosphonium hexafluorophosphate |
| TEA | triethylamine |
| TFA | trifluoroacetic acid |
| THF | tetrahydrofuran |
| TRIS | tris(hydroxymethyl)aminomethane |
| KOAc | potassium acetate |
| K$_3$PO$_4$ | potassium phosphate |
| MgSO$_4$ | magnesium sulfate |
| NaCl | sodium chloride |
| NaH | sodium hydride |
| NaHCO$_3$ | sodium bicarbonate |
| NaOH | sodium hydroxide |

| | |
|---|---|
| Na₂SO₃ | sodium sulfite |
| Na₂SO₄ | sodium sulfate |
| NH₃ | ammonia |
| NH₄Cl | ammonium chloride |
| NH₄OH | ammonium hydroxide |
| OTs | tosylate, para-toluenesulfonate |
| PBr₃ | phosphorous tribromide |
| Pd(PPh₃)₄ | tetrakis(triphenylphosphine) palladium (0) |
| (S,S)-EtDuPhosRh(I) | (+)-1,2-bis((2S,5S)-2,5-diethylphospholano)benzene (cyclooctadiene)rhodium (I) trifluoromethanesulfonate |

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Wuts et al. (*Greene's Protective Groups In Organic Synthesis*, 4th Edition, Wiley-Interscience (2006)).

Compounds of formula I of this invention can be obtained by condensation of an amine of formula III with a ketone of formula IV which contains a leaving group Z such as a bromide, iodide or tosylate and a protecting group PG such as benzyl as shown in Scheme 1. Both compounds of formula III and IV are commercially available or can be prepared by means known to one skilled in the art. This condensation is promoted by heating, either thermally or preferably by microwave irradiation. The protecting group can be removed by methods known in the art, such as BCl₃ at −78° C. in the presence of pentamethylbenzene. Subsequent alkylation using either an alcohol VI under Mitsunobu conditions or a bromide VII in the presence of base such as potassium carbonate provides the compounds of Formula I. Alcohols and bromides VI and VII are commercially available or can be prepared by methods known in the art.

Scheme 1

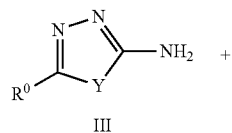

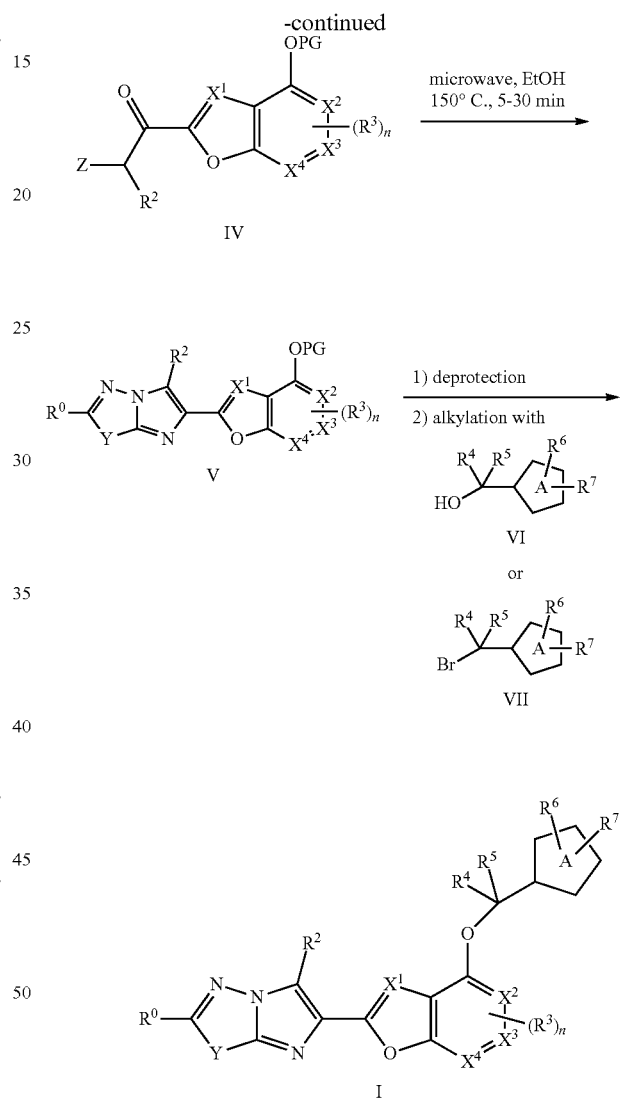

Alternatively, compounds of Formula I can be prepared from compounds of formula IX upon activation of the thiomethyl group by oxidation to a sulfone VII as shown in Scheme 2. This allows introduction of a variety of nucleophiles as groups R⁰ such as alcohols, thiols and amines in the presence of a base such as potassium carbonate or sodium hydride either neat or in a polar, aprotic solvent such as dimethylformamide to give compounds XI. Compounds XI can be converted to compounds of Formula I by removal of the protecting group (PG) and alkylation as discussed in Scheme 1.

Scheme 2

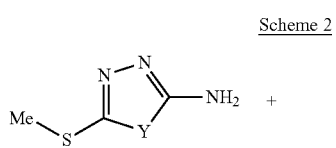

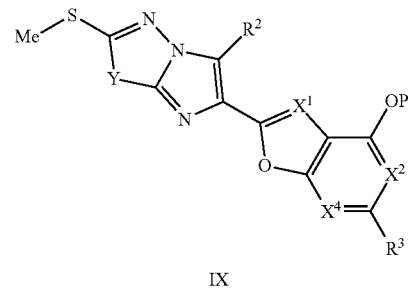

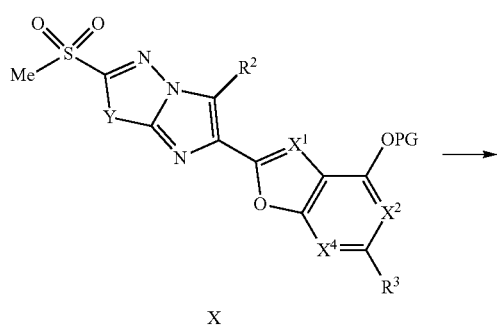

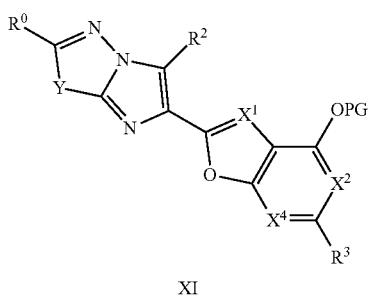

Substituted benzofurans bearing α-bromoketone substituents at the 2-position (XV) can be prepared as shown in Scheme 3. o-Hydroxy benzaldehydes XII can be prepared by methods known to one skilled in the art of organic synthesis, and can be condensed with ketones of formula XIII bearing a leaving group Q such as chloro, bromo or tosyloxy, to give benzofurans XIV. Bromination of compounds of formula XIV affords bromoketones XV, which can be condensed with a substituted aminoheterocycle III according to Scheme 1 to give compounds of Formula I. Bromoketones XV are a specific subset of compounds IV in Scheme 1.

Scheme 3

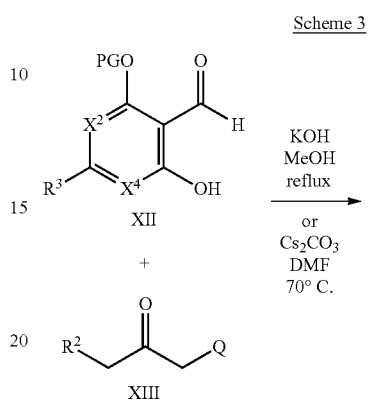

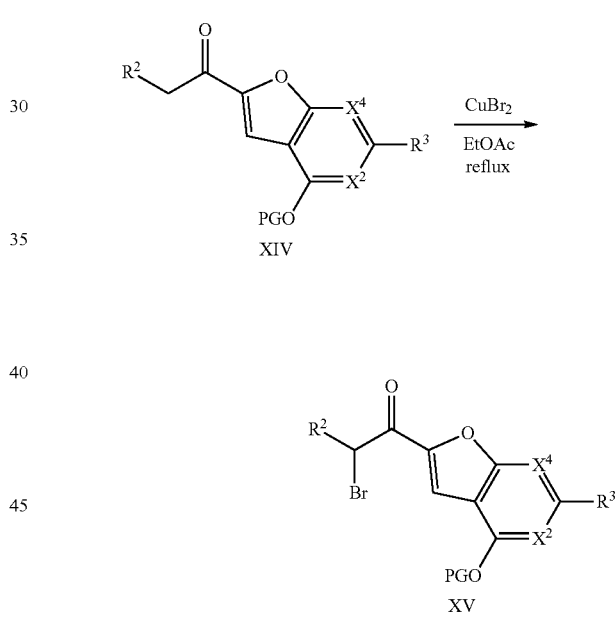

Benzoxazole compounds of Formula I can be prepared starting from substituted aminoheterocycle III and pyruvate esters of formula XVI which contain a leaving group Z such as a bromide, iodide or tosylate as shown in Scheme 4. Both compounds of formula III and XVI are commercially available or are available by means known to one skilled in the art. Following condensation and saponification of the ester to form acid XVIII, amino phenols of formula XIX are coupled to form amides of the formula XX, which can be cyclized under acid catalysis to form benzoxazole compounds of formula XXI. These can be deprotected and alkylated as shown in Scheme 1 to provide compounds of Formula I.

Scheme 4

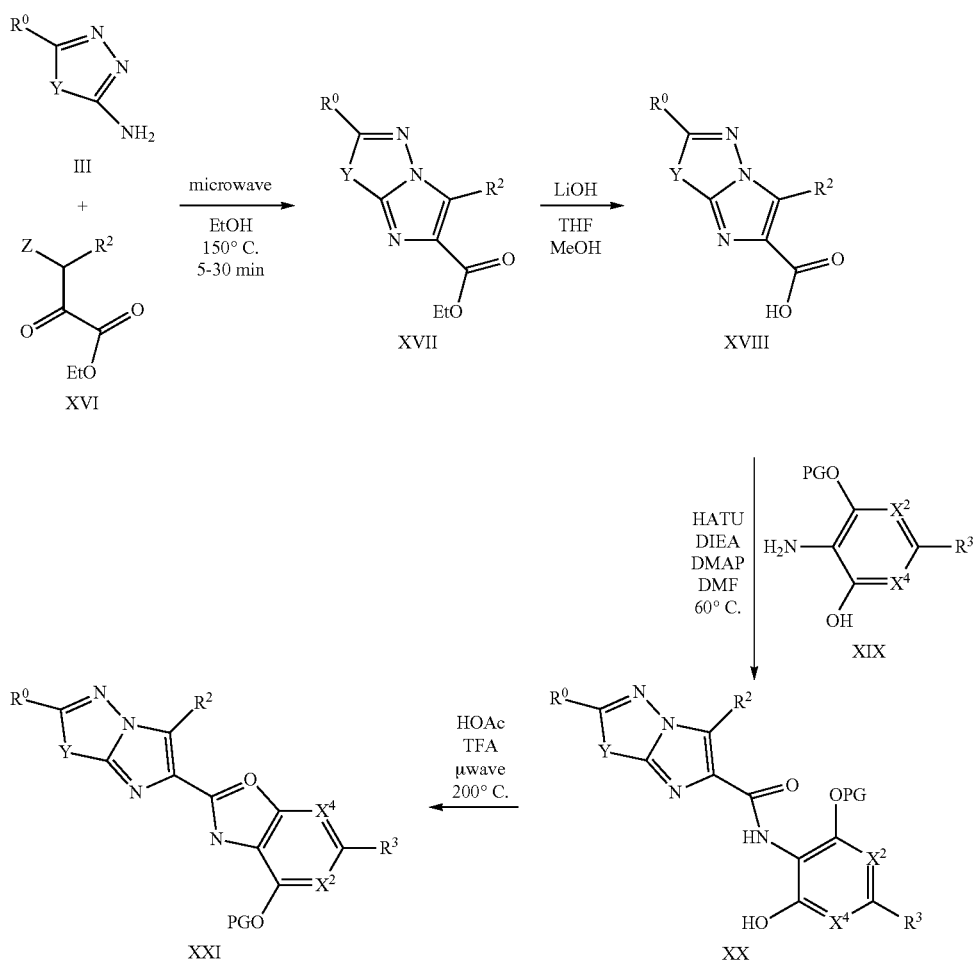

Aminoheterocycles XXIV can be prepared from carbon disulfide (XXII) via the thioxanthate intermediate XXIII. These aminoheterocycles are useful for the preparation of compounds of Formula I.

bromine gives pyridazinones XXVII. Chlorination, displacement with hydrazine, and subsequent hydrogenation provides aminoheterocycles XXX, which are a specific subset of compounds III in Scheme I. As such, these aminoheterocycles are useful for the preparation of compounds of Formula I.

Scheme 5

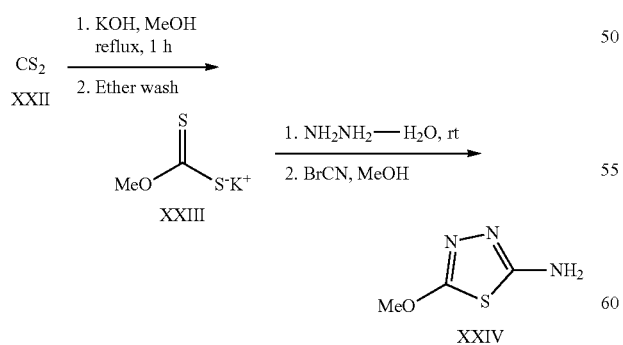

Scheme 6

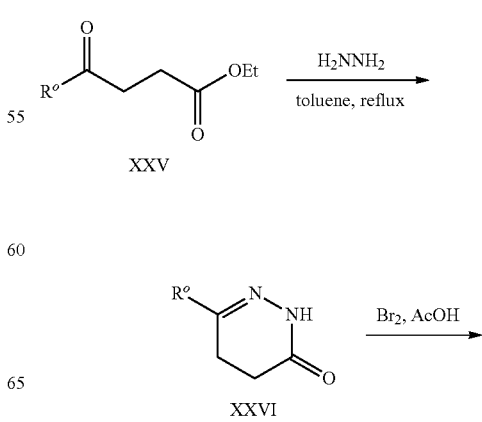

Aminoheterocycles XXX, which are useful intermediates for preparation of compounds of Formula I where Y=—CH$_2$CH$_2$—, can be prepared from ketoesters XXV. Cyclization with hydrazine, followed by oxidation with

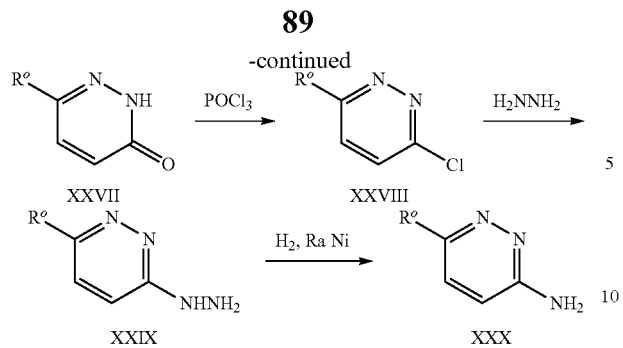

EXAMPLES

The following compounds of the invention have been prepared, isolated and characterized using the methods disclosed herein. They demonstrate a partial scope of the invention and are not meant to be limiting of the scope of the invention. In the experimental procedures, solution ratios express a volume relationship, unless stated otherwise. NMR chemical shifts (δ) are reported in parts per million (ppm). Products were analyzed by reverse phase analytical HPLC using the following methods:

Method A: Column: ZORBAX® XDB-C18 3.5 micron, 4.6×30 mm; Mobile Phase: A=MeOH:H₂O:TFA (95:5:05), B=MeOH:H₂O:TFA (5:95:05). Grad.: T=0:100% solv A; T=2:100% solv B; stop time: 4 min. Flow=3.0 mL/min.

Method B: Column: Agilent POROSHELL® 120; EC-C18, 2.7 um; 2.1×30 mm; Mobile Phase: Solv A: 5% MeOH: 95% H₂O+0.1% AcOH; Solv B: 95% MeOH: 5% H₂O+0.1% AcOH; Grad.: T=0:100% solv A; T=1:100% solv B; stop time: 4 min. Flow=1.0 mL/min.

Method C: SunfireC18 3.5 micron column (4.6×30 mm) eluted at 3 mL/min with a 2 min. gradient from 100% A to 100% B (A: 5% methanol, 94.95% water, 0.05% TFA; B: 5% water, 94.95% methanol, 0.05% TFA, UV 220 nm).

Method D: Eclipse XDB-C18 3.5 micron column (4.6×30 mm) eluted at 3 mL/min with a 2 min gradient from 100% A to 100% B (A: 5% methanol, 94.95% water, 0.05% TFA; B: 5% water, 94.95% methanol, 0.05% TFA, UV 220 nm).

Method E: Eclipse XDB-C18 3.5 micron column (4.6×30 mm) eluted at 3 mL/min with a 2 min gradient from 100% A to 100% B (A: 5% acetonitrile, 94.95% water, 0.05% TFA; B: 5% water, 94.95% acetonitrile, 0.05% TFA, UV 220 nm).

Method F: ZORBAX® SB-Phenyl 3.5 micron column (4.6×50 mm) eluted at 3 mL/min with a 2 min gradient from 100% A to 100% B (A: 5% methanol, 94.95% water, 0.05% TFA; B: 5% water, 94.95% methanol, 0.05% TFA, UV 220 nm).

Method G: Waters BEH C18 column (2.0×50 mm, 1.7-μm particles); Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min.

Method H: Waters BEH C18 column (2.0×50 mm, 1.7-μm particles); Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min.

Purification of products by reverse phase preparative HPLC was done using the following method:

Method A: Column: ZORBAX® SB-C18 PrepHT, 5 micron, 21.2×100 mm; Mobile Phase: A=MeOH:H₂O:TFA (5:95:0.05), B=MeOH:H₂O:TFA (95:5:0.05). Grad.: 0 to 2 min: isocratic 25% solvent B; 8 min gradient of 25 to 100% solvent B; stop time=15 min. Flow=20 mL/min, detection at UV 220 nm.

Example 1

2-Methoxy-6-(6-methoxy-4-((2-methylthiazol-4-yl)methoxy)benzofuran-2-yl) imidazo[2,1-b][1,3,4]thiadiazole

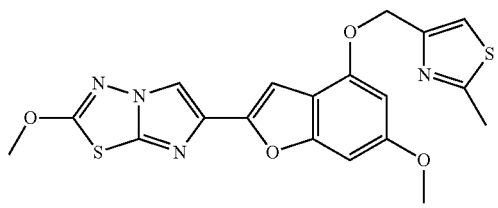 [SMILES: COc1cc(OCc2csc(C)n2)c2cc(-c3cn4nc(OC)sc4n3)oc2c1]

1A. (2-Methylthiazol-4-yl)methanol

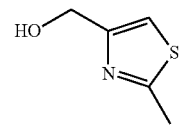

A solution of 2-methyl-thiazole-4-carboxylic acid ethyl ester (1.26 g, 7.36 mmol) in ethyl ether (10 mL) was cooled to −78° C. and treated with a solution of LAH (0.83 g, 21.9 mmol) in dry THF (30 mL) added dropwise over 10 min. After 3 hours, at −78° C., the mixture was quenched with sat. Na₂SO₄ (app. 20 mL). The mixture was allowed to warm up to 22° C. and was extracted with ethyl ether (4×50 mL). The combined extracts were washed with brine, dried over anhydrous MgSO₄ and concentrated to give an oil. Filtration on a silica gel pad (3×7 cm) and elution with ethyl acetate gave an oil which was distilled to afford the title material (0.664 g, 70%) as an oil which crystallized. B.p. 60-70° C./0.2 torr. HRMS(ESI) calcd for C₅H₈NOS [M+H]⁺ m/z 130.0321, found 130.0342. ¹H NMR (CDCl₃, 600 MHz) δ 6.99 (d, J=0.8 Hz, 1H), 4.70 (s, 1H), 2.98 (br s, 1H), 2.68 (s, 3H).

1B. 5-(Benzyloxy)-7-methoxy-2,2-dimethyl-4H-benzo[d][1,3]dioxin-4-one

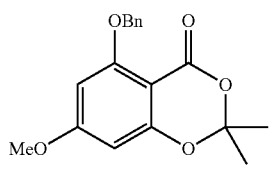 [SMILES: COc1cc(OCc2ccccc2)c2c(c1)OC(C)(C)OC2=O]

A solution of 5-hydroxy-7-methoxy-2,2-dimethyl-4H-benzo[d][1,3]dioxin-4-one (30.00 g, 0.134 mol, see Kamisuki, S. et al., *Tetrahedron*, 60:5695-5700 (2004) for preparation) in N,N-dimethylformamide (400 mL) was treated with powdered anhydrous potassium carbonate (19.41 g, 0.14 mol) added all at once. The resulting mixture was stirred in vacuo for 10 min. and then flushed with nitrogen. The reaction flask was placed in a water bath (22° C.) and treated with benzyl bromide (24.03 g, 0.14 mol) added dropwise over 15 min. The resulting mixture was then stirred at 22° C. for 18 h (no starting material left by tlc). The solid was filtered and washed with N,N-dimethylformamide. The filtrate was evaporated in vacuo and the residual oil was diluted with ethyl acetate (500 mL), washed with cold 0.1 N hydrochloric acid, saturated sodium bicarbonate and brine. After drying over anhydrous magnesium sulfate, evaporation of the solvent gave a thick syrup. Crystallization form ethyl acetate (50 mL) and hexane (150 mL) gave 35.17 g of 5-(benzyloxy)-7-methoxy-2,2-dimethyl-4H-benzo[d][1,3]dioxin-4-one as large colorless prisms. Chromatography of the mother liquors on silica gel (4×13 cm, elution toluene-ethyl acetate 0-5%) gave 6.64 g of additional material to afford a total yield of 41.81 g (99%). HRMS(ESI) calcd for $C_{18}H_{19}O_5$ [M+H]$^+$ m/z 315.1227, found 315.1386. $^1$H NMR (CDCl$_3$, 600 MHz) δ 1.68 (s, 6H), 3.77 (s, 3H), 5.19 (s, 2H), 5.19 (s, 2H), 6.04 (d, J=2.03 Hz, 1H), 6.15 (d, J=2.03 Hz, 1H), 7.27 (broad t, 1H), 7.36 (broad t, 2H), 7.52 (broad d, 2H).

1C.
2-(Benzyloxy)-6-hydroxy-4-methoxybenzaldehyde

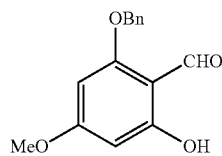

A solution of 5-(benzyloxy)-7-methoxy-2,2-dimethyl-4H-benzo[d][1,3]dioxin-4-one (Example 1B, 6.76 g, 21.5 mmol) in dichloromethane (120 mL) was cooled to −78° C. and treated with 43 mL (64.5 mmol) of a 1.5 M solution of diisobutylaluminum hydride in toluene added dropwise over 20 min. The resulting mixture was then stirred at −78° C. for 3 h. The reaction mixture was quenched by the careful addition of methanol (5 mL) added dropwise over 15 min, followed by 1N hydrochloric acid (50 mL) added dropwise over 15 min. The cooling bath was then removed and an additional 150 mL of 1N hydrochloric acid was added over 20 min. The mixture was then stirred at 22° C. for 2 h and diluted with dichloromethane (400 mL). The organic phase was collected and the aqueous phase (pH ~1) was extracted with dichloromethane (3×50 mL). The combined organic extracts were washed with brine, dried over anhydrous magnesium sulfate and concentrated in vacuo. The residual oil was diluted with tetrahydrofuran (70 mL), treated with 10 mL of 0.1N hydrochloric acid and stirred at 20° C. for 2 h. The reaction mixture was diluted with ethyl acetate (300 mL), washed with brine, dried over anhydrous magnesium sulfate, evaporated in vacuo to give a clear oil. Chromatography on silica gel (4×13 cm, elution toluene) gave 4.08 g (73% yield) of the title aldehyde as a clear oil which solidified on standing. LC (Method C): 2.237 min. HRMS (ESI) calcd for $C_{15}H_{15}O_4$ [M+H]$^+$ m/z 259.0965, found 259.1153. $^1$H NMR (CDCl$_3$, 600 MHz) δ 3.80 (s, 3H), 5.07 (s, 2H), 5.97 (d, J=2.1 Hz, 1H), 6.01 (d, J=2.1 Hz, 1H), 7.3-7.4 (m, 5H), 10.15 (s, 1H), 12.49 (s, 1H).

1D.
1-(4-(Benzyloxy)-6-methoxybenzofuran-2-yl)ethanone

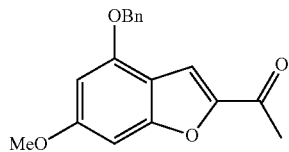 [SMILES: COc1cc(OCc2ccccc2)c2cc(C(C)=O)oc2c1]

A solution of 2-(benzyloxy)-6-hydroxy-4-methoxybenzaldehyde (Example 1C, 3.46 g, 13.4 mmol) in N,N-dimethylformamide (50 mL) was treated with powdered anhydrous cesium carbonate (4.58 g, 14.05 mmol) added all at once. The resulting mixture was stirred in vacuo for 10 min. and then flushed with nitrogen. The reaction flask was placed in a water bath (22° C.) and treated with chloroacetone (1.74 g, 18.7 mmol) added dropwise over 5 min. The resulting mixture was then stirred at 22° C. for 18 h (no starting aldehyde left by tlc and formation of the intermediate alkylated aldehyde). The solid was filtered and washed with N,N-dimethylformamide. The filtrate was evaporated in vacuo and the residual oil was diluted with ethyl acetate (300 mL), washed with cold 0.1 N hydrochloric acid, saturated sodium bicarbonate and brine. After drying over anhydrous magnesium sulfate, evaporation of the solvent gave a thick syrup. This syrup was diluted with tetrahydrofuran (50 mL) and ethyl acetate (50 mL), treated p-toluenesulfonic acid monohydrate (0.2 g) and stirred at 20° C. for 1 h (tlc indicated complete cyclization of the intermediate alkylated aldehyde to the benzofuran). The reaction mixture was diluted with ethyl acetate (300 mL), washed with saturated sodium bicarbonate and brine. After drying over anhydrous magnesium sulfate, evaporation of the solvent gave a thick syrup. Chromatography on silica gel (4×12 cm, elution toluene-ethyl acetate 2-4%) gave 3.51 g (88% yield) of the title benzofuran as a yellow solid. Recrystallization from ethyl acetate (10 mL) and hexane (20 mL) gave the title material as large yellow prisms (3.15 g). LC (Method D): 2.148 min. HRMS(ESI) calcd for $C_{18}H_{17}O_4$ [M+H]$^+$ m/z 297.1121, found 297.1092. $^1$H NMR (CDCl$_3$, 600 MHz) δ 2.51 (s, 3H), 3.82 (s, 3H), 5.13 (s, 2H), 6.37 (d, J=1.77 Hz, 1H), 6.63 (broad s, 1H), 7.34 (broad t, 1H), 7.39 (broad t, 2H), 7.44 (broad d, 2H), 7.55 (d, J=0.7 Hz, 1H).

1E. 1-(4-(Benzyloxy)-6-methoxybenzofuran-2-yl)-2-bromoethanone

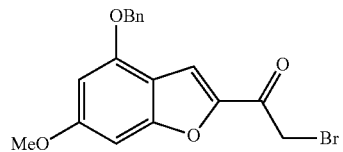

A 250-mL, three-necked flask is equipped with a magnetic stirring bar and purged with a nitrogen atmosphere was charged with anhydrous tetrahydrofuran (25 mL) followed by 9.3 mL (9.3 mmol) of a 1M solution of lithium bis(trimethylsilyl)amide in tetrahydrofuran. The mixture was cooled to −78° C. and treated with a solution of 1-(4-(benzyloxy)-6-methoxybenzofuran-2-yl)ethanone (Example 1D, 2.40 g, 8.1 mmole) in tetrahydrofuran (20 mL) added dropwise over 10 min. The resulting mixture was then stirred at −78° C. for 45 min. Then chlorotrimethylsilane (1.18 mL, 9.31 mmol) was added dropwise over 5 min and the resulting solution was stirred at −78° C. for another 20 min. The cooling bath was then removed and the mixture is allowed to warm to room temperature over 30 min. The reaction mixture was then quenched by addition to a cold solution of ethyl acetate (200 mL), saturated sodium bicarbonate (30 mL) and ice. The organic phase was rapidly dried over anhydrous magnesium sulfate (magnetic stirring) and evaporated in vacuo to give the silyl enol ether as an oil which is co-evaporated with toluene (20 mL). The silyl enol ether was then dissolved in dry tetrahydrofuran (40 mL), cooled to −20° C. and treated with solid sodium bicarbonate (0.10 g) followed by N-bromosuccinimide (1.44 g, 8.1 mmol) added in small portions over 15 min. The reaction mixture was allowed to warm to 0° C. over 2 h and then quenched by addition of ethyl acetate (300 mL) and saturated sodium bicarbonate. The organic phase was washed with brine, dried over anhydrous magnesium sulfate and evaporated to give an orange oil. Chromatography on silica gel (4×12 cm, elution toluene-ethyl acetate 0-5%) gave 2.62 g (86% yield) of the title bromomethylketone as a yellow solid. Recrystallization from ethyl acetate (10 mL) and hexane (20 mL) gave yellow prisms (2.30 g). LC (Method E): 1.977 min. HRMS(ESI) calcd for $C_{18}H_{16}BrO_4$ [M+H]$^+$ m/z 375.0226, found 375.0277. $^1$H NMR (CDCl$_3$, 600 MHz) δ 3.84 (s, 3H), 4.33 (s, 2H), 5.14 (s, 2H), 6.38 (d, J=1.76 Hz, 1H), 6.64 (broad s, 1H), 7.35 (broad t, 1H), 7.40 (broad t, 2H), 7.44 (broad d, 2H), 7.70 (s, 1H).

1EE. 1-(4-(Benzyloxy)-6-methoxybenzofuran-2-yl)-2-chloroethanone

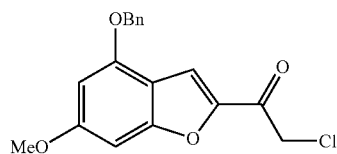 [SMILES: COc1cc(OCc2ccccc2)c2cc(C(=O)CCl)oc2c1]

Benzyltrimethylammonium dichloroiodate (117 g, 169 mmol) was added to a solution of 1-(4-(benzyloxy)-6-methoxybenzofuran-2-yl)ethanone (Example 1D, 50 g, 170 mmol) in THF (500 mL) in a 1 L multineck round bottom flask under nitrogen atmosphere. The reaction mixture was stirred at RT for 6 h, cooled to 0° C. and quenched with 10% NaHCO$_3$ solution. The organic layer was washed with 1 M sodium thiosulphate solution, water, and brine, dried over Na$_2$SO$_4$, and concentrated in vacuo (bath temperature<45° C.). The residue was triturated with 5% EtOAc in pet. ether and dried to obtain the title chloromethylketone as a pale yellow solid (48 g, 130 mmol, 78%). $^1$H NMR (300 MHz, DMSO-d$_6$) δ 3.84-3.82 (d, J=4.5 Hz, 3H) 4.98 (s, 2H), 5.27 (s, 2H), 6.62-6.61 (d, J=1.8 Hz, 1H), 6.92-6.93 (m, 1H), 7.54-7.36 (m, 5H), 8.10-8.09 (d, J=3 Hz, 1H); MS m/z: [M+H]$^+$ 331.0.

1F. 6-(4-(Benzyloxy)-6-methoxybenzofuran-2-yl)-2-bromoimidazo[2,1-b][1,3,4]thiadiazole

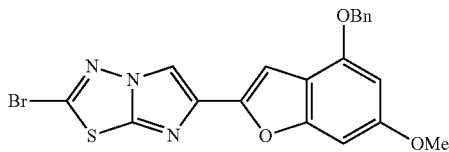 [SMILES: COc1cc(OCc2ccccc2)c2cc(-c3cn4nc(Br)sc4n3)oc2c1]

A mixture of 1-(4-(benzyloxy)-6-methoxybenzofuran-2-yl)-2-bromoethanone (Example 1E, 3.00 g, 8.0 mmol) and 5-bromo-1,3,4-thiadiazol-2-amine (1.65 g, 9.16 mmol) in isopropanol (100 mL) was heated in a pressure flask equipped with a magnetic stirring bar at 78-80° C. for 18 h (homogeneous after 20 min and then formation of a precipitate after 2 h). The cooled mixture is then transferred into five 20 mL microwave vials and then heated in a microwave apparatus to 150° C. for 30 min. Each vial was then diluted with dichloromethane (250 mL) washed with saturated sodium bicarbonate (25 mL) and brine (25 mL), dried over anhydrous magnesium sulfate. The fractions were combined and concentrated in vacuo. Chromatography of the orange-brown residual solid on silica gel (4×10 cm, slow elution with dichloromethane due to poor solubility) gave 2.96 g of the title imidazothiadiazole contaminated with some 1-(4-(benzyloxy)-6-methoxybenzofuran-2-yl)ethanone. The solid material was triturated with ethyl acetate (20 mL), filtered, washed with ethyl acetate (10 ml) and dried in vacuo to give 2.34 g (64% yield) of pure title imidazothiadiazole as an off white solid which is used as such for the next step. LC (Method E): 2.188 min. HRMS(ESI) calcd for $C_{20}H_{15}BrN_3O_3S$ [M+H]$^1$ m/z 456.00175, found 456.00397. $^1$H NMR (CDCl$_3$, 600 MHz) δ 3.82 (s, 3H), 5.16 (s, 2H), 6.38 (d, J=1.67 Hz, 1H), 6.66 (broad s, 1H), 7.15 (s, 1H), 7.31 (broad t, 1H), 7.38 (broad t, 2H), 7.45 (broad d, 2H), 8.02 (s, 1H).

Alternatively, Example 1F, 6-(4-(benzyloxy)-6-methoxybenzofuran-2-yl)-2-bromoimidazo[2,1-b][1,3,4]thiadiazole, was prepared as follows:

A 1000-mL, three-necked flask equipped with a magnetic stirring bar and purged with a nitrogen atmosphere was charged with dry NMP (200 mL) followed by 1-(4-(benzyloxy)-6-methoxybenzofuran-2-yl)-2-chloroethanone (Example 1EE, 50 g, 150 mmol) and 5-bromo-1,3,4-thiadiazol-2-amine (27.2 g, 151 mmol). The resulting mixture was stirred at 80° C. for 8 h. TLC (8:2 dichloromethane/pet. ether) and LC/MS showed intermediate uncyclized material (m/z 476) and the reaction mixture was stirred at 120° C. for 3 h. The reaction mixture was cooled to RT, quenched with water and extracted with EtOAc (3×). The combined organic layers were washed with brine, dried over Na$_2$SO$_4$, and concentrated in vacuo. The thick brown residue was purified by silica gel chromatography (0 to 100% dichloromethane in pet. ether) to give a brown solid. This material was triturated with EtOAc and dried to obtain the title imidazothiadiazole (24 g, 50 mmol, 33%) as a light brown solid. (See the procedure set forth above for analytical data).

1G. 6-(4-(Benzyloxy)-6-methoxybenzofuran-2-yl)-2-methoxyimidazo[2,1-b][1,3,4]thiadiazole

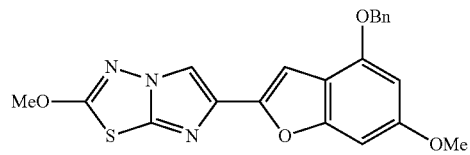

A solution of 6-(4-(benzyloxy)-6-methoxybenzofuran-2-yl)-2-bromoimidazo[2,1-b][1,3,4]thiadiazole (Example 1F, 2.30 g, 5.04 mmol) in a mixture of dichloromethane (180 mL) and methanol (45 mL) was treated at 22° C. with 4.2 mL of a 25 wt. % solution of sodium methoxide in methanol (0.2 mmol) added in one portion. More methanol (45 mL) was added and the mixture was stirred for 1 h. The reaction mixture was quenched by the addition of 25 mL of 1N hydrochloric acid followed by 20 ml of saturated sodium bicarbonate. The solvent was evaporated under reduced pressure and the residue was diluted with dichloromethane (400 mL), washed with brine, dried over anhydrous magnesium sulfate and evaporated in vacuo. Chromatography of the residue on silica gel (3×10 cm, elution with dichloromethane-ethyl acetate 0-4%) gave 1.70 g (83% yield) of the title compound as a white solid. This material was recrystallized from ethyl acetate (30 mL per gram, 80% recovery) to give white needles. LC (Method D): 2.293 min. HRMS(ESI) calcd for $C_{21}H_{18}N_3O_4S$ [M+H]$^+$ m/z 408.1013, found 408.1024. $^1$H NMR (CDCl$_3$, 600 MHz) δ 3.81 (s, 3H), 4.18 (s, 3H), 5.16 (s, 2H), 6.37 (d, J=1.75 Hz, 1H), 6.67 (broad s, 1H), 7.07 (s, 1H), 7.31 (broad t, 1H), 7.37 (broad t, 2H), 7.45 (broad d, 2H), 7.81 (s, 1H).

1H. 6-Methoxy-2-(2-methoxyimidazo[2,1-b][1,3,4]thiadiazol-6-yl)benzofuran-4-ol

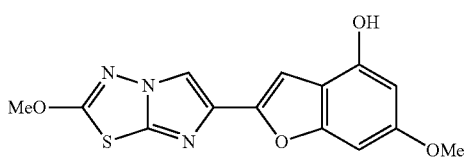 [SMILES: COc1cc(O)c2cc(-c3cn4nc(OC)sc4n3)oc2c1]

A mixture of 6-(4-(benzyloxy)-6-methoxybenzofuran-2-yl)-2-methoxyimidazo[2,1-b][1,3,4]thiadiazole (Example 1G, 1.250 g, 3.06 mmol) and pentamethylbenzene (3.17 g, 21.4 mmol) in dichloromethane (200 mL) was cooled to −78° C. under a nitrogen atmosphere and then treated immediately (to avoid crystallization) with 8 mL (8 mmol) of a 1 M solution of boron trichloride in dichloromethane added dropwise over 3 min. The resulting mixture was stirred at −78° C. for 1 h. The reaction mixture was then quenched by the addition of a solution of sodium bicarbonate (6 g) in water (100 mL) added in one portion. The cooling bath was removed and the resulting mixture was stirred at room temperature for 1 h. The solid formed was filtered, washed successively with water (50 m) and dichloromethane (50 mL). The filter cake was allowed to soak with anhydrous ethanol (15 ml) and then sucked dry. The white solid obtained was then dried under vacuum for 24 h to give 0.788 g (80% yield) of pure title material (>95% by hplc). The combined filtrate and washings were diluted with dichloromethane (600 mL) and stirred in a warm water bath till the organic phase was clear with no apparent solid in suspension. The organic phase was collected, dried over anhydrous magnesium sulfate and rapidly filtered while still warm. The filtrate was evaporated and the residue (product and pentamethylbenzene) was triturated with toluene (20 mL), the solid collected and washed with toluene (20 mL) to give 0.186 g (19% yield, 99% combined yield) of title material as a tan solid (>95% by hplc). LC (Method E): 1.444 min. HRMS(ESI) calcd for $C_{14}H_{12}N_3O_4S$ [M+H]$^+$ m/z 318.0543, found 318.0578. $^1$H NMR (DMSO-d$_6$, 600 MHz) δ 3.71 (s, 3H), 4.16 (s, 3H), 6.21 (d, J=1.87 Hz, 1H), 6.61 (broad s, 1H), 6.95 (s, 1H), 8.29 (s, 1H), 9.96 (s, 1H).

Example 1. 2-Methoxy-6-(6-methoxy-4-((2-methylthiazol-4-yl)methoxy)benzofuran-2-yl)imidazo[2,1-b][1,3,4]thiadiazole

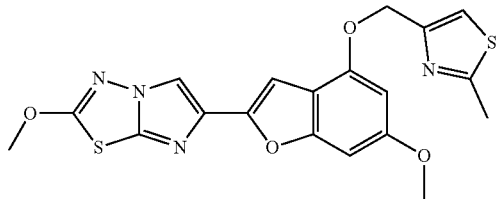 [SMILES: COc1cc(OCc2csc(C)n2)c2cc(-c3cn4nc(OC)sc4n3)oc2c1]

A mixture of 6-methoxy-2-(2-methoxyimidazo[2,1-b][1,3,4]thiadiazol-6-yl)benzofuran-4-ol (Example 1H, 0.100 g, 0.315 mmol) and triphenylphosphine (0.123 g, 0.47 mmol) was maintained under vacuum for 10 minutes. The mixture was flushed with nitrogen and then charged with dry THF (8 mL) and (2-methylthiazol-4-yl)methanol (Example 1A, 0.049 g, 0.38 mmol). The mixture was warmed to 50° C. and sonicated for 5 minutes. The cooled mixture was treated with a solution of DIAD (0.096 g, 0.47 mmol) in dry THF (2 mL) added in three portions dropwise over 20 minutes. The mixture was homogeneous after 40 min. and was stirred at 22° C. for 6 h. The reaction mixture was diluted with dichloromethane (250 mL), washed with sat. sodium bicarbonate, brine and dried over anhydrous MgSO$_4$. Evaporation gave a semi-solid residue which was purified by chromatography on silica gel (2.5×10 cm, dichloromethane/EtOAc 8:2) to provide the title material (0.103 g, 76%) as white cubes. LC (Method A): 2.224 min. HRMS(ESI) calcd for $C_{19}H_{17}N_4O_4S_2$ [M+H]$^+$ m/z 429.0686, found 429.0605. $^1$H NMR (CDCl$_3$, 600 MHz) δ 7.82 (s, 1H), 7.17 (s, 1H), 7.06 (s, 1H), 6.67 (m, 1H), 6.39 (d, J=1.89 Hz, 1H), 5.25 (d, J=0.9 Hz, 2H), 4.18 (s, 3H), 3.82 (s, 3H), 2.72 (s, 3H).

Example 2

2-Methoxy-6-(6-methoxy-4-((2-(trifluoromethyl)thiazol-4-yl)methoxy)benzofuran-2-yl)imidazo[2,1-b][1,3,4]thiadiazole

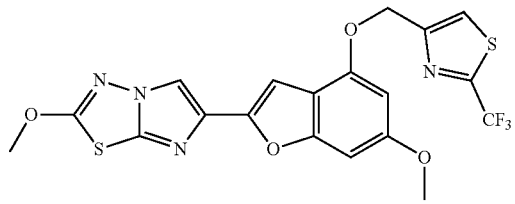 [SMILES: COc1cc(OCc2csc(C(F)(F)F)n2)c2cc(-c3cn4nc(OC)sc4n3)oc2c1]

2A. Ethyl 2-(trifluoromethyl)thiazole-4-carboxylate

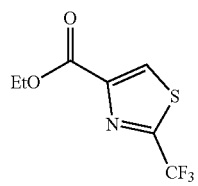

A mixture of 2,2,2-trifluoroacetamide (7.12 g, 63 mmol) and Lawesson's reagent (15.3 g, 37.8 mmol) in THF (60 mL) was heated at reflux for 18 hours. The reaction was then cooled down to RT and treated with ethyl bromopyruvate (8.0 mL, 63 mmol). The reaction was stirred at reflux for an additional 18 hours, then concentrated under vacuum and diluted with ethyl acetate. This mixture was washed with water (1×) and brine (1×), dried over anhydrous magnesium sulfate, filtered and concentrated. The residue was purified by silica gel chromatography (8×11 cm, toluene, then second time with 120 g silica gel, hexane/ethyl acetate) to give the title material (4.47 g, 32%) as a pale yellow solid. $^1$H NMR (CDCl$_3$, 400 MHz) δ 8.37 (s, 1H), 4.45 (q, J=7.0 Hz, 2H), 1.41 (t, J=7.0 Hz, 1H).

2B. (2-(Trifluoromethyl)thiazol-4-yl)methanol

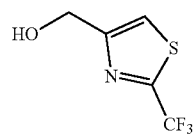

Ethyl 2-(trifluoromethyl)thiazole-4-carboxylate (Example 2A, 1.50 g, 6.66 mmol) was reacted as described in Example 1A and afforded the desired title material (0.95 g, 78%) as a clear oil after distillation (b.p.: 55-65° C./0.2 torr). $^1$H NMR (CDCl$_3$, 400 MHz) δ 7.47 (s, 1H), 4.85 (s, 2H), 2.25 (br s, 1H).

Example 2. 2-Methoxy-6-(6-methoxy-4-((2-(trifluoromethyl)thiazol-4-yl)methoxy)benzo furan-2-yl)imidazo[2,1-b][1,3,4]thiadiazole

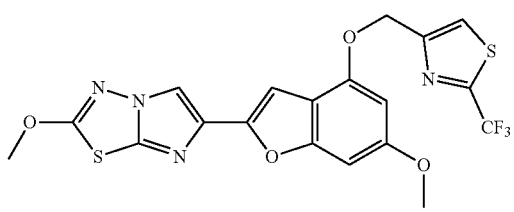 [SMILES: COc1cc(OCc2csc(C(F)(F)F)n2)c2cc(-c3cn4nc(OC)sc4n3)oc2c1]

6-Methoxy-2-(2-methoxyimidazo[2,1-b][1,3,4]thiadiazol-6-yl)benzofuran-4-ol (Example 1H, 0.100 g, 0.315 mmol) and (2-(trifluoromethyl)thiazol-4-yl)methanol (Example 2B, 0.075 g, 0.409 mmol) were reacted as described in Example 1 and afforded the title material (0.070, 46%) after crystallization in AcOEt. LC (Method B): 2.448 min. HRMS(ESI) calcd for C$_{19}$H$_{14}$F$_3$N$_4$O$_4$S$_2$ [M+H]$^+$ m/z 483.0403, found 483.0411. $^1$H NMR (CDCl$_3$, 600 MHz) δ 7.82 (s, 1H), 7.17 (s, 1H), 7.06 (s, 1H), 6.67 (m, 1H), 6.39 (d, J=1.89 Hz, 1H), 5.25 (d, J=0.9 Hz, 2H), 4.18 (s, 3H), 3.82 (s, 3H), 2.72 (s, 3H).

Example 3

2-Methoxy-6-(6-methoxy-4-((2-phenylthiazol-4-yl)methoxy)benzofuran-2-yl)imidazo[2,1-b][1,3,4]thiadiazole

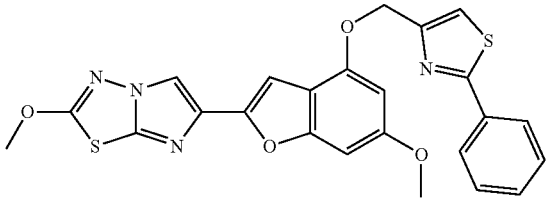 [SMILES: COc1cc(OCc2csc(-c3ccccc3)n2)c2cc(-c3cn4nc(OC)sc4n3)oc2c1]

3A. Methyl 2-phenylthiazole-4-carboxylate

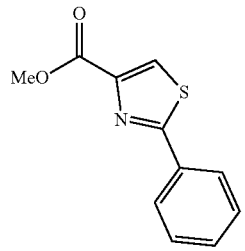 [SMILES: COC(=O)c1csc(-c2ccccc2)n1]

A solution of benzothioamide (4.0 g, 29.2 mmol) in THF (80 mL) was treated dropwise with methyl bromopyruvate (7.6 g, 39 mmol) and heated at reflux for 18 hours. The reaction was then concentrated under vacuum, diluted with ethyl acetate, washed with water (1×), brine (1×) and dried over anhydrous magnesium sulfate. The residue obtained after concentration was purified by silica gel chromatography (4.5×11 cm, 20% AcOEt/toluene), followed by a second purification with 20% AcOEt/hexane. The title material was obtained after concentration as a yellow oil (5.25, 77%). $^1$H NMR (CDCl$_3$, 400 MHz): 8.14 (s, 1H) 8.00 (m, 2H) 7.46-7.42 (m, 3H) 4.43 (q, J=7.0 Hz, 2H) 1.42 (t, J=7.3 Hz, 3H).

3B. (2-Phenylthiazol-4-yl)methanol

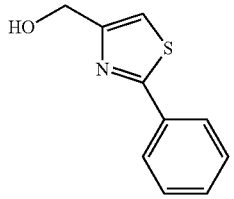 [SMILES: OCc1csc(-c2ccccc2)n1]

In a 250 mL round-bottom flask, methyl 2-phenylthiazole-4-carboxylate (Example 3A, 1.50 g, 6.43 mmol) was dissolved in ethyl ether (40 mL). The solution was cooled down to −78° C. and treated with lithium aluminum hydride (0.75 g, 19.76 mmol) portionwise over 20 minutes. The reaction was stirred at −78° C. for 3.5 hours, then treated with 20 mL of a saturated solution of $Na_2SO_4$. The reaction was allowed to reach RT and was diluted with ethyl acetate, washed with HCl 1N (1×), brine (1×), dried over anhydrous magnesium sulfate, filtered and concentrated. The residue was purified by silica gel chromatography (3×12 cm, 30% ethyl acetate/dichloromethane) to give a pale yellow oil (1.06 g) which was then distilled (bulb to bulb, bp: 110-120° C./0.2 torr) and provided the title material (0.88 g, 72%) as a clear oil. $^1$H NMR ($CDCl_3$, 400 MHz): 7.95-7.90 (m, 2H) 7.45-7.40 (m, 3H) 7.16 (s, 1H) 4.82 (s, 2H) 2.34 (br s, 1H).

Example 3. 2-Methoxy-6-(6-methoxy-4-((2-phenylthiazol-4-yl)methoxy)benzofuran-2-yl)imidazo[2,1-b][1,3,4]thiadiazole

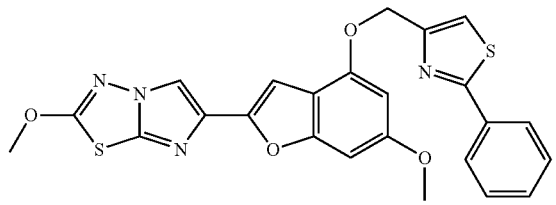 [SMILES: COc1cc(OCc2csc(-c3ccccc3)n2)c2cc(-c3cn4nc(OC)sc4n3)oc2c1]

A mixture of 6-methoxy-2-(2-methoxyimidazo[2,1-b][1,3,4]thiadiazol-6-yl)benzofuran-4-ol (Example 1H, 0.800 g, 2.52 mmol), triphenylphosphine (0.992 g, 3.78 mmol) and (2-phenylthiazol-4-yl)methanol (Example 3B, 0.555 g, 2.90 mmol) in a 200 mL flask fitted with an addition funnel was maintained under vacuum for ten minutes. The mixture was then flushed with nitrogen and charged with dry tetrahydrofuran (60 mL, distilled over lithium aluminum hydride). The solution was warmed to ~50° C. and then sonicated for 5 min. The cooled heterogeneous mixture was then treated at 22° C. with a solution of diisopropyl azodicarboxylate (0.663 g, 3.28 mmol) in tetrahydrofuran (15 mL), added dropwise over 2.5 h. The reaction was homogeneous (pale yellow) at the end of the addition. The mixture was then stirred for another 2.5 h (total 5 h). The reaction mixture was then diluted with dichloromethane (400 mL), washed with saturated sodium bicarbonate (20 mL), brine and dried (anhydrous magnesium sulfate). Evaporation gave a white solid which was chromatographed on silica gel (3×12 cm, elution dichloromethane-ethyl acetate 98.5:1.5 to 97:3). The fractions were collected and evaporated to give the desired compound (1.40 g) as a white solid, contaminated with hydrazide by tlc. Crystallization in ethyl acetate (40 mL) gave the pure title material (0.838 g, 68%) as a white solid. The mother liquors (0.475 g) were chromatographed on silica gel (3×12 cm, elution dichloromethane-ethyl acetate 98.5:1.5 to 97:3) to give after crystallization from ethyl acetate (30 mL) to provide additional desired compound (0.160 g, 13%, total 81%) as a white solid. LC (Method C): 2.480 min. HRMS(ESI) calcd for $C_{24}H_{19}N_4O_4S_2$ [M+H]$^+$ m/z 491.0842, found 491.0865. $^1$H NMR ($CDCl_3$, 400 MHz) 3.85 (s, 3H) 4.21 (s, 3H) 5.33-5.55 (m, 2H) 6.48 (d, J=1.96 Hz, 1H) 6.72 (dd, J=1.96, 0.78 Hz, 1H) 7.12 (s, 1H) 7.36-7.39 (m, 1H) 7.41-7.50 (m, 3H) 7.86 (s, 1H) 7.95-8.02 (m, 2H).

Example 4

2-Methoxy-6-(6-methoxy-4-((4-phenylthiazol-2-yl)methoxy)benzofuran-2-yl)imidazo[2,1-b][1,3,4]thiadiazole

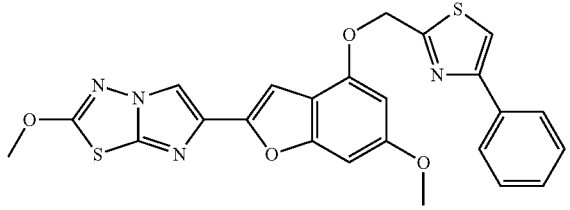 [SMILES: COc1cc(OCc2nc(-c3ccccc3)cs2)c2cc(-c3cn4nc(OC)sc4n3)oc2c1]

4A. Ethyl 2-amino-2-thioxoacetate

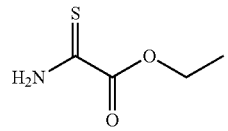

A solution of ethyl 2-amino-2-oxoacetate (5.00 g, 42.7 mmol) in tetrahydrofuran (150 mL) was treated with powdered (mortar and pestle) Lawesson's Reagent (9.50 g, 23.49 mmol) and the resulting orange clear solution was heated under reflux (bath temperature 85° C.) for 4 h (TLC product with higher Rf formed with some starting material left). The cooled mixture was concentrated under reduced pressure and the residue was diluted with ethyl acetate (400 mL) washed with saturated sodium bicarbonate, brine and dried over anhydrous magnesium sulfate. Evaporation gave an orange solid which was chromatographed on silica gel (3×10 cm, elution toluene-ethyl acetate 9:1) and provided the title material (3.189 g, 56%) of a yellow solid. LC (Method C): 0.816 min. $^1$H NMR ($CDCl_3$, 400 MHz) δ ppm: 1.41 (t, J=7.0 Hz, 3H), 4.38 (q, J=7.0 Hz, 2H), 7.69 (br s, 1H) 8.24 (br s, 1H).

4B. Ethyl 4-phenylthiazole-2-carboxylate

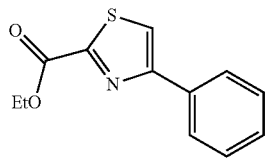 [SMILES: CCOC(=O)c1nc(-c2ccccc2)cs1]

A mixture of 2-bromo-1-phenylethanone (1.790 g, 8.99 mmol) and ethyl 2-amino-2-thioxoacetate (Example 4A, 1.20 g, 9.01 mmol) in benzene (80 mL) and ethanol (10 mL) was stirred at room temperature for 18 h. The mixture was heated at 80° C. for 1 h. The solvent was evaporated under reduced pressure and the residue was partitioned between ethyl acetate (300 mL) and saturated aqueous sodium bicarbonate (100 mL). The organic phase was washed with brine, dried over anhydrous magnesium sulfate and concentrated in vacuo. The residual clear oil was chromatographed on silica gel (4×10 cm, elution toluene-ethyl acetate 0-2-4%) and gave a yellow oil (1.588 g). This was distilled in vacuo (bp: 105-115° C./0.1 torr, bulb to bulb distillation, air bath temperature) to provide the title material (1.409 g, 67%) as a pale yellow syrup which solidified to an almost colorless solid upon standing. LC (Method C): 2.009 min. HRMS (ESI) calcd for $C_{12}H_{12}NO_2S$ [M+H]$^+$ m/z 234.0583, found 234.0597. $^1$H NMR (CDCl$_3$, 400 MHz) δ ppm: 1.48 (t, J=7.2 Hz, 3H), 4.52 (q, J=7.2 Hz, 2H), 7.35-7.49 (m, 3H), 7.75 (s, 1H), 7.93-8.00 (m, 2H).

4C. 2-(Hydroxymethyl)-4-phenylthiazole

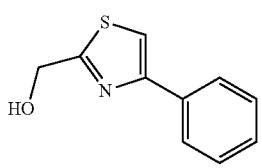 [SMILES: OCc1nc(-c2ccccc2)cs1]

A solution of ethyl 4-phenylthiazole-2-carboxylate (Example 4B, 1.300 g, 5.57 mmol) in diethyl ether (60 mL) in a 500 mL flask under a nitrogen atmosphere was cooled to −40° C. (dry ice-water-calcium chloride bath) and treated with solid LiAlH$_4$ (0.40 g, 10.54 mmol) added all at once. The mixture was stirred at −40° C. over 2.5 h. The reaction was quenched by dropwise addition of ethyl acetate (1 mL), water (0.4 mL) followed by 15% aqueous sodium hydroxide (0.4 mL) and water (1.2 mL). The bath was then removed and the mixture was stirred at room temperature for 50 min. The solid formed was filtered and washed with ether (50 mL). The combined filtrate and washing was washed with brine (20 mL) and dried over anhydrous magnesium sulfate. Evaporation gave a yellow oil which was purified by silica gel chromatography (2.5×8 cm, elution toluene-ethyl acetate 9:1, 8:2 to 7:3). The resulting light yellow oil (0.931 g) was then distilled in vacuo (bp: 105-110° C./0.1 torr, bulb to bulb, air bath temperature) to provide the title material (0.918 g, 86%) of a colorless syrup. LC (Method C): 1.672 min. HRMS(ESI) calcd for $C_{10}H_{10}NOS$ [M+H]$^+$ m/z 192.0478, found 192.0508. $^1$H NMR (CDCl$_3$, 400 MHz) δ ppm: 2.90 (br t, 1H), 5.02 (d, J=4.30 Hz, 2H), 7.31-7.38 (m, 1H), 7.39-7.45 (m, 2H), 7.46 (d, J=0.8 Hz, 1H), 7.85-7.92 (m, 2H).

4D. 2-(Bromomethyl)-4-phenylthiazole

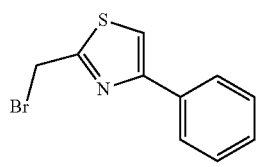 [SMILES: BrCc1nc(-c2ccccc2)cs1]

A solution of (4-phenylthiazol-2-yl)methanol (Example 4C, 0.530 g, 2.77 mmol) in dichloromethane (10 mL) was cooled to 0° C. (ice bath) and treated with PBr$_3$ (0.118 mL, 1.247 mmol) added dropwise over 2 min. A heavy white gum was immediately formed. After 10 min, the bath was removed and the solution was stirred at 22° C. for 4 h. The reaction mixture was quenched with ice (~10 g) and poured into a mixture of ethyl acetate (150 mL) and saturated sodium bicarbonate (50 mL). The organic phase was washed with brine, dried over anhydrous magnesium sulfate and concentrated in vacuo. The solid residue was chromatographed on silica gel (2.5×6 cm, elution toluene) to give the title material (0.561 g, 80%) as a light yellow oil which solidified in the fridge to a pale yellow solid. LC (Method C): 2.062 min. HRMS(ESI) calcd for $C_{10}H_9BrNS$ [M+H]$^+$ m/z 253.9634, found 253.9655. $^1$H NMR (CDCl$_3$, 400 MHz) δ ppm: 4.81 (s, 2H), 7.34-7.39 (m, 1H), 7.41-7.47 (m, 2H), 7.52 (s, 1H), 7.86-7.92 (m, 2H).

Example 4. 2-Methoxy-6-(6-methoxy-4-((4-phenylthiazol-2-yl)methoxy)benzofuran-2-yl)imidazo[2,1-b][1,3,4]thiadiazole

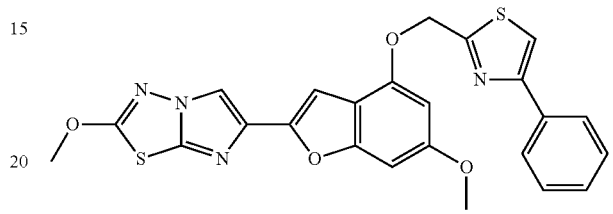

A suspension of 6-methoxy-2-(2-methoxyimidazo[2,1-b][1,3,4]thiadiazol-6-yl)benzofuran-4-ol (Example 1H, 0.080 g, 0.252 mmol) and 2-(bromomethyl)-4-phenylthiazole (0.128 g, 0.504 mmol) in N,N-Dimethylformamide (3 mL) was maintained under vacuum (10 mbar) for 5 minutes. The flask was then flushed with nitrogen and anhydrous freshly powdered (mortar and pestle) potassium carbonate (0.105 g, 0.756 mmol) was added all at once. The resulting mixture was stirred at room temperature with a few short sonication periods (~1 min) for 1 hour. The heterogeneous mixture became almost homogeneous (except the potassium carbonate) after 10 min and started to precipitate again to a cream solid. The reaction mixture was quenched with 1N hydrochloric acid (2 mL) and then partitioned between dichloromethane (150 mL) and saturated sodium bicarbonate (20 mL). The organic phase was washed with brine, dried over anhydrous magnesium sulfate and concentrated in vacuo. The solid pale yellow residue was chromatographed on silica gel (2.5×6 cm, elution dichloromethane-ethyl acetate 0-2-5%) to give the title material (0.116 g, 94%) as a pale yellow solid. Crystallization in ethyl acetate (12 mL) provided the title material (0.086 g) as a pale yellow solid. LC (Method C): 2.474 min. HRMS(ESI) calcd for $C_{24}H_{19}N_4O_4S_2$ [M+H]$^+$ m/z 491.0842, found 491.0864. $^1$H NMR (CDCl$_3$, 400 MHz) δ ppm: 3.86 (s, 3H), 4.22 (s, 3H), 5.54 (s, 2H), 6.48 (d, J=1.96 Hz, 1H), 6.75 (broad d, 1H), 7.15 (s, 1H), 7.32-7.39 (m, 1H), 7.41-7.49 (m, 2H), 7.53 (s, 1H), 7.87 (s, 1H), 7.90-7.95 (m, 2H).

Example 5

4-(4-(((6-Methoxy-2-(2-methoxyimidazo[2,1-b][1,3,4]thiadiazol-6-yl)benzofuran-4-yl)oxy)methyl)thiazol-2-yl)morpholine

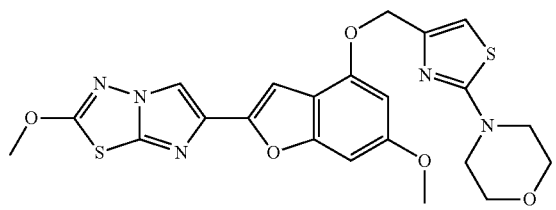 [SMILES: COc1cc(OCc2csc(N3CCOCC3)n2)c2cc(-c3cn4nc(OC)sc4n3)oc2c1]

5A. Methyl 2-morpholinothiazole-4-carboxylate

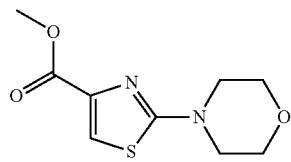

A solution of methyl 2-bromothiazole-4-carboxylate (0.20 g, 0.901 mmol) in THF (10 mL) was treated with morpholine (0.17 mL, 1.94 mmol) and refluxed for 18 h. The reaction was then diluted with ethyl acetate and washed with sat. NaHCO$_3$ (1×), brine (1×) and dried over anhydrous magnesium sulfate, filtered and concentrated. The residue was purified by silica gel chromatography (2.5×10 cm, 50% AcOEt/CH$_2$Cl$_2$) to give the title material (0.192 g, 92%) as a yellow solid. $^1$H NMR (CDCl$_3$, 400 MHz) δ ppm: 7.44 (s, 1H) 3.82 (s, 3H) 3.75 (m, 4H) 3.45 (m, 4H).

5B. (2-Morpholinothiazol-4-yl)methanol

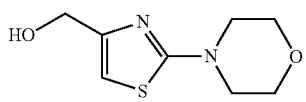

A solution of methyl 2-morpholinothiazole-4-carboxylate (0.76 g, 3.33 mmol) in ethyl ether (20 mL) was treated portion wise over 10 min. with lithium aluminum hydride (0.38 g, 10.01 mmol). The mixture was stirred at −78° C. for 4 hours, then slowly treated with ethyl acetate (10 mL) and sat. Na$_2$SO$_4$ (20 mL). The mixture was allowed to warm up to RT, diluted with ethyl acetate, washed with sat. NaHCO$_3$ (1×), brine (1×), dried over anhydrous magnesium sulfate, filtered and concentrated. The residue was purified on silica gel chromatography (3×10 cm, 25% AcOEt/CH$_2$Cl$_2$ to 100% AcOEt) to give the title material as a beige solid (0.458 g) which was then distilled (bulb to bulb, 135-145° C./0.2 torr) and afforded the desired product (0.455 g, 68%) as a white solid. LC (Method F): 0.873 min. HRMS(ESI) calcd for C$_8$H$_{13}$N$_2$O$_2$S [M+H]$^+$ m/z 201.07, found 201.2. $^1$H NMR (CDCl$_3$, 400 MHz) δ ppm: 6.43 (s, 1H) 4.53 (d, J=3.9 Hz, 2H) 3.79 (m, 4H) 3.44 (m, 4H) 2.17 (s, 1H).

Example 5. 4-(4-(((6-Methoxy-2-(2-methoxyimidazo[2,1-b][1,3,4]thiadiazol-6-yl)benzofuran-4-yl)oxy)methyl)thiazol-2-yl)morpholine

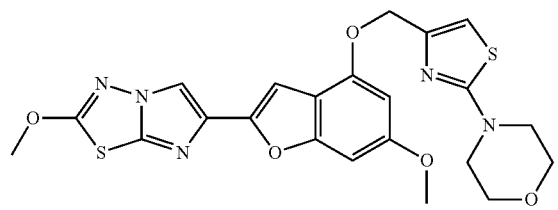 [SMILES: COc1cc(OCc2csc(N3CCOCC3)n2)c2cc(-c3cn4nc(OC)sc4n3)oc2c1]

6-Methoxy-2-(2-methoxyimidazo[2,1-b][1,3,4]thiadiazol-6-yl)benzofuran-4-ol (Example 1H, 0.10 g, 0.315 mmol), triphenylphosphine (0.124 g, 0.473 mmol) and (2-morpholinothiazol-4-yl)methanol (Example 5B, 0.086 g, 0.429 mmol) were added in a 25 mL round-bottom flask and purged under vacuum and nitrogen. Tetrahydrofuran (8 mL) was then added and the mixture was treated with DIAD (0.083 g, 0.410 mmol) in tetrahydrofuran (10 mL). The mixture was stirred at 22° C. for 1 hour and diluted with ethyl acetate. This was washed with sat. NaHCO$_3$ (1×) and brine (1×), dried over anhydrous magnesium sulfate, filtered and concentrated. The residue was purified on silica gel column chromatography (2.5×10 cm, 40% ethyl acetate in CH$_2$Cl$_2$) and the residue obtained after concentration was crystallized in ethyl acetate to give the title material as crystals (0.083 g, 53%) and as an amorphous impure solid from the mother liquor (0.169 g). LC (Method F): 2.466 min. HRMS(ESI) calcd for C$_{22}$H$_{22}$N$_5$O$_5$S$_2$ [M+H]$^+$ m/z 500.1057, found 500.1075. $^1$H NMR (CDCl$_3$, 400 MHz) δ ppm: 7.82 (s, 1H) 7.07 (s, 1H) 6.67 (d, J=2 Hz, 1H) 6.62 (s, 1H) 6.40 (d, J=1.5 Hz, 1H) 5.10 (s, 2H) 4.19 (s, 3H) 3.82 (s, 3H) 3.81 (m, 4H) 3.46 (m, 4H).

Example 6

2-Methoxy-6-(6-methoxy-4-((2-((2-methoxyethoxy)methyl)thiazol-4-yl)methoxy)benzofuran-2-yl)imidazo[2,1-b][1,3,4]thiadiazole

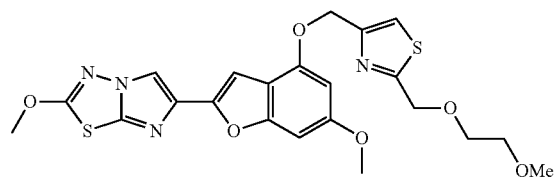 [SMILES: COCCOCc1nc(COc2cc(OC)cc3oc(-c4cn5nc(OC)sc5n4)cc23)cs1]

6A. 2-(2-Methoxyethoxy)acetamide

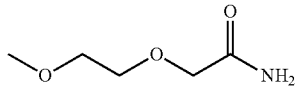

A solution of 2-(2-methoxyethoxy)acetic acid (5.0 g, 37.3 mmol) in CH$_2$Cl$_2$ (50 mL) was treated with oxalyl chloride (9.5 mL, 109 mmol) and DMF (2 drops) and the reaction was stirred for 3 hours. After evaporation under vacuum, the residue was co-evaporated with CH$_2$Cl$_2$ (2×) and then dissolved in THF (10 mL) and treated dropwise with a mixture of ammonium hydroxide (12 mL), THF (25 mL) and water (10 mL) for 5 min. The reaction was then stirred at 0-5° C. for 30 min. then at 22° C. for 1 h. The reaction was diluted with CH$_2$Cl$_2$, washed with water (1×), HCl 1N (1×), sat. NaHCO$_3$ (1×) and brine (1×), dried over anhydrous magnesium sulfate, filtered and concentrated. As the product appeared to be soluble in water, the aqueous phase was evaporated under vacuum and extracted with CH$_2$Cl$_2$ (5×200 mL), dried over anhydrous magnesium sulfate, filtered and concentrated to give the title material (3.59 g, 72%) as an oil which solidified. This was distilled (bulb to bulb, 105-115° C./0.2 torr) to provide the pure desired product (3.39 g) as a clear oil which solidified as a white solid. $^1$H NMR (CDCl$_3$, 400 MHz) δ ppm: 6.93 (very broad s, 1H), 5.43 (very broad s, 1H), 3.99 (s, 2H), 3.66-3.70 (m, 2H), 3.53-3.56 (m, 2H), 3.39 (s, 3H).

6B. 2-(2-Methoxyethoxy)ethanethioamide

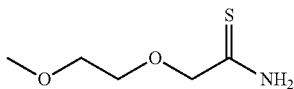

A solution of 2-(2-methoxyethoxy)acetamide (Example 6A, 3.39 g, 25.5 mmol) in THF (40 mL) was treated with Lawesson's reagent (6.55 g, 16.19 mmol) and the reaction was refluxed for 18 hours. The reaction was then allowed to cool down to RT and was concentrated under vacuum, diluted with ethyl acetate, washed with sat. NaHCO₃ (1×) and brine (1×). The aqueous phases were extracted with ethyl acetate (2×200 mL) and the organic extracts were dried over anhydrous magnesium sulfate, filtered and concentrated. The residue was purified by silica gel chromatography (3.5×11 cm, 30% AcOEt/CH₂Cl₂) to give the title material (3.26 g, 86%) as a yellow oil. ¹H NMR (CDCl₃, 400 MHz) δ ppm: 8.58 (very broad s, 1H), 7.50 (very broad s, 1H), 4.36 (s, 2H), 3.66-3.69 (m, 2H), 3.53-3.56 (m, 2H), 3.39 (s, 3H).

6C. Ethyl 2-((2-methoxyethoxy)methyl)thiazole-4-carboxylate

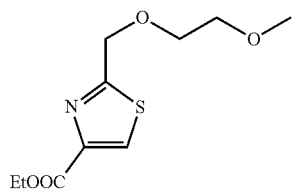 [SMILES: CCOC(=O)c1csc(COCCOC)n1]

To a solution of 2-(2-methoxyethoxy)ethanethioamide (Example 6B, 3.26 g, 21.85 mmol) in ethanol (60 mL) was added dropwise ethylbromopyruvate (3.7 mL, 29.5 mmol) and the mixture was refluxed for 18 hours. The reaction was then concentrated under vacuum, diluted with ethyl acetate, washed with water (1×), brine (1×), dried over anhydrous magnesium sulfate, filtered and concentrated. The residue was purified by silica gel column chromatography (3.5×10 cm, 30% ethyl acetate/CH₂Cl₂) to give the title material (4.36 g, 81%) as an oil. LC (Method F): 1.791 min. ¹H NMR (CDCl₃, 400 MHz) δ ppm: 8.16 (s, 1H), 4.87 (s, 2H), 4.41 (q, J=7.10 Hz, 2H), 3.74-3.77 (m, 2H), 3.57-3.60 (m, 2H), 3.39 (s, 3H), 1.39 (t, J=7.10 Hz, 3H).

6D. (2-((2-Methoxyethoxy)methyl)thiazol-4-yl)methanol

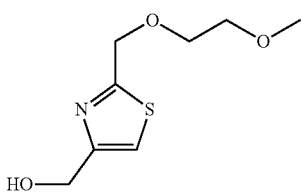

To a solution of ethyl 2-((2-methoxyethoxy)methyl)thiazole-4-carboxylate (Example 6C, 2.27 g, 9.25 mmol) in ether (50 mL) was added portion wise lithium aluminum hydride (1.06 g, 27.9 mmol) over 10 min. at −78° C. The reaction was then stirred at −78° C. for 1 hour. Ethyl acetate (10 mL) was then added to the reaction followed by water (20 mL) and the reaction was allowed to reach RT. The mixture was then diluted with ethyl acetate, washed with HCl 1N (1×) and brine (1×). The combined aqueous phases were extracted with ethyl acetate (2×300 mL), dried over anhydrous magnesium sulfate, filtered and concentrated. The residue was purified by silica gel chromatography (3.5×10 cm, ethyl acetate) to give the title material (0.357 g, 19%) as a brown oil. LC (Method F): 1.791 min. ¹H NMR (CDCl₃, 400 MHz) δ ppm: 7.16 (s, 1H), 4.82 (s, 2H), 4.74 (broad s, 2H), 3.7-3.75 (m, 2H), 3.54-3.61 (m, 2H), 3.38 (s, 3H), 2.28 (broad s, 1H).

6E. 4-(Bromomethyl)-2-((2-methoxyethoxy)methyl)thiazole

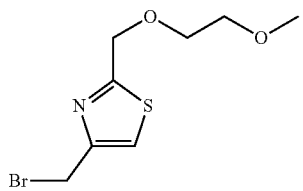

A solution of (2-((2-methoxyethoxy)methyl)thiazol-4-yl)methanol (0.35 g, 1.72 mmol) in ether (15 mL) was treated with PBr₃ (0.1 mL, 1.06 mmol) at RT. There is formation of a precipitate. The reaction was stirred at RT for 18 hours, then diluted with ethyl acetate and washed with sat. NaHCO₃ (1×) and brine (1×), dried over anhydrous magnesium sulfate, filtered and concentrated. The residue was purified by silica gel chromatography (3×10 cm, 20% ethyl acetate/CH₂Cl₂) to give the title material (0.233 g, 51%) as a clear oil. ¹H NMR (CDCl₃, 400 MHz) δ ppm: 7.27 (s, 1H), 4.83 (s, 2H), 4.55 (s, 2H), 3.73-3.76 (m, 2H), 3.57-3.60 (m, 2H), 3.39 (s, 3H).

Example 6. 2-Methoxy-6-(6-methoxy-4-((2-((2-methoxyethoxy)methyl)thiazol-4-yl)methoxy)benzofuran-2-yl)imidazo[2,1-b][1,3,4]thiadiazole

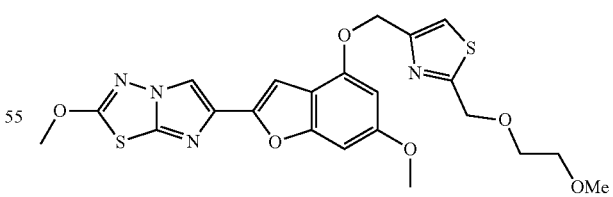

A suspension of 6-methoxy-2-(2-methoxyimidazo[2,1-b][1,3,4]thiadiazol-6-yl)benzofuran-4-ol (Example 1H, 0.10 g, 0.315 mmol) and 4-(bromomethyl)-2-((2-methoxyethoxy)methyl)thiazole (Example 6E, 0.10 g, 0.376 mmol) in DMF (5 mL) was purged under vacuum and nitrogen for 10 minutes. The mixture was then treated with potassium carbonate (0.10 g, 0.724 mmol) and the reaction was stirred at RT for 2.5 hours. The reaction was then diluted with dichloromethane, washed with water (1×), brine (1x), dried over anhydrous magnesium sulfate, filtered and concentrated. The residue was purified by silica gel chromatography (2.5×10 cm, 50% ethyl acetate/CH$_2$Cl$_2$) to give the title material which was crystallized in ethyl acetate and provided the desired title material (0.055 g, 35%) along with non-crystallized material (9 mgs, 6%). LC (Method F): 2.476 min. HRMS(ESI) calcd for C$_{22}$H$_{23}$N$_4$O$_6$S$_2$ [M+H]$^+$ m/z 503.1054, found 503.1066. $^1$H NMR (CDCl$_3$, 400 MHz) δ ppm: 7.82 (s, 1H), 7.35 (s, 1H), 7.05 (s, 1H), 6.68 (broad s, 1H), 6.39 (d, J=1.9 Hz, 1H), 5.28 (s, 2H), 4.86 (s, 2H), 4.19 (s, 3H), 3.82 (s, 3H), 3.74-3.77 (m, 2H), 3.58-3.61 (m, 2H), 3.39 (s, 3H).

Example 7

2-Methoxy-6-(6-methoxy-4-((5-phenyl-1,2,4-thiadiazol-3-yl)methoxy)benzofuran-2-yl)imidazo[2,1-b][1,3,4]thiadiazole

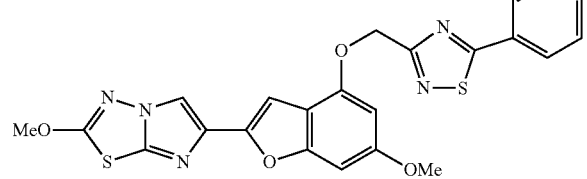

7A. Ethyl 5-phenyl-1,2,4-thiadiazole-3-carboxylate

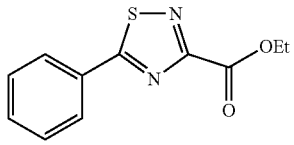 [SMILES: CCOC(=O)c1nsc(-c2ccccc2)n1]

A mixture of ethyl 2-oxo-1,3,4-oxathiazole-5-carboxylate (U.S. Publication No. 2005/0096362) (1.5 g, 8.56 mmol) and benzonitrile (4.37 ml, 42.8 mmol) in 1,2-dichlorobenzene (15.42 ml, 137 mmol) was heated to 160° C. for 4 days. The reaction was then cooled down to RT and the solvent was evaporated by heated the reaction at 75° C. at maximum vacuum. The residue was purified on silica gel chromatography (100% CH$_2$Cl$_2$ to 3% EtOAc in CH$_2$Cl$_2$) to provide the title material (0.064 g, 3%). LC (Method B): 2.021 min. HRMS(ESI) calcd for C$_{11}$H$_{11}$N$_2$O$_2$S [M+H]$^+$ m/z 235.0541, found 235. $^1$H NMR (CDCl$_3$, 400 MHz) δ ppm: 8.01-8.09 (m, 1H), 7.49-7.59 (m, 2H), 4.56 (q, J=7.17 Hz, 1H), 1.50 (t, J=7.24 Hz, 1H).

7B. (5-Phenyl-1,2,4-thiadiazol-3-yl)methanol

To a solution of ethyl 5-phenyl-1,2,4-thiadiazole-3-carboxylate (Example 7A, 230 mg, 0.982 mmol) in anhydrous ethanol (3 mL, 51.4 mmol) was added NaBH$_4$ (149 mg, 3.93 mmol) at 0° C. The reaction mixture was heated to 80° C. for 30 min, then HCl 1N (1 mL) was added and ethanol was evaporated. Dichloromethane was added to the reaction followed by brine and this was extracted with dichloromethane (3×). The organic layers were dried over anhydrous magnesium sulfate and concentrated. The residue was purified on silica gel column chromatography (100% CH$_2$Cl$_2$ up to 10% EtOAc/CH$_2$Cl$_2$) to provide the title material (25 mgs, 13%). LC (Method B): 1.858 min. LCMS (APCI) calcd for C$_9$H$_9$N$_2$OS [M+H]$^1$ m/z 193.04, found 193.0. $^1$H NMR (CDCl$_3$, 400 MHz) δ ppm: 7.89-8.03 (m, 2H), 7.46-7.62 (m, 3H), 4.99 (d, J=5.87 Hz, 2H), 2.81 (t, J=6.06 Hz, 1H).

Example 7. 2-Methoxy-6-(6-methoxy-4-((5-phenyl-1,2,4-thiadiazol-3-yl)methoxy)benzofuran-2-yl)imidazo[2,1-b][1,3,4]thiadiazole

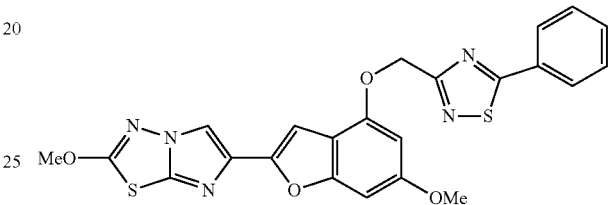

6-Methoxy-2-(2-methoxyimidazo[2,1-b][1,3,4]thiadiazol-6-yl)benzofuran-4-ol (Example 1H, 8.25 mg, 0.026 mmol) and (5-phenyl-1,2,4-thiadiazol-3-yl)methanol (Example 7B, 5 mg, 0.025 mmol) were put in a flask and this was flushed with N$_2$. Dry THF (4 mL) was added and to this resulting suspension was added tri-n-butylphosphine (0.017 mL, 0.065 mmol) and a solution of 1,1'-(azodicarbonyl)dipiperidine (16.57 mg, 0.065 mmol) in dry THF (2.5 mL) was added dropwise via a syringe pump over 2 h. The resulting being suspension was stirred for an additional 2 hours at RT, at which time LC showed that no starting material remained. The mixture was diluted with EtOAc, washed with 0.2N HCl, sat. aqueous NaHCO$_3$ and brine, dried over anhydrous magnesium sulfate, filtered and concentrated. The residue was purified on silica gel chromatography (50% dichloromethane/hexanes to 100% dichloromethane to 1% EtOAc/CH$_2$Cl$_2$ to 7% EtOAc/CH$_2$Cl$_2$) and lyophilized in MeCN/water to give the title material (6.2 mgs, 49%). LC (Method B): 2.615 min. HRMS(ESI) calcd for C$_{23}$H$_{18}$N$_5$O$_4$S$_2$ [M+H]$^+$ m/z 492.0795, found 492.0828. $^1$H NMR (CDCl$_3$, 400 MHz) δ ppm: 8.00 (dd, J=8.02, 1.37 Hz, 2H), 7.85 (s, 1H), 7.50-7.56 (m, 3H), 7.14 (s, 1H), 6.71-6.75 (m, 1H), 6.51 (d, J=1.57 Hz, 1H), 5.51 (s, 2H), 4.21 (s, 3H), 3.84 (s, 3H).

Example 8

2-Methoxy-6-(6-methoxy-4-((5-phenyl-1,3,4-thiadiazol-2-yl)methoxy)benzofuran-2-yl)imidazo[2,1-b][1,3,4]thiadiazole

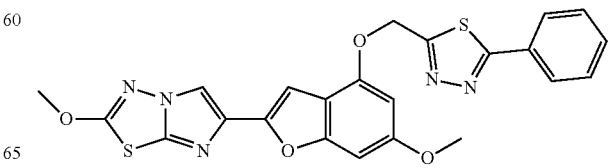

8A. Ethyl 5-phenyl-1,3,4-thiadiazole-2-carboxylate

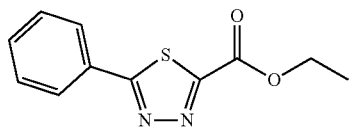 [SMILES: CCOC(=O)c1nnc(-c2ccccc2)s1]

To a solution of ethyl 2-(2-benzoylhydrazinyl)-2-oxoacetate (1 g, 4.23 mmol) in dry THF (5 ml, 61.0 mmol) was added the Lawesson's Reagent (1.079 g, 2.67 mmol). The reaction was stirred at r.t. for 2 h without any reaction. The mixture was then heated to 50° C. and then heated to reflux. Additional Lawesson's Reagent (1.079 g, 2.67 mmol) was added and after 16 h at reflux, the reaction was halfway completed. The mixture was evaporated to dryness and the residue was purified by silica gel column chromatography (50% $CH_2Cl_2$/hexanes up to 100% $CH_2Cl_2$) to provide the title material (0.35 g, 35%). LC (Method B): 2.063 min, LCMS (APCI) calcd for $C_{11}H_{11}N_2O_2S$ $[M+H]^+$ m/z 235.05, found 235.0. $^1H$ NMR ($CDCl_3$, 400 MHz) δ ppm: 1.49 (t, J=1.00 Hz, 3H), 4.55 (q, J=1.00 Hz, 2H), 7.45-7.65 (m, 3H), 8.02-8.07 (m, 2H).

8B. (5-Phenyl-1,3,4-thiadiazol-2-yl)methanol

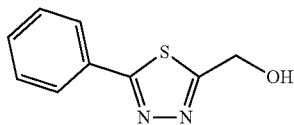 [SMILES: OCc1nnc(-c2ccccc2)s1]

To a solution of ethyl 5-phenyl-1,3,4-thiadiazole-2-carboxylate (350 mgs, 1.494 mmol) in anhydrous methanol (5 mL, 124 mmol) was added $NaBH_4$ (226 mgs, 5.98 mmol) at 0° C. The reaction mixture was stirred at ambient temperature for 16 h. AcOH (2 mL) was added and the reaction was concentrated to dryness. The residue was dissolved in EtOAc, brine and water and extracted with EtOAc (3×). The combined organic extracts were washed with sat. aqueous $NaHCO_3$ and brine, and dried over anhydrous magnesium sulfate. After filtration and evaporation, the residue was triturated with ethyl ether to give the title material as a first crop (150 mgs, 52%). LC (Method B): 2.022 min, LCMS (APCI) calcd for $C_9H_9N_2OS$ $[M+H]^+$ m/z 193.04, found 193.2. $^1H$ NMR ($CDCl_3$, 400 MHz) δ ppm: 7.92-8.03 (m, 2H), 7.44-7.59 (m, 3H), 5.14 (br. d, J=3.90 Hz, 2H), 2.63 (br. s., 1H).

Example 8. 2-Methoxy-6-(6-methoxy-4-((5-phenyl-1,3,4-thiadiazol-2-yl)methoxy)benzofuran-2-yl)imidazo[2,1-b][1,3,4]thiadiazole

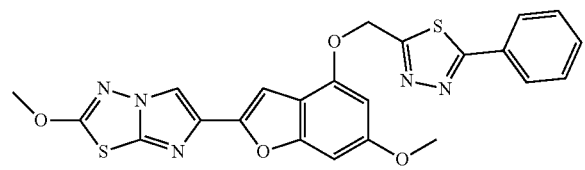 [SMILES: COc1cc(OCc2nnc(-c3ccccc3)s2)c2cc(-c3cn4nc(OC)sc4n3)oc2c1]

In a 200 mL round-bottomed flask, benzene was added to ethyl 5-phenyl-1,3,4-thiadiazole-2-carboxylate (Example 8B, 80 mgs, 0.252 mmol) and 6-methoxy-2-(2-methoxyimidazo[2,1-b][1,3,4]thiadiazol-6-yl)benzofuran-4-ol (Example 1H, 58.2 mgs, 0.303 mmol) and the mixture was sonicated for 30 sec. and concentrated in vacuo to remove traces of water in the starting material. Triphenylphosphine (99 mgs, 0.378 mmol) was added and the mixture was dried on high vacuum for 10 min. THF (40 mL) were added and the mixture was sonicated/heated for 5 min. Diisopropyl azodicarboxylate (68.6 µl, 0.353 mmol) in THF (4 mL) was added dropwise on app. 1 h and LC/MS showed that the reaction was not complete. Diisopropyl azodicarboxylate (2 drops) were added again and the mixture was diluted in $CH_2Cl_2$, washed with sat. aqueous $NaHCO_3$ (1×), brine (1×), and dried over anhydrous $MgSO_4$ and concentrated. The residue was purified on silica gel chromatography (100% $CH_2Cl_2$ up to 15% $EtOAc/CH_2Cl_2$) to give a residue which was triturated with MeCN and afforded the title material (36 mgs, 29%). LC (Method A): 2.901 min. HRMS(ESI) calcd for $C_{23}H_{17}N_5O_4S_2$ $[M+H]^+$ m/z 492.0722, found 492.0806. $^1H$ NMR ($CDCl_3$, 400 MHz) δ ppm: 7.96-8.02 (m, 2H), 7.87 (s, 1H), 7.45-7.55 (m, 3H), 7.10 (s, 1H), 6.73-6.78 (m, 1H), 6.48 (d, J=1.57 Hz, 1H), 5.63 (s, 2H), 4.22 (s, 3H), 3.86 (s, 3H).

Example 9

2-Methoxy-6-(6-methoxy-4-((1-phenyl-1H-1,2,3-triazol-4-yl)methoxy)benzofuran-2-yl)imidazo[2,1-b][1,3,4]thiadiazole

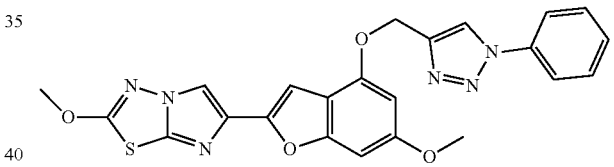

9A. 2-Methoxy-6-(6-methoxy-4-(prop-2-yn-1-yloxy)benzofuran-2-yl)imidazo[2,1-b][1,3,4]thiadiazole

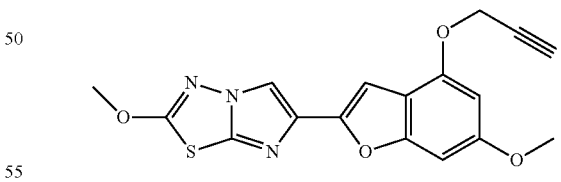

A solution of 6-methoxy-2-(2-methoxyimidazo[2,1-b][1,3,4]thiadiazol-6-yl)benzofuran-4-ol (Example 1H, 205 mgs, 0.646 mmol) in THF (10 mL) was treated at r.t. and under a nitrogen atmosphere, with propargyl alcohol (0.096 mL, 1.615 mmol), tri-n-butylphosphine (0.398 mL, 1.615 mmol) and dropwise, over a 25 min period with a solution of 1,1'-(azodicarbonyl)dipiperidine (408 mgs, 1.615 mmol) in THF (10 mL). The mixture was sonicated in a bath for 30 min and stirred at r.t. for another 30 min. The mixture was then dissolved in dichloromethane (50 mL) and washed with sat. aqueous $NaHCO_3$, brine and dried ($MgSO_4$). Evaporation of the solvent gave a solid that was purified by silica gel column chromatography ISCO to give the title material (180 mg, 0.507 mmol, 78% yield). $^1$H NMR (DMSO-$d_6$, 400 MHz) δ ppm: 8.38 (s, 1H), 6.92 (s, 1H), 6.86 (dd, J=1.8, 1.0 Hz, 1H), 6.53 (d, J=1.6 Hz, 1H), 4.94 (d, J=2.7 Hz, 2H), 4.21 (s, 3H), 3.77-3.84 (m, 3H), 3.60-3.66 (m, 1H).

9B. Azidobenzene

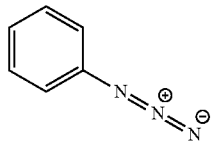

A solution of aniline (500 mgs, 5.37 mmol) in acetonitrile (10 mL, 191 mmol) was cooled down in an ice bath and treated with tert-butyl nitrite (680 mgs, 6.59 mmol) and dropwise with TMS-N$_3$ (0.713 mL, 5.37 mmol). The ice bath was removed and the mixture was stirred overnight at r.t. under N$_2$. Acetonitrile was carefully evaporated (NB: azidobenzene is also volatile) and the residue (750 mgs) was passed through a silica gel pad (20 g) and eluted with petroleum ether (35-55° C.). Evaporation of the solvent gave the title material as an oil (500 mgs, 4.20 mmol, 78% yield) that still contains some traces of solvent as shown by $^1$H NMR. $^1$H NMR (CDCl$_3$, 400 MHz) δ ppm: 7.32-7.41 (m, 2H), 7.12-7.19 (m, 1H), 7.01-7.09 (m, 2H).

Example 9. 2-Methoxy-6-(6-methoxy-4-((1-phenyl-1H-1,2,3-triazol-4-yl)methoxy)benzo furan-2-yl)imidazo[2,1-b][1,3,4]thiadiazole

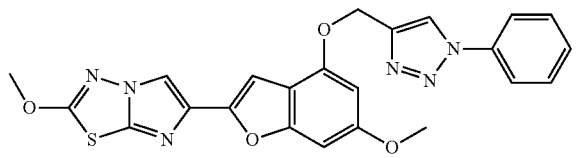 [SMILES: COc1cc(OCc2cn(-c3ccccc3)nn2)c2cc(-c3cn4nc(OC)sc4n3)oc2c1]

A solution of 2-methoxy-6-(6-methoxy-4-(prop-2-yn-1-yloxy)benzofuran-2-yl)imidazo[2,1-b][1,3,4]thiadiazole (Example 9A, 20 mgs, 0.056 mmol) and azidobenzene (Example 9B, 19 mgs, 0.159 mmol) in DMF (4 mL, 51.7 mmol) was treated at r.t. and under a nitrogen atmosphere with sodium (R)-2-((S)-1,2-dihydroxyethyl)-4-hydroxy-5-oxo-2,5-dihydrofuran-3-olate (8 mgs, 0.040 mmol) and copper(II) sulfate pentahydrate (5 mgs, 0.020 mmol). The mixture was stirred for 2 hours (reaction followed by HPLC) and was then diluted with dichloromethane (60 mL) and washed with sat. NaHCO$_3$, brine and dried (MgSO$_4$). The solvent was evaporated and the solid residue was triturated with acetonitrile (2×1 mL) and lyophilized to give the title material (13 mgs, 0.027 mmol, 49% yield). LC (Method A): 2.213 min. HRMS(ESI) calcd for C$_{23}$H$_{19}$N$_6$O$_4$S [M+H]$^+$ m/z 475.1183, found 475.1204. $^1$H NMR (DMSO-$d_6$, 400 MHz) δ ppm: 9.04 (s, 1H), 8.37 (s, 1H), 7.90-7.99 (m, 2H), 7.58-7.67 (m, 2H), 7.51 (tt, J=7.4, 1.2 Hz, 1H), 6.97-7.03 (m, 1H), 6.83-6.88 (m, 1H), 6.71 (d, J=1.6 Hz, 1H), 5.38 (s, 3H), 4.20 (s, 3H), 3.83 (s, 3H).

Example 10

2-Methoxy-6-(6-methoxy-4-((1-phenyl-1H-1,2,3-triazol-5-yl)methoxy)benzofuran-2-yl)imidazo[2,1-b][1,3,4]thiadiazole

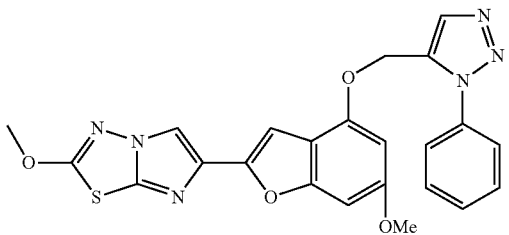 [SMILES: COc1cc(OCc2cnnn2-c2ccccc2)c2cc(-c3cn4nc(OC)sc4n3)oc2c1]

In a 5 mL microwave vial, was added 2-methoxy-6-(6-methoxy-4-(prop-2-yn-1-yloxy)benzofuran-2-yl)imidazo[2,1-b][1,3,4]thiadiazole (Example 9A, 27 mgs, 0.076 mmol), azidobenzene (Example 9B, 30 mgs, 0.252 mmol), anhydrous DMF (2.5 mL, 32.3 mmol) and (Cp*RuCl)$_4$ (12 mgs) under a nitrogen atmosphere. The vial was capped and heated at 110° C. for 20 min. in the microwave apparatus. The solvent was evaporated and the residue was purified by silica gel chromatography ISCO, concentrated and twice triturated with methanol (2×1 mL). To the solid was added acetonitrile (2 mL) and water (4 mL) and the mixture was freeze dried over the weekend to give the title material (5 mgs, 10.54 µmol, 14% yield). LC (Method F): 2.480 min. HRMS(ESI) calcd for C$_{23}$H$_{19}$N$_6$O$_4$S [M+H]$^+$ m/z 475.1183, found 475.1234. $^1$H NMR (DMSO-$d_6$, 400 MHz) δ ppm: 8.35 (s, 1H), 8.12 (s, 1H), 7.66-7.73 (m, 2H), 7.53-7.63 (m, 3H), 6.84 (dd, J=2.0, 0.8 Hz, 1H), 6.75 (d, J=0.8 Hz, 1H), 5.40 (s, 2H), 4.20 (s, 3H), 3.79 (s, 3H).

Preparation of Alcohols

The following alcohols were prepared according to the procedures described in Examples 3 to 8.

| Structure | Formula | Calc. [M + H]$^+$ m/z | Calc. [M + H]$^+$ – H$_2$O m/z | LCMS [M + H]$^+$ m/z | LCMS [M + H]$^+$ – H$_2$O m/z | HPLC Retention Time (Min)/Method | NMR |
|---|---|---|---|---|---|---|---|
| ![structure] F$_3$C-phenyl-thiazole-CH$_2$OH | C$_{11}$H$_8$F$_3$NOS | 260.04 | 242.04 | 260.00 | 242.00 | 1.943/A | $^1$H NMR (CDCl$_3$) δ ppm: 8.07 (d, J = 8.2 Hz, 2H) 7.71 (d, J = 8.2 Hz, 2H) 7.28 (s, 1H) 4.87 (d, J = 5.5 Hz, 2H) 2.31 (t, J = 5.5 Hz, 1H) |

-continued

| Structure | Formula | Calc. [M + H]+ m/z | Calc. [M + H]+ − H2O m/z | LCMS [M + H]+ m/z | LCMS [M + H]+ − H2O m/z | HPLC Retention Time (Min)/ Method | NMR |
|---|---|---|---|---|---|---|---|
| 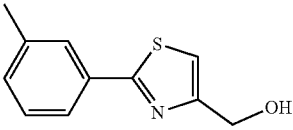 | $C_{11}H_{11}NOS$ | 206.0634 | 189.06 | 206.1 | 188.1 | 1.842/A | $^1$H NMR (CDCl$_3$) δ ppm: 7.78 (s, 1H) 7.70-7.75 (m, 1H) 7.30-7.36 (m, 1H) 7.23-7.27 (m, 1H) 7.16-7.19 (m, 1H) 4.84 (d, J = 5.5 Hz, 2H) 2.53 (t, J = 6.1 Hz, 1H) 2.42 (s, 3H) |
| 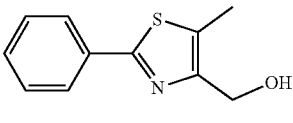 | $C_{11}H_{11}NOS$ | 206.0634 | | 206.0674 | | 1.616/C | $^1$H NMR (400 MHz, CDCl$_3$) δ ppm: 2.07 (t, J = 5.1 Hz, 1H) 2.46 (s, 3H) 4.83 (d, J = 5.1 Hz, 2H) 7.34-7.51 (m, 3H) 7.80-8.01 (m, 2H) |
| 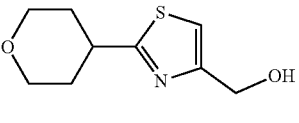 | $C_9H_{13}NO_2S$ | 200.074 | | 200.077 | | 1.139/C | $^1$H NMR (400 MHz, CDCl$_3$) δ ppm: 1.75-1.99 (m, 2H) 1.99-2.15 (m, 2H) 2.27-2.45 (m, 1H) 3.11-3.34 (m, 1H) 3.55 (td, J = 11.74, 1.96 Hz, 2H) 4.08 (ddd, J = 11.74, 4.11, 1.37 Hz, 2H) 4.76 (d, J = 5.87 Hz, 2H) 7.09 (d, J = 0.78 Hz, 1H) |
| 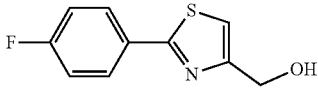 | $C_{10}H_8FNOS$ | 210.04 | 192.03 | 210 | | 1.607/A | $^1$H NMR (400 MHz, CDCl$_3$) δ ppm: 7.88-7.97 (m, 2H), 7.71 (t, J = 1.0 Hz, 1H), 7.10-7.18 (m, 2H), 4.91 (dd, J = 6.1, 1.0 Hz, 2H), 1.92 (t, J = 6.1 Hz, 1H) |
| 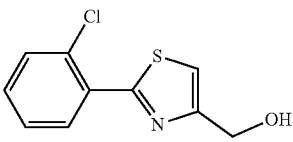 [SMILES: OCc1csc(-c2ccccc2Cl)n1] | $C_{10}H_8ClNOS$ | | | | | 1.819/A | $^1$H NMR (400 MHz, CDCl$_3$) δ ppm: $^1$H NMR (400 MHz, CDCl$_3$) δ ppm: 8.15-8.2 (m, 1H), 7.45-7.5 (m, 1H), 7.3-7.41 (m, 3H), 4.85 (d, J = 5.9 Hz, 2H), 2.33 (t, J = 5.9 Hz, 1H) |
| 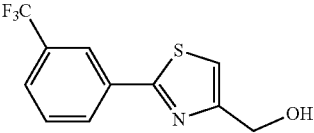 [SMILES: OCc1csc(-c2cccc(C(F)(F)F)c2)n1] | $C_{11}H_8F_3NOS$ | 260.0351 | | 260.0362 | | 1.987/A | $^1$H NMR (400 MHz, CDCl$_3$) δ ppm: 8.19 (s, 1H), 8.07 (d, J = 7.5 Hz, 1H), 7.65 (d, J = 7.9 Hz, 1H), 7.54 (broad t, 1H), 7.24 (s, 1H), 4.83 (s, 2H), 2.58 (broad s, 1H) |
| 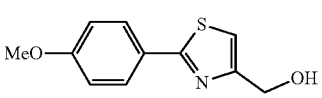 [SMILES: COc1ccc(-c2nc(CO)cs2)cc1] | $C_{11}H_{11}NO_2S$ | 222.0583 | | 222.0591 | | 1.712/A | $^1$H NMR (400 MHz, CDCl$_3$) δ ppm: 7.86 (d, J = 8.8 Hz, 2H), 7.08 (s, 1H), 6.93 (d, J = 8.8 |

-continued

| Structure | Formula | Calc. [M + H]+ m/z | Calc. [M + H]+ − H2O m/z | LCMS [M + H]+ m/z | LCMS [M + H]+ − H2O m/z | HPLC Retention Time (Min)/ Method | NMR |
|---|---|---|---|---|---|---|---|
| | | | | | | | Hz, 2H), 4.79 (d, J = 6.1 Hz, 2H), 3.84 (s, 3H), 2.31 (t, J = 6.1 Hz, 1H). |
| (2-methoxyphenyl)thiazole-4-methanol | $C_{11}H_{11}NO_2S$ | 222.0583 | | 222.0598 | | 1.659/A | $^1$H NMR (400 MHz, CDCl$_3$) δ ppm: 8.36 (dd, J = 8.8, 1.45 Hz, 1H), 7.35-7.40 (m, 1H), 7.21 (s, 1H), 7.06 (t, J = 7.8 Hz, 1H), 7.02 (d, J = 8.3 Hz, 1H), 4.83 (d, J = 5.9 Hz, 2H), 4.01 (s, 3H), 2.34 (t, J = 5.9 Hz, 1H). |
| cyclohexyl-thiazole-4-methanol | $C_{10}H_{15}NOS$ | 198.0947 | | 198.0956 | | 1.829/F | $^1$H NMR (400 MHz, CDCl$_3$) δ ppm: 7.01 (s, 1H), 4.72 (broad s, 2H), 2.91-3.0 (m, 1H), 2.56 (broad s, 1H), 2.08-2.13 (m, 2H), 1.72-1.85 (m, 2H), 1.7-1.72 (m, 1H), 1.14-1.54 (m, 5H). |
| piperidinyl-thiazole-4-methanol | $C_9H_{14}N_2OS$ | | | | | 1.188/F | $^1$H NMR (400 MHz, CDCl$_3$) δ ppm: 6.34 (s, 1H), 4.51 (d, J = 5.8 Hz, 2H), 3.41-3.44 (m, 4H), 2.17 (t, J = 5.8 Hz, 1H), 1.59-1.68 (m, 6H). |
| methylpiperazinyl-thiazole-4-methanol | $C_9H_{15}N_3OS$ | 214.1009 | | 214.1012 | | 0.534/F | $^1$H NMR (400 MHz, CDCl$_3$) δ ppm: 6.40 (s, 1H), 4.52 (s, 2H), 3.48 (t, J = 5.2 Hz, 4H), 2.50 (t, J = 5.2 Hz, 4H), 2.33 (s, 3H), 1.75 (broad s, 1H). |
| ethyl-thiazole-4-methanol | $C_6H_9NOS$ | 144.0478 | | 144.0502 | | 0.803/C | $^1$H NMR (400 MHz, CDCl$_3$) δ ppm: 1.39 (t, J = 7.63 Hz, 3 H) 2.90-3.15 (m, 3 H) 4.74 (d, J = 5.87 Hz, 2 H) 7.04 (s, 1 H) |
| (2,4-difluorophenyl)thiazole-4-methanol | $C_{10}H_7F_2NOS$ | 228.03 | 210.02 | 228 | 210 | | $^1$H NMR (400 MHz, CDCl$_3$) δ ppm: 8.29 (td, J = 8.7, 6.5 Hz, 1H), 7.29-7.33 (m, 1H), 6.92-7.05 (m, 2H), 4.86 (d, J = 6.0 Hz, 2H), 2.32 (t, J = 6.1 Hz, 1H) |
| (3-fluorophenyl)thiazole-4-methanol | $C_{10}H_8FNOS$ | 210.04 | 192.03 | 210 | 192 | 1.738/A | $^1$H NMR (400 MHz, CDCl$_3$) δ ppm: 7.65-7.74 (m, 2H), 7.41 (td, J = 7.9, 5.7 Hz, 1H), 7.23 (s, 1H), 7.13 (td, J = 8.4, 2.7 Hz, 1H), 4.84 (d, J = 5.9 Hz, 2H), 2.42 (t, J = 5.9 Hz, 1H) |

| Structure | Formula | Calc. [M + H]+ m/z | Calc. [M + H]+ − H2O m/z | LCMS [M + H]+ m/z | LCMS [M + H]+ − H2O m/z | HPLC Retention Time (Min)/ Method | NMR |
|---|---|---|---|---|---|---|---|
| 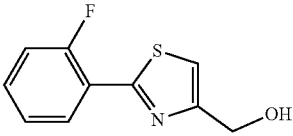 [SMILES: OCc1csc(-c2ccccc2F)n1] | C10H8FNOS | 210.04 | 192.03 | 210 | 192 | 1.741/A | 1H NMR (400 MHz, CDCl3) δ ppm: 8.21 (td, J = 7.7, 1.8 Hz, 1H), 7.31-7.40 (m, 1H), 7.27 (s, 1H), 7.11-7.24 (m, 2H), 4.82 (d, J = 6.0 Hz, 2H), 2.86 (t, J = 6.1 Hz, 1H) |
| 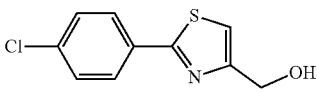 [SMILES: OCc1csc(-c2ccc(Cl)cc2)n1] | C10H8ClNOS | 226.01 | 208.00 | 226 | 208 | 1.902/A | 1H NMR (400 MHz, CDCl3) δ ppm: 7.87-7.91 (m, 2H), 7.39-7.45 (m, 2H), 7.21 (t, J = 1.0 Hz, 1H), 4.84 (d, J = 5.7 Hz, 2H), 2.31 (t, J = 5.7 Hz, 1H) |
| 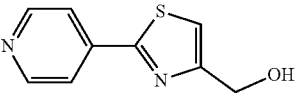 [SMILES: OCc1csc(-c2ccncc2)n1] | C9H8N2OS | 193.04 | 175.03 | 193 | 175 | 1.248/B | 1H NMR (400 MHz, CDCl3) δ ppm: 8.71 (d, J = 6.2 Hz, 2H), 7.81 (d, J = 6.2 Hz, 2H), 7.35 (s, 1H), 4.88 (d, J = 3.9 Hz, 2H), 2.45 (br. s., 1H) |
| 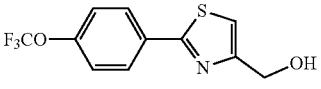 [SMILES: OCc1csc(-c2ccc(OC(F)(F)F)cc2)n1] | C11H8F3NO2S | 276.03 | 258.02 | 276 | 258 | 2.020/A | 1H NMR (400 MHz, CDCl3) δ ppm: 7.98 (dd, J = 8.1, 4.8 Hz, 2H), 7.29 (d, J = 8.1 Hz, 2H), 7.22 (s, 1H), 4.84 (d, J = 5.5 Hz, 2H), 2.47 (t, J = 5.5 Hz, 1H) |
| 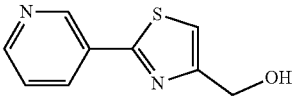 | C9H8N2OS | 193.04 | 175.03 | 193 | | 1.152/A | 1H NMR (400 MHz, CDCl3) δ ppm: 9.11 (d, J = 2.0 Hz, 1H), 8.66 (dd, J = 4.9, 1.4 Hz, 1H), 8.28 (dt, J = 8.2, 2.0 Hz, 1H), 7.58 (s, 1H), 7.53 (dd, J = 7.8, 4.7 Hz, 1H), 5.44 (t, J = 5.8 Hz, 1H), 4.65 (d, J = 5.9 Hz, 2H) |
| 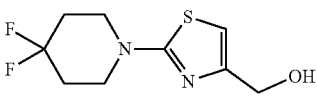 | C9H12F2N2OS | 235.07 | 217.06 | 235 | 217 | 1.293/A | 1H NMR (400 MHz, CDCl3) δ ppm: 6.46 (s, 1H), 4.55 (br. s., 2H), 3.66 (dd, J = 6.0 Hz, 4H), 2.17 (br. s., 1H), 2.02-2.15 (m, 4H) |
| 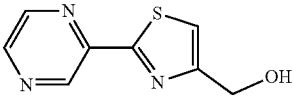 | C8H7N3OS | 194.04 | 176.03 | 194 | 176 | 1.577/B | 1H NMR (400 MHz, CDCl3) δ ppm: 9.43 (br. d, J = 1.60 Hz, 1H), 8.62 (d, J = 2.74 Hz, 1H), 8.56-8.60 (m, 1H), 7.40 (s, 1H), 4.89 (d, J = 5.87 Hz, 2H), 2.24 (t, J = 6.06 Hz, 1H) |
| 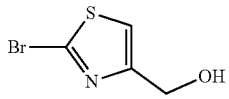 | C4H4BrNOS | 193.93 | 175.92 | | 176 | 1.101/A | 1H NMR (400 MHz, CDCl3) δ ppm: 7.18 (d, J = 0.78 Hz, 1H), 4.76 (d, J = 1.00 Hz, 2H), 2.28-2.71 (m, 1H) |

| Structure | Formula | Calc. [M + H]+ m/z | Calc. [M + H]+ − H2O m/z | LCMS [M + H]+ m/z | LCMS [M + H]+ − H2O m/z | HPLC Retention Time (Min)/ Method | NMR |
|---|---|---|---|---|---|---|---|
| 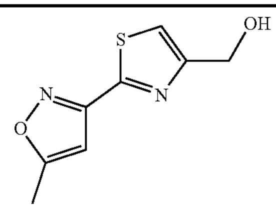 | C8H8N2O2S | 197.04 | 179.03 | 197 | 179 | 1.689/B | 1H NMR (400 MHz, CDCl3) δ ppm: 7.32 (s, 1H), 6.57 (br. d, J = 0.80 Hz, 1H), 4.86 (s, 2H), 2.52 (d, J = 0.78 Hz, 3H) |
| 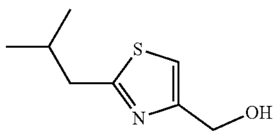 | C8H13NOS | 172.0791 | | 172.0788 | | 1.528/A | 1H NMR (CDCl3) δ ppm: 7.05 (s, 1H), 4.75 (s, 2H), 2.87 (d, J = 7.0 Hz, 2H), 2.39 (br. s, 1H), 2.01-2.19 (m, 1H), 1.00 (d, J = 6.6 Hz, 6H) |
| 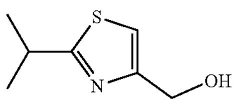 | C17H11NOS | 158.0634 | | 158.0634 | | 1.169/A | 1H NMR (400 MHz, CDCl3) δ ppm: 7.04 (s, 1H), 4.75 (br. s., 2H), 3.25-3.39 (m, 1H), 2.44 (br. s., 1H), 1 (d, J = 6.6 Hz, 6H) |
| 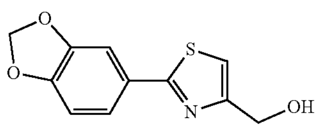 [SMILES: OCc1csc(-c2ccc3c(c2)OCO3)n1] | C11H9NO3S | 236.0376 | | 236.0386 | | 1.900/A | 1H NMR (DMSO-d6) δ ppm: 7.41-7.46 (m, 2H), 7.38 (t, J = 1.0 Hz, 1H), 7.02 (d, J = 7.8 Hz, 1H), 6.11 (s, 2H), 5.34 (br. s., 1H), 4.59 (broad s, 2H). |
| 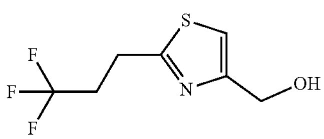 [SMILES: OCc1csc(CCC(F)(F)F)n1] | C7H8F3NOS | 212.0351 | | 212.035 | | 1.484/A | 1H NMR (400 MHz, CDCl3) δ ppm: 7.15 (s, 1H), 4.78 (s, 2H), 3.28-3.36 (m, 2H), 3.1 (broad s, 1H), 2.65-2.79 (m, 2H). |
| 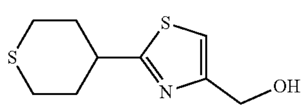 | C9H13NOS2 | 216.0511 | | 216.0516 | | 1.705/A | 1H NMR (400 MHz, CDCl3) δ ppm: 7.14 (s, 1H), 4.78 (s, 2H), 3.27 (broad s, 1H), 3.12-3.18 (m, 1H), 2.80-2.90 (m, 2H), 2.70-2.78 (m, 2H), 2.42-2.52 (m, 2H), 1.90-2.04 (m, 2H). |
| 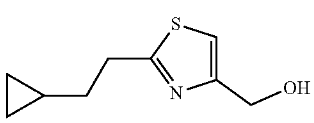 [SMILES: OCc1csc(CCC2CC2)n1] | C9H13NOS | 184.0791 | | 184.0787 | | 1.544/A | 1H NMR (400 MHz, CDCl3) δ ppm: 7.04 (s, 1H), 4.74 (d, J = 5.9 Hz, 2H), 3.09 (t, J = 7.9 Hz, 2H), 2.65 (t, J = 6.1 Hz, 1H), 1.63-1.74 (m, 2H), 0.71-0.84 (m, 1H), 0.40-0.53 (m, 2H), 0.05-0.12 (m, 2H) |
| 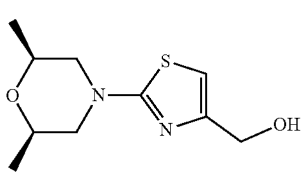 | C10H16N2O2S | 229.1005 | | 229.1015 | | 2.013/B | 1H NMR (400 MHz, CDCl3) δ ppm: 6.44 (s, 1H), 4.56 (d, J = 5.9 Hz, 2H), 3.69-3.81 (m, 4H), 2.73 (t, J = 11.5 Hz, 2H), 2.14 (t, J = 5.5 Hz, 1H), 1.26 (d, J = 5.9 Hz, 6H) |

-continued

| Structure | Formula | Calc. [M + H]+ m/z | Calc. [M + H]+ − H$_2$O m/z | LCMS [M + H]+ m/z | LCMS [M + H]+ − H$_2$O m/z | HPLC Retention Time (Min)/ Method | NMR |
|---|---|---|---|---|---|---|---|
| (thiomorpholine-thiazole-CH$_2$OH) | C$_8$H$_{12}$N$_2$OS$_2$ | 217.0464 | | 217.0467 | | 1.13/A | $^1$H NMR (400 MHz, CDCl$_3$) δ ppm: 6.42 (s, 1H), 4.54 (s, 2H), 3.78-3.90 (m, 4H), 2.67-2.76 (m, 4H), 2.05-2.18 (m, 1H) |
| (oxazepane-thiazole-CH$_2$OH) | C$_9$H$_{14}$N$_2$O$_2$S | 215.0849 | | 215.0845 | | 0.93/A | $^1$H NMR (400 MHz, CDCl$_3$) δ ppm: 6.35 (s, 1H), 4.54 (broad s, 2H), 3.83-3.89 (m, 2H), 3.76-3.81 (m, 4H), 3.68-3.76 (m, 2H), 2.47 (br. s., 1H), 2.02-2.10 (m, 2H). |

Preparation of Bromides

The following bromides were prepared according to the procedure described in Example 4.

| Structure | Formula | Calc. [M + H]+ m/z | LCMS [M + H]+ m/z | HPLC Retention Time (Min)/ Method | NMR |
|---|---|---|---|---|---|
| (2-phenyl-4-bromomethyl-thiazole) | C$_{10}$H$_8$BrNS | 253.9634 | 253.9654 | 2.10/A | $^1$H NMR (400 MHz, CDCl$_3$) δ ppm: 4.65 (s, 2H), 7.31 (s, 1H), 7.42-7.49 (m, 3H), 7.93-8.00 (m, 2H) |
| (2-(tetrahydropyran-4-yl)-4-bromomethyl-thiazole) | C$_9$H$_{12}$BrNOS | 261.9896 | 261.9903 | 1.535/A | $^1$H NMR (400 MHz, CDCl$_3$) δ ppm: 1.79-1.99 (m, 2H) 1.99-2.13 (m, 2H) 3.27 (tt, J = 11.69, 3.96 Hz, 1H) 3.54 (td, J = 11.74, 1.96 Hz, 2H) 4.00-4.17 (m, 2H) 4.57 (s, 2H) 7.21 (s, 1H) |
| (4-methyl-2-phenyl-5-bromomethyl-thiazole) | C$_{11}$H$_{10}$BrNS | | decomposed | | $^1$H NMR (400 MHz, CDCl$_3$) δ ppm: 2.47 (s, 3H) 4.74 (s, 2H) 7.40-7.47 (m, 3H) 7.87-7.94 (m, 2H) |
| (2-(4-fluorophenyl)-5-bromomethyl-thiazole) | C$_{10}$H$_7$BrFNS | 271.9539 | 271.9543 | 2.165/A | $^1$H NMR (400 MHz, CDCl$_3$) δ ppm: 7.88-7.97 (m, 2H), 7.78 (s, 1H), 7.09-7.19 (m, 2H), 4.76 (s, 2H). |
| (2-(2-chlorophenyl)-5-bromomethyl-thiazole) | C$_{10}$H$_7$BrClNS | | | | $^1$H NMR (400 MHz, CDCl$_3$) δ ppm: 8.2-8.5 (m, 1H), 7.45-7.5 (m, 1H), 7.44 (s, 1H), 7.3-7.4 (m, 2H), 4.65 (s, 2H). |
| (2-(3-trifluoromethylphenyl)-5-bromomethyl-thiazole) | C$_{11}$H$_7$BrF$_3$NS | | | | $^1$H NMR (400 MHz, CDCl$_3$) δ ppm: 8.20 (s, 1H), 8.10 (d, J = 7.8 Hz, 1H), 7.68 (d, J = 7.8 Hz, 1H), 7.56 (t, J = 7.8 Hz, 1H), 7.35 (s, 1H), 4.62 (s, 2H). |

-continued

| Structure | Formula | Calc. [M + H]+ m/z | LCMS [M + H]+ m/z | HPLC Retention Time (Min)/ Method | NMR |
|---|---|---|---|---|---|
| 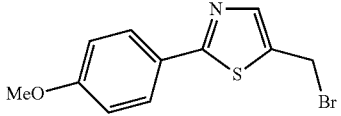 | C₁₁H₁₀BrNOS | | | | ¹H NMR (400 MHz, CDCl₃) δ ppm: 7.87 (d, J = 8.9 Hz, 2H), 7.21 (s, 1H), 6.93 (d, J = 8.9 Hz, 2H), 4.60 (s, 2H), 3.85 (s, 3H). |
| 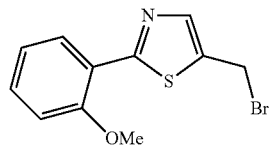 [SMILES: COc1ccccc1-c1ncc(CBr)s1] | C₁₁H₁₀BrNOS | | | | ¹H NMR (400 MHz, CDCl₃) δ ppm: 8.39 (dd, J = 7.8, 2.0 Hz, 1H), 7.36-7.41 (m, 1H), 7.34 (s, 1H), 7.05-7.09 (m, 1H), 7.01 (d, J = 8.16 Hz, 1H), 4.65 (s, 2H), 4.0 (s, 3H). |
| 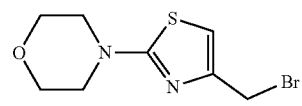 | C₈H₁₁BrN₂OS | 262.9848 | 262.9864 | 1.625/F | ¹H NMR (400 MHz, CDCl₃) δ ppm: 6.52 (s, 1H) 4.32 (s, 2H), 3.74 (t, J = 5.05 Hz, 4H), 3.40 (t, J = 5.05 Hz, 4H). |
| 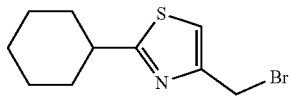 [SMILES: BrCc1csc(C2CCCCC2)n1] | C₁₀H₁₄BrNS | 260.0103 | 260.0127 | 2.184/F | ¹H NMR (400 MHz, CDCl₃) δ ppm: 7.13 (s, 1H), 4.54 (s, 2H), 2.94-3.03 (m, 1H), 2.10-2.14 (m, 2H), 1.80-1.86 (m, 2H), 1.69-1.75 (m, 1H), 1.2-1.54 (m, 5H). |
| 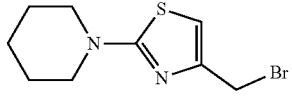 | C₉H₁₃BrN₂S | 261.0056 | 261.0067 | 1.604/F | ¹H NMR (400 MHz, CDCl₃) δ ppm: 6.49 (s, 1H), 4.36 (s, 2H), 3.42-3.45 (m, 4H), 1.59-1.69 (m, 6H). |
| 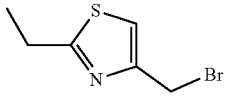 | C₆H₈BrNS | 205.96 207.96 | 206 208 | 1.748/F | ¹H NMR (400 MHz, CDCl₃) δ ppm: 7.17 (s, 1H), 4.56 (s, 2H), 3.04 (q, J = 7.4 Hz, 2H), 1.28-1.49 (m, 3H) |
| 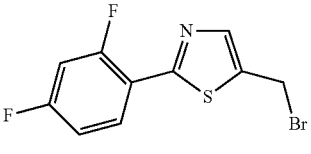 [SMILES: Fc1ccc(-c2ncc(CBr)s2)c(F)c1] | C₁₀H₆BrF₂NS | 289.94 291.94 | 290 292 | 2.134/A | ¹H NMR (400 MHz, CDCl₃) δ ppm: 8.33 (td, J = 8.7, 6.5 Hz, 1H), 7.42 (s, 1H), 6.91-7.05 (m, 2H), 4.66 (d, J = 0.8 Hz, 2H) |
| 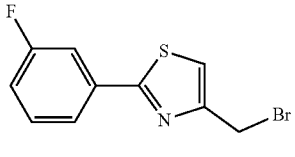 | C₁₀H₇BrFNS | 271.95 273.95 | 272 274 | 1.986/A | ¹H NMR (400 MHz, CDCl₃) δ ppm: 7.67-7.75 (m, 2H), 7.38-7.46 (m, 1H), 7.34 (s, 1H), 7.11-7.18 (m, 1H), 4.64 (s, 2H) |
| 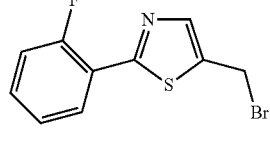 | C₁₀H₇BrFNS | 271.95 273.95 | 272 274 | 2.082/A | ¹H NMR (400 MHz, CDCl₃) δ ppm: 8.28-8.36 (m, 1H), 7.38-7.47 (m, 2H), 7.24-7.30 (m, 2H), 7.20 (dd, J = 11.3, 8.2 Hz, 1H), 4.67 (s, 2H) |
| 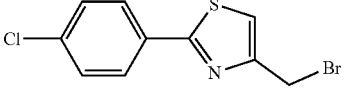 | C₁₀H₇BrClNS | 287.92 289.92 | 288 290 | 2.223/F | ¹H NMR (400 MHz, CDCl₃) δ ppm: 7.90 (d, J = 8.0 Hz, 2H), 7.43 (d, J = 8.0 Hz, 2H), 7.32 (s, 1H), 4.63 (s, 2H) |
| 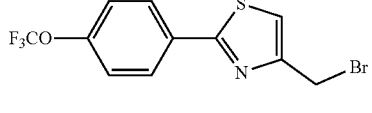 | C₁₁H₇BrF₃NOS | 337.95 339.94 | 338 340 | 2.251/A | ¹H NMR (400 MHz, CDCl₃) δ ppm: 8.00 (dd, J = 9.0, 1.0 Hz, 2H), 7.33 (s, 1H), 7.30 (dd, J = 9.0, 1.0 Hz, 2H), 4.64 (s, 2H) |

| Structure | Formula | Calc. [M + H]+ m/z | LCMS [M + H]+ m/z | HPLC Retention Time (Min)/ Method | NMR |
|---|---|---|---|---|---|
| 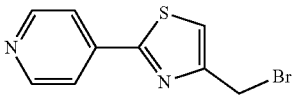 | C9H7BrN2S | 254.96<br>256.96 | 255<br>257 | 1.828/B | |
| 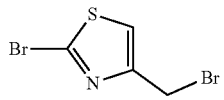 | C4H3Br2NS | 255.84<br>257.84 | 256<br>258 | 1.813/B | |
| 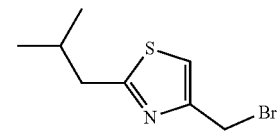 | C8H12BrNS | 233.9947 | 233.996 | 2.022/A | 1H NMR (400 MHz, CDCl3) δ ppm: 7.17 (s, 1H), 4.57 (s, 2H), 2.88 (d, J = 7.4 Hz, 2H), 2.05-2.16 (m, 1H), 1.00 (d, J = 6.7 Hz, 6H) |
| 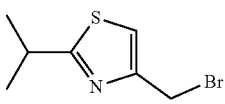 | C7H10BrNS | 219.979 | 219.9792 | 1.89/A | 1H NMR (400 MHz, CDCl3) δ ppm: 7.17 (s, 1H), 4.57 (s, 2H), 3.28-3.38 (m, 1H), 1.41 (d, J = 6.7 Hz, 6H) |
| 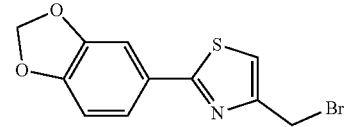 [SMILES: BrCc1csc(-c2ccc3c(c2)OCO3)n1] | C11H8BrNO2S | 297.9532 | 297.9545 | 2.185/A | 1H NMR (400 MHz, CDCl3) δ ppm: 7.43-7.53 (m, 2H), 7.26 (s, 1H), 6.88 (d, J = 7.8 Hz, 1H), 6.05 (s, 2H), 4.64 (s, 2H). |
| 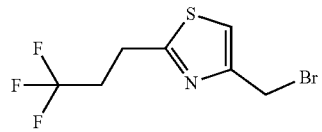 [SMILES: FC(F)(F)CCc1nc(CBr)cs1] | C7H7BrF3NS | 273.9507 | 273.9511 | 1.918/A | 1H NMR (400 MHz, CDCl3) δ ppm: 7.21 (s, 1H), 4.55 (s, 2H), 3.21-3.30 (m, 2H), 2.59-2.77 (m, 2H) |
| 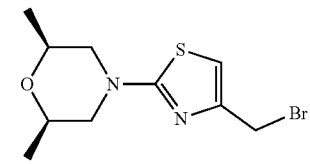 | C10H15BrN2OS | 291.0161 | 291.018 | 1.911/A | 1H NMR (400 MHz, CDCl3) δ ppm: 6.58 (s, 1H), 4.39 (s, 2H), 3.70-3.81 (m, 4H), 2.74 (dd, J = 12.9, 11.0 Hz, 2H), 1.26 (d, J = 6.3 Hz, 6H) |
| 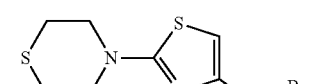 | C8H11BrN2S2 | 278.962 | 278.9636 | 1.912/A | 1H NMR (400 MHz, CDCl3) δ ppm: 6.57 (s, 1H), 4.37 (s, 2H), 3.79-3.90 (m, 4H), 2.67-2.79 (m, 4H). |
| 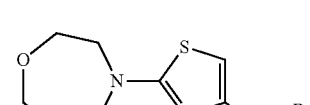 | C9H13BrN2OS | 277.0005 | 277.0017 | 1.437/A | 1H NMR (400 MHz, CDCl3) δ ppm: 6.53 (s, 1H), 4.47 (s, 2H), 3.87-3.94 (m, 2H), 3.84-3.87 (m, 2H), 3.75-3.83 (m, 4H), 2.03-2.10 (m, 2H). |

Examples 11 to 35

The following additional Examples have been prepared, isolated and characterized using the methods disclosed above.

| Ex. | Structure | Formula | Calc. [M + H]⁺ m/z | HPLC Retention Time (Min)/ Method | LCMS [M + H]⁺ m/z | NMR |
|---|---|---|---|---|---|---|
| 11 | 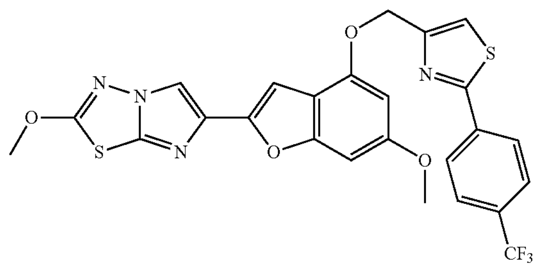 [SMILES: COc1cc(OCc2csc(-c3ccc(C(F)(F)F)cc3)n2)c2cc(-c3cn4nc(OC)sc4n3)oc2c1] | $C_{25}H_{17}F_3N_4O_4S_2$ | 559.0716 | 2.501/A | 559.0725 | $^1$H NMR (CDCl$_3$) δ ppm: 8.10 (d, J = 8.2 Hz, 2H), 7.86 (s, 1H), 7.72 (d, J = 8.2 Hz, 2H), 7.44-7.48 (m, 1H), 7.12 (s, 1H), 6.71-6.75 (m, 1H), 6.48 (d, J = 1.6 Hz, 1H), 5.41 (d, J = 0.8 Hz, 2H), 4.22 (s, 3H), 3.86 (s, 3H) |
| 12 | 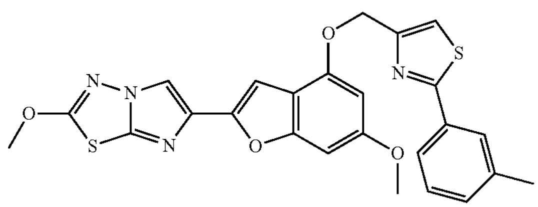 | $C_{25}H_{20}N_4O_4S_2$ | 505.0999 | 2.506/A | 505.1012 | $^1$H NMR (CDCl$_3$) δ ppm: 8.10 (d, J = 8.2 Hz, 2H) 7.86 (s, 1H) 7.72 (d, J = 8.2 Hz, 2H) 7.44-7.48 (m, 1H) 7.12 (s, 1H) 6.71-6.75 (m, 1H) 6.48 (d, J = 1.6 Hz, 1H) 5.41 (d, J = 0.8 Hz, 2H) 4.22 (s, 3H) 3.86 (s, 3H) |
| 13 | 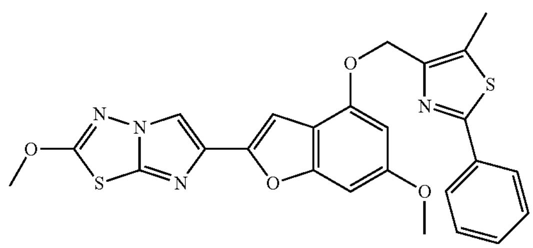 [SMILES: COc1cc(OCc2nc(-c3ccccc3)sc2C)c2cc(-c3cn4nc(OC)sc4n3)oc2c1] | $C_{25}H_{20}N_4O_4S_2$ | 505.0999 | 2.498/C | 505.1197 | $^1$H NMR (400 MHz, CDCl$_3$) δ ppm 2.53 (s, 3H) 3.87 (s, 3H) 4.21 (s, 3H) 5.31 (s, 2H) 6.44 (d, J = 1.56 Hz, 1H) 6.74 (broad d, 1H) 7.06 (s, 1H) 7.38-7.48 (m, 3H) 7.85 (s, 1H) 7.90-7.97 (m, 2H) |
| 14 | 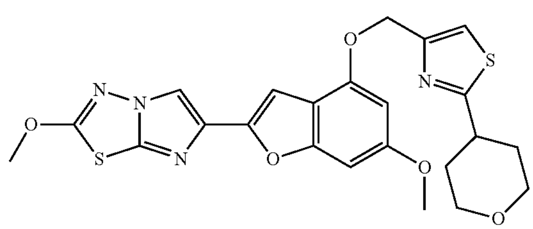 [SMILES: COc1cc(OCc2csc(C3CCOCC3)n2)c2cc(-c3cn4nc(OC)sc4n3)oc2c1] | $C_{23}H_{22}N_4O_5S_2$ | 499.1104 | 2.303/C | 499.1139 | $^1$H NMR (400 MHz, CDCl$_3$) δ ppm: 1.82-2.02 (m, 2H) 2.02-2.20 (m, 2H) 3.21-3.35 (m, 1H) 3.56 (td, J = 11.74, 1.96 Hz, 2H) 3.85 (s, 3H) 4.05-4.13 (m, 2H) 4.22 (s, 3H) 5.31 (s, 2H) 6.44 (d, J = 1.96 Hz, 1H) 6.71 (d, J = 0.78 Hz, 1H) 7.09 (s, 1H) 7.85 (s, 1H) |
| 15 | 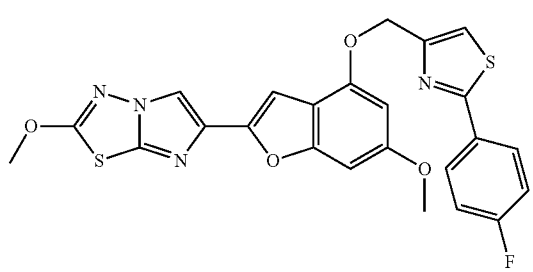 [SMILES: COc1cc(OCc2csc(-c3ccc(F)cc3)n2)c2cc(-c3cn4nc(OC)sc4n3)oc2c1] | $C_{24}H_{17}FN_4O_4S_2$ | 509.0748 | 2.637/B | 509.0769 | $^1$H NMR (400 MHz, CDCl$_3$) δ ppm: 7.9-7.97 (m, 2H), 7.82 (s, 1H), 7.33 (s, 1H), 7.13-7.15 (m, 2H), 7.12 (s, 1H), 6.70 (d, J = 1.87 Hz, 1H), 6.44 (d, J = 1.87 Hz, 1H), 5.36 (s, 2H), 4.19 (s, 3H), 3.83 (s, 3H). |

-continued

| Ex. | Structure | Formula | Calc. [M + H]+ m/z | HPLC Retention Time (Min)/ Method | LCMS [M + H]+ m/z | NMR |
|---|---|---|---|---|---|---|
| 16 | 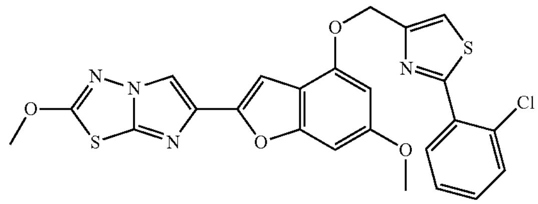 [SMILES: COc1cc(OCc2csc(-c3ccccc3Cl)n2)c2cc(-c3cn4nc(OC)sc4n3)oc2c1] | $C_{24}H_{17}ClN_4O_4S_2$ | 525.0453 | 2.502/A | 525.0458 | $^1$H NMR (400 MHz, CDCl$_3$) δ ppm: 8.2-8.25 (m, 1H), 7.83 (s, 1H), 7.52 (s, 1H), 7.48-7.50 (m, 1H), 7.31-7.39 (m, 2H), 7.10 (s, 1H), 6.70 (broad d, 1H), 6.46 (d, J = 1.88 Hz, 1H), 5.41 (s, 2H), 4.19 (s, 3H), 3.83 (s, 3H). |
| 17 | 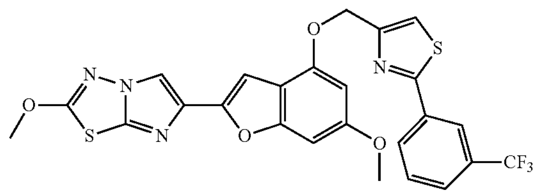 [SMILES: COc1cc(OCc2csc(-c3cccc(C(F)(F)F)c3)n2)c2cc(-c3cn4nc(OC)sc4n3)oc2c1] | $C_{25}H_{17}F_3N_4O_4S_2$ | 559.0716 | 2.534/A | 559.0752 | $^1$H NMR (400 MHz, CDCl$_3$) δ ppm: 8.23 (broad s, 1H), 8.12 (broad d, J = 7.9 Hz, 1H), 7.83 (s, 1H), 7.67 (broad d, J = 7.9 Hz, 1H), 7.57 (broad t, J = 7.9 Hz, 1H), 7.42 (s, 1H), 7.10 (s, 1H), 6.70 (broad d, 1H), 6.46 (d, J = 1.54 Hz, 1H), 5.39 (s, 2H), 4.19 (s, 3H), 3.83 (s, 3H). |
| 18 | 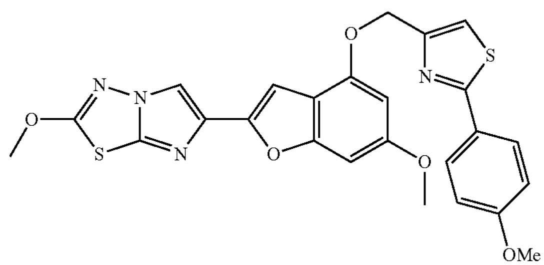 [SMILES: COc1ccc(-c2nc(COc3cc(OC)cc4oc(-c5cn6nc(OC)sc6n5)cc34)cs2)cc1] | $C_{25}H_{20}N_4O_5S_2$ | 521.0948 | 2.451/A | 521.0977 | $^1$H NMR (400 MHz, CDCl$_3$) δ ppm: 7.86-7.90 (m, 2H), 7.83 (s, 1H), 7.27 (s, 1H), 7.10 (s, 1H), 6.93-6.96 (m, 2H), 6.69 (broad d, 1H), 6.45 (d, J = 1.7 Hz, 1H), 5.36 (s, 2H), 4.19 (s, 3H), 3.85 (s, 3H), 3.83 (s, 3H). |
| 19 | 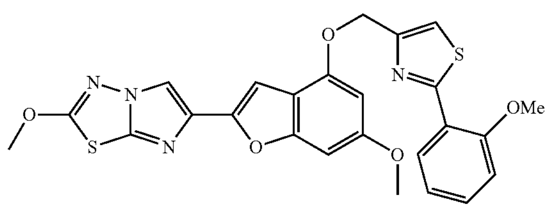 [SMILES: COc1cc(OCc2csc(-c3ccccc3OC)n2)c2cc(-c3cn4nc(OC)sc4n3)oc2c1] | $C_{25}H_{20}N_4O_5S_2$ | 521.0948 | 2.460/A | 521.0984 | $^1$H NMR (400 MHz, CDCl$_3$) δ ppm: 8.33 (dd, J = 7.84, 1.7 Hz, 1H), 7.77 (s, 1H), 7.35 (s, 1H), 7.29-7.34 (m, 1H), 7.05 (s, 1H), 6.95-7.04 (m, 2H), 6.62 (d, J = 2.0 Hz, 1H), 6.40 (d, J = 2.0 Hz, 1H), 5.34 (s, 2H), 4.12 (s, 3H), 3.96 (s, 3H), 3.76 (s, 3H). |
| 20 | 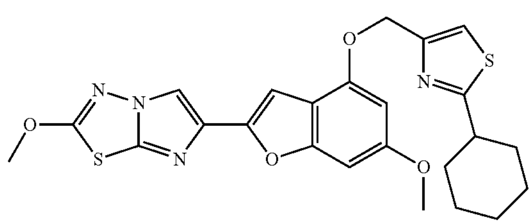 [SMILES: COc1cc(OCc2csc(C3CCCCC3)n2)c2cc(-c3cn4nc(OC)sc4n3)oc2c1] | $C_{24}H_{24}N_4O_4S_2$ | 497.1312 | 2.631/F | 497.1350 | $^1$H NMR (400 MHz, CDCl$_3$) δ ppm: 7.82 (s, 1H), 7.20 (s, 1H), 7.07 (s, 1H), 6.68 (broad d, 1H), 6.40 (d, J = 2.0 Hz, 1H), 5.27 (s, 2H), 4.19 (s, 3H), 3.82 (s, 3H), 2.95-3.03 (m, 1H), 2.13-2.16 (m, 2H), 1.82-1.87 (m, 2H), 1.7-1.75 (m, 1H), 1.12-1.58 (m, 5H). |

-continued

| Ex. | Structure | Formula | Calc. [M + H]+ m/z | HPLC Retention Time (Min)/ Method | LCMS [M + H]+ m/z | NMR |
|---|---|---|---|---|---|---|
| 21 | 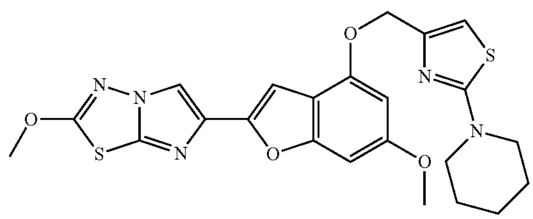 [SMILES: COc1cc(OCc2csc(N3CCCCC3)n2)c2cc(-c3cn4nc(OC)sc4n3)oc2c1] | C23H23N5O4S2 | 498.1264 | 2.409/F | 498.1329 | 1H NMR (400 MHz, CDCl3) δ ppm: 7.82 (s, 1H), 7.08 (s, 1H), 6.68 (broad s, 1H), 6.53 (s, 1H), 6.41 (broad s, 1H), 5.09 (s, 2H), 4.18 (s, 3H), 3.82 (s, 3H), 3.43-3.46 (m, 4H), 1.60-1.68 (m, 6H). |
| 22 | 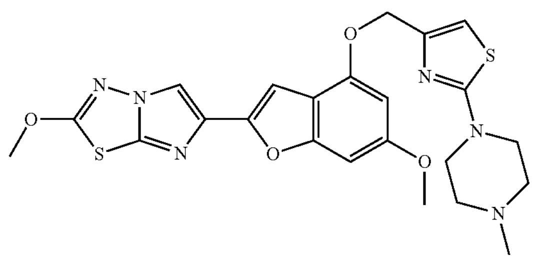 [SMILES: COc1cc(OCc2csc(N3CCN(C)CC3)n2)c2cc(-c3cn4nc(OC)sc4n3)oc2c1] | C23H24N6O4S2 | 513.1373 | 2.208/F | 513.1391 | 1H NMR (400 MHz, CDCl3) δ ppm: 7.85 (s, 1H), 7.10 (s, 1H), 6.70 (d, J = 0.8 Hz, 1H), 6.61 (s, 1H), 6.43 (d, J = 1.6 Hz, 1H), 5.12 (s, 2H), 4.21 (s, 3H), 3.84 (s, 3H), 3.53 (t, J = 1.0 Hz, 4H), 2.54 (t, J = 1.0 Hz, 4H), 2.36 (s, 3H). |
| 23 | 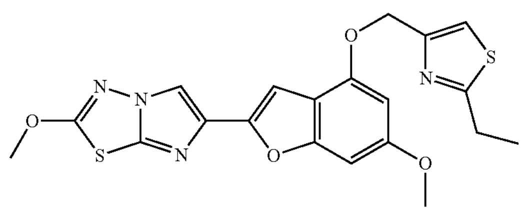 [SMILES: CCc1nc(COc2cc(OC)cc3oc(-c4cn5nc(OC)sc5n4)cc23)cs1] | C20H18N4O4S2 | 443.0842 | 2.491/F | 443.0796 | 1H NMR (400 MHz, CDCl3) δ ppm: 7.85 (s, 1H), 7.23 (s, 1H), 7.09 (s, 1H), 6.71 (d, J = 0.8 Hz, 1H), 6.43 (d, J = 1.6 Hz, 1H), 5.30 (s, 2H) 4.21 (s, 3H), 3.85 (s, 3H), 3.07 (q, J = 7.4 Hz, 2H), 1.43 (t, J = 7.6 Hz, 3H) |
| 24 | 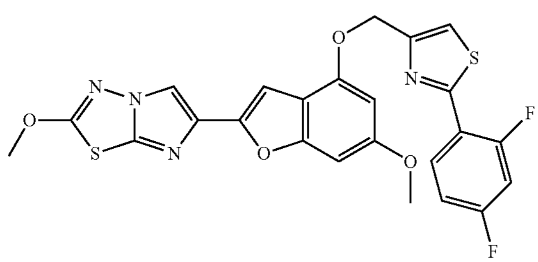 [SMILES: COc1cc(OCc2csc(-c3ccc(F)cc3F)n2)c2cc(-c3cn4nc(OC)sc4n3)oc2c1] | C24H16F2N4O4S2 | 527.0654 | 2.490/A | 527.0661 | 1H NMR (400 MHz, CDCl3) δ ppm: 8.33 (td, J = 8.6, 6.7 Hz, 1H), 7.86 (s, 1H), 7.49 (s, 1H), 7.12 (s, 1H), 6.93-7.06 (m, 2H), 6.72 (d, J = 1.6 Hz, 1H), 6.47 (d, J = 1.6 Hz, 1H), 5.41 (s, 1H), 4.22 (s, 3H), 3.85 (s, 3H) |
| 25 | 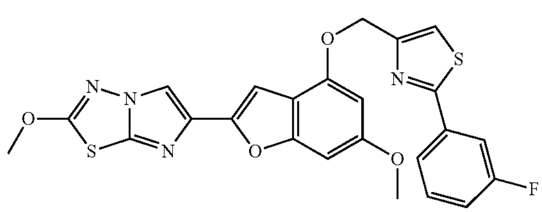 [SMILES: COc1cc(OCc2csc(-c3cccc(F)c3)n2)c2cc(-c3cn4nc(OC)sc4n3)oc2c1] | C24H17FN4O4S2 | 509.0748 | 2.475/A | 509.0757 | 1H NMR (400 MHz, CDCl3) δ ppm: 7.86 (s, 1H), 7.68-7.77 (m, 2H), 7.39-7.47 (m, 2H), 7.10-7.18 (m, 2H), 6.70-6.75 (m, 1H), 6.47 (d, J = 2.0 Hz, 1H), 5.40 (s, 2H), 4.21 (s, 3H), 3.85 (s, 3H) |

-continued

| Ex. | Structure | Formula | Calc. [M + H]+ m/z | HPLC Retention Time (Min)/ Method | LCMS [M + H]+ m/z | NMR |
|---|---|---|---|---|---|---|
| 26 | 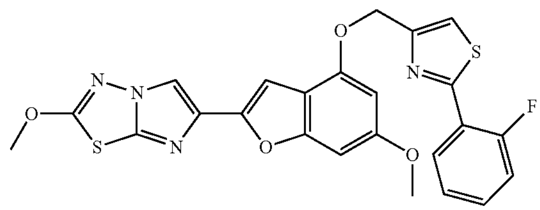 [SMILES: COc1cc(OCc2csc(-c3ccccc3F)n2)c2cc(-c3cn4nc(OC)sc4n3)oc2c1] | C₂₄H₁₇FN₄O₄S₂ | 509.0748 | 2.477/A | | ¹H NMR (400 MHz, CDCl₃) δ ppm: 8.28-8.36 (m, 1H), 7.86 (s, 1H), 7.51 (s, 1H), 7.38-7.46 (m, 1H), 7.28-7.31 (m, 1H), 7.18-7.25 (m, 1H), 7.13 (s, 1H), 6.73 (dd, J = 2.0, 0.8 Hz, 1H), 6.48 (d, J = 2.0 Hz, 1H), 5.43 (s, 2H), 4.22 (s, 3H), 3.85 (s, 3H) |
| 27 | 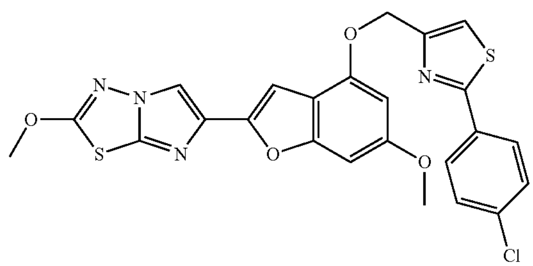 [SMILES: COc1cc(OCc2csc(-c3ccc(Cl)cc3)n2)c2cc(-c3cn4nc(OC)sc4n3)oc2c1] | C₂₄H₁₇ClN₄O₄S₂ | | 2.668/F | | ¹H NMR (400 MHz, CDCl₃) δ ppm: 8.28-8.36 (m, 1H), 7.86 (s, 1H), 7.51 (s, 1H), 7.38-7.46 (m, 1H), 7.28-7.31 (m, 1H), 7.18-7.25 (m, 1H), 7.13 (s, 1H), 6.73 (dd, J = 2.0, 0.8 Hz, 1H), 6.48 (d, J = 2.0 Hz, 1H), 5.43 (s, 2H), 4.22 (s, 3H), 3.85 (s, 3H) |
| 28 | 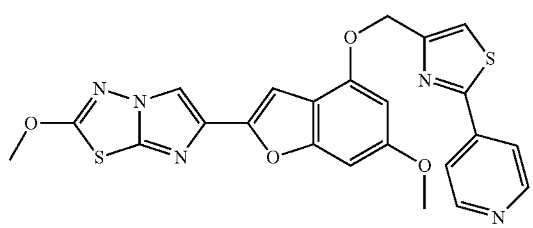 [SMILES: COc1cc(OCc2csc(-c3ccncc3)n2)c2cc(-c3cn4nc(OC)sc4n3)oc2c1] | C₂₃H₁₇N₅O₄S₂ | 492.0795 | 2.219/A | 492.0822 | ¹H NMR (400 MHz, CDCl₃) δ ppm: 8.68-8.73 (m, 2H), 7.83 (s, 1H), 7.79-7.83 (m, 2H), 7.49 (s, 1H), 7.07-7.11 (m, 1H), 6.71 (d, J = 0.8 Hz, 1H), 6.44 (d, J = 2.0 Hz, 1H), 5.38-5.41 (m, 2H), 4.19 (s, 3H), 3.83 (s, 3H) |
| 29 | 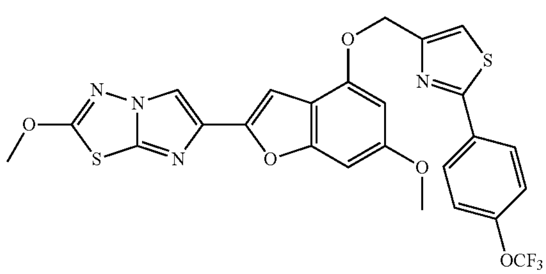 [SMILES: COc1cc(OCc2csc(-c3ccc(OC(F)(F)F)cc3)n2)c2cc(-c3cn4nc(OC)sc4n3)oc2c1] | C₂₅H₁₇F₃N₄O₅S₂ | 575.0665 | 2.549/A | 575.0691 | ¹H NMR (400 MHz, CDCl₃) δ ppm: 8.01 (d, J = 8.6 Hz, 2H), 7.86 (s, 1H), 7.40 (d, J = 0.8 Hz, 1H), 7.31 (d, J = 8.6 Hz, 2H), 7.12 (s, 1H), 6.70-6.75 (m, 1H), 6.45-6.50 (m, 1H), 5.39 (s, 2H), 4.22 (s, 3H), 3.85 (s, 3H) |
| 30 | 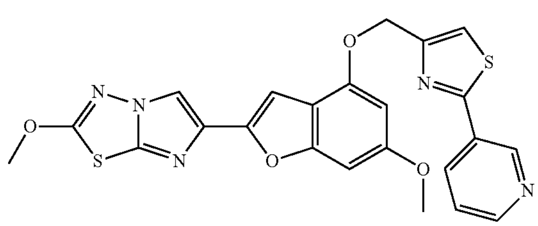 [SMILES: COc1cc(OCc2csc(-c3cccnc3)n2)c2cc(-c3cn4nc(OC)sc4n3)oc2c1] | C₂₃H₁₇N₅O₄S₂ | 492.0795 | 2.344/A | 492.0815 | ¹H NMR (400 MHz, CDCl₃) δ ppm: 9.20 (d, J = 2.3 Hz, 1H), 8.68 (dd, J = 5.1, 1.6 Hz, 1H), 8.24-8.31 (m, 1H), 7.86 (s, 1H), 7.46 (s, 1H), 7.41 (dd, J = 7.8, 4.7 Hz, 1H), 7.12 (s, 1H), 6.71-6.76 (m, 1H), 6.48 (d, J = 2.0 Hz, 1H), 5.42 (s, 2H), 4.22 (s, 3H), 3.86 (s, 3H) |

-continued

| Ex. | Structure | Formula | Calc. [M + H]+ m/z | HPLC Retention Time (Min)/ Method | LCMS [M + H]+ m/z | NMR |
|---|---|---|---|---|---|---|
| 31 | 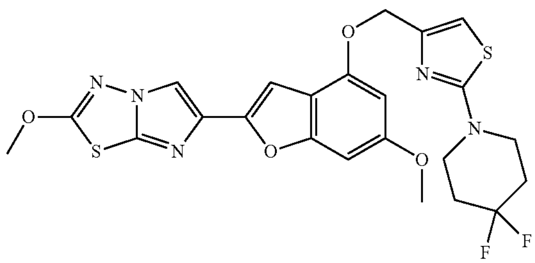 [SMILES: COc1cc(OCc2csc(N3CCC(F)(F)CC3)n2)c2cc(-c3cn4nc(OC)sc4n3)oc2c1] | $C_{23}H_{21}F_2N_5O_4S_2$ | 534.1076 | 2.428/A | 534.1097 | $^1$H NMR (400 MHz, CDCl$_3$) δ ppm: 7.85 (s, 1H), 7.10 (s, 1H), 6.70 (d, J = 1.6 Hz, 1H), 6.64 (s, 1H), 6.44 (d, J = 1.6 Hz, 1H), 5.11 (s, 2H), 4.21 (s, 3H), 3.85 (s, 3H), 3.63-3.73 (m, 4H), 2.03-2.20 (m, 4H) |
| 32 | 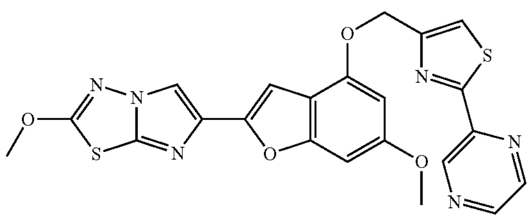 [SMILES: COc1cc(OCc2csc(-c3cnccn3)n2)c2cc(-c3cn4nc(OC)sc4n3)oc2c1] | $C_{22}H_{16}N_6O_4S_2$ | 493.0747 | 2.371/A | 493.0750 | $^1$H NMR (400 MHz, CDCl$_3$) δ ppm: 3.86 (s, 1H), 4.22 (s, 1H), 5.43 (s, 1H), 6.45-6.52 (m, 1H), 6.73 (s, 1H), 7.06-7.19 (m, 1H), 7.08-7.15 (m, 1H), 7.57 (s, 1H), 7.82-7.90 (m, 1H), 8.53-8.67 (m, 2H), 9.46 (s, 1H) |
| 33 | 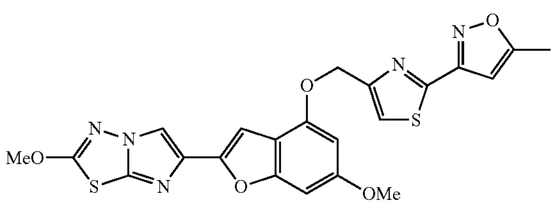 [SMILES: COc1cc(OCc2csc(-c3cc(C)on3)n2)c2cc(-c3cn4nc(OC)sc4n3)oc2c1] | $C_{22}H_{17}N_5O_5S_2$ | 496.0744 | 2.330/A | 496.0757 | $^1$H NMR (400 MHz, CDCl$_3$) δ ppm: 2.53 (d, J = 1.17 Hz, 3H), 3.85 (s, 3H), 4.22 (s, 3H), 5.40 (d, J = 0.78 Hz, 2H), 6.45 (d, J = 1.96 Hz, 1H), 6.56-6.63 (m, 1H), 6.73 (dd, J = 1.96, 0.78 Hz, 1H), 7.07-7.14 (m, 1H), 7.49 (t, J = 0.98 Hz, 1H), 7.86 (s, 1H) |
| 34 | 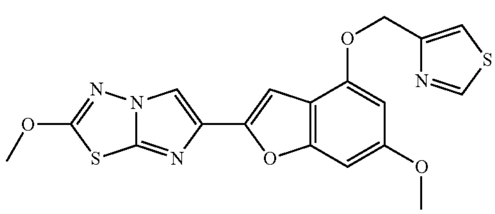 [SMILES: COc1cc(OCc2cscn2)c2cc(-c3cn4nc(OC)sc4n3)oc2c1] | $C_{18}H_{14}N_4O_4S_2$ | 415.0529 | 2.193/A | 415.0546 | $^1$H NMR (400 MHz, CDCl$_3$) δ ppm: 3.85 (s, 3H), 4.22 (s, 3H), 5.38-5.43 (m, 2H), 6.45 (d, J = 1.96 Hz, 1H), 6.70-6.74 (m, 1H), 7.10 (s, 1H), 7.40-7.49 (m, 1H), 7.85 (s, 1H), 8.85 (d, J = 1.96 Hz, 1H) |
| 35 | 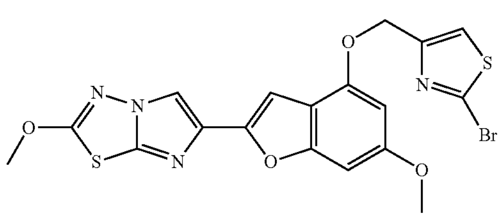 [SMILES: COc1cc(OCc2csc(Br)n2)c2cc(-c3cn4nc(OC)sc4n3)oc2c1] | $C_{18}H_{13}BrN_4O_4S_2$ | 494.9614 | 2.333/A | 494.9620 | $^1$H NMR (400 MHz, CDCl$_3$) δ ppm: 3.85 (s, 3H), 4.19-4.25 (m, 3H), 5.30 (s, 2H), 6.40 (s, 1H), 6.72 (s, 1H), 7.08 (s, 1H), 7.30-7.38 (m, 1H), 7.86 (s, 1H) |

Example 36

4-(4-(((6-Methoxy-2-(2-methoxyimidazo[2,1-b][1,3,4]thiadiazol-6-yl)benzofuran-4-yl)oxy)methyl)thiazol-2-yl)-N,N-dimethylbenzamide

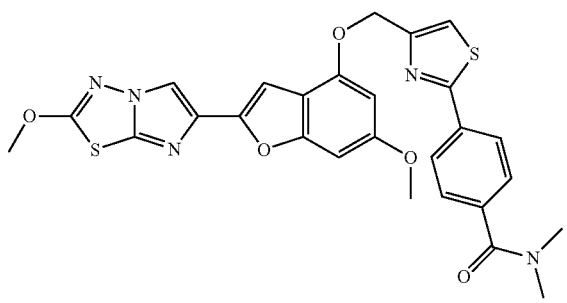

36A. 4-(4-(((tert-Butyldimethylsilyl)oxy)methyl)thiazol-2-yl)-N,N-dimethylbenzamide

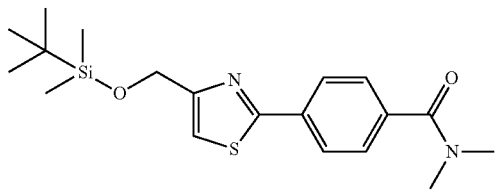 [SMILES: CN(C)C(=O)c1ccc(-c2nc(CO[Si](C)(C)C(C)(C)C)cs2)cc1]

In a 350 mL glass pressure flask, a mixture of 2-bromo-4-(((tert-butyldimethylsilyl)oxy)-methyl)thiazole (Example 37B, 3.00 g, 9.73 mmol), (4-(dimethylcarbamoyl)phenyl)-boronic acid (2.82 g, 14.61 mmol) in toluene (90 mL) and EtOH (30 mL) was treated with 2 M Na$_2$CO$_3$ (6.0 mL, 12.0 mmol) and the resulting heterogeneous mixture was flushed with nitrogen for 10 min. To this mixture was added Pd(dppf)Cl2.DCM (0.50 g, 0.61 mmol) and the sealed vial was heated at 95° C. for 2 h. The cooled reaction mixture was then partitioned between ethyl acetate and saturated sodium bicarbonate. The organic phase was separated, washed with brine, dried over anhydrous magnesium sulfate and concentrated in vacuo. The light yellow syrup obtained was chromatographed on silica gel (elution with 0-20% ethyl acetate-dichloromethane) to give 3.24 g (88%) of the title material as a clear syrup. LC (Method A): 2.401 min. $^1$H NMR (DMSO-d$_6$, 400 MHz) δ ppm: 7.97 (d, J=8.2 Hz, 2H), 7.52 (d, J=8.2 Hz, 2H), 7.48-7.54 (s, 1H), 4.83 (s, 2H), 3.00 (br. s., 3H), 2.93 (br. s., 3H), 0.91 (s, 9H), 0.11 (s, 6H).

36B. 4-(4-(Hydroxymethyl)thiazol-2-yl)-N,N-dimethylbenzamide

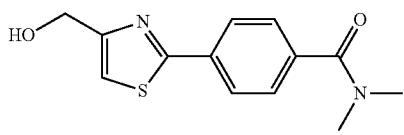 [SMILES: CN(C)C(=O)c1ccc(-c2nc(CO)cs2)cc1]

A solution of 4-(4-(((tert-butyldimethylsilyl)oxy)methyl)thiazol-2-yl)-N,N-dimethylbenzamide (3.24 g, 8.6 mmol) in tetrahydrofuran (150 mL) was treated with triethylamine trihydrofluoride (7.0 mL, 43.0 mmol) and the resulting clear solution was stirred at 23° C. for 18 h. The reaction mixture was then quenched with saturated aqueous sodium bicarbonate (100 mL) and stirred for 10 min. The reaction mixture was extracted with dichloromethane (3×250 mL) and the combined organic phase was washed with saturated sodium bicarbonate and brine, dried over anhydrous magnesium sulfate and concentrated in vacuo. The residue obtained was chromatographed on silica gel (elution with 50-100% ethyl acetate-dichloromethane) to give 1.98 g (88%) of the title material as a white solid. LC (Method A): 1.762 min. HRMS(ESI) Anal. Calcd for C$_{13}$H$_{15}$N$_2$O$_2$S [M+H]$^+$ m/z 263.0849; found 263.0865. $^1$H NMR (CDCl$_3$, 400 MHz) δ ppm: 7.96 (d, J=7.8 Hz, 2H), 7.49 (d, J=7.8 Hz, 2H), 7.22 (s, 1H), 4.82 (s, 2H), 3.13 (br. s., 3H), 3.00 (br. s., 3H), 2.66 (br. s., 1H).

Example 36. 4-(4-(((6-Methoxy-2-(2-methoxyimidazo[2,1-b][1,3,4]thiadiazol-6-yl)benzofuran-4-yl)oxy)methyl)thiazol-2-yl)-N,N-dimethylbenzamide

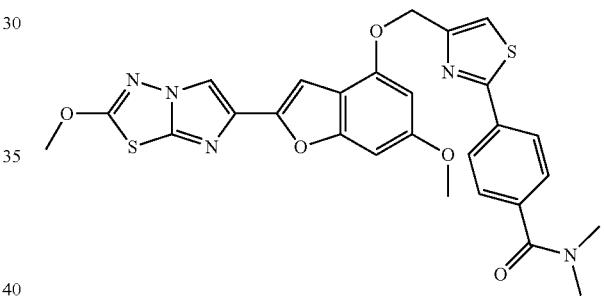

A mixture of 6-methoxy-2-(2-methoxyimidazo[2,1-b][1,3,4]thiadiazol-6-yl)benzofuran-4-ol (Example 1H, 1.00 g, 3.15 mmol) and 4-(4-(hydroxymethyl)thiazol-2-yl)-N,N-dimethylbenzamide (Example 36B, 0.950 g, 3.62 mmol) in dry tetrahydrofuran (80 mL) was treated at 22° C. and under nitrogen with tri-n-butylphosphine (2.0 mL, 8.11 mmol) added in one portion, followed by a solution of 1,1'-(azodicarbonyl)dipiperidine (2.00 g, 7.93 mmol) in tetrahydrofuran (20 mL) added dropwise over 40 min. After another 2 h at 22° C., the reaction mixture was partitioned between dichloromethane and saturated aqueous sodium bicarbonate. The organic phase was washed with brine, dried over anhydrous magnesium sulfate and concentrated in vacuo to give a glassy residue. Chromatography on silica gel (elution gradient of ethyl acetate in dichloromethane) gave 1.343 g (66%) of the title material as a white solid after trituration in acetonitrile. LC (Method A): 2.597 min. HRMS(ESI) Anal. Calcd for C$_{27}$H$_{24}$N$_5$O$_5$S$_2$ [M+H]$^+$ m/z 562.1213; found 562.1216. $^1$H NMR (CDCl$_3$, 400 MHz) δ ppm: 8.02 (d, J=8.0 Hz, 2H), 7.86 (s, 1H), 7.52 (d, J=8.0 Hz, 2H), 7.42 (s, 1H), 7.12 (s, 1H), 6.73 (br s, 1H), 6.48 (br s, 1H), 5.41 (s, 2H), 4.22 (s, 3H), 3.86 (s, 3H), 3.15 (br s, 3H), 3.02 (br s, 3H).

Example 37

Methyl 4-(4-(((6-methoxy-2-(2-methoxyimidazo[2,1-b][1,3,4]thiadiazol-6-yl)benzofuran-4-yl)oxy)methyl)thiazol-2-yl)benzoate

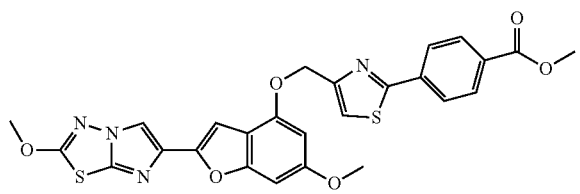

37A. (2-Bromothiazol-4-yl)methanol

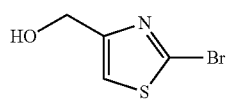

A solution of methyl 2-bromothiazole-4-carboxylate (0.500 g, 2.25 mmol) in EtOH (10 mL) in a 50 mL flask under a nitrogen atmosphere was cooled to 0° C. and treated with NaBH$_4$ (170 mg, 4.50 mmol) portion-wise over 5 min. After stirring for 15 min at 0° C., the reaction mixture was heated at 90° C. for 1 h. The cooled mixture was then quenched with saturated aqueous NH$_4$Cl (15 mL) and stirring was continued for 20 min. Ethyl acetate (50 mL) was then added and the organic phase was separated, washed with brine, dried over MgSO$_4$ and concentrated to give the title compound (0.212 g, 49%) which was used as such in the next step. $^1$H NMR (CDCl$_3$, 400 MHz) δ ppm: 7.18 (s, 1H), 4.76 (s, 2H), 2.21 (br s, 1H).

37B. 2-Bromo-4-(((tert-butyldimethylsilyl)oxy)methyl)thiazole

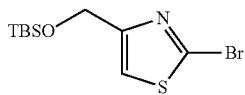 [SMILES: CC(C)(C)[Si](C)(C)OCc1csc(Br)n1]

To an ice-cold solution of (2-bromothiazol-4-yl)methanol (0.212 g, 1.09 mmol) in DMF (10 mL) was added TBDMSCl (0.329 g, 2.19 mmol), followed by imidazole (0.171 g, 2.51 mmol). The reaction mixture was then allowed to warm to room temperature over 10 min and stirred for 18 h under N$_2$. The reaction was quenched by the addition of EtOH at 0° C. and the mixture was stirred at 20° C. for 10 min before being partitioned with EtOAc and saturated aqueous NaHCO$_3$. The organic layer was separated, washed with brine, dried over MgSO$_4$ and filtered. The residue was purified on the ISCO using a REDISEP® 12 g column (0 to 5% EtOAc-DCM) to afford the desired product as yellow oil (0.333 g, 99%). LCMS (APCI): calcd for C$_{10}$H$_{19}$BrNOSSi [M+H]$^+$ m/z 308.01, found 308.0. $^1$H NMR (CDCl$_3$, 400 MHz) δ ppm: 7.14 (t, J=1.5 Hz, 1H), 4.83 (d, J=1.6 Hz, 2H), 0.95 (s, 9H), 0.12 (s, 6H).

37C. Methyl 4-(4-(((tert-butyldimethylsilyl)oxy)methyl)thiazol-2-yl)benzoate

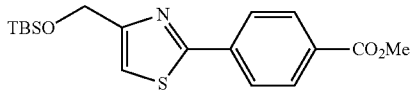 [SMILES: COC(=O)c1ccc(-c2nc(CO[Si](C)(C)C(C)(C)C)cs2)cc1]

A mixture of 2-bromo-4-(((tert-butyldimethylsilyl)oxy)methyl)thiazole (0.150 g, 0.487 mmol) and (4-(methoxycarbonyl)phenyl)boronic acid (0.119 g, 0.662 mmol) in tetrahydrofuran (4 mL) was treated with potassium fluoride (0.085 g, 1.460 mmol), 2-(di-t-butylphosphino)biphenyl (0.015 g, 0.049 mmol) and palladium(II) acetate (5.5 mg, 0.024 mmol). The reaction mixture was purged with nitrogen for 5 min and then heated at 70° C. for 16 h. The cooled reaction mixture was concentrated and the residue chromatographed on silica gel (ISCO, elution gradient of dichloromethane in hexane) to give 0.050 g (28%) of the title material. LC (Method B): 2.793 min. LCMS (APCI): calcd for C$_{18}$H$_{26}$NO$_3$SSi [M+H]$^+$ m/z 364.14; found 364.2. $^1$H NMR (400 MHz, acetone-d$_6$) δ ppm: 8.11 (s, 4H), 7.51 (s, 1H), 4.92 (d, J=1.17 Hz, 2H), 3.92 (s, 3H), 0.97 (s, 9H), 0.16 (s, 6H).

37D. Methyl 4-(4-(hydroxymethyl)thiazol-2-yl)benzoate

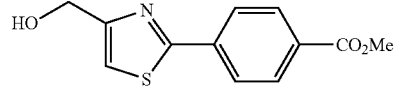

A solution of methyl 4-(4-(((tert-butyldimethylsilyl)oxy)methyl)thiazol-2-yl)benzoate (0.050 g, 0.138 mmol) in dry tetrahydrofuran (10 mL) under nitrogen was treated dropwise with triethylamine trihydrofluoride (0.112 mL, 0.688 mmol) and the solution was stirred at room temperature for 16 h. The reaction mixture was then partitioned with dichloromethane-saturated aqueous sodium bicarbonate and the organic phase was separated, washed with brine, dried over anhydrous magnesium sulfate and concentrated in vacuo. This gave 0.030 g (88%) of the title material as a beige foam which was used as such for the next step. LC (Method B): 2.049 min. LCMS (APCI): calcd for C$_{12}$H$_{12}$NO$_3$S [M+H]$^+$ m/z 250.05; found 250.2. $^1$H NMR (400 MHz, acetone-d$_6$) δ ppm: 8.09 (s, 4H), 7.51 (s, 1H), 4.73-4.87 (m, 2H), 3.91 (s, 3H), 2.83 (br s, 1H).

Example 37. Methyl 4-(4-(((6-methoxy-2-(2-methoxyimidazo[2,1-b][1,3,4]thiadiazol-6-yl)benzofuran-4-yl)oxy)methyl)thiazol-2-yl)benzoate

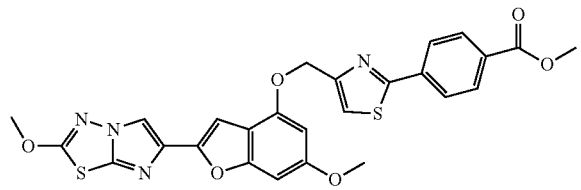

The title compound was prepared according to the general coupling procedure described in Example 36 to give a solid. LC (Method A): 2.488 min. HRMS(ESI) calcd for $C_{26}H_{21}N_4O_6S_2$ [M+H]$^+$ m/z 549.0903; found 549.0913. $^1$H NMR (400 MHz, DMSO-d$_6$) δ ppm: 8.37 (s, 1H), 8.05-8.16 (m, 4H), 8.01 (s, 1H), 7.03 (s, 1H), 6.85 (br s, 1H), 6.65 (d, J=1.96 Hz, 1H), 5.40 (s, 2H), 4.20 (s, 3H), 3.89 (s, 3H), 3.82 (s, 3H).

Example 38

2-(4-(4-(((6-methoxy-2-(2-methoxyimidazo[2,1-b][1,3,4]thiadiazol-6-yl)benzofuran-4-yl)oxy)methyl)thiazol-2-yl)phenyl)propan-2-ol

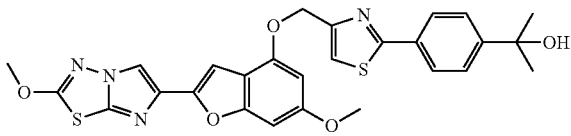 [SMILES: COc1cc(OCc2csc(-c3ccc(C(C)(C)O)cc3)n2)c2cc(-c3cn4nc(OC)sc4n3)oc2c1]

38A. 2-(4-(4-(((tert-Butyldimethylsilyl)oxy)methyl)thiazol-2-yl)phenyl)propan-2-ol

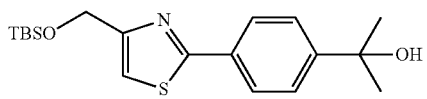 [SMILES: CC(C)(O)c1ccc(-c2nc(CO[Si](C)(C)C(C)(C)C)cs2)cc1]

An ice-cold solution of methyl 4-(4-(((tert-butyldimethylsilyl)oxy)methyl)thiazol-2-yl)benzoate (Example 37C, 0.150 g, 0.413 mmol) in tetrahydrofuran (5 mL) was treated with methylmagnesium bromide (1 M in butyl ether, 1.65 mL, 1.65 mmol). The cooling bath was then removed and the mixture was stirred at room temperature for 30 min before being partitioned between ethyl acetate and an aqueous solution of citric acid. The organic layer was separated, washed with brine, dried over anhydrous sodium sulfate and concentrated to give 0.100 g (67%) of the title material, which was used as such for the next step. LC (Method B): 2.773 min. LCMS (APCI): calcd for $C_{19}H_{30}NO_2SSi$ [M+H]$^+$ m/z 364.18; found 364.2.

38B. 2-(4-(4-(Hydroxymethyl)thiazol-2-yl)phenyl)propan-2-ol

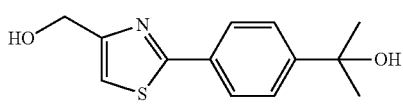 [SMILES: CC(C)(O)c1ccc(-c2nc(CO)cs2)cc1]

This compound was prepared according to the deprotection procedure described in Example 37D. LC (Method A): 1.584 min. HRMS(ESI): calcd for $C_{13}H_{16}NO_2S$ [M+H]$^+$ m/z 250.0902; found 250.0895. $^1$H NMR (400 MHz, CDCl$_3$) δ ppm: 7.92 (m, J=8.22 Hz, 2H), 7.57 (m, J=8.22 Hz, 2H), 7.18 (s, 1H), 4.84 (d, J=5.87 Hz, 2H), 2.20-2.29 (m, 1H), 1.77 (s, 1H), 1.62 (s, 6H).

Example 38. 2-(4-(4-(((6-Methoxy-2-(2-methoxyimidazo[2,1-b][1,3,4]thiadiazol-6-yl)benzofuran-4-yl)oxy)methyl)thiazol-2-yl)phenyl)propan-2-ol

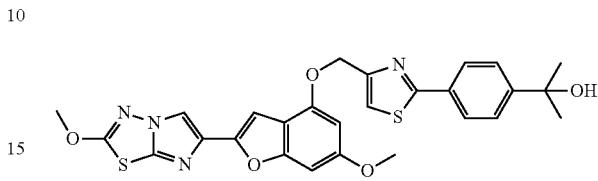

The title compound was prepared according to the Mitsunobu coupling procedure described in Example 36. LC (Method A): 2.379 min. HRMS(ESI): calcd for $C_{27}H_{25}N_4O_5S_2$ [M+H]$^+$ m/z 549.1266; found 549.1221. $^1$H NMR (400 MHz, CDCl$_3$) δ ppm: 7.95 (m, J=8.4 Hz, 2H), 7.86 (s, 1H), 7.59 (m, J=8.4 Hz, 2H), 7.36 (s, 1H), 7.12 (s, 1H), 6.72 (s, 1H), 6.45-6.52 (m, 1H), 5.40 (s, 2H), 4.22 (s, 3H), 3.85 (s, 3H), 1.77 (s, 1H), 1.63 (s, 6H).

Example 39

4-(4-(((6-Methoxy-2-(2-methoxyimidazo[2,1-b][1,3,4]thiadiazol-6-yl)benzofuran-4-yl)oxy)methyl)thiazol-2-yl)-N-(2-methoxyethyl)-N-methylbenzamide

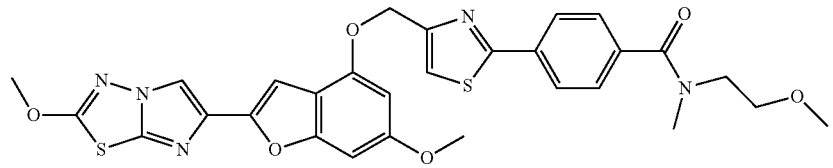

39A. tert-Butyl 4-(4-(((tert-butyldimethylsilyl)oxy)methyl)thiazol-2-yl)benzoate

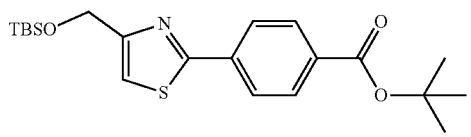

A mixture of 2-bromo-4-(((tert-butyldimethylsilyl)oxy)methyl)thiazole (Example 37B, 1.542 g, 5.000 mmol) and (4-(tert-butoxycarbonyl)phenyl)boronic acid (1.388 g, 6.25 mmol) in toluene-tert-butanol (3:1, 60 mL) was purged with a stream of N$_2$ bubbles for 15 min in a sealable flask. To this mixture was added Pd(dppf)Cl$_2$.DCM (0.204 g, 0.250 mmol) and 2 M Na$_2$CO$_3$ (3.13 mL, 6.25 mmol), the flask was sealed and the mixture was stirred at 95° C. (oil bath temperature) for 4 h. Another 0.25 equiv of the boronic acid and 2 M Na₂CO₃ were added, together with a small amount of the catalyst. The mixture was heated at 95° C. for another 2 h before being allowed to cool to room temperature and then partitioned with EtOAc-water. The organic phase was separated, washed (brine), dried (Na₂SO₄) and evaporated to give a dark brown gum. Flash chromatography (Isco/0-10% EtOAc-hexane) of this gum afforded the title compound (1.065 g, 52.5%) as a colorless gum. This material was used as such in the next step. LC (Method B): 3.407 min. LCMS (APCI): calcd for $C_{21}H_{32}NO_3SSi$ [M+H]⁺ m/z 406.19; found 406.2. ¹H NMR (400 MHz, CDCl₃) δ ppm: 8.04 (d, J=8.6 Hz, 2H), 7.98 (d, J=8.6 Hz, 2H), 7.26 (s, 1H), 4.79 (s, 2H), 1.47 (s, 9H), 0.82 (s, 9H), 0.10 (s, 6H).

39B. tert-Butyl 4-(4-(hydroxymethyl)thiazol-2-yl)benzoate

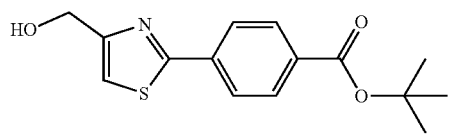

To a solution of tert-butyl 4-(4-(((tert-butyldimethylsilyl) oxy)methyl)thiazol-2-yl)benzoate (1.058 g, 2.61 mmol) in dry THF (25 mL) under N₂ was added triethylamine trihydrofluoride (1.274 mL, 7.82 mmol) dropwise and the mixture was stirred at room temperature for 18 h. The resulting mixture was partitioned with EtOAc-saturated aqueous NaHCO₃ and the organic phase was separated, dried (Na₂SO₄) and evaporated to give the title compound (0.760 g, 100%) as a colorless gum which crystallized on standing in vacuo. This material was essentially pure and was used as such in the next step. LC (Method B): 2.239 min. LCMS (APCI): calcd for $C_{15}H_{18}NO_3S$ [M+H]⁺ m/z 292.10; found 292.2. ¹H NMR (400 MHz, CDCl₃) δ ppm: 8.18-7.92 (m, 4H), 7.27 (s, 1H), 4.86 (d, J=5.87 Hz, 2H), 2.41-2.22 (m, 1H), 1.63 (s, 9H).

39C. tert-Butyl 4-(4-(((6-methoxy-2-(2-methoxyimidazo[2,1-b][1,3,4]thiadiazol-6-yl)benzofuran-4-yl) oxy)methyl)thiazol-2-yl)benzoate

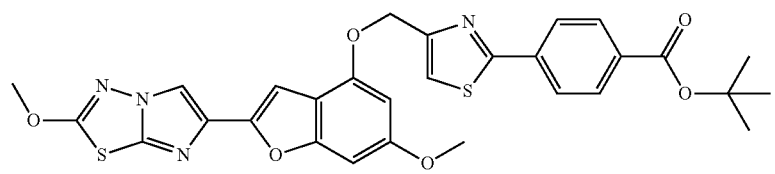 [SMILES: COc1cc(OCc2csc(-c3ccc(C(=O)OC(C)(C)C)cc3)n2)c2cc(-c3cn4nc(OC)sc4n3)oc2c1]

The title compound was prepared according to the general Mitsunobu coupling procedure described in Example 36. LC (Method A) 2.599 min. HRMS(ESI): calcd for $C_{29}H_{27}N_4O_6S_2$ [M+H]⁺ m/z 591.1372; found 591.1363. ¹H NMR (400 MHz, CDCl₃) δ ppm: 7.99-8.10 (m, 4H), 7.86 (s, 1H), 7.44 (s, 1H), 7.12 (s, 1H), 6.71-6.75 (m, 1H), 6.46-6.49 (m, 1H), 5.42 (s, 2H), 4.22 (s, 3H), 3.86 (s, 3H), 1.63 (s, 9H).

39D. 4-(4-(((6-Methoxy-2-(2-methoxyimidazo[2,1-b][1,3,4]thiadiazol-6-yl)benzofuran-4-yl)oxy) methyl)thiazol-2-yl)benzoic Acid

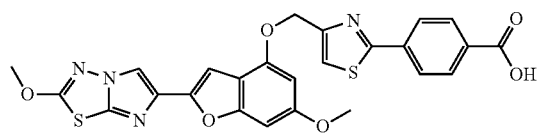 [SMILES: COc1cc(OCc2csc(-c3ccc(C(=O)O)cc3)n2)c2cc(-c3cn4nc(OC)sc4n3)oc2c1]

To a solution of tert-butyl 4-(4-(((6-methoxy-2-(2-methoxyimidazo[2,1-b][1,3,4]thia-diazol-6-yl)benzofuran-4-yl)oxy)methyl)thiazol-2-yl)benzoate (0.841 g, 1.424 mmol) in DCM (6 mL) was added TFA (3 mL) and the resulting pale yellowish solution was stirred at room temperature for 4 h before the volatiles were removed in vacuo. The residue was triturated with a minimum volume of DCM and the resulting solid was filtered and then lyophilized from DMSO. This gave the essentially pure title compound (0.701 g, 92%) as a solid which was used as such in the next step. LC (Method A): 2.347 min. HRMS(ESI): calcd for $C_{25}H_{19}N_4O_6S_2$ [M+H]⁺ m/z 535.0746; found 535.0742. ¹H NMR (400 MHz, DMSO-d₆) δ ppm: 13.18 (br s, 1H), 8.37 (s, 1H), 8.03-8.13 (m, 4H), 8.00 (s, 1H), 7.01-7.06 (m, 1H), 6.85 (d, J=0.78 Hz, 1H), 6.65 (d, J=1.96 Hz, 1H), 5.40 (s, 2H), 4.20 (s, 3H), 3.82 (s, 3H).

Example 39. 4-(4-(((6-Methoxy-2-(2-methoxyimidazo[2,1-b][1,3,4]thiadiazol-6-yl)benzofuran-4-yl)oxy)methyl)thiazol-2-yl)-N-(2-methoxyethyl)-N-methylbenzamide

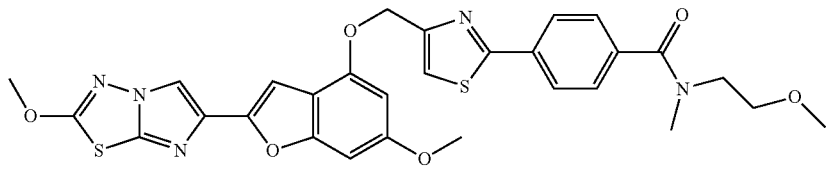

To a solution of 4-(4-(((6-methoxy-2-(2-methoxyimidazo[2,1-b][1,3,4]thiadiazol-6-yl)benzofuran-4-yl)oxy)methyl)thiazol-2-yl)benzoic acid (0.050 g, 0.094 mmol) in DMF (3 mL) was added DIEA (0.082 mL, 0.468 mmol), followed by 2-methoxy-N-methylethanamine (0.0092 g, 0.103 mmol) and finally HATU (0.039 g, 0.103 mmol). The resulting mixture was stirred at room temperature for 2 h before being evaporated to dryness. The residue was partitioned with DCM-water and the organic phase was separated, washed (saturated aqueous $NaHCO_3$), dried ($Na_2SO_4$) and adsorbed directly on a silica gel pre-column. Flash chromatography (Isco, elution gradient 0-80% EtOAc-DCM), followed by lyophilization obtained material from MeCN-water afforded the title compound (0.044 g, 78%) as a solid. LC (Method A): 2.325 min. HRMS(ESI): calcd. for $C_{29}H_{28}N_5O_6S_2$ [M+H]$^+$ m/z 606.1481; found 606.1469. $^1$H NMR (400 MHz, CDCl$_3$) δ ppm: 8.01 (m, J=7.83 Hz, 2H), 7.86 (s, 1H), 7.49-7.56 (m, 2H), 7.41 (s, 1H), 7.12 (s, 1H), 6.73 (s, 1H), 6.45-6.49 (m, 1H), 5.41 (s, 2H), 4.22 (s, 3H), 3.86 (s, 3H), 3.65-3.81 (m, 2H), 3.45-3.53 (m, 2H), 3.37-3.45 (m, 2H), 3.24-3.37 (m, 1H), 3.12-3.21 (m, 2H), 3.06-3.11 (m, 1H).

Example 40

4-(4-(((6-Methoxy-2-(2-methoxyimidazo[2,1-b][1,3,4]thiadiazol-6-yl)benzofuran-4-yl)oxy)methyl)thiazol-2-yl)-N-methylbenzamide

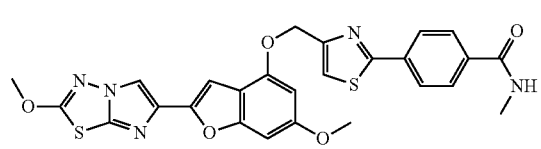 [SMILES: CNC(=O)c1ccc(-c2nc(COc3cc(OC)cc4oc(-c5cn6nc(OC)sc6n5)cc34)cs2)cc1]

The title compound was prepared according to the general amide coupling method described in Example 39. LC (Method A): 2.239 min. HRMS(ESI): calcd for $C_{26}H_{22}N_5O_5S_2$ [M+H]$^+$ m/z 548.1062; found 548.1058. $^1$H NMR (400 MHz, CDCl$_3$) δ ppm: 8.04 (d, J=8.22 Hz, 2H), 7.81-7.89 (m, 3H), 7.44 (s, 1H), 7.12 (s, 1H), 6.66-6.78 (m, 1H), 6.44-6.50 (m, 1H), 6.14-6.24 (m, 1H), 5.41 (s, 2H), 4.22 (s, 3H), 3.85 (s, 3H), 3.06 (d, J=5.09 Hz, 3H).

Example 41

N-(tert-Butyl)-4-(4-(((6-methoxy-2-(2-methoxyimidazo[2,1-b][1,3,4]thiadiazol-6-yl)benzofuran-4-yl)oxy)methyl)thiazol-2-yl)benzamide

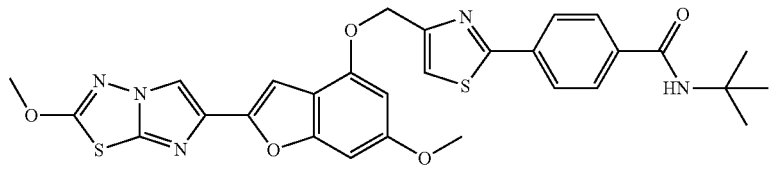

The title compound was prepared according to the general amide coupling method described in Example 39. LC (Method A): 2.458 min. HRMS(ESI): calcd for $C_{29}H_{28}N_5O_5S_2$ [M+H]$^+$ m/z 590.1532; found 590.1536. $^1$H NMR (400 MHz, CDCl$_3$) δ ppm: 8.03 (m, 2H), 7.86 (s, 1H), 7.81 (m, 2H), 7.43 (s, 1H), 7.12 (s, 1H), 6.73 (s, 1H), 6.48 (br s, 1H), 5.98 (s, 1H), 5.41 (s, 2H), 4.22 (s, 3H), 3.86 (s, 3H), 1.51 (s, 9H).

Example 42

4-(5-Isopropyl-4-(((6-methoxy-2-(2-methoxyimidazo[2,1-b][1,3,4]thiadiazol-6-yl)benzofuran-4-yl)oxy)methyl)thiazol-2-yl)-N,N-dimethylbenzamide

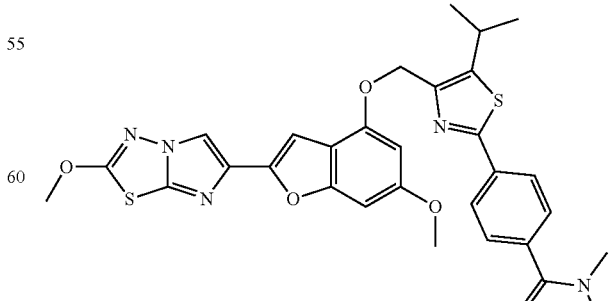

42A. Methyl 2-bromo-5-isopropylthiazole-4-carboxylate

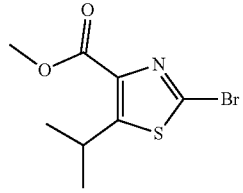

To a solution of methyl 2-amino-5-isopropylthiazole-4-carboxylate (1.000 g, 4.99 mmol) in CH$_3$CN (10 mL) was added isopentyl nitrite (1.073 mL, 7.99 mmol) followed by copper(I) bromide (1.433 g, 9.99 mmol) and the resulting mixture was heated at 80° C. for 3 h. The reaction mixture was then concentrated under reduced pressure and the residue was partitioned between EtOAc and water. The organic phase was separated, filtered through a CELITE® pad and concentrated. The residue was purified on the ISCO using a REDISEPR® 24 g column (0 to 40% EtOAc-hexanes) to give the desired product as a light red oil (0.787 g, 60%). LCMS (APCI): calcd for C$_8$H$_{11}$BrNO$_2$S [M+H]$^+$ m/z 263.962, found 264.0. $^1$H NMR (CDCl$_3$, 400 MHz) δ ppm: 4.17 (dt, J=13.7, 6.8 Hz, 1H), 3.94 (s, 3H), 1.35 (s, 3H), 1.33 (s, 3H).

42B. (2-Bromo-5-isopropylthiazol-4-yl)methanol

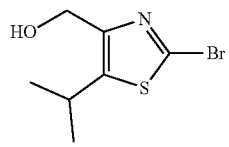

The compound was prepared according to the procedure described in Example 37A. The reaction mixture was quenched with MeOH (10 mL) and stirred at room temperature for 10 min before being concentrated under reduced pressure. The residue was dissolved in DCM, washed with saturated aqueous NaHCO$_3$, water and brine, dried over MgSO$_4$ and evaporated. The crude product was purified on the ISCO using a REDISEP® 12 g column (0 to 15% MeOH-DCM) to give the desired product as a white solid (0.509 g, 72%). LCMS (APCI): calcd for C$_7$H$_{11}$BrNOS [M+H]$^+$ m/z 234.97, found 218.0 (M+H-OH). $^1$H NMR (CDCl$_3$, 400 MHz) δ ppm: 4.64 (d, J=6.3 Hz, 2H), 3.32 (dt, J=13.7, 6.8 Hz, 1H), 2.26 (t, J=6.2 Hz, 1H), 1.30 (d, J=6.8 Hz, 6H).

42C. 2-Bromo-4-(((tert-butyldimethylsilyl)oxy)methyl)-5-isopropylthiazole

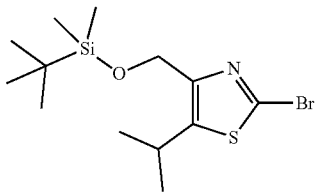 [SMILES: CC(C)c1sc(Br)nc1CO[Si](C)(C)C(C)(C)C]

The compound was prepared according to the procedure described in Example 37B. The crude product was purified on the ISCO using a REDISEP® 12 g column (0 to 50% EtOAc-hexanes) to give the pure product as a colorless oil (0.744 g, 99%). LCMS (APCI): calcd for C$_{13}$H$_{25}$BrNOSSi [M+H]$^+$ m/z 350.05, found 350.1. $^1$H NMR (CDCl$_3$, 400 MHz) δ ppm: 4.73 (s, 2H), 3.47 (dt, J=13.7, 7.0 Hz, 1H), 1.29 (d, J=7.0 Hz, 6H), 0.91 (s, 9H), 0.10 (s, 6H).

42D. 4-(4-(((tert-Butyldimethylsilyl)oxy)methyl)-5-isopropylthiazol-2-yl)-N,N-dimethyl benzamide

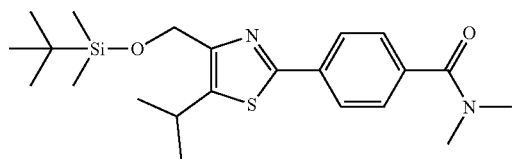 [SMILES: CC(C)c1sc(-c2ccc(C(=O)N(C)C)cc2)nc1CO[Si](C)(C)C(C)(C)C]

In a 75 mL sealable tube were added 2-bromo-4-(((tert-butyldimethylsilyl)oxy) methyl)-5-isopropylthiazole (0.200 g, 0.571 mmol), (4-(dimethylcarbamoyl) phenyl)boronic acid (0.166 g, 0.859 mmol) and Pd(dppf)Cl$_2$.DCM (0.030 g, 0.037 mmol) in a mixture of toluene-ethanol (3:1, 6.5 mL). The resulting orange solution was degassed with a stream of nitrogen bubbles for 15 min and then a 2 M aqueous solution of Na$_2$CO$_3$ (0.342 mL, 0.685 mmol) was added, the reaction vessel was sealed and the mixture was heated at 95° C. (bath temperature) for 4 h. The cooled dark brown reaction mixture was diluted with EtOAc and washed with saturated aqueous NaHCO$_3$ and brine, dried over MgSO$_4$ and evaporated. The residue was purified on the ISCO using a REDISEP® 12 g column (0 to 60% EtOAc-DCM) to give the title compound as a colorless oil (0.080 g, 34%). LCMS (APCI): calcd for C$_{22}$H$_{35}$N$_2$O$_2$SSi [M+H]$^+$ m/z 419.21, found 419.2. $^1$H NMR (CDCl$_3$, 400 MHz) δ ppm: 7.91-7.96 (m, 2H), 7.45-7.49 (m, 2H), 4.84 (s, 2H), 3.51 (dt, J=13.6, 6.7 Hz, 1H), 3.13 (br. s., 3H), 3.01 (br. s., 3H), 1.36 (s, 3H), 1.35 (s, 3H), 0.93 (s, 9H), 0.13 (s, 6H).

42E. 4-(4-(Hydroxymethyl)-5-isopropylthiazol-2-yl)-N,N-dimethylbenzamide

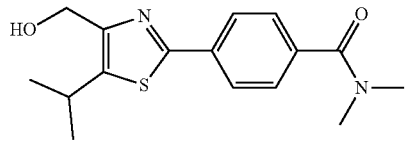 [SMILES: CC(C)c1sc(-c2ccc(C(=O)N(C)C)cc2)nc1CO]

The reaction was done according to the procedure of Example 37D. The reaction mixture was diluted with DCM, washed with saturated aqueous NaHCO$_3$, water, and brine, dried over MgSO$_4$ and evaporated. The crude material was purified on the ISCO using a REDISEP® 4 g column (0 to 15% MeOH-DCM) to give the desired product as a yellow solid (0.056 g, 96%). LCMS (APCI): calcd for C$_{16}$H$_{21}$N$_2$O$_2$S [M+H]$^+$ m/z 305.125, found 305.1. $^1$H NMR (CDCl$_3$, 400 MHz) δ ppm: 7.4 (d, J=8.2 Hz, 2H), 7.49 (d, J=8.2 Hz, 2H), 4.74 (d, J=5.9 Hz, 2H), 3.34 (dt, J=13.6, 6.7 Hz, 1H), 3.14 (br. s., 3H), 3.01 (br. s., 3H), 2.45 (t, J=5.9 Hz, 1H), 1.36 (d, J=7.0 Hz, 6H).

149

Example 42. 4-(5-Isopropyl-4-(((6-methoxy-2-(2-methoxyimidazo[2,1-b][1,3,4]thiadiazol-6-yl)benzofuran-4-yl)oxy)methyl)thiazol-2-yl)-N,N-dimethylbenzamide

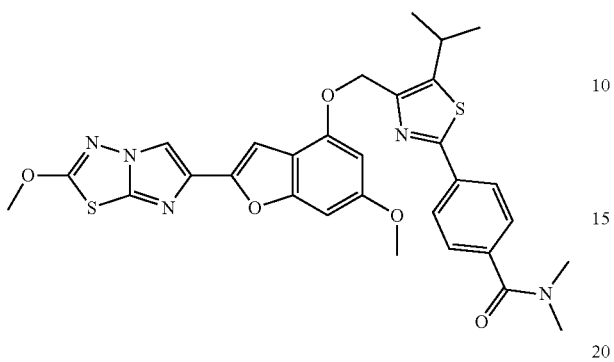

The title compound was prepared according to the procedure used for the synthesis of Example 36. The crude product was suspended in CH$_3$CN, sonicated, filtered and dried (×2) to give the title compound as an off-white solid (0.018 g, 16%). LC (Method C): 2.359 min. HRMS(ESI): calcd for C$_{30}$H$_{30}$N$_5$O$_5$S$_2$ [M+H]$^+$ m/z 604.161, found 604.1690. $^1$H NMR (CDCl$_3$, 400 MHz) δ ppm: 7.95-8.00 (m, J=8.2 Hz, 2H), 7.84 (s, 1H), 7.47-7.52 (m, J=8.2 Hz, 2H), 7.02 (s, 1H), 6.71 (s, 1H), 6.60 (d, J=1.6 Hz, 1H), 5.32 (s, 2H), 4.21 (s, 3H), 3.86 (s, 3H), 3.50 (dt, J=13.8, 7.0 Hz, 1H), 3.14 (br s, 3H), 3.02 (br s, 3H), 1.37 (d, J=7.0 Hz, 6H).

Example 43

6-(4-((2-(2-Fluoropyridin-4-yl)-5-isopropylthiazol-4-yl)methoxy)-6-methoxybenzofuran-2-yl)-2-methoxyimidazo[2,1-b][1,3,4]thiadiazole

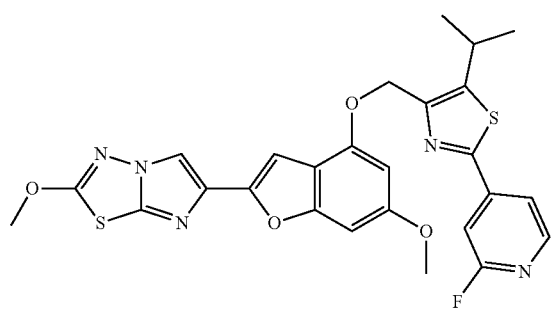 [SMILES: COc1cc(OCc2nc(-c3ccnc(F)c3)sc2C(C)C)c2cc(-c3cn4nc(OC)sc4n3)oc2c1]

43A. 4-(((tert-Butyldimethylsilyl)oxy)methyl)-2-(2-fluoropyridin-4-yl)-5-isopropylthiazole

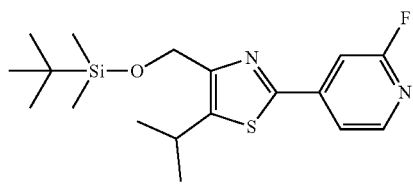 [SMILES: CC(C)c1sc(-c2ccnc(F)c2)nc1CO[Si](C)(C)C(C)(C)C]

150

The compound was prepared according to the procedure described for Example 42D. The crude product was purified on the ISCO using a REDISEP® 12 g column (0 to 5% EtOAc-DCM) to give the product as a white solid (0.078 g, 38%). LCMS (APCI): calcd for C$_{18}$H$_{28}$FN$_2$OSSi [M+H]$^+$ m/z 367.16, found 367.2. $^1$H NMR (CDCl$_3$, 400 MHz) δ ppm: 8.26 (d, J=5.3 Hz, 1H), 7.64 (dt, J=5.3, 1.6 Hz, 1H), 7.42 (s, 1H), 4.85 (s, 2H), 3.54 (dt, J=13.7, 6.8 Hz, 1H), 1.38 (s, 3H), 1.36 (s, 3H), 0.93 (s, 9H), 0.13 (s, 6H).

43B. (2-(2-Fluoropyridin-4-yl)-5-isopropylthiazol-4-yl)methanol

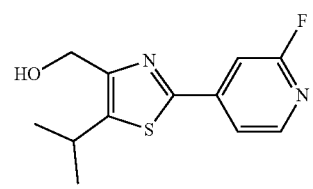 [SMILES: CC(C)c1sc(-c2ccnc(F)c2)nc1CO]

The compound was prepared using the procedure described in Example 37D. The reaction mixture was diluted with DCM, washed with saturated aqueous NaHCO$_3$, water and brine, dried over MgSO$_4$ and evaporated. The crude product was purified on the ISCO using a REDISEP® 4 g column (0 to 15% MeOH-DCM) to give the desired product as a colorless solid (0.048 g, 89%). LCMS (APCI): calcd for C$_{12}$H$_{13}$FN$_2$OS [M+H]$^+$ m/z 253.073, found 253.1. $^1$H NMR (CDCl$_3$, 400 MHz) δ ppm: 8.28 (d, J=5.1 Hz, 1H), 7.65 (dt, J=5.5, 1.6 Hz, 1H), 7.41-7.45 (m, 1H), 4.77 (d, J=5.9 Hz, 2H), 3.38 (dt, J=13.7, 6.8 Hz, 1H), 2.36 (t, J=5.9 Hz, 1H), 1.38 (d, J=6.9 Hz, 6H).

Example 43. 6-(4-((2-(2-Fluoropyridin-4-yl)-5-isopropylthiazol-4-yl)methoxy)-6-methoxybenzofuran-2-yl)-2-methoxyimidazo[2,1-b][1,3,4]thiadiazole

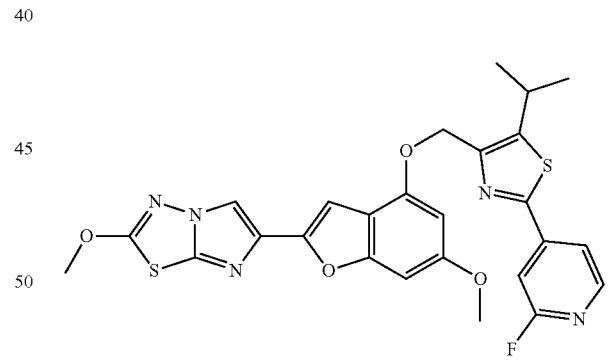

The title compound was prepared according to the procedure used for the synthesis of Example 36. The crude product was suspended in CH$_3$CN, sonicated and filtered. The resulting solid was purified on the ISCO using a REDISEP® 4 g column (0 to 40% EtOAc-DCM) to give the title compound as a yellow solid (0.063 g, 60%). LC (Method C): 2.457 min. HRMS(ESI): calcd for C$_{26}$H$_{23}$FN$_5$O$_4$S$_2$ [M+H]$^+$ m/z 552.110, found 552.1181. $^1$H NMR (CDCl$_3$, 400 MHz) δ ppm: 8.29 (d, J=5.5 Hz, 1H), 7.84 (s, 1H), 7.68 (dt, J=5.5, 1.6 Hz, 1H), 7.46 (s, 1H), 7.02 (s, 1H), 6.72 (d, J=0.8 Hz, 1H), 6.58 (d, J=2.0 Hz, 1H), 5.34 (s, 2H), 4.21 (s, 3H), 3.87 (s, 3H), 3.53 (dt, J=13.6, 7.0 Hz, 1H), 1.39 (d, J=7.0 Hz, 6H).

Example 44

4-(5-Ethyl-4-(((6-methoxy-2-(2-methoxyimidazo[2,1-b][1,3,4]thiadiazol-6-yl)benzofuran-4-yl)oxy)methyl)thiazol-2-yl)-N,N-dimethylbenzamide

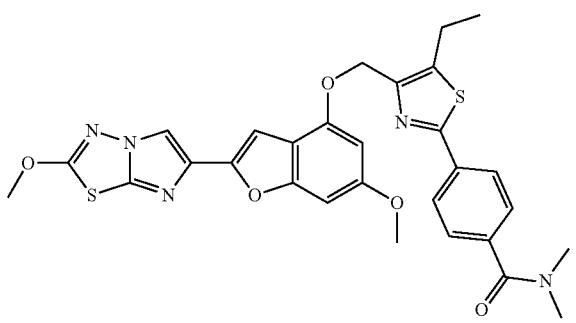

44A. (2-Bromo-5-ethylthiazol-4-yl)methanol

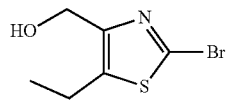

The compound was prepared using the procedure described in Example 37A. The reaction mixture was quenched with MeOH (10 mL) and stirred at room temperature for 10 min. Then the mixture was concentrated under reduced pressure and the residue was dissolved in DCM, washed with saturated aqueous NaHCO$_3$, water and brine, dried over MgSO$_4$ and evaporated to give the desired product as colorless oil (0.156 g, 88%). LCMS (APCI): calcd for C$_6$H$_9$BrNOS [M+H]$^+$ m/z 220.95, found 205.9 (M+H-OH). $^1$H NMR (CDCl$_3$, 400 MHz) δ ppm: 4.63 (br. s., 2H), 2.82 (q, J=7.4 Hz, 2H), 2.29 (br. s., 1H), 1.28 (t, J=7.4 Hz, 3H).

44B. 2-Bromo-4-(((tert-butyldimethylsilyl)oxy)methyl)-5-ethylthiazole

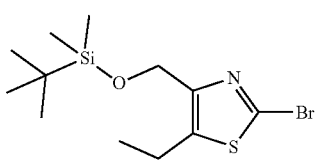 [SMILES: CCc1sc(Br)nc1CO[Si](C)(C)C(C)(C)C]

The compound was prepared according to the procedure described in Example 37B. The crude product was purified on the ISCO using a REDISEP® 12 g column (0 to 50% EtOAc-hexanes) to give the title compound as a colorless oil (0.173 g, 73%). LCMS (APCI): calcd for C$_{12}$H$_{23}$BrNOSSi [M+H]$^+$ m/z 336.04, found 337.1. $^1$H NMR (CDCl$_3$, 400 MHz) δ ppm: 4.73 (s, 2H), 2.88 (q, J=7.7 Hz, 2H), 1.28 (t, J=7.6 Hz, 3H), 0.91 (s, 9H), 0.10 (s, 6H).

44C. 4-(4-(((tert-Butyldimethylsilyl)oxy)methyl)-5-ethylthiazol-2-yl)-N,N-dimethyl benzamide

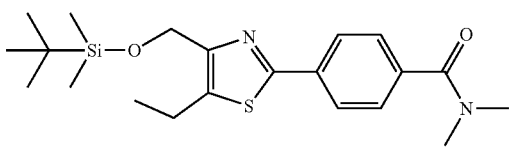 [SMILES: CCc1sc(-c2ccc(C(=O)N(C)C)cc2)nc1CO[Si](C)(C)C(C)(C)C]

The compound was prepared according to the procedure described for Example 36A. The crude product was purified on the ISCO using a REDISEP® 4 g column (0 to 60% EtOAc-DCM) to give the title compound as brownish oil (0.155 g, 75%). LCMS (APCI): calcd for C$_{21}$H$_{33}$N$_2$O$_2$SSi [M+H]$^+$ m/z 405.20, found 405.2. $^1$H NMR (CDCl$_3$, 400 MHz) δ ppm: 7.90-7.96 (m, J=7.8 Hz, 2H), 7.44-7.50 (m, J=8.2 Hz, 2H), 4.84 (s, 2H), 3.13 (br s, 3H), 3.01 (br s, 3H), 2.96 (q, J=7.4 Hz, 2H), 1.34 (t, J=7.5 Hz, 3H), 0.93 (s, 9H), 0.13 (s, 6H).

44D. 4-(5-Ethyl-4-(hydroxymethyl)thiazol-2-yl)-N,N-dimethylbenzamide

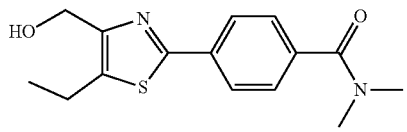

The compound was prepared according to the procedure described in Example 36B. The reaction mixture was diluted with DCM, washed with saturated aqueous NaHCO$_3$, water and brine, dried over MgSO$_4$ and evaporated. The crude product was purified on the ISCO using a REDISEP® 4 g column (0 to 15% MeOH-DCM) to give the desired product as a colorless oil (0.094 g, 85%). LCMS (APCI): calcd for C$_{15}$H$_{19}$N$_2$O$_2$S [M+H]$^+$ m/z 291.109, found 291.1. $^1$H NMR (CDCl$_3$, 400 MHz) δ ppm: 7.91-7.96 (m, J=8.2 Hz, 2H), 7.46-7.51 (m, J=8.2 Hz, 2H), 4.73 (d, J=5.9 Hz, 2H), 3.14 (br. s., 3H), 3.01 (br. s., 3H), 2.89 (q, J=7.7 Hz, 2H), 2.40 (t, J=5.9 Hz, 1H), 1.34 (t, J=7.6 Hz, 3H).

Example 44. 4-(5-Ethyl-4-(((6-methoxy-2-(2-methoxyimidazo[2,1-b][1,3,4] thiadiazol-6-yl)benzofuran-4-yl)oxy)methyl)thiazol-2-yl)-N,N-dimethylbenzamide

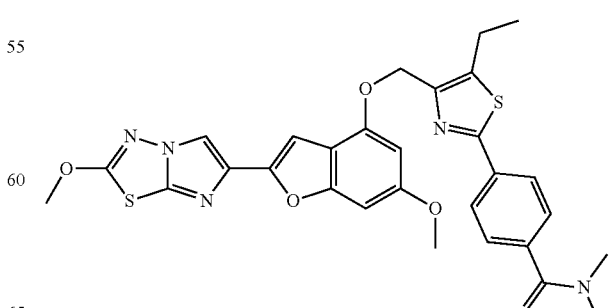

The title compound was prepared according to the procedure described for the synthesis of Example 36. The crude product was suspended in CH₃CN, sonicated and filtered before being purified on the ISCO using a REDISEP® 4 g column (0 to 70% EtOAc-DCM) to give the title compound as an off-white solid (0.059 g, 49%). LC (Method C): 2.409 min. HRMS(ESI): calcd for $C_{29}H_{28}N_5O_5S_2$ [M+H]⁺ m/z 590.145, found 590.1505. ¹H NMR (CDCl₃, 400 MHz) δ ppm: 7.94-8.00 (m, J=8.2 Hz, 2H), 7.84 (s, 1H), 7.46-7.52 (m, J=7.8 Hz, 2H), 7.04 (s, 1H), 6.71 (d, J=0.8 Hz, 1H), 6.58 (d, J=2.0 Hz, 1H), 5.32 (s, 2H), 4.21 (s, 3H), 3.86 (s, 3H), 3.14 (br s, 3H), 2.95-3.06 (m, 5H), 1.35 (t, J=7.6 Hz, 3H).

Example 45 tert-Butyl 4-(4-(((6-methoxy-2-(2-methoxyimidazo[2,1-b][1,3,4]thiadiazol-6-yl)benzofuran-4-yl)oxy)methyl)-5-methylthiazol-2-yl)benzoate

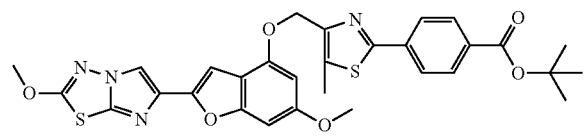 [SMILES: COc1cc(OCc2nc(-c3ccc(C(=O)OC(C)(C)C)cc3)sc2C)c2cc(-c3cn4nc(OC)sc4n3)oc2c1]

45A. (2-Bromo-5-methylthiazol-4-yl)methanol

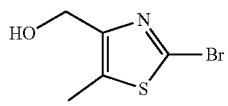

The compound was prepared according to the procedure described in Example 37A. The reaction mixture was quenched with MeOH (10 mL) and stirred at room temperature for 10 min. Then the mixture was concentrated under reduced pressure and the residue was dissolved in DCM, washed with saturated aqueous NaHCO₃, water and brine, dried over MgSO₄ and evaporated to give the desired product as colorless oil (0.843 g, 96%). LCMS (APCI): calcd for $C_5H_7BrNOS$ [M+H]⁺ m/z 207.94, found 208.0.

45B. 2-Bromo-4-(((tert-butyldimethylsilyl)oxy)methyl)-5-methylthiazole

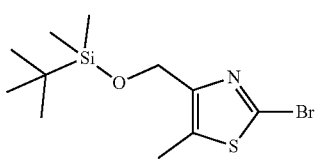 [SMILES: Cc1sc(Br)nc1CO[Si](C)(C)C(C)(C)C]

The compound was prepared according to the procedure described in Example 37B. The crude product was purified on the ISCO using a REDISEP® 40 g column (50 to 100% DCM-hexanes) to give the title compound as a colorless oil (0.682 g, 52%). LCMS (APCI): calcd for $C_{11}H_{21}BrNOSSi$ [M+H]⁺ m/z 322.03, found 322.0. ¹H NMR (CDCl₃, 400 MHz) δ ppm: 4.64 (s, 2H), 2.34 (s, 3H), 0.81 (s, 9H), 0.00 (s, 6H).

45C. tert-Butyl 4-(4-(((tert-butyldimethylsilyl)oxy)methyl)-5-methylthiazol-2-yl)benzoate

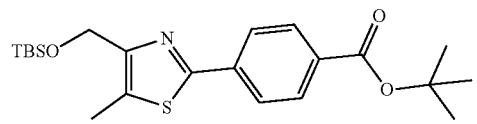 [SMILES: Cc1sc(-c2ccc(C(=O)OC(C)(C)C)cc2)nc1CO[Si](C)(C)C(C)(C)C]

In a sealable vial, a suspension of (4-(tert-butoxycarbonyl)phenyl)boronic acid (0.611 g, 2.75 mmol) and 2-bromo-4-(((tert-butyldimethylsilyl)oxy)methyl)-5-methylthiazole (0.682 g, 2.116 mmol) in toluene (34 mL) and ethanol (9.3 mL) was treated with 2 M aqueous sodium carbonate (1.27 mL, 2.54 mmol) and then purged with nitrogen for 5 min. To this mixture was added [1,1'-bis(diphenylphosphino)ferrocene]palladium (II) dichloride.DCM (0.091 g, 0.133 mmol), the vial was sealed and the mixture was heated at 95° C. for 4 h. The cooled reaction mixture was partitioned with ethyl acetate-saturated aqueous sodium bicarbonate and the organic phase was separated, washed with brine, dried over anhydrous magnesium sulfate and evaporated in vacuo. Chromatography of the residue on silica gel (ISCO, elution gradient of dichloromethane in hexane) gave 0.654 g (74%) of the title compound. LC (Method A): 2.966 min. HRMS (ESI): calcd for $C_{22}H_{34}NO_3SSi$ [M+H]⁺ m/z 420.2029; found 420.2038. ¹H NMR (400 MHz, CDCl₃) δ ppm: 7.97-8.10 (m, 2H), 7.85-7.97 (m, 2H), 4.86 (s, 2H), 2.54 (s, 3H), 1.62 (s, 9H), 0.94 (s, 9H), 0.14 (s, 6H).

45D. tert-Butyl 4-(4-(hydroxymethyl)-5-methylthiazol-2-yl)benzoate

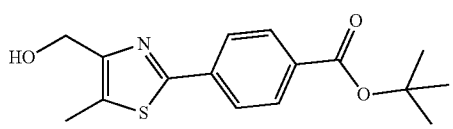 [SMILES: Cc1sc(-c2ccc(C(=O)OC(C)(C)C)cc2)nc1CO]

The title compound was prepared according to the method described in Example 37D. LC (Method A): 2.225 min. HRMS(ESI): calcd for $C_{16}H_{20}NO_3S$ [M+H]⁺ m/z 306.1164; found 306.1161. ¹H NMR (400 MHz, CDCl₃) δ ppm: 7.99-8.07 (m, 2H), 7.87-7.99 (m, 2H), 4.74 (d, J=5.77 Hz, 2H), 2.50 (s, 3H), 2.35 (t, J=5.77 Hz, 1H), 1.62 (s, 9H).

Example 45. tert-Butyl 4-(4-(((6-methoxy-2-(2-methoxyimidazo[2,1-b][1,3,4]thiadiazol-6-yl)benzofuran-4-yl)oxy)methyl)-5-methylthiazol-2-yl)benzoate

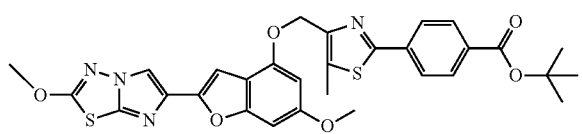 [SMILES: COc1cc(OCc2nc(-c3ccc(C(=O)OC(C)(C)C)cc3)sc2C)c2cc(-c3cn4nc(OC)sc4n3)oc2c1]

The title compound was prepared according to the general Mitsunobu coupling procedure described in Example 36. LC (Method A): 2.761 min. HRMS(ESI): calcd for $C_{30}H_{29}N_4O_6S_2$ [M+H]$^+$ m/z 605.1529; found 605.1518. $^1$H NMR (400 MHz, CDCl$_3$) δ ppm: 8.00-8.07 (m, 2H), 7.92-7.99 (m, 2H), 7.84 (s, 1H), 7.06 (s, 1H), 6.69-6.73 (m, 1H), 6.55-6.59 (m, 1H), 5.34 (s, 2H), 4.21 (s, 3H), 3.85 (s, 3H), 2.59 (s, 3H), 1.62 (s, 9H).

Example 46

4-(4-(((6-Methoxy-2-(2-methoxyimidazo[2,1-b][1,3,4]thiadiazol-6-yl)benzofuran-4-yl)oxy)methyl)-5-methylthiazol-2-yl)benzoic Acid

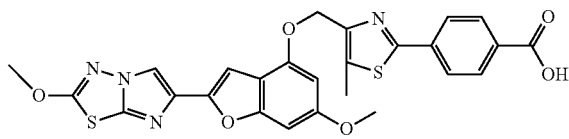 [SMILES: COc1cc(OCc2nc(-c3ccc(C(=O)O)cc3)sc2C)c2cc(-c3cn4nc(OC)sc4n3)oc2c1]

The title compound was prepared from Example 45 above according to the general deprotection method described in Example 39D. LC (Method A): 2.436 min. HRMS(ESI): calcd for $C_{26}H_{21}N_4O_6S_2$ [M+H]$^+$ m/z 549.0903; found 549.0898. $^1$H NMR (400 MHz, DMSO-d$_6$) δ ppm: 13.07 (br s, 1H), 8.30 (s, 1H), 7.92-8.01 (m, 4H), 6.87 (s, 1H), 6.76-6.79 (m, 1H), 6.60-6.64 (m, 1H), 5.27 (s, 2H), 4.13 (s, 3H), 3.75 (s, 3H), 2.52 (s, 3H).

Example 47

4-(4-(((6-Methoxy-2-(2-methoxyimidazo[2,1-b][1,3,4]thiadiazol-6-yl)benzofuran-4-yl)oxy)methyl)-5-methylthiazol-2-yl)-N-(2,2,2-trifluoroethyl)benzamide

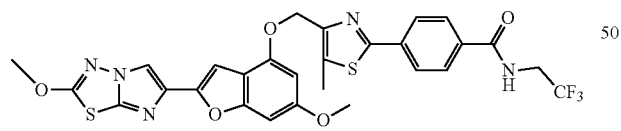

The title compound was prepared from Example 46 according to the general amide coupling method described in Example 39. LC (Method A): 2.412 min. HRMS(ESI): calcd for $C_{28}H_{23}F_3N_5O_5S_2$ [M+H]$^+$ m/z 630.1093; found 630.1092. $^1$H NMR (400 MHz, CDCl$_3$) δ ppm: 7.99 (d, J=8.22 Hz, 2H), 7.76-7.88 (m, 3H), 7.03 (s, 1H), 6.69 (s, 1H), 6.54 (s, 1H), 6.32 (t, J=6.46 Hz, 1H), 5.31 (s, 2H), 4.06-4.22 (m, 5H), 3.83 (s, 3H), 2.57 (s, 3H).

Example 48

N-(Cyanomethyl)-4-(4-(((6-methoxy-2-(2-methoxyimidazo[2,1-b][1,3,4]thiadiazol-6-yl)benzofuran-4-yl)oxy)methyl)-5-methylthiazol-2-yl)-N-methylbenzamide

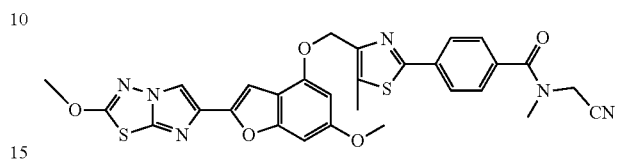

The title compound was prepared from Example 46 according to the general amide coupling method described in Example 39. LC (Method A): 2.327 min. HRMS(ESI): calcd for $C_{29}H_{25}N_6O_5S_2$ [M+H]$^+$ m/z 601.1328; found 601.1328. $^1$H NMR (400 MHz, CDCl$_3$) δ ppm: 8.00 (m, 2H), 7.84 (s, 1H), 7.52-7.59 (m, 2H), 7.05 (s, 1H), 6.69-6.74 (m, 1H), 6.53-6.59 (m, 1H), 5.33 (s, 2H), 4.48 (br s, 2H), 4.21 (s, 3H), 3.86 (s, 3H), 3.19 (s, 3H), 2.59 (s, 3H).

Example 49

4-(4-(((6-Methoxy-2-(2-methoxyimidazo[2,1-b][1,3,4]thiadiazol-6-yl)benzofuran-4-yl)oxy)methyl)-5-methylthiazol-2-yl)-N-methylbenzamide

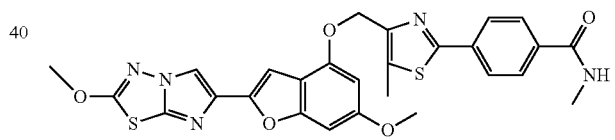

The title compound was prepared from Example 46 according to the general amide coupling method described in Example 39. LC (Method A): 2.364 min. HRMS(ESI): calcd for $C_{27}H_{24}N_5O_5S_2$ [M+H]$^+$ m/z 562.1219; found 562.1215. $^1$H NMR (400 MHz, CDCl$_3$) δ ppm: 7.98 (d, J=8.22 Hz, 2H), 7.78-7.86 (m, 3H), 7.05 (s, 1H), 6.65-6.76 (m, 1H), 6.53-6.59 (m, 1H), 6.12-6.24 (m, 1H), 5.33 (s, 2H), 4.21 (s, 3H), 3.85 (s, 3H), 3.05 (d, J=5.09 Hz, 3H), 2.58 (s, 3H).

Preparation of Alcohols

The following additional alcohols were prepared according to the procedures described in Examples 36 to 49.

| Structure | Formula | Calc. [M + H]+ m/z | LCMS [M + H]+ m/z | HPLC Retention Time (Min)/ Method | NMR |
|---|---|---|---|---|---|
| 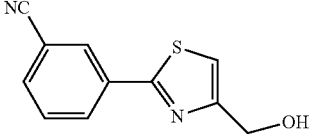 [SMILES: N#Cc1cccc(-c2nc(CO)cs2)c1] | C₁₁H₈N₂OS | 217.0 | 217.0 | 1.804/ A | ¹H NMR (400 MHz, CDCl₃) δ ppm: 8.27 (s, 1H), 8.17 (d, J = 7.8 Hz, 1H), 7.71 (d, J = 7.8 Hz, 1H), 7.57 (t, J = 7.8 Hz, 1H), 7.30 (s, 1H), 4.86 (d, J = 6.0 Hz, 2H), 2.26 (t, J = 6.0 Hz, 1H). |
| 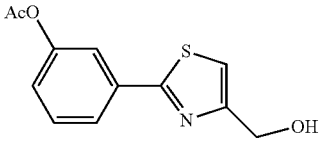 [SMILES: CC(=O)Oc1cccc(-c2nc(CO)cs2)c1] | C₁₂H₁₁NO₃S | 250.0532 | 250.0566 | 1.813/ A | ¹H NMR (400 MHz, CDCl₃) δ ppm: 7.80 (d, J = 7.8 Hz, 1H), 7.72 (broad s, 1H), 7.46 (t, J = 7.8 Hz, 1H), 7.21 (s, 1H), 7.17 (dd, J = 8.2, 2.3 Hz, 1H), 4.83 (d, J = 5.5 Hz, 2H), 2.34 (s, 3H), 2.26 (br. t., 1H). |
| 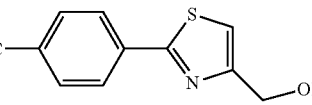 | C₁₁H₈N₂OS | | | 1.809/ A | ¹H NMR (400 MHz, CDCl₃) δ ppm: 8.07 (d, J = 8.2 Hz, 2H), 7.74 (d, J = 8.2 Hz, 2H), 7.33 (s, 1H), 4.87 (d, J = 5.9 Hz, 2H), 2.22 (t, J = 5.9 Hz, 1H). |
| 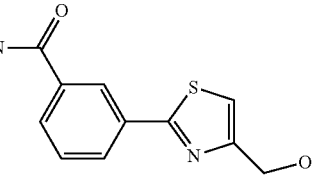 | C₁₃H₁₄N₂O₂S | 263.0849 | 263.0854 | 1.744/ A | ¹H NMR (400 MHz, CDCl₃) δ ppm: 7.96-8.04 (m, 2H), 7.43-7.54 (m, 2H), 7.22 (s, 1H), 4.84 (d, J = 6.0 Hz, 2H), 3.15 (broad s, 3H), 3.02 (broad s, 3H), 2.33 (t, J = 6.0 Hz, 1H). |
| 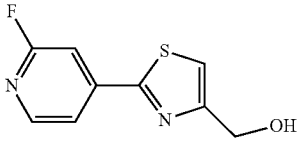 [SMILES: OCc1csc(-c2ccnc(F)c2)n1] | C₉H₇FN₂OS | 211.0336 | 211.032 | 1.633/ A | ¹H NMR (400 MHz, CDCl₃) δ ppm: 8.32 (d, J = 5.1 Hz, 1H), 7.70 (dt, J = 5.1, 1.7 Hz, 1H), 7.49 (t, J = 1.4 Hz, 1H), 7.39 (s, 1H), 4.89 (d, J = 5.9 Hz, 2H), 2.24 (t, J = 5.9 Hz, 1H). |
| 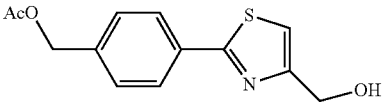 [SMILES: CC(=O)OCc1ccc(-c2nc(CO)cs2)cc1] | C₁₃H₁₃NO₃S | 264.0689 | 264.0687 | 1.928/ A | ¹H NMR (400 MHz, CDCl₃) δ ppm: 7.95 (d, J = 8.2 Hz, 2H), 7.44 (d, J = 8.2 Hz, 2H), 7.20 (s, 1H), 5.15 (s, 2H), 4.84 (d, J = 6.0 Hz, 2H), 2.29 (t, J = 6.0 Hz, 1H), 2.14 (s, 3H). |
| 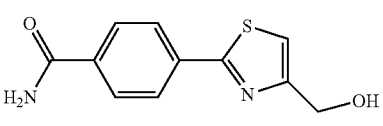 [SMILES: Cc1sc(-c2ccc(C(N)=O)cc2)nc1CO] | C₁₁H₁₀N₂O₂S | 235.0536 | 235.0537 | 1.528/ A | ¹H NMR (400 MHz, DMSO-d₆) δ ppm: 8.08 (br. s., 1H), 7.95-8.02 (m, 4H), 7.55 (s, 1H), 7.46 (br. s., 1H), 5.41 (t, J = 5.3 Hz, 1H), 4.64 (d, J = 5.3 Hz, 2H). |
| 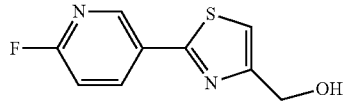 | C₉H₇FN₂OS | | | 1.357/ A | ¹H NMR (400 MHz, DMSO-d₆) δ ppm: 8.78 (d, J = 2.7 Hz, 1H), 8.43-8.52 (m, 1H), 7.57 (d, J = 1.1 Hz, 1H), 7.33 (dd, J = 8.6, 2.3 Hz, 1H), 5.43 (br. t., 1H), 4.64 (broad d, 2H). |
| 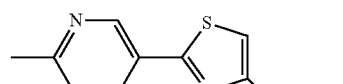 | C₁₀H₁₀N₂OS | 207.0587 | 207.0593 | 0.853/ A | ¹H NMR (400 MHz, CDCl₃) δ ppm: 9.05 (d, J = 2.3 Hz, 1H), 8.12 (dd, J = 8.2, 2.3 Hz, 1H), 7.24 (d, J = 8.2 Hz, 1H), 7.26 (s, 1H), 4.85 (d, J = 5.4 Hz, 2H), 2.62 (s, 3H), 2.38 (t, J = 5.4 Hz, 1H). |
| 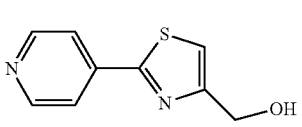 | C₉H₈N₂OS | 193.043 | 207.0437 | 0.710/ A | ¹H NMR (400 MHz, CDCl₃) δ ppm: 8.67-8.77 (m, 2H), 7.77-7.87 (m, 2H), 7.35 (s, 1H), 4.88 (d, J = 5.9 Hz, 2H), 2.32 (t, J = 5.9 Hz, 1H). |
| 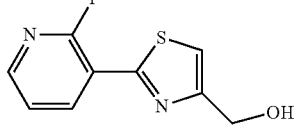 | C₉H₇FN₂OS | | | 1.412/ A | ¹H NMR (400 MHz, CDCl₃) δ ppm: 8.67-8.79 (m, 1H), 8.28 (broad d, J = 5.1 Hz, 1H), 7.40 (s, 1H), 7.31-7.38 (m, 1H), 4.88 (d, J = 6.0 Hz, 2H), 2.23 (t, J = 6.0 Hz, 1H). |

| Structure | Formula | Calc. [M + H]+ m/z | LCMS [M + H]+ m/z | HPLC Retention Time (Min)/ Method | NMR |
|---|---|---|---|---|---|
| (pyridine-thiazole-CH2OH with MeO) | C10H10N2O2S | 223.0536 | 223.053 | 1.168/ A | 1H NMR (400 MHz, CDCl3) δ ppm: 8.74 (d, J = 1.6 Hz, 1H), 8.38 (d, J = 3.1 Hz, 1H), 7.77-7.80 (m, 1H), 7.28 (s, 1H), 4.87 (d, J = 5.9 Hz, 2H), 3.95 (s, 3H), 2.27 (t, J = 5.9 Hz, 1H). |
| (chloropyridine-thiazole-CH2OH) | C9H7ClN2OS | 227.004 | 227.0036 | 1.529/ A | 1H NMR (400 MHz, CDCl3) δ ppm: 8.94 (d, J = 2.6 Hz, 1H), 8.21 (dd, J = 8.7, 2.6 Hz, 1H), 7.43 (d, J = 8.7 Hz, 1H), 7.30 (s, 1H), 4.86 (d, J = 5.9, Hz, 2H), 2.21 (t, J = 5.9 Hz, 1H). |
| (methylsulfonyl-phenyl-thiazole-CH2OH) | C11H11NO3S2 | 270.0252 | 270.026 | 1.337/ A | 1H NMR (400 MHz, CDCl3) δ ppm: 8.12-8.19 (m, 2H), 7.99-8.06 (m, 2H), 7.34 (s, 1H), 4.88 (d, J = 5.9 Hz. 2H), 3.10 (s, 3H), 2.24 (t, J = 5.9 Hz, 1H). |
| (pyridine-thiazole-CH2OH) | C9H8N2OS | 193.043 | 193.0445 | 0.836/ A | 1H NMR (400 MHz, CDCl3) δ ppm: 9.18 (d, J = 2.0 Hz, 1H), 8.67 (dd, J = 4.8, 1.6 Hz, 1H), 8.22-8.27 (m, 1H), 7.40 (dd, J = 8.0, 4.8 Hz, 1H), 7.28 (s, 1H), 4.87 (d, J = 5.9 Hz, 2H), 2.37 (t, J = 5.9 Hz, 1H). |
| (N,N-dimethylbenzamide-thiazole-CH2OH) | C14H16N2O2S | 277.1005 | 277.1013 | 1.845/ A | 1H NMR (400 MHz, CDCl3) δ ppm: 7.92 (~ d, J = 8.2 Hz, 2H), 7.48 ((~ d, J = 8.2 Hz, 2H), 4.73 (d, J = 5.9 Hz, 2H), 3.13 (br. s., 3H), 3.01 (br. s., 3H), 2.49 (s, 3H), 2.48 (t, J = 5.9 Hz, 1H). |
| (benzamide-thiazole-CH2OH) | C12H12N2O2S | 249.0692 | 249.0692 | 1.658/ A | 1H NMR (400 MHz, DMSO-d6) δ ppm: 8.06 (br. s., 1H), 7.90-8.00 (m, 4H), 7.44 (br. s., 1H), 5.14 (t, J = 5.5 Hz, 1H), 4.55 (d, J = 5.5 Hz, 2H), 2.5 (Me under DMSO). |
| (fluoropyridine-methylthiazole-CH2OH) | C10H9FN2OS | 225.0492 | 225.0494 | 1.551/ A | 1H NMR (400 MHz, CDCl3) δ ppm: 8.29 (d, J = 5.5 Hz, 1H), 7.64 (d, J = 5.5 Hz, 1H), 7.41 (s, 1H), 4.76 (d, J = 5.9 Hz, 2H), 2.54 (s, 3H), 2.30 (t, J = 5.9 Hz, 1H). |
| (AcO-CH2-phenyl-methylthiazole-CH2OH) | C14H15NO3S | 278.0845 | 278.0849 | 1.996/ A | 1H NMR (400 MHz, CDCl3) δ ppm: 7.90 (s, 1H), 7.80-7.84 (m, 1H), 7.37-7.46 (m, 2H), 5.16 (s, 2H), 4.73 (d, J = 5.9 Hz, 2H), 2.48 (s, 3H), 2.43 (t, J = 5.9 Hz, 1H), 2.14 (s, 3H). |

Examples 50 to 82

The following additional Examples have been prepared, isolated and characterized using the methods disclosed above.

| Ex. | Structure | Formula | Calc. M + H]+ [m/z] | HPLC Retention Time (Min)/ Method | LCMS [M + H]+ m/z | NMR |
|---|---|---|---|---|---|---|
| 50 | 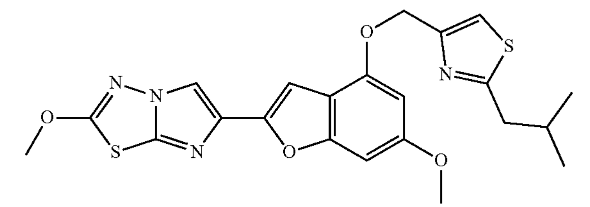 [SMILES: COc1cc(OCc2csc(CC(C)C)n2)c2cc(-c3cn4nc(OC)sc4n3)oc2c1] | C22H22N4O4S2 | 471.1155 | 2.574/A | 471.1236 | 1H NMR (CDCl3) δ ppm: 7.85 (s, 1H), 7.23 (s, 1H), 7.09 (s, 1H), 6.71 (br. d, 1H), 6.43 (d, J = 2.0 Hz, 1H), 5.31 (s,2H), 4.21 (s, 3H), 3.85 (s, 3H), 2.90 (d, J = 7.4 Hz, 2H), 2.10-2.18 (m, 1H), 1.02 (d, J = 6.7 Hz, 6H) |
| 51 | 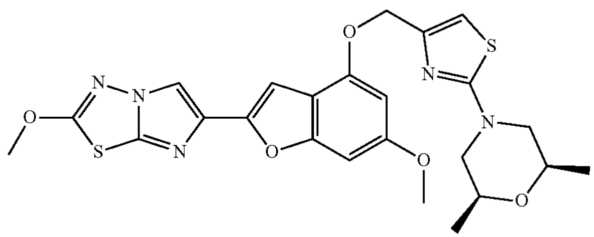 | C24H25N5O5S2 | 528.137 | 2.572/A | 528.1415 | 1H NMR (CDCl3) δ ppm: 7.85 (s, 1H), 7.10 (s, 1H), 6.70 (br. d, 1H), 6.62 (s, 1H), 6.43 (d, J = 2.0 Hz, 1H), 5.12 (s, 2H), 4.21 (s, 3H), 3.84 (s, 3H), 3.70-3.82 (m, 4H), 2.76 (dd, J = 12.9, 11.0 Hz, 2H), 1.27 (d, J = 6.3Hz, 6H) |
| 52 | 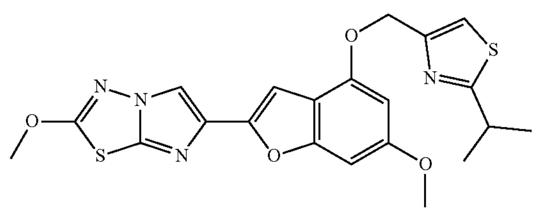 [SMILES: COc1cc(OCc2csc(C(C)C)n2)c2cc(-c3cn4nc(OC)sc4n3)oc2c1] | C21H20N4O4S2 | 457.0999 | 2.517/A | 457.1057 | 1H NMR (CDCl3) δ ppm: 7.85 (s, 1H), 7.23 (s, 1H), 7.10 (s, 1H), 6.71 (br. d, 1H), 6.44 (d, J = 2.0 Hz, 1H), 5.30 (s, 2H), 4.21 (s, 3H), 3.85 (s, 3H), 3.3-3.4 (m, 1H), 1.44 (d, J = 7.0 Hz, 6H) |
| 53 | 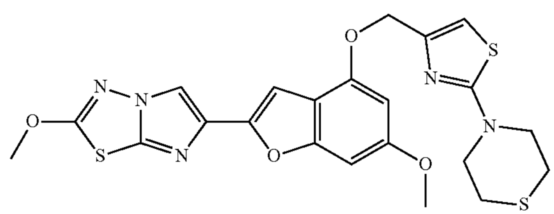 [SMILES: COc1cc(OCc2csc(N3CCSCC3)n2)c2cc(-c3cn4nc(OC)sc4n3)oc2c1] | C22H21N5O4S3 | 516.0828 | 2.481/A | 516.0887 | 1H NMR (CDCl3) δ ppm: 7.85 (s, 1H), 7.10 (s, 1H), 6.70 (br. d, 1H), 6.61 (s, 1H), 6.44 (d, J =1.6 Hz, 1H), 5.10 (s, 2H), 4.21 (s, 3H), 3.85-3.90 (m, 4H), 3.85 (s, 3H), 2.68-2.79 (m, 4H) |

| Ex. | Structure | Formula | Calc. M + H]+ [m/z | HPLC Retention Time (Min)/ Method | LCMS [M + H]+ m/z | NMR |
|---|---|---|---|---|---|---|
| 54 | 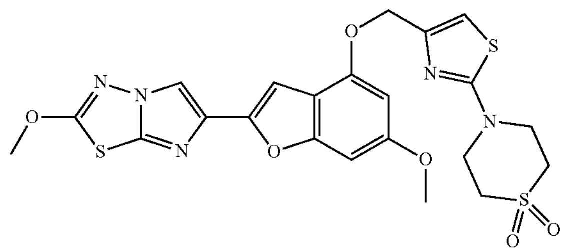 [SMILES: COc1cc(OCc2csc(N3CCS(=O)(=O)CC3)n2)c2cc(-c3cn4nc(OC)sc4n3)oc2c1] | $C_{22}H_{21}N_5O_6S_3$ | 548.0727 | 2.47/A | 548.0744 | 1H NMR (400 MHz, DMSO-$d_6$) δ ppm: 8.37 (s, 1H), 7.04 (s, 1H), 6.98 (d, J = 0.8 Hz, 1H), 6.83 (br. d, 1H), 6.57 (d, J = 2.0 Hz, 1H), 5.07 (s, 2H), 4.20 (s, 3H), 3.89-3.99 (m, 4H), 3.80 (s, 3H), 3.21-3.28 (m, 4H). |
| 55 | 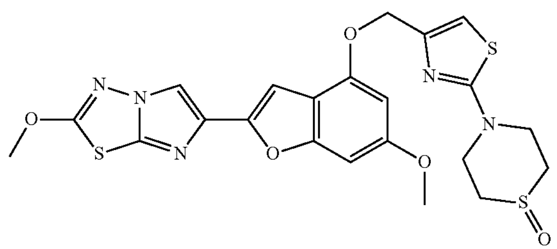 [SMILES: COc1cc(OCc2csc(N3CCS(=O)CC3)n2)c2cc(-c3cn4nc(OC)sc4n3)oc2c1] | $C_{22}H_{21}N_5O_5S_3$ | 532.0778 | 2.526/A | 532.0839 | 1H NMR (400 MHz, DMSO-$d_6$) δ ppm: 8.37 (s, 1H), 6.99 (s, 1H), 6.97 (s, 1H), 6.82 (br. d, 1H), 6.58 (d, J = 2.0 Hz, 1H), 5.07 (s, 2H), 4.20 (s, 3H), 3.82-3.96 (m, 4H), 3.80 (s, 3H), 2.91-3.06 (m, 2H), 2.75-2.85 (m, 2H). |
| 56 | 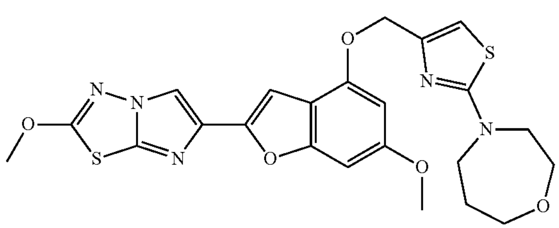 [SMILES: COc1cc(OCc2csc(N3CCCOCC3)n2)c2cc(-c3cn4nc(OC)sc4n3)oc2c1] | $C_{23}H_{23}N_5O_5S_2$ | 514.1213 | 2.411/A | 514.1258 | 1H NMR (400 MHz, CDCl$_3$) δ ppm: 7.86 (s, 1H), 7.09 (s, 1H), 6.72 (br. s, 1H), 6.60 (s, 1H), 6.49 (br. s, 1H), 5.37 (s, 2H), 4.22 (s, 3H), 3.90-4.0 (m, 4H), 3.85 (s, 3H), 3.78-3.88 (m, 4H), 2.09-2.21 (m, 2H). |
| 57 | 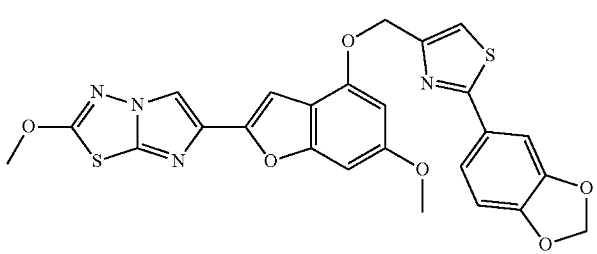 [SMILES: COc1cc(OCc2csc(-c3ccc4c(c3)OCO4)n2)c2cc(-c3cn4nc(OC)sc4n3)oc2c1] | $C_{25}H_{18}N_4O_6S_2$ | 535.0741 | 2.681/A | 535.0766 | 1H NMR (400 MHz, CDCl$_3$) δ ppm: 7.87 (br. s., 1H), 7.49-7.62 (m, 3H), 7.39 (br. s., 1H), 6.90 (d, J = 8.2 Hz, 1H), 6.71 (br. s, 1H), 6.50 (br. s, 1H), 6.06 (s, 2H), 5.42 (s, 2H), 4.27 (s, 3H), 3.86 (s, 3H), |

| Ex. | Structure | Formula | Calc. M + H]+ [m/z] | HPLC Retention Time (Min)/ Method | LCMS [M + H]+ m/z | NMR |
|---|---|---|---|---|---|---|
| 58 | 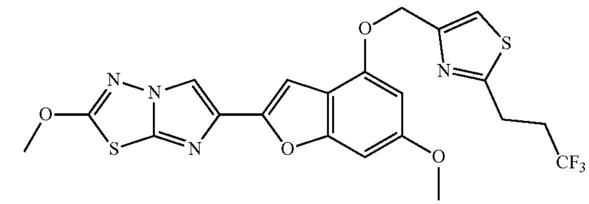 [SMILES: COc1cc(OCc2csc(CCC(F)(F)F)n2)c2cc(-c3cn4nc(OC)sc4n3)oc2c1] | C21H17F4N4O4S2 | 511.0716 | 2.499/A | 511.0773 | 1H NMR (400 MHz, CDCl3) δ ppm: 7.86 (s, 1H), 7.32 (d, J = 0.8 Hz, 2H), 6.70 (br. d, 1H), 6.44 (d, J = 2.0 Hz, 1H), 5.28 (br. s, 2H), 4.27 (s, 3H), 3.86 (s, 3H), 3.26-3.35 (m, 2H), 2.63-2.79 (m, 2H). |
| 59 | 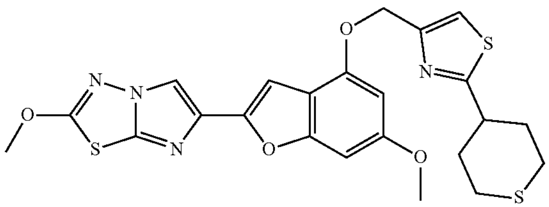 [SMILES: COc1cc(OCc2csc(C3CCSCC3)n2)c2cc(-c3cn4nc(OC)sc4n3)oc2c1] | C23H22N4O4S3 | 515.0876 | 2.613/A | 515.091 | 1H NMR (400 MHz, DMSO-d6) δ ppm: 8.37 (s, 1H), 7.71 (s, 1H), 6.98 (s, 1H), 6.84 (br. d, 1H), 6.61 (d, J = 2.0 Hz, 1H), 5.27 (s, 2H), 4.21 (s, 3H), 3.81 (s, 3H), 3.10-3.18 (m, 1H), 2.75-2.86 (m, 2H), 2.63-2.74 (m, 2H), 2.30-2.42 (m, 2H), 1.72-1.88 (m, 2H). |
| 60 | 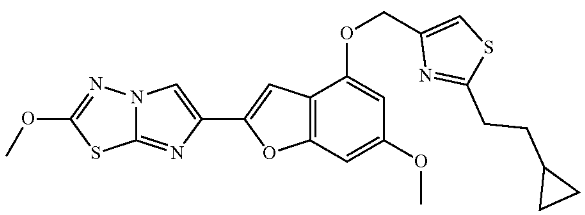 [SMILES: COc1cc(OCc2csc(CCC3CC3)n2)c2cc(-c3cn4nc(OC)sc4n3)oc2c1] | C23H22N4O4S2 | 483.1155 | 2.549/A | 483.1191 | 1H NMR (400 MHz, CDCl3) δ ppm: 7.85 (s, 1H), 7.22 (s, 1H), 7.09 (s, 1H), 6.71 (br. d, 1H), 6.43 (d, J = 1.5 Hz, 1H), 5.30 (s, 2H), 4.21 (s, 3H), 3.85 (s, 3H), 3.09-3.17 (m, 2H), 1.68-1.78 (m, 2H), 0.74-0.88 (m, 1H), 0.44-0.52 (m, 2H), 0.06-0.15 (m, 2H). |
| 61 | 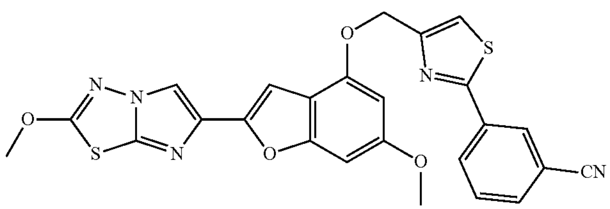 [SMILES: COc1cc(OCc2csc(-c3cccc(C#N)c3)n2)c2cc(-c3cn4nc(OC)sc4n3)oc2c1] | C25H17N5O4S2 | 516.0795 | 2.561/A | 516.0823 | 1H NMR (400 MHz, CDCl3) δ ppm: 8.29 (s, 1H), 8.19 (d, J = 8.2 Hz, 1H), 7.86 (s, 1H), 7.72 (d, J = 7.8 Hz, 1H), 7.59 (br. t, 1H), 7.47 (s, 1H), 7.12 (s, 1H), 6.73 (br. d, 1H), 6.47 (d, J = 2.0 Hz, 1H), 5.41 (s, 2H), 4.22 (s, 3H), 3.86 (s, 3H). |

-continued

| Ex. | Structure | Formula | Calc. M + H]+ [m/z] | HPLC Retention Time (Min)/ Method | LCMS [M + H]+ m/z | NMR |
|---|---|---|---|---|---|---|
| 62 | 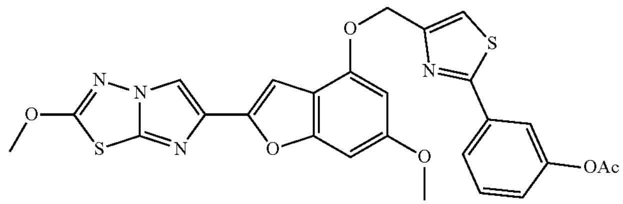 [SMILES: COc1cc(OCc2csc(-c3cccc(OC(C)=O)c3)n2)c2cc(-c3cn4nc(OC)sc4n3)oc2c1] | C26H20N4O6S2 | 549.0897 | 2.538/A | 549.0534 | 1H NMR (400 MHz, CDCl3) δ ppm: 7.86 (s, 1H), 7.82 (d, J = 7.8 Hz, 1H), 7.74 (br. s, 1H), 7.47 (br. t, J = 7.8 Hz, 1H), 7.39 (s, 1H), 7.18 (dd, J = 7.8, 1.6 Hz, 1H), 7.12 (s, 1H), 6.73 (br. d, 1H), 6.46 (d, J = 2.0 Hz, 1H), 5.39 (s, 2H), 4.22 (s, 3H), 3.85 (s, 3H), 2.34 (s, 3H). |
| 63 | 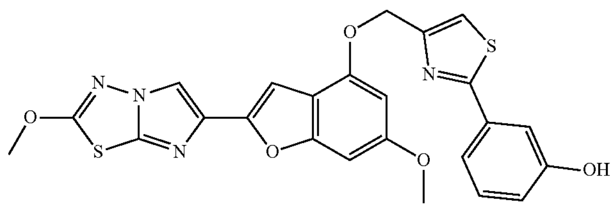 | C24H18N4O5S2 | 507.0729 | 2.459/A | 507.0831 | 1H NMR (400 MHz, CDCl3) δ ppm: 9.77 (s, 1H), 8.37 (s, 1H), 7.86 (s, 1H), 7.35-7.41 (m, 2H), 7.27-7.34 (m, 1H), 7.03 (s, 1H), 6.88-6.92 (m, 1H), 6.85 (br. d, 1H), 6.65 (d, J = 1.6 Hz, 1H), 5.36 (s, 2H), 4.20 (s, 3H), 3.82 (s, 3H). |
| 64 | 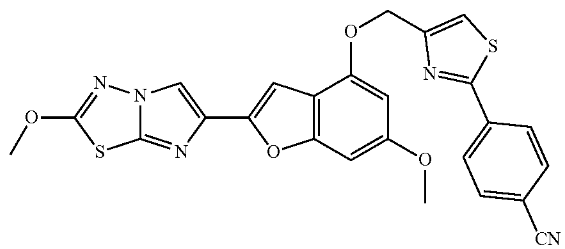 [SMILES: COc1cc(OCc2csc(-c3ccc(C#N)cc3)n2)c2cc(-c3cn4nc(OC)sc4n3)oc2c1] | C25H17N5O4S2 | 516.0795 | 2.607/A | 516.0805 | 1H NMR (400 MHz, CDCl3) δ ppm: 8.09 (broad d, J = 8.6 Hz, 2H), 7.86 (s, 1H), 7.75 (br. d, J = 8.6 Hz, 2H), 7.50 (s, 1H), 7.11 (s, 1H), 6.73 (br. d, 1H), 6.46 (d, J = 2.0 Hz, 1H), 5.41 (s, 2H), 4.22 (s, 3H), 3.86 (s, 3H). |
| 65 | 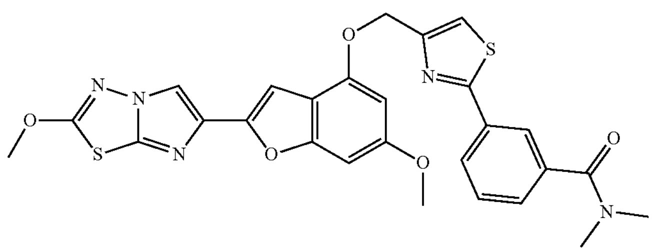 | C27H23N5O5S2 | 562.1213 | 2.592/A | 562.1235 | 1H NMR (400 MHz, CDCl3) δ ppm: 7.99-8.06 (m, 2H), 7.86 (s, 1H), 7.47 -7.55 (m, 2H),7.41(s, 1H), 7.12 (s, 1H), 6.73 (br. d, 1H), 6.47 (d, J = 2.0 Hz, 1H), 5.40 (s, 2H), 4.22 (s, 3H), 3.85 (s, 3H), 3.15 (br. s, 3H), 3.04 (br. s, 3H). |

-continued

| Ex. | Structure | Formula | Calc. M + H]+ [m/z | HPLC Retention Time (Min)/ Method | LCMS [M + H]+ m/z | NMR |
|---|---|---|---|---|---|---|
| 66 | 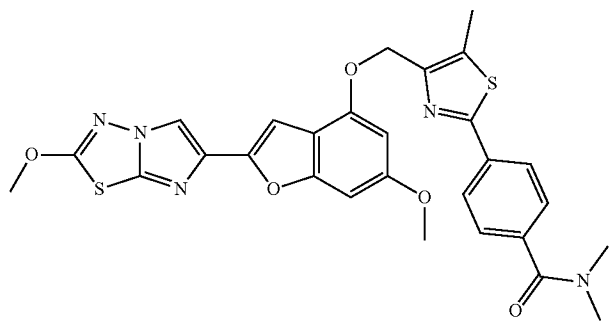 | C28H25N5O5S2 | 576.137 | 2.571/A | 576.1386 | 1H NMR (400 MHz, CDCl3) δ ppm: 7.95 (d, J = 8.2 Hz, 2H), 7.84 (s, 1H), 7.49 (d, J = 8.2 Hz, 2H), 7.05 (s, 1H), 6.71 (br. s., 1H), 6.56 (d, J = 1.2 Hz, 1H), 5.33 (s, 2H), 4.20 (s, 3H), 3.85 (s, 3H), 3.13 (br. s., 3H), 3.02 (br. s., 3H), 2.58 (s, 3H). |
| 67 | 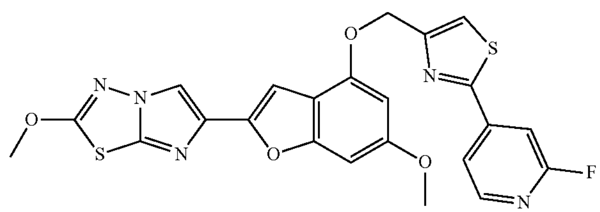 [SMILES: COc1cc(OCc2csc(-c3ccnc(F)c3)n2)c2cc(-c3cn4nc(OC)sc4n3)oc2c1] | C23H16NFN3O4S2 | 510.0701 | 2.602/A | 510.0739 | 1H NMR (400 MHz, CDCl3) δ ppm: 8.33 (d, J = 5.1 Hz, 1H), 7.86 (s, 1H), 7.73 (d, J = 5.1 Hz, 1H), 7.56 (s, 1H), 7.51 (s, 1H), 7.12 (s, 1H), 6.73 (br. d, 1H), 6.46 (d, J = 1.2 Hz, 1H), 5.42 (s, 2H), 4.22 (s, 3H), 3.86 (s, 3H). |
| 68 | 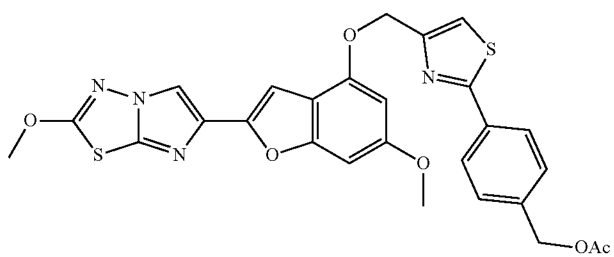 [SMILES: COc1cc(OCc2csc(-c3ccc(COC(C)=O)cc3)n2)c2cc(-c3cn4nc(OC)sc4n3)oc2c1] | C27H22N4O6S2 | 563.1054 | 2.634/A | 563.1053 | 1H NMR (400 MHz, CDCl3) δ ppm: 7.97 (d, J = 8.6 Hz, 2H), 7.86 (s, 1H), 7.45 (d, J = 8.6 Hz, 2H), 7.39 (s, 1H), 7.12 (s, 1H), 6.73 (br. d, 1H), 6.48 (d, J = 1.6 Hz, 1H), 5.40 (s, 2H), 5.16 (s, 2H), 4.22 (s, 3H), 3.85 (s, 3H), 2.14 (s, 3H). |

| Ex. | Structure | Formula | Calc. M + H]+ [m/z] | HPLC Retention Time (Min)/ Method | LCMS [M + H]+ m/z | NMR |
|---|---|---|---|---|---|---|
| 69 | 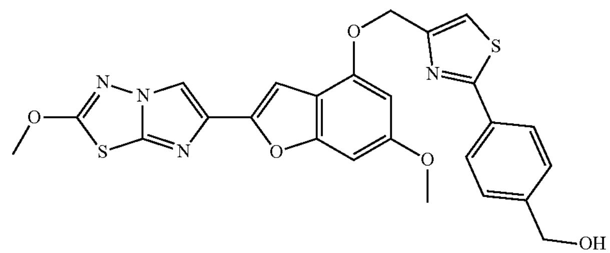 [SMILES: COc1cc(OCc2csc(-c3ccc(CO)cc3)n2)c2cc(-c3cn4nc(OC)sc4n3)oc2c1] | C25H20N4O5S2 | 521.0948 | 2.500/A | 521.0948 | 1H NMR (400 MHz, DMSO-d6) δ ppm: 8.36 (s, 1H), 7.92 (d, J = 8.4 Hz, 2H), 7.85 (s, 1H), 7.44 (d, J = 8.4 Hz, 2H), 7.02 (s, 1H), 6.84 (br. d, 1H), 6.64 (d, J = 2.0 Hz, 1H), 5.36 (s, 2H), 5.31 (t, J = 5.6 Hz, 1H), 4.55 (d, J = 5.6 Hz, 2H), 4.19 (s, 3H), 3.81 (s, 3H). |
| 70 | 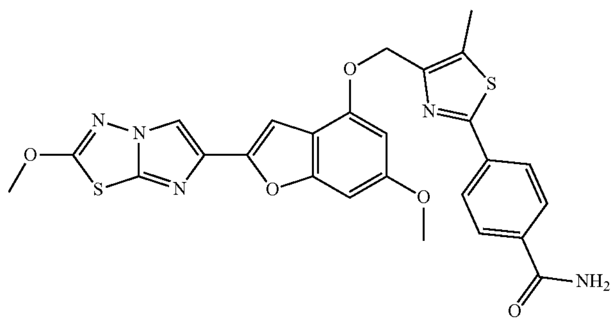 [SMILES: COc1cc(OCc2nc(-c3ccc(C(N)=O)cc3)sc2C)c2cc(-c3cn4nc(OC)sc4n3)oc2c1] | C26H21N5O5S2 | 548.1057 | 2.445/A | 548.1054 | 1H NMR (400 MHz, DMSO-d6) δ ppm: 8.37 (s, 1H), 8.07 (broad s, 1H), 7.93-8.01 (m, 4H), 7.46 (br. s., 1H), 6.93 (s, 1H), 6.85 (broad d, 1H), 6.69 (d, J = 2.0 Hz, 1H), 5.32 (s, 2H), 4.19 (s, 3H), 3.82 (s, 3H), 2.58 (s, 3H). |
| 71 | 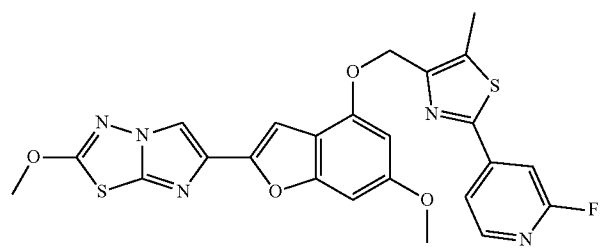 [SMILES: COc1cc(OCc2nc(-c3ccnc(F)c3)sc2C)c2cc(-c3cn4nc(OC)sc4n3)oc2c1] | C24H18FN5O4S2 | 524.0857 | 2.382/A | 524.0882 | 1H NMR (400 MHz, CDCl3) δ ppm: 8.29 (d, J = 5.5 Hz, 1H), 7.84 (s, 1H), 7.65-7.68 (m, 1H), 7.44 (br. s, 1H), 7.05 (s, 1H), 6.72 (br. d, 1H), 6.55 (d, J = 2.0 Hz, 1H), 5.35 (s, 2H), 4.21 (s, 3H), 3.86 (s, 3H), 2.62 (s, 3H). |

-continued

| Ex. | Structure | Formula | Calc. M + H]+ [m/z] | HPLC Retention Time (Min)/ Method | LCMS [M + H]+ m/z | NMR |
|---|---|---|---|---|---|---|
| 72 | 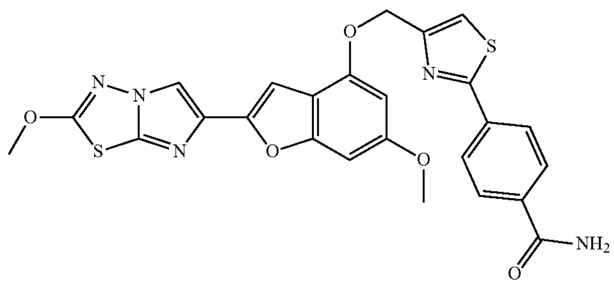 [SMILES: COc1cc(OCc2csc(-c3ccc(C(N)=O)cc3)n2)c2cc(-c3cn4nc(OC)sc4n3)oc2c1] | C25H19BrN5O5S2 | 534.09 | 2.457/A | 534.0902 | 1H NMR (400 MHz, CDCl3) δ ppm: 8.37 (s, 1H), 8.09 (br. s., 1H), 7.98-8.07 (m, 4H), 7.97 (s, 1H), 7.48 (br. s., 1H), 7.03 (s, 1H), 6.85 (broad d, 1H), 6.66 (d, J = 2.0 Hz, 1H), 5.39 (s, 2H), 4.20 (s, 3H), 3.82 (s, 3H). |
| 73 | 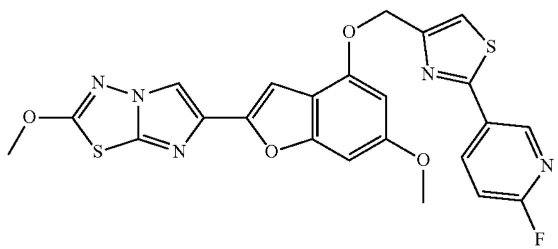 [SMILES: COc1cc(OCc2csc(-c3ccc(F)nc3)n2)c2cc(-c3cn4nc(OC)sc4n3)oc2c1] | C23H16FN5O4S2 | 510.0701 | 2.347/A | 510.0706 | 1H NMR (400 MHz, CDCl3) δ ppm: 8.80 (d, J = 2.7 Hz, 1H), 8.39 (ddd, J = 8.6, 7.4, 2.7 Hz, 1H), 7.86 (s, 1H), 7.44 (s, 1H), 7.12 (br. s, 1H), 7.05 (dd, J = 8.6, 2.7 Hz, 1H), 6.74 (br. d, 1H), 6.47 (d, J = 2.0 Hz, 1H), 5.40 (s, 2H), 4.22 (s, 3H), 3.86 (s, 3H). |
| 74 | 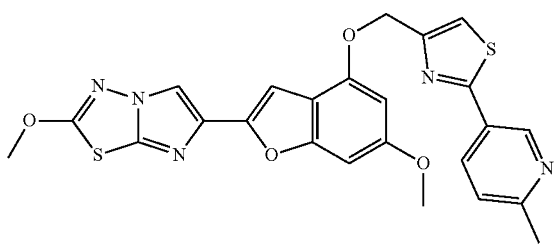 [SMILES: COc1cc(OCc2csc(-c3ccc(C)nc3)n2)c2cc(-c3cn4nc(OC)sc4n3)oc2c1] | C24H19N5O4S2 | 506.0951 | 2.176/A | 506.0952 | 1H NMR (400 MHz, CDCl3) δ ppm: 9.06 (d, J = 2.0 Hz, 1H), 8.16 (dd, J = 8.0, 2.5 Hz, 1H), 7.86 (s, 1H), 7.41 (s, 1H), 7.26 (d, 1H), 7.12 (s, 1H), 6.73 (br. d, 1H), 6.48 (d, J = 2.0 Hz, 1H), 5.41 (s, 2H), 4.22 (s, 3H), 3.85 (s, 3H), 2.63 (s, 3H). |
| 75 | 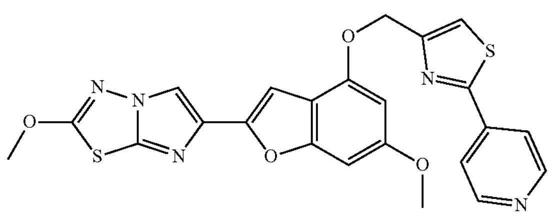 [SMILES: COc1cc(OCc2csc(-c3ccncc3)n2)c2cc(-c3cn4nc(OC)sc4n3)oc2c1] | C23H17N5O4S2 | 492.0795 | 2.143/A | 492.0796 | 1H NMR (400 MHz, CDCl3) δ ppm: 8.70-8.77 (m, 2H), 7.86 (s, 1H), 7.82-7.86 (m, 2H), 7.52 (br. s, 1H), 7.12 (s, 1H), 6.73 (br. d, 1H), 6.47 (d, J = 2.0 Hz, 1H), 5.42 (s, 2H), 4.22 (s, 3H), 3.86 (s, 3H). |

-continued

| Ex. | Structure | Formula | Calc. M + H]+ [m/z] | HPLC Retention Time (Min)/ Method | LCMS [M + H]+ m/z | NMR |
|---|---|---|---|---|---|---|
| 76 | 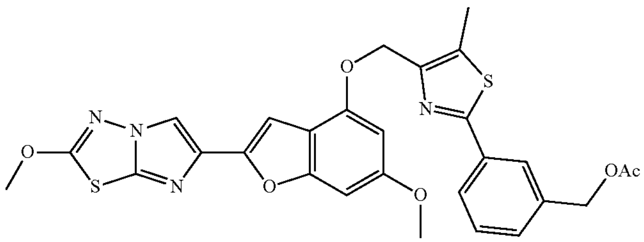 [SMILES: COc1cc(OCc2nc(-c3cccc(COC(C)=O)c3)sc2C)c2cc(-c3cn4nc(OC)sc4n3)oc2c1] | C28H24N4O6S2 | 577.121 | 2.660/A | 577.1213 | 1H NMR (400 MHz, CDCl3) δ ppm: 7.93 (s, 1H), 7.86 (broad d, J = 7.4 Hz, 1H), 7.84 (s, 1H), 7.37-7.47 (m, 2H), 7.06 (s, 1H), 6.71 (broad d, 1H), 6.57 (d, J = 1.6 Hz, 1H), 5.33 (s, 2H), 5.17 (s, 2H), 4.21 (s, 3H), 3.85 (s, 3H), 2.57 (s, 3H), 2.14 (s, 3H). |
| 77 | 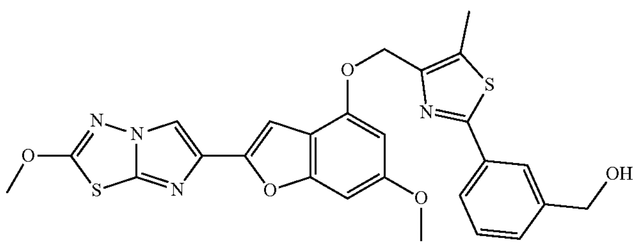 [SMILES: COc1cc(OCc2nc(-c3cccc(CO)c3)sc2C)c2cc(-c3cn4nc(OC)sc4n3)oc2c1] | C26H22N4O5S2 | 535.1104 | 2.535/A | 535.1102 | 1H NMR (400 MHz, DMSO-d6) δ ppm: 8.37 (s, 1H), 7.88 (s, 1H), 7.75 (broad d, J = 7.8 Hz, 1H), 7.37-7.48 (m, 2H), 6.93 (s, 1H), 6.84 (broad d, 1H), 6.69 (d, J = 1.6 Hz, 1H), 5.33 (t, J = 5.9 Hz, 1H), 5.31 (s, 2H), 4.57 (d, J = 5.9 Hz, 2H), 4.19 (s, 3H), 3.82 (s, 3H), 2.56 (s, 3H). |
| 78 | 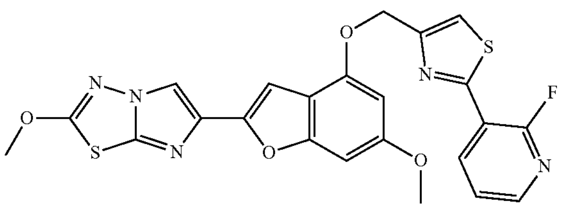 [SMILES: COc1cc(OCc2csc(-c3cccnc3F)n2)c2cc(-c3cn4nc(OC)sc4n3)oc2c1] | C23H16FN5O4S2 | 510.0701 | 2.452/A | 510.0691 | 1H NMR (400 MHz, CDCl3) δ ppm: 8.76 (ddd, J = 9.5, 7.5, 2.2 Hz, 1H), 8.24-8.33 (m, 1H), 7.86 (s, 1H), 7.57 (br. s, 1H), 7.32-7.41 (m, 1H), 7.12 (br. s, 1H), 6.73 (br. d, 1H), 6.47 (d, J = 2.0 Hz, 1H), 5.42 (s, 2H), 4.22 (s, 3H), 3.86 (s, 3H). |
| 79 | 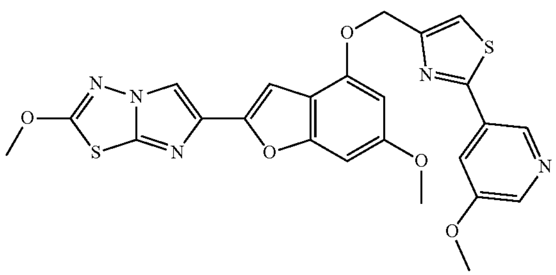 [SMILES: COc1cncc(-c2nc(COc3cc(OC)cc4oc(-c5cn6nc(OC)sc6n5)cc34)cs2)c1] | C24H19N5O5S2 | 522.09 | 2.383/A | 522.0874 | 1H NMR (400 MHz, CDCl3) δ ppm: 8.75 (s, 1H), 8.38 (d, J = 2.7 Hz, 1H), 7.86 (s, 1H), 7.82 (br. s, 1H), 7.45 (s, 1H), 7.12 (s, 1H), 6.73 (br. d, 1H), 6.48 (d, J = 1.6 Hz, 1H), 5.41 (s, 2H), 4.22 (s, 3H), 3.96 (s, 3H), 3.86 (s, 3H). |

| Ex. | Structure | Formula | Calc. M + H]+ [m/z] | HPLC Retention Time (Min)/ Method | LCMS [M + H]+ m/z | NMR |
|---|---|---|---|---|---|---|
| 80 | 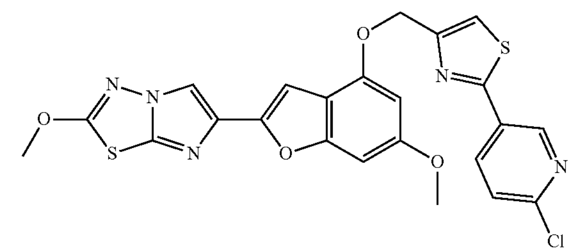 [SMILES: COc1cc(OCc2csc(-c3ccc(Cl)nc3)n2)c2cc(-c3cn4nc(OC)sc4n3)oc2c1] | C₂₃H₁₆ClN₅O₄S₂ | 526.0405 | 2.429/A | 526.0402 | ¹H NMR (400 MHz, CDCl₃) δ ppm: 8.96 (d, J = 2.2 Hz, 1H), 8.24 (dd, J = 8.7, 2.2 Hz, 1H), 7.86 (s, 1H), 7.47 (s, 1H), 7.44 (d, J = 8.7 Hz, 1H), 7.11 (s, 1H), 6.73 (br. d, 1H), 6.47 (d, J = 2.0 Hz, 1H), 5.40 (s, 2H), 4.22 (s, 3H), 3.86 (s, 3H). |
| 81 | 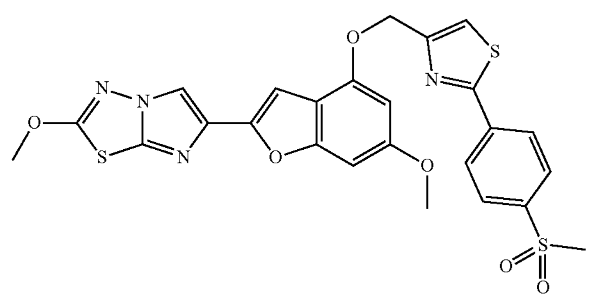 | C₂₅H₂₀N₄O₆S₃ | 569.0618 | 2.310/A | 569.0624 | ¹H NMR (400 MHz, CDCl₃) δ ppm: 8.14-8.22 (m, 2H), 8.00-8.07 (m, 2H), 7.86 (s, 1H), 7.51 (s, 1H), 7.12 (s, 1H), 6.73 (br. d, 1H), 6.47 (d, J = 1.6 Hz, 1H), 5.42 (s, 2H), 4.22 (s, 3H), 3.86 (s, 3H), 3.11 (s, 3H). |
| 82 | 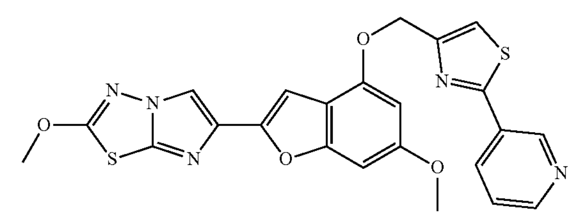 [SMILES: COc1cc(OCc2csc(-c3cccnc3)n2)c2cc(-c3cn4nc(OC)sc4n3)oc2c1] | C₂₃H₁₇N₅O₄S₂ | 492.0795 | 2.307/A | 492.0798 | ¹H NMR (400 MHz, CDCl₃) δ ppm: 9.16-9.24 (m, 1H), 8.68 (dd, J = 4.7, 1.6 Hz, 1H), 8.25-8.30 (m, 1H), 7.86 (s, 1H), 7.46 (s, 1H), 7.38-7.44 (m, 1H), 7.12 (s, 1H), 6.73 (br. d, 1H), 6.48 (d, J = 2.0 Hz, 1H), 5.42 (s, 2H), 4.22 (s, 3H), 3.86 (s, 3H). |

Example 83

2-Methoxy-6-(6-methoxy-4-(1-(2-phenylthiazol-4-yl)ethoxy)benzofuran-2-yl)imidazo[2,1-b][1,3,4]thiadiazole

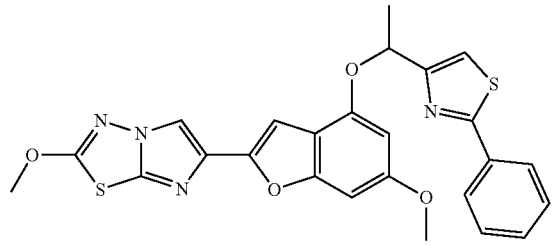 [SMILES: COc1cc(OC(C)c2csc(-c3ccccc3)n2)c2cc(-c3cn4nc(OC)sc4n3)oc2c1]

83A. 2-Phenylthiazole-4-carboxylic Acid

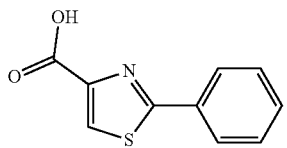 [SMILES: O=C(O)c1csc(-c2ccccc2)n1]

A solution of ethyl 2-phenylthiazole-4-carboxylate (Example 4B, 3.046 g, 13.06 mmol) in methanol (20 mL) was treated with a solution of NaOH (1.044 g, 26.1 mmol) in water (10 mL) added dropwise over 2 min and the resulting solution was stirred at room temperature for 1 h. The methanol was then evaporated under reduced pressure and the residual paste was diluted with a mixture of water (30 mL) and ethyl acetate (200 mL). The pH was adjusted to ~3 with concentrated hydrochloric acid, the organic phase was separated and the aqueous phase was re-extracted with ethyl acetate (2×150 mL). The combined organic extract was washed with brine (3×35 mL) and dried over anhydrous magnesium sulfate. After concentration of the solvent under reduced pressure, the solid residue obtained was dried in vacuo for 18 h to yield 2.629 g (98%) of the title compound as a white crystalline solid. LC (Method A): 1.842 min. HRMS(ESI) Anal. Calcd for $C_{10}H_8NO_2S$ [M+H]$^+$ m/z 206.027; found 206.0266. $^1$H NMR (CDCl$_3$, 400 MHz) δ ppm: 8.30 (s, 1H), 7.94-8.05 (m, 2H), 7.4-7.55 (m, 3H).

83B. N-Methoxy-N-methyl-2-phenylthiazole-4-carboxamide

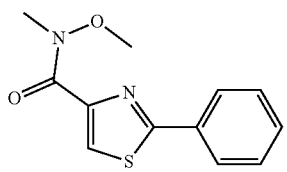 [SMILES: CON(C)C(=O)c1csc(-c2ccccc2)n1]

A mixture of 2-phenylthiazole-4-carboxylic acid (1.00 g, 4.87 mmol) in dichloromethane (20 mL) was treated with oxalyl chloride (1.237 g, 9.75 mmol) and a drop of N,N-dimethylformamide and the resulting mixture was stirred at 22° C. for 4 h. The solvent was evaporated under reduced pressure and the residual solid was co-evaporated with toluene (10 mL). This solid was diluted with dichloromethane (10 mL) and added dropwise over 2 min to an ice-cold mixture of N,O-dimethylhydroxylamine hydrochloride (0.713 g, 7.31 mmol) and triethylamine (2.03 mL, 14.62 mmol) in dichloromethane (20 mL). The cooling bath was then removed and the mixture with a white precipitate was stirred at room temperature for 1 h. The reaction mixture was quenched by addition of saturated aqueous sodium bicarbonate (30 mL) and dichloromethane (200 mL). The organic phase was washed with brine, dried over anhydrous magnesium sulfate and concentrated in vacuo to give a clear oil. This oil was chromatographed on silica gel (elution toluene-ethyl acetate; 8:2 to 7:3) to give 1.054 g (87%) of the title compound as a clear oil. LC (Method A): 2.022 min. HRMS(ESI) Anal. Calcd for $C_{12}H_{13}N_2O_2S$ [M+H]$^+$ m/z 249.0692; found 249.0694. $^1$H NMR (CDCl$_3$, 400 MHz) δ ppm: 8.03 (s, 1H), 7.91-8.01 (m, 2H), 7.39-7.55 (m, 3H), 3.90 (s, 3H), 3.51 (br s, 3H).

83C. 1-(2-Phenylthiazol-4-yl)ethanone

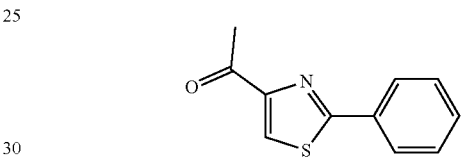

A solution of N-methoxy-N-methyl-2-phenylthiazole-4-carboxamide (1.00 g, 4.03 mmol) in dry tetrahydrofuran (20 mL) at 0° C. was treated with methylmagnesium bromide (1 M in butyl ether, 6.0 mL, 6.0 mmol) dropwise over 2 min. The resulting pale yellow solution was stirred at 0° C. for 30 min and then the reaction mixture was quenched by addition to a mixture of ice (ca. 200 g) and concentrated hydrochloric acid (2 mL). The aqueous phase was extracted with ethyl acetate and the organic extract was washed with saturated aqueous sodium bicarbonate and brine. The organic phase was dried over anhydrous magnesium sulfate and concentrated in vacuo to give a white solid. This solid was chromatographed on silica gel (elution with 0-5% ethyl acetate-toluene) to give 0.806 g (98%) of the title compound as colorless prisms. LC (Method A): 2.017 min. HRMS(ESI) Anal. Calcd for $C_{11}H_{10}NOS$ [M+H]$^+$ m/z 204.0478; found 204.0484. $^1$H NMR (CDCl$_3$, 400 MHz) δ ppm: 8.14 (d, J=1.6 Hz, 1H), 7.95-8.05 (m, 2H), 7.43-7.57 (m, 3H), 2.76 (d, J=1.6 Hz, 3H).

83D. 1-(2-Phenylthiazol-4-yl)ethanol

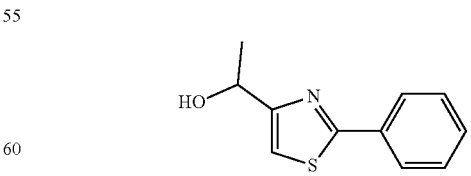

A solution of 1-(2-phenylthiazol-4-yl)ethanone (0.410 g, 2.017 mmol) in dry tetrahydrofuran (5 mL) was cooled to 0° C. and treated with sodium borohydride (0.114 g, 3.03 mmol), followed by methanol (0.040 mL, 1.0 mmol). The resulting purple mixture was stirred at 0° C. for 15 min and then at 23° C. for 5 h. The mixture was re-cooled in ice and treated dropwise with 1 mL of 50% aqueous acetic. The mixture was then partitioned between ethyl acetate (200 mL) and saturated aqueous sodium bicarbonate. The organic phase was separated, washed with saturated sodium bicarbonate and brine, dried over anhydrous magnesium sulfate and evaporated under reduced pressure to give a yellow syrup. This material was chromatographed on silica gel (elution with 20-40% ethyl acetate-toluene) to give 0.392 g (95%) of the title material as a pale yellow syrup. LC (Method A): 1.874 min. HRMS(ESI) Anal. Calcd for $C_{11}H_{12}NOS$ $[M+H]^+$ m/z 206.0634; found 206.0638. $^1H$ NMR (CDCl$_3$, 400 MHz) δ ppm: 7.9-8.0 (m, 2H), 7.4-7.5 (m, 3H), 7.12 (s, 1H), 5.05 (q, J=6.3 Hz, 1H), 2.87 (br s, 1H), 1.63 (d, J=6.3 Hz, 3H).

Example 83. 2-Methoxy-6-(6-methoxy-4-(1-(2-phenylthiazol-4-yl)ethoxy)benzofuran-2-yl)imidazo[2,1-b][1,3,4]thiadiazole

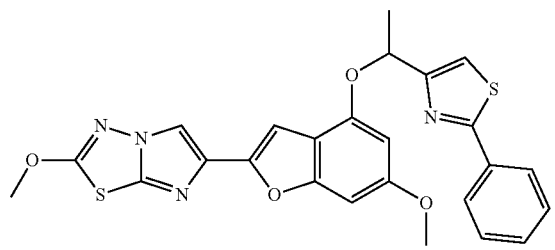 [SMILES: COc1cc(OC(C)c2csc(-c3ccccc3)n2)c2cc(-c3cn4nc(OC)sc4n3)oc2c1]

A mixture of 6-methoxy-2-(2-methoxyimidazo[2,1-b][1,3,4]thiadiazol-6-yl)benzofuran-4-ol (Example 1H, 0.080 g, 0.252 mmol) and 1-(2-phenylthiazol-4-yl)ethanol (0.062 g, 0.303 mmol) in dry tetrahydrofuran (10 mL) was treated at 22° C. and under nitrogen with tri-n-butylphosphine (0.157 mL, 0.63 mmol) added in one portion, followed by a solution of 1,1'-(azodicarbonyl)dipiperidine (0.083 g, 0.328 mmol) in tetrahydrofuran (4 mL) added dropwise over 30 min. After another 2 h at 22° C., the reaction mixture was partitioned between dichloromethane and saturated sodium bicarbonate. The organic phase was washed with brine, dried over anhydrous magnesium sulfate and concentrated in vacuo to give a glassy residue. Chromatography on silica gel (elution gradient of ethyl acetate in dichloromethane) gave 0.078 g (61%) of the title compound as a white solid, after trituration with acetonitrile. LC (Method A): 2.596 min. HRMS(ESI) Anal. Calcd for $C_{25}H_{20}N_4O_5S_2$ $[M+H]^+$ m/z 505.0999; found 505.1001. $^1H$ NMR (CDCl$_3$, 400 MHz) δ ppm: 7.95-8.0 (m, 2H), 7.86 (s, 1H), 7.40-7.50 (m, 3H), 7.23 (s, 1H), 7.14 (s, 1H), 6.68 (br d, 1H), 6.39 (d, J=2.0 Hz, 1H), 5.73 (q, J=6.5 Hz, 1H), 4.22 (s, 3H), 3.79 (s, 3H), 1.82 (d, J=6.5 Hz, 3H).

Example 84

4-(5-Chloro-4-(((6-methoxy-2-(2-methoxyimidazo[2,1-b]thiadiazol-6-yl)benzofuran-4-yl)oxy)thiazol-2-yl)morpholine

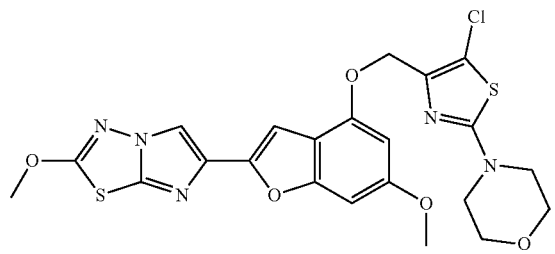 [SMILES: COc1cc(OCc2nc(N3CCOCC3)sc2Cl)c2cc(-c3cn4nc(OC)sc4n3)oc2c1]

84A. Methyl and Ethyl-2-morpholinothiazole-4-carboxylate

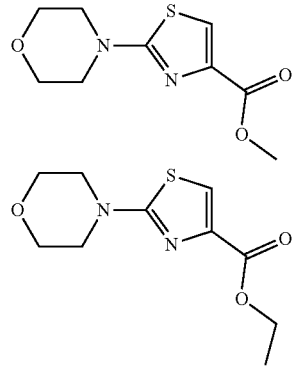

A solution of morpholine (3.0 mL, 34.2 mmol) in EtOH (50 mL) was treated with methyl 2-bromothiazole-4-carboxylate (1.65 g, 7.43 mmol) and DIEA (6.8 mL, 39.4 mmol) and the resulting mixture was refluxed for 18 h under N$_2$. The reaction mixture was then concentrated under reduced pressure and the residue was purified on the ISCO using a REDISEP® 24 g column (0 to 30% EtOAc-DCM) to give the product (1.22 g, 72%; mixture of methyl and ethyl esters) as a yellow oil. This mixture was used as such in the next step. LCMS (APCI): calcd for $C_{10}H_{15}N_2O_3S$ $[M+H]^+$ m/z 277.03, found 277.1; LCMS (APCI): calcd for $C_9H_{13}N_2O_3S$ $[M+H]^+$ m/z 229.06, found 229.1.

84B. 5-Chloro-2-morpholinothiazole-4-carboxylic acid ethyl ester and 5-Chloro-2-morpholinothiazole-4-carboxylic Acid methyl ester

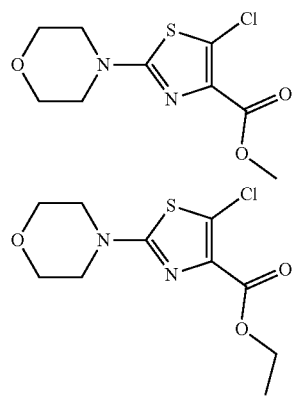

A mixture of 2-morpholinothiazole-4-carboxylic acid ethyl and methyl ester (1.22 g, 5.04 mmol) in a mixture of DCM-CHCl$_3$-acetic acid (1:1:1, 9 mL) was treated at 22° C. with N-chlorosuccinimide (0.807 g, 6.04 mmol). The resulting mixture was stirred at room temperature for 2 h, then more NCS was added (0.050 g) and the mixture was stirred at 40° C. for 18 h. CELITE® was then added and the mixture was concentrated. DCM was added, followed by saturated aqueous NaHCO$_3$ and the organic layer was separated, washed with brine, dried over MgSO$_4$ and evaporated to dryness. The residue was purified on the ISCO using a REDISEP® 24 g column (0 to 30% EtOAc-DCM) to give the title esters as a white solid (0.746 g, 54%). This mixture was used as such in the next step. LCMS (APCI): calcd for $C_{10}H_{14}ClN_2O_3S$ [M+H]$^+$ m/z 277.03, found 277.1; LCMS (APCI): calcd for $C_9H_{12}ClN_2O_3S$ [M+H]$^+$ m/z 263.02, found 263.0. $^1$H NMR (CDCl$_3$, 400 MHz) δ ppm: 4.38 (q, J=7.0 Hz, 1H), 3.91 (s, 1H), 3.76-3.83 (m, 4H), 3.40-3.49 (m, 4H), 1.40 (t, J=7.0 Hz, 2H).

84C. (5-Chloro-2-morpholinothiazol-4-yl)methanol

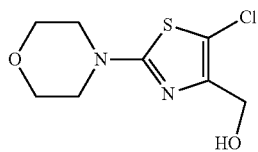 [SMILES: OCc1nc(N2CCOCC2)sc1Cl]

A mixture of 2-morpholinothiazole-4-carboxylic acid ethyl and methyl esters (0.746 g, 2.70 mmol) in Et$_2$O (50 mL) was cooled at −78° C. and treated with LAH (0.307 g, 8.09 mmol). The cooling bath was then removed and the resulting mixture was stirred for 2.5 h at room temperature. The reaction mixture was re-cooled at −78° C. and quenched by the dropwise addition of ethyl acetate (5 mL) over 5 min. After 10 min, water (8.0 mL) was added dropwise over 5 min then an aqueous solution of 1 N NaOH (8.5 mL) and finally water (10 mL). The cooling bath was removed and the heterogeneous mixture was stirred at room temperature until it became white (ca. 30 min). The suspension was then filtered and the filter-cake washed with diethyl ether (10 mL). The combined filtrate was washed with brine and dried over anhydrous magnesium sulfate. Evaporation gave the desired compound as an off-white solid (0.249 g, 39%). This material was used as such in the next step. LCMS (APCI): calcd for $C_8H_{12}ClN_2O_2S$ [M+H]$^+$ m/z 235.02, found 235.1. $^1$H NMR (CDCl$_3$, 400 MHz) δ ppm: 4.52 (d, J=5.7 Hz, 2H), 3.76-3.84 (m, 4H), 3.37-3.44 (m, 4H), 2.32 (t, J=5.7 Hz, 1H).

Example 84. 4-(5-Chloro-4-(((6-methoxy-2-(2-methoxyimidazo[2,1-b] thiadiazol-6-yl) benzofuran-4-yl)oxy)thiazol-2-yl)morpholine

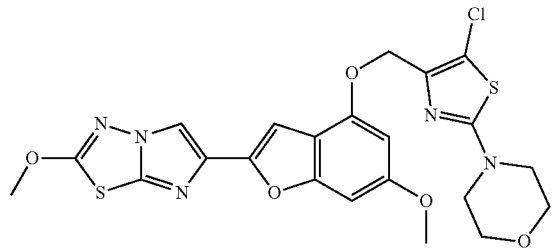 [SMILES: COc1cc(OCc2nc(N3CCOCC3)sc2Cl)c2cc(-c3cn4nc(OC)sc4n3)oc2c1]

6-Methoxy-2-(2-methoxyimidazo[2,1-b][1,3,4]thiadiazol-6-yl)benzofuran-4-ol (Example 1H, 0.070 g, 0.22 mmol) and (5-chloro-2-morpholinothiazol-4-yl)methanol (0.057 g, 0.24 mmol) were added to a 25 mL round-bottom flask which was then flushed with N$_2$. Then dry THF (4 mL) and tri-n-butylphosphine (0.14 mL, 0.55 mmol) were added and the reaction mixture was treated dropwise with a solution of 1,1' (azodicarbonyl)dipiperidine (0.139 g, 0.55 mmol) in dry THF (3.5 mL) over 1 h. The resulting beige suspension was stirred for an additional 2 h at room temperature and then it was diluted with EtOAc, washed with NaHCO$_3$ and brine, dried over MgSO$_4$ and evaporated to dryness. The residue was purified on the ISCO using a REDISEP® 4 g column (0 to 40% EtOAc-DCM). The obtained solid was suspended in MeOH, sonicated, filtered and dried in vacuo to give the title compound (0.082 g, 70%) as a white solid. LC (Method C): 2.366 min. HRMS(ESI): calcd for $C_{22}H_{21}ClN_5O_5S_2$ [M+H]$^+$ m/z 534.059, found 534.0719. $^1$H NMR (CDCl$_3$, 400 MHz) δ ppm: 7.83 (s, 1H), 7.08 (s, 1H), 6.70 (d, J=1.6 Hz, 1H), 6.51 (d, J=1.6 Hz, 1H), 5.05 (s, 2H), 4.21 (s, 3H), 3.85 (s, 3H), 3.77-3.83 (m, 4H), 3.39-3.46 (m, 4H).

Example 85

6-(4-((5-Chloro-2-phenylthiazol-4-yl)methoxy)-6-methoxybenzofuran-2-yl)-2-methoximidazo[2,1-b][1,3,4]thiadiazole

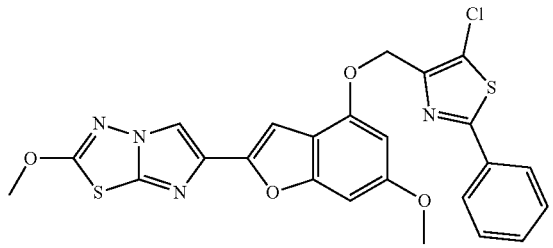 [SMILES: COc1cc(OCc2nc(-c3ccccc3)sc2Cl)c2cc(-c3cn4nc(OC)sc4n3)oc2c1]

85A. Ethyl 2-phenylthiazole-4-carboxylate

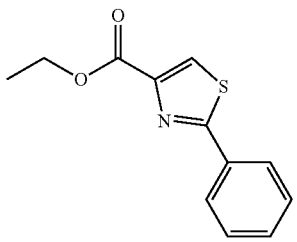 [SMILES: CCOC(=O)c1csc(-c2ccccc2)n1]

A solution of benzothioamide (3.00 g, 21.87 mmol) in EtOH (70 mL) was treated dropwise with ethyl bromopyruvate (5.10 g, 26.2 mmol) and stirred at room temperature for 30 min before being heated at reflux for 1.5 h. The cooled mixture was diluted with ethyl acetate (200 mL), washed (aqueous NaHCO$_3$, brine), dried over anhydrous MgSO$_4$ and evaporated. The residue was purified on the ISCO using a REDISEP® 80 g column (10 to 20% EtOAc-hexane) to give the title compound (4.82 g, 94%) as a yellow oil. LCMS (APCI): calcd for $C_{12}H_{12}NO_2S$ [M+H]$^+$ m/z 234.05, found 234.1. $^1$H NMR (CDCl$_3$, 400 MHz) δ ppm: 8.14-8.19 (m, 1H), 7.98-8.07 (m, 2H), 7.41-7.51 (m, 3H), 4.46 (q, J=7.2 Hz, 2H), 1.44 (t, J=7.2 Hz, 3H).

85B. 5-Chloro-2-phenylthiazole-4-carboxylic Acid ethyl ester

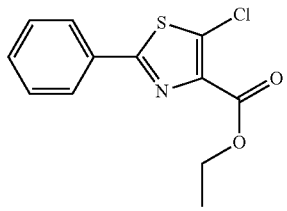 [SMILES: CCOC(=O)c1nc(-c2ccccc2)sc1Cl]

Ethyl 2-phenylthiazole-4-carboxylate (0.300 g, 1.29 mmol) was treated according to the method described in Example 84B above. The crude residue was purified on the ISCO using a REDISEP® 24 g column (0 to 30% EtOAc-hexane) to give the title material as a colorless oil (0.066 g, 19%). LCMS (APCI): calcd for $C_{12}H_{11}ClNO_2S$ $[M+H]^+$ m/z 268.01, found 268.0. $^1$H NMR (CDCl$_3$, 400 MHz) δ ppm: 7.87-7.94 (m, 2H), 7.42-7.50 (m, 3H), 4.48 (q, J=7.0 Hz, 2H), 1.46 (t, J=7.1 Hz, 3H).

85C. (5-Chloro-2-phenylthiazol-4-yl)methanol

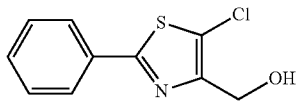 [SMILES: OCc1nc(-c2ccccc2)sc1Cl]

5-Chloro-2-phenylthiazole-4-carboxylic acid ethyl ester (0.066 g, 0.25 mmol) was reduced according to the method described in Example 5B to yield the title compound (0.048 g, 86%) as a pale yellow solid. LCMS (APCI): calcd for $C_{10}H_9ClNOS$ $[M+H]^+$ m/z 226.00, found 226.0. $^1$H NMR (CDCl$_3$, 400 MHz) δ ppm: 7.86 (dd, J=6.5, 2.2 Hz, 2H), 7.39-7.50 (m, 3H), 4.77 (s, 2H), 2.39 (br s, 1H).

Example 85. 6-(4-((5-Chloro-2-phenylthiazol-4-yl)methoxy)-6-methoxy benzofuran-2-yl)-2-methoxy-imidazo[2,1-b][1,3,4]thiadiazole

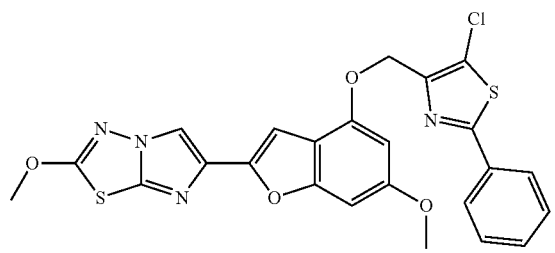 [SMILES: COc1cc(OCc2nc(-c3ccccc3)sc2Cl)c2cc(-c3cn4nc(OC)sc4n3)oc2c1]

6-Methoxy-2-(2-methoxyimidazo[2,1-b][1,3,4]thiadiazol-6-yl)benzofuran-4-ol (Example 1H, 0.058 g, 0.18 mmol) and (5-chloro-2-phenylthiazol-4-yl)methanol (0.041 g, 0.18 mmol) were reacted as described in Example 36. The crude residue was purified on the ISCO using a REDISEP® Gold 12 g column (5 to 20% EtOAc-DCM) and the obtained product was triturated with CH$_3$CN-MeOH. The resulting solid was re-purified on the ISCO using a REDISEP® 4 g column (0 to 10% EtOAc-DCM) to give the pure title compound as a pale yellow solid (0.048 g, 50%). LC (Method C): 2.569 min. LCMS (APCI): calcd for $C_{24}H_{18}ClN_4O_4S_2$ $[M+H]^+$ m/z 525.04, found 525.10. $^1$H NMR (CDCl$_3$, 400 MHz) δ ppm: 7.86 (dt, J=3.8, 3.0 Hz, 2H), 7.81 (s, 1H), 7.39-7.46 (m, 3H), 7.06 (s, 1H), 6.70 (s, 1H), 6.55 (d, J=2.0 Hz, 1H), 5.28 (s, 2H), 4.18 (s, 3H), 3.84 (s, 3H).

Example 86

4-(4-(((6-Methoxy-2-(2-methoxyimidazo[2,1-b][1,3,4]thiadiazol-6-yl)benzofuran-4-yl)oxy)methyl)-5-(trifluoromethyl)thiazol-2-yl)morpholine

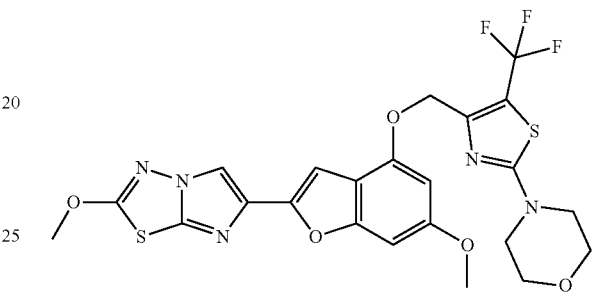

86A. Methyl 2-morpholino-5-(trifluoromethyl)thiazole-4-carboxylate

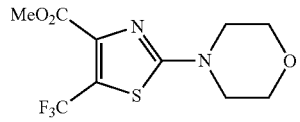

This product was prepared adapting the methodology described by Nagib, D. A. et al., (*Nature*, 480:224 (2011)). Thus, a 50 mL round-bottomed flask was charged with methyl 2-morpholinothiazole-4-carboxylate (0.200 g, 0.876 mmol) [cf. Example 84A], potassium phosphate dibasic (1.831 g, 10.51 mmol) [previously dried at 105° C. in vacuo overnight] and dichlorotris(1,10-phenanthroline)-ruthenium (II) hydrate (0.030 g, 0.04 mmol) and the mixture was maintained under vacuum for 10 min. The flask was then flushed with nitrogen, charged with acetonitrile (10 mL), degassed under light vacuum for 2 min and then again flushed with nitrogen. Then trifluoromethanesulfonyl chloride (0.742 mL, 7.01 mmol) was added all at once and the orange suspension was stirred and irradiated with a 13 W Globe fluorescent light bulb for 24 h. The reaction mixture was then quenched by addition to a mixture of ethyl acetate (200 mL) and water (50 mL). The organic phase was separated, washed successively with saturated aqueous sodium bicarbonate (20 mL) and brine, dried over anhydrous magnesium sulfate and evaporated under reduced pressure. The obtained pale yellow oily residue was chromatographed on silica gel (elution with dichloromethane-ethyl acetate, 90:10) to give 0.189 g (72%) of the title material as long white plates. LC (Method A): 2.047 min. HRMS(ESI): Anal. Calcd for $C_{10}H_{12}F_3N_2O_3S$ $[M+H]^+$ m/z 297.0515; found 297.0526. $^1$H NMR (CDCl$_3$, 400 MHz) δ ppm: 3.94 (s, 3H), 3.78-3.87 (m, 4H), 3.50-3.59 (m, 4H).

86B. (2-Morpholino-5-(trifluoromethyl)thiazol-4-yl)methanol

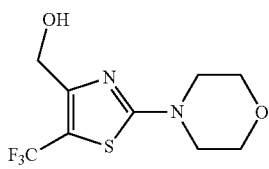 [SMILES: OCc1nc(N2CCOCC2)sc1C(F)(F)F]

A solution of methyl 2-morpholino-5-(trifluoromethyl)thiazole-4-carboxylate (0.177 g, 0.597 mmol) in tetrahydrofuran (4 mL) under nitrogen was cooled to 0° C. and treated with methanol (0.048 mL, 1.19 mmol), followed by lithium borohydride (0.026 g, 1.195 mmol) added all at once. After 30 min the cooling bath was removed and the resulting turbid solution was stirred at room temperature for 2.5 h. The reaction mixture was re-cooled in ice, quenched with 50% aqueous acetic acid (two drops) and diluted with ethyl acetate (100 mL). This mixture was washed with saturated sodium bicarbonate and brine, dried over anhydrous magnesium sulfate and concentrated under reduced pressure. The white solid residue obtained was chromatographed on silica gel (elution with ethyl acetate) to give 0.144 g (90%) of the title material as a white solid. LC (Method A): 1.833 min. HRMS(ESI): Anal. Calcd for $C_9H_{12}F_3N_2O_2S$ [M+H]$^+$ m/z 269.0566; found 269.0573. $^1$H NMR (CDCl$_3$, 400 MHz) δ ppm: 4.62 (d, J=5.9 Hz, 2H), 3.82 (d, J=5.0 Hz, 4H), 3.51 (d, J=5.0 Hz, 4H), 2.57 (t, J=5.9 Hz, 1H).

Example 86. 4-(4-(((6-Methoxy-2-(2-methoxyimidazo[2,1-b][1,3,4]thiadiazol-6-yl)benzofuran-4-yl)oxy)methyl)-5-(trifluoromethyl)thiazol-2-yl)morpholine

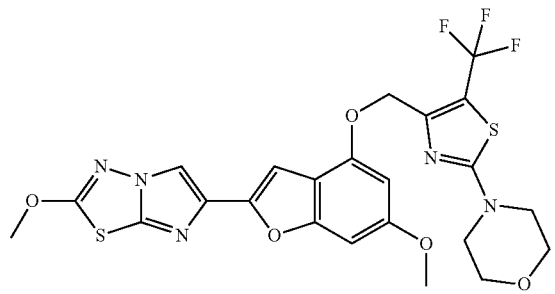 [SMILES: COc1cc(OCc2nc(N3CCOCC3)sc2C(F)(F)F)c2cc(-c3cn4nc(OC)sc4n3)oc2c1]

A mixture of 6-methoxy-2-(2-methoxyimidazo[2,1-b][1,3,4]thiadiazol-6-yl)benzofuran-4-ol (Example 1H, 0.080 g, 0.252 mmol) and 2-morpholino-5-(trifluoromethyl)thiazol-4-yl)methanol (0.074 g, 0.277 mmol) in dry tetrahydrofuran (10 mL) was treated at 22° C. and under nitrogen with tri-n-butylphosphine (0.128 g, 0.63 mmol) added in one portion, followed by a solution of 1,1'-(azodicarbonyl)dipiperidine (0.102 g, 0.403 mmol) in tetrahydrofuran (2 mL) added dropwise over 30 min. After another 2 h at 22° C., the reaction mixture was partitioned between dichloromethane and saturated sodium bicarbonate. The organic phase was washed with brine, dried over anhydrous magnesium sulfate and concentrated in vacuo to give a glassy residue. Chromatography on silica gel (elution gradient of ethyl acetate in dichloromethane) gave 0.104 g (73%) of the title compound as a white solid, after trituration in acetonitrile. LC (Method A): 2.576 min. HRMS(ESI): Anal. Calcd for $C_{23}H_{21}F_3N_5O_5S_2$ [M+H]$^+$ m/z 568.0931; found 568.0978. $^1$H NMR (400 MHz, CDCl$_3$) δ ppm: 7.84 (s, 1H), 7.06 (s, 1H), 6.71 (br. s, 1H), 6.47 (d, J=1.6 Hz, 1H), 5.13 (s, 2H), 4.21 (s, 3H), 3.85 (s, 3H), 3.79-3.84 (m, 4H), 3.48-3.55 (m, 4H).

Example 87

4-(((6-Methoxy-2-(2-methoxyimidazo[2,1-b][1,3,4]thiadiazol-6-yl)benzofuran-4-yl)oxy)methyl)-5-methylthiazol-2-amine

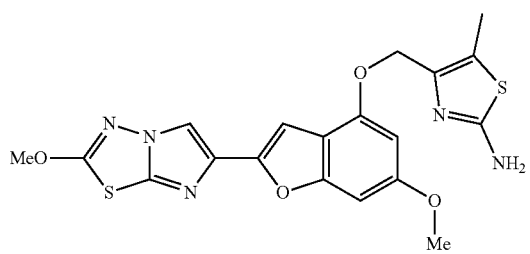 [SMILES: COc1cc(OCc2nc(N)sc2C)c2cc(-c3cn4nc(OC)sc4n3)oc2c1]

87A. Methyl 2-((tert-butoxycarbonyl)amino)-5-methylthiazole-4-carboxylate

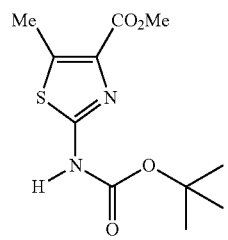

A solution of methyl 2-amino-5-methylthiazole-4-carboxylate (1.00 g, 5.81 mmol) in tetrahydrofuran (20 mL) was treated with di-tert-butyl dicarbonate (1.27 g, 5.81 mmol), added all at once, followed by triethylamine (1.619 mL, 11.61 mmol) and DMAP (0.040 g, 0.327 mmol). The resulting solution was stirred at 22° C. for 18 h. The reaction mixture was then diluted with ethyl acetate (200 mL) and water (50 mL) and the organic phase was washed successively with water, cold 0.1 N hydrochloric acid, saturated aqueous sodium bicarbonate, brine and dried over anhydrous magnesium sulfate. Evaporation of the solvent under reduced pressure gave a clear oil which was chromatographed on silica gel (elution with toluene-ethyl acetate, 8:2 to 7:3) to give 1.319 g (83%) of the title material as a pale yellow solid. LC (Method A): 2.049 min. LCMS (APCI): Anal. Calcd for $C_{11}H_{15}N_2O_4S$ [M−H]$^-$ m/z 271; found 271. $^1$H NMR (CDCl$_3$, 400 MHz) δ ppm: 8.24 (br. s, 1H), 3.90 (s, 3H), 2.69 (s, 3H), 1.53 (s, 9H).

87B. Methyl 2-((tert-butoxycarbonyl)(2,4-dimethoxybenzyl)amino)-5-methylthiazole-4-carboxylate, and (Z)-Methyl 2-((tert-butoxycarbonyl)imino)-3-(2,4-dimethoxybenzyl)-5-methyl-2,3-dihydrothiazole-4-carboxylate

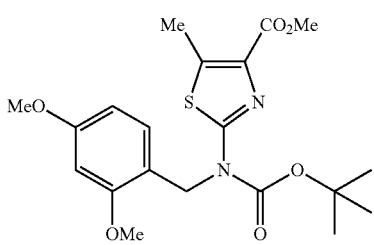

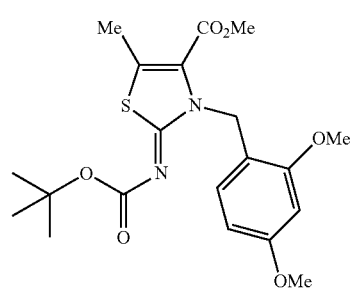

A mixture of methyl 2-((tert-butoxycarbonyl)amino)-5-methylthiazole-4-carboxylate (1.18 g, 4.33 mmol) and (2,4-dimethoxyphenyl)methanol (0.802 g, 4.77 mmol) in dry tetrahydrofuran (40 mL) was treated at 22° C. with tri-n-butylphosphine (2.67 mL, 10.83 mmol), added all at once, followed by a solution of 1,1'-(azodicarbonyl)dipiperidine (2.187 g, 8.67 mmol) in tetrahydrofuran (25 mL) added dropwise over 40 min. The mixture was stirred for another 2 h and then it was partitioned between ethyl acetate (250 mL) and saturated aqueous sodium bicarbonate (20 mL). The organic phase was separated, washed with brine, dried over anhydrous magnesium sulfate and concentrated in vacuo to give a gel-like residue. Chromatography on silica gel (elution with 0-5% ethyl acetate-toluene) gave 0.993 g (54%) of methyl 2-((tert-butoxycarbonyl)(2,4-dimethoxybenzyl)amino)-5-methylthiazole-4-carboxylate as a white solid. LC (Method A): 2.388 min. HRMS(ESI): Anal. Calcd for $C_{20}H_{27}N_2O_6S$ [M+H]$^+$ m/z 423.1584; found 423.1474. $^1$H NMR (CDCl$_3$, 400 MHz) δ ppm: 6.96 (d, J=8.2 Hz, 1H), 6.43 (broad s, 1H), 6.38 (br d, J=8.2 Hz, 1H), 5.28 (s, 2H), 3.86 (s, 3H), 3.79 (s, 3H), 3.78 (s, 3H), 2.66 (s, 3H), 1.43 (s, 9H). Further elution gave 0.287 g (16%) of (Z)-methyl 2-((tert-butoxycarbonyl)imino)-3-(2,4-dimethoxybenzyl)-5-methyl-2,3-dihydrothiazole-4-carboxylate as a white solid. LC (Method A): 2.310 min. HRMS(ESI): Anal. Calcd for $C_{20}H_{27}N_2O_6S$ [M+H]$^+$ m/z 423.1584; found 423.1481. $^1$H NMR (CDCl$_3$, 400 MHz) δ ppm: 6.84 (d, J=8.2 Hz, 1H), 6.34-6.40 (m, 2H), 5.58 (s, 2H), 3.77 (s, 3H), 3.76 (s, 3H), 3.73 (s, 3H), 2.42 (s, 3H), 1.55 (s, 9H).

87C. tert-Butyl 2,4-dimethoxybenzyl(4-(hydroxymethyl)-5-methylthiazol-2-yl)carbamate

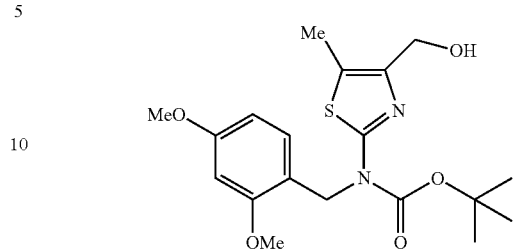

A solution of methyl 2-((tert-butoxycarbonyl)(2,4-dimethoxybenzyl)amino)-5-methylthiazole-4-carboxylate (0.650 g, 1.538 mmol) in tetrahydrofuran (15 mL) and under nitrogen was cooled at 0° C. and treated with methanol (0.124 mL, 3.08 mmol), followed by lithium borohydride (0.134 g, 6.15 mmol), added all at once. After 10 min the cooling bath was removed and the resulting turbid solution was stirred at room temperature for 6 h. The reaction mixture was re-cooled in ice and quenched with 50% aqueous acetic acid (1 mL). After the evolution of hydrogen has ceased, the reaction mixture was diluted with dichloromethane (250 mL), washed with saturated sodium bicarbonate and brine, and then dried over anhydrous magnesium sulfate. After concentration under reduced pressure, the solid residue obtained was chromatographed on silica-gel (elution dichloromethane-ethyl acetate 95:5 to 9:1) to give 0.488 g (80%) of the title material as a white solid. LC (Method A): 2.213 min. HRMS(ESI): Anal. Calcd for $C_{19}H_{27}N_2O_5S$ [M+H]$^+$ m/z 395.1635; found 395.1627. $^1$H NMR (CDCl$_3$, 400 MHz) δ ppm: 6.91 (d, J=8.5 Hz, 1H), 6.45 (d, J=2.1 Hz, 1H), 6.38 (dd, J=8.5, 2.1 Hz, 1H), 5.23 (s, 2H), 4.49 (d, J=5.8 Hz, 2H), 3.82 (s, 3H), 3.78 (s, 3H), 2.32 (t, J=5.8 Hz, 1H), 2.29 (s, 3H), 1.46 (s, 9H).

87D. tert-Butyl 2,4-dimethoxybenzyl(4-(((6-methoxy-2-(2-methoxyimidazo[2,1-b][1,3,4]thiadiazol-6-yl)benzofuran-4-yl)oxy)methyl)-5-methylthiazol-2-yl)carbamate

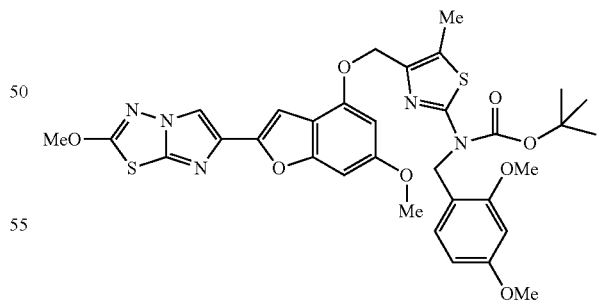

A mixture of 6-methoxy-2-(2-methoxyimidazo[2,1-b][1,3,4]thiadiazol-6-yl)benzofuran-4-ol (Example 1H, 0.378 g, 1.19 mmol) and tert-butyl 2,4-dimethoxybenzyl(4-(hydroxymethyl)-5-methylthiazol-2-yl)carbamate (0.469 g, 1.19 mmol) in dry tetrahydrofuran (30 mL) was treated at 22° C. with tri-n-butylphosphine (0.88 mL, 3.57 mmol), added in one portion, followed by a solution of 1,1'-(azodicarbonyl)dipiperidine (0.450 g, 1.785 mmol) in tetrahydrofuran (10 mL) added dropwise over 40 min. After another 2 h at 22° C., the reaction mixture was partitioned between dichloromethane (300 mL) and saturated aqueous sodium bicarbonate. The organic phase was washed with brine, dried over anhydrous magnesium sulfate and concentrated in vacuo to give a glassy residue. Chromatography on silica gel (elution with 0-5% ethyl acetate-dichloromethane) gave 0.622 g (75%) of the title material as a white solid. LC (Method A): 2.703 min. HRMS(ESI): Anal. Calcd for $C_{33}H_{36}N_5O_8S_2$ [M+H]$^+$ m/z 694.2005; found 694.2006. $^1$H NMR (CDCl$_3$, 400 MHz) δ ppm: 7.83 (s, 1H), 7.01 (s, 1H), 6.95 (d, J=8.5 Hz, 1H), 6.67 (s, 1H), 6.47 (br s, 1H), 6.43 (d, J=2.2 Hz, 1H), 6.37 (dd, J=8.5, 2.2 Hz, 1H), 5.26 (s, 2H), 5.11 (s, 2H), 4.21 (s, 3H), 3.80 (s, 3H), 3.79 (s, 3H), 3.78 (s, 3H), 2.41 (s, 3H), 1.44 (s, 9H).

Example 87. 4-(((6-Methoxy-2-(2-methoxyimidazo [2,1-b][1,3,4]thiadiazol-6-yl)benzofuran-4-yl)oxy) methyl)-5-methylthiazol-2-amine

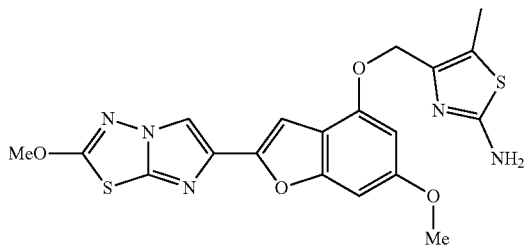 [SMILES: COc1cc(OCc2nc(N)sc2C)c2cc(-c3cn4nc(OC)sc4n3)oc2c1]

To a mixture of tert-butyl 2,4-dimethoxybenzyl(4-(((6-methoxy-2-(2-methoxyimidazo-[2,1-b][1,3,4]thiadiazol-6-yl)benzofuran-4-yl)oxy)methyl)-5-methylthiazol-2-yl)carbamate (0.643 g, 0.927 mmol) and 1,2,3,4,5-pentamethylbenzene (2.40 g, 16.19 mmol) in dichloromethane (10 mL) was added 2,2,2-trifluoroacetic acid (15 mL, 196 mmol) in one portion and the resulting clear solution was stirred at 23° C. for 3 h. The volatiles were then evaporated under reduced pressure and the residue was partitioned between dichloromethane (500 mL) and saturated aqueous sodium bicarbonate. The aqueous phase was separated and back-extracted with dichloromethane (2×50 mL) and the combined organic extract was washed with brine, dried over anhydrous magnesium sulfate and evaporated under reduced pressure to give a white residue. This solid residue was chromatographed on silica gel (elution with 1-5% MeOH-dichloromethane) to give 0.351 g (85%) of the title compound as a white solid. LC (Method A): 2.189 min. HRMS(ESI): Anal. Calcd for $C_{19}H_{18}N_5O_4S_2$ [M+H]$^+$ m/z 444.0795; found 444.0797. $^1$H NMR (DMSO-d$_6$, 400 MHz) δ ppm: 8.37 (s, 1H), 6.89 (s, 1H), 6.80 (s, 1H), 6.74 (br s, 2H), 6.57 (d, J=1.6 Hz, 1H), 4.93 (s, 2H), 4.20 (s, 3H), 3.80 (s, 3H), 2.26 (s, 3H).

Example 88

4-(((6-Methoxy-2-(2-methoxyimidazo[2,1-b][1,3,4] thiadiazol-6-yl)benzofuran-4-yl)oxy)methyl)-2-morpholinothiazole-5-carbaldehyde

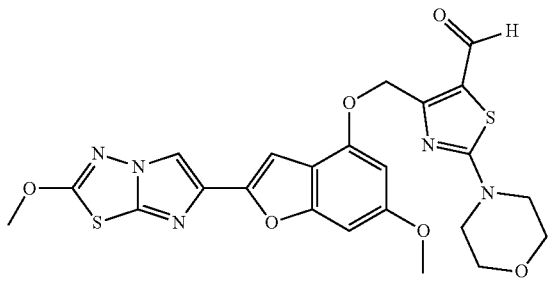 [SMILES: COc1cc(OCc2nc(N3CCOCC3)sc2C=O)c2cc(-c3cn4nc(OC)sc4n3)oc2c1]

88A. 4-(4-(((tert-Butyldimethylsilyl)oxy)methyl) thiazol-2-yl)morpholine

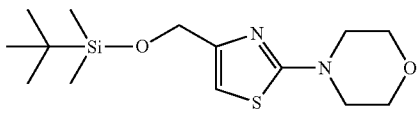 [SMILES: CC(C)(C)[Si](C)(C)OCc1csc(N2CCOCC2)n1]

A mixture of 2-bromo-4-(((tert-butyldimethylsilyl)oxy) methyl)thiazole (Example 37B, 2.46 g, 7.98 mmol) and morpholine (3.13 mL, 35.9 mmol) in THF (7 mL) in a 50 mL pressure vial was heated at 83° C. for 48 h. The cooled mixture was then evaporated under vacuum and the residue was diluted with ethyl acetate (200 mL) and washed successively with water, cold 0.1N HCl, saturated sodium bicarbonate and brine. After drying over anhydrous magnesium sulfate, the solvent was evaporated and the light yellow oily residue obtained was purified by flash chromatography on the Isco (40 g cartridge, elution with 0-9% ethyl acetate-DCM) to give a yellow oil (1.98 g, 79%). Distillation (Kugelrohr) of this oil in vacuo gave 1.85 g (74%) of the title compound as a light yellow oil: bp 105-115° C./0.04 torr. LC (Method F): 2.205 min. HRMS(ESI): calcd for $C_{14}H_{27}N_2O_2SSi$ [M+H]$^+$ m/z 315.156, found 315.158. $^1$H NMR (CDCl$_3$, 400 MHz) δ ppm: 6.47 (t, J=1.5 Hz, 1H), 4.67 (d, J=1.5 Hz, 2H), 3.74-3.90 (m, 4H), 3.39-3.51 (m, 4H), 0.95 (s, 9H), 0.11 (s, 6H).

88B. 4-(((tert-Butyldimethylsilyl)oxy)methyl)-2-morpholinothiazole-5-carbaldehyde

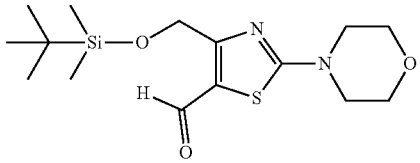 [SMILES: CC(C)(C)[Si](C)(C)OCc1nc(N2CCOCC2)sc1C=O]

A solution of 4-(4-(((tert-butyldimethylsilyl)oxy)methyl) thiazol-2-yl)morpholine (0.400 g, 1.272 mmol) in anhydrous THF (10 mL) was cooled to −78° C. under nitrogen and then a solution of BuLi (1.6 M in hexanes, 1.11 ml, 1.780 mmol) was added dropwise over 10 min. The resulting mixture was stirred at −78° C. for 30 min and then dry DMF (0.591 mL, 7.63 mmol) was added dropwise. The mixture was stirred for 2 h at −78° C. and then allowed to warm up to room temperature. After reaction completion (LC), saturated aqueous NH₄Cl (3 mL) was added and the resulting mixture was stirred for 10 min at 20° C., then diluted in DCM (50 mL) and washed with brine. The organic phase was dried (MgSO₄) and evaporated and the residue was purified on the ISCO using a REDISEP® 12 g column (60 to 100% DCM-hexanes) to give the title product as a bright yellow solid (0.20 g, 46%). LCMS (APCI): calcd for $C_{15}H_{27}N_2O_3SSi$ [M+H]⁺ m/z 343.14, found 343.1. ¹H NMR (CDCl₃, 400 MHz) δ ppm: 10.22 (s, 1H), 4.91 (s, 2H), 3.78-3.83 (m, 4H), 3.56-3.63 (m, 4H), 0.94 (s, 9H), 0.14 (s, 6H).

88C. 4-(Hydroxymethyl)-2-morpholinothiazole-5-carbaldehyde

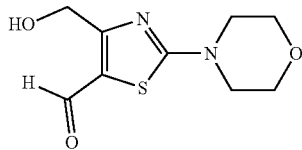 [SMILES: O=Cc1sc(N2CCOCC2)nc1CO]

To a solution of 4-(((tert-butyldimethylsilyl)oxy)methyl)-2-morpholinothiazole-5-carbaldehyde (0.200 g, 0.584 mmol) in dry THF (5 mL) under N₂ was added TBAF (2.7 M in THF, 0.427 mL, 1.168 mmol) dropwise and the mixture was stirred at room temperature for 2 h. The reaction mixture was then diluted with DCM and washed with aqueous NaHCO₃ and brine, and then it was dried over MgSO₄ and evaporated. The crude product was purified on the ISCO using a REDISEP® 4 g column (0 to 15% MeOH-DCM) to yield the product as a yellow solid (0.102 g, 77%). LCMS (APCI): calcd for $C_9H_{13}N_2O_3S$ [M+H]⁺ m/z 229.06, found 229.1. ¹H NMR (CDCl₃, 400 MHz) δ ppm: 9.88 (s, 1H), 4.84 (d, J=5.9 Hz, 2H), 3.78-3.87 (m, 4H), 3.59-3.68 (m, 4H), 2.77 (t, J=5.1 Hz, 1H).

Example 88. 4-(((6-Methoxy-2-(2-methoxyimidazo[2,1-b][1,3,4] thiadiazol-6-yl)benzofuran-4-yl)oxy)methyl)-2-morpholinothiazole-5-carbaldehyde

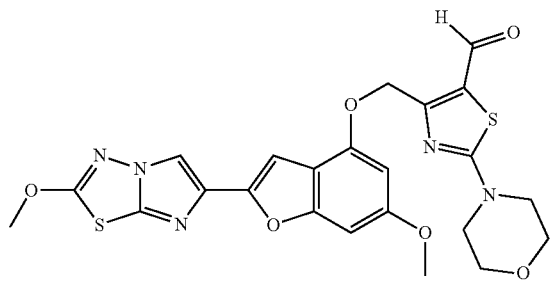 [SMILES: COc1cc(OCc2nc(N3CCOCC3)sc2C=O)c2cc(-c3cn4nc(OC)sc4n3)oc2c1]

6-Methoxy-2-(2-methoxyimidazo[2,1-b][1,3,4]thiadiazol-6-yl)benzofuran-4-ol (Example 1H, 0.139 g, 0.438 mmol) and 4-(hydroxymethyl)-2-morpholinothiazole-5-carbaldehyde (0.100 g, 0.438 mmol) were reacted as described in Example 86. The reaction mixture was concentrated in vacuo and the crude residue was suspended in CH₃CN, sonicated and filtered. The resulting solid was purified on the ISCO using a REDISEP® Gold 4 g column (0 to 60% EtOAc-DCM). The obtained material was suspended in CH₃CN, sonicated, filtered and dried to give the title compound as an off-white solid (0.100 g, 43%). LC (Method C): 2.287 min. HRMS(ESI): calcd for $C_{23}H_{22}N_5O_6S_2$ [M+H]⁺ m/z 528.093, found 528.0988. ¹H NMR (CDCl₃, 400 MHz) δ ppm: 10.15 (s, 1H), 7.85 (s, 1H), 7.03 (s, 1H), 6.74 (s, 1H), 6.45 (d, J=1.6 Hz, 1H), 5.36 (s, 2H), 4.22 (s, 3H), 3.85 (s, 3H), 3.81-3.85 (m, 4H), 3.65 (t, J=4.7 Hz, 4H).

Example 89

(4-(((6-Methoxy-2-(2-methoxyimidazo[2,1-b][1,3,4] thiadiazol-6-yl) benzofuran-4-yl)oxy)methyl)-2-morpholinothiazol-5-yl)methanol

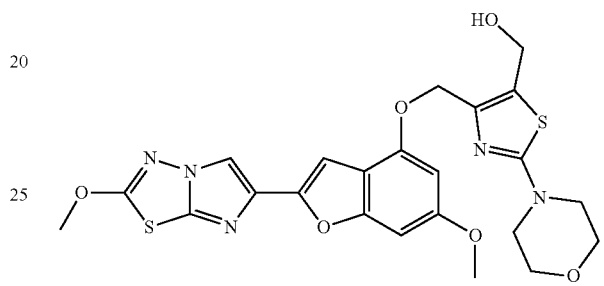

A solution of 4-(((6-methoxy-2-(2-methoxyimidazo[2,1-b][1,3,4]thiadiazol-6-yl) benzofuran-4-yl)oxy)methyl)-2-morpholinothiazole-5-carbaldehyde (0.088 g, 0.167 mmol) in dry THF (10 mL) in a 50 mL flask under a nitrogen atmosphere was cooled to 0° C. and treated with MeOH (6.75 µl, 0.167 mmol) followed by LiBH₄ (3.63 mg, 0.167 mmol). The resulting mixture was stirred at 0° C. for 1 h before to be quenched with MeOH (5 mL) and stirred at room temperature for 10 min. Then the reaction mixture was diluted with DCM, washed with aqueous NaHCO₃ and brine, dried over MgSO₄ and evaporated. The residue was purified on the ISCO using a REDISEP® 4 g column (0 to 100% EtOAc-DCM) to give the title compound as a white solid (0.084 g, 95%). LC (Method C): 2.062 min. HRMS (ESI): calcd for $C_{23}H_{24}N_5O_6S_2$ [M+H]⁺ m/z 530.109, found 530.114. ¹H NMR (CDCl₃, 400 MHz) δ ppm: 7.84 (s, 1H), 7.04 (d, J=0.8 Hz, 1H), 6.72 (d, J=0.8 Hz, 1H), 6.48-6.53 (m, 1H), 5.11-5.17 (m, 2H), 4.77-4.83 (m, 2H), 4.26 (s, 1H), 4.21 (s, 2H), 3.79-3.87 (m, 7H), 3.45-3.52 (m, 4H), 1.91 (t, J=6.3 Hz, 1H).

Example 90

4-(4-(((6-Methoxy-2-(2-methoxyimidazo[2,1-b][1,3,4]thiadiazol-6-yl)benzofuran-4-yl)oxy)methyl)-5-(methoxymethyl)thiazol-2-yl)morpholine

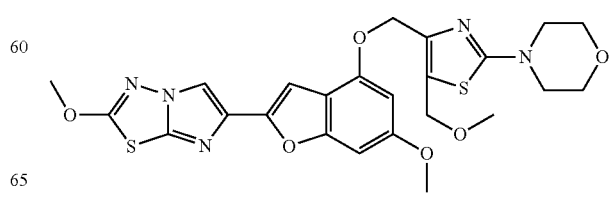

90A. Ethyl 4-(((tert-butyldimethylsilyl)oxy)methyl)-2-morpholinothiazole-5-carboxylate

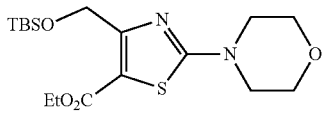

A solution of 4-(4-(((tert-butyldimethylsilyl)oxy)methyl)thiazol-2-yl)morpholine (Example 88A, 0.060 g, 0.191 mmol) in dry THF (2 mL) was cooled at −78° C. under N$_2$ and then n-butyllithium (1.5 M in hexanes, 0.165 mL, 0.248 mmol) was added dropwise. The resulting pale yellow solution was stirred for 35 min at the same temperature and then ethyl chloroformate (0.027 mL, 0.286 mmol) was added dropwise. The resulting mixture was allowed to warm to room temperature over 2 h and then it was partitioned between ethyl acetate and saturated aqueous ammonium chloride. The organic phase was separated, washed with brine, dried over anhydrous magnesium sulfate and evaporated in vacuo. Chromatography of the residue on silica gel (ISCO, elution gradient of ethyl acetate in dichloromethane) gave 0.065 g (88%) of the title compound. LC (Method B): 2.999 min. LCMS (APCI): calcd for C$_{17}$H$_{31}$N$_2$O$_4$SSi [M+H]$^+$ m/z 387.18; found 387.2.

90B. (4-(((tert-Butyldimethylsilyl)oxy)methyl)-2-morpholinothiazol-5-yl)methanol

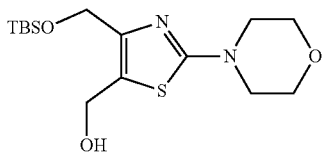 [SMILES: CC(C)(C)[Si](C)(C)OCc1nc(N2CCOCC2)sc1CO]

To an ice-cold solution of ethyl 4-(((tert-butyldimethylsilyl)oxy)methyl)-2-morpholinothiazole-5-carboxylate (0.065 g, 0.168 mmol) in tetrahydrofuran (5 mL) was added methanol (0.020 mL, 0.504 mmol), followed by lithium borohydride (0.0073 g, 0.336 mmol). After 15 min at 0° C., the cooling bath was removed and the reaction mixture was allowed to warm to ambient temperature while being stirred for 3 h. The reaction mixture was then partitioned with dichloromethane-saturated aqueous ammonium chloride and the aqueous phase was separated and back-extracted with dichloromethane (×3). The combined organic extract was washed with brine, dried over anhydrous magnesium sulfate and evaporated in vacuo. Chromatography of the residue on silica gel (ISCO, elution gradient of ethyl acetate in dichloromethane) gave 0.048 g (83%) of the title compound. LC (Method A): 2.017 min. HRMS(ESI): calcd for C$_{15}$H$_{29}$N$_2$O$_3$SSi [M+H]$^+$ m/z 345.1668; found 345.1662. $^1$H NMR (400 MHz, CDCl$_3$) δ ppm: 4.74 (s, 2H), 4.68 (d, J=6.2 Hz, 2H), 3.74-3.84 (m, 4H), 3.36-3.47 (m, 4H), 2.63 (t, J=6.2 Hz, 1H), 0.94 (s, 9H), 0.15 (s, 6H).

90C. 4-(4-(((tert-Butyldimethylsilyl)oxy)methyl)-5-(methoxymethyl)thiazol-2-yl)morpholine

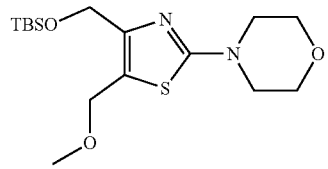 [SMILES: COCc1sc(N2CCOCC2)nc1CO[Si](C)(C)C(C)(C)C]

To a solution of (4-(((tert-butyldimethylsilyl)oxy)methyl)-2-morpholinothiazol-5-yl)methanol (0.048 g, 0.139 mmol) in N,N-dimethylformamide (2.5 mL), cooled at −15° C. under nitrogen, was added sodium hydride (60% dispersion in oil, 0.017 g, 0.418 mmol) and the mixture was stirred at −15° C. to −10° C. for 25 min. Iodomethane (0.044 mL, 0.697 mmol) was then added and the resulting mixture was stirred at the same temperature for 4 h, before being partitioned between ether and saturated aqueous ammonium chloride. The aqueous phase was separated and back-extracted with ether (×3), and the combined organic extract was washed with brine, dried over anhydrous magnesium sulfate and evaporated in vacuo. This gave the title compound (0.050 g, 100%) which was used as such in the next step without further purification. LC (Method A): 2.224 min. HRMS(ESI): calcd for C$_{16}$H$_{31}$N$_2$O$_3$SSi [M+H]$^+$ m/z 359.1825; found 359.1819.

90D. (5-(Methoxymethyl)-2-morpholinothiazol-4-yl)methanol

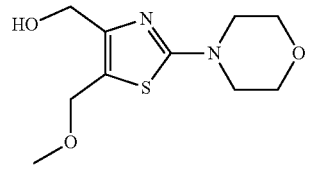 [SMILES: COCc1sc(N2CCOCC2)nc1CO]

A solution of 4-(4-(((tert-butyldimethylsilyl)oxy)methyl)-5-(methoxymethyl)thiazol-2-yl)morpholine (0.050 g, 0.139 mmol) in dry tetrahydrofuran (4 mL) under nitrogen was treated dropwise with triethylamine trihydrofluoride (0.136 mL, 0.837 mmol) and the resulting mixture was stirred at room temperature for 36 h. The reaction mixture was then partitioned with dichloromethane-saturated aqueous sodium bicarbonate and the organic phase was separated, washed with brine, dried over anhydrous magnesium sulfate and evaporated in vacuo. Chromatography of the residue on silica gel (ISCO, elution gradient of ethyl acetate in dichloromethane) gave 0.025 g (74%) of the title compound as a white crystalline solid. LC (Method A): 0.933 min. HRMS (ESI): calcd for C$_{10}$H$_{17}$N$_2$O$_3$S [M+H]$^+$ m/z 245.0960; found 245.0954. $^1$H NMR (400 MHz, CDCl$_3$) δ ppm: 4.55 (s, 2H), 4.49 (s, 2H), 3.77-3.84 (m, 4H), 3.41-3.49 (m, 4H), 3.35 (s, 3H), 2.46 (br s, 1H).

Example 90. 4-(4-(((6-Methoxy-2-(2-methoxyimidazo[2,1-b][1,3,4]thiadiazol-6-yl)benzo furan-4-yl) oxy)methyl)-5-(methoxymethyl)thiazol-2-yl)morpholine

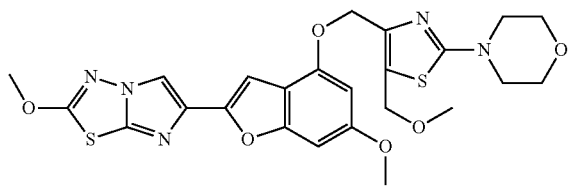 [SMILES: COCc1sc(N2CCOCC2)nc1COc1cc(OC)cc2oc(-c3cn4nc(OC)sc4n3)cc12]

The title compound was prepared according to the general Mitsunobu coupling procedure described in Example 86. LC (Method A): 2.191 min. HRMS(ESI): calcd for $C_{24}H_{26}N_5O_6S_2$ [M+H]$^+$ m/z 544.1325; found 544.1322. $^1$H NMR (400 MHz, CDCl$_3$) δ ppm: 7.83 (s, 1H), 7.03 (s, 1H), 6.70 (d, J=0.78 Hz, 1H), 6.47-6.52 (m, 1H), 5.10 (s, 2H), 4.60 (s, 2H), 4.20 (s, 3H), 3.77-3.89 (m, 7H), 3.43-3.52 (m, 4H), 3.33 (s, 3H).

Example 91

2-(4-(((6-Methoxy-2-(2-methoxyimidazo[2,1-b][1,3,4]thiadiazol-6-yl)benzofuran-4-yl)oxy)methyl)-2-morpholinothiazol-5-yl)propan-2-ol

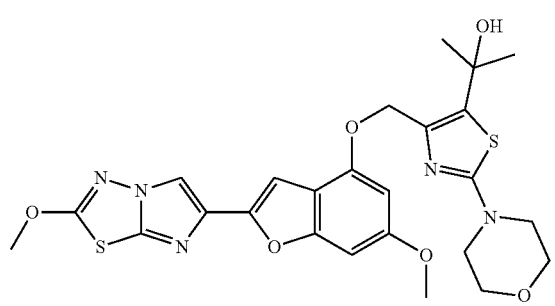 [SMILES: COc1cc(OCc2nc(N3CCOCC3)sc2C(C)(C)O)c2cc(-c3cn4nc(OC)sc4n3)oc2c1]

91A. 2-(4-(((tert-Butyldimethylsilyl)oxy)methyl)-2-morpholinothiazol-5-yl)propan-2-ol

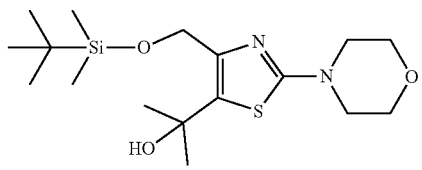 [SMILES: CC(C)(O)c1sc(N2CCOCC2)nc1CO[Si](C)(C)C(C)(C)C]

A solution of 4-(4-(((tert-butyldimethylsilyl)oxy)methyl)thiazol-2-yl)morpholine (Example 88A, 0.100 g, 0.318 mmol) in dry THF (5 mL) was cooled at −78° C. under nitrogen and then a solution of n-BuLi (1.26 M in hexanes, 0.454 mL, 0.572 mmol) was added dropwise over 10 min. The resulting mixture was stirred at −78° C. for 30 min and then dry acetone (1.0 mL, 13.62 mmol) was added dropwise. The reaction mixture was allowed to warm to room temperature and was stirred for another 2 h before being quenched with saturated aqueous NH$_4$Cl (5 mL). The mixture was diluted with DCM (50 mL), washed with brine and, after concentration under reduced pressure, the crude material was purified on the ISCO using a REDISEP® 4 g column (0 to 50% EtOAc-DCM) to give the desired product (0.040 g, 25%) as a colorless oil which was used as such in the next step. LC (Method A): 2.072 min. LCMS (APCI): calcd for $C_{17}H_{33}N_2O_3SSi$ [M+H]$^+$ m/z 373.20, found 373.20.

91B. 2-(4-(Hydroxymethyl)-2-morpholinothiazol-5-yl)propan-2-ol

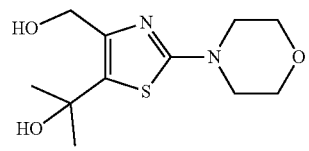 [SMILES: CC(C)(O)c1sc(N2CCOCC2)nc1CO]

To a solution of 2-(4-(((tert-butyldimethylsilyl)oxy) methyl)-2-morpholinothiazol-5-yl)propan-2-ol (0.040 g, 0.107 mmol) in dry THF (2 mL) under N$_2$ was added triethylamine trihydrofluoride (0.105 mL, 0.644 mmol) dropwise and the mixture was stirred at room temperature overnight. The reaction mixture was then diluted with DCM and the solution was washed with aqueous NaHCO$_3$, dried over MgSO$_4$ and evaporated. The residue was purified on the ISCO using a REDISEP® 4 g column (0 to 15% MeOH-DCM) to give the title compound as a white solid (0.019 g, 69%). LCMS (APCI): calcd for $C_{11}H_{19}N_2O_3S$ [M+H]$^+$ m/z 259.104, found 259.1. $^1$H NMR (CDCl$_3$, 400 MHz) δ ppm: 4.70 (s, 2H), 3.76-3.83 (m, 4H), 3.36-3.43 (m, 4H), 3.07 (br. s., 1H), 2.94 (br. s., 1H), 1.63 (s, 6H).

Example 91. 2-(4-(((6-Methoxy-2-(2-methoxyimidazo[2,1-b][1,3,4]thiadiazol-6-yl) benzofuran-4-yl) oxy)methyl)-2-morpholinothiazol-5-yl)propan-2-ol

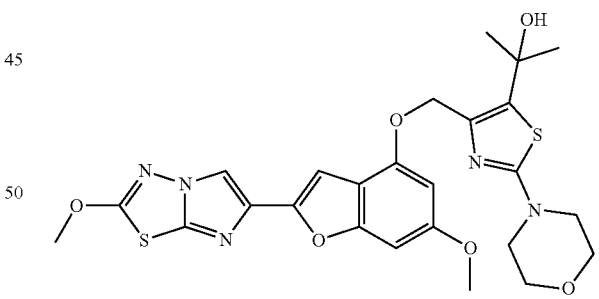

6-Methoxy-2-(2-methoxyimidazo[2,1-b][1,3,4]thiadiazol-6-yl)benzofuran-4-ol (Example 1H, 0.023 g, 0.074 mmol) and 2-(4-(hydroxymethyl)-2-morpholinothiazol-5-yl) propan-2-ol (0.019 g, 0.074 mmol) were reacted as described in Example 86. The reaction mixture was concentrated in vacuo and the residue was suspended in CH$_3$CN, sonicated and filtered. The resulting solid was purified on the ISCO using a REDISEP® Gold 4 g column (0 to 70% EtOAc-DCM) and the obtained material was suspended in CH$_3$CN, sonicated, filtered and dried to give the title compound as an off-white solid (0.005 g, 13%). LC (Method C): 2.047 min. HRMS(ESI): calcd for $C_{25}H_{28}N_5O_6S_2$ [M+H]$^+$ m/z 558.140, found 558.1482. $^1$H NMR (CDCl$_3$, 400 MHz) δ ppm: 7.84 (s, 1H), 7.03 (s, 1H), 6.68-6.72 (m, 1H), 6.57 (d, J=2.0 Hz, 1H), 5.24 (s, 2H), 4.21 (s, 3H), 3.85 (s, 3H), 3.78-3.84 (m, 4H), 3.41-3.47 (m, 4H), 2.89 (s, 1H), 1.64 (s, 6H).

Example 92

3-(4-(((6-Methoxy-2-(2-methoxyimidazo[2,1-b][1,3,4]thiadiazol-6-yl)benzofuran-4-yl)oxy)methyl)thiazol-2-yl)-8-oxa-3-azabicyclo[3.2.1]octane

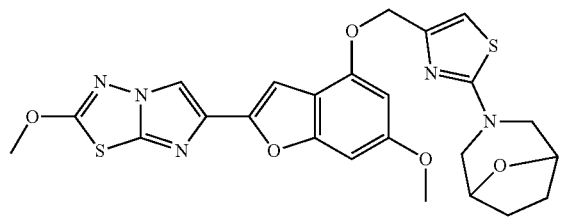 [SMILES: COc1cc(OCc2csc(N3CC4CCC(C3)O4)n2)c2cc(-c3cn4nc(OC)sc4n3)oc2c1]

92A. Methyl 2-(8-oxa-3-azabicyclo[3.2.1]octan-3-yl)thiazole-4-carboxylate

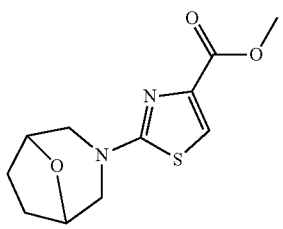 [SMILES: COC(=O)c1csc(N2CC3CCC(C2)O3)n1]

A solution of bicyclomorpholine (0.52 mL, 4.75 mmol) in THF (10 mL) was treated with methyl 2-bromothiazole-4-carboxylate (1.0 g, 4.24 mmol) and DIEA (1.66 mL, 9.50 mmol) and the resulting mixture was refluxed for 18 h under N$_2$. The reaction mixture was then concentrated under reduced pressure and the residue was purified on the ISCO using a REDISEP® 24 g column (0 to 40% EtOAc-DCM) to give the desired product as a yellow gum (0.740 g, 62%). LCMS (APCI): calcd for C$_{11}$H$_{15}$N$_2$O$_3$S [M+H]$^+$ m/z 255.07, found 255.1. $^1$H NMR (CDCl$_3$, 400 MHz) δ ppm: 7.48 (s, 1H), 4.48 (d, J=2.7 Hz, 2H), 3.89 (s, 3H), 3.58 (d, J=12.1 Hz, 2H), 3.37 (dd, J=11.9, 2.5 Hz, 2H), 1.98-2.07 (m, 2H), 1.86-1.94 (m, 2H).

92B. (2-(8-Oxa-3-azabicyclo[3.2.1]octan-3-yl)thiazole-4-yl)methanol

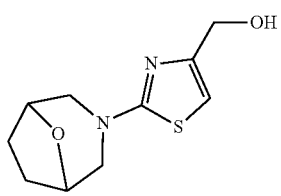 [SMILES: OCc1csc(N2CC3CCC(C2)O3)n1]

A solution of methyl 2-(8-oxa-3-azabicyclo[3.2.1]octan-3-yl)thiazole-4-carboxylate (0.740 g, 2.91 mmol) in dry THF (15 mL) in a 50 mL flask under a nitrogen atmosphere was cooled to 0° C. and treated with LiBH$_4$ (0.127 g, 5.82 mmol) followed by MeOH (0.24 mL, 5.82 mmol). After 10 min at 0° C. the bath was removed and the reaction mixture was stirred at room temperature overnight. The reaction mixture was then quenched with MeOH (10 mL), concentrated under reduced pressure and the residue was dissolved in DCM and dried over MgSO$_4$. The volatiles were removed under reduced pressure and the residue was purified on the ISCO using a REDISEP® 24 g column (0 to 15% MeOH-DCM) to give the title alcohol (0.60 g, 91%) as a colorless oil which solidified on standing in vacuo to give a white solid. LCMS (APCI): calcd for C$_{10}$H$_{15}$N$_2$O$_2$S [M+H]$^+$ m/z 227.08, found 227.1. $^1$H NMR (CDCl$_3$, 400 MHz) δ ppm: 6.41 (s, 1H), 4.53 (s, 2H), 4.02 (dt, J=12.2, 6.2 Hz, 2H), 3.49 (d, J=11.7 Hz, 2H), 3.30 (dd, J=12.1, 2.0 Hz, 2H), 2.78 (br. s., 1H), 1.96-2.03 (m, 2H), 1.88-1.92 (m, 2H).

Example 92. 3-(4-(((6-Methoxy-2-(2-methoxyimidazo[2,1-b][1,3,4]thiadiazol-6-yl)benzofuran-4-yl)oxy)methyl)thiazol-2-yl)-8-oxa-3-azabicyclo[3.2.1]octane

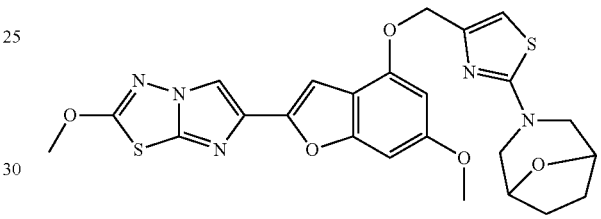

6-Methoxy-2-(2-methoxyimidazo[2,1-b][1,3,4]thiadiazol-6-yl)benzofuran-4-ol (Example 1H, 0.070 g, 0.22 mmol) and (2-(8-oxa-3-azabicyclo[3.2.1]octan-3-yl)thiazol-4-yl)methanol (0.055 g, 0.24 mmol) were reacted as described in Example 86. The crude material was purified on the ISCO using a REDISEP® Gold 4 g column (0 to 45% EtOAc-DCM) and the obtained material was triturated with CH$_3$CN to give the title compound as a cream solid (0.032 g, 28%). LC (Method C): 2.262 min. HRMS(ESI): calcd for C$_{24}$H$_{24}$N$_5$O$_5$S$_2$ [M+H]$^+$ m/z 526.114, found 526.124. $^1$H NMR (CDCl$_3$, 400 MHz) δ ppm: 8.37 (s, 1H), 6.98 (s, 1H), 6.92 (s, 1H), 6.82 (s, 1H), 6.56 (d, J=2.0 Hz, 1H), 4.42 (br. s., 2H), 4.20 (s, 3H), 3.80 (s, 3H), 3.47 (d, J=11.7 Hz, 3H), 3.14-3.19 (m, 3H), 1.86 (d, J=8.2 Hz, 2H), 1.76-1.80 (m, 2H).

Example 93

3-(4-(((6-Methoxy-2-(2-methoxyimidazo[2,1-b]thiadiazol-6-yl) benzofuran-4-yl)oxy)methyl)-5-methylthiazol-2-yl)-8-oxa-3-azabicyclo-[3.2.1]-octane

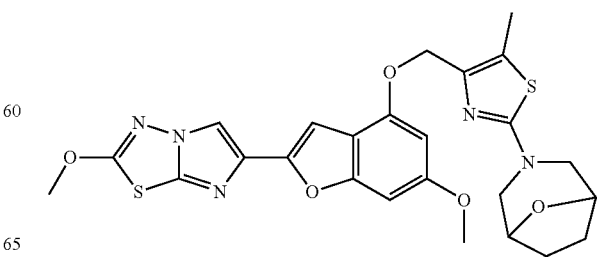

93A. 3-(4-(((tert-Butyldimethylsilyl)oxy)methyl)thiazol-2-yl)-8-oxa-3-azabicyclo[3.2.1]octane

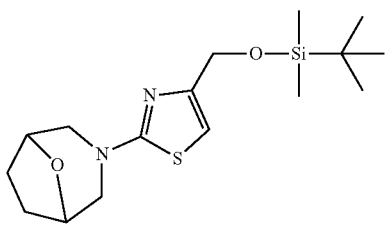 [SMILES: CC(C)(C)[Si](C)(C)OCc1csc(N2CC3CCC(C2)O3)n1]

To a solution of (2-(8-oxa-3-azabicyclo[3.2.1]octan-3-yl)thiazol-4-yl)methanol (0.490 g, 2.165 mmol) in DMF (10 mL) cooled at 0° C. under $N_2$, was added TBDMS-Cl (0.653 g, 4.33 mmol) and then imidazole (0.339 g, 4.98 mmol). The reaction mixture was brought to room temperature over 10 min and was stirred at the same temperature for 18 h. The mixture was then re-cooled at 0° C. and EtOH (2 mL) was added. After 10 min the mixture was allowed to warm to room temperature and was then partitioned between EtOAc and saturated aqueous $NaHCO_3$. The organic layer was washed with brine, dried over $MgSO_4$, filtered and evaporated. The residue was purified on the ISCO using a REDISEP® 12 g column (0 to 20% EtOAc-DCM) to give the desired product as a colorless oil (0.70 g, 95%). LCMS (APCI): calcd for $C_{16}H_{29}N_2O_2SSi$ [M+H]$^+$ m/z 341.16, found 341.2. $^1$H NMR (CDCl$_3$, 400 MHz) δ ppm: 6.30 (s, 1H), 4.55 (s, 2H), 4.32-4.37 (m, 2H), 3.38 (d, J=11.7 Hz, 2H), 3.18 (dd, J=11.7, 2.3 Hz, 2H), 1.84-1.91 (m, 2H), 1.76-1.83 (m, 2H), 0.83 (s, 9H), 0.00 (s, 6H).

93B. 3-(4-(((tert-Butyldimethylsilyl)oxy)methyl)-5-methylthiazol-2-yl)-8-oxa-3-azabicyclo[3.2.1]octane

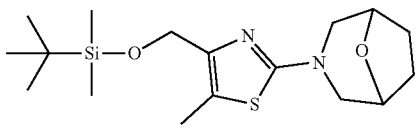 [SMILES: Cc1sc(N2CC3CCC(C2)O3)nc1CO[Si](C)(C)C(C)(C)C]

A solution of 3-(4-(((tert-butyldimethylsilyl)oxy)methyl)thiazol-2-yl)-8-oxa-3-azabicyclo[3.2.1]octane (0.700 g, 2.055 mmol) in anhydrous THF (20 mL) was cooled at −78° C. under nitrogen and a solution of BuLi (1.6 M in hexanes, 2.70 mL, 4.32 mmol) was added dropwise over 10 min. The resulting mixture was stirred at −78° C. for 30 min and then it was treated dropwise with iodomethane (0.257 mL, 4.11 mmol). The cooling bath was removed and the mixture was stirred for 2 h at room temperature before being quenched with saturated aqueous NH$_4$Cl (5 mL). After stirring for 10 min, the mixture was diluted with DCM (100 mL) and washed with brine. The organic phase was dried (MgSO$_4$) and evaporated and the residue was purified on the ISCO using a REDISEP® 24 g column (0 to 40% EtOAc-DCM) to give the desired product as a yellow oil (0.514 g, 71%). LCMS (APCI): calcd for $C_{17}H_{31}N_2O_2SSi$ [M+H]$^+$ m/z 355.18, found 355.2. $^1$H NMR (CDCl$_3$, 400 MHz) δ ppm: 4.55-4.61 (m, 2H), 4.40-4.47 (m, 2H), 3.44 (d, J=12.1 Hz, 2H), 3.24 (dd, J=12.1, 2.3 Hz, 2H), 2.31 (s, 3H), 1.93-2.01 (m, 2H), 1.85-1.93 (m, 2H), 0.92 (s, 9H), 0.10 (s, 6H).

93C. (2-(8-Oxa-3-azabicyclo[3.2.1]octan-3-yl)-5-methylthiazol-4-yl)methanol

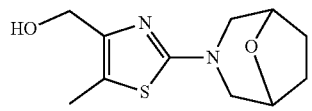

To a solution of 3-(4-(((tert-butyldimethylsilyl)oxy)methyl)-5-methylthiazol-2-yl)-8-oxa-3-azabicyclo[3.2.1]octane (0.514 g, 1.450 mmol) in dry THF (10 mL) under $N_2$ was added triethylamine trihydrofluoride (1.3 mL, 7.98 mmol) dropwise and the mixture was stirred at room temperature overnight. The reaction mixture was then quenched with MeOH and concentrated under reduced pressure. The residue was purified on the ISCO using a REDISEP® 12 g column (0 to 15% MeOH-DCM) to give the title product as an off-white solid (0.278 g, 80%). LCMS (APCI): calcd for $C_{11}H_{17}N_2O_2S$ [M+H]$^+$ m/z 241.09, found 241.1. $^1$H NMR (CDCl$_3$, 400 MHz) δ ppm: 4.35-4.41 (m, 4H), 3.62 (t, J=5.7 Hz, 1H), 3.45 (d, J=12.1 Hz, 2H), 3.10 (dd, J=12.1, 2.3 Hz, 2H), 2.26 (s, 3H), 1.86-1.94 (m, 2H), 1.79-1.86 (m, 2H).

Example 93. 3-(4-(((6-Methoxy-2-(2-methoxyimidazo[2,1-b]thiadiazol-6-yl) benzofuran-4-yl)oxy)methyl)-5-methylthiazol-2-yl)-8-oxa-3-azabicyclo[3.2.1]-octane

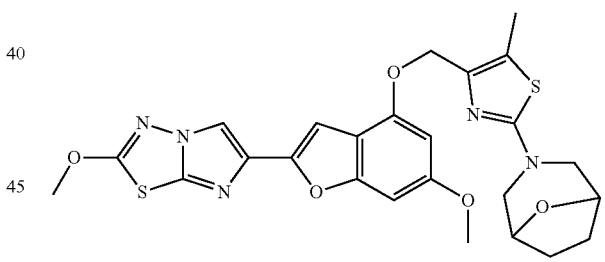

6-Methoxy-2-(2-methoxyimidazo[2,1-b][1,3,4]thiadiazol-6-yl)benzofuran-4-ol (Example 1H, 0.070 g, 0.22 mmol) and (2-(8-oxa-3-azabicyclo[3.2.1]octan-3-yl)-5-methylthiazol-4-yl)methanol (0.058 g, 0.24 mmol) were reacted as described in Example 86. The reaction mixture was concentrated under vacuum and the residue was suspended in CH$_3$CN, sonicated and filtered. The resulting solid was purified on the ISCO using a REDISEP® Gold 4 g column (0 to 70% EtOAc-DCM) to give the title compound as a white solid (0.056 g, 47%). LC (Method C): 2.182 min. LCMS (APCI): calcd for $C_{25}H_{26}N_5O_5S_2$ [M+H]$^+$ m/z 540.130, found 540.1. $^1$H NMR (CDCl$_3$, 400 MHz) δ ppm: 8.33 (s, 1H), 6.87 (s, 1H), 6.78 (s, 1H), 6.57 (d, J=1.6 Hz, 1H), 4.96 (s, 2H), 4.37 (br. s., 2H), 4.17 (s, 3H), 3.77 (s, 3H), 3.37 (d, J=11.7 Hz, 2H), 3.08 (dd, J=11.8, 2.2 Hz, 2H), 2.28 (s, 3H), 1.78-1.87 (m, 2H), 1.68-1.78 (m, 2H).

Example 94

4-(4-(((6-Methoxy-2-(2-methoxyimidazo[2,1-b][1,3,4]thiadiazol-6-yl)benzofuran-4-yl)oxy)methyl)-5-methylthiazol-2-yl)morpholine

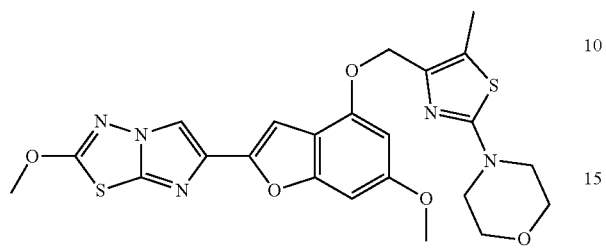

94A. Methyl 5-methyl-2-morpholinothiazole-4-carboxylate

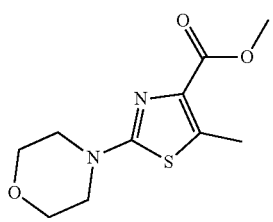 [SMILES: COC(=O)c1nc(N2CCOCC2)sc1C]

A solution of methyl 2-bromo-5-methylthiazole-4-carboxylate (2.80 g, 11.86 mmol) and morpholine (4.5 mL, 51.7 mmol) in THF (10 mL) was heated at reflux under nitrogen for 18 h. The volatiles were then removed under reduced pressure and the crude product was purified on the ISCO using a REDISEP® 40 g column (0 to 40% EtOAc-DCM), to give the title compound (2.20 g, 77%) as a yellow solid. LCMS (APCI): calcd for $C_{10}H_{15}N_2O_3S$ [M+H]$^+$ m/z 243.07, found 243.1. $^1$H NMR (CDCl$_3$, 400 MHz) δ ppm: 3.89 (s, 3H), 3.77-3.83 (m, 4H), 3.41-3.47 (m, 4H), 2.64 (s, 3H).

Alternatively, Example 94A, methyl 5-methyl-2-morpholinothiazole-4-carboxylate, was prepared as follows:

94AA. Methyl 3-bromo-2-oxobutanoate

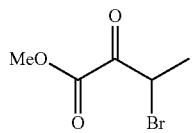

A 5 L 4-neck round bottom flask equipped with a mechanical stirrer, temperature thermocouple, condenser and a 1 L addition funnel, was charged copper(II) bromide (962 g, 4310 mmol) and ethyl acetate (2 L). A solution of methyl 2-ketobutyrate (250 g, 2150 mmol) in CHCl$_3$ (828 mL) was added dropwise. A scrubber (400 mL 1 N NaOH) was connected and the reaction mixture was heated to reflux (75° C.). The reaction started as a dark green color and as heating progressed, it became a light green with a white precipitate forming. NMR after one hour at reflux indicated that the reaction was complete. The reaction was cooled to RT and filtered through a pad of CELITE®. The filtrate was concentrated to an oil, dissolved in methylene chloride (500 mL) and filtered again through CELITE®. The filtrate was then passed through a pad of silica gel and eluted with ethyl acetate. Concentration of the filtrate provided the title bromoketoester (399 g, 2040 mmol, 95%) as a yellow oil. $^1$H NMR (400 MHz, CDCl$_3$) δ 5.18 (q, J=6.7 Hz, 1H), 3.94 (s, 3H), 1.83 (d, J=6.8 Hz, 3H).

94AAA. Morpholine-4-carbothioamide

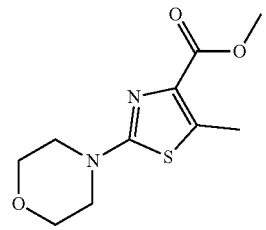 [SMILES: COC(=O)c1nc(N2CCOCC2)sc1C]

To a solution of morpholine (199 g, 2280 mmol) in CHCl$_3$ (1 L) was added isothiocyanatotrimethylsilane (150 g, 1140 mmol) dropwise. A white precipitate formed almost immediately, and the reaction was stirred for 1 h at RT. The reaction was then filtered and the resulting solid was washed with additional CHCl$_3$ and dried in vacuo to give the title thiourea as a white solid. (137 g, 937 mmol, 82%). $^1$H NMR (400 MHz, DMSO-d$_6$) δ 3.81-3.71 (m, 2H), 3.17-3.08 (m, 2H).

94A. Methyl 5-methyl-2-morpholinothiazole-4-carboxylate

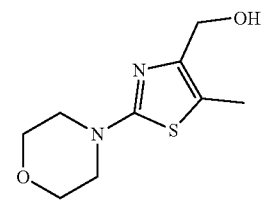

To a solution of morpholine-4-carbothioamide (Example 94AAA, 175 g, 1200 mmol) in methanol (500 mL) was charged methyl 3-bromo-2-oxobutanoate (Example 94AA, 233 g, 1200 mmol). The reaction was then heated to reflux for 1 hour, cooled to RT, and filtered. The filtrate was concentrated and the crude product was purified on by silica gel chromatography. The title thiazole (206 g, 850 mmol, 71%) was isolated as a yellow oil. (See the procedure set forth above for analytical data).

94B. (5-Methyl-2-morpholinothiazol-4-yl)methanol

The compound was prepared according to the protocol described for Example 92B. The crude product was purified on the ISCO using a REDISEP® Gold 24 g column (0 to 50% EtOAc-DCM) to give the title compound as a white solid (0.086 g, 51%). LCMS (APCI): calcd for $C_9H_{15}N_2O_2S$ [M+H]+ m/z 215.08, found 215.1. $^1$H NMR (CDCl$_3$, 400 MHz) δ ppm: 4.48 (d, J=4.7 Hz, 2H), 3.77-3.83 (m, 4H), 3.37-3.43 (m, 4H), 2.30 (t, J=4.7 Hz, 1H), 2.28 (s, 3H).

Example 94. 4-(4-(((6-Methoxy-2-(2-methoxyimidazo[2,1-b][1,3,4]thiadiazol-6-yl) benzofuran-4-yl) oxy)methyl)-5-methylthiazol-2-yl)morpholine

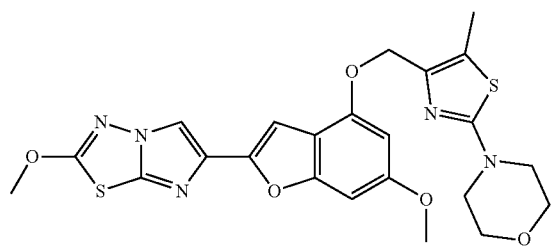 [SMILES: COc1cc(OCc2nc(N3CCOCC3)sc2C)c2cc(-c3cn4nc(OC)sc4n3)oc2c1]

The title compound was prepared according to the protocol described for Example 86. The crude product was purified on the ISCO using a REDISEP® 4 g column (0 to 40% EtOAc-DCM) and the obtained solid was suspended in MeOH, sonicated, filtered and dried to give the title compound as an off-white solid (0.094 g, 53%). LC (Method C): 2.314 min. HRMS(ESI): calcd for $C_{23}H_{24}N_5O_5S_2$ [M+H]+ m/z 514.122, found 514.126. $^1$H NMR (CDCl$_3$, 400 MHz) δ ppm: 7.83 (s, 1H), 7.06 (d, J=0.8 Hz, 1H), 6.69 (d, J=0.8 Hz, 1H), 6.50 (d, J=2.0 Hz, 1H), 5.05 (s, 2H), 4.21 (s, 3H), 3.85 (s, 3H), 3.78-3.84 (m, 4H), 3.39-3.46 (m, 4H), 2.37 (s, 3H).

Example 95

2-Methoxy-6-(6-methoxy-4-((5-methyl-2-(tetrahydro-2H-pyran-4-yl)thiazol-4-yl)methoxy)benzofuran-2-yl)imidazo[2,1-b][1,3,4]thiadiazole

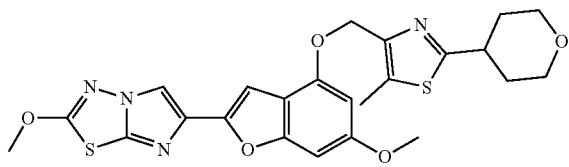 [SMILES: COc1cc(OCc2nc(C3CCOCC3)sc2C)c2cc(-c3cn4nc(OC)sc4n3)oc2c1]

95A. 4-(((tert-Butyldimethylsilyl)oxy)methyl)-2-(tetrahydro-2H-pyran-4-yl)thiazole

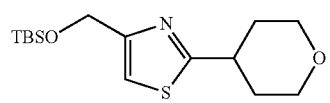

To a solution of (2-(tetrahydro-2H-pyran-4-yl)thiazol-4-yl)methanol (0.075 g, 0.376 mmol) in dichloromethane (5 mL) at room temperature was added imidazole (0.0384 g, 0.565 mmol), followed by tert-butylchlorodimethylsilane (0.071 g, 0.470 mmol). The resulting reaction mixture was stirred at room temperature for 18 h and then it was quenched with methanol and concentrated under reduced pressure. The crude residue was purified by column chromatography (Isco, 24 g cartridge) eluting with a gradient of ethyl acetate in dichloromethane (from 0 to 50%) to give the pure title compound (0.102 g, 86%). LC (Method A): 2.416 min. LCMS (APCI) calcd for $C_{15}H_{28}NO_2SSi$ [M+H]+ m/z 314.16, found 314.2. $^1$H NMR (CDCl$_3$, 400 MHz) δ ppm: 0.11 (s, 6H), 0.94 (s, 9H), 1.82-1.94 (m, 2H), 1.99-2.07 (m, 2H), 3.16-3.26 (m, 1H), 3.53 (td, J=2.5, 11.7 Hz, 2H), 4.02-4.09 (m, 2H), 4.84 (s, 2H), 7.06 (s, 1H).

95B. (5-Methyl-2-(tetrahydro-2H-pyran-4-yl)thiazol-4-yl)methanol

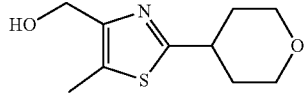

To a solution of 4-(((tert-butyldimethylsilyl)oxy)methyl)-2-(tetrahydro-2H-pyran-4-yl)thiazole (1.38 g, 4.40 mmol) in dry THF (50 mL), at −78° C. under nitrogen, was added n-BuLi (1.5 M in hexanes, 4.40 mL, 6.60 mmol) dropwise. The reaction mixture was stirred for 20 min at the same temperature before methyl iodide (0.826 mL, 13.20 mmol) was added. The resulting reaction mixture was then warmed to −20° C. over 2 h and then it was quenched with methanol and concentrated under reduced pressure. The crude residue obtained was dissolved in dichloromethane, washed with water and brine, dried (MgSO$_4$) and evaporated. The crude product (1.44 g, 100%) was used as such for the next step. LC (Method A): 2.648 min. LCMS (APCI): calcd for $C_{16}H_{30}NO_2SSi$ [M+H]+ m/z 328.18, found 328.2.

To a solution of 4-(((tert-butyldimethylsilyl)oxy)methyl)-5-methyl-2-(tetrahydro-2H-pyran-4-yl)thiazole (1.44 g, 4.40 mmol) in THF (30 mL) at room temperature was added TBAF (75% solution in water, 2.381 mL, 6.60 mmol) and the resulting mixture was stirred at room temperature for 2 h. Another equivalent of TBAF (75% solution in water, 1.587 mL, 4.40 mmol) was then added and stirring was continued for another 3 h at room temperature. The reaction mixture was quenched with water and the product was extracted with dichloromethane (3×). The combined organic extracts were washed with brine, dried over MgSO$_4$, filtered and concentrated. The crude residue obtained was purified by column chromatography (Isco, 40 g cartridge) eluting with a gradient of ethyl acetate in dichloromethane (0 to 100%) to give the title compound as a white solid (0.782 g, 83%). LC (Method A): 1.255 min. LCMS (APCI): calcd for $C_{10}H_{16}NO_2S$ [M+H]+ m/z 214.09, found 214.2. $^1$H NMR (DMSO-d$_6$, 400 MHz) δ ppm: 1.59-1.72 (m, 2H), 1.85-1.94 (m, 2H), 2.38 (s, 3H), 3.08-3.20 (m, 1H), 3.43 (td, J=1.6, 11.3 Hz, 2H), 3.87-3.93 (m, 2H), 4.42 (s, 2H), 4.98 (br s, 1H).

95C. 4-(Bromomethyl)-5-methyl-2-(tetrahydro-2H-pyran-4-yl)thiazole

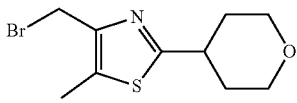

To a solution of (5-methyl-2-(tetrahydro-2H-pyran-4-yl)thiazol-4-yl)methanol (250 mg, 1.172 mmol) in dichloromethane (25 mL) cooled at 0° C., tribromophosphine (0.055 mL, 0.586 mmol) was added. After 5 min stirring, the cooling bath was removed and the solution was stirred at room temperature for 3 h. The reaction mixture was poured into a mixture of ethyl acetate and saturated aqueous sodium bicarbonate and the organic layer was washed with brine, dried over MgSO$_4$, filtered and concentrated. The crude residue obtained was purified by column chromatography (Isco, 12 g cartridge) eluting with a mixture of ethyl acetate in dichloromethane (1:1) to give the product as a white solid (0.285 g, 88%). LC (Method A): 1.828 min. LCMS (APCI): calcd for C$_{10}$H$_{15}$BrNOS [M+H]$^+$ m/z 276.01, found 276.0. $^1$H NMR (DMSO-d$_6$, 400 MHz) δ ppm: 1.58-1.72 (m, 2H), 1.87-1.96 (m, 2H), 2.39 (s, 3H), 3.10-3.22 (m, 1H), 3.43 (td, J=2.0, 11.3 Hz, 2H), 3.87-3.94 (m, 2H), 4.70 (s, 2H).

Example 95. 2-Methoxy-6-(6-methoxy-4-((5-methyl-2-(tetrahydro-2H-pyran-4-yl)thiazol-4-yl)methoxy)benzofuran-2-yl)imidazo[2,1-b][1,3,4]thiadiazole

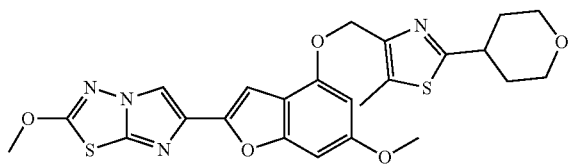 [SMILES: COc1cc(OCc2nc(C3CCOCC3)sc2C)c2cc(-c3cn4nc(OC)sc4n3)oc2c1]

To a solution of 6-methoxy-2-(2-methoxyimidazo[2,1-b][1,3,4]thiadiazol-6-yl)benzofuran-4-ol (Example 1H, 0.060 g, 0.189 mmol) and 4-(bromomethyl)-5-methyl-2-(tetrahydro-2H-pyran-4-yl)thiazole (0.055 g, 0.199 mmol) in DMF (5 mL) under nitrogen was added potassium carbonate (0.065 g, 0.473 mmol) and the resulting mixture was stirred at room temperature for 1.25 h. The crude reaction mixture was dissolved with dichloromethane, washed with water and brine, dried over MgSO$_4$, filtered and concentrated. The crude residue obtained was purified by column chromatography (Isco, 12 g cartridge) eluting with a gradient of ethyl acetate in dichloromethane (from 0 to 50%). The white solid obtained was triturated in acetonitrile to give the title compound as a white solid (0.050 g, 52%). LC (Method A): 2.348 min. LCMS(ESI): calcd for C$_{24}$H$_{25}$N$_4$O$_5$S$_2$ [M+H]$^+$ m/z 513.1266, found 513.1299. $^1$H NMR (DMSO-d$_6$, 400 MHz) δ ppm: 1.62-1.75 (m, 2H), 1.91-1.98 (m, 2H), 2.46 (s, 3H), 3.15-3.25 (m, 1H), 3.45 (td, J=1.6, 11.3 Hz, 2H), 3.81 (s, 3H), 3.87-3.94 (m, 2H), 4.20 (s, 3H), 5.19 (s, 2H), 6.64 (s, 1H), 6.83 (s, 1H), 6.89 (s, 1H), 8.37 (s, 1H).

Example 96

4-(4-(((6-Methoxy-2-(2-methoxyimidazo[2,1-b][1,3,4]thiadiazol-6-yl)benzofuran-4-yl)oxy)methyl)oxazol-2-yl)morpholine

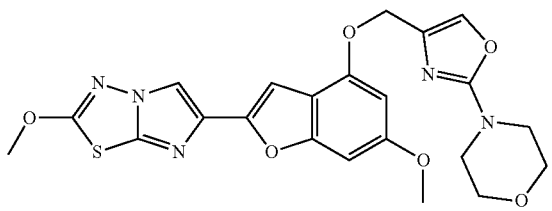 [SMILES: COc1cc(OCc2coc(N3CCOCC3)n2)c2cc(-c3cn4nc(OC)sc4n3)oc2c1]

96A. Ethyl 2-morpholinooxazole-4-carboxylate

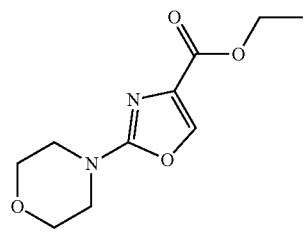 [SMILES: CCOC(=O)c1coc(N2CCOCC2)n1]

To a solution of morpholine (1.5 mL, 17.22 mmol) in dry THF (10 mL) was added ethyl 2-bromooxazole-4-carboxylate (1.00 g, 4.55 mmol). Then the mixture was heated at 95° C. for 18 h under N$_2$. The reaction mixture was concentrated under reduced pressure and the crude material was purified on the ISCO using a REDISEP® 24 g column (0 to 60% EtOAc-DCM) to give the title compound as a yellow oil (1.02 g, 99%). LCMS (APCI): calcd for C$_{10}$H$_{15}$N$_2$O$_4$ [M+H]$^+$ m/z 227.10, found 227.1. $^1$H NMR (CDCl$_3$, 400 MHz) δ ppm: 7.80 (s, 1H), 4.36 (q, J=7.0 Hz, 2H), 3.73-3.81 (m, 4H), 3.51-3.59 (m, 4H), 1.36 (t, J=7.1 Hz, 3H).

96B. (2-Morpholinooxazol-4-yl)methanol

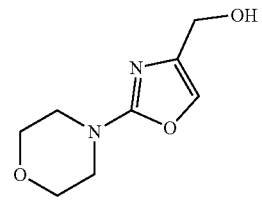 [SMILES: OCc1coc(N2CCOCC2)n1]

The compound was prepared from ethyl 2-morpholinooxazole-4-carboxylate (1.029 g, 4.55 mmol) by using the protocol described in Example 92B. The crude product mixture was purified on the ISCO using a REDISEP® Gold 12 g column (0 to 15% MeOH-DCM) to give the title compound as a white solid (0.354 g, 42%). LCMS (APCI): calcd for C$_8$H$_{13}$N$_2$O$_3$ [M+H]$^+$ m/z 185.09, found 185.1. $^1$H NMR (CDCl$_3$, 400 MHz) δ ppm: 7.18 (s, 1H), 4.48 (d, J=5.7 Hz, 2H), 3.73-3.82 (m, 4H), 3.44-3.54 (m, 4H), 2.65 (t, J=5.7 Hz, 1H).

Example 96. 4-(4-(((6-Methoxy-2-(2-methoxyimidazo[2,1-b][1,3,4]thiadiazol-6-yl)benzofuran-4-yl)oxy)methyl)oxazol-2-yl)morpholine

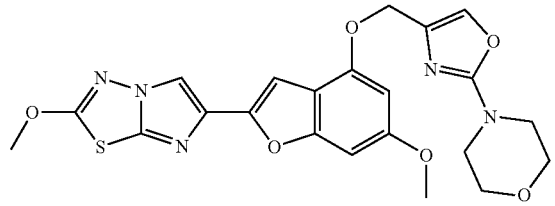 [SMILES: COc1cc(OCc2coc(N3CCOCC3)n2)c2cc(-c3cn4nc(OC)sc4n3)oc2c1]

The title compound was prepared according to the general procedure described for Example 86. The crude product was purified on the ISCO using a REDISEP® Gold 4 g column (0 to 80% EtOAc-DCM) and the obtained material was suspended in CH$_3$CN, sonicated, filtered and dried to give the title compound as a white solid (0.060 g, 56%). LC (Method C): 2.173 min. HRMS(ESI): calcd for C$_{22}$H$_{22}$N$_5$O$_6$S [M+H]$^+$ m/z 483.129, found 484.132. $^1$H NMR (CDCl$_3$, 400 MHz) δ ppm: 7.84 (s, 1H), 7.29 (s, 1H), 7.07 (s, 1H), 6.70 (s, 1H), 6.43 (d, J=1.6 Hz, 1H), 5.02 (s, 2H), 4.21 (s, 3H), 3.85 (s, 3H), 3.77-3.82 (m, 4H), 3.50-3.55 (m, 4H).

Example 97

4-(4-(((6-Methoxy-2-(2-methoxyimidazo[2,1-b][1,3,4]thiadiazol-6-yl)benzofuran-4-yl)oxy)methyl)-5-methyloxazol-2-yl)morpholine

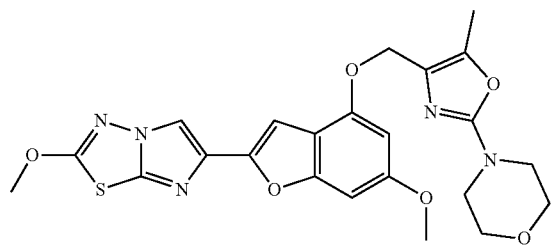 [SMILES: COc1cc(OCc2nc(N3CCOCC3)oc2C)c2cc(-c3cn4nc(OC)sc4n3)oc2c1]

97A. 4-(4(((tert-Butyldimethylsilyl)oxy)methyl)oxazol-2-yl)morpholine

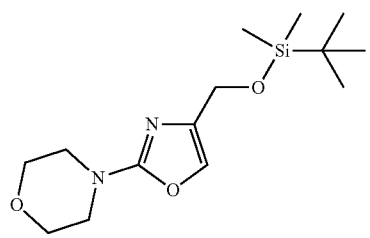 [SMILES: CC(C)(C)[Si](C)(C)OCc1coc(N2CCOCC2)n1]

The title compound was prepared from (2-morpholinooxazol-4-yl)methanol (0.250 g, 1.36 mmol) by using the protocol described for Example 92C. The crude product mixture was purified on the ISCO using a REDISEP® Gold 12 g column (0 to 15% MeOH-DCM) to give the title compound as a white solid (0.354 g, 42%). LCMS (APCI): calcd for C$_{14}$H$_{27}$N$_2$O$_3$Si [M+H]$^+$ m/z 299.17, found 299.2. $^1$H NMR (CDCl$_3$, 400 MHz) δ ppm: 7.11 (t, J=1.4 Hz, 1H), 4.57 (d, J=1.6 Hz, 2H), 3.74-3.81 (m, 4H), 3.44-3.50 (m, 4H), 0.91-0.95 (m, 9H), 0.12 (s, 6H).

97B. 4-(4-(((tert-Butyl(ethyl)(methyl)silyl)oxy)methyl)-5-methyloxazol-2-yl)morpholine

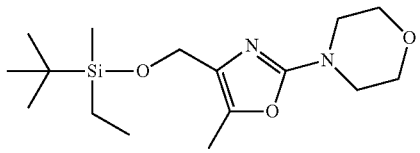 [SMILES: CC[Si](C)(OCc1nc(N2CCOCC2)oc1C)C(C)(C)C]

The title compound was prepared from 4-(4(((tert-butyldimethylsilyl)oxy)methyl)oxazol-2-yl)morpholine (0.296 g, 0.99 mmol) according to the protocol described in Example 93B. The crude product mixture was purified on the ISCO using a REDISEP® Gold 12 g column (0 to 60% EtOAc-DCM) to give the title compound as a colorless oil (0.127 g, 32%). LCMS (APCI): calcd for C$_{16}$H$_{31}$N$_2$O$_3$Si [M+H]$^+$ m/z 327.20, found 327.2. $^1$H NMR (CDCl$_3$, 400 MHz) δ ppm: 4.53 (s, 2H), 3.73-3.80 (m, 4H), 3.39-3.46 (m, 4H), 2.24 (d, J=0.8 Hz, 3H), 0.97-1.04 (m, 3H), 0.91-0.96 (m, 9H), 0.73 (s, 1H), 0.60 (s, 1H), 0.11 (s, 3H).

97C. (5-Methyl-2-morpholinooxazol-4-yl)methanol

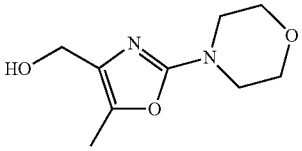

The title compound was prepared from 4-(4(((tert-butyl(ethyl)(methyl)silyl)oxy)methyl)-5-methyloxazol-2-yl)morpholine (0.124 g, 0.38 mmol) according to the protocol described in Example 93C. The crude product mixture was purified on the ISCO using a REDISEP® Gold 4 g column (0 to 15% MeOH-DCM) to give an oil which was dissolved in DCM (100 mL) and washed with 1N HCl (2×30 mL). The aqueous layer was basified with solid Na$_2$CO$_3$ to pH 8 and then it was back-extracted with DCM (5×20 mL). The combined organic phase was dried over MgSO$_4$, filtered and concentrated to give the desired product as the free base (0.035 g, 34%). LCMS (APCI): calcd for C$_9$H$_{15}$N$_2$O$_3$ [M+H]$^+$ m/z 199.11, found 199.1. $^1$H NMR (CDCl$_3$, 400 MHz) δ ppm: 4.42 (br s, 2H), 3.74-3.81 (m, 4H), 3.41-3.48 (m, 4H), 2.18-2.26 (m, 4H).

Example 97. 4-(4-(((6-Methoxy-2-(2-methoxyimidazo[2,1-b][1,3,4] thiadiazol-6-yl)benzofuran-4-yl)oxy)methyl)-5-methyloxazol-2-yl)morpholine

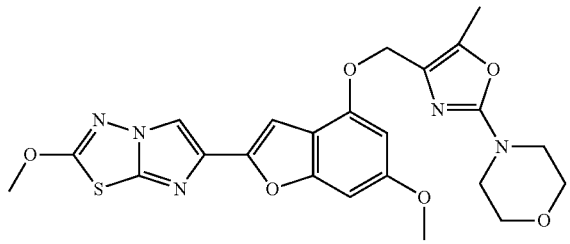 [SMILES: COc1cc(OCc2nc(N3CCOCC3)oc2C)c2cc(-c3cn4nc(OC)sc4n3)oc2c1]

6-Methoxy-2-(2-methoxyimidazo[2,1-b][1,3,4]thiadiazol-6-yl)benzofuran-4-ol (Example 1H, 0.042 g, 0.13 mmol) and (2-(8-oxa-3-azabicyclo[3.2.1]octan-3-yl)-5-methylthiazol-4-yl)methanol (0.026 g, 0.13 mmol) were reacted as described in Example 86. The reaction mixture was concentrated in vacuo and the residue was suspended in CH$_3$CN, sonicated and filtered. The resulting solid was purified on the ISCO using a REDISEP® Gold 4 g column (0 to 70% EtOAc-DCM) and the obtained material was suspended in CH$_3$CN, sonicated, filtered and dried to give the title compound as an off-white solid (0.022 g, 34%). LC (Method C): 2.126 min. LCMS (APCI): calcd for C$_{23}$H$_{24}$N$_5$O$_6$S [M+H]$^+$ m/z 498.14, found 498.1. $^1$H NMR (CDCl$_3$, 400 MHz) δ ppm: 7.84 (s, 1H), 7.05 (s, 1H), 6.70 (s, 1H), 6.45 (d, J=2.0 Hz, 1H), 4.95 (s, 2H), 4.21 (s, 3H), 3.85 (s, 3H), 3.77-3.81 (m, 4H), 3.45-3.50 (m, 4H), 2.28 (s, 3H).

Example 98

3-(4-(((6-Methoxy-2-(2-methoxyimidazo[2,1-b][1,3,4]thiadiazol-6-yl) benzofuran-4-yl)oxy)methyl)oxazol-2-yl)-8-oxa-3-azabicyclo[3.2.1]octane

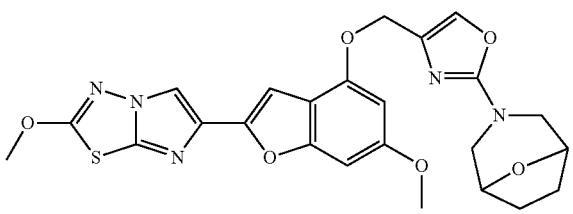 [SMILES: COc1cc(OCc2coc(N3CC4CCC(C3)O4)n2)c2cc(-c3cn4nc(OC)sc4n3)oc2c1]

98A. Ethyl 2-(8-oxa-3-azabicyclo[3.2.1]octan-3-yl)oxazole-4-carboxylate

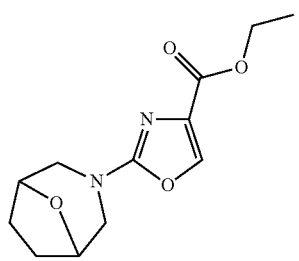 [SMILES: CCOC(=O)c1coc(N2CC3CCC(C2)O3)n1]

To a solution of 8-oxa-3-azabicyclo[3.2.1]octane (0.292 mL, 2.65 mmol) in THF (10 mL) was added ethyl 2-bromooxazole-4-carboxylate (0.583 g, 2.65 mmol) followed by DIEA (0.926 mL, 5.30 mmol). The mixture was heated to reflux for 18 h under N$_2$. The cooled reaction mixture was then concentrated under reduced pressure and the crude residue was purified on the ISCO using a REDISEP® 24 g column (0 to 45% EtOAc-DCM) to give the desired product as a pale yellow solid (0.592 g, 89%). LCMS (APCI): calcd for C$_{12}$H$_{17}$N$_2$O$_4$ [M+H]$^+$ m/z 253.11, found 253.1. $^1$H NMR (CDCl$_3$, 400 MHz) δ ppm: 7.78 (s, 1H), 4.43 (d, J=2.2 Hz, 2H), 4.35 (q, J=7.2 Hz, 2H), 3.66 (d, J=12.4 Hz, 2H), 3.34 (dd, J=12.3, 2.2 Hz, 2H), 1.92-2.04 (m, 2H), 1.84-1.92 (m, 2H), 1.36 (t, J=7.0 Hz, 3H).

98B. (2-(8-Oxa-3-azabicyclo[3.2.1]octan-3-yl)oxazol-4-yl)methanol

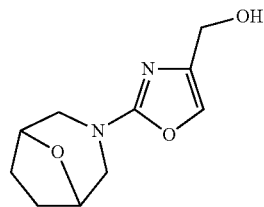 [SMILES: OCc1coc(N2CC3CCC(C2)O3)n1]

The title compound was prepared from ethyl 2-(8-oxa-3-azabicyclo[3.2.1]octan-3-yl)oxazole-4-carboxylate according to the method described in Example 92B. The crude product mixture was purified on the ISCO using a REDISEP® 4 g column (0 to 15% MeOH-DCM) and the obtained material was suspended in MeOH, sonicated, filtered and dried to give the desired product as a white solid (0.382 g, 77%). LCMS (APCI): calcd for C$_{10}$H$_{15}$N$_2$O$_3$ [M+H]$^+$ m/z 211.11, found 211.1. $^1$H NMR (CDCl$_3$, 400 MHz) δ ppm: 7.35 (s, 1H), 4.98 (t, J=5.5 Hz, 1H), 4.34-4.40 (m, 2H), 4.20 (d, J=5.5 Hz, 2H), 3.45 (d, J=12.1 Hz, 2H), 3.10 (dd, J=12.1, 2.3 Hz, 2H), 1.79-1.89 (m, 2H), 1.71-1.79 (m, 2H).

Example 98. 3-(4-(((6-Methoxy-2-(2-methoxyimidazo[2,1-b][1,3,4]thiadiazol-6-yl)benzofuran-4-yl)oxy)methyl)oxazol-2-yl)-8-oxa-3-azabicyclo[3.2.1]octane

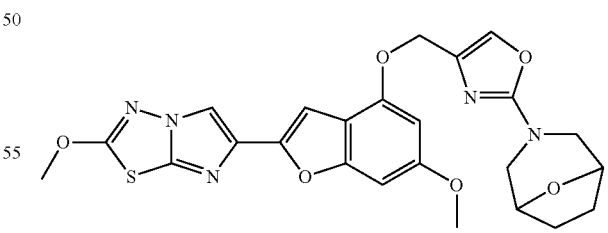

The title compound was prepared according to the procedure described for the synthesis of Example 92B. The crude product mixture was purified on the ISCO using a REDISEP® Gold 12 g column (0 to 80% EtOAc-DCM) and the obtained material was suspended again in CH$_3$CN, sonicated, filtered and dried to give the title compound as a white solid (0.046 g, 41%). LC (Method C): 2.218 min. LCMS (APCI): calcd for C$_{24}$H$_{24}$N$_5$O$_6$S [M+H]$^+$ m/z 510.15, found 510.2. $^1$H NMR (DMSO-d$_6$, 400 MHz) δ ppm: 8.30 (s, 1H), 7.66 (s, 1H), 6.87 (s, 1H), 6.75 (s, 1H), 6.52 (d, J=1.6 Hz, 1H), 4.89 (s, 2H), 4.32 (br s, 2H), 4.14 (s, 3H), 3.74 (s, 3H), 3.43 (d, J=12.1 Hz, 2H), 3.09 (dd, J=12.1, 2.0 Hz, 2H), 1.74-1.84 (m, 2H), 1.66-1.74 (m, 2H).

Example 99 tert-Butyl 4-(4-(((6-methoxy-2-(2-methoxyimidazo [2,1-b][1,3,4] thiadiazol-6-yl)benzofuran-4-yl)oxy) methyl)thiazol-2-yl)piperazine-1-carboxylate

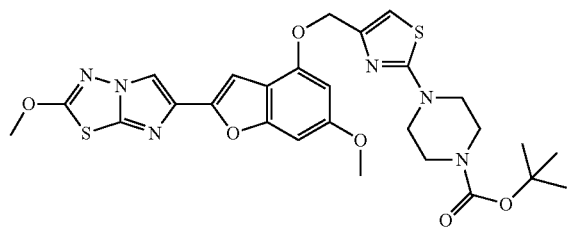 [SMILES: COc1cc(OCc2csc(N3CCN(C(=O)OC(C)(C)C)CC3)n2)c2cc(-c3cn4nc(OC)sc4n3)oc2c1]

99A. Methyl 2-(4-(tert-butoxycarbonyl)piperazin-1-yl)thiazole-4-carboxylate

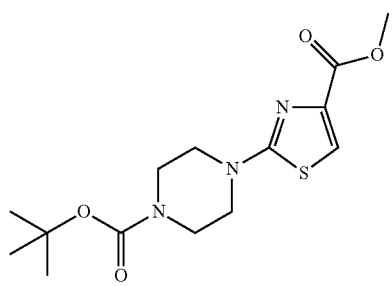 [SMILES: COC(=O)c1csc(N2CCN(C(=O)OC(C)(C)C)CC2)n1]

To a solution of tert-butyl piperazine-1-carboxylate (3.77 g, 20.26 mmol) in MeOH (40 mL) was added methyl 2-bromothiazole-4-carboxylate (1.50 g, 6.75 mmol), followed by DIEA (6.25 mL, 35.8 mmol). The mixture was then heated to reflux for 18 h under N$_2$. The cooled mixture was then concentrated under reduced pressure and the residue was purified on the ISCO using a REDISEP® 40 g column (0 to 30% EtOAc-DCM) to give the product as a cream solid (0.579 g, 26%). LCMS (APCI): calcd for C$_{14}$H$_{22}$N$_3$O$_4$S [M+H]$^+$ m/z 328.13, found 328.2. $^1$H NMR (CDCl$_3$, 400 MHz) δ ppm: 7.50 (s, 1H), 3.90 (s, 3H), 3.55 (br s, 8H), 1.47-1.51 (m, 9H).

99B. Methyl 2-(4-(tert-butoxycarbonyl)piperazin-1-yl)thiazole-4-carboxylate

The compound was prepared according to the procedure described in Example 92. The crude product was purified on the ISCO using a REDISEP® 24 g column (0 to 20% MeOH-DCM) to give the title compound as a white foam (0.494 g, 93%). LCMS (APCI): calcd for C$_{13}$H$_{22}$N$_3$O$_3$S [M+H]$^+$ m/z 300.13, found 300.1. $^1$H NMR (CDCl$_3$, 400 MHz) δ ppm: 6.45 (s, 1H), 4.56 (br s, 2H), 3.53-3.61 (m, 4H), 3.49 (br s, 4H), 3.35-3.44 (m, 1H), 1.49 (s, 9H).

Example 99. tert-Butyl 4-(4-(((6-methoxy-2-(2-methoxyimidazo[2,1-b][1,3,4] thiadiazol-6-yl)benzofuran-4-yl)oxy)methyl)thiazol-2-yl)piperazine-1-carboxylate

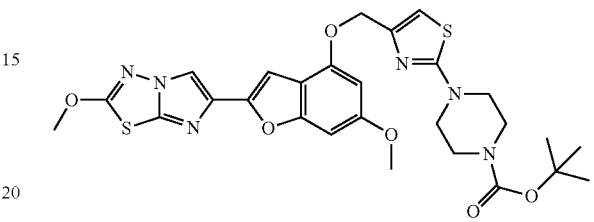

The title compound was prepared according to the procedure described in Example 86 and was isolated as an off-white solid (0.339 g, 38%). LC (Method C): 1.602 min. HRMS(ESI): calcd for C$_{27}$H$_{31}$N$_6$O$_6$S$_2$ [M+H]$^+$ m/z 599.175, found 599.177. $^1$H NMR (CDCl$_3$, 400 MHz) δ ppm: 7.85 (s, 1H), 7.10 (s, 1H), 6.70 (s, 1H), 6.64 (s, 1H), 6.44 (d, J=2.0 Hz, 1H), 5.16 (s, 2H), 4.21 (s, 3H), 3.85 (s, 3H), 3.59 (d, J=5.5 Hz, 4H), 3.55 (br s, 4H), 1.49 (s, 9H).

Example 100

2-Methoxy-6-(6-methoxy-4-((2-(4-(methylsulfonyl) piperazin-1-yl) thiazol-4-yl)methoxy)benzofuran-2-yl)imidazo[2,1-b][1,3,4]thiadiazole

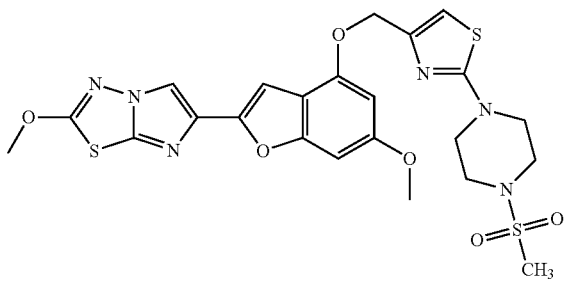

100A. Methyl 2-(4-(methylsulfonyl)piperazin-1-yl) thiazole-4-carboxylate

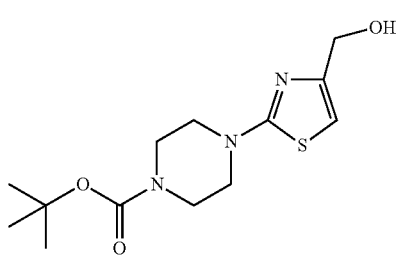 [SMILES: CC(C)(C)OC(=O)N1CCN(c2nc(CO)cs2)CC1]

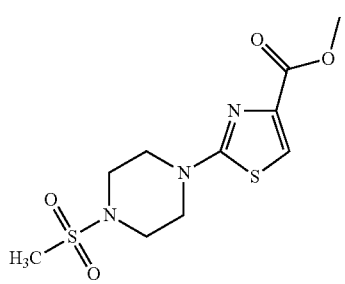

To a solution of methyl 2-(4-(tert-butoxycarbonyl)piperazin-1-yl)thiazole-4-carboxylate (0.20 g, 0.61 mmol) in DCM (5 mL) was added trifluoroacetic acid (2 mL, 26 mmol). The resulting mixture was stirred at room temperature for 3 h and then it was concentrated under reduced pressure and the crude residue used as such in the next step. The resulting methyl 2-(piperazin-1-yl)thiazole-4-carboxylate TFA salt (0.32 g, 0.94 mmol) was dissolved in DCM (10 mL), treated with triethylamine (1.10 mL, 7.92 mmol) and stirred at 25° C. for 5 min. The mixture was then cooled at 0° C. and methanesulfonyl chloride (0.10 mL, 1.29 mmol) was added and the mixture was stirred at 0° C. for 4 h before being allowed to stir overnight at 25° C. The reaction mixture was then diluted with DCM and washed with saturated aqueous NaHCO$_3$ and brine, dried over MgSO$_4$ and evaporated. The residue was purified on the ISCO using a REDISEP® 24 g column (0 to 35% EtOAc-DCM) to give the desired product as a white solid (0.281, 98%). LCMS (APCI): calcd for C$_{10}$H$_{16}$N$_3$O$_4$S$_2$ [M+H]$^+$ m/z 306.06, found 306.1. $^1$H NMR (CDCl$_3$, 400 MHz) δ ppm: 7.49-7.53 (m, 1H), 3.85-3.91 (m, 3H), 3.63-3.72 (m, 4H), 3.30-3.39 (m, 4H), 2.80 (s, 3H).

100B. (2-(4-(Methylsulfonyl)piperazin-1-yl)thiazol-4-yl)methanol

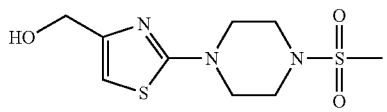

The compound was prepared according to the procedure described in Example 92B. The crude product was purified on the ISCO using a REDISEP® 24 g column (0 to 20% MeOH-DCM) to give the title compound as a white foam (0.215 g, 84%). LCMS (APCI): calcd for C$_9$H$_{16}$N$_3$O$_3$S$_2$ [M+H]$^+$ m/z 278.06, found 278.1. $^1$H NMR (CDCl$_3$, 400 MHz) δ ppm: 6.50 (s, 1H), 4.59 (s, 2H), 3.80 (br s, 3H), 3.55-3.69 (m, 1H), 3.39-3.48 (m, 4H), 3.33-3.39 (m, 1H), 2.80-2.88 (m, 3H).

Example 100. 2-Methoxy-6-(6-methoxy-4-((2-(4-(methylsulfonyl)piperazin-1-yl) thiazol-4-yl)methoxy)benzofuran-2-yl)imidazo[2,1-b][1,3,4]thiadiazole

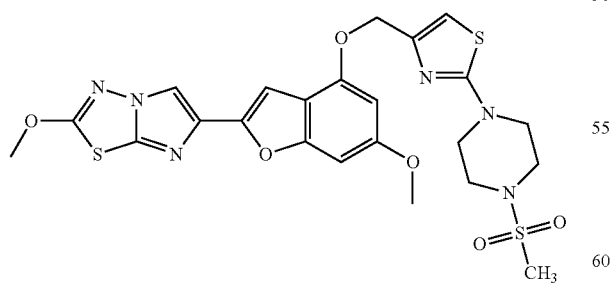

The title compound was prepared and purified according to the method described in Example 86 and was isolated as an off-white solid (0.038 g, 30%). LC (Method C): 2.225 min. HRMS(ESI): calcd for C$_{23}$H$_{25}$N$_6$O$_6$S$_3$ [M+H]$^+$ m/z 577.0998, found 577.1017. $^1$H NMR (CDCl$_3$, 400 MHz) δ ppm: 8.37 (s, 1H), 7.00 (s, 1H), 6.98 (s, 1H), 6.82 (d, J=0.8 Hz, 1H), 6.57 (d, J=1.6 Hz, 1H), 5.07 (s, 2H), 4.20 (s, 3H), 3.80 (s, 3H), 3.51-3.58 (m, 4H), 3.21-3.28 (m, 4H), 2.92 (s, 3H).

Example 101

4-((4-(4-(((6-Methoxy-2-(2-methoxyimidazo[2,1-b][1,3,4]thiadiazol-6-yl)benzofuran-4-yl)oxy)methyl)thiazol-2-yl)piperazin-1-yl)sulfonyl)benzonitrile

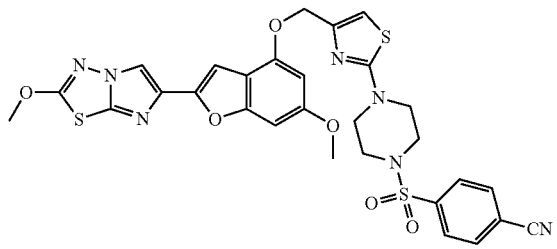 [SMILES: COc1cc(OCc2csc(N3CCN(S(=O)(=O)c4ccc(C#N)cc4)CC3)n2)c2cc(-c3cn4nc(OC)sc4n3)oc2c1]

101A. Methyl 2-(4-((4-cyanophenyl)sulfonyl)piperazin-1-yl)thiazole-4-carboxylate

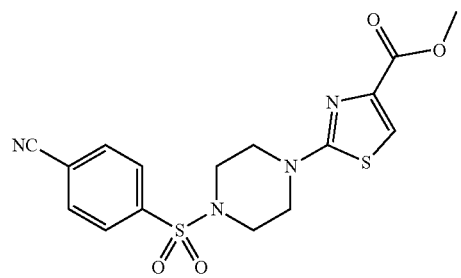 [SMILES: COC(=O)c1csc(N2CCN(S(=O)(=O)c3ccc(C#N)cc3)CC2)n1]

The compound was prepared according to the procedure described in Example 100A above. The crude product was purified on the ISCO using a REDISEP® 24 g column (0 to 40% EtOAc-DCM) to give the desired product as a white solid (0.222 g, 93%). LCMS (APCI): calcd for C$_{16}$H$_{17}$N$_4$O$_4$S$_2$ [M+H]$^+$ m/z 393.07, found 393.1. $^1$H NMR (CDCl$_3$, 400 MHz) δ ppm: 7.83-7.93 (m, 4H), 7.50 (s, 1H), 3.87-3.91 (m, 3H), 3.66-3.73 (m, 3H), 3.57-3.62 (m, 1H), 3.16-3.25 (m, 4H).

101B. 4-((4-(4-(hydroxymethyl)thiazol-2-yl)piperazin-1-yl)sulfonyl)benzonitrile

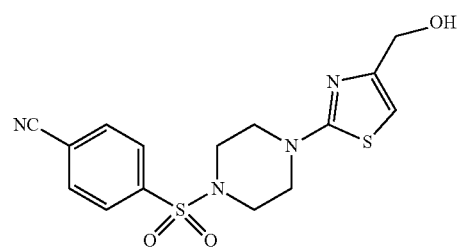 [SMILES: N#Cc1ccc(S(=O)(=O)N2CCN(c3nc(CO)cs3)CC2)cc1]

The compound was prepared according to the procedure described in Example 92B. The crude product was purified on the ISCO using a REDISEP® 24 g column (0 to 15% MeOH-DCM) to give the desired product as a white solid (0.103 g, 50%). LCMS (APCI): calcd for $C_{15}H_{17}N_4O_3S_2$ [M+H]$^+$ m/z 365.06, found 365.1. $^1$H NMR (CDCl$_3$, 400 MHz) δ ppm: 7.83-7.95 (m, 4H), 6.47 (s, 1H), 4.56 (s, 2H), 3.84 (br s, 3H), 3.54-3.67 (m, 1H), 3.23-3.31 (m, 3H), 3.15-3.22 (m, 1H).

Example 101. 4-((4-(4-(((6-Methoxy-2-(2-methoxy-imidazo[2,1-b][1,3,4] thiadiazol-6-yl)benzofuran-4-yl)oxy)methyl)thiazol-2-yl)piperazin-1 yl)sulfonyl)benzonitrile

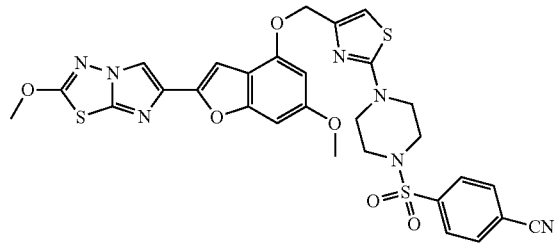 [SMILES: COc1cc(OCc2csc(N3CCN(S(=O)(=O)c4ccc(C#N)cc4)CC3)n2)c2cc(-c3cn4nc(OC)sc4n3)oc2c1]

The title compound was prepared according to the procedure described in Example 86. The crude product was purified on the ISCO using a REDISEP® 4 g column (0 to 60% EtOAc-DCM) to give the title compound as a cream solid (0.051 g, 41%). LC (Method C): 2.339 min. HRMS (ESI): calcd for $C_{29}H_{26}N_7O_6S_3$ [M+H]$^+$ m/z 664.1107, found 664.1118. $^1$H NMR (CDCl$_3$, 400 MHz) δ ppm: 7.83-7.94 (m, 5H), 7.20 (s, 1H), 6.69 (s, 2H), 6.42 (d, J=2.0 Hz, 1H), 5.18 (s, 2H), 4.25 (s, 3H), 3.84 (s, 3H), 3.81 (br s, 4H), 3.23-3.30 (m, 4H).

Example 102

6-(4-((2-(4-(Isopropylsulfonyl)piperazin-1-yl)thi-azol-4-yl)methoxy)-6-methoxybenzo-furan-2-yl)-2-methoxyimidazo[2,1-b][1,3,4]thiadiazole

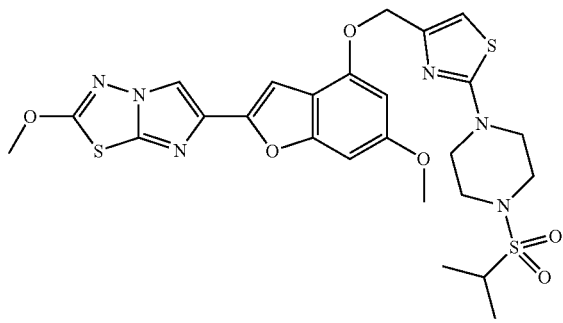 [SMILES: COc1cc(OCc2csc(N3CCN(S(=O)(=O)C(C)C)CC3)n2)c2cc(-c3cn4nc(OC)sc4n3)oc2c1]

102A. Methyl 2-(4-(isopropylsulfonyl)piperazin-1-yl)thiazole-4-carboxylate

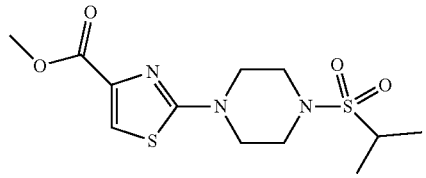 [SMILES: COC(=O)c1csc(N2CCN(S(=O)(=O)C(C)C)CC2)n1]

The compound was prepared according to the procedure described in Example 100A. The crude product was purified on the ISCO using a REDISEP® 24 g column (0 to 55% EtOAc-DCM) to give the desired product as a white solid (0.080 g, 56%). LCMS (APCI): calcd for $C_{12}H_{20}N_3O_4S_2$ [M+H]$^+$ m/z 334.08, found 334.1. $^1$H NMR (CDCl$_3$, 400 MHz) δ ppm: 7.53 (s, 1H), 3.89-3.94 (m, 3H), 3.64-3.70 (m, 3H), 3.46-3.58 (m, 5H), 3.17-3.27 (m, 1H), 1.37 (d, J=7.0 Hz, 6H).

102B. (2-(4-(Isopropylsulfonyl)piperazin-1-yl)thi-azol-4-yl)methanol

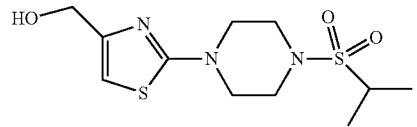

The compound was prepared according to the procedure described in Example 92B. The crude product was purified on the ISCO using a REDISEP® 4 g column (0 to 15% MeOH-DCM) to give the desired product as a white foam (0.070 g, 96%). LCMS (APCI): calcd for $C_{11}H_{20}N_3O_3S_2$ [M+H]$^+$ m/z 306.09, found 306.1. $^1$H NMR (CDCl$_3$, 400 MHz) δ ppm: 6.49 (s, 1H), 4.61 (s, 1H), 4.53 (s, 1H), 3.81 (br s, 3H), 3.46-3.63 (m, 5H), 3.15-3.29 (m, 1H), 1.61 (br s, 1H), 1.37 (d, J=6.7 Hz, 6H).

Example 102. 6-(4-((2-(4-(Isopropylsulfonyl)piper-azin-1-yl)thiazol-4-yl) methoxy)-6-methoxybenzo-furan-2-yl)-2-methoxyimidazo[2,1-b][1,3,4]thiadiaz-ole

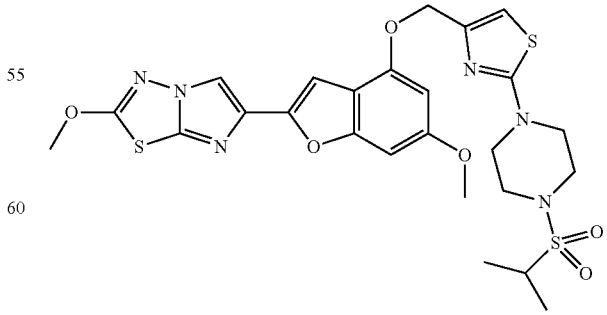

The title compound was prepared according to the procedure described in Example 86. The crude product was purified on the ISCO using a REDISEP® 4 g column (0 to 60% EtOAc-DCM) to give title compound as a cream solid (0.082 g, 71%). LC (Method C): 2.266 min. HRMS(ESI): calcd for $C_{25}H_{29}N_6O_6S_3$ [M+H]⁺ m/z 605.1311, found 605.1327. ¹H NMR (CDCl₃, 400 MHz) δ ppm: 8.36 (s, 1H), 6.98 (d, J=3.5 Hz, 2H), 6.80-6.84 (m, 1H), 6.56 (d, J=2.0 Hz, 1H), 5.06 (s, 2H), 4.20 (s, 3H), 3.79 (s, 3H), 3.45-3.50 (m, 4H), 3.36-3.39 (m, 4H), 3.29 (s, 1H), 1.23 (d, J=6.7 Hz, 6H).

Example 103

8-(4-(((6-Methoxy-2-(2-methoxyimidazo[2,1-b][1,3,4]thiadiazol-6-yl) benzofuran-4-yl)oxy)methyl)thiazol-2-yl)-1,4-dioxa-8-azaspiro[4.5]decane

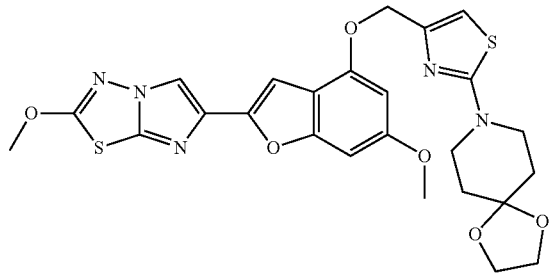 [SMILES: COc1cc(OCc2csc(N3CCC4(CC3)OCCO4)n2)c2cc(-c3cn4nc(OC)sc4n3)oc2c1]

103A. Methyl 2-(1,4-dioxa-8-azaspiro[4.5]decan-8-yl)thiazole-4-carboxylate

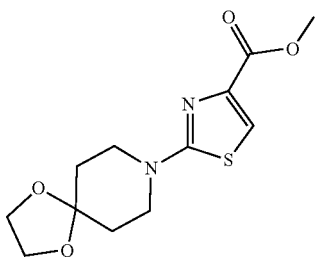 [SMILES: COC(=O)c1csc(N2CCC3(CC2)OCCO3)n1]

The compound was prepared according to the procedure described in Example 92A. The crude product was purified on the ISCO using a REDISEP® 24 g column (0 to 55% EtOAc-DCM) to give the desired product as a colorless oil (0.416 g, 65%). LCMS (APCI): calcd for $C_{12}H_{17}N_2O_4S$ [M+H]⁺ m/z 285.09, found 285.1. ¹H NMR (CDCl₃, 400 MHz) δ ppm: 7.46 (s, 1H), 4.00 (s, 4H), 3.89 (s, 3H), 3.64-3.73 (m, 4H), 1.77-1.86 (m, 4H).

103B. (2-(1,4-Dioxa-8-azaspiro[4.5]decan-8-yl)thiazol-4-yl)methanol

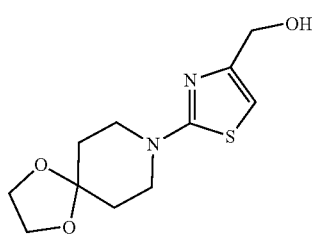 [SMILES: OCc1csc(N2CCC3(CC2)OCCO3)n1]

The compound was prepared according to the procedure described in Example 92B. The crude product was purified on the ISCO using a REDISEP® 4 g column (0 to 15% MeOH-DCM) to give the desired product as a colorless oil (0.124 g, 69%). LCMS (APCI): calcd for $C_{11}H_{17}N_2O_3S$ [M+H]⁺ m/z 257.10, found 257.1. ¹H NMR (CDCl₃, 400 MHz) δ ppm: 6.39 (s, 1H), 4.55 (br s, 2H), 3.99-4.02 (m, 5H), 3.65-3.73 (m, 4H), 1.81-1.88 (m, 4H).

Example 103. 8-(4-(((6-Methoxy-2-(2-methoxyimidazo[2,1-b][1,3,4]thiadiazol-6-yl)benzofuran-4-yl)oxy)methyl)thiazol-2-yl)-1,4-dioxa-8-azaspiro[4.5]decane

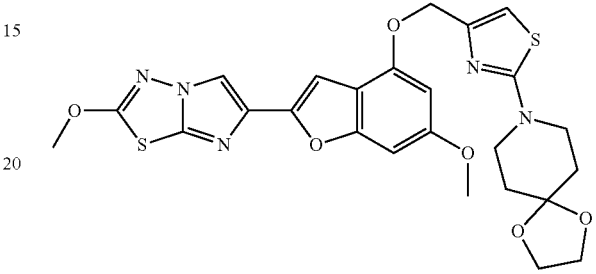

The title compound was prepared according to the procedure described in Example 86. The crude product was purified on the ISCO using a REDISEP® 4 g (0 to 50% EtOAc-DCM) to give the title compound as a cream solid (0.083 g, 38%). LC (Method C): 2.395 min. HRMS(ESI): calcd for $C_{25}H_{26}N_5O_6S_2$ [M+H]⁺ m/z 556.1325, found 556.1352. ¹H NMR (CDCl₃, 400 MHz) δ ppm: 7.85 (s, 1H), 7.09 (s, 1H), 6.68-6.73 (m, 1H), 6.60 (s, 1H), 6.46 (d, J=2.0 Hz, 1H), 5.25 (br s, 2H), 4.21 (s, 3H), 4.01 (s, 4H), 3.83-3.86 (m, 3H), 3.78 (br. s., 3H), 1.84-1.92 (m, 4H).

Example 104

6-(4-(((6-Methoxy-2-(2-methoxyimidazo[2,1-b][1,3,4]thiadiazol-6-yl) benzofuran-4-yl)oxy)methyl)thiazol-2-yl)-2-oxa-6-azaspiro[3.3]heptane

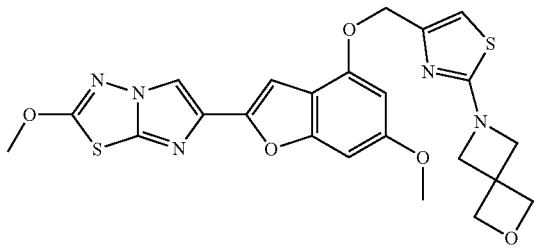 [SMILES: COc1cc(OCc2csc(N3CC4(COC4)C3)n2)c2cc(-c3cn4nc(OC)sc4n3)oc2c1]

104A. Methyl 2-(2-oxa-6-azaspiro[3.3]heptan-6-yl)thiazole-4-carboxylate

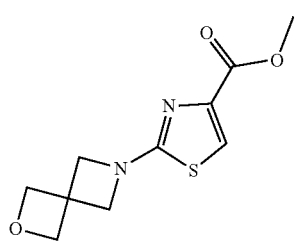 [SMILES: COC(=O)c1csc(N2CC3(COC3)C2)n1]

The compound was prepared according to the procedure described in Example 92A. The crude product was purified on the ISCO using a REDISEP® 24 g column (0 to 100% EtOAc-DCM) to give the desired product as a white solid (0.145 g, 34%). LCMS (APCI): calcd for $C_{10}H_{13}N_2O_3S$ [M+H]$^+$ m/z 241.06, found 241.1. $^1$H NMR (CDCl$_3$, 400 MHz) δ ppm: 7.51 (s, 1H), 4.85 (s, 4H), 4.30 (s, 4H), 3.90 (s, 3H).

104B. (2-(2-Oxa-6-azaspiro[3.3]heptan-6-yl)thiazol-4-yl)methanol

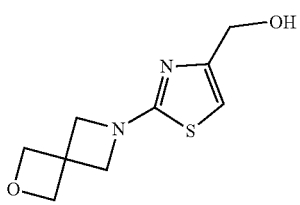 [SMILES: OCc1csc(N2CC3(COC3)C2)n1]

The compound was prepared according to the procedure described in Example 92B. The reaction mixture was quenched with MeOH (10 mL) and stirred at room temperature for 10 min. Then the mixture was concentrated under reduced pressure, dissolved in DCM and washed with aqueous NaHCO$_3$, water and brine, dried over MgSO$_4$ and evaporated. The product was isolated as a white gum (0.053 g, 41%). $^1$H NMR (CDCl$_3$, 400 MHz) δ ppm: 6.45-6.47 (m, 1H), 4.85-4.86 (m, 4H), 4.56 (d, J=6.1 Hz, 2H), 4.24 (s, 4H), 2.11 (t, J=6.1 Hz, 1H).

Example 104. 6-(4-(((6-Methoxy-2-(2-methoxyimidazo[2,1-b][1,3,4]thiadiazol-6-yl)benzofuran-4-yl)oxy)methyl)thiazol-2-yl)-2-oxa-6-azaspiro[3.3]heptane

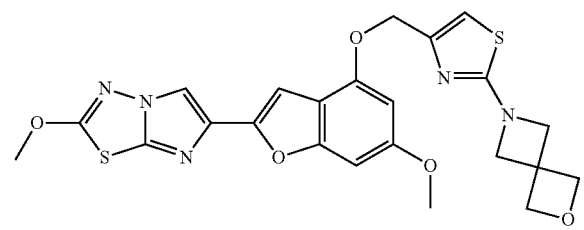 [SMILES: COc1cc(OCc2csc(N3CC4(COC4)C3)n2)c2cc(-c3cn4nc(OC)sc4n3)oc2c1]

The title compound was prepared according to the procedure described in Example 86. The crude product was purified on the ISCO using a REDISEP® 4 g column (0 to 100% EtOAc-DCM) to give the title compound as a white solid (0.070 g, 62%). LC (Method C): 2.081 min. HRMS (ESI): calcd for $C_{23}H_{22}N_5O_5S_2$ [M+H]$^+$ m/z 512.1062, found 512.1067. $^1$H NMR (CDCl$_3$, 400 MHz) δ ppm: 7.85 (s, 1H), 7.09 (s, 1H), 6.70 (s, 1H), 6.63 (s, 1H), 6.41 (d, J=2.0 Hz, 1H), 5.12 (s, 2H), 4.87 (s, 4H), 4.27 (s, 4H), 4.22 (s, 3H), 3.84 (s, 3H).

Example 105

4-(5-Ethyl-4-(((6-methoxy-2-(2-methoxyimidazo[2,1-b][1,3,4] thiadiazol-6-yl)benzofuran-4-yl)oxy)methyl)thiazol-2-yl)morpholine

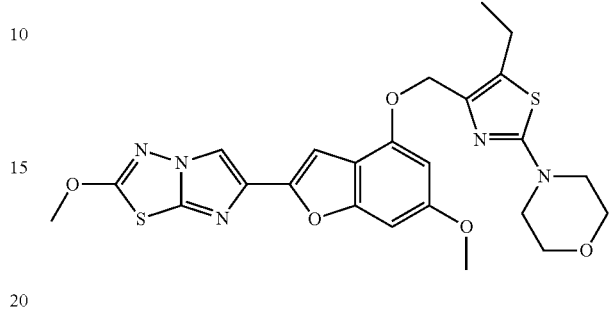

105A. Methyl 5-ethyl-2-morpholinothiazole-4-carboxylate

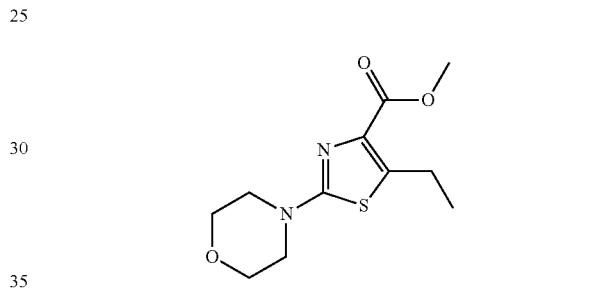

The compound was prepared according to the procedure described in Example 92A. The crude product was purified on the ISCO using a REDISEP® 12 g column (0 to 50% EtOAc-DCM) to give the desired product as a white solid (0.349 g, 68%). LCMS (APCI): calcd for $C_{11}H_{17}N_2O_3S$ [M+H]$^+$ m/z 257.09, found 257.1. $^1$H NMR (CDCl$_3$, 400 MHz) δ ppm: 3.88 (s, 3H), 3.75-3.85 (m, 4H), 3.41-3.50 (m, 4H), 3.14 (q, J=7.6 Hz, 2H), 1.27 (t, J=7.4 Hz, 3H).

105B. (5-Ethyl-2-morpholinothiazol-4-yl)methanol

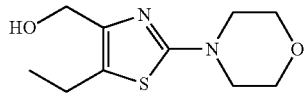

The compound was prepared according to the procedure described in Example 92B. The reaction mixture was quenched with MeOH (10 mL) and stirred at room temperature for 10 min. Then the mixture was concentrated under reduced pressure, diluted with DCM, washed with NaHCO$_3$, water and brine, dried over MgSO$_4$ and evaporated. The residue was purified on the ISCO using a REDISEP® 12 g column (0 to 15% MeOH-DCM) to give the desired product as a white solid (0.235 g, 76%). LCMS (APCI): calcd for $C_{10}H_{17}N_2O_2S$ [M+H]$^+$ l229.10, found 229.1. $^1$H NMR (CDCl$_3$, 400 MHz) δ ppm: 4.48 (d, J=5.9 Hz, 2H), 3.77-3.85 (m, 4H), 3.37-3.46 (m, 4H), 2.68 (q, J=7.4 Hz, 2H), 2.25 (t, J=5.9 Hz, 1H), 1.22 (t, J=7.4 Hz, 3H).

Example 105. 4-(5-Ethyl-4-(((6-methoxy-2-(2-methoxyimidazo[2,1-b][1,3,4] thiadiazol-6-yl)benzofuran-4-yl)oxy)methyl)thiazol-2-yl)morpholine

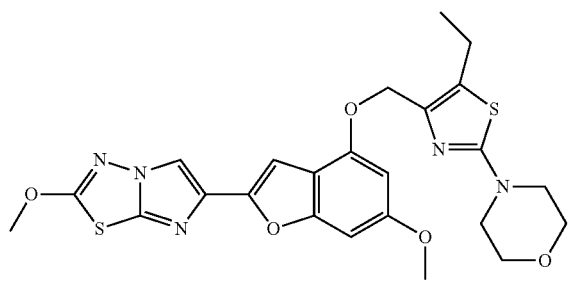 [SMILES: CCc1sc(N2CCOCC2)nc1COc1cc(OC)cc2oc(-c3cn4nc(OC)sc4n3)cc12]

The title compound was prepared according to the procedure described for the synthesis of Example 86. The crude product was purified on the ISCO using a REDISEP® 4 g column (0 to 60% EtOAc-DCM) and the obtained solid was suspended in CH$_3$CN, sonicated, filtered and dried to give the title compound as an off-white solid (0.086 g, 74%). LC (Method C): 2.263 min. HRMS(ESI): calcd for C$_{24}$H$_{26}$N$_5$O$_5$S$_2$ [M+H]$^+$ m/z 528.1375, found 528.1374. $^1$H NMR (CDCl$_3$, 400 MHz) δ ppm: 7.83 (s, 1H), 7.04 (s, 1H), 6.69 (dd, J=2.0, 0.8 Hz, 1H), 6.52 (d, J=2.0 Hz, 1H), 5.05 (s, 2H), 4.21 (s, 3H), 3.85 (s, 3H), 3.79-3.84 (m, 4H), 3.42-3.47 (m, 4H), 2.78 (q, J=7.6 Hz, 2H), 1.23 (t, J=7.6 Hz, 3H).

Example 106

3-((4-(((6-Methoxy-2-(2-methoxyimidazo[2,1-b][1,3,4]thiadiazol-6-yl)benzofuran-4-yl)oxy)methyl)thiazol-2-yl)(methyl)amino)propanenitrile

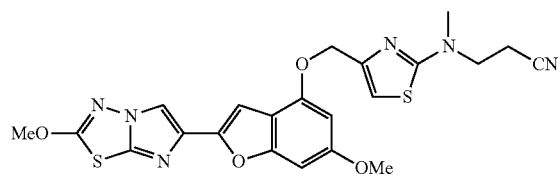 [SMILES: COc1cc(OCc2csc(N(C)CCC#N)n2)c2cc(-c3cn4nc(OC)sc4n3)oc2c1]

106A. Methyl 2-((2-cyanoethyl)(methyl)amino)thiazole-4-carboxylate

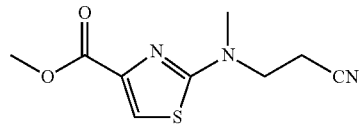

In a sealable tube, a solution of methyl 2-bromothiazole-4-carboxylate (0.500 g, 2.252 mmol) and 3-(methylamino)propanenitrile (0.176 mL, 1.876 mmol) in dioxane (8 mL) was treated with cesium carbonate (0.611 g, 1.876 mmol), palladium(II) acetate (0.021 g, 0.094 mmol) and Xantphos (0.065 g, 0.113 mmol). The system was purged with nitrogen for 5 min and then the tube was sealed and the mixture heated at 100° C. for 16 h. The cooled reaction mixture was then partitioned between ethyl acetate and saturated aqueous sodium bicarbonate. The organic phase was washed with brine, dried over anhydrous magnesium sulfate and concentrated in vacuo. The residue obtained was chromatographed on silica gel (ISCO, elution gradient of methanol in dichloromethane) to give 0.300 g (59%) of the title compound. LC (Method B): 1.927 min. LCMS (APCI): calcd for C$_9$H$_{12}$N$_3$O$_2$S [M+H]$^+$ m/z 226.07; found 226.0.

106B. 3-((4-(Hydroxymethyl)thiazol-2-yl)(methyl)amino)propanenitrile

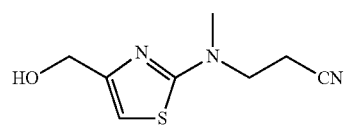

A solution of methyl 2-((2-cyanoethyl)(methyl)amino)thiazole-4-carboxylate (0.300 g, 1.332 mmol) in ethanol (5 mL) at 0° C. was treated with sodium borohydride (0.151 g, 4.00 mmol), followed by calcium chloride (0.177 g, 1.598 mmol) and then stirred at room temperature for 4 h. The reaction mixture was then partitioned between ethyl acetate and saturated aqueous sodium bicarbonate, the organic phase was separated, washed with brine, dried over anhydrous magnesium sulfate and concentrated in vacuo. The residue obtained was chromatographed on silica gel (ISCO, elution gradient of ethyl acetate in dichloromethane) to give 0.048 g (18%) of the title material as an oil which crystallized on standing to give a white solid. LC (Method B): 1.376 min. LCMS (APCI): calcd for C$_8$H$_{12}$N$_3$OS [M+H]$^+$ m/z 198.07; found 198.0. $^1$H NMR (400 MHz, CDCl$_3$) δ ppm: 6.43 (s, 1H), 4.52 (s, 2H), 3.80 (t, J=6.55 Hz, 2H), 3.18 (br s, 1H), 3.15 (s, 3H), 2.73 (t, J=6.55 Hz, 2H).

Example 106. 3-((4-(((6-Methoxy-2-(2-methoxyimidazo[2,1-b][1,3,4]thiadiazol-6-yl)benzofuran-4-yl)oxy)methyl)thiazol-2-yl)(methyl)amino)propanenitrile

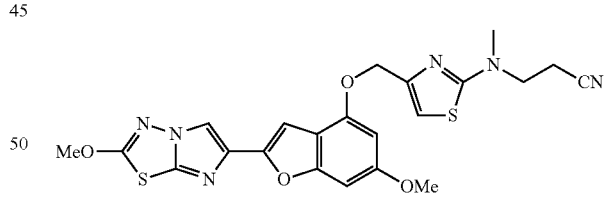

A mixture of 6-methoxy-2-(2-methoxyimidazo[2,1-b][1,3,4]thiadiazol-6-yl)benzofuran-4-ol (Example 1H, 0.064 g, 0.203 mmol) and 3-((4-(hydroxymethyl)thiazol-2-yl)(methyl)-amino)propanenitrile (0.048 g, 0.243 mmol) in dry THF (3.5 mL) under nitrogen was treated at 22° C. with tri-n-butylphosphine (0.132 mL, 0.507 mmol), followed by a solution of 1,1'-(azodicarbonyl)dipiperidine (0.129 g, 0.507 mmol) in dry THF (2.5 mL) added dropwise (via syringe pump) over 1 h. The resulting beige suspension was stirred for an additional 1 h and then it was partitioned between ethyl acetate and saturated aqueous sodium bicarbonate. The organic phase was separated, washed with brine, dried over anhydrous magnesium sulfate and concentrated in vacuo. The residue obtained was chromatographed on silica gel (ISCO, elution gradient of ethyl acetate in dichloromethane) to give 0.085 g (85%) of the title compound as a white solid. LC (Method A): 2.179 min. HRMS(ESI): calcd for $C_{22}H_{21}N_6O_4S_2$ [M+H]$^+$ m/z 497.1066; found: 497.1113. $^1$H NMR (400 MHz, CDCl$_3$) δ ppm: 7.85 (s, 1H), 7.09 (s, 1H), 6.68-6.72 (m, 1H), 6.62 (br s, 1H), 6.46 (d, J=1.96 Hz, 1H), 5.11 (s, 2H), 4.21 (s, 3H), 3.82-3.89 (m, 5H), 3.20 (s, 3H), 2.80 (t, J=6.46 Hz, 2H).

Example 107

(S)-2-Methoxy-6-(6-methoxy-4-((2-(2-(methoxymethyl)pyrrolidin-1-yl)thiazol-4-yl)methoxy)benzofuran-2-yl)imidazo[2,1-b][1,3,4]thiadiazole

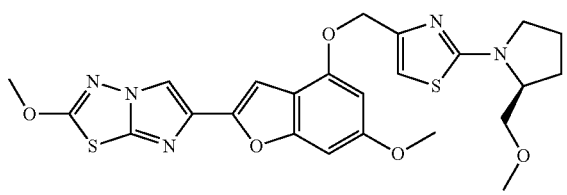 [SMILES: COC[C@@H]1CCCN1c1nc(COc2cc(OC)cc3oc(-c4cn5nc(OC)sc5n4)cc23)cs1]

107A. (S)-4-(((tert-Butyldimethylsilyl)oxy)methyl)-2-(2-(methoxymethyl)pyrrolidin-1-yl)thiazole

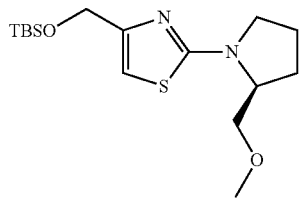 [SMILES: COC[C@@H]1CCCN1c1nc(CO[Si](C)(C)C(C)(C)C)cs1]

A solution of 2-bromo-4-(((tert-butyl dimethyl silyl)oxy)methyl)thiazole (Example 37B, 0.500 g, 1.622 mmol) and (S)-2-(methoxymethyl)pyrrolidine (0.224 g, 1.946 mmol) in 1,4-dioxane (5 mL) was treated with triethylamine (0.678 mL, 4.87 mmol) and the resulting mixture was heated at 100° C. for 18 h. The cooled reaction mixture was concentrated in vacuo and the residue was chromatographed on silica gel (ISCO, elution gradient of ethyl acetate in dichloromethane) to give 0.175 g (31%) of the title material. LC (Method B): 2.685 min. LCMS (APCI): calcd for $C_{16}H_{31}N_2O_2SSi$ [M+H]$^+$ m/z 343.19; found 343.2. $^1$H NMR (400 MHz, CDCl$_3$) δ ppm: 6.35 (s, 1H), 4.68 (s, 2H), 4.02 (dt, J=6.65, 3.33 Hz, 1H), 3.61 (dd, J=9.39, 3.4 Hz, 1H), 3.40-3.56 (m, 2H), 3.28-3.39 (m, 4H), 1.91-2.16 (m, 4H), 0.95 (s, 9H), 0.12 (s, 6H).

107B. (S)-(2-(2-(Methoxymethyl)pyrrolidin-1-yl)thiazol-4-yl)methanol

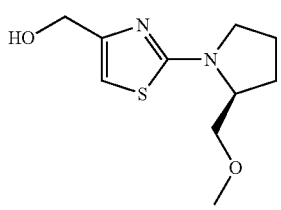

The title compound was prepared according to the deprotection procedure described in Example 93C. LC (Method B): 1.431 min. LCMS (APCI): calcd for $C_{10}H_{17}N_2O_2S$ [M+H]$^+$ m/z 229.10; found 229.2. $^1$H NMR (400 MHz, CDCl$_3$) δ ppm: 6.33 (s, 1H), 4.54 (s, 2H), 3.96-4.08 (m, 1H), 3.38-3.63 (m, 4H), 3.27-3.37 (m, 4H), 1.92-2.19 (m, 4H).

Example 107. (S)-2-Methoxy-6-(6-methoxy-4-((2-(2-(methoxymethyl)pyrrolidin-1-yl)thiazol-4-yl)methoxy)benzofuran-2-yl)imidazo[2,1-b][1,3,4]thiadiazole

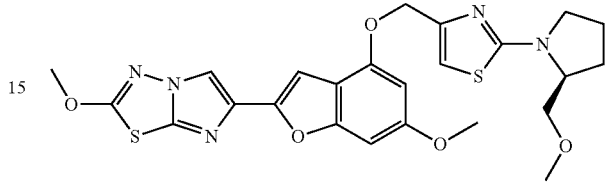

The title compound was prepared according to the general coupling procedure described in Example 106. LC (Method A): 2.090 min. HRMS(ESI): calcd for $C_{24}H_{26}N_5O_5S_2$ [M+H]$^+$ m/z 528.1375; found 528.1352. $^1$H NMR (400 MHz, CDCl$_3$) δ ppm: 7.83 (s, 1H), 7.10 (s, 1H), 6.69 (s, 1H), 6.53 (s, 1H), 6.45 (s, 1H), 5.13 (s, 2H), 4.19 (s, 3H), 4.05 (br s, 1H), 3.84 (s, 3H), 3.58-3.66 (m, 1H), 3.43-3.58 (m, 2H), 3.31-3.43 (m, 4H), 1.94-2.19 (m, 4H).

Example 108

N-(4-Bromo-2-methylphenyl)-4-(((6-methoxy-2-(2-methoxyimidazo[2,1-b][1,3,4]thiadiazol-6-yl)benzofuran-4-yl)oxy)methyl)thiazol-2-amine

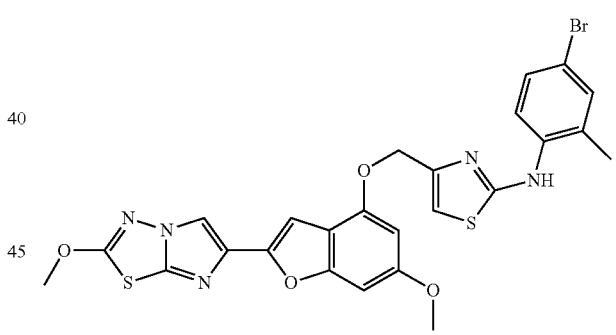

108A. Ethyl 2-((4-bromo-2-methylphenyl)(tert-butoxycarbonyl)amino)thiazole-4-carboxylate

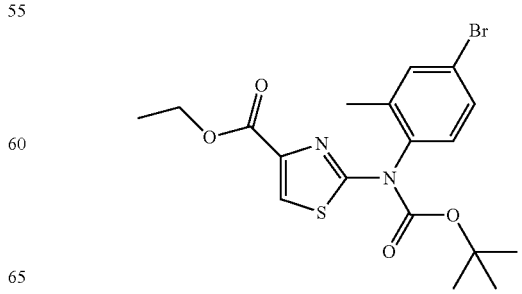

A suspension of ethyl 2-((4-bromo-2-methylphenyl)amino)thiazole-4-carboxylate (0.083 g, 0.243 mmol; obtained by the condensation of 1-(4-bromo-2-methylphenyl)thiourea with ethyl bromopyruvate) in THF (2 mL) was treated, under nitrogen, with di-tert-butyl dicarbonate (0.169 mL, 0.730 mmol), DMAP (0.015 g, 0.122 mmol) and triethylamine (0.102 mL, 0.730 mmol). The mixture was stirred for 3 h at room temperature before being concentrated under reduced pressure. The obtained solid residue was purified on the ISCO using a REDISEP® Gold 12 g column (elution with hexanes-EtOAc) to give the title material (0.080 g, 74.5%) as a solid. LC (Method F): 2.341 min. LCMS (APCI) calcd for $C_{18}H_{22}BrN_2O_4S$ [M+H]$^+$ m/z 441.05, found 441.2. $^1$H NMR (400 MHz, CDCl$_3$) δ ppm: 7.82 (s, 1H), 7.45 (d, J=2.0 Hz, 1H), 7.40 (dd, J=8.2, 2.3 Hz, 1H), 7.06 (d, J=8.2 Hz, 1H), 4.28 (q, J=7.2 Hz, 2H), 2.09 (s, 3H), 1.44 (s, 9H), 1.32 (t, J=7.0 Hz, 3H).

108B. tert-Butyl (4-bromo-2-methylphenyl)(4-(hydroxymethyl)thiazol-2-yl)carbamate

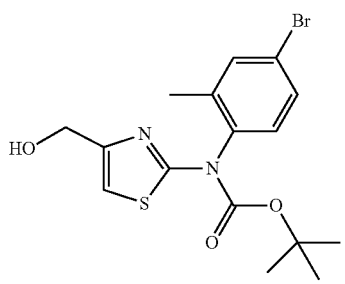 [SMILES: Cc1cc(Br)ccc1N(C(=O)OC(C)(C)C)c1nc(CO)cs1]

An ice-cold solution of ethyl 2-((4-bromo-2-methylphenyl)(tert-butoxycarbonyl)amino)-thiazole-4-carboxylate (0.080 g, 0.181 mmol) in THF (3 mL) under nitrogen was treated with NaBH$_4$ (0.0274 g, 0.725 mmol) and methanol (0.147 mL, 3.63 mmol). After 30 min, the ice bath was removed and the reaction was stirred at room temperature for 5.5 h. At this point, more NaBH$_4$ (0.013 g) and methanol (0.3 mL) were added and stirring was continued for 30 min. The resulting turbid solution was cooled in an ice bath and quenched with acetic acid (0.5 mL). The reaction mixture was diluted with ethyl acetate (40 mL), washed with saturated aqueous sodium bicarbonate (2×20 mL) and brine (20 mL) and then dried over anhydrous magnesium sulfate. Evaporation of the solvent gave a foamy residue which was purified on the ISCO using a REDISEP® Gold 4 g column (elution with hexanes-EtOAc) to give title material (0.064 g, 88%). LC (Method F): 2.216 min. LCMS (APCI): calcd for $C_{16}H_{20}BrN_2O_3S$ [M+H]$^+$ m/z 399.04, found 399.0. $^1$H NMR (400 MHz, CDCl$_3$) δ ppm: 7.45 (d, J=2.3 Hz, 1H), 7.40 (dd, J=8.4, 2.2 Hz, 1H), 7.02 (d, J=8.6 Hz, 1H), 6.81 (s, 1H), 4.49 (d, J=6.3 Hz, 2H), 2.09 (s, 3H), 1.96 (t, J=6.3 Hz, 1H), 1.44 (s, 9H).

108C. tert-Butyl (4-bromo-2-methylphenyl)(4-(((6-methoxy-2-(2-methoxyimidazo[2,1-b][1,3,4]thiadiazol-6-yl)benzofuran-4-yl)oxy)methyl)thiazol-2-yl)carbamate

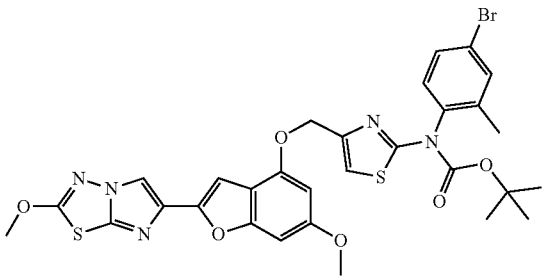 [SMILES: COc1cc(OCc2csc(N(C(=O)OC(C)(C)C)c3ccc(Br)cc3C)n2)c2cc(-c3cn4nc(OC)sc4n3)oc2c1]

To solid 6-methoxy-2-(2-methoxyimidazo[2,1-b][1,3,4]thiadiazol-6-yl)benzofuran-4-ol (Example 1H, 0.045 g, 0.142 mmol) was added, at room temperature under nitrogen, tert-butyl (4-bromo-2-methylphenyl)(4-(hydroxymethyl)thiazol-2-yl)carbamate (0.062 g, 0.156 mmol) and tri-n-butylphosphine (0.175 mL, 0.709 mmol) and the mixture was pumped under high vacuum for 20 min. Anhydrous THF (3 mL) was then added, followed by the dropwise addition of a solution of 1,1'-(azodicarbonyl)dipiperidine (0.089 g, 0.355 mmol) in THF (3 mL), dropwise over 20 min. The mixture was stirred at room temperature for another 3 h, before being diluted with dichloromethane (75 mL), washed with saturated aqueous NaHCO$_3$ (2×20 mL), water (20 mL) and brine (20 mL), and finally dried (MgSO$_4$). Evaporation of the solvent gave a semi-solid which was purified on the ISCO using a REDISEP® Gold 24 g column (elution with hexanes-EtOAc) to give a solid that was further triturated with acetonitrile (1 mL) and lyophilized to give the title compound (0.088 g, 89%) as a solid. LC (Method F): 2.630 min. HRMS(ESI): calcd for $C_{30}H_{29}BrN_5O_6S_2$ [M+H]$^+$ m/z 698.0743, found 698.0753. $^1$H NMR (400 MHz, DMSO-d$_6$) δ ppm: 8.36 (s, 1H), 7.59 (d, J=2.0 Hz, 1H), 7.48 (dd, J=8.4, 2.2 Hz, 1H), 7.40 (s, 1H), 7.25 (d, J=8.2 Hz, 1H), 6.89-6.94 (m, 1H), 6.79 (s, 1H), 6.48 (d, J=1.6 Hz, 1H), 5.02 (s, 2H), 4.21 (s, 3H), 3.77 (s, 3H), 2.00 (s, 3H), 1.37 (s, 9H).

Example 108. N-(4-Bromo-2-methylphenyl)-4-(((6-methoxy-2-(2-methoxyimidazo[2,1-b][1,3,4]thiadiazol-6-yl)benzofuran-4-yl)oxy)methyl)thiazol-2-amine

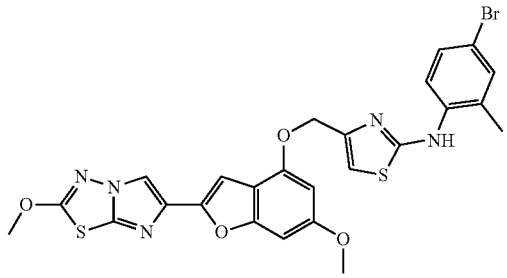

To a solution of tert-butyl (4-bromo-2-methylphenyl)(4-(((6-methoxy-2-(2-methoxyimidazo[2,1-b][1,3,4]thiadiazol-6-yl)benzofuran-4-yl)oxy)methyl)thiazol-2-yl)carbamate (0.030 g, 0.043 mmol) in dichloromethane (4 mL) was added a 95% solution of TFA (0.5 mL) in water. The mixture was stirred at room temperature for 3 h, then toluene (5 mL) was added and the mixture was concentrated. Toluene (5 mL) was added to the concentrate and the volatiles were evaporated to give a solid, which was subsequently triturated with acetonitrile (1 mL). The mixture was filtered and the obtained solid was lyophilized from MeCN-water to give the title compound (0.025 g, 97%) as a white powder. LC (Method F): 2.535 min. HRMS(ESI): calcd for $C_{25}H_{21}BrN_5O_4S_2$ [M+H]$^+$ m/z 598.0218, found 598.0214. $^1$H NMR (400 MHz, DMSO-d$_6$) δ ppm: 9.37 (s, 1H), 8.37 (s, 1H), 7.96 (d, J=8.6 Hz, 1H), 7.40 (d, J=2.0 Hz, H), 7.33 (dd, J=8.6, 2.3 Hz, 1H), 6.98 (d, J=7.4 Hz, 2H), 6.83 (d, J=1.2 Hz, 1H), 6.62 (d, J=2.0 Hz, 1H), 5.11 (s, 2H), 4.20 (s, 3H), 3.80 (s, 3H), 2.26 (s, 3H).

Example 109 tert-Butyl 4-(4-(((6-methoxy-2-(2-methoxyimidazo[2,1-b][1,3,4]thiadiazol-6-yl)benzofuran-4-yl)oxy)methyl)thiazol-2-yl)piperidine-1-carboxylate

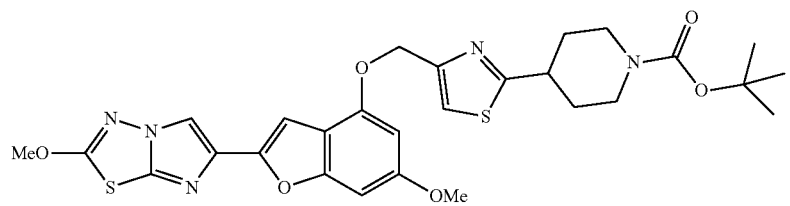 [SMILES: COc1cc(OCc2csc(C3CCN(C(=O)OC(C)(C)C)CC3)n2)c2cc(-c3cn4nc(OC)sc4n3)oc2c1]

109A. Ethyl 2-(1-(tert-butoxycarbonyl)piperidin-4-yl)thiazole-4-carboxylate

To a suspension of tert-butyl 4-carbamothioylpiperidine-1-carboxylate (1.50 g, 6.14 mmol) in ethanol (6 mL) at 0° C. was added dropwise a solution of ethyl 3-bromo-2-oxopropanoate (0.788 mL, 6.26 mmol) in ethanol (6 mL). The ice bath was then removed and the reaction mixture was stirred at ambient temperature overnight. Triethylamine (1.5 mL, 10.76 mmol) was then added and the mixture was concentrated to near dryness and the concentrate was diluted with ethyl acetate, washed with brine, dried (MgSO$_4$) and evaporated to dryness. The residue was purified by flash chromatography using hexanes-ethyl acetate as eluent to give ethyl 2-(1-(tert-butoxycarbonyl)piperidin-4-yl)thiazole-4-carboxylate (1.55 g, 74.2%) as a nearly colorless oil that crystallized on standing to give a white solid. LC (Method A): 2.115 min. $^1$H NMR (DMSO-d$_6$, 400 MHz) δ ppm: 8.42 (s, 1H), 7.20 (br s, 2H), 4.29 (q, J=7.0 Hz, 2H), 4.00 (m, 1H), 3.24 (m, 1H), 2.88 (br s, 1H), 2.03 (m, 2H), 1.54 (m, 2H), 1.29 (t, J=7.2 Hz, 3H).

109B. tert-Butyl 4-(4-(hydroxymethyl)thiazol-2-yl)piperidine-1-carboxylate

To a stirred solution of ethyl 2-(1-(tert-butoxycarbonyl)piperidin-4-yl)thiazole-4-carboxylate (1.430 g, 4.20 mmol) in THF (21 mL) at ambient temperature was added lithium borohydride (0.183 g, 8.40 mmol), followed by MeOH (0.340 mL, 8.40 mmol). The resulting mixture was stirred at room temperature for 16 h before being quenched with saturated aqueous NH$_4$Cl and extracted with EtOAc. The organic phase was separated, dried (MgSO$_4$), filtered and concentrated to dryness. The residue was purified by flash chromatography using DCM-EtOAc as eluent to give the product as a clear, colorless oil. This oil was taken up in acetonitrile-water and lyophilized to give tert-butyl 4-(4-(hydroxymethyl)thiazol-2-yl)piperidine-1-carboxylate (0.996 g, 79%) as a white solid. LC (Method A): 1.875 min. $^1$H NMR (DMSO-d$_6$, 400 MHz) δ ppm: 7.27 (m, 1H), 5.26 (t, J=5.2 Hz, 1H), 4.52 (d, J=4.7 Hz, 2H), 3.99 (d, J=11.3 Hz, 2H), 3.15 (m, 1H), 2.87 (br s, 2H), 2.00 (m, 2H), 1.51 (m, 2H), 1.40 (s, 9H).

Example 109. tert-Butyl 4-(4-(((6-methoxy-2-(2-methoxyimidazo[2,1-b][1,3,4]thiadiazol-6-yl)benzofuran-4-yl)oxy)methyl)thiazol-2-yl)piperidine-1-carboxylate

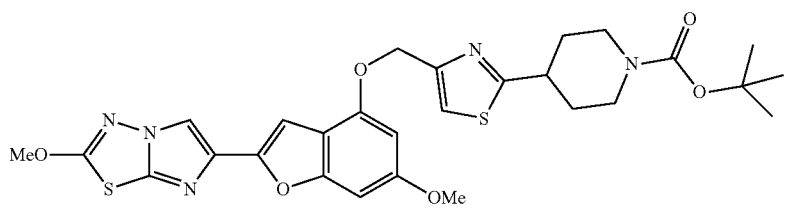 [SMILES: COc1cc(OCc2csc(C3CCN(C(=O)OC(C)(C)C)CC3)n2)c2cc(-c3cn4nc(OC)sc4n3)oc2c1]

To a suspension of 6-methoxy-2-(2-methoxyimidazo[2,1-b][1,3,4]thiadiazol-6-yl)benzofuran-4-ol (Example 1H, 0.339 g, 1.069 mmol) and tert-butyl 4-(4-(hydroxymethyl)thiazol-2-yl)piperidine-1-carboxylate (0.319 g, 1.069 mmol) in dry THF (8 mL) was added tri-n-butylphosphine (0.694 mL, 2.67 mmol), followed by a solution of ADDP (0.674 g, 2.67 mmol) in THF (2 mL) added dropwise over 30 min via syringe pump. After stirring for another 30 min, the reaction mixture was partitioned between EtOAc and saturated aqueous NaHCO₃. The organic phase was separated, washed with brine, dried (MgSO₄), filtered and concentrated to dryness. The residue was purified by flash chromatography using DCM-EtOAc as eluent to give the title compound (0.432 g, 67.6%) as a white solid. LC (Method A): 2.479 min. HRMS(ESI): calcd for $C_{28}H_{32}N_5O_6S_2$ [M+H]⁺ m/z 598.1794, found 598.1806. ¹H NMR (DMSO-d₆, 400 MHz) δ ppm: 8.37 (s, 1H), 7.70 (s, 1H), 6.98 (d, J=0.8 Hz, 1H), 6.83 (dd, J=0.8, 1.6 Hz, 1H), 6.61 (d, J=2.0 Hz, 1H), 5.26 (s, 2H), 4.20 (s, 3H), 4.00 (m, 2H), 3.80 (s, 3H), 3.22 (m, 1H), 2.90 (br s, 1H), 2.04 (m, 2H), 1.55 (m, 2H), 1.40 (s, 9H).

Example 110

(4-(4-(((6-Methoxy-2-(2-methoxyimidazo[2,1-b][1,3,4]thiadiazol-6-yl)benzofuran-4-yl)oxy)methyl)thiazol-2-yl)piperidin-1-yl)(phenyl)methanone

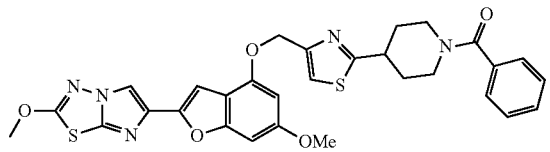 [SMILES: COc1cc(OCc2csc(C3CCN(C(=O)c4ccccc4)CC3)n2)c2cc(-c3cn4nc(OC)sc4n3)oc2c1]

To a stirred suspension of tert-butyl 4-(4-(((6-methoxy-2-(2-methoxyimidazo[2,1-b][1,3,4]thiadiazol-6-yl)benzofuran-4-yl)oxy)methyl)thiazol-2-yl)piperidine-1-carboxylate (0.406 g, 0.679 mmol) in DCM (8 mL) was added TFA (1 mL) and the mixture was stirred at room temperature for 4 h, before being concentrated to dryness. The residue was partitioned with EtOAc-saturated aqueous NaHCO₃ and the organic phase was separated, dried with MgSO₄, filtered and concentrated to dryness to give 2-methoxy-6-(6-methoxy-4-((2-(piperidin-4-yl)thiazol-4-yl)methoxy)benzofuran-2-yl)imidazo[2,1-b][1,3,4]thiadiazole (TFA salt, 0.415 g, 100%) as a beige solid. LC (Method A): 1.990 min. LCMS (APCI): calcd for $C_{23}H_{24}N_5O_4S_2$ [M+H]⁺ m/z 498.13, found 498.20.

To a stirred solution of 2-methoxy-6-(6-methoxy-4-((2-(piperidin-4-yl)thiazol-4-yl)methoxy)benzofuran-2-yl)imidazo[2,1-b][1,3,4]thiadiazole (0.025 g, 0.050 mmol) in DMF (1 mL) was added DIEA (0.044 mL, 0.250 mmol) and benzoic acid (0.0067 g, 0.055 mmol), followed by HATU (0.021 g, 0.055 mmol). The reaction mixture was stirred for 1 h, before being diluted with DMF (1 mL) and submitted directly to purification by preparative HPLC (Method A). Product-containing fractions were concentrated to dryness and the residue was lyophilized from MeCN-water to give the title compound (0.012 g, 39.9%) as an amorphous white solid. LC (Method A): 2.328 min. HRMS(ESI): calcd for $C_{30}H_{28}N_5O_5S_2$ [M+H]⁺ m/z 602.1532, found 602.1532. ¹H NMR (DMSO-d₆, 400 MHz) δ ppm: 8.37 (s, 1H), 7.72 (s, 1H), 7.46-7.39 (m, 5H), 6.98 (d, J=0.8 Hz, 1H), 6.83 (dd, J=0.8, 1.6 Hz, 1H), 6.61 (d, J=2.0 Hz, 1H), 5.26 (s, 2H), 4.52 (br s, 1H), 4.20 (s, 3H), 3.80 (s, 3H), 3.65 (br s, 1H), 3.08 (m, 3H), 2.10 (m, 2H), 1.69 (m, 2H).

Example 111

6-(4-((2-(1-(Isopropylsulfonyl)piperidin-4-yl)thiazol-4-yl)methoxy)-6-methoxybenzofuran-2-yl)-2-methoxyimidazo[2,1-b][1,3,4]thiadiazole

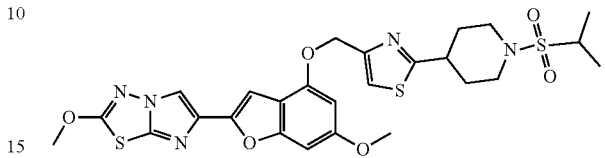

To a stirred solution of 2-methoxy-6-(6-methoxy-4-((2-(piperidin-4-yl)thiazol-4-yl)methoxy)benzofuran-2-yl)imidazo[2,1-b][1,3,4]thiadiazole (0.025 g, 0.050 mmol) in DMF (1 mL) was added DIEA (0.044 mL, 0.250 mmol) and propane-2-sulfonyl chloride (5.61 µl, 0.050 mmol). The reaction mixture was stirred at room temperature for 1 h, before being diluted with DMF (1 mL) and purified by preparative HPLC (Method A). Product-containing fractions were concentrated to dryness and the residue was lyophilized from MeCN-water to give the title compound (0.007 g, 0.012 mmol, 23.19%) as an amorphous white solid. LC (Method A): 2.283 min. HRMS(ESI): calcd for $C_{26}H_{30}N_5O_6S_3$ [M+H]⁺ m/z 604.1358, found 604.1373. ¹H NMR (DMSO-d₆, 400 MHz) δ ppm: 8.37 (s, 1H), 7.72 (s, 1H), 6.98 (d, J=0.8 Hz, 1H), 6.83 (dd, J=0.8, 2.0 Hz, 1H), 6.61 (d, J=2.0 Hz, 1H), 5.27 (s, 2H), 4.20 (s, 3H), 3.81 (s, 3H), 3.72 (m, 2H), 3.24 (m, 2H), 3.06 (m, 2H), 2.12 (m, 2H), 1.67 (m, 2H), 1.22 (d, J=7.0 Hz, 6H).

Example 112

2-Methoxy-6-(6-methoxy-4-((2-(1-(methylsulfonyl)piperidin-4-yl)thiazol-4-yl)methoxy)benzofuran-2-yl)imidazo[2,1-b][1,3,4]thiadiazole

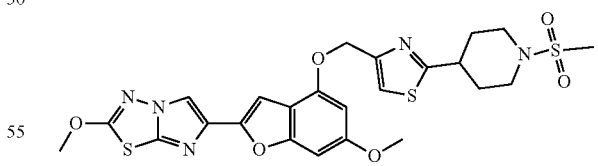

The title compound was prepared according to the method described in Example 111 above and was isolated as a solid. LC (Method A): 2.172 min. HRMS(ESI): calcd for $C_{24}H_{26}N_5O_6S_3$ [M+H]⁺ m/z 576.1040, found 576.1041. ¹H NMR (DMSO-d₆, 400 MHz) δ ppm: 8.37 (s, 1H), 7.73 (s, 1H), 6.99 (s, 1H), 6.84 (dd, J=0.8, 1.6 Hz, 1H), 6.61 (d, J=2.0 Hz, 1H), 5.27 (s, 2H), 4.20 (s, 3H), 3.81 (s, 3H), 3.64 (m, 2H), 3.18 (m, 1H), 2.90 (m, 2H), 2.89 (s, 3H), 2.18 (m, 2H), 1.75 (m, 2H).

Example 113

2-Methoxy-6-(6-methoxy-4-((2-(1-(phenylsulfonyl)piperidin-4-yl)thiazol-4-yl)methoxy)benzofuran-2-yl)imidazo[2,1-b][1,3,4]thiadiazole

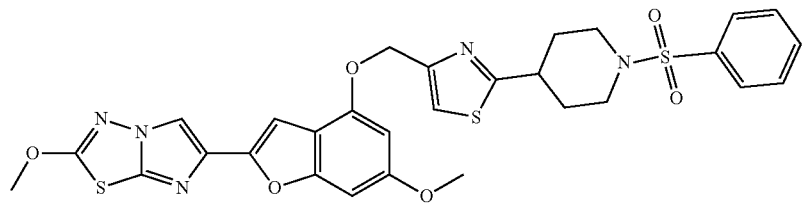 [SMILES: COc1cc(OCc2csc(C3CCN(S(=O)(=O)c4ccccc4)CC3)n2)c2cc(-c3cn4nc(OC)sc4n3)oc2c1]

The title compound was prepared according to the method described in Example 111 above and was isolated as a solid. LC (Method A): 2.014 min. HRMS(ESI): calcd for $C_{29}H_{28}N_5O_6S_3$ [M+H]$^+$ m/z 638.1202, found 638.1422. $^1$H NMR (DMSO-d$_6$, 400 MHz) δ ppm: 8.37 (s, 1H), 7.79-7.64 (m, 6H), 6.97 (d, J=0.8 Hz, 1H), 6.83 (dd, J=0.8, 1.6 Hz, 1H), 6.59 (d, J=2.0 Hz, 1H), 5.23 (s, 2H), 4.20 (s, 3H), 3.80 (s, 3H), 3.71 (m, 2H), 3.06 (m, 1H), 2.45 (m, 2H), 2.13 (m, 2H), 1.72 (m, 2H).

Example 114

2-Methoxy-6-(6-methoxy-4-((2-(1-((trifluoromethyl)sulfonyl)piperidin-4-yl)thiazol-4-yl)methoxy)benzofuran-2-yl)imidazo[2,1-b][1,3,4]thiadiazole

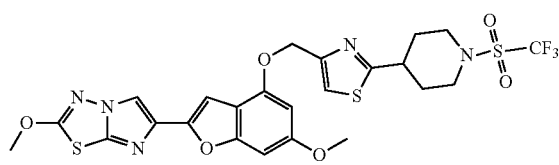 [SMILES: COc1cc(OCc2csc(C3CCN(S(=O)(=O)C(F)(F)F)CC3)n2)c2cc(-c3cn4nc(OC)sc4n3)oc2c1]

The title compound was prepared according to the method described in Example 111 above and was isolated as a solid. LC (Method A): 2.403 min. HRMS(ESI): calcd for $C_{24}H_{23}F_3N_5O_6S_3$ [M+H]$^+$ m/z 630.0763, found 630.0821. $^1$H NMR (DMSO-d$_6$, 400 MHz) δ ppm: 8.37 (s, 1H), 7.74 (s, 1H), 6.98 (d, J=0.8 Hz, 1H), 6.84 (dd, J=0.8, 1.6 Hz, 1H), 6.61 (d, J=1.6 Hz, 1H), 5.27 (s, 2H), 4.20 (s, 3H), 3.89 (m, 2H), 3.80 (s, 3H), 2.23 (m, 2H), 1.74 (m, 2H).

Example 115

6-(4-((2-(4,4-Difluorocyclohexyl)thiazol-4-yl)methoxy)-6-methoxybenzofuran-2-yl)-2-methoxyimidazo[2,1-b][1,3,4]thiadiazole

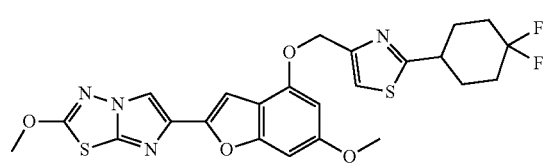 [SMILES: COc1cc(OCc2csc(C3CCC(F)(F)CC3)n2)c2cc(-c3cn4nc(OC)sc4n3)oc2c1]

115A. 4,4-Difluorocyclohexanecarboxamide

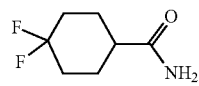

To a stirred solution of 4,4-difluorocyclohexanecarboxylic acid (1.50 g, 9.14 mmol) in DCM (22 mL) was added oxalyl chloride (1.600 mL, 18.28 mmol) and the reaction mixture was stirred for 1 h at room temperature before being evaporated to dryness. The residue was taken up in dry THF (4.5 mL) and was added with stirring to ice-cold concentrated aqueous ammonia (22 mL). The mixture was stirred at 0° C. for 2 min and then at room temperature for 30 min, before being diluted with water and extracted with EtOAc. The organic phase was dried (MgSO$_4$), filtered and concentrated to dryness to give 4,4-difluorocyclohexanecarboxamide (1.02 g, 68.4%) as a white solid. This material was used as such in the next step. LC (Method F): 2.567 min. $^1$H NMR (DMSO-d$_6$, 400 MHz) δ ppm: 7.29 (br s, 1H), 6.79 (br s, 1H), 2.26-2.18 (m, 1H), 2.07-1.97 (m, 2H), 1.86-1.70 (m, 4H), 1.62-1.51 (m, 2H).

115B. 4,4-Difluorocyclohexanecarbothioamide

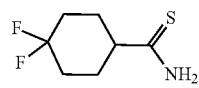

To a solution of 4,4-difluorocyclohexanecarboxamide (1.00 g, 6.13 mmol) in THF (10 mL) was added Lawesson's reagent (1.239 g, 3.06 mmol) and the mixture was heated in a sealed vessel at 65° C. for 6 h. The cooled mixture was partitioned between EtOAc-saturated aqueous NaHCO$_3$ and the organic phase was washed with brine, dried (MgSO$_4$), filtered and concentrated to dryness. The residue was purified by flash chromatography using hexanes-EtOAc as eluent to give 4,4-difluorocyclohexanecarbothioamide (0.634 g, 3.54 mmol, 57.7%) as a white solid. LC (Method F): 1.432 min. $^1$H NMR (DMSO-d$_6$, 400 MHz) δ ppm: 9.42 (br s, 1H), 9.15 (br s, 1H), 2.63 (m, 1H), 2.10-2.01 (m, 2H), 1.90-1.80 (m, 1H), 1.79-1.72 (m, 5H).

115C. Ethyl 2-(4,4-difluorocyclohexyl)thiazole-4-carboxylate

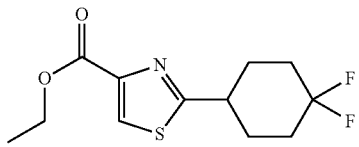 [SMILES: CCOC(=O)c1csc(C2CCC(F)(F)CC2)n1]

A sealable vessel was charged with 4,4-difluorocyclohexanecarbothioamide (0.600 g, 3.35 mmol), ethyl bromopyruvate (0.505 mL, 4.02 mmol) and i-PrOH (15 mL) and the mixture was heated at 85° C. for 3 h. The cooled mixture was partitioned between EtOAc-saturated aqueous NaHCO$_3$ and the organic phase was dried (MgSO$_4$), filtered and concentrated to dryness. The residue was purified by column chromatography using hexanes-EtOAc as eluent to give ethyl 2-(4,4-difluorocyclohexyl)thiazole-4-carboxylate (0.600 g, 2.179 mmol, 65.1%) as a white solid. LC (Method F): 2.089 min. $^1$H NMR (DMSO-d$_6$, 400 MHz) δ ppm: 8.43 (s, 1H), 4.29 (q, J=7.0 Hz, 2H), 3.27 (m, 1H), 2.20-1.91 (m, 6H), 1.75 (m, 2H), 1.30 (t, J=7.2 Hz, 3H).

115D. (2-(4,4-Difluorocyclohexyl)thiazol-4-yl)methanol

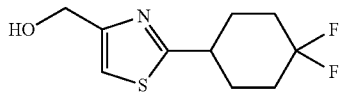

To an ice-cold solution of ethyl 2-(4,4-difluorocyclohexyl)thiazole-4-carboxylate (0.580 g, 2.107 mmol) in THF (11 mL) was added LiBH$_4$ (0.092 g, 4.20 mmol) all at once, followed by MeOH (0.170 mL, 4.20 mmol). The resulting mixture was stirred at 0° C. for 5 min and then at ambient temperature for 4 h. The mixture was then cooled in an ice-bath, quenched by dropwise addition of saturated aqueous NH$_4$Cl and extracted with ethyl acetate. The organic phase was then washed with brine, dried (MgSO$_4$), filtered and concentrated to dryness. The residue was purified by flash chromatography using a gradient of 0 to 100% EtOAc in hexanes to give (2-(4,4-difluorocyclohexyl)thiazol-4-yl)methanol (0.398 g, 81%) as a clear, colorless oil. LC (Method F): 1.776 min. $^1$H NMR (DMSO-d$_6$, 400 MHz) δ ppm: 7.28 (m, 1H), 5.26 (br s, 1H), 4.52 (s, 2H), 3.17 (m, 1H), 2.14-1.90 (m, 6H), 1.78-1.67 (m, 2H).

Example 115. 6-(4-((2-(4,4-Difluorocyclohexyl)thiazol-4-yl)methoxy)-6-methoxybenzofuran-2-yl)-2-methoxyimidazo[2,1-b][1,3,4]thiadiazole

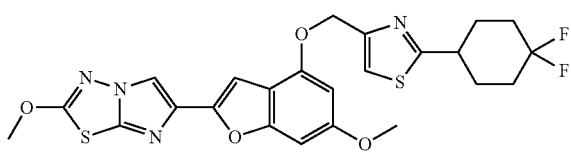 [SMILES: COc1cc(OCc2csc(C3CCC(F)(F)CC3)n2)c2cc(-c3cn4nc(OC)sc4n3)oc2c1]

The title compound was prepared according to the method described in Example 109 and was isolated as a solid. LC (Method F): 2.556 min. HRMS(ESI): calcd for C$_{24}$H$_{23}$FN$_4$O$_4$S$_2$ [M+H]$^+$ m/z 533.1145, found 533.1161. $^1$H NMR (DMSO-d$_6$, 400 MHz) δ ppm: 8.37 (s, 1H), 7.71 (s, 1H), 6.98 (m, 1H), 6.61 (m, 1H), 5.28 (m, 2H), 4.20 (s, 3H), 3.80 (s, 3H), 3.24 (m, 1H), 2.18-1.92 (m, 6H), 1.76 (m, 2H).

Example 116

5-(4-((((6-Methoxy-2-(2-methoxyimidazo[2,1-b][1,3,4]thiadiazol-6-yl)benzofuran-4-yl)oxy)methyl)thiazol-2-yl)isoxazole

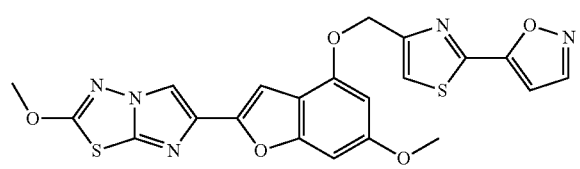 [SMILES: COc1cc(OCc2csc(-c3ccno3)n2)c2cc(-c3cn4nc(OC)sc4n3)oc2c1]

116A. Ethyl 2-(isoxazol-5-yl)thiazole-4-carboxylate

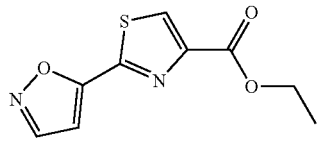

To a suspension of isoxazole-5-carbothioamide (0.500 g, 3.90 mmol) in ethanol (10 mL) was added ethyl 3-bromo-2-oxopropanoate (0.598 mL, 4.29 mmol) and the resulting mixture was heated to 90° C. for 1.5 h. The cooled reaction mixture was evaporated to dryness and the residue was then partitioned between ethyl acetate and saturated aqueous sodium bicarbonate. The organic phase was separated, washed with brine, dried over anhydrous magnesium sulfate and concentrated in vacuo. The residue obtained was chromatographed on silica gel (ISCO, elution gradient of ethyl acetate in dichloromethane) to give 0.800 g (92%) of the title material as a reddish solid. LC (Method B): 2.167 min. LCMS(ESI): calcd. for C$_9$H$_9$N$_2$O$_3$S [M+H]$^+$ m/z 225.03; found: 225.0. $^1$H NMR (400 MHz, CDCl$_3$) δ ppm: 8.36-8.42 (m, 1H), 8.28-8.34 (m, 1H), 6.94-7.10 (m, 1H), 4.35-4.53 (m, 2H), 1.31-1.48 (m, 3H).

116B. (2-(Isoxazol-5-yl)thiazol-4-yl)methanol

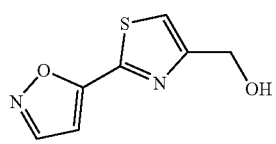 [SMILES: OCc1csc(-c2ccno2)n1]

A solution of ethyl 2-(isoxazol-5-yl)thiazole-4-carboxylate (0.087 g, 0.388 mmol) in THF (2 mL) at 0° C. was treated with methanol (0.056 mL, 1.395 mmol), followed by lithium borohydride (0.030 g, 1.395 mmol). After 15 min, the cooling bath was removed and the reaction mixture was stirred at 22° C. for 3 h. The reaction mixture was then quenched with saturated aqueous NH₄Cl and diluted with dichloromethane. The aqueous phase was separated and back-extracted (×3) with dichloromethane and the combined organic extract was dried over MgSO₄ and evaporation under reduced pressure gave 0.039 g (56%) of the title material which was used as such for next step. LC (Method B): 1.818 min. LCMS (APCI): calcd. for $C_7H_7N_2O_2S$ [M+H]⁺ m/z 183.02; found: 183.0. ¹H NMR (400 MHz, CDCl₃) δ ppm: 8.36 (d, J=1.8 Hz, 1H), 7.41 (s, 1H), 6.87 (d, J=1.8 Hz, 1H), 4.87 (d, J=5.4 Hz, 2H), 3.00 (t, J=5.4 Hz, 1H).

Example 116. 5-(4-(((6-Methoxy-2-(2-methoxyimidazo[2,1-b][1,3,4]thiadiazol-6-yl)benzofuran-4-yl)oxy)methyl)thiazol-2-yl)isoxazole

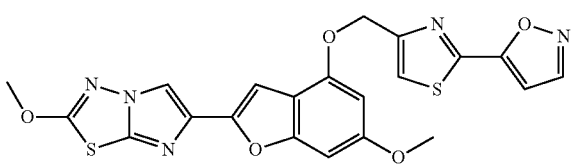

A mixture of 6-methoxy-2-(2-methoxyimidazo[2,1-b][1,3,4]thiadiazol-6-yl)benzofuran-4-ol (Example 1H, 0.032 g, 0.100 mmol) and (2-(isoxazol-5-yl)thiazol-4-yl)methanol (0.020 g, 0.110 mmol) in dry THF (2.5 mL) under nitrogen was treated at 22° C. with tri-n-butylphosphine (0.065 mL, 0.249 mmol), followed by a solution of 1,1'-(azodicarbonyl)dipiperidine (0.064 g, 0.249 mmol) in dry THF (2.5 mL), added dropwise (via syringe pump) over 1 h. The resulting beige suspension was stirred for an additional 1 h at room temperature and then it was partitioned between ethyl acetate and saturated aqueous sodium bicarbonate. The organic phase was separated, washed with brine, dried over anhydrous magnesium sulfate and concentrated in vacuo. The residue obtained was chromatographed on silica gel (ISCO, elution gradient of ethyl acetate in dichloromethane) and the obtained material was triturated with methanol to give (after filtration and drying in vacuo) 0.013 g (27%) of the title compound. LC (Method A): 2.289 min. HRMS (ESI): calcd for $C_{21}H_{16}N_5O_5S_2$ [M+H]⁺ m/z 482.0593; found: 482.0602. ¹H NMR (400 MHz, CDCl₃) δ ppm: 8.38 (d, J=1.96 Hz, 1H), 7.86 (s, 1H), 7.58 (s, 1H), 7.10 (s, 1H), 6.89 (d, J=1.96 Hz, 1H), 6.69-6.76 (m, 1H), 6.43 (d, J=1.57 Hz, 1H), 5.37-5.45 (m, 2H), 4.21 (s, 3H), 3.85 (s, 3H).

Example 117

5-(4-(((6-methoxy-2-(2-methoxyimidazo[2,1-b][1,3,4]thiadiazol-6-yl)benzofuran-4-yl)oxy)methyl)thiazol-2-yl)oxazole

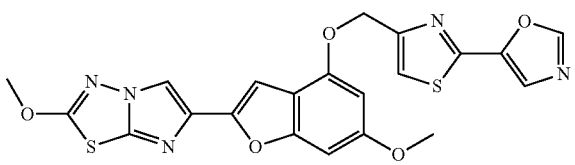 [SMILES: COc1cc(OCc2csc(-c3cnco3)n2)c2cc(-c3cn4nc(OC)sc4n3)oc2c1]

117A. Ethyl 2-(oxazol-5-yl)thiazole-4-carboxylate

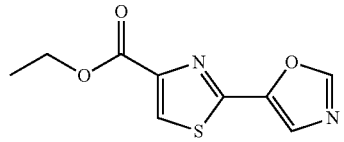

Oxazole-5-carbothioamide (0.390 g, 3.04 mmol) was reacted with ethyl 3-bromo-2-oxopropanoate (0.263 mL, 1.884 mmol) as described in Example 116A above to give 0.085 g (22%) of the title material. LC (Method B): 1.811 min. LCMS (APCI): calcd for $C_9H_9N_2O_3S$ [M+H]⁺ m/z 225.03; found: 225.0. ¹H NMR (400 MHz, CDCl₃) δ ppm: 8.21 (s, 1H), 7.98 (s, 1H), 7.80 (s, 1H), 4.44 (q, J=7.04 Hz, 2H), 1.41 (t, J=7.04 Hz, 3H).

117B. (2-(Oxazol-5-yl)thiazol-4-yl)methanol

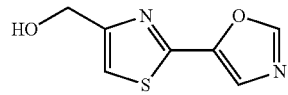 [SMILES: OCc1csc(-c2cnco2)n1]

Ethyl 2-(oxazol-5-yl)thiazole-4-carboxylate (0.112 g, 0.499 mmol) was treated with lithium borohydride (0.022 g, 0.999 mmol) as described in Example 116B above to give 0.024 g (26%) of the title compound after flash chromatography. LC (Method B): 1.462 min. HRMS(ESI): calcd for $C_7H_7N_2O_2S$ [M+H]⁺ m/z 183.0228; found 183.0222. ¹H NMR (400 MHz, CDCl₃) δ ppm: 7.99 (s, 1H), 7.80 (s, 1H), 7.32 (s, 1H), 4.86 (s, 2H), 2.90 (br s, 1H).

Example 117. 5-(4-(((6-Methoxy-2-(2-methoxyimidazo[2,1-b][1,3,4]thiadiazol-6-yl)benzofuran-4-yl)oxy)methyl)thiazol-2-yl)oxazole

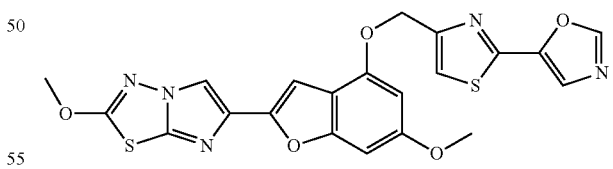

Reaction of 6-methoxy-2-(2-methoxyimidazo[2,1-b][1,3,4]thiadiazol-6-yl)benzofuran-4-ol (Example 1H, 0.079 g, 0.249 mmol) with (2-(oxazol-5-yl)thiazol-4-yl)methanol (0.050 g, 0.274 mmol), as described in Example 116 above, gave 0.035 g (29%) of the title compound as a beige solid. LC (Method A): 2.278 min. HRMS(ESI): calcd for $C_{21}H_{16}N_5O_5S_2$ [M+H]⁺ m/z 482.0593; found 482.0595. ¹H NMR (400 MHz, CDCl₃) δ ppm: 7.98 (s, 1H), 7.86 (s, 1H), 7.69 (s, 1H), 7.46 (s, 1H), 7.11 (s, 1H), 6.72 (br d, 1H), 6.44 (d, J=1.96 Hz, 1H), 5.39 (s, 2H), 4.22 (s, 3H), 3.85 (s, 3H).

Example 118

4-(4-(((6-Methoxy-2-(2-methoxyimidazo[2,1-b][1,3,4]thiadiazol-6-yl)benzofuran-4-yl)oxy)methyl)thiazol-2-yl)tetrahydro-2H-pyran-4-ol

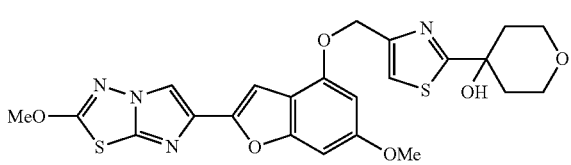 [SMILES: COc1cc(OCc2csc(C3(O)CCOCC3)n2)c2cc(-c3cn4nc(OC)sc4n3)oc2c1]

118A. 4-(4-(((tert-Butyldimethylsilyl)oxy)methyl)thiazol-2-yl)tetrahydro-2H-pyran-4-ol

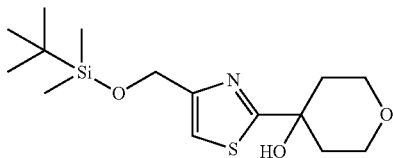 [SMILES: CC(C)(C)[Si](C)(C)OCc1csc(C2(O)CCOCC2)n1]

A solution of 2-bromo-4-(((tert-butyldimethylsilyl)oxy)methyl)thiazole (Example 37B, 3.39 g, 11.00 mmol) in dry THF (55 mL) was cooled at −78° C. under $N_2$ and then 1.45 M n-butyllithium (9.10 mL, 13.20 mmol) was added dropwise. The resulting mixture was stirred for 30 min to give a pale brown solution. To this mixture was slowly added a solution of dihydro-2H-pyran-4(3H)-one (1.219 mL, 13.20 mmol) in dry THF (5 mL) and the mixture was kept at −78° C. for 1 h, to give a pale brown solution. The reaction was quenched by the addition of saturated aqueous $NH_4Cl$ (15 mL) and then the cooling bath was removed and the mixture was partitioned with EtOAc-water. The organic phase was separated, washed (brine), dried ($Na_2SO_4$) and evaporated to give a pale yellow oil. Flash chromatography (Isco/0-30% acetone-hexane) afforded 4-(4-(((tert-butyldimethylsilyl)oxy)methyl)thiazol-2-yl)tetrahydro-2H-pyran-4-ol (2.97 g, 82%) as a colorless oil which crystallized on standing in vacuo. LC (Method A): 2.262 min. HRMS(ESI): calcd for $C_{15}H_{28}NO_3SSi$ [M+H]$^+$ m/z 330.156; found 330.158. $^1$H NMR (400 MHz, DMSO-d$_6$): δ 7.23 (s, 1H), 5.99 (s, 1H), 4.64 (s, 2H), 3.64 (m, 4H), 2.00 (ddd, J=5.48, 11.35, 13.69 Hz, 2H), 1.56 (br d, J=12.91 Hz, 2H), 0.81 (s, 9H), 0.00 (s, 6H).

118B. 4-(4-(Hydroxymethyl)thiazol-2-yl)tetrahydro-2H-pyran-4-ol

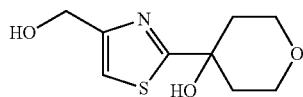

To a solution of 4-(4-(((tert-butyldimethylsilyl)oxy)methyl)thiazol-2-yl)tetrahydro-2H-pyran-4-ol (2.96 g, 8.98 mmol) in dry THF (40 mL) under $N_2$ was added triethylamine trihydrofluoride (3.66 mL, 22.46 mmol) dropwise and the mixture was stirred at room temperature for 16 h. The mixture was then concentrated to half volume and the concentrate was diluted with DCM and then saturated aqueous $NaHCO_3$ was added (Caution: vigorous gas evolution!). The organic phase was separated, washed (saturated aqueous $NaHCO_3$), dried ($Na_2SO_4$) and evaporated to give only a small amount of a pale yellow residue. The aqueous phase was subsequently saturated with solid NaCl and the mixture was extracted with DCM (×6). The combined organic extracts were dried ($Na_2SO_4$) and evaporated to give a white solid. The aqueous phase was then neutralized with conc. HCl (pH 7) and re-extracted with DCM (×5). The organic extract was again dried ($Na_2SO_4$) and evaporated to give additional material as an off-white solid. These solids were combined to give 4-(4-(hydroxymethyl)thiazol-2-yl)tetrahydro-2H-pyran-4-ol (1.145 g, 59.2%) as a cream solid which was used as such in the next step without further purification. LC (Method A): 0.861 min. HRMS(ESI): calcd for $C_9H_{14}NO_3S$ [M+H]$^+$ m/z 216.069; found 216.070. $^1$H NMR (400 MHz, DMSO-d$_6$): δ 7.24 (s, 1H), 6.00 (s, 1H), 5.21 (t, J=5.87 Hz, 1H), 4.48 (d, J=5.87 Hz, 2H), 3.68 (m, 4H), 2.04 (m, 2H), 1.60 (br d, J=13.30 Hz, 2H).

Example 118. 4-(4-(((6-Methoxy-2-(2-methoxyimidazo[2,1-b][1,3,4]thiadiazol-6-yl)benzofuran-4-yl)oxy)methyl)thiazol-2-yl)tetrahydro-2H-pyran-4-ol

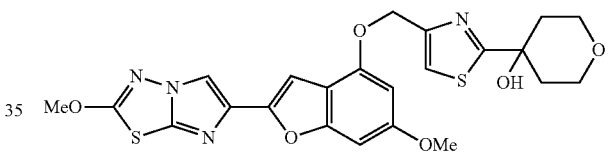

To a flame-dried flask was added 6-methoxy-2-(2-methoxyimidazo[2,1-b][1,3,4]thiadiazol-6-yl)benzofuran-4-ol (Example 1H, 0.040 g, 0.126 mmol) and 4-(4-(hydroxymethyl)thiazol-2-yl)tetrahydro-2H-pyran-4-ol (0.034 g, 0.158 mmol), then the flask was flushed with $N_2$ and dry THF (2 mL) was added. To the resulting suspension was added tri-n-butylphosphine (0.082 mL, 0.315 mmol) and then a solution of 1,1'-(azodicarbonyl)dipiperidine (0.080 g, 0.315 mmol) in dry THF (2 mL) was added dropwise (via syringe pump) over 30 min. The resulting mixture was stirred at room temperature for another 1 h and then it was diluted with EtOAc, washed (saturated aqueous $NaHCO_3$, $H_2O$, brine), dried ($Na_2SO_4$) and evaporated to give a pale yellow gum. Flash chromatography (Isco/0-30% ether-DCM, then 0-100% EtOAc-DCM and finally 0-3% MeOH-DCM) gave 4-(4-(((6-methoxy-2-(2-methoxyimidazo[2,1-b][1,3,4]thiadiazol-6-yl)benzofuran-4-yl)oxy)methyl)thiazol-2-yl)tetrahydro-2H-pyran-4-ol (0.049 g, 76%) as a colorless gum which was lyophilized from MeCN-water as an off-white solid. LC (Method A): 2.106 min. HRMS(ESI): calcd for $C_{23}H_{23}N_4O_6S_2$ [M+H]$^+$ m/z 515.106; found 515.107. $^1$H NMR (400 MHz, DMSO-d$_6$): δ 8.33 (s, 1H), 7.66 (s, 1H), 6.95 (s, 1H), 6.80 (s, 1H), 6.59 (d, J=1.57 Hz, 1H), 5.23 (s, 2H), 4.17 (s, 3H), 3.77 (s, 3H), 3.70 (m, 4H), 2.08 (ddd, J=5.48, 10.96, 13.30 Hz, 1H), 1.64 (br d, J=12.52 Hz, 2H).

Example 119

6-(4-((2-(4-Fluorotetrahydro-2H-pyran-4-yl)thiazol-4-yl)methoxy)-6-methoxybenzofuran-2-yl)-2-methoxyimidazo[2,1-b][1,3,4]thiadiazole

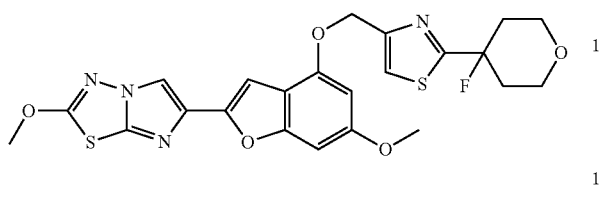

119A.
4-(4-Methylthiazol-2-yl)tetrahydro-2H-pyran-4-ol

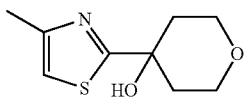

A solution of 4-methylthiazole (0.910 mL, 10.0 mmol) in dry THF (45 mL) was cooled at −78° C. under $N_2$ and then n-butyllithium (1.45 M in hexanes, 7.59 mL, 11.00 mmol) was added dropwise. The resulting mixture was stirred for 15 min to give a bright yellow solution. To this mixture was slowly added a solution of dihydro-2H-pyran-4(3H)-one (1.108 mL, 12.00 mmol) in dry THF (5 mL) and the mixture was kept at −78° C. for 1 h, to give a pale yellow solution. The reaction was then quenched by the addition of saturated aqueous $NH_4Cl$ (5 mL) and the mixture was partitioned with EtOAc-water. The organic phase was separated, washed (brine), dried ($Na_2SO_4$) and evaporated to give a pale yellow oil which solidified on standing in vacuo. Flash chromatography (Isco/0-50% acetone-hexane) afforded 4-(4-methylthiazol-2-yl)tetrahydro-2H-pyran-4-ol (1.535 g, 77%) as a white crystalline solid. This material was used as such in the next step. LC (Method A): 1.091 min. HRMS: calcd for $C_9H_{14}NO_2S$ $[M+1]^+$ m/z 200.075; found 200.075. $^1H$ NMR (400 MHz, DMSO-$d_6$) δ ppm: 1.59 (br d, J=12.52 Hz, 2H), 2.04 (ddd, J=5.87, 10.56, 13.30 Hz, 2H), 2.29 (s, 3H), 3.72-3.62 (m, 4H), 5.95 (s, 1H), 7.08 (s, 1H).

119B. (2-(4-Fluorotetrahydro-2H-pyran-4-yl)-4-methylthiazole

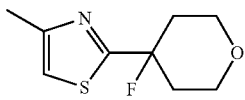

To a solution of 4-(4-methylthiazol-2-yl)tetrahydro-2H-pyran-4-ol (0.022 g, 0.110 mmol) in dichloromethane (1.75 mL), cooled at 0° C. under nitrogen, was added DAST (0.018 mL, 0.138 mmol) dropwise. The resulting reaction mixture was allowed to stir at 0° C. for 2 h and then saturated aqueous sodium carbonate was added and the heterogeneous mixture was stirred vigorously for 15 min to ensure complete quenching. The mixture was then partitioned with dichloromethane and saturated aqueous bicarbonate solution. The organic layer was separated, dried over magnesium sulfate and concentrated under reduced pressure. The crude product (0.021 g, 95%) was used as such for the next step. LC (Method A): 1.722 min. LCMS (APCI): calcd for $C_9H_{13}FNOS$ $[M+H]^+$ m/z 202.07, found 202.2. $^1H$ NMR (CDCl$_3$, 400 MHz) δ ppm: 2.00-2.11, (m, 2H), 2.28-2.49 (m, 2H), 2.45 (s, 3H), 3.79-3.98 (m, 4H), 6.88 (s, 1H).

119C. 4-(Bromomethyl)-2-(4-fluorotetrahydro-2H-pyran-4-yl)thiazole

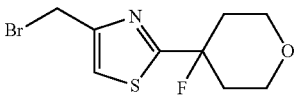 [SMILES: FC1(c2nc(CBr)cs2)CCOCC1]

A sealed tube was charged with 2-(4-fluorotetrahydro-2H-pyran-4-yl)-4-methylthiazole (0.021 g, 0.104 mmol), carbon tetrachloride (2 mL), NBS (0.0204 g, 0.115 mmol) and benzoyl peroxide (0.002 g, 8.26 μmol). The reaction mixture was then stirred at 85° C. for 2.5 h. After cooling, the crude reaction mixture was taken up in dichloromethane and the solid present was removed by filtration. The filtrate was concentrated and the crude residue was purified by preparative HPLC (Method A) to give pure the title compound (0.010 g, 34%). LC (Method A): 1.784 min. LCMS (APCI): calcd for $C_9H_{12}BrFNOS$ $[M+H]^+$ m/z 279.98, found 280.0. $^1H$ NMR (CD$_3$OD, 400 MHz) δ ppm: 1.96-2.09 (m, 2H), 2.26-2.46 (m, 2H), 3.77-3.96 (m, 4H), 4.62 (s, 2H), 7.60 (s, 1H).

Example 119. 6-(4-((2-(4-Fluorotetrahydro-2H-pyran-4-yl)thiazol-4-yl)methoxy)-6-methoxybenzofuran-2-yl)-2-methoxyimidazo[2,1-b][1,3,4]thiadiazole

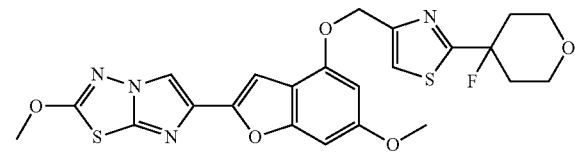 [SMILES: COc1cc(OCc2csc(C3(F)CCOCC3)n2)c2cc(-c3cn4nc(OC)sc4n3)oc2c1]

To a solution of 6-methoxy-2-(2-methoxyimidazo[2,1-b][1,3,4]thiadiazol-6-yl)benzofuran-4-ol (Example 1H, 0.009 g, 0.028 mmol) and 4-(bromomethyl)-2-(4-fluorotetrahydro-2H-pyran-4-yl)thiazole (0.010 g, 0.036 mmol), stirred in DMF (1 mL) under a nitrogen atmosphere, was added potassium carbonate (0.009 g, 0.065 mmol) and the resulting reaction mixture was stirred at room temperature for 2 h. The crude reaction mixture was diluted with dichloromethane, washed with water and brine, dried over MgSO$_4$, filtered and concentrated. The crude residue obtained was purified by preparative HPLC (Method A) to give the pure title compound (0.010 g, 68%). LC (Method A): 2.376 min. LCMS (ESI): calcd for $C_{23}H_{22}FN_4O_5S_2$ $[M+H]^+$ m/z 517.1016, found 517.1054. $^1H$ NMR (DMSO-$d_6$, 400 MHz) δ ppm: 2.01-2.15 (m, 2H), 2.17-2.39 (m, 2H), 3.63-3.77 (m, 2H), 3.78-3.90 (m, 2H), 3.81 (s, 3H), 4.20 (s, 3H), 5.32 (s, 2H), 6.62 (d, J=2.0 Hz, 1H), 6.84 (d, J=0.8 Hz, 1H), 7.00 (s, 1H), 7.93 (s, 1H), 8.37 (s, 1H).

Example 120

2-Methoxy-6-(6-methoxy-4-((2-(4-methoxytetrahydro-2H-pyran-4-yl)thiazol-4-yl)methoxy)benzofuran-2-yl)imidazo[2,1-b][1,3,4]thiadiazole

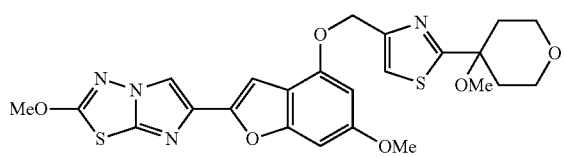 [SMILES: COc1cc(OCc2csc(C3(OC)CCOCC3)n2)c2cc(-c3cn4nc(OC)sc4n3)oc2c1]

120A. 4-(((tert-Butyldimethylsilyl)oxy)methyl)-2-(4-methoxytetrahydro-2H-pyran-4-yl)thiazole

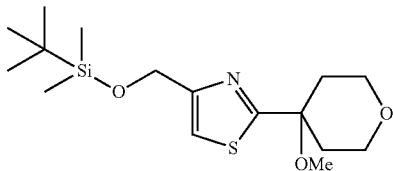 [SMILES: COC1(c2nc(CO[Si](C)(C)C(C)(C)C)cs2)CCOCC1]

To a suspension of sodium hydride (0.097 g, 2.428 mmol) [Note: 60% NaH in oil was washed free of oil with hexanes (×2) before dry THF was added to the reaction flask] in dry THF (5 mL) under $N_2$ was added a solution of 4-(4-(((tert-butyldimethylsilyl)oxy)methyl)thiazol-2-yl)tetrahydro-2H-pyran-4-ol (Example 118A, 0.400 g, 1.214 mmol) in dry THF (3 mL) and the mixture was stirred at room temperature until there was no more gas evolution (ca. 30 min). To the resulting pale yellow mixture was added iodomethane (0.091 mL, 1.457 mmol) dropwise and stirring was continued at room temperature for 16 h. The reaction mixture was then quenched by the careful addition of saturated aqueous $NH_4Cl$ (5 mL) and was subsequently partitioned with EtOAc-water. The organic phase was separated, dried ($Na_2SO_4$) and evaporated to give a nearly colorless oil. Flash chromatography (Isco/0-50% EtOAc-hexane) afforded 4-(((tert-butyldimethylsilyl)oxy)methyl)-2-(4-methoxytetrahydro-2H-pyran-4-yl)thiazole (0.362 g, 87%) as a colorless oil which was used as such in the next step. LC (Method A): 2.442 min. HRMS(ESI): calcd for $C_{16}H_{30}NO_3SSi$ $[M+H]^+$ m/z 344.171; found 344.173. $^1H$ NMR (400 MHz, DMSO-$d_6$): δ 7.42 (s, 1H), 4.67 (s, 2H), 3.58 (m, 4H), 2.99 (s, 3H), 2.01 (m, 2H), 1.87 (m, 2H), 0.81 (s, 9H), 0.00 (s, 6H).

120B. (2-(4-Methoxytetrahydro-2H-pyran-4-yl)thiazol-4-yl)methanol

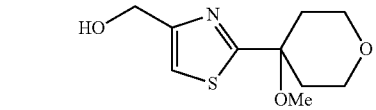 [SMILES: COC1(c2nc(CO)cs2)CCOCC1]

To a solution of 4-(((tert-butyldimethylsilyl)oxy)methyl)-2-(4-methoxytetrahydro-2H-pyran-4-yl)thiazole (0.358 g, 1.042 mmol) in dry THF (10 mL) under $N_2$ was added triethylamine trihydrofluoride (0.848 mL, 5.21 mmol) dropwise and the mixture was stirred at room temperature for 5 h. The mixture was then diluted with DCM and the solution was washed (saturated aqueous $NaHCO_3$), dried ($Na_2SO_4$) and evaporated to give (2-(4-methoxytetrahydro-2H-pyran-4-yl)thiazol-4-yl)methanol (0.227 g, 95%) as a nearly colorless gum which was used as such in the next step. LC (Method A): 1.301 min. HRMS(ESI): calcd for $C_{10}H_{16}NO_3S$ $[M+H]^+$ m/z 230.085; found 230.085. $^1H$ NMR (400 MHz, DMSO-$d_6$): δ 7.38 (t, J=1.17 Hz, 1H), 5.23 (t, J=5.48 Hz, 1H), 4.48 (dt, J=1.17, 5.48 Hz, 2H), 3.58 (m, 4H), 2.99 (s, 3H), 2.01 (m, 2H), 1.87 (m, 2H).

Example 120. 2-Methoxy-6-(6-methoxy-4-((2-(4-methoxytetrahydro-2H-pyran-4-yl)thiazol-4-yl)methoxy)benzofuran-2-yl)imidazo[2,1-b][1,3,4]thiadiazole

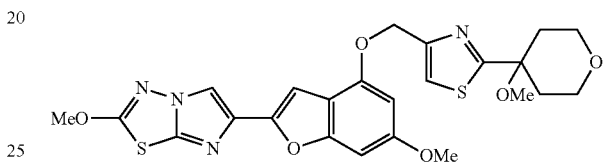

To a flame-dried flask was added 6-methoxy-2-(2-methoxyimidazo[2,1-b][1,3,4]thiadiazol-6-yl)benzofuran-4-ol (Example 1H, 0.040 g, 0.126 mmol) and (2-(4-methoxytetrahydro-2H-pyran-4-yl)thiazol-4-yl)methanol (0.036 g, 0.158 mmol), then the flask was flushed with $N_2$ and dry THF (2 mL) was added. To the resulting suspension was added tri-n-butylphosphine (0.082 mL, 0.315 mmol) and then a solution of 1,1'-(azodicarbonyl)dipiperidine (0.080 g, 0.315 mmol) in dry THF (2 mL) was added dropwise (via syringe pump) over 30 min. The resulting mixture was stirred at room temperature for another 1 h and then it was diluted with EtOAc, washed (saturated aqueous $NaHCO_3$, $H_2O$, brine), dried ($Na_2SO_4$) and evaporated to give a pale yellow gum. Flash chromatography (Isco/0-50% ether-DCM) gave 2-methoxy-6-(6-methoxy-4-((2-(4-methoxytetrahydro-2H-pyran-4-yl)thiazol-4-yl)methoxy)benzofuran-2-yl)imidazo[2,1-b][1,3,4]thiadiazole (0.045 g, 67.5%) as a white solid. LC (Method A): 2.348 min. HRMS(ESI): calcd for $C_{24}H_{25}N_4O_6S_2$ $[M+H]^+$ m/z 529.122; found 529.124. $^1H$ NMR (400 MHz, DMSO-$d_6$): δ 8.33 (s, 1H), 7.84 (s, 1H), 6.95 (s, 1H), 6.80 (s, 1H), 6.59 (d, J=1.57 Hz, 1H), 5.23 (s, 2H), 4.17 (s, 3H), 3.77 (s, 3H), 3.64 (m, 4H), 3.06 (s, 3H), 2.09 (m, 2H), 1.95 (m, 2H).

Example 121

4-(4-(((6-Methoxy-2-(2-methoxyimidazo[2,1-b][1,3,4]thiadiazol-6-yl)benzofuran-4-yl)oxy)methyl)thiazol-2-yl)-2,6-dimethyltetrahydro-2H-pyran-4-ol

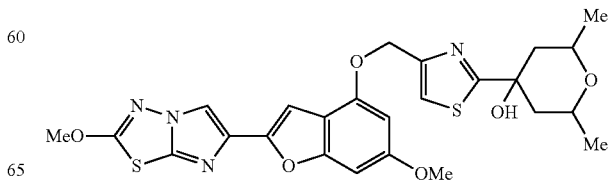

121A. 4-(4-(((tert-Butyldimethylsilyl)oxy)methyl)thiazol-2-yl)-2,6-dimethyltetrahydro-2H-pyran-4-ol

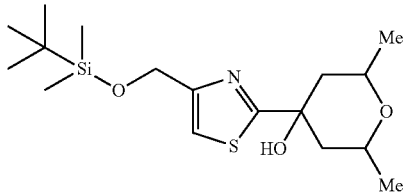 [SMILES: CC1CC(O)(c2nc(CO[Si](C)(C)C(C)(C)C)cs2)CC(C)O1]

A solution of 2-bromo-4-(((tert-butyldimethylsilyl)oxy)methyl)thiazole (Example 37B, 5.00 g, 16.22 mmol) in dry THF (75 mL) was cooled at −78° C. under $N_2$ and then 1.45 M n-butyllithium (11.89 mL, 17.84 mmol) was added dropwise. The resulting mixture was stirred for 15 min to give a pale brown solution. To this mixture was slowly added a solution of 3,5-dimethyldihydro-2H-pyran-4(3H)-one (2.494 g, 19.46 mmol) [Aube, J. et al., *J. Org. Chem.*, 69:1716 (2004)] in dry THF (5 mL) and stirring was continued at −78° C. for 2 h to give a light brown solution. The reaction was then quenched by the addition of saturated aqueous $NH_4Cl$ (10 mL), the cooling bath was removed and the mixture was partitioned with EtOAc-water. The organic phase was separated, washed (water, brine), dried ($Na_2SO_4$) and evaporated to give a pale yellow oil. Flash chromatography (Isco/0-100% EtOAc-toluene) gave the impure product as a colorless oil (2.11 g). This material was rechromatographed (Isco/0-50% ether-chloroform) to give 4-(4-(((tert-butyldimethylsilyl)oxy)methyl)thiazol-2-yl)-2,6-dimethyltetrahydro-2H-pyran-4-ol (1.767 g, 30.5%) as a viscous oil which solidified on standing. This material was used as such in the next step. LC (Method A): 2.352 min. HRMS(ESI): calcd for $C_{17}H_{32}NO_3SSi$ [M+H]$^+$ m/z 358.187; found 358.188. $^1$H NMR (400 MHz, DMSO-d$_6$): δ 7.30 (s, 1H), 5.94 (s, 1H), 4.64 (s, 2H), 3.78 (ddq, J=1.57, 6.26, 12.52 Hz, 2H), 1.98 (d, J=12.52 Hz, 2H), 1.36 (t, J=12.52 Hz, 2H), 1.00 (d, J=6.26 Hz, 6H), 0.80 (s, 9H), 0.00 (s, 6H).

121B. 4-(4-(Hydroxymethyl)thiazol-2-yl)-2,6-dimethyltetrahydro-2H-pyran-4-ol

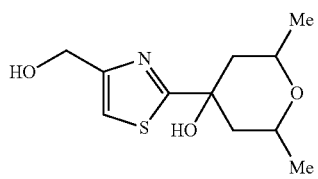

To a solution of 4-(4-(((tert-butyldimethylsilyl)oxy)methyl)thiazol-2-yl)-2,6-dimethyltetrahydro-2H-pyran-4-ol (1.742 g, 4.87 mmol) in dry THF (30 mL) under $N_2$ was added triethylamine trihydrofluoride (2.380 mL, 14.61 mmol) dropwise and the mixture was stirred at room temperature for 14 h. The mixture was then diluted with DCM and the solution was washed (saturated aqueous NaHCO$_3$), dried (Na$_2$SO$_4$) and evaporated to give the product (0.800 g, 68%) as a pale yellow solid. The aqueous phase was saturated with solid NaCl and extracted with EtOAc (×2) to give (after separation, drying and evaporation of the combined organic phase) an additional 0.329 g (28%) of the product as a white crystalline solid. The solids were combined to give 4-(4-(hydroxymethyl)thiazol-2-yl)-2,6-dimethyltetrahydro-2H-pyran-4-ol (1.129 g, 95%) which was essentially pure and was used as such in the next step. LC (Method A): 1.210 min. HRMS(ESI): calcd for $C_{11}H_{18}NO_3S$ [M+H]$^+$ m/z 244.100; found 244.101. $^1$H NMR (400 MHz, DMSO-d$_6$): δ 7.29 (s, 1H), 5.95 (s, 1H), 5.20 (t, J=5.87 Hz, 1H), 4.48 (d, J=5.48 Hz, 2H), 3.78 (ddq, J=1.96, 6.26, 11.35 Hz, 2H), 2.02 (d, J=12.91 Hz, 2H), 1.39 (t, J=11.74 Hz, 2H), 1.04 (d, J=6.26 Hz, 6H).

Example 121. 4-(4-(((6-Methoxy-2-(2-methoxyimidazo[2,1-b][1,3,4]thiadiazol-6-yl)benzofuran-4-yl)oxy)methyl)thiazol-2-yl)-2,6-dimethyltetrahydro-2H-pyran-4-ol

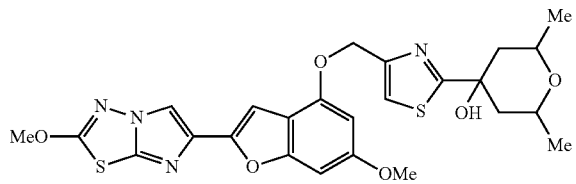 [SMILES: COc1cc(OCc2csc(C3(O)CC(C)OC(C)C3)n2)c2cc(-c3cn4nc(OC)sc4n3)oc2c1]

To a flame-dried flask was added 6-methoxy-2-(2-methoxyimidazo[2,1-b][1,3,4]thiadiazol-6-yl)benzofuran-4-ol (Example 1H, 0.600 g, 1.891 mmol) and 4-(4-(hydroxymethyl)thiazol-2-yl)-2,6-dimethyltetrahydro-2H-pyran-4-ol (0.552 g, 2.269 mmol), then the flask was flushed with $N_2$ and dry THF (20 mL) was added. To the resulting suspension was added tri-n-butylphosphine (1.228 mL, 4.73 mmol) and then a solution of 1,1'-(azodicarbonyl)dipiperidine (1.205 g, 4.73 mmol) in dry THF (8 mL) was added dropwise (via syringe pump) over 30 min. The resulting mixture was stirred at room temperature for another 1 h and then it was quenched with saturated aqueous NaHCO$_3$ and partitioned with DCM-water. The organic extract was separated, dried (Na$_2$SO$_4$) and evaporated to give a pale yellow solid. Flash chromatography (Isco/0-100% EtOAc-DCM) gave a solid which was triturated with MeCN to give (after filtration, washing with a minimum volume of MeCN and drying in vacuo) 4-(4-(((6-methoxy-2-(2-methoxyimidazo[2,1-b][1,3,4]thiadiazol-6-yl)benzofuran-4-yl)oxy)methyl)thiazol-2-yl)-2,6-dimethyltetrahydro-2H-pyran-4-ol (679 mg, 66%) as a cream solid. LC (Method A): 2.202 min. HRMS(ESI): calcd for $C_{25}H_{27}N_4O_6S_2$ [M+H]$^+$ m/z 543.137; found 543.140. $^1$H NMR (400 MHz, DMSO-d$_6$): δ 8.30 (s, 1H), 7.68 (s, 1H), 6.89 (s, 1H), 6.76 (s, 1H), 6.59 (d, J=1.96 Hz, 1H), 6.01 (s, 1H), 5.22 (s, 2H), 4.14 (s, 3H), 3.76 (m, 2H), 3.73 (s, 3H), 2.00 (d, J=11.76 Hz, 2H), 1.37 (t, J=11.74 Hz, 2H), 0.99 (d, J=6.26 Hz, 6H).

Example 122

6-(4-((2-(4-Fluoro-2,6-dimethyltetrahydro-2H-pyran-4-yl)thiazol-4-yl)methoxy)-6-methoxybenzofuran-2-yl)-2-methoxy-imidazo[2,1-b][1,3,4]thiadiazole

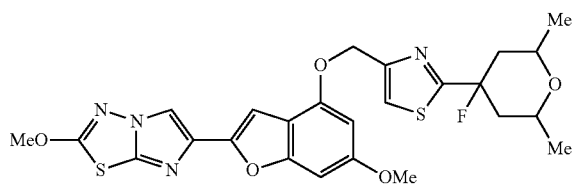 [SMILES: COc1cc(OCc2csc(C3(F)CC(C)OC(C)C3)n2)c2cc(-c3cn4nc(OC)sc4n3)oc2c1]

To an ice-cold suspension of 4-(4-(((6-methoxy-2-(2-methoxyimidazo[2,1-b][1,3,4]thiadiazol-6-yl)benzofuran-4-yl)oxy)methyl)thiazol-2-yl)-2,6-dimethyltetrahydro-2H-pyran-4-ol (0.023 g, 0.042 mmol) in DCM (3 mL) under N₂ was added DAST (0.014 mL, 0.106 mmol) dropwise and the resulting mixture was stirred at 0° C. for 20 min. Another aliquot of DAST (0.007 mL, 0.053 mmol) was added, the cooling bath was removed and the resulting pale yellow solution was stirred at room temperature for 16 h. The reaction mixture was then re-cooled at 0° C. and quenched by the dropwise addition of saturated aqueous NaHCO₃ (3 mL). The mixture was vigorously stirred at 0° C. for 5 min and then the cooling bath was removed and stirring was continued until no more gas evolution was observed. The organic phase was subsequently separated and applied directly to a silica gel pre-column. Flash chromatography (Isco/0-100% EtOAc-hexane) afforded 6-(4-((2-(4-fluoro-2,6-dimethyltetrahydro-2H-pyran-4-yl)thiazol-4-yl)methoxy)-6-methoxybenzofuran-2-yl)-2-methoxy-imidazo[2,1-b][1,3,4]thiadiazole (0.020 g, 87% yield) as a colorless gum which was lyophilized from MeCN-water to give a white solid. NMR indicated that this was a 3:2 mixture of isomers. LC (Method A): 2.470 min. HRMS(ESI): calcd for C₂₅H₂₆FN₄O₅S₂ [M+H]⁺ m/z 545.133; found 545.135. ¹H NMR (400 MHz, DMSO-d₆): δ 8.31 (s, 0.4H), 8.30 (s, 0.6H), 7.97 (s, 0.6H), 7.84 (s, 0.4H), 6.93 (s, 0.4H), 6.91 (s, 0.6H), 6.77 (m, 1H), 6.58 (d, J=1.96 Hz, 0.6H), 6.56 (d, J=1.57 Hz, 0.4H), 5.29 (s, 1.2H), 5.23 (s, 0.8H), 4.14 (s, 3H), 3.76 (m, 0.8H), 3.74 (s, 1.2H), 3.73 (s, 1.8H), 3.53 (m, 1.2H), 2.38 (dd, J=1.96, 12.52 Hz, 1H), 2.07 (m, 1H), 1.83-1.61 (m, 2H), 1.10 (d, J=6.26 Hz, 2.4H), 1.08 (d, J=6.26 Hz, 3.6H).

Example 123

3-(4-(((6-Methoxy-2-(2-methoxyimidazo[2,1-b][1,3,4]thiadiazol-6-yl)benzo-furan-4-yl)oxy)methyl)thiazol-2-yl)tetrahydrofuran-3-ol

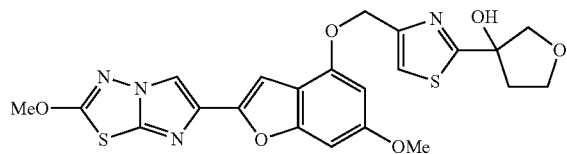 [SMILES: COc1cc(OCc2csc(C3(O)CCOC3)n2)c2cc(-c3cn4nc(OC)sc4n3)oc2c1]

123A. 3-(4-(((tert-Butyldimethylsilyl)oxy)methyl)thiazol-2-yl)tetrahydrofuran-3-ol

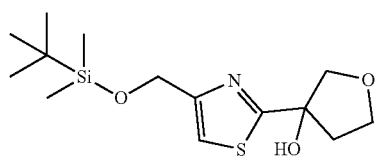 [SMILES: CC(C)(C)[Si](C)(C)OCc1csc(C2(O)CCOC2)n1]

A solution of 2-bromo-4-(((tert-butyldimethylsilyl)oxy)methyl)thiazole (Example 37B, 1.542 g, 5.000 mmol) in dry THF (20 mL) was cooled at −78° C. under N₂ and then 1.45 M n-butyllithium (3.79 mL, 5.50 mmol) was added dropwise. The resulting mixture was stirred for 15 min to give a pale yellow-brown solution. To this mixture was slowly added a solution of dihydrofuran-3(2H)-one (0.517 g, 6.00 mmol) in dry THF (2.5 mL) and the mixture was stirred at −78° C. for 1 h, to give a light brown solution. The reaction was then quenched by the addition of saturated aqueous NH₄Cl (5 mL), the cooling bath was removed and the mixture was partitioned with EtOAc-water. The organic phase was separated, washed (brine), dried (Na₂SO₄) and evaporated to give a pale yellow oil. Flash chromatography (Isco/0-50% EtOAC-hexane) afforded 3-(4-(((tert-butyldimethylsilyl)oxy)methyl)thiazol-2-yl)tetrahydrofuran-3-ol (1.052 g, 66.7%) as an oil which crystallized on standing in vacuo. This material was used as such in the next step. LC (Method A): 2.226 min. HRMS(ESI): calcd for C₁₄H₂₆NO₃SSi [M+H]⁺ m/z 316.140; found 316.147. ¹H NMR (400 MHz, DMSO-d₆): δ 7.28 (s, 1H), 6.32 (s, 1H), 4.65 (s, 2H), 3.92 (m, 2H), 3.78 (q, J=9.00 Hz, 2H), 2.36 (dt, J=9.00, 12.52 Hz, 1H), 2.09 (dt, J=5.09, 12.52 Hz, 1H), 0.82 (s, 9H), 0.00 (s, 6H).

123B. 3-(4-(Hydroxymethyl)thiazol-2-yl)tetrahydrofuran-3-ol

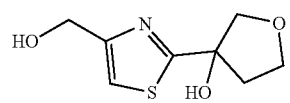 [SMILES: OCc1csc(C2(O)CCOC2)n1]

To a solution of 3-(4-(((tert-butyldimethylsilyl)oxy)methyl)thiazol-2-yl)tetrahydrofuran-3-ol (1.022 g, 3.24 mmol) in dry THF (20 mL) under N₂ was added triethylamine trihydrofluoride (1.319 mL, 8.10 mmol) dropwise and the mixture was stirred at room temperature for 16 h. The mixture was then diluted with DCM and then saturated aqueous NaHCO₃ was added (Caution: vigorous gas evolution). The organic phase was separated, washed (saturated aqueous NaHCO₃), dried (Na₂SO₄) and evaporated to give a colorless gum which solidified on standing in vacuo. The aqueous phase was saturated with solid NaCl and back-extracted with DCM to give (after drying as before) additional colorless gum which also solidified on standing. These solids were combined to give 3-(4-(hydroxymethyl)thiazol-2-yl)tetrahydrofuran-3-ol as a cream solid. This material was used as such in the next step without further purification. LC (Method A): 0.734 min. HRMS(ESI): calcd for C₉H₁₂NO₃S [M+H]⁺ m/z 202.054; found 202.055. ¹H NMR (400 MHz, DMSO-d₆): δ 7.18 (s, 1H), 6.23 (s, 1H), 5.12 (br s, 1H), 4.37 (s, 2H), 3.85 (dd, J=1.57, 9.00 Hz, 1H), 3.84 (d, J=9.00 Hz, 1H), 3.74 (d, J=9.00 Hz, 1H), 3.68 (d, J=9.00 Hz, 1H), 2.29 (dt, J=9.00, 12.91 Hz, 1H), 2.02 (dt, J=5.09, 12.52 Hz, 1H).

Example 123. 3-(4-(((6-Methoxy-2-(2-methoxyimidazo[2,1-b][1,3,4]thiadiazol-6-yl)benzofuran-4-yl)oxy)methyl)thiazol-2-yl)tetrahydrofuran-3-ol

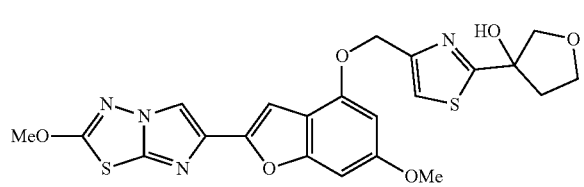 [SMILES: COc1cc(OCc2csc(C3(O)CCOC3)n2)c2cc(-c3cn4nc(OC)sc4n3)oc2c1]

249

To a flame-dried flask was added 6-methoxy-2-(2-methoxyimidazo[2,1-b][1,3,4]thiadiazol-6-yl)benzofuran-4-ol (Example 1H, 0.063 g, 0.200 mmol) and 3-(4-(hydroxymethyl)thiazol-2-yl)tetrahydrofuran-3-ol (0.040 g, 0.200 mmol), then the flask was flushed with $N_2$ and dry THF (5 mL) was added. To the resulting suspension was added tri-n-butylphosphine (0.123 mL, 0.500 mmol) and then a solution of 1,1'-(azodicarbonyl)dipiperidine (0.127 g, 0.500 mmol) in dry THF (2 mL) was added dropwise (via syringe pump) over 30 min. The resulting mixture was stirred at room temperature for another 1 h and then it was diluted with EtOAc, washed (saturated aqueous $NaHCO_3$, $H_2O$, brine), dried ($Na_2SO_4$) and evaporated to give a pale yellow semi-solid. Flash chromatography (Isco/0-100% EtOAc-DCM) gave 3-(4-(((6-methoxy-2-(2-methoxyimidazo[2,1-b][1,3,4]thiadiazol-6-yl)benzofuran-4-yl)oxy)methyl)thiazol-2-yl)tetrahydrofuran-3-ol (0.015 g, 14.98%) as a solid. LC (Method A): 2.161 min. HRMS(ESI): calcd for $C_{22}H_{21}N_4O_6S_2$ $[M+H]^+$ m/z 501.090; found 501.092. $^1$H NMR (400 MHz, DMSO-$d_6$): δ 8.33 (s, 1H), 7.71 (s, 1H), 6.95 (s, 1H), 6.80 (s, 1H), 6.58 (d, J=1.57 Hz, 1H), 6.44 (s, 1H), 5.23 (s, 2H), 4.17 (s, 3H), 3.98 (d, J=5.09 Hz, 1H), 3.96 (d, J=5.48 Hz, 1H), 3.88 (d, J=9.00 Hz, 1H), 3.83 (d, J=9.00 Hz, 1H), 3.77 (s, 3H), 2.43 (m, 1H), 2.16 (dt, J=5.09, 12.52 Hz, 2H).

Example 124

4-(4-(((6-Methoxy-2-(2-methoxyimidazo[2,1-b][1,3,4]thiadiazol-6-yl)benzofuran-4-yl)oxy)methyl)-5-methylthiazol-2-yl)tetrahydro-2H-pyran-4-ol

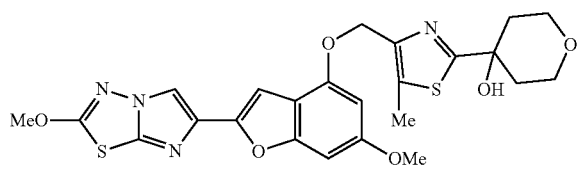 [SMILES: COc1cc(OCc2nc(C3(O)CCOCC3)sc2C)c2cc(-c3cn4nc(OC)sc4n3)oc2c1]

124A. (5-Methylthiazol-4-yl)methanol

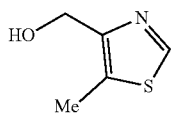

To an ice-cold solution of ethyl 5-methylthiazole-4-carboxylate (2.57 g, 15.00 mmol) in dry THF (50 mL) under $N_2$ was added lithium borohydride (0.654 g, 30.0 mmol) all at once, followed by MeOH (1.214 mL, 30.0 mmol) dropwise. The cooling bath was then removed and the mixture was stirred at room temperature for 16 h. The mixture was then re-cooled at 0° C. and cautiously quenched by the slow addition of saturated aqueous $NH_4Cl$ (20 mL) with vigorous stirring. The cooling bath was then removed and the mixture was partitioned with EtOAc-water. The organic phase was separated and then it was washed with water and brine. The combined aqueous phase was saturated with solid NaCl and back-extracted with EtOAc (×4). The combined organic phase was dried ($Na_2SO_4$) and evaporated to give a yellow oil which was purified by flash chromatography (Isco/0-

250

100% EtOAc-DCM) to give (5-methylthiazol-4-yl)methanol (1.144 g, 59.0%) as a nearly colorless oil which crystallized on standing in vacuo to give a solid. This material was used as such in the next step. LC (Method X): 0.620 min. HRMS(ESI): calcd for $C_5H_8NOS$ $[M+H]^+$ m/z 130.032; found 130.032. $^1$H NMR (400 MHz, DMSO-$d_6$): δ 8.75 (s, 1H), 4.98 (br s, 1H), 4.46 (s, 2H), 2.40 (s, 3H).

124B. 4-(((tert-Butyldimethylsilyl)oxy)methyl)-5-methylthiazole

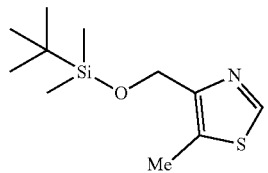

To a solution of (5-methylthiazol-4-yl)methanol (1.134 g, 8.78 mmol) and imidazole (1.793 g, 26.3 mmol) in DMF (40 mL) under $N_2$ was added tert-butyldimethylchlorosilane (1.455 g, 9.66 mmol) and the resulting mixture was stirred at room temperature under $N_2$ for 16 h. The solution was then concentrated under reduced pressure and the residual oil was partitioned with EtOAc-saturated aqueous $NH_4Cl$. The organic phase was separated, washed (water, brine), dried ($Na_2SO_4$) and evaporated to give a pale yellow, viscous oil. Flash chromatography (Isco/0-10% EtOAc-DCM) afforded 4-(((tert-butyldimethylsilyl)oxy)methyl)-5-methylthiazole (1.484 g, 69.4%) as a colorless oil which was used as such in the next step. LC (Method A): 2.272 min. HRMS(ESI): calcd for $C_{11}H_{22}NOSSi$ $[M+H]^+$ m/z 244.119; found 244.123. $^1$H NMR (400 MHz, $CDCl_3$): δ 8.46 (s, 1H), 4.74 (s, 2H), 2.43 (s, 3H), 0.82 (s, 9H), 0.00 (s, 6H).

124C. 4-(4-(((tert-Butyldimethylsilyl)oxy)methyl)-5-methylthiazol-2-yl)tetrahydro-2H-pyran-4-ol

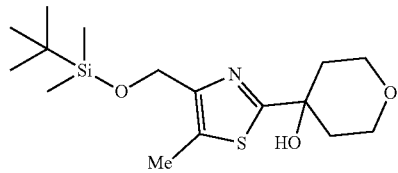 [SMILES: Cc1sc(C2(O)CCOCC2)nc1CO[Si](C)(C)C(C)(C)C]

A solution of 4-(((tert-butyldimethylsilyl)oxy)methyl)-5-methylthiazole (1.480 g, 6.08 mmol) in dry THF (45 mL) was cooled at −78° C. under $N_2$ and then n-butyllithium (1.45 M in hexanes, 5.03 mL, 7.30 mmol) was added dropwise. The initially colorless solution became bright purple near the end of the addition and the resulting mixture was stirred for 15 min at the same temperature. To this purple solution was slowly added a solution of dihydro-2H-pyran-4(3H)-one (0.674 mL, 7.30 mmol) in dry THF (3 mL) and the solution was kept at −78° C. for 1 h, to give a pale orange solution. The reaction was then quenched by the addition of saturated aqueous $NH_4Cl$ (10 mL) and then the cooling bath was removed and the mixture was partitioned with EtOAc-water. The organic phase was separated, washed (brine), dried ($Na_2SO_4$) and evaporated to give a pale yellow oil. Flash chromatography (Isco/0-30% acetone-hexane) afforded 4-(4-(((tert-butyldimethylsilyl)oxy)methyl)-5-methylthiazol-2-yl)tetrahydro-2H-pyran-4-ol (1.865 g, 89%) as a colorless oil which was used as such in the next step. LC (Method A): 2.297 min. HRMS(ESI): calcd for $C_{16}H_{30}NO_3SSi$ [M+H]$^+$ m/z 344.172; found 344.176. $^1$H NMR (400 MHz, DMSO-$d_6$): δ 5.92 (s, 1H), 4.59 (s, 2H), 3.66 (m, 4H), 2.34 (s, 3H), 2.00 (m, 2H), 1.57 (d, J=12.91 Hz, 2H), 0.81 (s, 9H), 0.00 (s, 6H).

124D. 4-(4-(Hydroxymethyl)-5-methylthiazol-2-yl)tetrahydro-2H-pyran-4-ol

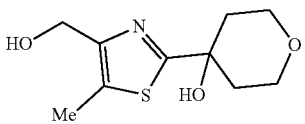 [SMILES: Cc1sc(C2(O)CCOCC2)nc1CO]

To a solution of 4-(4-(((tert-butyldimethylsilyl)oxy)methyl)-5-methylthiazol-2-yl)tetrahydro-2H-pyran-4-ol (1.861 g, 5.42 mmol) in dry THF (15 mL) under $N_2$ was added triethylamine trihydrofluoride (2.65 mL, 16.25 mmol) dropwise and the mixture was stirred at room temperature for 18 h. The mixture was then concentrated to about one-half volume under reduced pressure and the concentrate was diluted with DCM and the solution was washed (saturated aqueous $NaHCO_3$), dried ($Na_2SO_4$) and evaporated to give 4-(4-(hydroxymethyl)-5-methylthiazol-2-yl)tetrahydro-2H-pyran-4-ol (1.114 g, 90%) as a white solid. This material was essentially pure and was used as such in the next step. LC (Method A): 1.062 min. HRMS(ESI): calcd for $C_{10}H_{16}NO_3S$ [M+H]$^+$ m/z 230.085; found 230.086. $^1$H NMR (400 MHz, DMSO-$d_6$): δ 5.90 (s, 1H), 4.93 (t, J=5.87 Hz, 1H), 4.38 (d, J=5.48 Hz, 2H), 3.67 (m, 4H), 2.34 (s, 3H), 2.02 (m, 2H), 1.58 (d, J=11.74 Hz, 2H).

Example 124. 4-(4-(((6-Methoxy-2-(2-methoxyimidazo[2,1-b][1,3,4]thiadiazol-6-yl)benzofuran-4-yl)oxy)methyl)-5-methylthiazol-2-yl)tetrahydro-2H-pyran-4-ol

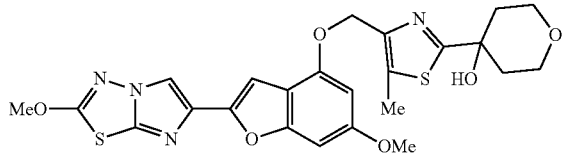 [SMILES: COc1cc(OCc2nc(C3(O)CCOCC3)sc2C)c2cc(-c3cn4nc(OC)sc4n3)oc2c1]

To a flame-dried flask was added 6-methoxy-2-(2-methoxyimidazo[2,1-b][1,3,4]thiadiazol-6-yl)benzofuran-4-ol (Example 1H, 0.060 g, 0.189 mmol) and 4-(4-(hydroxymethyl)-5-methylthiazol-2-yl)tetrahydro-2H-pyran-4-ol (0.054 g, 0.236 mmol), then the flask was flushed with $N_2$ and dry THF (3 mL) was added. To the resulting suspension was added tri-n-butylphosphine (0.123 mL, 0.473 mmol) and then a solution of 1,1'-(azodicarbonyl)dipiperidine (0.120 g, 0.473 mmol) in dry THF (2 mL) was added dropwise (via syringe pump) over 30 min. The resulting mixture was stirred at room temperature for another 1 h and then it was diluted with EtOAc, washed (saturated aqueous $NaHCO_3$, $H_2O$, brine), dried ($Na_2SO_4$) and evaporated to give a pale yellow semi-solid. Flash chromatography (Isco/0-100% EtOAc-DCM) gave 4-(4-(((6-methoxy-2-(2-methoxyimidazo[2,1-b][1,3,4]thiadiazol-6-yl)benzofuran-4-yl)oxy)methyl)-5-methylthiazol-2-yl)tetrahydro-2H-pyran-4-ol (0.077 g, 77%) as a white solid. LC (Method A): 2.214 min. HRMS(ESI): calcd for $C_{24}H_{25}N_4O_6S_2$ [M+H]$^+$ m/z 529.122; found 529.125. $^1$H NMR (400 MHz, DMSO-$d_6$): δ 8.30 (s, 1H), 6.83 (s, 1H), 6.76 (s, 1H), 6.59 (d, J=1.57 Hz, 1H), 5.98 (s, 1H), 5.13 (s, 2H), 4.13 (s, 3H), 3.74 (s, 3H), 3.65 (m, 4H), 2.39 (s, 3H), 2.02 (m, 2H), 1.58 (d, J=12.91 Hz, 2H).

Example 125

6-(4-((2-(4-Fluorotetrahydro-2H-pyran-4-yl)-5-methylthiazol-4-yl)methoxy)-6-methoxybenzofuran-2-yl)-2-methoxyimidazo[2,1-b][1,3,4]-thiadiazole

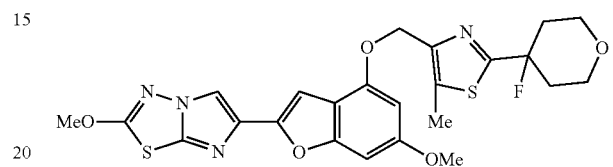

To an ice-cold suspension of 4-(4-(((6-methoxy-2-(2-methoxyimidazo[2,1-b][1,3,4]thiadiazol-6-yl)benzofuran-4-yl)oxy)methyl)-5-methylthiazol-2-yl)tetrahydro-2H-pyran-4-ol (0.025 g, 0.047 mmol) in DCM (3 mL) under $N_2$ was added DAST (0.016 mL, 0.118 mmol) dropwise and the resulting mixture was stirred at 0° C. for 20 min. The cooling bath was then removed and the resulting pale yellow solution was stirred at room temperature for 1 h. The reaction mixture was then re-cooled at 0° C. and quenched by the dropwise addition of saturated aqueous $NaHCO_3$ (3 mL). The mixture was vigorously stirred at 0° C. for 5 min and then the cooling bath was removed, the mixture was diluted with DCM and additional saturated aqueous $NaHCO_3$ and stirring was continued until no more gas evolution was observed. The organic phase was then separated and applied directly to a silica gel pre-column. Flash chromatography (Isco/0-100% EtOAc-hexane) afforded 6-(4-((2-(4-fluorotetrahydro-2H-pyran-4-yl)-5-methylthiazol-4-yl)methoxy)-6-methoxybenzo-furan-2-yl)-2-methoxyimidazo[2,1-b][1,3,4]thiadiazole (0.020 g, 80%) as a colorless gum which was lyophilized from MeCN-water to give a white solid. LC (Method A): 2.405 min. HRMS(ESI): calcd for $C_{24}H_{24}FN_4O_5S_2$ [M+H]$^+$ m/z 531.117; found 531.118. $^1$H NMR (400 MHz, DMSO-$d_6$): δ 8.30 (s, 1H), 6.83 (s, 1H), 6.77 (s, 1H), 6.58 (d, J=1.96 Hz, 1H), 5.18 (s, 2H), 4.13 (s, 3H), 3.74 (s, 3H), 3.74 (m, 2H), 3.62 (dt, J=1.96, 10.96 Hz, 2H), 2.45 (s, 3H), 2.23-2.10 (m, 2H), 1.99 (m, 2H).

Examples 126 and 127

8-(4-(((6-Methoxy-2-(2-methoxyimidazo[2,1-b][1,3,4]thiadiazol-6-yl)benzofuran-4-yl)oxy)methyl)-thiazol-2-yl)-1,4-dioxaspiro[4.5]decan-8-ol, and 6-(4-((2-(1,4-Dioxaspiro-[4.5]dec-7-en-8-yl)thiazol-4-yl)methoxy)-6-methoxybenzofuran-2-yl)-2-methoxyimidazo[2,1-b][1,3,4]thiadiazole, respectively

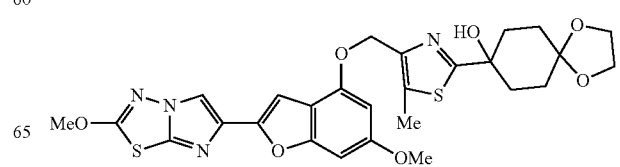

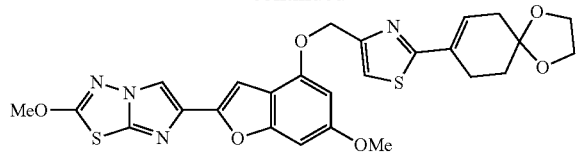

126A. 8-(4-(((tert-Butyldimethylsilyl)oxy)methyl)thiazol-2-yl)-1,4-dioxaspiro-[4.5]decan-8-ol

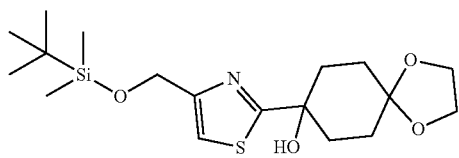 [SMILES: CC(C)(C)[Si](C)(C)OCc1csc(C2(O)CCC3(CC2)OCCO3)n1]

A solution of 2-bromo-4-(((tert-butyldimethylsilyl)oxy)methyl)thiazole (Example 37B, 1.00 g, 3.24 mmol) in dry THF (15 mL) was cooled at −78° C. under $N_2$ and then n-butyllithium (1.45 M in hexanes, 2.68 mL, 3.89 mmol) was added dropwise. The resulting mixture was stirred for 30 min to give a light yellow-brown solution. To this mixture was added dropwise a solution of 1,4-dioxaspiro[4.5]decan-8-one (0.608 g, 3.89 mmol) in dry THF (4 mL) and the mixture was kept at −78° C. for 2 h. The reaction was then quenched by the addition of saturated aqueous $NH_4Cl$ (5 mL), then the cooling bath was removed and the mixture was partitioned with EtOAc-water. The organic phase was separated, washed (brine), dried ($Na_2SO_4$) and evaporated to give a light yellow oil which was purified by flash chromatography (Isco/0-100% EtOAc-hexane) to give 8-(4-(((tert-butyldimethylsilyl)oxy)-methyl)thiazol-2-yl)-1,4-dioxaspiro[4.5]decan-8-ol (0.920 g, 73.6%) as a colorless gum which crystallized on standing in vacuo. This material was used as such in the next step. LC (Method A): 2.287 min. HRMS(ESI): calcd for $C_{18}H_{32}NO_4SSi$ $[M+H]^+$ m/z 386.182; found 386.182. $^1$H NMR (400 MHz, DMSO-$d_6$): δ 7.20 (s, 1H), 5.85 (s, 1H), 4.64 (s, 2H), 3.81 (s, 4H), 2.03 (dt, J=3.91, 12.91 Hz, 2H), 1.78 (dt, J=4.30, 13.30 Hz, 2H), 1.68 (d, J=12.91 Hz, 2H), 1.53 (d, J=12.52 Hz, 2H), 0.82 (s, 9H), 0.00 (s, 6H).

126B. 8-(4-(Hydroxymethyl)thiazol-2-yl)-1,4-dioxaspiro[4.5]decan-8-ol

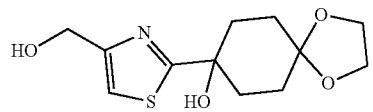 [SMILES: OCc1csc(C2(O)CCC3(CC2)OCCO3)n1]

To a solution of 8-(4-(((tert-butyldimethylsilyl)oxy)methyl)thiazol-2-yl)-1,4-dioxaspiro[4.5]decan-8-ol (0.916 g, 2.376 mmol) in dry THF (10 mL) under $N_2$ was added triethylamine trihydrofluoride (1.160 mL, 7.13 mmol) dropwise and the mixture was stirred at room temperature for 18 h. The mixture was then partitioned with EtOAc-saturated aqueous $NaHCO_3$ and the organic phase was washed (brine), dried ($Na_2SO_4$) and evaporated to give 8-(4-(hydroxymethyl)thiazol-2-yl)-1,4-dioxaspiro[4.5]decan-8-ol (0.579 g, 90%) as a colorless gum which crystallized on standing in vacuo. This material was essentially pure and was used as such in the next step. LC (Method A): 1.148 min. HRMS (ESI): calcd for $C_{12}H_{18}NO_4S$ $[M+H]^+$ m/z 272.096; found 272.095. $^1$H NMR (400 MHz, DMSO-$d_6$): δ 7.20 (s, 1H), 5.86 (s, 1H), 5.20 (t, J=5.48 Hz, 1H), 4.46 (d, J=5.09 Hz, 2H), 3.84 (s, 4H), 2.07 (dt, J=3.91, 12.91 Hz, 2H), 1.81 (dt, J=4.30, 13.30 Hz, 2H), 1.70 (d, J=12.91 Hz, 2H), 1.55 (d, J=12.52 Hz, 2H).

Examples 126 and 127. 8-(4-(((6-Methoxy-2-(2-methoxyimidazo[2,1-b][1,3,4]thiadiazol-6-yl)benzofuran-4-yl)oxy)methyl)-thiazol-2-yl)-1,4-dioxaspiro[4.5]decan-8-ol and 6-(4-((2-(1,4-dioxaspiro-[4.5]dec-7-en-8-yl)thiazol-4-yl)methoxy)-6-methoxybenzofuran-2-yl)-2-methoxyimidazo[2,1-b][1,3,4]thiadiazole

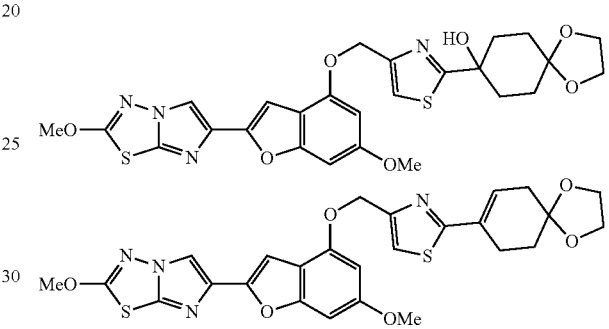

To a flame-dried flask was added 6-methoxy-2-(2-methoxyimidazo[2,1-b][1,3,4]thiadiazol-6-yl)benzofuran-4-ol (Example 1H, 0.600 g, 1.891 mmol) and 8-(4-(hydroxymethyl)thiazol-2-yl)-1,4-dioxaspiro[4.5]decan-8-ol (0.539 g, 1.985 mmol), then the flask was flushed with $N_2$ and dry THF (15 mL) was added. To the resulting suspension was added tri-n-butylphosphine (1.228 mL, 4.73 mmol) and then a solution of 1,1'-(azodicarbonyl)dipiperidine (1.205 g, 4.73 mmol) in dry THF (10 mL) was added over ca. 30 min (via syringe pump). The resulting mixture was stirred at room temperature for another 1 h and then it was diluted with EtOAc, washed (saturated aqueous $NaHCO_3$, $H_2O$, brine), dried ($Na_2SO_4$) and evaporated to give a light amber semi-solid. Flash chromatography (Isco/0-100% EtOAc-DCM) afforded 2 major products. Fraction 1 was identified as 6-(4-((2-(1,4-dioxaspiro[4.5]dec-7-en-8-yl)thiazol-4-yl)methoxy)-6-methoxybenzofuran-2-yl)-2-methoxyimidazo[2,1-b][1,3,4]thiadiazole (0.127 g, 12.15%) and was isolated as a white foam. This material was lyophilized from MeCN-water to give a cream solid. LC (Method A): 2.362 min. HRMS(ESI): calcd for $C_{26}H_{25}N_4O_6S_2$ $[M+H]^+$ m/z 553.121; found 553.122. $^1$H NMR (400 MHz, DMSO-$d_6$): δ 8.34 (s, 1H), 7.67 (s, 1H), 6.97 (s, 1H), 6.80 (s, 1H), 6.57 (s, 1H), 6.50 (br s, 1H), 5.24 (s, 2H), 4.17 (s, 3H), 3.89 (s, 4H), 3.77 (s, 3H), 2.63 (br s, 2H), 2.38 (br s, 2H), 1.79 (t, J=6.26 Hz, 2H). Fraction 2 was identified as 8-(4-(((6-methoxy-2-(2-methoxyimidazo[2,1-b][1,3,4]thiadiazol-6-yl)benzofuran-4-yl)oxy)methyl)thiazol-2-yl)-1,4-dioxaspiro-[4.5]decan-8-ol (0.254 g, 23.54%) and was isolated as an off-white foam. This material was lyophilized from MeCN-water to give a cream solid. LC (Method A): 2.193 min. HRMS(ESI): calcd for $C_{26}H_{27}N_4O_7S_2$ $[M+H]^+$ m/z 571.132; found 571.132. $^1$H NMR (400 MHz, DMSO-$d_6$): δ 8.29 (s, 1H), 7.58 (s, 1H), 6.89 (s, 1H), 6.75 (s, 1H), 6.53 (s, 1H), 5.92 (s, 1H), 5.16 (s, 2H), 4.12 (s, 3H), 3.80 (s, 4H), 3.73 (s, 3H), 2.06 (dt, J=3.13, 12.91 Hz, 2H), 1.78 (dt, J=3.52, 13.30 Hz, 2H), 1.70 (d, J=13.30 Hz, 2H), 1.53 (d, J=12.52 Hz, 2H).

Example 128

4-Hydroxy-4-(4-(((6-methoxy-2-(2-methoxyimidazo[2,1-b][1,3,4]thiadiazol-6-yl)benzofuran-4-yl)oxy)methyl)thiazol-2-yl)cyclohexan-one

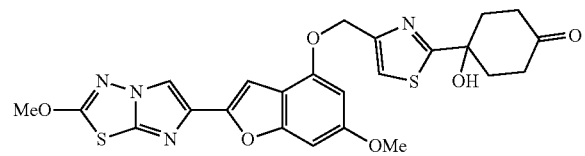 [SMILES: COc1cc(OCc2csc(C3(O)CCC(=O)CC3)n2)c2cc(-c3cn4nc(OC)sc4n3)oc2c1]

To a mixture of 8-(4-(((6-methoxy-2-(2-methoxyimidazo[2,1-b][1,3,4]thiadiazol-6-yl)benzofuran-4-yl)oxy)methyl)thiazol-2-yl)-1,4-dioxaspiro[4.5]decan-8-ol (0.013 g, 0.023 mmol) in DCM (1 mL) was added TFA (0.2 mL) and the resulting solution was stirred at room temperature in a sealed flask for 18 h. The volatiles were then evaporated to give the impure product as a solid. Flash chromatography (Isco/0-100% EtOAc-DCM) afforded 4-hydroxy-4-(4-(((6-methoxy-2-(2-methoxyimidazo[2,1-b][1,3,4]thiadiazol-6-yl)benzofuran-4-yl)oxy)-methyl)thiazol-2-yl)cyclohexanone (0.009 g, 75%) as a white solid. LC (Method A): 2.208 min. HRMS(ESI): calcd for $C_{24}H_{23}N_4O_6S_2$ $[M+H]^+$ m/z 527.105; found 527.106. $^1$H NMR (400 MHz, DMSO-$d_6$): δ 8.30 (s, 1H), 7.66 (s, 1H), 6.91 (s, 1H), 6.76 (s, 1H), 6.54 (d, J=1.57 Hz, 1H), 6.39 (s, 1H), 5.19 (s, 2H), 4.14 (s, 3H), 3.73 (s, 3H), 2.60 (m, 2H), 2.25 (dt, J=4.70, 14.09 Hz, 2H), 2.18 (m, 2H), 2.06 (m, 2H).

Example 129 tert-Butyl 4-hydroxy-4-(4-(((6-methoxy-2-(2-methoxyimidazo[2,1-b][1,3,4]thiadiazol-6-yl)benzofuran-4-yl)oxy)methyl)thiazol-2-yl)piperidine-1-carboxylate

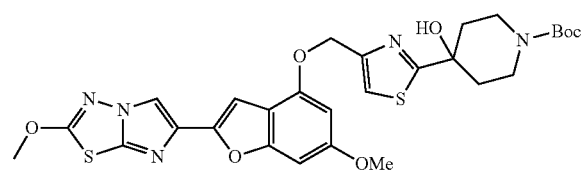 [SMILES: COc1cc(OCc2csc(C3(O)CCN(C(=O)OC(C)(C)C)CC3)n2)c2cc(-c3cn4nc(OC)sc4n3)oc2c1]

129A. tert-Butyl 4-(4-(((tert-butyldimethylsilyl)oxy)methyl)thiazol-2-yl)-4-hydroxypiperidine-1-carboxylate

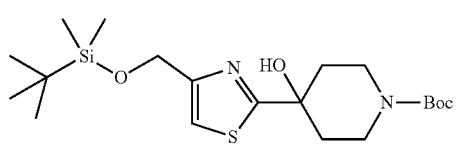 [SMILES: CC(C)(C)OC(=O)N1CCC(O)(c2nc(CO[Si](C)(C)C(C)(C)C)cs2)CC1]

A solution of 4-(((tert-butyldimethylsilyl)oxy)methyl)thiazole (0.738 g, 3.22 mmol) in dry THF (8 mL) was cooled at −78° C. under $N_2$ and then n-butyllithium (1.45 M in hexanes, 2.440 mL, 3.54 mmol) was added dropwise. The resulting mixture was stirred for 35 min to give a pale brown solution. To this mixture was slowly added a solution of tert-butyl 4-oxopiperidine-1-carboxylate (0.769 g, 3.86 mmol) in dry THF (2 mL) and the mixture was stirred at −78° C. for 2 h to give a light brown solution. The reaction was then quenched by the addition of saturated aqueous $NH_4Cl$ (5 mL), the cooling bath was removed and the mixture was partitioned with EtOAc-water. The organic phase was separated, washed with brine, dried ($MgSO_4$) and evaporated to give a yellow oil. This oil was purified by flash chromatography using hexanes-EtOAc as eluent to give tert-butyl 4-(4-(((tert-butyldimethylsilyl)oxy)methyl)thiazol-2-yl)-4-hydroxypiperidine-1-carboxylate (0.850 g, 61.6%) as a clear, colorless gum. LC (Method A): 2.427 min. LCMS (APCI): calcd for $C_{20}H_{37}N_2O_4SSi$ $[M+H]^+$ m/z 429.22, found 429.20.

129B. tert-Butyl 4-hydroxy-4-(4-(hydroxymethyl)thiazol-2-yl)piperidine-1-carboxylate

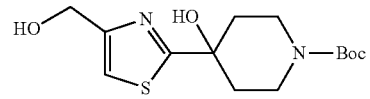

To a stirred solution of tert-butyl 4-(4-(((tert-butyldimethylsilyl)oxy)methyl)thiazol-2-yl)-4-hydroxypiperidine-1-carboxylate (0.850 g, 1.983 mmol) in THF (11 mL) was added triethylamine trihydrofluoride (1.60 mL, 9.83 mmol) and the reaction mixture was stirred at room temperature for 4 h. The resulting mixture was then partitioned with EtOAc-saturated aqueous $NaHCO_3$ and the organic phase was separated, dried ($MgSO_4$), filtered and concentrated to dryness. The residue was purified by flash chromatography using DCM-EtOAc as eluent to give tert-butyl 4-hydroxy-4-(4-(hydroxymethyl)thiazol-2-yl)piperidine-1-carboxylate (0.476 g, 77%) as a clear, colorless oil. LC (Method A): 1.670 min. $^1$H NMR (DMSO-$d_6$, 400 MHz) δ ppm: 7.27 (m, 1H), 6.09 (s, 1H), 5.23 (t, J=5.7 Hz, 1H), 4.50 (d, J=4.7 Hz, 2H), 6.82 (d, J=11.3 Hz, 2H), 3.12 (br s, 1H), 1.90 (m, 2H), 1.68 (d, J=12.9 Hz, 2H), 1.41 (s, 9H).

Example 129. tert-Butyl 4-hydroxy-4-(4-(((6-methoxy-2-(2-methoxyimidazo[2,1-b][1,3,4]thiadiazol-6-yl)benzofuran-4-yl)oxy)methyl)thiazol-2-yl)piperidine-1-carboxylate

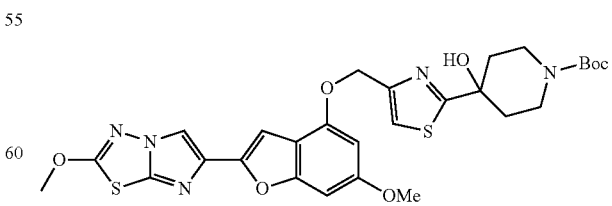

To a suspension of 6-methoxy-2-(2-methoxyimidazo[2,1-b][1,3,4]thiadiazol-6-yl)benzofuran-4-ol (Example 1H, 0.202 g, 0.636 mmol) and tert-butyl 4-hydroxy-4-(4-(hydroxymethyl)thiazol-2-yl)piperidine-1-carboxylate (0.200 g, 0.636 mmol) in dry THF (8 mL) was added tri-n-butylphosphine (0.413 mL, 1.590 mmol), followed by a solution of ADDP (0.401 g, 1.590 mmol) in THF (2 mL) added dropwise over 30 min via syringe pump. After stirring for another 30 min, the reaction mixture was partitioned between EtOAc and saturated aqueous NaHCO$_3$. The organic phase was separated, washed with brine, dried (MgSO$_4$), filtered and concentrated to dryness. The residue was purified by flash chromatography using DCM-EtOAc as eluent to give the title compound (0.263 g, 0.429 mmol, 67.4%) as a white solid. LC (Method A): 2.387 min. HRMS(ESI): calcd for $C_{28}H_{32}N_5O_7S_2$ [M+H]$^+$ m/z 614.1743, found 614.1755. $^1$H NMR (DMSO-d$_6$, 400 MHz) δ ppm: 8.37 (s, 1H), 7.70 (s, 1H), 6.97 (d, J=0.8 Hz, 1H), 6.83 (dd, J=0.8, 1.6 Hz, 1H), 6.61 (d, J=1.6 Hz, 1H), 6.19 (br s, 1H), 5.25 (s, 2H), 4.20 (s, 3H), 3.84 (m, 2H), 3.80 (s, 3H), 3.14 (br s, 1H), 1.94 (m, 2H), 1.72 (d, J=12.9 Hz, 2H), 1.41 (s, 9H).

Example 130

(4-Hydroxy-4-(4-(((6-methoxy-2-(2-methoxyimidazo[2,1-b][1,3,4]thiadiazol-6-yl)benzofuran-4-yl)oxy)methyl)thiazol-2-yl)piperidin-1-yl)(phenyl)methanone

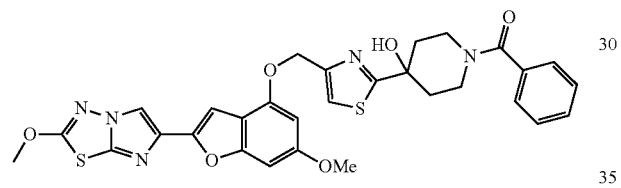

To a stirred suspension of tert-butyl 4-hydroxy-4-(4-(((6-methoxy-2-(2-methoxyimidazo[2,1-b][1,3,4]thiadiazol-6-yl)benzofuran-4-yl)oxy)methyl)thiazol-2-yl)piperidine-1-carboxylate (0.662 g, 1.079 mmol) in DCM (10 mL) was added TFA (3 mL) and the resulting solution was stirred for 4 h at room temperature, before being concentrated to dryness to give an amber colored oil. This crude oil was partitioned with EtOAc-saturated aqueous NaHCO$_3$ and the organic phase was separated, dried (MgSO$_4$), filtered and concentrated to dryness to 4-(4-(((6-methoxy-2-(2-methoxyimidazo[2,1-b][1,3,4]thiadiazol-6-yl)benzofuran-4-yl)oxy)methyl)thiazol-2-yl)piperidin-4-ol 2,2,2-trifluoroacetate (0.554 g, 1.079 mmol, 100%) as a beige solid. LC (Method A): 1.980 min. HRMS(ESI): calcd for $C_{23}H_{24}N_5O_5S_2$ [M+H]$^+$ m/z 514.1219, found 514.1228. To a stirred solution of 4-(4-(((6-methoxy-2-(2-methoxyimidazo[2,1-b][1,3,4]thiadiazol-6-yl)benzofuran-4-yl)oxy)methyl)thiazol-2-yl)piperidin-4-ol (0.031 g, 0.050 mmol) in DMF (1 mL) was added DIEA (0.070 mL, 0.400 mmol) and benzoic acid (0.0073 g, 0.060 mmol), followed by HATU (0.023 g, 0.060 mmol). The reaction mixture was stirred for 1 h and then it was diluted with DMF (1 mL) and purified by preparative HPLC (Method A). Fractions containing the desired product were concentrated to dryness and the residue was lyophilized from MeCN-water to give the title compound (0.022 g, 71.2%) as an amorphous white solid. LC (Method A): 2.257 min. HRMS(ESI): calcd for $C_{30}H_{28}N_5O_6S_2$ [M+H]$^+$ m/z 618.1481, found 618.1484. $^1$H NMR (DMSO-d$_6$, 400 MHz) δ ppm: 8.37 (s, 1H), 7.71 (s, 1H), 7.46-7.40 (m, 5H), 6.98 (d, J=0.8 Hz, 1H), 6.84 (dd, J=0.8, 1.6 Hz, 1H), 6.63 (d, J=1.6 Hz, 1H), 6.30 (br s, 1H), 5.26 (s, 2H), 4.36 (br s, 1H), 4.20 (s, 3H), 3.80 (s, 3H), 3.48 (m, 2H), 3.24 (br s, 1H), 2.03 (br s, 2H), 1.79 (m, 2H).

Example 131

4-(4-(((6-Methoxy-2-(2-methoxyimidazo[2,1-b][1,3,4]thiadiazol-6-yl)benzofuran-4-yl)-oxy)methyl)-5-(trifluoromethyl)thiazol-2-yl)tetrahydro-2H-pyran-4-ol

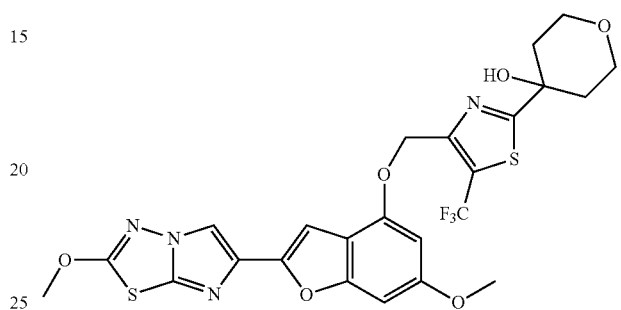

131A. Ethyl 5-iodothiazole-4-carboxylate

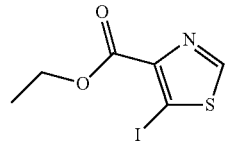

To a solution of ethyl 2-aminothiazole-4-carboxylate (2.92 g, 16.96 mmol) in dichloromethane (100 mL) was added NIS (5.00 g, 22.22 mmol). The resulting reaction mixture was stirred at room temperature for 24 h and then it was diluted with ethyl acetate, washed with water and brine, dried over MgSO$_4$, filtered and concentrated to give ethyl 2-amino-5-iodothiazole-4-carboxylate (4.75 g, 90%) that was used as such for the next step. LC (Method A): 1.549 min. LCMS (APCI): calcd for $C_6H_8IN_2O_2S$ [M+H]$^+$ m/z 298.94, found 299.0.

A solution of ethyl 2-amino-5-iodothiazole-4-carboxylate (4.75 g, 15.93 mmol) in DMF (70 mL) was cooled in an ice bath under nitrogen and then tert-butylnitrite (2.74 mL, 23.04 mmol) was added and the mixture was stirred at room temperature for 2 h. The reaction mixture was poured into brine, and the mixture was extracted 3 times with ethyl acetate. The combined organic extracts were washed with brine, dried over MgSO$_4$, filtered and concentrated. The crude residue obtained was purified by column chromatography (Isco, 8 g cartridge) eluting with a gradient of ethyl acetate in hexanes (from 0 to 50%) to give the pure title compound (0.825 g, 18%). LC (Method A): 1.601 min. LCMS (APCI): calcd for $C_6H_7INO_2S$ [M+H]$^+$ m/z 283.92, found 283.9. $^1$H NMR (CDCl$_3$, 400 MHz) δ ppm: 1.45 (t, J=7.0 Hz, 3H), 4.46 (q, J=7.0 Hz, 2H), 8.95 (s, 1H).

131B. Ethyl 5-(trifluoromethyl)thiazole-4-carboxylate

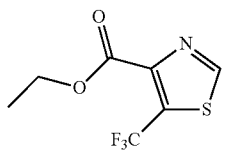

To a sealable tube charged with ethyl 5-iodothiazole-4-carboxylate (0.825 g, 2.91 mmol) and dry DMF (20 mL) was added methyl 2,2-difluoro-2-(fluorosulfonyl)acetate (0.742 mL, 5.83 mmol), followed by copper (I) iodide (1.110 g, 5.83 mmol). The reaction vessel was sealed and the reaction mixture was stirred overnight at 85° C. (bath temperature). The cooled reaction mixture was taken up in ether and filtered through a pad of CELITE®. The filtrate was then washed with water and brine, dried over MgSO$_4$, filtered and concentrated. The crude residue obtained was purified by column chromatography (Isco, 24 g cartridge) eluting with a gradient of EtOAc in hexanes (from 0 to 50%) to give the desired compound as a yellow solid (0.438 g, 67%). LC (Method A): 1.750 min. LCMS (APCI): calcd for $C_7H_7F_3NO_2S$ [M+H]$^+$ m/z 226.01, found 226.0. $^1$H NMR (CDCl$_3$, 400 MHz) δ ppm: 1.43 (t, J=7.4 Hz, 3H), 4.48 (q, J=7.4 Hz, 2H), 8.90 (s, 1H).

131C. (5-(Trifluoromethyl)thiazol-4-yl)methanol

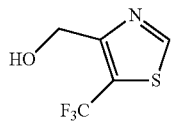 [SMILES: OCc1ncsc1C(F)(F)F]

To an ice-cold solution of ethyl 5-(trifluoromethyl)thiazole-4-carboxylate (0.425 g, 1.887 mmol) in dry THF (50 mL) under nitrogen was added lithium borohydride (0.082 g, 3.77 mmol) all at once, followed by dropwise addition of methanol (0.153 mL, 3.77 mmol). The cooling bath was then removed and the mixture was stirred at room temperature for 1 h. The mixture was recooled at 0° C. and cautiously quenched by the slow addition of saturated aqueous NH$_4$Cl (10 mL) with vigorous stirring. The cooling bath was then removed and the mixture was partitioned with ethyl acetate-water. The organic phase was separated, washed with brine, dried over MgSO$_4$, filtered and concentrated. The crude residue obtained was purified by column chromatography (Isco, 12 g cartridge) eluting with a gradient of EtOAc in hexanes (from 0 to 100%) to give the desired product as a pale yellow oil (0.200 g, 58%). LC retention time (Method A): 1.248 min. LCMS (APCI): calcd for $C_5H_5F_3NOS$ [M+H]$^+$ m/z 184.00, found 184.0. $^1$H NMR (CDCl$_3$, 400 MHz) δ ppm: 4.90 (s, 2H), 8.96 (s, 1H).

131D. 4-(((tert-Butyldimethylsilyl)oxy)methyl)-5-(trifluoromethyl)thiazole

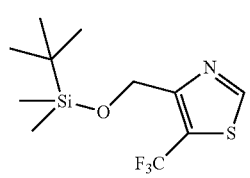 [SMILES: CC(C)(C)[Si](C)(C)OCc1ncsc1C(F)(F)F]

To a solution of (5-(trifluoromethyl)thiazol-4-yl)methanol (0.200 g, 1.092 mmol) in dichloromethane (10 mL) at room temperature was added imidazole (0.112 g, 1.638 mmol), followed by tert-butylchlorodimethylsilane (0.206 g, 1.365 mmol). The resulting reaction mixture was stirred at room temperature for 1 h and then the reaction was quenched with MeOH and concentrated under reduced pressure. The crude residue was purified by column chromatography (Isco, 12 g cartridge), eluting with a gradient of ethyl acetate in hexanes (from 0 to 50%) to give the desired product as a colorless oil (0.145 g, 45%). LC (Method A): 2.409 min. LCMS (APCI): calcd for $C_{11}H_{19}F_3NOSSi$ [M+H]$^+$ m/z 298.09, found 298.2. $^1$H NMR (CDCl$_3$, 400 MHz) δ ppm: 0.11 (s, 6H), 0.91 (s, 9H), 4.92 (s, 2H), 8.84 (s, 1H).

131E. 4-(4-(((tert-Butyldimethylsilyl)oxy)methyl)-5-(trifluoromethyl)thiazol-2-yl)tetrahydro-2H-pyran-4-ol

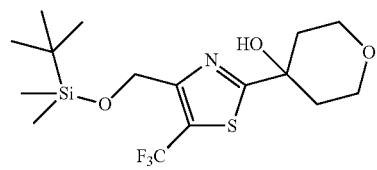 [SMILES: CC(C)(C)[Si](C)(C)OCc1nc(C2(O)CCOCC2)sc1C(F)(F)F]

A solution of 4-(((tert-butyldimethylsilyl)oxy)methyl)-5-(trifluoromethyl)thiazole (0.145 g, 0.488 mmol) in dry THF (5 mL) was cooled at −78° C. under nitrogen before n-butyllithium (1.5 M in hexanes, 0.390 mL, 0.585 mmol) was added dropwise. The solution obtained was stirred for 15 min at −78° C. before a solution of dihydro-2H-pyran-4(3H)-one (0.054 mL, 0.585 mmol) in dry THF (1 mL) was slowly added. The resulting reaction mixture was stirred at −78° C. for 1 h and then it was quenched by the addition of saturated aqueous NH$_4$Cl (1.5 mL). The cooling bath was then removed and the mixture was diluted with ethyl acetate. The organic phase was separated, washed (brine), dried (MgSO$_4$), filtered and evaporated to give a pale yellow oil. The crude residue obtained was purified by column chromatography (Isco, 12 g cartridge) eluting with a gradient of EtOAc in hexanes (from 0 to 50%) to give the desired compound as a pale yellow oil (0.185 g, 95%). LC (Method A): 2.415 min. LCMS (APCI): calcd for $C_{16}H_{27}F_3NO_3SSi$ [M+H]$^+$ m/z 398.14, found 398.2. $^1$H NMR (CDCl$_3$, 400 MHz) δ ppm: 0.10 (s, 6H), 0.91 (s, 9H), 1.61 (br s, 1H), 1.75-1.82 (m, 2H), 2.25-2.36 (m, 2H), 3.83-3.97 (m, 4H), 4.84 (d, J=0.8 Hz, 2H).

131F. 4-(4-(Hydroxymethyl)-5-(trifluoromethyl)thiazol-2-yl)tetrahydro-2H-pyran-4-ol

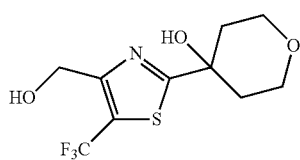 [SMILES: OCc1nc(C2(O)CCOCC2)sc1C(F)(F)F]

To a solution of 4-(4-(((tert-butyldimethylsilyl)oxy)methyl)-5-(trifluoromethyl)thiazol-2-yl)tetrahydro-2H-pyran-4-ol (0.185 g, 0.465 mmol) in THF (3 mL) at room temperature was added TBAF (75% solution in water, 0.252 mL, 0.698 mmol). After 30 min stirring another equivalent of TBAF (75% solution in water, 0.168 mL, 0.465 mmol) was added and the mixture was stirred for another 1 h. The resulting mixture was quenched with brine and then dichloromethane was added. The isolated organic layer was washed with brine, dried over MgSO$_4$, filtered and concentrated. The crude residue obtained was purified by column chromatography (Isco, 12 g cartridge) eluting with a gradient of ethyl acetate in hexanes (from 0 to 100%) to give the desired compound as a colorless oil (0.101 g, 77%). LC (Method A): 1.504 min. LCMS (APCI): calcd for $C_{10}H_{13}F_3NO_3S$ [M+H]$^1$ m/z 284.06, found 284.0. $^1$H NMR (CDCl$_3$, 400 MHz) δ ppm: 1.65 (br s, 1H), 1.79 (dd, J=2.0, 14.0 Hz, 2H), 2.28-2.38 (m, 2H), 2.71 (br s, 1H), 3.82-3.97 (m, 4H), 4.81 (d, J=1.2 Hz, 2H).

Example 131. 4-(4-(((6-Methoxy-2-(2-methoxyimidazo[2,1-b][1,3,4]thiadiazol-6-yl)benzofuran-4-yl)oxy)methyl)-5-(trifluoromethyl)thiazol-2-yl)tetrahydro-2H-pyran-4-ol

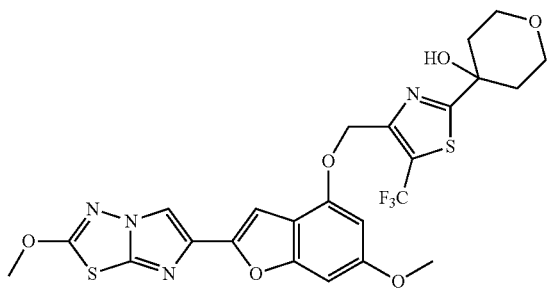 [SMILES: COc1cc(OCc2nc(C3(O)CCOCC3)sc2C(F)(F)F)c2cc(-c3cn4nc(OC)sc4n3)oc2c1]

To a mixture of 6-methoxy-2-(2-methoxyimidazo[2,1-b][1,3,4]thiadiazol-6-yl)benzofuran-4-ol (Example 1H, 0.090 g, 0.284 mmol) and 4-(4-(hydroxymethyl)-5-(trifluoromethyl)thiazol-2-yl)tetrahydro-2H-pyran-4-ol (0.100 g, 0.355 mmol) under nitrogen was added dry THF (5 mL). To the resulting suspension was added tri-n-butylphosphine (0.184 mL, 0.709 mmol), followed by the dropwise addition of a solution of 1,1'-(azodicarbonyl)dipiperidine (0.181 g, 0.709 mmol) in dry THF (2.5 mL). The resulting reaction mixture was stirred at room temperature for 45 min and then it was diluted with ethyl acetate and washed with saturated aqueous NaHCO$_3$, dried over MgSO$_4$, filtered and concentrated. The crude residue obtained was purified by column chromatography (Isco, 24 g cartridge) eluting with a gradient of EtOAc in DCM (from 0 to 50%) to give the title compound as a white solid (0.108 g, 65%). LC (Method A): 2.689 min. HRMS(ESI): calcd for $C_{24}H_{22}F_3N_4O_6S_2$ [M+H]$^+$ m/z 583.0933, found 523.0967. $^1$H NMR (DMSO-d$_6$, 400 MHz) δ ppm: 1.70 (d, J=13.3 Hz, 2H), 2.06-2.17 (m, 2H), 3.62-3.83 (m, 4H), 3.81 (s, 3H), 4.20 (s, 3H), 5.37 (s, 2H), 6.63 (d, J=9.0 Hz, 2H), 6.86 (s, 2H), 8.38 (s, 1H).

Example 132

6-(4-((2-(4-Fluorotetrahydro-2H-pyran-4-yl)-5-(trifluoromethyl)thiazol-4-yl)methoxy)-6-methoxybenzofuran-2-yl)-2-methoxyimidazo[2,1-b][1,3,4]thiadiazole

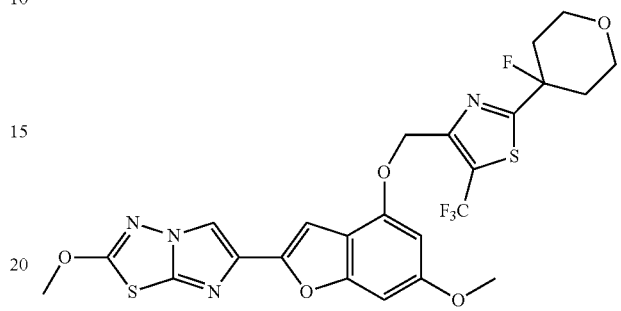

To an ice-cold suspension of 4-(4-(((6-methoxy-2-(2-methoxyimidazo[2,1-b][1,3,4]thiadiazol-6-yl)benzofuran-4-yl)oxy)methyl)-5-(trifluoromethyl)thiazol-2-yl)tetrahydro-2H-pyran-4-ol (0.052 g, 0.089 mmol) in dichloromethane (10 mL) under nitrogen was added DAST (0.029 mL, 0.223 mmol) dropwise. The resulting mixture was stirred at 0° C. for 20 min and then the cooling bath was removed and the resulting pale yellow solution was stirred at room temperature for 1 h. The reaction mixture was re-cooled to 0° C., quenched by the dropwise addition of saturated aqueous NaHCO$_3$ (5 mL) and vigorously stirred for 15 min to ensure complete quenching. The resulting mixture was diluted with dichloromethane and saturated aqueous sodium bicarbonate, then the organic layer was separated, dried over magnesium sulfate and concentrated under reduced pressure. The crude residue obtained was purified by column chromatography (Isco, 24 g cartridge) eluting with a gradient of EtOAc in DCM (from 0 to 50%) to give the title compound as a white solid (0.045 g, 86%). LC (Method A): 2.492 min. LCMS(ESI): calcd for $C_{24}H_{21}F_4N_4O_5S_2$ [M+H]$^+$ m/z 585.0890, found 585.0904. $^1$H NMR (DMSO-d$_6$, 400 MHz) δ ppm: 2.03-2.39 (m, 4H), 3.69 (td, J=2.0, 11.7 Hz, 2H), 3.82 (s, 3H), 3.85-3.92 (m, 2H), 4.20 (s, 3H), 5.43 (s, 2H), 6.65 (d, J=1.6 Hz, 1H), 6.87 (s, 2H), 8.38 (s, 1H).

Example 133

1-(4-(((6-Methoxy-2-(2-methoxyimidazo[2,1-b][1,3,4]thiadiazol-6-yl)benzofuran-4-yl)oxy)methyl)thiazol-2-yl)cyclohexanol

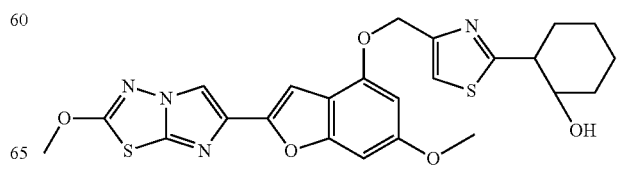

133A:
1-(4-(Hydroxymethyl)thiazol-2-yl)cyclohexanol

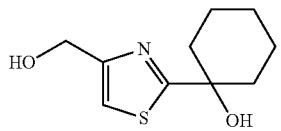 [SMILES: OCc1csc(C2(O)CCCCC2)n1]

General Method: A solution of 2-bromo-4-(((tert-butyldimethylsilyl)oxy)methyl)-thiazole (Example 37B, 0.195 g, 0.632 mmol) in dry THF (5 mL) was cooled at −78° C. under nitrogen before n-butyllithium (1.5 M in hexanes, 0.506 mL, 0.759 mmol) was added dropwise. The resulting mixture was stirred for 15 min and then a solution of cyclohexanone (0.075 mg, 0.759 mmol) in dry THF (1 mL) was added and stirring was continued at −78° C. for 1 h. The reaction was then quenched by the addition of saturated aqueous $NH_4Cl$ (1.5 mL) and then the cooling bath was removed and the mixture was diluted with ethyl acetate. The organic phase was separated, washed (brine), dried ($MgSO_4$), filtered and evaporated to give a pale yellow oil. The crude 1-(4-(((tert-butyldimethylsilyl)-oxy)methyl)thiazol-2-yl)cyclohexanol obtained (0.185 g, 89%) was used as such for the next step. LC (Method A): 2.391 min. LCMS (APCI): calcd for $C_{16}H_{30}NO_2SSi$ [M+H]$^+$ m/z 328.18, found 328.2.

To a solution of crude 1-(4-(((tert-butyldimethylsilyl)oxy)methyl)thiazol-2-yl)cyclo-hexanol (0.185 g, 0.480 mmol) in THF (3 mL) at room temperature was added TBAF (75% solution in water, 0.260 mL, 0.720 mmol). After 30 min another equivalent of TBAF (75% solution in water, 0.173 mL, 0.480 mmol) was added and the resulting mixture was stirred for another 1 h. The reaction mixture was then quenched with brine and DCM was added. The isolated organic layer was washed with brine, dried over $MgSO_4$, filtered and concentrated. The crude residue obtained was purified by column chromatography (Isco, 12 g cartridge) eluting with a gradient of ethyl acetate in hexanes (from 0 to 100%) to give the desired compound as a colorless oil (0.076 g, 74%). LC (Method A): 1.319 min. LCMS (APCI): calcd for $C_{10}H_{16}NO_2S$ [M+H]$^+$ m/z 214.09, found 214.2. $^1$H NMR (DMSO-d$_6$, 400 MHz) δ ppm: 1.18-1.32 (m, 1H), 1.48-1.75 (m, 7H), 1.84 (td, J=3.9, 12.9 Hz, 2H), 4.50 (dd, J=0.8, 5.9 Hz, 2H), 5.22 (t, J=5.9 Hz, 1H), 5.69 (s, 1H), 7.21 (s, 1H).

Example 133. 1-(4-(((6-Methoxy-2-(2-methoxyimidazo[2,1-b][1,3,4]thiadiazol-6-yl)benzofuran-4-yl)oxy)methyl)thiazol-2-yl)cyclohexanol

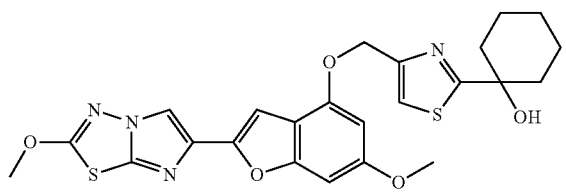 [SMILES: COc1cc(OCc2csc(C3(O)CCCCC3)n2)c2cc(-c3cn4nc(OC)sc4n3)oc2c1]

To a mixture of 6-methoxy-2-(2-methoxyimidazo[2,1-b][1,3,4]thiadiazol-6-yl)benzofuran-4-ol (Example 1H, 0.090 g, 0.284 mmol) and 1-(4-(hydroxymethyl)-thiazol-2-yl)cyclohexanol (0.076 g, 0.355 mmol) under nitrogen at room temperature was added dry THF (5 mL). To the resulting suspension was added tri-n-butylphosphine (0.184 mL, 0.709 mmol) and then a solution of 1,1'-(azodicarbonyl)dipiperidine (0.181 g, 0.709 mmol) in dry THF (2.5 mL) was added dropwise and the resulting mixture was stirred at room temperature for 45 min. The reaction mixture was then diluted with ethyl acetate and washed with saturated aqueous $NaHCO_3$, dried over $MgSO_4$, filtered and concentrated. The crude residue obtained was purified by column chromatography (Isco, 24 g cartridge) eluting with a gradient of ethyl acetate in dichloromethane (from 0 to 50%) to give the title compound as a white solid (0.104 g, 72%). LC (Method A): 2.339 min. LCMS(ESI): calcd for $C_{24}H_{25}N_4O_5S_2$ [M+H]$^+$ m/z 513.1266, found 513.1256. $^1$H NMR (DMSO-d$_6$, 400 MHz) δ ppm: 1.20-1.36 (m, 1H), 1.48-1.79 (m, 7H), 1.88 (td, J=3.5, 12.5 Hz, 2H), 3.81 (s, 3H), 4.20 (s, 3H), 5.24 (s, 2H), 5.80 (s, 1H), 6.61 (d, J=2.0 Hz, 1H), 6.82-6.84 (m, 1H), 6.98 (s, 1H), 7.64 (s, 1H), 8.37 (s, 1H).

Example 134

6-(4-((2-(1-Fluorocyclohexyl)thiazol-4-yl)methoxy)-6-methoxybenzofuran-2-yl)-2-methoxyimidazo[2,1-b][1,3,4]thiadiazole

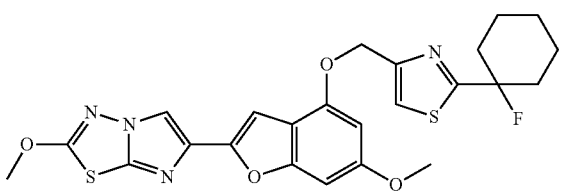 [SMILES: COc1cc(OCc2csc(C3(F)CCCCC3)n2)c2cc(-c3cn4nc(OC)sc4n3)oc2c1]

To an ice-cold suspension of 1-(4-(((6-methoxy-2-(2-methoxyimidazo[2,1-b][1,3,4]thiadiazol-6-yl)benzofuran-4-yl)oxy)methyl)thiazol-2-yl)cyclohexanol (0.050 g, 0.098 mmol) in dichloromethane (10 mL) under nitrogen was added DAST (0.032 mL, 0.244 mmol) dropwise. The resulting mixture was stirred at 0° C. for 15 min and then the cooling bath was removed and the resulting pale yellow solution was stirred at room temperature for 1 h. The reaction mixture was re-cooled at 0° C., quenched by the dropwise addition of saturated aqueous $NaHCO_3$ (5 mL) and stirred vigorously for 15 min to ensure complete quenching. The mixture was further diluted with dichloromethane and saturated aqueous sodium bicarbonate solution and the organic layer was separated, dried over magnesium sulfate and concentrated under reduced pressure. The crude residue obtained was purified by column chromatography (Isco, 24 g cartridge) eluting with a gradient of ethyl acetate in dichloromethane (from 0 to 50%) to give the title compound as a white solid (0.037 g, 74%). LC (Method A): 2.524 min. LCMS(ESI): calcd for $C_{24}H_{24}FN_4O_4S_2$ [M+H]$^+$ m/z 515.1223, found 515.1203. $^1$H NMR (DMSO-d$_6$, 400 MHz) δ ppm: 1.30-1.46 (m, 1H), 1.56-1.73 (m, 5H), 1.95-2.13 (m, 4H), 3.81 (s, 3H), 4.20 (s, 3H), 5.30 (s, 2H), 6.62 (d, J=2.0 Hz, 1H), 6.83-6.85 (m, 1H), 6.99 (s, 1H), 7.88 (s, 1H), 8.37 (s, 1H).

Example 135

4,4-Difluoro-1-(4-((((6-methoxy-2-(2-methoxyimidazo[2,1-b][1,3,4]thiadiazol-6-yl)benzofuran-4-yl)oxy)methyl)thiazol-2-yl)cyclohexanol

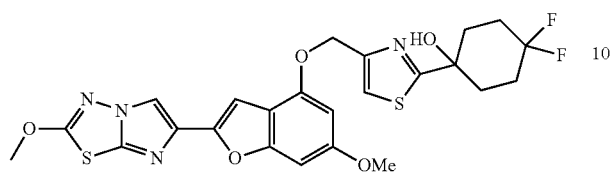

135A. 1-(4-(((tert-Butyldimethylsilyl)oxy)methyl)thiazol-2-yl)-4,4-difluorocyclohexanol

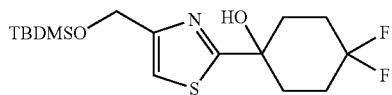 [SMILES: CC(C)(C)[Si](C)(C)OCc1csc(C2(O)CCC(F)(F)CC2)n1]

A solution of 2-bromo-4-(((tert-butyldimethylsilyl)oxy)methyl)thiazole (Example 37B, 0.500 g, 1.622 mmol) in dry THF (8 mL) was cooled at −78° C. under $N_2$ and then n-butyllithium (1.45 M in hexanes, 0.714 mL, 1.784 mmol) was added dropwise. The resulting mixture was stirred for 35 min to give a pale brown solution. To this mixture was slowly added a solution of 4,4-difluorocyclohexanone (0.218 g, 1.622 mmol) in dry THF (2 mL) and the mixture was stirred at −78° C. for 2 h to give a light brown solution. The reaction was then quenched by the addition of saturated aqueous $NH_4Cl$ (5 mL), the cooling bath was removed and the mixture was partitioned with EtOAc-water. The organic phase was separated, washed with brine, dried ($MgSO_4$) and evaporated to give a pale yellow oil. This oil was purified by flash chromatography using DCM-EtOAc as eluent to give 1-(4-(((tert-butyldimethylsilyl)oxy)methyl)thiazol-2-yl)-4,4-difluorocyclohexanol (0.289 g, 49.0%) as a beige solid. LC (Method A): 2.354 min. $^1$H NMR (DMSO-$d_6$, 400 MHz) δ ppm: 7.32 (s, 1H), 6.21 (s, 1H), 4.70 (s, 2H), 2.21-1.99 (m, 6H), 1.86 (m, 2H), 0.88 (s, 9H), 0.06 (s, 6H).

135B. 4,4-Difluoro-1-(4-(hydroxymethyl)thiazol-2-yl)cyclohexanol

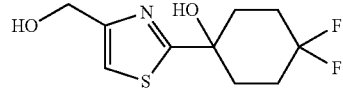

To a solution of 1-(4-(((tert-butyldimethylsilyl)oxy)methyl)thiazol-2-yl)-4,4-difluorocyclohexanol (0.289 g, 0.795 mmol) in dry THF (10 mL) under $N_2$ was added triethylamine trihydrofluoride (0.647 mL, 3.97 mmol) dropwise and the mixture was stirred at room temperature for 16 h. The mixture was then diluted with EtOAc and the solution was washed (saturated aqueous $NaHCO_3$), dried ($MgSO_4$) and evaporated to give 4,4-difluoro-1-(4-(hydroxymethyl)thiazol-2-yl)cyclohexanol (0.164 g, 83%) as a white solid. This material was used as such in the next step without further purification. LC (Method A): 1.332 min. $^1$H NMR (DMSO-$d_6$, 400 MHz) δ ppm: 7.28 (s, 1H), 6.18 (s, 1H), 5.25 (t, J=5.9 Hz, 1H), 4.50 (d, J=5.5 Hz, 2H), 2.21-1.99 (m, 6H), 1.88 (m, 2H).

Example 135. 4,4-Difluoro-1-(4-((((6-methoxy-2-(2-methoxyimidazo-[2,1-b][1,3,4]thiadiazol-6-yl)benzofuran-4-yl)oxy)methyl)thiazol-2-yl)cyclohexanol

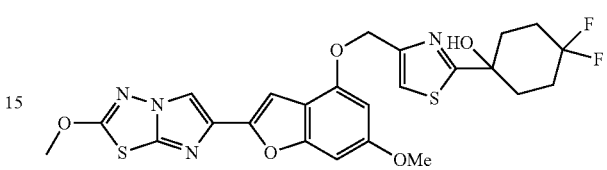

To a suspension of 6-methoxy-2-(2-methoxyimidazo[2,1-b][1,3,4]thiadiazol-6-yl)benzofuran-4-ol (Example 1H, 0.186 g, 0.586 mmol) and 4,4-difluoro-1-(4-(hydroxymethyl)thiazol-2-yl)cyclohexanol (0.146 g, 0.586 mmol) in dry THF (8 mL) was added tri-n-butylphosphine (0.380 mL, 1.464 mmol), followed by a solution of ADDP (0.369 g, 1.464 mmol) in THF (2 mL), added dropwise over 30 min via syringe pump. After stirring for another 30 min, the reaction mixture was partitioned between EtOAc and saturated aqueous $NaHCO_3$. The organic phase was separated, washed with brine, dried ($MgSO_4$), filtered and concentrated to dryness. The residue was purified by flash chromatography using DCM-EtOAc as eluent to give a beige solid with a yellow tinge. This solid was further triturated with acetonitrile and the resulting solid was filtered, rinsed with diethyl ether and dried under vacuum to give the title compound (0.250 g, 78%) as a beige solid. LC (Method A): 2.322 min. HRMS(ESI): calcd for $C_{24}H_{23}F_2N_4O_5S_2$ [M+H]$^+$ m/z 549.1078, found 549.1101. $^1$H NMR (DMSO-$d_6$, 400 MHz) δ ppm: 8.37 (s, 1H), 7.71 (s, 1H), 6.98 (s, 1H), 6.83 (s, 1H), 6.62 (d, J=1.6 Hz, 1H), 6.29 (br s, 1H), 5.26 (s, 2H), 4.20 (s, 3H), 3.80 (s, 3H), 2.20-2.01 (m, 6H), 1.91 (m, 2H).

Example 136

2-Methoxy-6-(6-methoxy-4-((2-(1,4,4-trifluorocyclohexyl)thiazol-4-yl)methoxy)benzofuran-2-yl)imidazo[2,1-b][1,3,4]thiadiazole

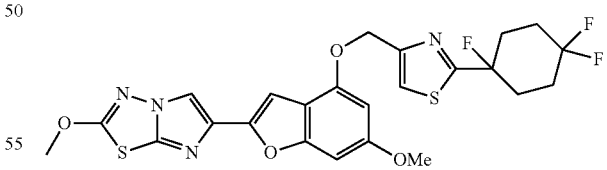

To an ice-cold mixture of 4,4-difluoro-1-(4-((((6-methoxy-2-(2-methoxyimidazo[2,1-b][1,3,4]thiadiazol-6-yl)benzofuran-4-yl)oxy)methyl)thiazol-2-yl)cyclohexanol (0.050 g, 0.091 mmol) in dichloromethane (4 mL) under $N_2$ was added DAST (0.036 mL, 0.273 mmol) dropwise. The reaction mixture was stirred at 0° C. for 1 h before being quenched with saturated aqueous $NaHCO_3$. The resulting mixture was extracted with EtOAc, after which the organic phase was washed with brine, dried ($MgSO_4$), filtered and concentrated to dryness. The residue was purified by flash chromatography using a gradient of 0 to 100% EtAOc in DCM to give the title compound (0.007 g, 0.013 mmol, 13.95%) as a white solid. LC (Method A): 2.322 min. HRMS(ESI): calcd for $C_{24}H_{22}F_3N_4O_4S_2$ [M+H]$^+$ m/z 551.1035, found 551.1055. $^1$H NMR (DMSO-d$_6$, 400 MHz) δ ppm: 8.37 (s, 1H), 7.94 (s, 1H), 6.99 (s, 1H), 6.84 (d, J=0.8 Hz, 1H), 6.62 (d, J=2.0 Hz, 1H), 5.31 (s, 2H), 4.20 (s, 3H), 3.81 (s, 3H), 2.34-2.07 (m, 8H).

Preparation of Alcohols

The following additional alcohols were prepared according to the general procedure described in Example 133A;

| Structure | Formula | Calc. [M + H]$^+$ m/z | LCMS found [M + H]$^+$ m/z | HPLC retention time (min)/ method | NMR |
|---|---|---|---|---|---|
| 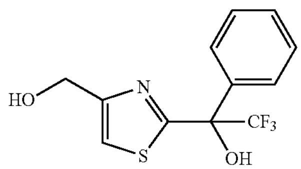 [SMILES: OCc1csc(C(O)(c2ccccc2)C(F)(F)F)n1] | $C_{12}H_{10}F_3NO_2S$ | 290.046 | 290.047 | 1.661/A | $^1$H NMR (DMSO-d$_6$, 400 MHz) δ ppm: 4.59 (dd, J = 0.8, 5.5 Hz, 2H), 5.37 (t, J = 5.9 Hz, 1H), 7.37-7.45 (m, 3H), 7.51-7.52 (m, 1H), 7.70-7.74 (m, 2H), 8.28 (s, 1H). |
| 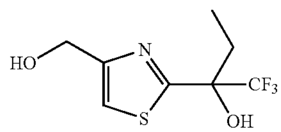 | $C_8H_{10}F_3NO_2S$ | 242.046 | 242.047 | 1.254/A | $^1$H NMR (DMSO-d$_6$, 400 MHz) δ ppm: 0.74 (t, J = 7.4 Hz, 3H), 1.95-2.08 (m, 1H), 2.18-2.31 (m, 1H), 4.55 (d, J = 5.5 Hz, 2H), 5.32 (t, J = 5.9 Hz, 1H), 7.23 (s, 1H), 7.46 (s, 1H). |
| 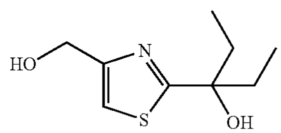 | $C_9H_{15}NO_2S$ | 202.09 | 202.2 | 1.165/A | $^1$H NMR (DMSO-d$_6$, 400 MHz) δ ppm: 0.73 (t, J = 7.4 Hz, 6H), 1.67-1.90 (m, 4H), 4.51 (dd, J = 0.8, 5.5 Hz, 2H), 5.21 (t, J = 5.9 Hz, 1H), 5.38 (s, 1H), 7.20-7.21 (m, 1H). |
| 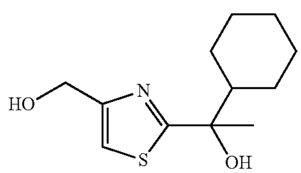 [SMILES: CC(O)(c1nc(CO)cs1)C1CCCCC1] | $C_{12}H_{19}NO_2S$ | 242.12 | 242.2 | 1.702/A | $^1$H NMR (CD$_3$OD, 400 MHz) δ ppm: 1.00-1.32 (m, 5H), 1.41-1.50 (m, 1H), 1.53 (s, 3H), 1.59-1.88 (m, 5H), 4.65 (s, 2H), 7.23 (s, 1H). |
| 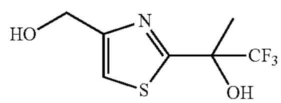 | $C_7H_8F_3NO_2S$ | 228.030 | 228.030 | 1.134/A | $^1$H NMR (DMSO-d$_6$, 400 MHz) δ ppm: 1.73 (s, 3H), 4.55 (d, J = 5.1 Hz, 2H), 5.33 (t, J = 5.9 Hz, 1H), 7.47-7.49 (m, 1H), 7.52 (br s, 1H). |
| 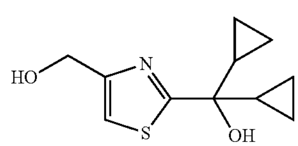 [SMILES: OCc1csc(C(O)(C2CC2)C2CC2)n1] | $C_{11}H_{15}NO_2S$ | 226.090 | 226.090 | 1.389/A | $^1$H NMR (DMSO-d$_6$, 400 MHz) δ ppm: 0.18-0.27 (m, 2H), 0.33-0.51 (m, 6H), 1.28-1.39 (m, 2H), 4.52 (d, J = 3.5 Hz, 2H), 5.22 (br s, 2H), 7.21 (s, 1H). |
| 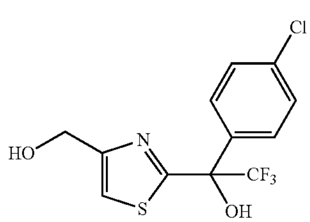 [SMILES: OCc1csc(C(O)(c2ccc(Cl)cc2)C(F)(F)F)n1] | $C_{12}H_9ClF_3NO_2S$ | 324.01 | 324.0 | 1.905/A | $^1$H NMR (DMSO-d$_6$, 400 MHz) δ ppm: 4.59 (d, J = 3.9 Hz, 2H), 5.34-5.42 (m, 1H), 7.48-7.55 (m, 3H), 7.75 (d, J = 8.6 Hz, 2H), 8.45 (s, 1H). |
| 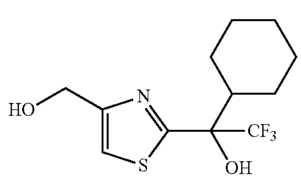 [SMILES: OCc1csc(C(O)(C2CCCCC2)C(F)(F)F)n1] | $C_{12}H_{16}F_3NO_2S$ | 296.093 | 296.094 | 1.837/A | $^1$H NMR (DMSO-d$_6$, 400 MHz) δ ppm: 0.95-1.38 (m, 6H), 1.53-1.86 (m, 4H), 2.18-2.30 (m, 1H), 4.54 (d, J = 3.9 Hz, 2H), 5.33 (t, J = 4.7 Hz, 1H), 7.07 (br s, 1H), 7.42 (s, 1H). |

-continued

| Structure | Formula | Calc. [M + H]+ m/z | LCMS found [M + H]+ m/z | HPLC retention time (min)/ method | NMR |
|---|---|---|---|---|---|
| HO-(thiazole with OMe, OH, Me substituents) | C₉H₁₅NO₃S | 218.09 | 218.2 | 1.008/A | ¹H NMR (DMSO-d₆, 400 MHz) δ ppm: 1.47 (s, 3H), 1.94-2.10 (m, 2H), 3.14 (s, 3H), 3.15-.324 (m, 1H), 3.38-3.46 (m, 1H), 4.50 (dd, J = 0.8, 5.5 Hz, 2H), 5.23 (t, J = 5.9 Hz, 1H), 5.85 (s, 1H), 7.22 (s, 1H). |

Examples 137 to 147

The following additional Examples have been prepared, isolated and characterized using the methods disclosed in Examples 133 and 134 above.

| Ex. | Structure | Formula | Calc. [M + H]+ m/z | LCMS found [M + H]+ m/z | HPLC retention time (min)/ method | NMR |
|---|---|---|---|---|---|---|
| 137 | (structure) | C₂₆H₁₉F₃N₄O₅S₂ | 589.082 | 589.084 | 2.354/A | ¹H NMR (DMSO-d₆, 400 MHz) δ ppm: 3.80 (s, 3H), 4.20 (s, 3H), 5.37 (s, 2H), 6.65 (d, J = 1.6 Hz, 1H), 6.83-6.84 (m, 1H), 6.99 (s, 1H), 7.38-7.42 (m, 3H), 7.71-7.76 (m, 2H), 7.93 (s, 1H), 8.39 (d, J = 10.2 Hz, 2H). |
| 138 | (structure) | C₂₂H₁₉F₃N₄O₅S₂ | 541.082 | 541.080 | 2.258/A | ¹H NMR (DMSO-d₆, 400 MHz) δ ppm: 0.75 (t, J = 7.0 Hz, 3H), 1.99-2.10 (m, 1H), 2.24-2.34 (m, 1H), 3.80 (s, 3H), 4.20 (s, 3H), 5.31 (s, 2H), 6.61 (d, J = 2.0 Hz, 1H), 6.82-6.84 (m, 1H), 6.97 (d, J = 0.8 Hz, 1H), 7.35 (s, 1H), 7.88 (s, 1H), 8.37 (s, 1H). |
| 139 | (structure) | C₂₂H₁₈F₄N₄O₄S₂ | 543.078 | 543.079 | 2.472/A | ¹H NMR (DMSO-d₆, 400 MHz) δ ppm: 0.86 (t, J = 7.4 Hz, 3H), 2.34-2.47 (m, 2H), 3.80 (s, 3H), 4.20 (s, 3H), 5.37 (s, 2H), 6.61 (d, J = 2.0 Hz, 1H), 6.83-6.85 (m, 1H), 6.98 (s, 1H), 8.13 (s, 1H), 8.37 (s, 1H). |
| 140 | (structure) | C₂₃H₂₄N₄O₅S₂ | 501.126 | 501.128 | 2.302/A | ¹H NMR (DMSO-d₆, 400 MHz) δ ppm: 0.74 (t, J = 7.4 Hz, 6H), 1.71-1.92 (m, 4H), 3.80 (s, 3H), 4.20 (s, 3H), 5.25 (s, 2H), 5.49 (s, 1H), 6.60 (d, J = 2.0 Hz, 1H), 6.81-6.83 (m, 1H), 6.96 (s, 1H), 7.62 (s, 1H), 8.37 (s, 1H). |

-continued

| Ex. | Structure | Formula | Calc. [M + H]+ m/z | LCMS found [M + H]+ m/z | HPLC retention time (min)/ method | NMR |
|---|---|---|---|---|---|---|
| 141 | 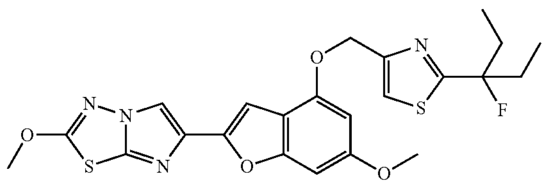 [SMILES: CCC(F)(CC)c1nc(COc2cc(OC)cc3oc(-c4cn5nc(OC)sc5n4)cc23)cs1] | C23H23FN4O4S2 | 503.122 | 503.122 | 2.492/ A | 1H NMR (DMSO-d6, 400 MHz) δ ppm: 0.81 (t, J = 7.4 Hz, 6H), 1.97-2.18 (m, 4H), 3.80 (s, 3H), 4.20 (s, 3H), 5.31 (s, 2H), 5.60 (d, J = 2.0 Hz, 1H), 6.82-6.84 (m, 1H), 6.97 (s, 1H), 7.84 (s, 1H), 8.37 (s, 1H). |
| 142 | 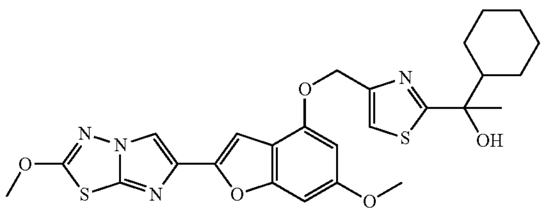 [SMILES: COc1cc(OCc2csc(C(C)(O)C3CCCCC3)n2)c2cc(-c3cn4nc(OC)sc4n3)oc2c1] | C26H28N4O5S2 | 541.157 | 541.157 | 2.423/ A | 1H NMR (DMSO-d6, 400 MHz) δ ppm; 0.82-1.20 (m, 4H), 1.43-1.83 (m, 7H), 1.47 (s, 3H), 3.79 (s, 3H), 4.20 (s, 3H), 5.26 (s, 2H), 5.71 (s, 1H), 6.60 (d, J = 2.0 Hz, 1H), 6.80-6.82 (m, 1H), 6.96 (d, J = 0.8 Hz, 1H), 7.61 (s, 1H), 8.36 (s, 1H). |
| 143 | 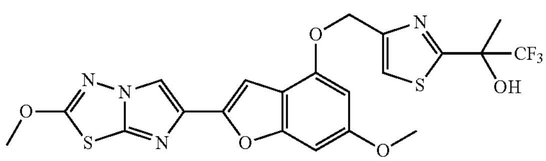 [SMILES: COc1cc(OCc2csc(C(C)(O)C(F)(F)F)n2)c2cc(-c3cn4nc(OC)sc4n3)oc2c1] | C21H17F3N4O5S2 | 527.067 | 527.067 | 2.240/ A | 1H NMR (DMSO-d6, 400 MHz) δ ppm: 1.77 (s, 3H), 3.81 (s, 3H), 4.20 (s, 3H), 5.30 (s, 2H), 6.62 (d, J = 2.0 Hz, 1H), 6.82-6.85 (m, 1H), 6.98 (s, 1H), 7.64 (br s, 1H), 7.91 (s, 1H), 8.37 (s, 1H). |
| 144 | 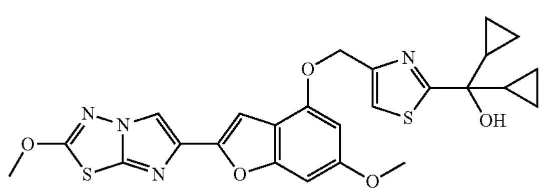 [SMILES: COc1cc(OCc2csc(C(O)(C3CC3)C3CC3)n2)c2cc(-c3cn4nc(OC)sc4n3)oc2c1] | C25H24N4O5S2 | 525.126 | 525.126 | 2.318/ A | 1H NMR (DMSO-d6, 400 MHz) δ ppm: 0.20-0.29 (m, 2H), 0.36-0.54 (m, 6H), 1.32-1.41 (m, 2H), 3.81 (s, 3H), 4.20 (s, 3H), 5.26 (s, 2H), 5.36 (s, 1H), 6.62 (d, J = 2.0 Hz, 1H), 6.82-6.83 (m, 1H), 6.98 (s, 1H), 7.63 (s, 1H), 8.36 (s, 1H). |
| 145 | 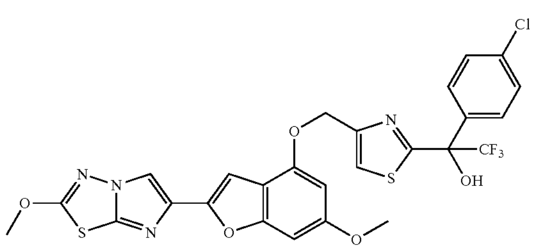 [SMILES: COc1cc(OCc2csc(C(O)(c3ccc(Cl)cc3)C(F)(F)F)n2)c2cc(-c3cn4nc(OC)sc4n3)oc2c1] | C26H18ClF3N4O5S2 | 623.043 | 623.044 | 2.462/ A | 1H NMR (DMSO-d6, 400 MHz) δ ppm: 3.80 (s, 3H), 4.20 (s, 3H), 5.37 (s, 2H), 6.65 (d, J = 1.6 Hz, 1H), 6.83-6.84 (m, 1H), 6.99 (s, 1H), 7.47-7.52 (m, 2H), 7.77 (d, J = 8.6 Hz, 2H), 7.95 (s, 1H), 8.37 (s, 1H), 8.56 (s, 1H). |

-continued

| Ex. | Structure | Formula | Calc. [M + H]+ m/z | LCMS found [M + H]+ m/z | HPLC retention time (min)/ method | NMR |
|---|---|---|---|---|---|---|
| 146 | 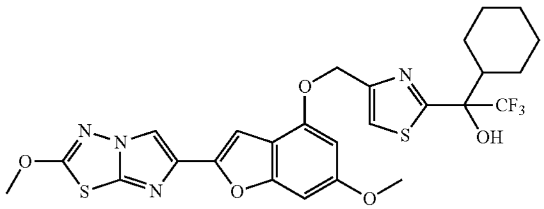 [SMILES: COc1cc(OCc2csc(C(O)(C3CCCCC3)C(F)(F)F)n2)c2cc(-c3cn4nc(OC)sc4n3)oc2c1] | C26H25F3N4O5S2 | 595.129 | 595.130 | 2.467/ A | 1H NMR (DMSO-d6, 400 MHz) δ ppm; 0.91-1.88 (m, 10H), 2.20-2.31 (m, 1H), 3.79 (s, 3H), 4.20 (s, 3H). 5.31 (s, 2H), 6.60 (d, J = 2.0 Hz, 1H), 6.80-6.82 (m, 1H), 6.96 (s, 1H), 7.17 (br s, 1H), 7.83 (s, 1H), 8.36 (s, 1H). |
| 147 | 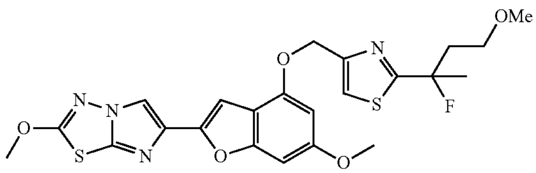 [SMILES: COCCC(C)(F)c1nc(COc2cc(OC)cc3oc(-c4cn5nc(OC)sc5n4)cc23)cs1] | C23H23FN4O5S2 | 517.121 | 517.123 | 2.226/ A | 1H NMR (DMSO-d6, 400 MHz) δ ppm: 1.77 (d, J = 22.3 Hz, 3H), 2.22-2.44 (m, 2H), 3.15 (s, 3H), 3.29-3.36 (m, 1H), 3.39-3.47 (m, 1H), 3.80 (s, 3H), 4.20 (s, 3H), 5.30 (s, 2H), 6.61 (d, J = 1.6 Hz, 1H), 6.82-6.85 (m, 1H), 6.98 (d, J = 0.8 Hz, 1H), 7.87 (s, 1H), 8.37 (s, 1H). |

Examples 148 and 149 tert-Butyl 4-(4-(((6-methoxy-2-(2-methoxyimidazo [2,1-b][1,3,4]thiadiazol-6-yl)benzofuran-4-yl)oxy) methyl)thiazol-2-yl)cyclohex-3-enecarboxylate and tert-Butyl 4-hydroxy-4-(4-(((6-methoxy-2-(2-methoxyimidazo[2,1-b][1,3,4]thiadiazol-6-yl)benzofuran-4-yl)oxy)methyl)thiazol-2-yl)cyclohexanecarboxylate, respectively 148A. 4-Oxocyclohexanecarboxylic Acid

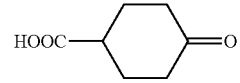

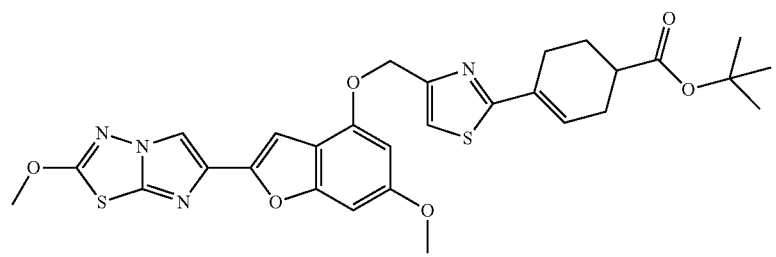

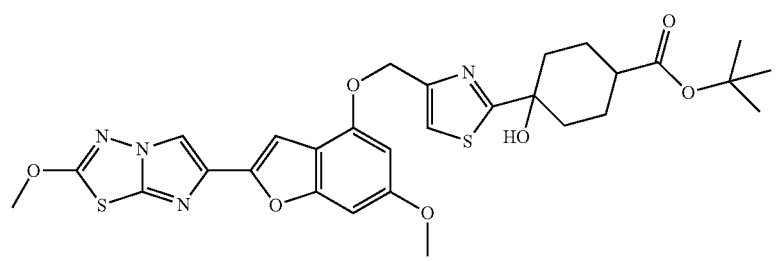

To a solution of ethyl 4-oxocyclohexanecarboxylate (5.00 g, 29.4 mmol) in a mixture of methanol (30 mL) and THF (125 mL) was added an aqueous solution of NaOH (3 N, 29.4 mL, 88 mmol) and the resulting reaction mixture was heated at 60° C. for 3 h. The cooled mixture was concentrated under reduced pressure, the aqueous concentrate was acidified (pH 1) with 1N HCl and the mixture was extracted with DCM (×3). The combined organic extract was washed with brine, dried over MgSO$_4$, filtered and concentrated to give the title compound (3.175 g, 76%). $^1$H NMR (DMSO-d$_6$, 400 MHz) δ ppm: 1.70-1.86 (m, 2H), 2.03-2.14 (m, 2H), 2.18-2.30 (m, 2H), 2.32-2.46 (m, 2H), 2.66-2.77 (m, 1H), 12.32 (br s, 1H).

148B. tert-Butyl 4-oxocyclohexanecarboxylate

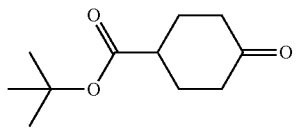

To an ice-cold solution of 4-oxocyclohexanecarboxylic acid (3.175 g, 22.34 mmol) in pyridine (12 mL, 148 mmol) and tert-butanol (17 mL, 178 mmol) was added neat POCl$_3$ (3.0 mL, 32.2 mmol). The cooling bath was then removed and the reaction mixture was stirred at room temperature for 4 h. The crude mixture was then poured in water and the product was extracted with EtOAc (3×). The combined organic extract was washed with 2 N HCl (×2) and brine, dried over MgSO$_4$, filtered and concentrated. The crude residue obtained was used as such without further purification (3.02 g, 68%). $^1$H NMR (DMSO-d$_6$, 400 MHz) δ ppm: 1.41 (s, 9H), 1.70-1.85 (m, 2H), 2.01-2.13 (m, 2H), 2.18-2.29 (m, 2H), 2.32-2.45 (m, 2H), 2.63-2.75 (m, 1H).

148C. tert-Butyl 4-hydroxy-4-(4-(hydroxymethyl)thiazol-2-yl)cyclohexanecarboxylate

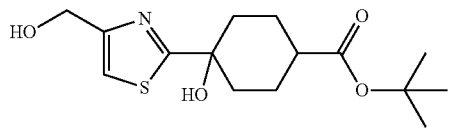 [SMILES: CC(C)(C)OC(=O)C1CCC(O)(c2nc(CO)cs2)CC1]

To a solution of 2-bromo-4-(((tert-butyldimethylsilyl)oxy)methyl)thiazole (Example 37B, 0.200 g, 0.649 mmol) in dry THF (5 mL), cooled at −78° C. under nitrogen, was added n-butyllithium (1.5 M in hexanes, 0.519 mL, 0.778 mmol) dropwise. The resulting mixture was stirred for 5 min before a pre-cooled (−78° C.) solution of tert-butyl 4-oxocyclohexanecarboxylate (0.129 g, 0.649 mmol) in dry THF (1 mL) was cannulated into the reaction mixture. The resulting mixture was stirred at −78° C. for 1.5 h and then the reaction was quenched by the addition of saturated aqueous NH$_4$Cl (3 mL). The cooling bath was then removed and the mixture was diluted with ethyl acetate. The organic phase was separated, washed (brine), dried (MgSO$_4$), filtered and evaporated to give the crude product, tert-butyl 4-(4-(((tert-butyldimethylsilyl)oxy)methyl)thiazol-2-yl)-4-hydroxycyclohexanecarboxylate, (0.177 g, 64%), as a pale yellow oil. This material was used as such in the next step without further purification. LC (Method A): 2.447 min. LCMS (APCI): calcd for C$_{21}$H$_{38}$NO$_4$SSi [M+H]$^+$ m/z 428.23, found 428.2.

To a solution of tert-butyl 4-(4-(((tert-butyldimethylsilyl)oxy)methyl)thiazol-2-yl)-4-hydroxycyclohexanecarboxylate (0.277 g, 0.415 mmol) in THF (5 mL) at room temperature was added TBAF (75% solution in water, 0.299 mL, 0.829 mmol). The resulting mixture was stirred for 1 h and then the reaction was quenched with brine and the resulting mixture was diluted with dichloromethane. The organic layer was separated, washed with brine, dried over MgSO$_4$, filtered and concentrated. The crude residue obtained was purified by column chromatography (Isco, 12 g cartridge) eluting with a gradient of ethyl acetate in dichloromethane (from 0 to 100%) to give the desired compound as viscous, colorless oil which was a mixture of cis- and trans-isomers (0.073 g, 56%). LC (Method A): 1.768, 1.789 min. LCMS (APCI): calcd for C$_{15}$H$_{24}$NO$_4$S [M+H]$^+$ m/z 314.14, found 314.2. $^1$H NMR (DMSO-d$_6$, 400 MHz) δ ppm: 1.40 (s, 9H), 1.52-1.93 (m, 7H), 2.01-2.12 (m, 1H), 2.17-2.28 (m, 1H), 4.50 (s, 2H), 5.23 (t, J=5.1 Hz, 1H), 5.78 (d, J=11.7 Hz, 1H), 7.24 (d, J=11.3 Hz, 1H).

Examples 148 and 149. tert-Butyl 4-(4-(((6-methoxy-2-(2-methoxyimidazo[2,1-b][1,3,4]thiadiazol-6-yl)benzofuran-4-yl)oxy)methyl)thiazol-2-yl)cyclohex-3-enecarboxylate and tert-Butyl 4-hydroxy-4-(4-(((6-methoxy-2-(2-methoxyimidazo[2,1-b][1,3,4]thiadiazol-6-yl)benzofuran-4-yl)oxy)methyl)thiazol-2-yl)cyclohexanecarboxylate, respectively

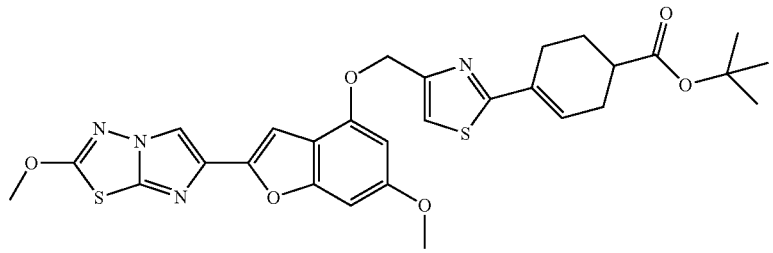

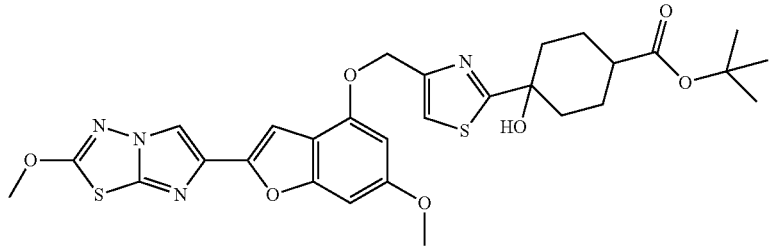

To a mixture of 6-methoxy-2-(2-methoxyimidazo[2,1-b][1,3,4]thiadiazol-6-yl)benzofuran-4-ol (Example 1H, 0.070 g, 0.221 mmol) and tert-butyl 4-hydroxy-4-(4-(hydroxymethyl)thiazol-2-yl)cyclohexanecarboxylate (0.069 g, 0.221 mmol) was added dry THF (5 mL) and the flask was flushed with nitrogen. To the resulting suspension was added tri-n-butylphosphine (0.143 mL, 0.551 mmol), followed by the dropwise addition of a solution of 1,1'-(azodicarbonyl)dipiperidine (0.141 g, 0.551 mmol) in dry THF (2.5 mL). The resulting reaction mixture was stirred at room temperature for 1.5 h and then it was diluted with ethyl acetate, washed with saturated aqueous $NaHCO_3$, dried over $MgSO_4$, filtered and concentrated. The crude residue obtained was purified by flash chromatography (Isco, 24 g cartridge) using a 0-100% gradient of EtOAc in DCM to give two fractions. Fraction 1 was obtained as a solid which was further triturated with MeOH to give (after filtration, washing with MeOH and drying in vacuo) tert-butyl 4-(4-(((6-methoxy-2-(2-methoxyimidazo[2,1-b][1,3,4]thiadiazol-6-yl)benzofuran-4-yl)oxy)methyl)thiazol-2-yl)cyclohex-3-enecarboxylate (0.011 g, 8%) as a white solid. LC (Method A): 2.567 min. HRMS(ESI) calcd for $C_{29}H_{31}N_4O_6S_2$ $[M+H]^+$ m/z 595.168, found 595.168. $^1$H NMR (DMSO-$d_6$, 400 MHz) δ ppm: 1.38 (s, 9H), 1.64 (m, 1H), 2.00 (m, 1H), 2.25-2.65 (m, 5H), 3.77 (s, 3H), 4.17 (s, 3H), 5.23 (s, 2H), 6.57 (d, J=1.57 Hz, 1H), 6.61 (br s, 1H), 6.80 (s, 1H), 6.97 (s, 1H), 7.66 (s, 1H), 8.33 (s, 1H). Fraction 2 was further purified by preparative HPLC (Method A) to give tert-butyl 4-hydroxy-4-(4-(((6-methoxy-2-(2-methoxyimidazo[2,1-b][1,3,4]thiadiazol-6-yl)benzofuran-4-yl)oxy)methyl)thiazol-2-yl)cyclohexanecarboxylate as a white solid which was a mixture of cis- and trans-isomers (0.010 g, 7%). LC (Method A): 2.320 min. HRMS(ESI): calcd for $C_{29}H_{33}N_4O_7S_2$ $[M+H]^+$ m/z 613.1791, found 613.1789. $^1$H NMR (DMSO-$d_6$, 400 MHz) δ ppm: 1.39 (s, 4.5H), 1.41 (s, 4.5H), 1.61-1.98 (m, 7H), 2.04-2.16 (m, 1H), 2.21-2.31 (m, 1H), 3.80 (s, 3H), 4.21 (s, 3H), 5.24 (s, 1H), 5.25 (s, 1H), 5.87 (br s, 1H), 6.60 (d, J=2.0 Hz, 0.5H), 6.61 (d, J=2.0 Hz, 0.5H), 6.81-6.84 (m, 1H), 6.97 (d, J=0.8 Hz, 0.5H), 6.98 (d, J=0.8 Hz, 0.5H), 7.65 (s, 0.5H), 7.68 (s, 0.5H), 8.36 (s, 0.5H), 8.37 (s, 0.5H).

Example 150

4-Hydroxy-4-(4-(((6-methoxy-2-(2-methoxyimidazo[2,1-b][1,3,4]thiadiazol-6-yl)benzofuran-4-yl)oxy)methyl)thiazol-2-yl)cyclohexanecarboxylic Acid

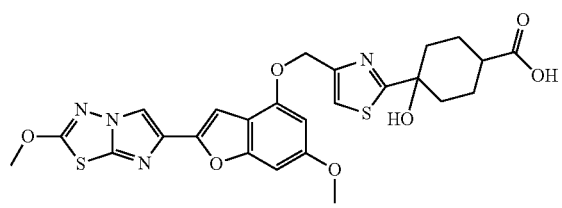 [SMILES: COc1cc(OCc2csc(C3(O)CCC(C(=O)O)CC3)n2)c2cc(-c3cn4nc(OC)sc4n3)oc2c1]

To a solution of tert-butyl 4-hydroxy-4-(4-(((6-methoxy-2-(2-methoxyimidazo[2,1-b][1,3,4]thiadiazol-6-yl)benzofuran-4-yl)oxy)methyl)thiazol-2-yl)cyclohexanecarboxylate (0.486 g, 0.587 mmol) in dichloromethane (20 mL) at room temperature was added TFA (2.261 mL, 29.3 mmol) and the mixture was stirred for 1.5 h. The resulting mixture was diluted with toluene and the volatiles were then removed under reduced pressure. The orange oil obtained was co-evaporated with methanol (×2) to give the crude title compound (0.297 g, 91%) as an orange solid which was a mixture of cis- and trans-isomers. This material was used as such for the next step without further purification. LC (Method A): 2.110, 2.142 min. HRMS(ESI): calcd for $C_{25}H_{25}N_4O_7S_2$ $[M+H]^+$ m/z 557.1165, found 557.1169. $^1$H NMR (DMSO-$d_6$, 400 MHz) δ ppm: 1.60-2.15 (m, 8H), 2.24-2.35 (m, 1H), 2.21-2.31 (m, 1H), 3.81 (s, 3H), 4.21 (s, 3H), 5.24 (d, J=5.4 Hz, 1H), 5.26 (s, 1H), 5.90 (s, 0.5H), 5.92 (s, 0.5H), 6.61 (d, J=2.0 Hz, 0.5H), 6.62 (d, J=2.0 Hz, 0.5H), 6.82-6.85 (m, 1H), 6.99 (d, J=0.4 Hz, 0.5H), 7.00 (d, J=0.8 Hz, 0.5H), 7.66 (s, 0.5H), 7.67 (s, 0.5H), 8.38 (s, 1H).

Example 151

(4-Hydroxy-4-(4-(((6-methoxy-2-(2-methoxyimidazo[2,1-b][1,3,4]thiadiazol-6-yl)benzofuran-4-yl)oxy)methyl)thiazol-2-yl)cyclohexyl)(pyrrolidin-1-yl)methanone

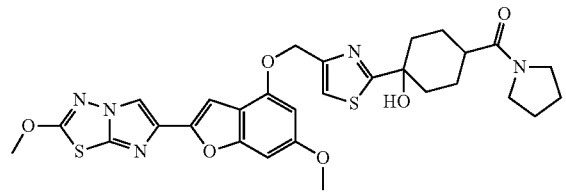 [SMILES: COc1cc(OCc2csc(C3(O)CCC(C(=O)N4CCCC4)CC3)n2)c2cc(-c3cn4nc(OC)sc4n3)oc2c1]

To a solution of 4-hydroxy-4-(4-(((6-methoxy-2-(2-methoxyimidazo[2,1-b][1,3,4]thiadiazol-6-yl)benzofuran-4-yl)oxy)methyl)thiazol-2-yl)cyclohexanecarboxylic acid (0.025 g, 0.045 mmol) and pyrrolidine (3.71 µl, 0.045 mmol) in DMF (1 mL) was added DIEA (0.039 mL, 0.225 mmol), followed by HATU (0.0214 g, 0.056 mmol). The resulting reaction mixture was stirred at room temperature for 3 h and then it was diluted with ethyl acetate and washed with saturated aqueous $NaHCO_3$, and brine. The organic layer was separated, dried over $MgSO_4$, filtered and concentrated. The crude residue obtained was purified by preparative HPLC (Method A) to give two fractions. Fraction 1 was identified as Isomer A of the title compound (0.008 g, 25%). LC (Method A): 2.236 min. HRMS(ESI): calcd for $C_{29}H_{32}N_5O_6S_2$ $[M+H]^+$ m/z 610.1794, found 610.1777. $^1$H NMR (DMSO-d$_6$, 400 MHz) δ ppm: 1.60-1.91 (m, 11), 2.28-2.36 (m, 2H), 3.24 (t, J=7.0 Hz, 2H), 3.45 (t, J=6.7 Hz, 2H), 3.80 (s, 3H), 4.19 (s, 3H), 5.25 (s, 2H), 5.80 (br s, 1H), 6.61 (d, J=2.0 Hz, 1H), 6.81-6.84 (m, 1H), 7.00 (s, 1H), 7.72 (s, 1H), 8.38 (s, 1H). Fraction 2 was re-purified by preparative HPLC (Method A) to give pure Isomer B of the title compound (0.004 g, 14%). LC (Method A): 2.301 min. HRMS(ESI): calcd for C$_{29}$H$_{32}$N$_5$O$_6$S$_2$ [M+H]$^+$ m/z 610.1794, found 610.1791. $^1$H NMR (DMSO-d$_6$, 400 MHz) δ ppm: 1.51-1.60 (m, 2H), 1.70-2.04 (m, 11H), 3.27 (t, J=6.7 Hz, 2H), 3.48 (t, J=6.7 Hz, 2H), 3.81 (s, 3H), 4.20 (s, 3H), 5.23 (s, 2H), 5.90 (s, 1H), 6.60 (d, J=1.6 Hz, 1H), 6.82-6.84 (m, 1H), 6.97 (d, J=0.8 Hz, 1H), 7.64 (s, 1H), 8.37 (s, 1H).

Example 152

N-(Cyanomethyl)-4-hydroxy-4-(4-(((6-methoxy-2-(2-methoxyimidazo[2,1-b][1,3,4]thiadiazol-6-yl)benzofuran-4-yl)oxy)methyl)thiazol-2-yl)-N-methyl-cyclohexanecarboxamide

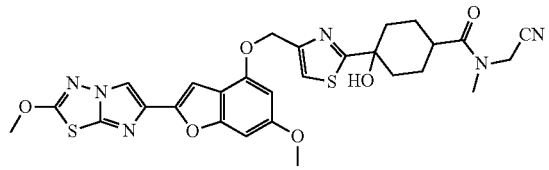 [SMILES: COc1cc(OCc2csc(C3(O)CCC(C(=O)N(C)CC#N)CC3)n2)c2cc(-c3cn4nc(OC)sc4n3)oc2c1]

The title compound was prepared from 4-hydroxy-4-(4-(((6-methoxy-2-(2-methoxyimidazo[2,1-b][1,3,4]thiadiazol-6-yl)benzofuran-4-yl)oxy)methyl)thiazol-2-yl)cyclohexanecarboxylic acid and 2-(methylamino)acetonitrile according to the method described in Example 151 above. The crude product mixture was separated into its two isomers using preparative HPLC (Method A). Isomer A. LC (Method A): 2.143 min. HRMS(ESI): calcd for C$_{28}$H$_{29}$N$_6$O$_6$S$_2$ [M+H]$^1$ m/z 609.1590, found 609.1581. $^1$H NMR (DMSO-d$_6$, 400 MHz) δ ppm: 1.61-1.88 (m, 7H), 2.27-2.34 (m, 1H), 2.78-2.89 (m, 1H), 3.11 (s, 3H), 3.81 (s, 3H), 4.20 (s, 3H), 4.36 (s, 2H), 5.26 (s, 2H), 5.88 (br s, 1H), 6.62 (d, J=2.0 Hz, 1H), 6.81-6.85 (m, 1H), 7.00 (d, J=0.8 Hz, 1H), 7.72 (s, 1H), 8.37 (s, 1H). Isomer B. LC (Method A): 2.177 min. HRMS(ESI): calcd for C$_{28}$H$_{29}$N$_6$O$_6$S$_2$ [M+H]$^+$ m/z 609.1590, found 609.1580. $^1$H NMR (DMSO-d$_6$, 400 MHz) δ ppm: 1.49-1.62 (m, 2H), 1.74-1.90 (m, 4H), 1.96-2.10 (m, 2H), 2.72-2.85 (m, 1H), 3.13 (s, 3H), 3.81 (s, 3H), 4.20 (s, 3H), 4.37 (s, 2H), 5.23 (s, 2H), 5.94 (br s, 1H), 6.59 (d, J=1.6 Hz, 1H), 6.82-6.85 (m, 1H), 6.97 (s, 1H), 7.65 (s, 1H), 8.37 (s, 1H).

Example 153

6-(4-((2-(4-(4-Bromophenyl)tetrahydro-2H-pyran-4-yl)thiazol-4-yl)methoxy)-6-methoxybenzofuran-2-yl)-2-methoxyimidazo[2,1-b][1,3,4]thiadiazole

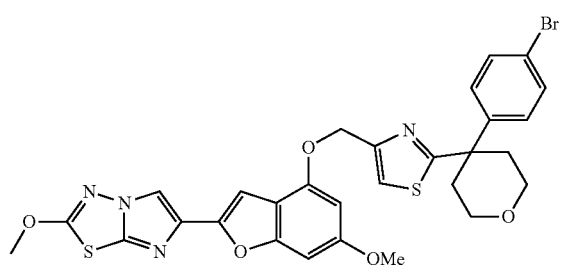 [SMILES: COc1cc(OCc2csc(C3(c4ccc(Br)cc4)CCOCC3)n2)c2cc(-c3cn4nc(OC)sc4n3)oc2c1]

153A. 4-(4-Bromophenyl)tetrahydro-2H-pyran-4-carbonitrile

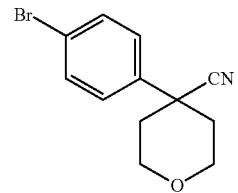 [SMILES: N#CC1(c2ccc(Br)cc2)CCOCC1]

A solution of 2-(4-bromophenyl)acetonitrile (1.00 g, 5.10 mmol) in dry THF (5.85 mL) was treated with 17 M sodium hydroxide (9.00 mL, 153 mmol), tetrabutylammonium hydrogen sulfate (0.173 g, 0.510 mmol) and 1-chloro-2-(2-chloroethoxy)ethane (0.628 mL, 5.36 mmol). The reaction mixture was heated to reflux for 4 h, then the cooled mixture was diluted with EtOAc, washed with 1N HCl, water and saturated aqueous NaHCO$_3$. The organic phase was dried over MgSO$_4$, filtered and concentrated to dryness. The residue was then purified by flash chromatography using a gradient of 0 to 100% EtOAc in hexanes to give 4-(4-bromophenyl)tetrahydro-2H-pyran-4-carbonitrile (1.11 g, 82%) as a clear yellow oil. LC (Method F): 2.080 min. $^1$H NMR (DMSO-d$_6$, 400 MHz) δ ppm: 7.66 (ddd, J=2.0, 2.7, 8.6 Hz, 2H), 7.52 (ddd, J=2.0, 2.7, 8.6 Hz), 4.01 (m, 2H), 3.64 (m, 2H), 2.12-1.99 (m, 4H).

153B. 4-(4-Bromophenyl)tetrahydro-2H-pyran-4-carboxamide

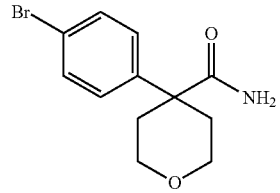

4-(4-Bromophenyl)tetrahydro-2H-pyran-4-carbonitrile (1.09 g, 4.10 mmol) was stirred in concentrated sulphuric acid (3 mL) at room temperature for 40 h. The mixture was then poured onto ice and the resulting suspension was filtered and the filter-cake washed thoroughly with water until the pH of the wash was neutral. The resulting white solid was rinsed with hexanes and then dried under reduced pressure to give 4-(4-bromophenyl)tetrahydro-2H-pyran-4-carboxamide (1.065 g, 92%). LC (Method F): 1.835 min. $^1$H NMR (DMSO-d$_6$, 400 MHz) δ ppm: 7.53 (dt, J=2.5, 9.0 Hz, 2H), 7.32 (dt, J=2.5, 9.0 Hz, 2H), 7.23 (br s, 1H), 7.06 (br s, 1H), 3.73 (dt, J=3.7, 11.7 Hz, 2H), 3.46 (dt, J=2.0, 11.7 Hz, 2H), 2.40 (d, J=13.3 Hz, 2H), 1.77 (m, 2H).

153C. 4-(4-Bromophenyl)tetrahydro-2H-pyran-4-carbothioamide

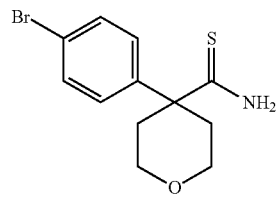 [SMILES: NC(=S)C1(c2ccc(Br)cc2)CCOCC1]

To a stirred solution of 4-(4-bromophenyl)tetrahydro-2H-pyran-4-carboxamide (1.00 g, 3.52 mmol) in THF (12 mL) was added Lawesson's reagent (0.712 g, 1.760 mmol) all at once and the reaction mixture was heated to reflux for 6 h. The cooled reaction mixture was then concentrated to near dryness and partitioned with EtOAc-saturated aqueous NaHCO$_3$. The organic phase was dried (MgSO$_4$), filtered and concentrated to dryness and the residue was purified by flash chromatography using hexanes-EtOAc as eluent to give 4-(4-bromophenyl)tetrahydro-2H-pyran-4-carbothioamide as a white solid (0.771 g, 73.0%). LC (Method F): 1.993 min. $^1$H NMR (DMSO-d$_6$, 400 MHz) δ ppm: 9.70 (s, 1H), 8.92 (s, 1H), 7.54 (ddd, J=2.0, 2.7, 8.6 Hz, 2H), 7.40 ((ddd, J=2.0, 2.7, 8.6 Hz, 2H), 3.59 (m, 4H), 2.60 (m, 2H), 2.07 (m, 2H).

153D. Ethyl 2-(4-(4-bromophenyl)tetrahydro-2H-pyran-4-yl)thiazole-4-carboxylate

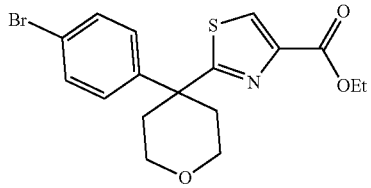 [SMILES: CCOC(=O)c1csc(C2(c3ccc(Br)cc3)CCOCC2)n1]

To a mixture of 4-(4-bromophenyl)tetrahydro-2H-pyran-4-carbothioamide (0.725 g, 2.415 mmol) in isopropanol (10 mL) was added ethyl bromopyruvate (0.365 mL, 2.90 mmol) and the reaction mixture was heated to reflux for 2.75 h. The cooled mixture was partitioned between EtOAc and saturated aqueous NaHCO$_3$ and the organic phase was washed with brine, dried (MgSO$_4$), filtered and concentrated to dryness. The residue was purified by flash chromatography using a gradient of 0 to 100% EtOAc in hexanes to give ethyl 2-(4-(4-bromophenyl)tetrahydro-2H-pyran-4-yl)thiazole-4-carboxylate (0.288 g, 30.1%) as a clear, colorless oil. LC (Method F): 2.320 min. $^1$H NMR (DMSO-d$_6$, 400 MHz) δ ppm: 8.46 (s, 1H), 7.55 (dt, J=2.4, 9.0 Hz, 2H), 7.38 (dt, J=2.4, 9.0 Hz, 2H), 4.29 (q, J=7.0 Hz, 2H), 3.70 (m, 2H), 3.57 (m, 2H), 2.56 (m, 2H), 2.35 (m, 2H), 1.29 (t, J=7.0 Hz, 3H).

153E. (2-(4-(4-Bromophenyl)tetrahydro-2H-pyran-4-yl)thiazol-4-yl)methanol

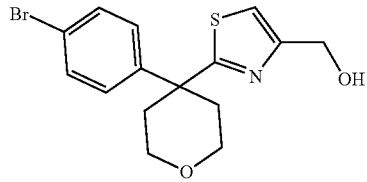 [SMILES: OCc1csc(C2(c3ccc(Br)cc3)CCOCC2)n1]

To an ice-cold solution of ethyl 2-(4-(4-bromophenyl)tetrahydro-2H-pyran-4-yl)thiazole-4-carboxylate (0.288 g, 0.727 mmol) in THF (3.6 mL) was added LiBH$_4$ (0.0314 g, 1.441 mmol) all at once, followed by MeOH (0.058 mL, 1.441 mmol). The resulting mixture was stirred at 0° C. for 5 min and then at ambient temperature for 16 h. The mixture was then re-cooled at 0° C. and carefully quenched by the dropwise addition of saturated aqueous NH$_4$Cl. The resulting mixture was extracted with ethyl acetate, after which the organic phase was washed with brine, dried (MgSO$_4$), filtered and evaporated to dryness. The obtained residue was purified by flash chromatography using a gradient of 0 to 100% EtOAc in hexanes to give (2-(4-(4-bromophenyl)tetrahydro-2H-pyran-4-yl)thiazol-4-yl)methanol (0.226 g, 89%) as a white solid. LC (Method F): 2.111 min. $^1$H NMR (DMSO-d$_6$, 400 MHz) δ ppm: 7.52 (m, 2H), 7.35 (m, 3H), 5.28 (t, J=5.7 Hz, 1H), 4.53 (dd, J=1.2, 5.9 Hz, 2H), 3.72 (m, 1H), 3.69 (t, J=4.3 Hz, 1H), 3.55 (m, 2H), 2.55 (m, 1H), 2.29 (m, 2H).

Example 153. 6-(4-((2-(4-(4-Bromophenyl)tetrahydro-2H-pyran-4-yl)thiazol-4-yl)methoxy)-6-methoxybenzofuran-2-yl)-2-methoxyimidazo[2,1-b][1,3,4]thiadiazole

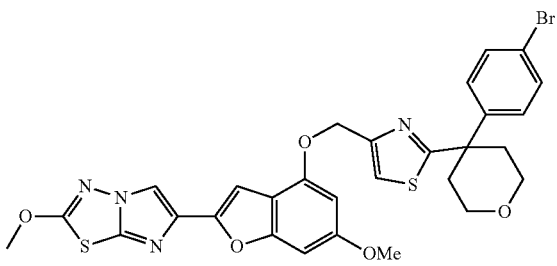 [SMILES: COc1cc(OCc2csc(C3(c4ccc(Br)cc4)CCOCC3)n2)c2cc(-c3cn4nc(OC)sc4n3)oc2c1]

To a flame-dried flask containing 6-methoxy-2-(2-methoxyimidazo[2,1-b][1,3,4]thiadiazol-6-yl)benzofuran-4-ol (Example 1H, 0.035 g, 0.110 mmol) and (2-(4-(4-bromophenyl)tetrahydro-2H-pyran-4-yl)thiazol-4-yl)methanol (0.039 g, 0.110 mmol) was added dry THF (4 mL), followed by tri-n-butylphosphine (0.072 mL, 0.276 mmol). To the resulting suspension was added a solution of ADDP (0.070 g, 0.276 mmol) in THF (1 mL) dropwise over 30 min via syringe pump. After stirring for 1.5 h, the reaction mixture was diluted with EtOAc, then washed with 1N HCl, saturated aqueous NaHCO$_3$, water and brine. The organic phase was dried (MgSO$_4$) and evaporated and the crude material was triturated with DMSO, filtered, rinsed with acetonitrile and dried in vacuo to give the title compound (0.035 g, 48.6%) as a beige solid. LC (Method F): 2.732 min. HRMS(ESI): calcd for C$_{29}$H$_{26}$BrN$_4$O$_5$S$_2$ [M+H]$^+$ m/z 653.0528, found 653.0530. $^1$H NMR (DMSO-d$_6$, 400 MHz) δ ppm: 8.36 (s, 1H), 7.75 (s, 1H), 7.52 (d, J=8.6 Hz, 2H), 7.36 (d, J=8.6 Hz, 2H), 6.98 (s, 1H), 6.83 (s, 1H), 6.62 (d, J=2.0 Hz, 1H), 5.29 (s, 2H), 4.20 (s, 3H), 3.80 (s, 3H), 3.74-3.70 (m, 2H), 3.56 (m, 2H), 2.57 (m, 2H), 2.35-2.28 (m, 2H).

Example 154

6-(4-((2-(4-(4-Chlorophenyl)tetrahydro-2H-pyran-4-yl)thiazol-4-yl)methoxy)-6-methoxybenzofuran-2-yl)-2-methoxyimidazo[2,1-b][1,3,4]thiadiazole

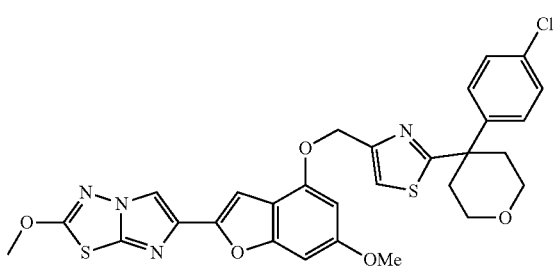 [SMILES: COc1cc(OCc2csc(C3(c4ccc(Cl)cc4)CCOCC3)n2)c2cc(-c3cn4nc(OC)sc4n3)oc2c1]

154A. (2-(4-(4-Chlorophenyl)tetrahydro-2H-pyran-4-yl)thiazol-4-yl)methanol

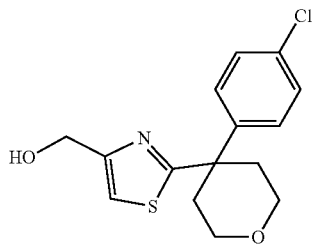 [SMILES: OCc1csc(C2(c3ccc(Cl)cc3)CCOCC2)n1]

The alcohol was prepared according to the method described in Example 153 above. LC (Method F): 2.076 min. $^1$H NMR (DMSO-$d_6$, 400 MHz) δ ppm: 7.40 (m, 4H), 7.34 (m, 1H), 5.28 (t, J=5.7 Hz, 1H), 4.53 (dd, J=1.2, 5.9 Hz, 2H), 3.71 (m, 2H), 3.55 (m, 2H), 2.54 (m, 2H), 2.30 (m, 2H).

Example 154. 6-(4-((2-(4-(4-Chlorophenyl)tetrahydro-2H-pyran-4-yl)thiazol-4-yl)methoxy)-6-methoxybenzofuran-2-yl)-2-methoxyimidazo[2,1-b][1,3,4]thiadiazole

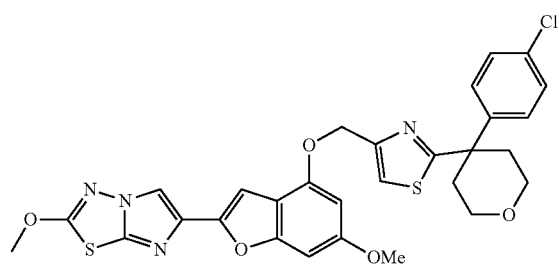 [SMILES: COc1cc(OCc2csc(C3(c4ccc(Cl)cc4)CCOCC3)n2)c2cc(-c3cn4nc(OC)sc4n3)oc2c1]

The title compound was prepared according to the method described in Example 153 above and was isolated as a solid. LC (Method F): 2.728 min. HRMS(ESI): calcd for $C_{29}H_{26}ClN_4O_5S_2$ [M+H]$^+$ m/z 609.1028, found 609.1077. $^1$H NMR (DMSO-$d_6$, 400 MHz) δ ppm: 8.37 (s, 1H), 7.75 (s, 1H), 7.41 (m, 4H), 6.98 (d, J=0.8 Hz, 1H), 6.83 (dd, J=0.8, 1.6 Hz, 1H), 6.62 (d, J=1.6 Hz, 1H), 5.29 (s, 2H), 4.20 (s, 3H), 3.80 (s, 3H), 3.75-3.70 (m, 2H), 3.56 (m, 2H), 2.58 (m, 2H), 2.32 (m, 2H).

Example 155

6-(4-((2-(4-(3-Chlorophenyl)tetrahydro-2H-pyran-4-yl)thiazol-4-yl)methoxy)-6-methoxybenzofuran-2-yl)-2-methoxyimidazo[2,1-b][1,3,4]thiadiazole

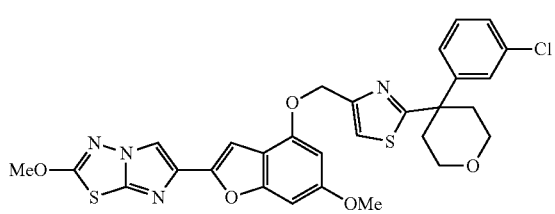 [SMILES: COc1cc(OCc2csc(C3(c4cccc(Cl)c4)CCOCC3)n2)c2cc(-c3cn4nc(OC)sc4n3)oc2c1]

155A. (2-(4-(3-Chlorophenyl)tetrahydro-2H-pyran-4-yl)thiazol-4-yl)methanol

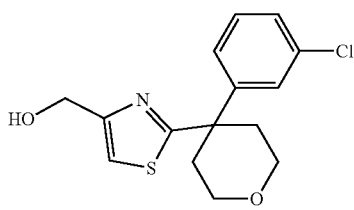 [SMILES: OCc1csc(C2(c3cccc(Cl)c3)CCOCC2)n1]

The alcohol was prepared according to the method described in Example 153 above. LC (Method F): 2.057 min. $^1$H NMR (DMSO-$d_6$, 400 MHz) δ ppm: 7.40-7.35 (m, 4H), 7.32-7.29 (m, 1H), 5.29 (m, 1H), 4.53 (s, 1H), 3.74 (m, 1H), 3.71 (t, J=4.3 Hz, 1H), 3.56 (dd, J=2.3, 9.4 Hz, 1H), 3.53 (dd, J=2.3, 9.4 Hz, 1H), 2.56 (dd, J=2.0, 11.7 Hz, 2H), 2.33 (dd, J=3.9, 9.4 Hz, 1H), 2.29 (m, 1H).

Example 155. 6-(4-((2-(4-(3-Chlorophenyl)tetrahydro-2H-pyran-4-yl)thiazol-4-yl)methoxy)-6-methoxybenzofuran-2-yl)-2-methoxyimidazo[2,1-b][1,3,4]thiadiazole

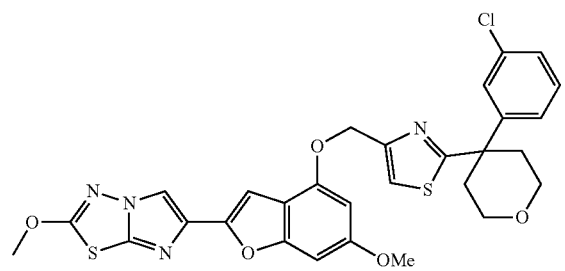 [SMILES: COc1cc(OCc2csc(C3(c4cccc(Cl)c4)CCOCC3)n2)c2cc(-c3cn4nc(OC)sc4n3)oc2c1]

The title compound was prepared according to the method described in Example 153 above and was isolated as a solid. LC (Method F): 2.679 min. HRMS(ESI): calcd for $C_{29}H_{26}ClN_4O_5S_2$ [M+H]$^+$ m/z 609.1033, found 609.1042. $^1$H NMR (DMSO-$d_6$, 400 MHz) δ ppm: 8.36 (s, 1H), 7.77 (s, 1H), 7.42-7.35 (m, 3H), 7.30 (m, 1H), 6.98 (d, J=0.8 Hz, 1H), 6.83 (dd, J=0.8, 1.6 Hz, 1H), 6.62 (d, J=1.6 Hz, 1H), 5.30 (s, 2H), 4.20 (s, 3H), 3.80 (s, 3H), 3.73 (dt, J=4.3, 12.1 Hz, 2H), 3.55 (m, 2H), 2.60 (m, 2H), 2.37-2.30 (m, 2H).

Example 156

6-(4-((2-(4-(2-Fluorophenyl)tetrahydro-2H-pyran-4-yl)thiazol-4-yl)methoxy)-6-methoxybenzofuran-2-yl)-2-methoxyimidazo[2,1-b][1,3,4]thiadiazole

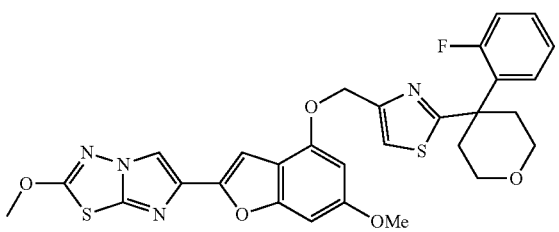 [SMILES: COc1cc(OCc2csc(C3(c4ccccc4F)CCOCC3)n2)c2cc(-c3cn4nc(OC)sc4n3)oc2c1]

156A. (2-(4-(2-Fluorophenyl)tetrahydro-2H-pyran-4-yl)thiazol-4-yl)methanol

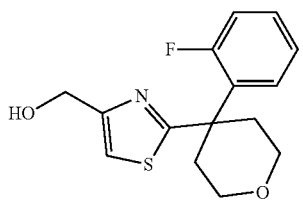 [SMILES: OCc1csc(C2(c3ccccc3F)CCOCC2)n1]

The alcohol was prepared according to the method described in Example 153 above. LC (Method F): 1.948 min. ¹H NMR (DMSO-d₆, 400 MHz) δ ppm: 7.48 (dt, J=2.0, 8.2 Hz, 1H), 7.38-7.33 (m, 1H), 7.31 (m, 1H), 7.23 (dt, J=1.6, 7.8 Hz, 1H), 7.13 (ddd, J=1.2, 8.2, 12.9 Hz, 1H), 5.27 (br s, 1H), 4.52 (s, 2H), 3.73-3.62 (m, 4H), 2.44 (m, 4H).

Example 156. 6-(4-((2-(4-(2-Fluorophenyl)tetrahydro-2H-pyran-4-yl)thiazol-4-yl)methoxy)-6-methoxybenzofuran-2-yl)-2-methoxyimidazo[2,1-b][1,3,4]thiadiazole

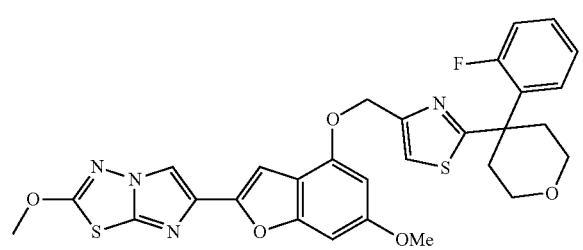 [SMILES: COc1cc(OCc2csc(C3(c4ccccc4F)CCOCC3)n2)c2cc(-c3cn4nc(OC)sc4n3)oc2c1]

The title compound was prepared according to the method described in Example 153 above and was isolated as a solid. LC (Method F): 2.633 min. HRMS(ESI): calcd for $C_{29}H_{26}FN_4O_5S_2$ [M+H]⁺ m/z 593.1329, found 593.1356. ¹H NMR (DMSO-d₆, 400 MHz) δ ppm: 8.37 (s, 1H), 7.73 (s, 1H), 7.51 (dt, J=1.6, 8.2 Hz, 1H), 7.37 (m, 1H), 7.25 (dt, J=1.2, 7.4 Hz, 1H), 7.15 (ddd, J=1.2, 8.2, 12.9 Hz, 1H), 6.98 (s, 1H), 6.83 (dd, J=0.8, 2.0 Hz, 1H), 6.61 (d, J=2.0 Hz, 1H), 5.28 (s, 2H), 4.20 (s, 3H), 3.80 (s, 3H), 3.74-3.63 (m, 4H), 2.58-2.42 (m, 4H).

Example 157

2-Methoxy-6-(6-methoxy-4-((2-(4-(p-tolyl)tetrahydro-2H-pyran-4-yl)thiazol-4-yl)methoxy)benzofuran-2-yl)imidazo[2,1-b][1,3,4]thiadiazole

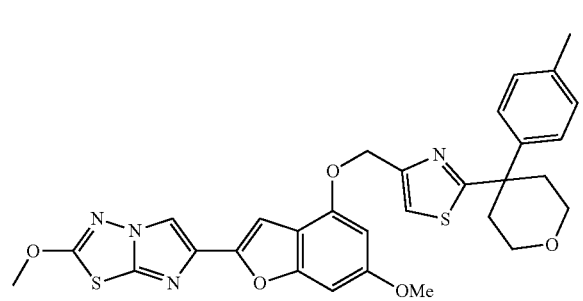 [SMILES: COc1cc(OCc2csc(C3(c4ccc(C)cc4)CCOCC3)n2)c2cc(-c3cn4nc(OC)sc4n3)oc2c1]

157A. (2-(4-(p-Tolyl)tetrahydro-2H-pyran-4-yl)thiazol-4-yl)methanol

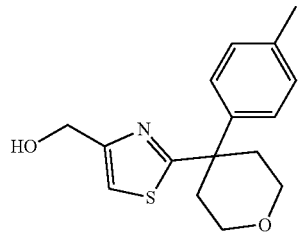 [SMILES: Cc1ccc(C2(c3nc(CO)cs3)CCOCC2)cc1]

The alcohol was prepared according to the method described in Example 153 above. LC (Method F): 2.043 min. ¹H NMR (DMSO-d₆, 400 MHz) δ ppm: 7.29 (t, J=1.2 Hz, 1H), 7.27 (m, 2H), 7.14 (d, J=7.8 Hz, 2H), 5.26 (t, J=5.5 Hz, 1H), 4.53 (d, J=4.3 Hz, 2H), 3.72-3.66 (m, 2H), 3.57 (m, 1H), 3.55 (dd, J=2.7, 9.0 Hz, 1H), 2.53 (m, 2H), 2.29 (m, 2H), 2.25 (s, 3H).

Example 157. 2-Methoxy-6-(6-methoxy-4-((2-(4-(p-tolyl)tetrahydro-2H-pyran-4-yl)thiazol-4-yl)methoxy)benzofuran-2-yl)imidazo[2,1-b][1,3,4]thiadiazole

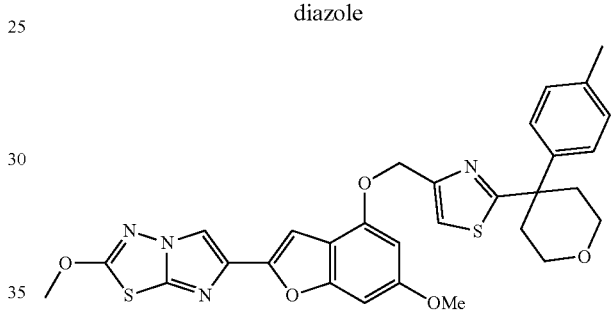

The title compound was prepared according to the method described in Example 153 above and was isolated as a solid. LC (Method F): 2.662 min. HRMS(ESI): calcd for $C_{30}H_{29}N_4O_5S_2$ [M+H]⁺ m/z 589.1579, found 589.1593. ¹H NMR (DMSO-d₆, 400 MHz) δ ppm: 8.37 (s, 1H), 7.71 (s, 1H), 7.29 (d, J=8.2 Hz, 2H), 7.14 (d, J=8.2 Hz, 2H), 6.98 (s, 1H), 6.83 (dd, J=0.8, 1.6 Hz, 1H), 6.26 (d, J=2.0 Hz, 1H), 5.28 (s, 2H), 4.20 (s, 3H), 3.80 (s, 3H), 3.71 (m, 2H), 3.57 (m, 2H), 2.56 (m, 2H), 2.32 (m, 2H), 2.25 (s, 3H).

Example 158

2-Methoxy-6-(6-methoxy-4-((2-(4-(3-methoxyphenyl)tetrahydro-2H-pyran-4-yl)thiazol-4-yl)methoxy)benzofuran-2-yl)imidazo[2,1-b][1,3,4]thiadiazole

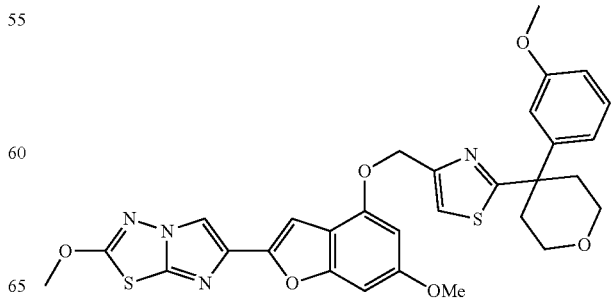

158A. (2-(4-(3-Methoxyphenyl)tetrahydro-2H-pyran-4-yl)thiazol-4-yl)methanol

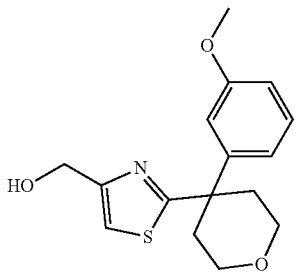 [SMILES: COc1cccc(C2(c3nc(CO)cs3)CCOCC2)c1]

The alcohol was prepared according to the method described in Example 153 above. LC (Method F): 1.953 min. $^1$H NMR (DMSO-d$_6$, 400 MHz) δ ppm: 7.32 (s, 1H), 7.26 (t, J=8.0 Hz, 1H), 6.96 (dd, J=1.2, 7.8 Hz, 1H), 6.88 (m, 1H), 6.80 (dd, J=2.3, 8.0 Hz, 1H), 5.28 (t, J=5.7 Hz, 1H), 4.53 (d, J=5.5 Hz, 2H), 3.72 (m, 2H), 3.72 (s, 3H), 3.54 (m, 2H), 2.53 (m, 2H), 2.29 (ddd, J=3.5, 9.2, 13.3 Hz, 2H).

Example 158. 2-Methoxy-6-(6-methoxy-4-((2-(4-(3-methoxyphenyl)tetrahydro-2H-pyran-4-yl)thiazol-4-yl)methoxy)benzofuran-2-yl)imidazo[2,1-b][1,3,4]thiadiazole

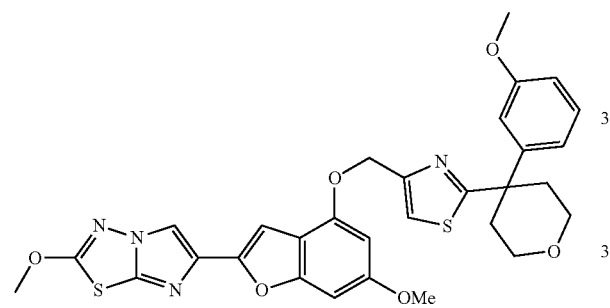

The title compound was prepared according to the method described in Example 153 above and was isolated as a solid. LC (Method F): 2.675 min. HRMS(ESI): calcd for $C_{30}H_{29}N_4O_6S_2$ [M+H]$^+$ m/z 605.1529, found 605.1544. $^1$H NMR (DMSO-d$_6$, 400 MHz) δ ppm: 836 (s, 1H), 7.74 (s, 1H), 7.25 (t, J=8.0 Hz, 1H), 6.98 (m, 2H), 6.90 (m, 1H), 6.82 (m, 1H), 6.81 (m, 1H), 6.62 (d, J=1.6 Hz, 1H), 5.29 (s, 2H), 4.20 (s, 3H), 3.80 (s, 3H), 3.73 (m, 2H), 3.71 (s, 3H), 3.56 (m, 2H), 2.57 (m, 2H), 2.32 (m, 2H).

Example 159

2-Methoxy-6-(6-methoxy-4-((2-(4-(4-methoxyphenyl)tetrahydro-2H-pyran-4-yl)thiazol-4-yl)methoxy)benzofuran-2-yl)imidazo[2,1-b][1,3,4]thiadiazole

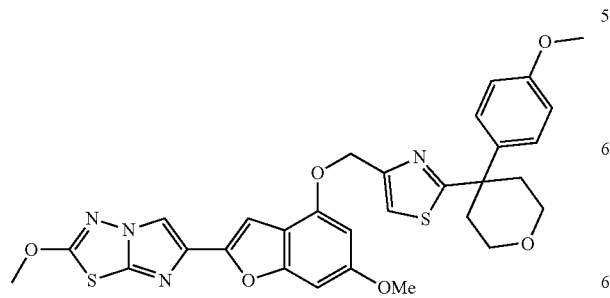

159A. (2-(4-(4-Methoxyphenyl)tetrahydro-2H-pyran-4-yl)thiazol-4-yl)methanol

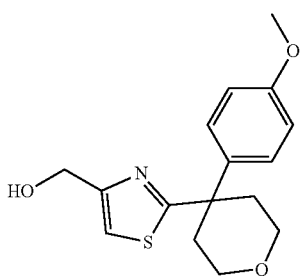 [SMILES: COc1ccc(C2(c3nc(CO)cs3)CCOCC2)cc1]

The alcohol was prepared according to the method described in Example 153 above. LCMS (APCI): calcd for $C_{16}H_{20}NO_3S$ [M+H]$^+$ m/z 306.12, found 306.20.

Example 159. 2-Methoxy-6-(6-methoxy-4-((2-(4-(4-methoxyphenyl)tetrahydro-2H-pyran-4-yl)thiazol-4-yl)methoxy)benzofuran-2-yl)imidazo[2,1-b][1,3,4]thiadiazole

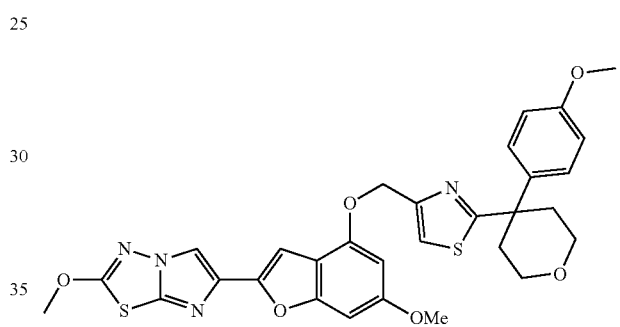

The title compound was prepared according to the method described in Example 153 above and was isolated as a solid. LC (Method F): 2.440 min. HRMS(ESI): calcd for $C_{30}H_{29}N_4O_6S_2$ [M+H]$^+$ m/z 605.1529, found 605.1557. $^1$H NMR (DMSO-d$_6$, 400 MHz) δ ppm: 8.36 (s, 1H), 7.70 (s, 1H), 7.32 (d, J=8.6 Hz, 2H), 6.98 (s, 1H), 6.88 (d, J=9.0 Hz, 2H), 6.83 (s, 1H), 6.62 (d, J=1.6 Hz, 1H), 5.28 (s, 2H), 4.20 (s, 3H), 3.80 (s, 3H), 3.72 (s, 3H), 3.70 (m, 2H), 3.60 (m, 2H), 2.55 (m, 2H), 2.30 (m, 2H).

Example 160

Methyl 4-(4-(4-(((6-methoxy-2-(2-methoxyimidazo[2,1-b][1,3,4]thiadiazol-6-yl)benzofuran-4-yl)oxy)methyl)thiazol-2-yl)tetrahydro-2H-pyran-4-yl)benzoate

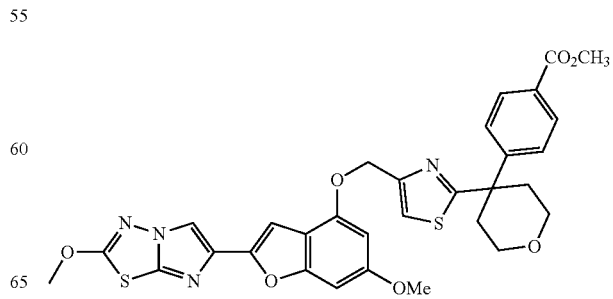

160A. 2-(4-(4-Bromophenyl)tetrahydro-2H-pyran-4-yl)-4-(((tert-butyldimethylsilyl)-oxy)methyl)thiazole

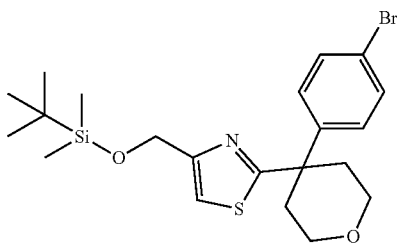 [SMILES: CC(C)(C)[Si](C)(C)OCc1csc(C2(c3ccc(Br)cc3)CCOCC2)n1]

To a stirred solution of (2-(4-(4-bromophenyl)tetrahydro-2H-pyran-4-yl)thiazol-4-yl)methanol (Example 153E, 0.163 g, 0.460 mmol) and imidazole (0.047 g, 0.690 mmol) in DCM (7.5 mL) at ambient temperature was added tert-butylchlorodimethylsilane (0.087 g, 0.575 mmol). The reaction mixture was stirred overnight, then quenched with MeOH and concentrated to dryness. The residue was purified by column chromatography using hexanes-EtOAc as eluent to give 2-(4-(4-bromophenyl)tetrahydro-2H-pyran-4-yl)-4-(((tert-butyldimethylsilyl)oxy)methyl)thiazole (0.214 g, 99%) as a clear, colorless oil. LC (Method A): 2.683 min. $^1$H NMR (DMSO-$d_6$, 400 MHz) δ ppm: 7.46 (d, J=8.8 Hz, 2H), 7.32 (s, 1H), 7.28 (d, J=8.8 Hz, 2H), 4.66 (s, 2H), 3.65 (m, 2H), 3.49 (m, 2H), 2.48 (m, 2H), 2.23 (m, 2H), 0.81 (s, 9H), 0.00 (s, 6H).

160B. Methyl 4-(4-(4-(((tert-butyldimethylsilyl)oxy)methyl)thiazol-2-yl)tetrahydro-2H-pyran-4-yl)benzoate and Methyl 4-(4-(4-(hydroxymethyl)thiazol-2-yl)tetrahydro-2H-pyran-4-yl)benzoate

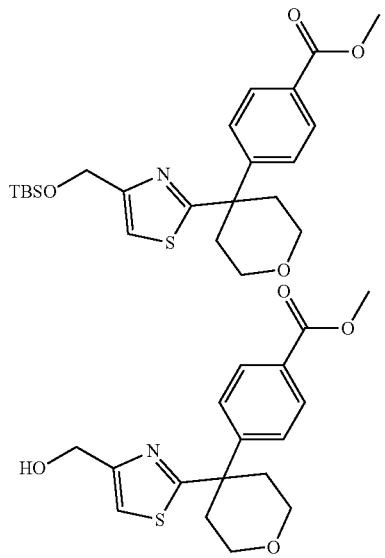

To a mixture of Pd(OAc)$_2$ (0.002 g, 9.14 μmol) and Xantphos (0.0106 g, 0.018 mmol) was added as a solution of 2-(4-(4-bromophenyl)tetrahydro-2H-pyran-4-yl)-4-(((tert-butyldimethylsilyl)oxy)methyl)thiazole (0.214 g, 0.457 mmol) in Et$_3$N (2 mL, 14.35 mmol) after which MeOH (0.185 mL, 4.57 mmol) was added. The reaction mixture was placed under high vacuum and then back-filled with CO (g) (using a CO-filled balloon). The vessel was sealed and then heated with stirring at 70° C. (oil bath temperature) for 24 h. The cooled mixture was filtered through CELITE® and the filter-cake was washed with additional MeOH. The filtrate was evaporated and the residue was purified by flash chromatography using hexanes-EtOAc as eluent to give methyl 4-(4-(4-(((tert-butyldimethylsilyl)oxy)methyl)thiazol-2-yl)tetrahydro-2H-pyran-4-yl)benzoate (0.052 g, 25.4%) as a clear, colorless oil. LC (Method A): 2.552 min. LCMS (APCI): calcd for $C_{23}H_{34}NO_4SSi$ [M+H]$^+$ m/z 448.20, found 448.20. Further elution afforded methyl 4-(4-(4-(hydroxymethyl)thiazol-2-yl)tetrahydro-2H-pyran-4-yl)benzoate (0.029 g, 19.04%) as a white solid. LC (Method A): 1.769 min. LCMS (APCI): calcd for $C_{17}H_{21}NO_4S$ [M+H]$^+$ m/z 334.11, found 334.20.

Example 160. Methyl 4-(4-(4-(((6-methoxy-2-(2-methoxyimidazo[2,1-b][1,3,4]thiadiazol-6-yl)benzofuran-4-yl)oxy)methyl)thiazol-2-yl)tetrahydro-2H-pyran-4-yl)benzoate

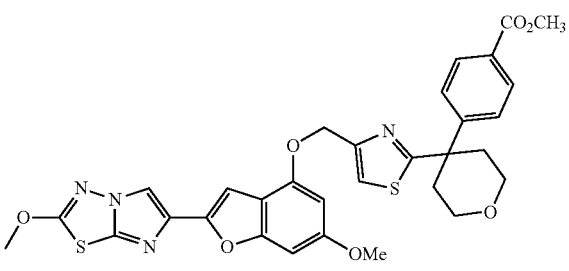 [SMILES: COC(=O)c1ccc(C2(c3nc(COc4cc(OC)cc5oc(-c6cn7nc(OC)sc7n6)cc45)cs3)CCOCC2)cc1]

The title compound was prepared according to the method described in Example 153 above and was isolated as a solid. LC (Method A): 2.588 min. HRMS(ESI): calcd for $C_{31}H_{29}N_4O_7S_2$ [M+H]$^+$ m/z 633.1478, found 633.1493. $^1$H NMR (DMSO-$d_6$, 400 MHz) δ ppm: 8.36 (s, 1H), 7.91 (d, J=8.6 Hz, 2H), 7.76 (s, 1H), 7.56 (d, J=8.2 Hz, 2H), 6.97 (s, 1H), 6.82 (m, 1H), 6.61 (d, J=1.6 Hz, 1H), 5.30 (s, 2H), 4.20 (s, 3H), 3.82 (s, 3H), 3.80 (s, 3H), 3.74 (dt, J=3.9, 12.1 Hz, 2H), 3.57 (m, 2H), 2.62 (m, 2H), 2.36 (m, 2H).

Example 161

4-(4-(4-(((6-Methoxy-2-(2-methoxyimidazo[2,1-b][1,3,4]thiadiazol-6-yl)benzofuran-4-yl)oxy)methyl)thiazol-2-yl)tetrahydro-2H-pyran-4-yl)-N,N-dimethylbenzamide

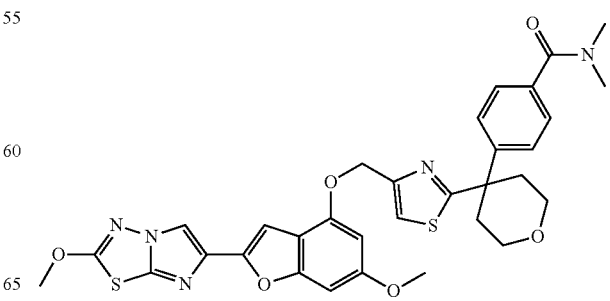

161A. 4-(4-(4-(((tert-butyldimethylsilyl)oxy)methyl)thiazol-2-yl)tetrahydro-2H-pyran-4-yl)-N,N-dimethylbenzamide

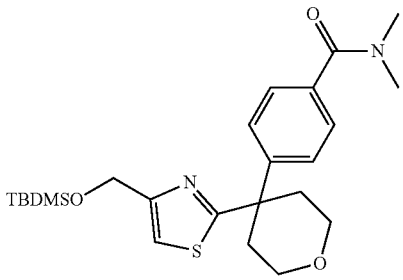 [SMILES: CN(C)C(=O)c1ccc(C2(c3nc(CO[Si](C)(C)C(C)(C)C)cs3)CCOCC2)cc1]

To a stirred solution of methyl 4-(4-(4-(((tert-butyldimethylsilyl)oxy)methyl)thiazol-2-yl)tetrahydro-2H-pyran-4-yl)benzoate (Example 160B, 0.863 g, 1.928 mmol) in MeOH (10 mL) was added 1 N sodium hydroxide (2.121 mL, 2.121 mmol). The reaction mixture was stirred at ambient temperature for 2 h and then at 55° C. for 1 h. The cooled mixture was neutralized (pH 7) with 1N HCl and stirring was continued for 10 min. The resulting slurry was filtered and the residue was washed with water and then dried in vacuo to give 4-(4-(4-(((tert-butyldimethylsilyl)oxy)methyl)thiazol-2-yl)tetrahydro-2H-pyran-4-yl)benzoic acid (0.305 g, 0.703 mmol, 36.5%) as a white solid. LC (Method A): 2.418 min. LCMS (APCI): calcd for $C_{22}H_{32}NO_4SSi$ $[M+H]^+$ m/z 434.18, found 434.20.

To a stirred solution of 4-(4-(4-(((tert-butyldimethylsilyl)oxy)methyl)thiazol-2-yl)tetrahydro-2H-pyran-4-yl)benzoic acid (0.100 g, 0.231 mmol) in DMF (3 mL) was added dimethylamine (0.115 mL, 0.231 mmol), DIEA (0.201 mL, 1.153 mmol) and HATU (0.088 g, 0.231 mmol). After stirring at room temperature for 2 h, the mixture was partitioned between EtOAc and saturated aqueous NaHCO₃. The organic phase was separated, dried (MgSO₄), filtered and concentrated to dryness. The residue was purified by flash chromatography using DCM-EtOAc as eluent to give 4-(4-(4-(((tert-butyldimethylsilyl)oxy)methyl)thiazol-2-yl)tetrahydro-2H-pyran-4-yl)-N,N-dimethylbenzamide (0.088 g, 83%) as a white solid. LC (Method A): 2.343 min. ¹H NMR (DMSO-d₆, 400 MHz) δ ppm: 7.43 (m, 2H), 7.37 (m, 3H), 4.73 (d, J=0.8 Hz, 2H), 4.34 (t, J=5.1 Hz, 1H), 3.74 (m, 2H), 3.56 (m, 2H), 3.44 (m, 1H), 2.95 (br s, 2H), 2.88 (br s, 2H), 2.58 (m, 2H), 2.33 (m, 2H), 0.87 (s, 9H), 0.06 (s, 6H).

161B. 4-(4-(4-(Hydroxymethyl)thiazol-2-yl)tetrahydro-2H-pyran-4-yl)-N,N-dimethylbenzamide

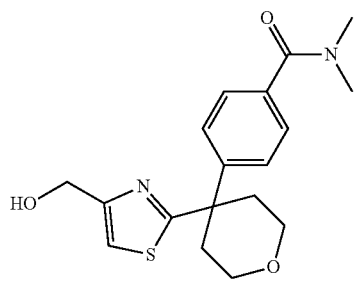 [SMILES: CN(C)C(=O)c1ccc(C2(c3nc(CO)cs3)CCOCC2)cc1]

To a stirred solution of 4-(4-(4-(((tert-butyldimethylsilyl)oxy)methyl)thiazol-2-yl)tetrahydro-2H-pyran-4-yl)-N,N-dimethylbenzamide (0.088 g, 0.191 mmol) in THF (1 mL) was added triethylamine trihydrofluoride (0.156 mL, 0.955 mmol) and the mixture was stirred at room temperature for 4 h. The resulting mixture was partitioned between EtOAc and saturated aqueous NaHCO₃ and the organic phase was separated, dried (MgSO₄), filtered and concentrated to dryness. The residue was purified by flash chromatography using DCM-EtOAc as eluent to give 4-(4-(4-(hydroxymethyl)thiazol-2-yl)tetrahydro-2H-pyran-4-yl)-N,N-dimethylbenzamide (0.044 g, 66.5%) as a clear, colorless oil. LC (Method A): 1.492 min. LCMS (APCI): calcd for $C_{18}H_{23}N_2O_3S$ $[M+H]^+$ m/z 347.14, found 347.20.

Example 161. 4-(4-(4-(((6-Methoxy-2-(2-methoxyimidazo[2,1-b][1,3,4]thiadiazol-6-yl)benzofuran-4-yl)oxy)methyl)thiazol-2-yl)tetrahydro-2H-pyran-4-yl)-N,N-dimethylbenzamide

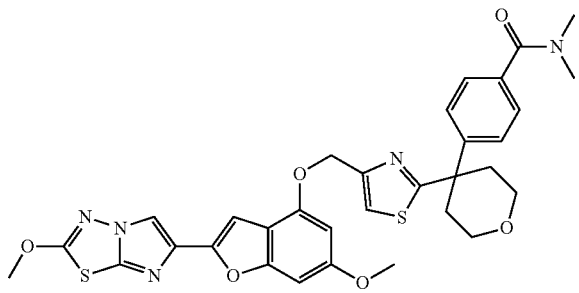

To a suspension of 6-methoxy-2-(2-methoxyimidazo[2,1-b][1,3,4]thiadiazol-6-yl)benzofuran-4-ol (Example 1H, 0.040 g, 0.127 mmol) and 4-(4-(4-(hydroxymethyl)thiazol-2-yl)tetrahydro-2H-pyran-4-yl)-N,N-dimethylbenzamide (0.044 g, 0.127 mmol) in dry THF (8 mL) was added tri-n-butylphosphine (0.082 mL, 0.318 mmol) and then a solution of ADDP (0.080 g, 0.318 mmol) in THF (2 mL) was added dropwise over 30 min via syringe pump. After stirring for another 30 min, the reaction mixture was partitioned between EtOAc and saturated aqueous NaHCO₃. The organic phase was separated, washed with brine, dried (MgSO₄), filtered and concentrated to dryness. The residue was purified by flash column chromatography using 0 to 10% of MeOH:NH₄OH (9:1) in DCM as eluent to give the slightly impure product. The obtained material was further triturated with MeCN and the resulting slurry was filtered, washed with a minimum volume of MeCN and dried under reduced pressure to give the title compound (0.040 g, 48.8%) as a white solid. LC (Method A): 2.297 min. HRMS(ESI): calcd for $C_{32}H_{32}N_5O_6S_2$ $[M+H]^+$ m/z 646.1794 found, 646.1870. ¹H NMR (DMSO-d₆, 400 MHz) δ ppm: 8.36 (s, 1H), 7.76 (s, 1H), 7.40 (dd, J=8.4, 38.5 Hz, 4H), 6.97 (d, J=0.8 Hz, 1H), 6.83 (dd, J=0.8, 1.6 Hz, 1H), 6.62 (d, J=1.6 Hz, 1H), 5.30 (s, 2 h), 4.20 (s, 3H), 3.80 (s, 3H), 3.75 (m, 2H), 3.57 (m, 2H), 2.95 (br s, 3H), 2.87 (br s, 3H), 2.61 (m, 2H), 2.35 (m, 2H).

Example 162

2-Methoxy-6-(6-methoxy-4-((2-(4-phenyltetrahydro-2H-pyran-4-yl)thiazol-4-yl)methoxy)benzofuran-2-yl)imidazo[2,1-b][1,3,4]thiadiazole

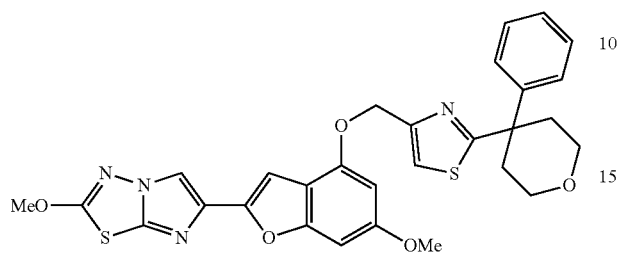

162A. (2-(4-Phenyltetrahydro-2H-pyran-4-yl)thiazol-4-yl)methanol

The alcohol was prepared according to the method described in Example 153 above. LC (Method F): 1.936 min. $^1$H NMR (DMSO-d$_6$, 400 MHz) δ ppm: 7.39 (m, 2H), 7.34 (m, 3H), 7.22 (m, 1H), 5.27 (t, J=5.9 Hz, 1H), 4.54 (m, 2H), 3.72 (m, 2H), 3.58 (dd, J=2.3, 9.4 Hz, 1H), 3.55 (dd, J=2.3, 9.4 Hz, 1H), 2.56 (m, 2H), 2.33 (m, 1H), 2.30 (dd, J=3.9, 9.4 Hz, 1H).

Example 162. 2-Methoxy-6-(6-methoxy-4-((2-(4-phenyltetrahydro-2H-pyran-4-yl)thiazol-4-yl)methoxy)benzofuran-2-yl)imidazo[2,1-b][1,3,4]thiadiazole

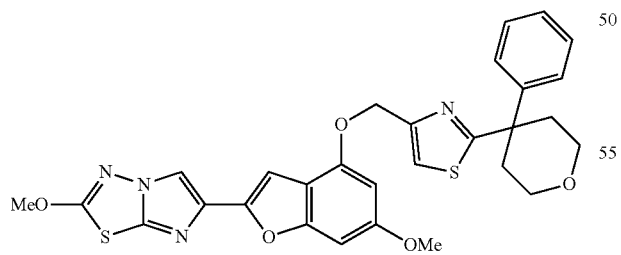

The title compound was prepared according to the method described in Example 153 above and was isolated as a solid. LC (Method F): 2.651 min. HRMS(ESI): calcd for C$_{29}$H$_{27}$N$_4$O$_5$S$_2$ [M+H]$^+$ m/z 575.1423, found 575.1442. $^1$H NMR (DMSO-d$_6$, 400 MHz) δ ppm: 8.36 (s, 1H), 7.73 (s, 1H), 7.41 (m, 2H), 7.33 (m, 2H), 7.23 (m, 1H), 6.98 (d, J=0.8 Hz, 1H), 6.83 (dd, J=0.8, 1.6 Hz, 1H), 6.63 (d, J=2.0 Hz, 1H), 5.30 (s, 2H), 4.20 (s, 3H), 3.80 (s, 3H), 3.73 (dt, J=4.3, 11.3 Hz, 2H), 3.57 (m, 2H), 2.60 (m, 2H), 2.34 (m, 2H).

Example 163

6-(4-((2-(3-(4-Chlorophenyl)tetrahydrofuran-3-yl)thiazol-4-yl)methoxy)-6-methoxybenzofuran-2-yl)-2-methoxyimidazo[2,1-b][1,3,4]thiadiazole

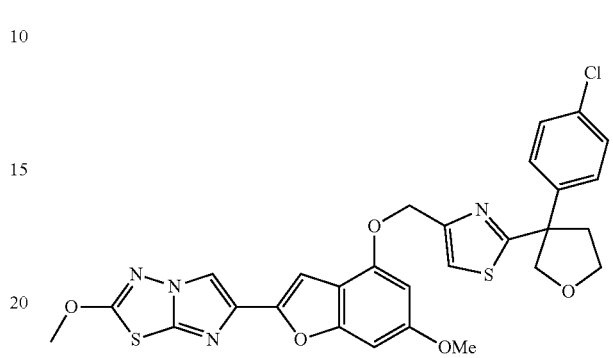

163A. 3-(4-Chlorophenyl)tetrahydrofuran-3-carbonitrile

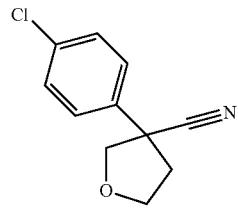 [SMILES: N#CC1(c2ccc(Cl)cc2)CCOC1]

To a stirred suspension of NaH (60% in oil, 0.792 g, 19.79 mmol) (Note: previously washed twice with hexanes and dried in vacuo) in NMP (17 mL) cooled at −20° C. was added dropwise a mixture of 2-(4-chlorophenyl)acetonitrile (1.00 g, 6.60 mmol) and 1-chloro-2-(chloromethoxy)ethane (0.851 g, 6.60 mmol) in diethyl ether (4 mL). The mixture was then allowed to warm to room temperature over 24 h. The reaction was slowly quenched with ice-water and the resulting mixture was extracted with ether (×3). The combined organic layer was washed with water and brine, dried (MgSO$_4$), concentrated and evaporated. The residue was purified by flash chromatography using hexanes-EtOAc as eluent to give 3-(4-chlorophenyl)tetrahydrofuran-3-carbonitrile (0.621 g, 45.3%) as an orange oil. LC (Method F): 1.970 min. $^1$H NMR (DMSO-d$_6$, 400 MHz) δ ppm: 7.54 (m, 4H), 4.39 (d, J=9.0 Hz, 1H), 4.06 (dd, J=5.7, 8.2 Hz, 2H), 3.84 (d, J=8.6 Hz, 1H), 2.77 (m, 1H), 2.48 (m, 1H).

163B. 3-(4-Chlorophenyl)tetrahydrofuran-3-carboxamide

A solution of 3-(4-chlorophenyl)tetrahydrofuran-3-carbonitrile (0.615 g, 2.96 mmol) in concentrated H$_2$SO$_4$ (4 mL) was stirred overnight at ambient temperature. The reaction mixture was then carefully quenched with crushed ice and the mixture was stirred for 1 h. The resulting suspension was filtered and the filter-cake was washed with water, then diethyl ether and finally it was dried under reduced pressure to give 3-(4-chlorophenyl)-tetrahydrofuran-3-carboxamide (0.466 g, 69.7%) as a beige solid. LC (Method F): 1.699 min. $^1$H NMR (DMSO-d$_6$, 400 MHz) δ ppm: 7.40 (m, 2H), 7.32 (m, 2H), 7.30 (br s, 1H), 7.07 (br s, 1H), 4.45 (d, J=8.2 Hz, 1H), 3.79 (m, 1H), 3.75 (d, J=7.8 Hz, 1H), 3.72 (d, J=8.6 Hz, 1H), 2.82 (ddd, J=5.1, 7.4, 12.5 Hz, 1H), 2.10 (m, 1H).

163C. 3-(4-Chlorophenyl)tetrahydrofuran-3-carbothioamide

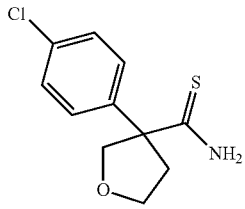 [SMILES: NC(=S)C1(c2ccc(Cl)cc2)CCOC1]

To a stirred solution of 3-(4-chlorophenyl)tetrahydrofuran-3-carboxamide (0.450 g, 1.994 mmol) in THF (15 mL) was added 2,4-bis(4-methoxyphenyl)-1,3,2,4-dithiadiphosphetane 2,4-disulfide (0.403 g, 0.997 mmol) all at once and the mixture was heated to reflux for 2 h. The resulting mixture was then concentrated to near dryness and the concentrate was partitioned between EtOAc and saturated aqueous NaHCO$_3$. The organic phase was separated, dried (MgSO$_4$), filtered and concentrated to dryness. The residue was purified by flash chromatography using hexanes-EtOAc as eluent to give 3-(4-chlorophenyl)-tetrahydrofuran-3-carbothioamide (0.356 g, 73.9%) as a white solid. LC (Method F): 1.864 min. $^1$H NMR (DMSO-d$_6$, 400 MHz) δ ppm: 9.71 (br s, 1H), 9.00 (br s, 1H), 7.43 (m, 4H), 4.43 (d, J=9.0 Hz, 1H), 3.99 (d, J=8.6 Hz, 1H), 3.84-3.71 (m, 2H), 2.91 (m, 1H), 2.33 (m, 1H).

163D. Ethyl 2-(3-(4-chlorophenyl)tetrahydrofuran-3-yl)thiazole-4-carboxylate

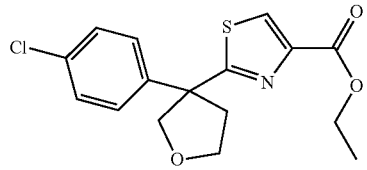 [SMILES: CCOC(=O)c1csc(C2(c3ccc(Cl)cc3)CCOC2)n1]

To a mixture of 3-(4-chlorophenyl)tetrahydrofuran-3-carbothioamide (0.345 g, 1.427 mmol) in i-PrOH (10 mL) was added ethyl bromopyruvate (0.215 mL, 1.713 mmol) and the reaction mixture was heated to reflux for 3 h. The cooled mixture was partitioned between EtOAc and saturated aqueous NaHCO$_3$ and the organic phase was washed with brine, dried (MgSO$_4$), filtered and concentrated to dryness. The residue was purified by flash chromatography using a gradient of 0 to 100% EtOAc in hexanes to give ethyl 2-(3-(4-chlorophenyl)tetrahydrofuran-3-yl)thiazole-4-carboxylate (0.200 g, 41.5%) as a clear, yellow oil. LC (Method F): 2.248 min. $^1$H NMR (DMSO-d$_6$, 400 MHz) δ ppm: 8.45 (s, 1H), 7.41 (m, 4H), 4.58 (d, J=8.6 Hz, 1H), 4.29 (q, J=7.0 Hz, 2H), 4.11 (d, J=8.6 Hz, 1H), 3.97-3.86 (m, 2H), 2.98 (m, 1H), 2.59 (m, 1H), 1.29 (t, J=7.0 Hz, 3H).

163E. (2-(3-(4-Chlorophenyl)tetrahydrofuran-3-yl)thiazol-4-yl)methanol

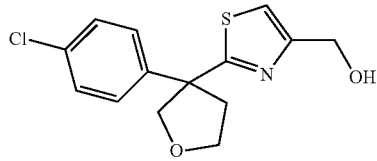 [SMILES: OCc1csc(C2(c3ccc(Cl)cc3)CCOC2)n1]

To an ice-cold solution of ethyl 2-(3-(4-chlorophenyl)tetrahydrofuran-3-yl)thiazole-4-carboxylate (0.200 g, 0.592 mmol) in THF (3 mL) was added LiBH$_4$ (0.026 g, 1.184 mmol) all at once, followed by MeOH (0.048 mL, 1.184 mmol). The resulting mixture was stirred at 0° C. for 5 min and then at ambient temperature for 4 h. The mixture was then re-cooled at 0° C., quenched by dropwise addition of saturated aqueous NH$_4$Cl and then extracted with ethyl acetate. The organic phase was separated, washed with brine, dried (MgSO$_4$), filtered and concentrated to dryness. The residue was purified by column chromatography using a gradient of 0 to 100% EtOAc in hexanes to give (2-(3-(4-chlorophenyl)tetrahydrofuran-3-yl)thiazol-4-yl)methanol (0.146 g, 83%) as a clear, colorless oil. LC (Method F): 1.990 min. $^1$H NMR (DMSO-d$_6$, 400 MHz) δ ppm: 7.39 (m, 4H), 7.32 (s, 1H), 5.28 (br s, 1H), 4.54 (d, J=8.6 Hz, 1H), 4.51 (s, 2H), 4.09 (d, J=8.2 Hz, 1H), 3.95-3.84 (m, 2H), 2.95 (ddd, J=4.7, 7.0, 12.1 Hz, 1H), 2.55 (m, 1H).

Example 163. 6-(4-((2-(3-(4-Chlorophenyl)tetrahydrofuran-3-yl)thiazol-4-yl)methoxy)-6-methoxybenzofuran-2-yl)-2-methoxyimidazo[2,1-b][1,3,4]thiadiazole

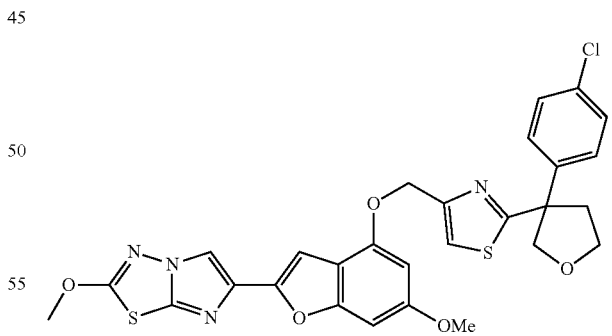

To a suspension of 6-methoxy-2-(2-methoxyimidazo[2,1-b][1,3,4]thiadiazol-6-yl)benzofuran-4-ol (Example 1H, 0.032 g, 0.101 mmol) and (2-(3-(4-chlorophenyl)tetrahydrofuran-3-yl)thiazol-4-yl)methanol (0.030 g, 0.101 mmol) in dry THF (8 mL) was added tri-n-butylphosphine (0.066 mL, 0.254 mmol) and then a solution of ADDP (0.064 g, 0.254 mmol) in THF (2 mL) was added dropwise over 30 min via syringe pump. After stirring for another 30 min, the reaction mixture was partitioned between EtOAc and saturated aqueous NaHCO₃. The organic phase was separated, washed with brine, dried (MgSO₄), filtered and concentrated to dryness. The residue was purified by flash chromatography using DCM-EtOAc as eluent to give the product as a yellow-beige solid. This material was further triturated with acetonitrile, the mixture was filtered and the filter-cake was rinsed with diethyl ether and then dried under vacuum. This gave pure 6-(4-((2-(3-(4-chlorophenyl)tetrahydrofuran-3-yl) thiazol-4-yl)methoxy)-6-methoxybenzofuran-2-yl)-2-methoxyimidazo[2,1-b][1,3,4]thiadiazole (0.041 g, 67.9%) as a white solid. LC (Method F): 2.619 min. HRMS(ESI): calcd for $C_{28}H_{24}ClN_4O_5S_2$ [M+H]⁺ m/z 595.0877, found 595.0888. ¹H NMR (DMSO-d₆, 400 MHz) δ ppm: 8.37 (s, 1H), 7.74 (s, 1H), 7.40 (s, 4H), 6.98 (s, 1H), 6.83 (d, J=0.8 Hz, 1H), 6.60 (d, J=1.6 Hz, 1H), 5.26 (s, 2H), 4.59 (d, J=8.6 Hz, 1H), 4.20 (s, 3H), 4.12 (d, J=8.6 Hz, 1H), 3.98-3.87 (m, 2H), 3.80 (s, 3H), 2.99 (m, 1H), 2.62-2.55 (m, 1H).

Example 164

2-Methoxy-6-(6-methoxy-4-((2-(3-(p-tolyl)tetrahydrofuran-3-yl)thiazol-4-yl)methoxy)benzofuran-2-yl)imidazo[2,1-b][1,3,4]thiadiazole

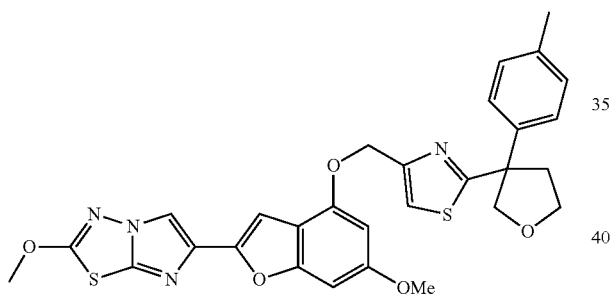

164A. (2-(3-(p-Tolyl)tetrahydrofuran-3-yl)thiazol-4-yl)methanol

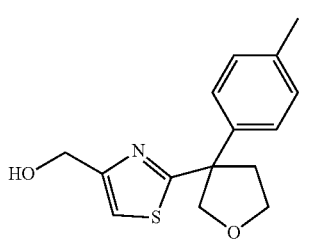 [SMILES: Cc1ccc(C2(c3nc(CO)cs3)CCOC2)cc1]

The alcohol was prepared according to the method described in Example 163 above. LC (Method F): 1.995 min. ¹H NMR (DMSO-d₆, 400 MHz) δ ppm: 7.28 (s, 1H), 7.22 (m, 2H), 7.14 (d, J=8.2 Hz, 2H), 5.26 (t, J=5.7 Hz, 1H), 4.55 (d, J=8.2 Hz, 1H), 4.50 (dd, J=0.8, 5.9 Hz, 2H), 4.07 (d, J=8.2 Hz, 1H), 3.93-3.83 (m, 2H), 2.94 (ddd, J=4.7, 7.2, 12.1 Hz, 1H), 2.53 (m, 1H).

Example 164. 2-Methoxy-6-(6-methoxy-4-((2-(3-(p-tolyl)tetrahydrofuran-3-yl)thiazol-4-yl)methoxy)benzofuran-2-yl)imidazo[2,1-b][1,3,4]thiadiazole

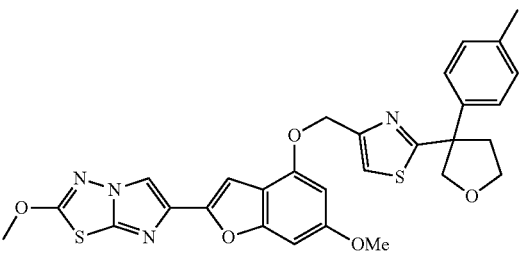

The title compound was prepared according to the method described in Example 163 above and was isolated as a solid. LC (Method F): 2.628 min. HRMS(ESI): calcd for $C_{29}H_{27}N_4O_5S_2$ [M+H]⁺ m/z 575.1423, found 575.1441. ¹H NMR (DMSO-d₆, 400 MHz) δ ppm: 8.37 (s, 1H), 7.70 (s, 1H), 7.25 (d, J=8.2 Hz, 2H), 7.15 (d, J=7.8 Hz, 2H), 6.98 (s, 1H), 6.83 (s, 1H), 6.61 (d, J=1.6 Hz, 1H), 5.26 (s, 2H), 4.59 (d, J=8.2 Hz, 1H), 4.20 (s, 3H), 4.10 (d, J=8.2 Hz, 1H), 3.96-3.86 (m, 2H), 3.80 (s, 3H), 2.98 (m, 1H), 2.56 (dt, J=8.2, 12.5 Hz, 1H), 2.26 (s, 3H).

Example 165

6-(4-((2-(3-(3-Chlorophenyl)tetrahydrofuran-3-yl)thiazol-4-yl)methoxy)-6-methoxybenzofuran-2-yl)-2-methoxyimidazo[2,1-b][1,3,4]thiadiazole

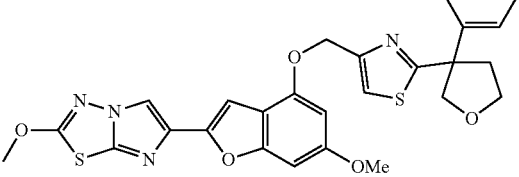

165A. (2-(3-(3-Chlorophenyl)tetrahydrofuran-3-yl)thiazol-4-yl)methanol

The alcohol was prepared according to the method described in Example 163 above. LC (Method F): 2.004 min. ¹H NMR (DMSO-d₆, 400 MHz) δ ppm: 7.37-7.27 (m, 5H), 5.25 (t, J=5.7 Hz, 1H), 4.53 (d, J=8.6 Hz, 1H), 4.48 (d, J=5.1 Hz, 2H), 4.07 (d, J=8.6 Hz, 1H), 3.89 (m, 1H), 3.83 (q, J=7.8 Hz, 1H), 2.93 (ddd, J=4.7, 7.4, 12.5 Hz, 1H), 2.54 (dt, J=8.2, 12.5 Hz, 1H).

Example 165. 6-(4-((2-(3-(3-Chlorophenyl)tetrahydrofuran-3-yl)thiazol-4-yl)methoxy)-6-methoxybenzofuran-2-yl)-2-methoxyimidazo[2,1-b][1,3,4]thiadiazole

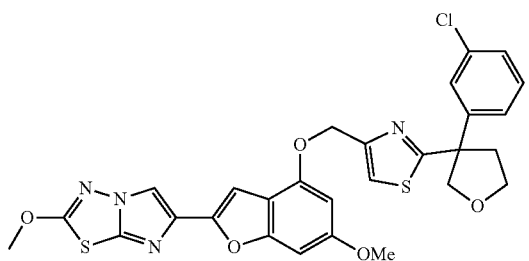 [SMILES: COc1cc(OCc2csc(C3(c4cccc(Cl)c4)CCOC3)n2)c2cc(-c3cn4nc(OC)sc4n3)oc2c1]

The title compound was prepared according to the method described in Example 163 above and was isolated as a solid. LC (Method F): 2.650 min. HRMS(ESI): calcd for C₂₈H₂₄ClN₄O₅S₂ [M+H]⁺ m/z 595.0877, found 595.0896. ¹H NMR (DMSO-d₆, 400 MHz) δ ppm: 8.65 (s, 1H), 8.02 (d, J=9.4 Hz, 1H), 7.98 (m, 2H), 7.93 (s, 1H), 7.55-7.49 (m, 3H), 7.26 (s, 1H), 7.19 (d, J=9.0 Hz, 1H), 6.78 (dd, J=2.1, 10.0 Hz, 2H), 5.44 (s, 2H), 3.80 (s, 3H), 2.53 (s, 3H).

Example 166

6-(4-((2-(3-(2-Fluorophenyl)tetrahydrofuran-3-yl)thiazol-4-yl)methoxy)-6-methoxybenzofuran-2-yl)-2-methoxyimidazo[2,1-b][1,3,4]thiadiazole

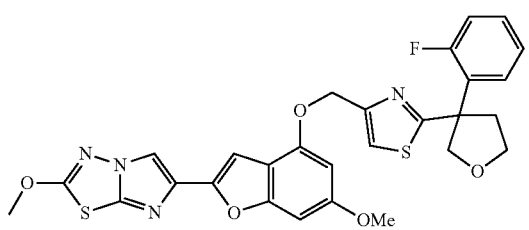 [SMILES: COc1cc(OCc2csc(C3(c4ccccc4F)CCOC3)n2)c2cc(-c3cn4nc(OC)sc4n3)oc2c1]

166A. (2-(3-(2-Fluorophenyl)tetrahydrofuran-3-yl)thiazol-4-yl)methanol

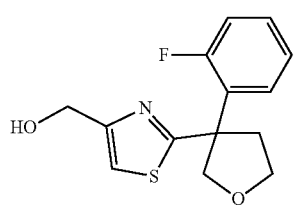 [SMILES: OCc1csc(C2(c3ccccc3F)CCOC2)n1]

The alcohol was prepared according to the method described in Example 163 above. LC (Method F): 1.900 min. ¹H NMR (DMSO-d₆, 400 MHz) δ ppm: 7.52 (dt, J=1.6, 7.8 Hz, 1H), 7.38 (m, 1H), 7.28 (s, 1H), 7.23 (dt, J=1.2, 7.6 Hz, 1H), 7.18 (ddd, J=1.2, 8.2, 11.7 Hz, 1H), 5.26 (t, J=5.9 Hz, 1H), 4.58 (dd, J=3.1, 8.6 Hz, 1H), 4.48 (d, J=5.5 Hz, 2H), 4.09 (d, J=8.6 Hz, 1H), 3.91 (m, 2H), 2.97 (m, 1H), 2.55 (m, 1H).

Example 166. 6-(4-((2-(3-(2-Fluorophenyl)tetrahydrofuran-3-yl)thiazol-4-yl)methoxy)-6-methoxybenzofuran-2-yl)-2-methoxyimidazo[2,1-b][1,3,4]thiadiazole

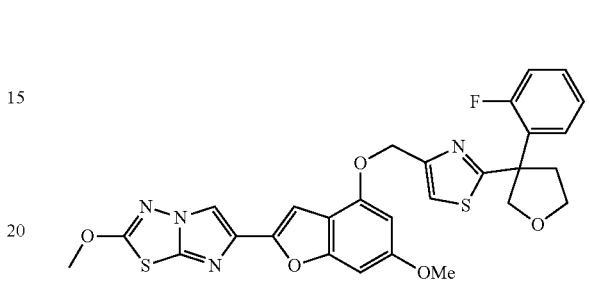

The title compound was prepared according to the method described in Example 163 above and was isolated as a solid. LC (Method F): 2.627 min. HRMS(ESI): calcd for C₂₈H₂₄FN₄O₅S₂ [M+H]⁻ m/z 579.1172, found 579.1202. ¹H NMR (DMSO-d₆, 400 MHz) δ ppm: 8.36 (s, 1H), 7.70 (s, 1H), 7.55 (dt, J=1.6, 7.8 Hz, 1H), 7.39 (m, 1H), 7.25 (dt, J=1.2, 7.4 Hz, 1H), 7.20 (ddd, J=0.8, 8.2, 11.7 Hz, 1H), 6.97 (s, 1H), 6.82 (d, J=0.8 Hz, 1H), 6.59 (d, J=1.6 Hz, 1H), 5.23 (s, 2H), 4.62 (dd, J=2.7, 8.6 Hz, 1H), 4.20 (s, 3H), 4.12 (d, J=8.6 Hz, 1H), 3.94 (m, 1H), 3.80 (s, 3H), 3.01 (m, 1H), 2.58 (dt, J=8.4, 12.5 Hz, 1H).

Example 167

2-Methoxy-6-(6-methoxy-4-((2-(4-methyltetrahydro-2H-pyran-4-yl)thiazol-4-yl)methoxy)benzofuran-2-yl)imidazo[2,1-b][1,3,4]thiadiazole

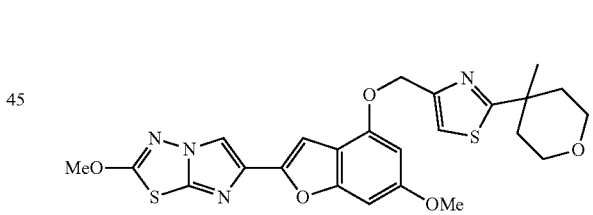

167A. Methyl 4-methyltetrahydro-2H-pyran-4-carboxylate

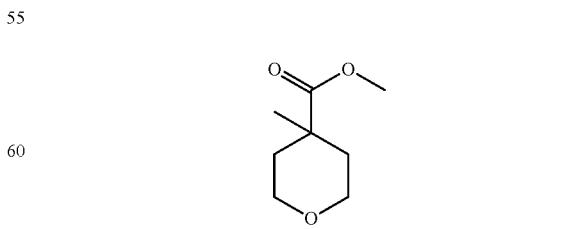

To a stirred solution of methyl tetrahydro-2H-pyran-4-carboxylate (0.926 mL, 6.94 mmol) in anhydrous THF (20 mL), at −78° C. under nitrogen, was added LDA (1 M in xx, 8.32 mL, 8.32 mmol) dropwise over 30 min. The mixture was then allowed to warm to 0° C. for 15 min and then it was re-cooled to −78° C. and iodomethane (0.867 mL, 13.87 mmol) was added dropwise over 5 min. The solution was stirred at −78° C. for 30 min and then at 0° C. for 3 h before being quenched with saturated aqueous NH₄Cl and extracted with ethyl acetate. The organic phase was washed with water and brine, dried (MgSO₄), filtered and evaporated to give a colorless oil. This material was purified by flash chromatography using a gradient of 0 to 100% EtOAc in hexanes to give methyl 4-methyltetrahydro-2H-pyran-4-carboxylate (0.666 g, 60.7%) as a clear, colorless oil. LC (Method F): 1.549 min. ¹H NMR (DMSO-d₆, 400 MHz) δ ppm: 3.67 (dt, J=4.5, 12.2 Hz, 2H), 3.64 (s, 3H), 3.33 (m, 2H), 1.91 (m, 2H), 1.43 (dd, J=3.9, 9.8 Hz, 1H), 1.40 (dd, J=3.9, 9.8 Hz, 1H), 1.16 (s, 3H).

167B. 4-Methyltetrahydro-2H-pyran-4-carboxylic Acid

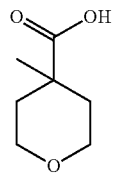

To a stirred solution of methyl 4-methyltetrahydro-2H-pyran-4-carboxylate (0.600 g, 3.79 mmol) in MeOH (15 mL) was added 1 N sodium hydroxide (7.59 mL, 7.59 mmol) and the mixture was stirred at ambient temperature for 24 h. The mixture was then concentrated to remove the MeOH and the aqueous concentrate was washed with EtOAc. The aqueous phase was acidified to pH 1 using concentrated HCl and then extracted with EtOAc. The organic extract was dried (MgSO₄), filtered and concentrated to dryness to give 4-methyltetrahydro-2H-pyran-4-carboxylic acid (0.316 g, 57.8%) as a clear, colorless oil. ¹H NMR (DMSO-d₆, 400 MHz) δ ppm: 12.21 (s, 1H), 3.67 (dt, J=4.5, 12.1 Hz, 2H), 3.35 (m, 2H), 1.89 (m, 2H), 1.36 (ddd, J=3.9, 9.8, 13.7 Hz, 2H), 1.15 (s, 3H).

167C. 4-Methyltetrahydro-2H-pyran-4-carboxamide

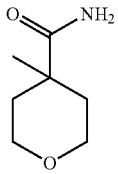

To a stirred solution of 4-methyltetrahydro-2H-pyran-4-carboxylic acid (0.300 g, 2.081 mmol) in DCM (5 mL) was added oxalyl chloride (0.364 mL, 4.16 mmol) and the reaction mixture was stirred for 1 h before being concentrated to dryness. The residue was taken up in THF (1 mL) and this solution was added with stirring to concentrated aqueous ammonia (5 mL) at 0° C. The mixture was stirred at 0° C. for 2 min and then at ambient temperature for 30 min before being diluted with water and extracted with EtOAc. The aqueous phase was concentrated to dryness to give a white solid which was suspended in EtOAc (20 mL) and the mixture heated with stirring at 60° C. for 20 min and then hot-filtered. The filtrate was combined with the original organic extract and evaporated to dryness to give 4-methyltetrahydro-2H-pyran-4-carboxamide (0.255 g, 86%) as a white solid which was used as such in the next step. ¹H NMR (DMSO-d₆, 400 MHz) δ ppm: 7.18 (br s, 1H), 6.86 (br s, 1H), 3.61 (m, 2H), 3.37 (m, 2H), 1.92 (m, 2H), 1.33 (dd, J=3.9, 9.4 Hz, 1H), 1.30 (m, 1H), 1.09 (s, 3H).

167D. 4-Methyltetrahydro-2H-pyran-4-carbothioamide

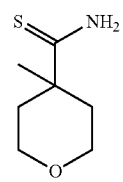

To a stirred solution of 4-methyltetrahydro-2H-pyran-4-carboxamide (0.250 g, 1.746 mmol) in THF (4 mL) was added Lawesson's reagent (0.353 g, 0.873 mmol) and the reaction mixture was heated at reflux for 6 h. The cooled mixture was concentrated to near dryness then partitioned with EtOAc-saturated aqueous NaHCO₃. The organic phase was separated and the aqueous phase was saturated with (solid) NaCl and back-extracted with EtOAc. The combined organic extract was dried (MgSO₄), filtered and concentrated to dryness. The residue was purified by flash column using hexanes-EtOAc as eluent to give 4-methyltetrahydro-2H-pyran-4-carbothioamide (0.052 g, 18.7%) as a white solid. ¹H NMR (DMSO-d₆, 400 MHz) δ ppm: 9.61 (br s, 1H), 8.79 (br s, 1H), 3.58 (m, 2H), 3.48 (m, 2H), 2.13 (m, 2H), 1.52 (m, 2H), 1.18 (s, 3H).

167E. Ethyl 2-(4-methyltetrahydro-2H-pyran-4-yl)thiazole-4-carboxylate

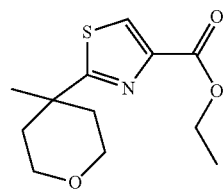 [SMILES: CCOC(=O)c1csc(C2(C)CCOCC2)n1]

To a mixture of 4-methyltetrahydro-2H-pyran-4-carbothioamide (0.052 g, 0.327 mmol) in i-PrOH (5 mL) was added ethyl bromopyruvate (0.049 mL, 0.392 mmol) and the reaction mixture was heated to reflux for 3 h. The cooled mixture was partitioned between EtOAc-saturated aqueous NaHCO₃ and the organic phase was washed with brine, dried (MgSO₄), filtered and concentrated to dryness. The residue was purified by flash chromatography using a gradient of 0 to 100% EtOAc in hexanes to give ethyl 2-(4-methyltetrahydro-2H-pyran-4-yl)thiazole-4-carboxylate (44 mg, 0.172 mmol, 52.8% yield) as a clear, colorless oil. The crude material was used as such without further purification. LC (Method F): 2.003 min.

167F. (2-(4-Methyltetrahydro-2H-pyran-4-yl)thiazol-4-yl)methanol

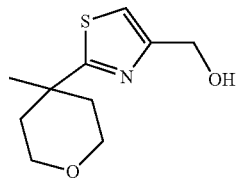

To an ice-cold solution of ethyl 2-(4-methyltetrahydro-2H-pyran-4-yl)thiazole-4-carboxylate (0.045 g, 0.176 mmol) in THF (1 mL) was added LiBH$_4$ (0.008 g, 0.352 mmol) all at once, followed by MeOH (0.014 mL, 0.352 mmol). The resulting mixture was stirred at 0° C. for 5 min and then at ambient temperature for 16 h. The mixture was then re-cooled at 0° C. and quenched by slow addition of saturated aqueous NH$_4$Cl. The resulting mixture was extracted with ethyl acetate, after which the organic phase was washed with brine, dried (MgSO$_4$), filtered and concentrated to dryness. The residue was purified by flash chromatography using a gradient of 0 to 100% EtOAc in hexanes to give (2-(4-methyltetrahydro-2H-pyran-4-yl)thiazol-4-yl)methanol (0.028 g, 74.5% yield) as a clear, colorless oil. LC (Method F): 1.564 min.

Example 167. 2-Methoxy-6-(6-methoxy-4-((2-(4-methyltetrahydro-2H-pyran-4-yl)thiazol-4-yl)methoxy)benzofuran-2-yl)imidazo[2,1-b][1,3,4]thiadiazole

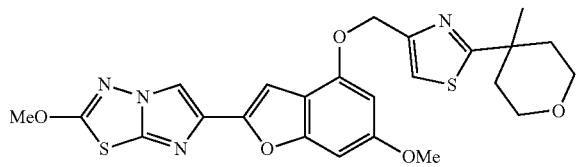 [SMILES: COc1cc(OCc2csc(C3(C)CCOCC3)n2)c2cc(-c3cn4nc(OC)sc4n3)oc2c1]

To a mixture of 6-methoxy-2-(2-methoxyimidazo[2,1-b][1,3,4]thiadiazol-6-yl)benzofuran-4-ol (Example 1H, 0.042 g, 0.131 mmol) and (2-(4-methyltetrahydro-2H-pyran-4-yl)thiazol-4-yl)methanol (0.028 g, 0.131 mmol) in dry THF (4 mL) was added tri-n-butylphosphine (0.085 mL, 0.328 mmol) and the resulting suspension was charged with a solution of ADDP (0.083 g, 0.328 mmol) in THF (1 mL), added dropwise over 30 min via syringe pump. After stirring for 1.5 h, the reaction mixture was diluted with EtOAc and then washed with 1N HCl, saturated aqueous NaHCO$_3$, water and brine. The organic solution was evaporated and the obtained crude residue was dissolved in DMSO and purified by preparative HPLC (ZORBAX® SB-C18 column 21.2×100 mm, eluted with CH$_3$CN-water-0.1% TFA). Product-containing fractions were concentrated to dryness and the residue was lyophilized from CH$_3$CN-water to give the title compound (0.038 g, 0.074 mmol, 56.5%) as an amorphous white solid. LC (Method F): 2.590 min. HRMS(ESI): calcd for C$_{24}$H$_{25}$N$_4$O$_5$S$_2$ [M+H]$^+$ m/z 513.1266, found 513.1305. TH NMR (DMSO-d$_6$, 400 MHz) δ ppm: 8.37 (s, 1H), 7.74 (s, 1H), 6.99 (d, J=0.8 Hz, 1H), 6.83 (dd, J=0.8, 1.6 Hz, 1H), 6.62 (d, J=2.0 Hz, 1H), 5.28 (s, 2H), 4.20 (s, 3H), 3.81 (s, 3H), 3.70 (m, 2H), 3.53 (dd, J=3.1, 7.8 Hz, 1H), 3.50 (dd, J=3.1, 7.8 Hz, 1H), 2.12 (m, 2H), 1.74 (m, 2H), 1.38 (s, 3H).

Example 168

6-(4-((2-(Chroman-4-yl)thiazol-4-yl)methoxy)-6-methoxybenzofuran-2-yl)-2-methoxyimidazo[2,1-b][1,3,4]thiadiazole

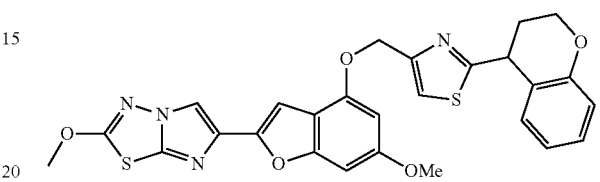

168A. (2-(Chroman-4-yl)thiazol-4-yl)methanol

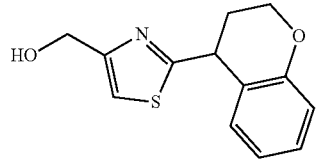 [SMILES: OCc1csc(C2CCOc3ccccc32)n1]

The alcohol was prepared according to the method described in Example 167. LC (Method F): 1.894 min. $^1$H NMR (DMSO-d$_6$, 400 MHz) δ ppm: 7.30 (m, 1H), 7.16 (m, 1H), 7.09 (dd, J=1.2, 7.4 Hz, 1H), 6.86 (dd, J=1.2, 7.4 Hz, 1H), 6.82 (m, 1H), 5.29 (t, J=5.7 Hz, 1H), 4.56 (m, 1H), 4.54 (dd, J=1.2, 5.9 Hz, 2H), 4.24 (m, 1H), 4.13-4.08 (m, 1H), 2.32-2.28 (m, 2H).

Example 168. 6-(4-((2-(Chroman-4-yl)thiazol-4-yl)methoxy)-6-methoxybenzofuran-2-yl)-2-methoxyimidazo[2,1-b][1,3,4]thiadiazole

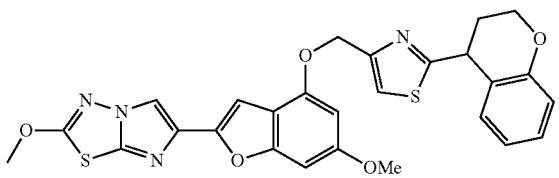 [SMILES: COc1cc(OCc2csc(C3CCOc4ccccc43)n2)c2cc(-c3cn4nc(OC)sc4n3)oc2c1]

The title compound was prepared according to the method described in Example 167 above and was isolated as a solid. LC (Method F): 2.638 min. HRMS(ESI): calcd for C$_{27}$H$_{23}$N$_4$O$_5$S$_2$ [M+H]$^+$ m/z 547.1110, found 547.1130. $^1$H NMR (DMSO-d$_6$, 400 MHz) δ ppm: 8.37 (s, 1H), 7.72 (s, 1H), 7.18 (m, 1H), 7.13 (m, 1H), 6.98 (d, J=0.8 Hz, 1H), 6.88-6.82 (m, 3H), 6.61 (d, J=2.0 Hz, 1H), 5.29 (s, 2H), 4.63 (t, J=5.1 Hz, 1H), 4.25 (m, 1H), 4.20 (s, 3H), 4.13-4.08 (m, 1H), 3.80 (s, 3H), 2.34 (q, J=5.5 Hz, 2H).

Example 169

6-(4-((2-(2H-Chromen-4-yl)thiazol-4-yl)methoxy)-6-methoxybenzofuran-2-yl)-2-methoxyimidazo[2,1-b][1,3,4]thiadiazole

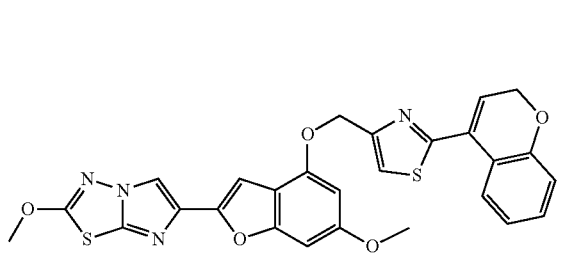 [SMILES: COc1cc(OCc2csc(C3=CCOc4ccccc43)n2)c2cc(-c3cn4nc(OC)sc4n3)oc2c1]

169A.
4-(4-(Hydroxymethyl)thiazol-2-yl)chroman-4-ol

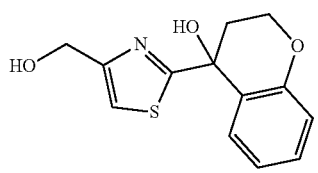 [SMILES: OCc1csc(C2(O)CCOc3ccccc32)n1]

The alcohol was prepared according to the method described in Example 118. LC (Method F): 1.519 min. $^1$H NMR (DMSO-$d_6$, 400 MHz) δ ppm: 7.33 (d, J=1.2 Hz, 1H), 7.15 (m, 1H), 7.02 (m, 1H), 6.81 (m, 2H), 6.73 (s, 1H), 5.22 (t, J=5.9 Hz, 1H), 4.46-4.41 (m, 3H), 4.30 (m, 1H), 2.50 (m, 1H), 2.17 (ddd, J=2.7, 5.7, 13.7 Hz, 1H).

169B. 4-(4-(((6-Methoxy-2-(2-methoxyimidazo[2,1-b][1,3,4]thiadiazol-6-yl)benzofuran-4-yl)oxy)methyl)thiazol-2-yl)chroman-4-ol

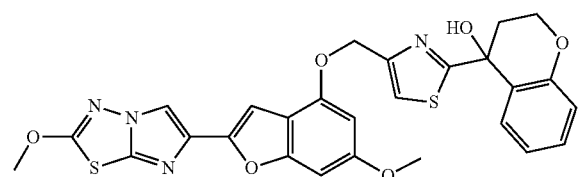

The title compound was prepared from 6-methoxy-2-(2-methoxyimidazo[2,1-b][1,3,4]thiadiazol-6-yl)benzofuran-4-ol (Example 1H) and 4-(4-(hydroxymethyl)thiazol-2-yl)chroman-4-ol according to the method described in Example 118 and was isolated as a solid. LC (Method A): 2.478 min. HRMS(ESI): calcd for $C_{27}H_{23}N_4O_6S_2$ [M+H]$^+$ m/z 563.1059, found 563.1059. $^1$H NMR (DMSO-$d_6$, 400 MHz) δ ppm: 8.36 (s, 1H), 7.75 (s, 1H), 7.17 (m, 1H), 7.05 (m, 1H), 6.95 (s, 1H), 6.83 (m, 4H), 6.55 (m, 1H), 5.20 (s, 2H), 4.45 (m, 1H), 4.31 (m, 1H), 4.20 (s, 3H), 3.77 (s, 3H), 2.54 (m, 1H), 2.21 (m, 1H).

Example 169. 6-(4-((2-(2H-Chromen-4-yl)thiazol-4-yl)methoxy)-6-methoxybenzofuran-2-yl)-2-methoxyimidazo[2,1-b][1,3,4]thiadiazole

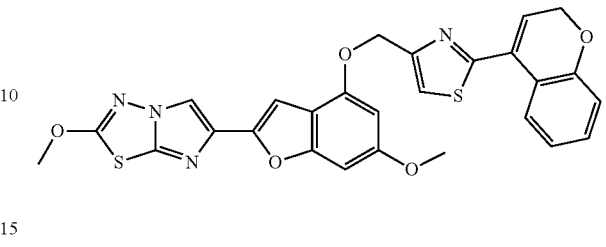

To an ice-cold solution of 4-(4-(((6-methoxy-2-(2-methoxyimidazo[2,1-b][1,3,4]thiadiazol-6-yl)benzofuran-4-yl)oxy)methyl)thiazol-2-yl)chroman-4-ol (0.025 g, 0.044 mmol) in DCM (5 mL) was added DAST (0.018 mL, 0.133 mmol) and the reaction mixture was stirred at 0° C. for 5 min and then at room temperature for 20 min. The reaction was then quenched at 0° C. with saturated aqueous NaHCO$_3$ and diluted with DCM. The organic phase was separated, dried (MgSO4), filtered and concentrated to dryness. The residue was purified by preparative HPLC (Method A). The product-containing fractions were evaporated and the residue was lyophilized from MeCN-water to give 6-(4-((2-(2H-chromen-4-yl)thiazol-4-yl)methoxy)-6-methoxybenzofuran-2-yl)-2-methoxyimidazo[2,1-b][1,3,4]thiadiazole (0.007 g, 28.9%) as an amorphous white solid. LC (Method F): 2.206 min. HRMS(ESI): calcd for $C_{27}H_{21}N_4O_5S_2$ [M+H]$^+$ m/z 545.0953, found 545.0956. $^1$H NMR (DMSO-$d_6$, 400 MHz) δ ppm: 8.37 (s, 1H), 7.90 (dd, J=1.6, 7.8 Hz, 1H), 7.89 (s, 1H), 7.23 (m, 1H), 7.02 (d, J=0.8 Hz, 1H), 6.94 (dt, J=1.2, 7.4 Hz, 1H), 6.90 (dd, J=1.2, 7.8 Hz, 1H), 6.85 (d, J=0.8 Hz, 1H), 6.67 (d, J=2.0 Hz, 1H), 6.57 (t, J=4.1 Hz, 1H), 5.39 (s, 2H), 4.85 (d, J=3.9 Hz, 2H), 4.20 (s, 3H), 3.81 (s, 3H).

Example 170

(R)—N-(4-(4-(((6-Methoxy-2-(2-methoxyimidazo[2,1-b][1,3,4]thiadiazol-6-yl)benzofuran-4-yl)oxy)methyl)thiazol-2-yl)tetrahydro-2H-pyran-4-yl)-2-methylpropane-2-sulfinamide

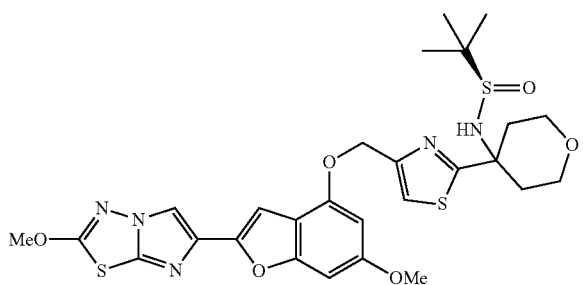 [SMILES: COc1cc(OCc2csc(C3(N[S@](=O)C(C)(C)C)CCOCC3)n2)c2cc(-c3cn4nc(OC)sc4n3)oc2c1]

170A. (R)—N-(Dihydro-2H-pyran-4(3H)-ylidene)-2-methylpropane-2-sulfinamide

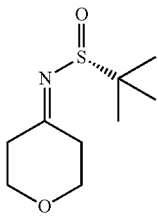

To a stirred solution of dihydro-2H-pyran-4(3H)-one (2.40 g, 23.97 mmol) in THF (50 mL) at room temperature under nitrogen was added titanium (IV) ethoxide (8.80 mL, 42.0 mmol) followed by (R)-(+)-2-methylpropane-2-sulfinamide (2.58 g, 21.29 mmol). The reaction was stirred at room temperature for 3 h and then it was quenched by pouring it into a mixture of cold saturated aqueous NaHCO$_3$ (50 mL) and EtOAc (50 mL), with rapid stirring. The resulting slurry was filtered and the residue rinsed with EtOAc. The aqueous layer of the filtrate was separated and re-extracted with EtOAc. The combined organics were dried (Na$_2$SO$_4$) and concentrated to give a light yellow oil. Flash chromatography (Isco/0-100% EtOAc-hexane) afforded (R)—N-(dihydro-2H-pyran-4(3H)-ylidene)-2-methylpropane-2-sulfinamide (2.045 g, 47.2%) as a clear, colorless oil which crystallized on standing in vacuo. This material was used as such in the next step. LC (Method A): 1.199 min. HRMS(ESI): calcd for C$_9$H$_{18}$NO$_2$S [M+H]$^+$ m/z 204.106; found 204.106.

170B. (R)—N-(4-(4-(((tert-Butyldimethylsilyl)oxy)methyl)thiazol-2-yl)tetrahydro-2H-pyran-4-yl)-2-methylpropane-2-sulfinamide

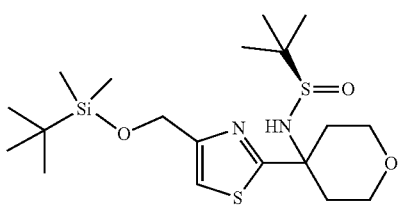 [SMILES: CC(C)(C)[S@@](=O)NC1(c2nc(CO[Si](C)(C)C(C)(C)C)cs2)CCOCC1]

A solution of 2-bromo-4-(((tert-butyldimethylsilyl)oxy)methyl)thiazole (Example 37B, 2.58 g, 8.37 mmol) in dry THF (40 mL) was cooled at −78° C. under N$_2$ and then 1.45 M n-butyllithium (6.93 mL, 10.04 mmol) was added dropwise. The resulting mixture was stirred for 30 min to give a light yellow-brown solution. To this mixture was added a solution of (R)—N-(dihydro-2H-pyran-4(3H)-ylidene)-2-methylpropane-2-sulfinamide (2.042 g, 10.04 mmol) in dry THF (10 mL) over 5 min and the mixture was kept at −78° C. for 2 h. The reaction was then quenched by the addition of saturated aqueous NH$_4$Cl (10 mL) and then the cooling bath was removed and the mixture was partitioned with EtOAc-water. The organic phase was separated, the aqueous phase was back-extracted with EtOAc and the combined organic phase was washed (brine), dried (Na$_2$SO$_4$) and evaporated to give a pale yellow oil. Flash chromatography (Isco/0-5% [10% NH$_4$OH-MeOH]-DCM) afforded (R)—N-(4-(4-(((tert-butyldimethylsilyl)oxy)-methyl)thiazol-2-yl)tetrahydro-2H-pyran-4-yl)-2-methylpropane-2-sulfinamide (3.05 g, 84%) as a nearly colorless gum. This material was used as such in the next step. LC (Method A): 2.394 min. HRMS(ESI): calcd for C$_{19}$H$_{37}$N$_2$O$_3$S$_2$Si [M+H]$^+$ m/z 433.201; found 433.203. $^1$H NMR (400 MHz, DMSO-d$_6$): δ 7.35 (s, 1H), 5.60 (s, 1H), 4.65 (s, 2H), 3.69 (m, 2H), 3.49 (m, 1H), 3.38 (m, 1H), 2.27 (m, 1H), 2.09 (m, 3H), 1.02 (s, 9H), 0.81 (s, 9H), 0.00 (s, 6H).

170C. (R)—N-(4-(4-(Hydroxymethyl)thiazol-2-yl)tetrahydro-2H-pyran-4-yl)-2-methylpropane-2-sulfinamide

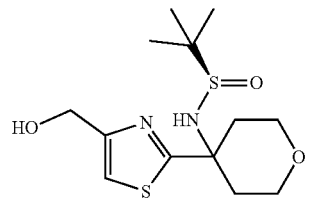 [SMILES: CC(C)(C)[S@@](=O)NC1(c2nc(CO)cs2)CCOCC1]

To a solution of (R)—N-(4-(4-(((tert-butyldimethylsilyl)oxy)methyl)thiazol-2-yl)tetrahydro-2H-pyran-4-yl)-2-methylpropane-2-sulfinamide (3.045 g, 7.04 mmol) in dry THF (25 mL) under N$_2$ was added triethylamine trihydrofluoride (3.44 mL, 21.11 mmol) dropwise and the mixture was stirred at room temperature for 2 days. The mixture was then diluted with DCM and the solution was washed (saturated aqueous NaHCO$_3$), dried (Na$_2$SO$_4$) and evaporated to give (R)—N-(4-(4-(hydroxymethyl)thiazol-2-yl)tetrahydro-2H-pyran-4-yl)-2-methylpropane-2-sulfinamide (2.074 g, 93%) as a colorless oil which crystallized on standing in vacuo. This material was essentially pure and was used as such in the next step. LC (Method A): 1.426 min. HRMS(ESI): calcd for C$_{13}$H$_{23}$N$_2$O$_3$S$_2$ [M+H]$^+$ m/z 319.115; found 319.115. $^1$H NMR (400 MHz, DMSO-d$_6$): δ 7.31 (s, 1H), 5.58 (s, 1H), 5.22 (t, J=5.87 Hz, 1H), 4.47 (d, J=5.87 Hz, 2H), 3.69 (m, 2H), 3.49 (m, 1H), 3.39 (m, 1H), 2.25 (m, 1H), 2.09 (m, 3H), 1.03 (s, 9H).

Example 170. (R)—N-(4-(4-(((6-Methoxy-2-(2-methoxyimidazo[2,1-b][1,3,4]thiadiazol-6-yl)benzofuran-4-yl)oxy)methyl)thiazol-2-yl)tetrahydro-2H-pyran-4-yl)-2-methylpropane-2-sulfinamide

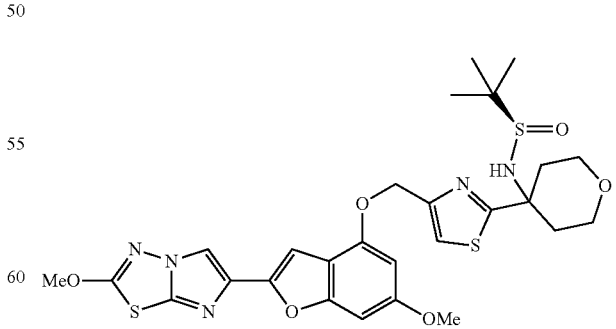

To a flame-dried flask was added 6-methoxy-2-(2-methoxyimidazo[2,1-b][1,3,4]thiadiazol-6-yl)benzofuran-4-ol (Example 1H, 0.200 g, 0.630 mmol) and (R)—N-(4-(4-(hydroxymethyl)thiazol-2-yl)tetrahydro-2H-pyran-4-yl)-

2-methylpropane-2-sulfinamide (0.241 g, 0.756 mmol), then the flask was flushed with N₂ and dry THF (8 mL) was added. To the resulting suspension was added tri-n-butylphosphine (0.409 mL, 1.576 mmol) and then a solution of 1,1'-(azodicarbonyl)dipiperidine (0.402 g, 1.576 mmol) in dry THF (5 mL) was added dropwise (via syringe pump) over 30 min. The resulting mixture was stirred at room temperature for another 1 h and then it was diluted with EtOAc, washed (saturated aqueous NaHCO₃, H₂O, brine), dried (Na₂SO₄) and evaporated to give a pale yellow gum. Flash chromatography (Isco/0-5% [10% NH₄OH-MeOH]-DCM) gave a solid which was triturated with a minimum volume of MeCN. The resulting suspension was filtered and the filter-cake was washed with a little MeCN and then dried in vacuo to give (R)—N-(4-(4-(((6-methoxy-2-(2-methoxyimidazo[2,1-b][1,3,4]thiadiazol-6-yl)benzofuran-4-yl)oxy)methyl)thiazol-2-yl)tetrahydro-2H-pyran-4-yl)-2-methylpropane-2-sulfinamide (0.294 g, 76%) as a white solid. LC (Method A): 2.240 min. HRMS(ESI): calcd for $C_{27}H_{32}N_5O_6S_3$ [M+H]⁺ m/z 618.151; found 618.150. ¹H NMR (400 MHz, DMSO-d₆): δ 8.33 (s, 1H), 7.77 (s, 1H), 6.95 (s, 1H), 6.80 (s, 1H), 6.59 (d, J=1.57 Hz, 1H), 5.72 (s, 1H), 5.25 (s, 2H), 4.17 (s, 3H), 3.77 (s, 3H), 3.73 (m, 2H), 3.55 (m, 1H), 3.46 (m, 1H), 2.31 (m, 1H), 2.18 (m, 3H), 1.08 (s, 9H).

Example 171

N-(4-(4-(((6-Methoxy-2-(2-methoxyimidazo[2,1-b][1,3,4]thiadiazol-6-yl)benzofuran-4-yl)oxy)methyl)thiazol-2-yl)tetrahydro-2H-pyran-4-yl)-2-methylpropane-2-sulfonamide

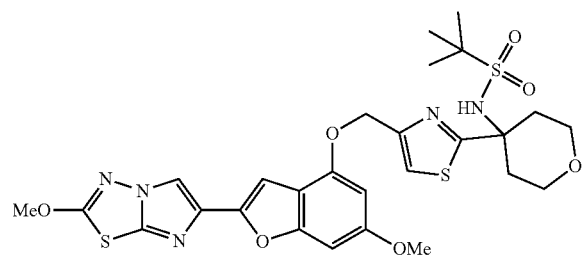 [SMILES: COc1cc(OCc2csc(C3(NS(=O)(=O)C(C)(C)C)CCOCC3)n2)c2cc(-c3cn4nc(OC)sc4n3)oc2c1]

To a solution of (R)—N-(4-(4-(((6-methoxy-2-(2-methoxyimidazo[2,1-b][1,3,4]thiadiazol-6-yl)benzofuran-4-yl)oxy)methyl)thiazol-2-yl)tetrahydro-2H-pyran-4-yl)-2-methylpropane-2-sulfinamide (0.050 g, 0.081 mmol) in DCM (3 mL) under N₂ was added 70% 3-chloroperoxybenzoic acid (0.030 g, 0.121 mmol) all at once and the resulting yellow mixture was stirred at room temperature for 6 h. The reaction mixture was then diluted with DCM and this mixture was washed (0.1 N NaOH, saturated aqueous NaHCO₃, brine), dried (Na₂SO₄) and evaporated to give a dark green solid. Flash chromatography (Isco/0-100% acetone-hexane) afforded N-(4-(4-(((6-methoxy-2-(2-methoxyimidazo[2,1-b][1,3,4]thiadiazol-6-yl)benzofuran-4-yl)oxy)methyl)thiazol-2-yl)tetrahydro-2H-pyran-4-yl)-2-methylpropane-2-sulfonamide (0.004 g, 7.80%) as an off-white solid. LC (Method A): 2.258 min. HRMS(ESI): calcd for $C_{27}H_{32}N_5O_7S_3$ [M+H]⁺ m/z 634.146; found 634.147. ¹H NMR (400 MHz, DMSO-d₆): δ 8.33 (s, 1H), 7.75 (s, 1H), 7.17 (s, 1H), 6.90 (s, 1H), 6.76 (s, 1H), 6.55 (d, J=1.96 Hz, 1H), 5.21 (s, 2H), 4.14 (s, 3H), 3.74 (s, 3H), 3.70 (m, 2H), 3.47 (m, 2H), 2.24 (m, 4H), 1.12 (s, 9H).

Example 172

4-(4-(((6-Methoxy-2-(2-methoxyimidazo[2,1-b][1,3,4]thiadiazol-6-yl)benzofuran-4-yl)oxy)methyl)thiazol-2-yl)tetrahydro-2H-pyran-4-amine, HCl

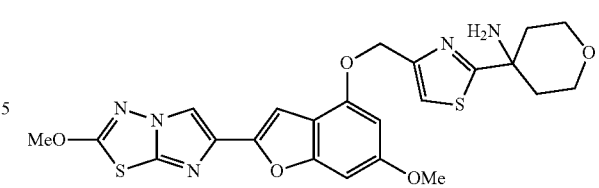

Method A: To a solution of (R)—N-(4-(4-(((6-methoxy-2-(2-methoxyimidazo[2,1-b][1,3,4]thiadiazol-6-yl)benzofuran-4-yl)oxy)methyl)thiazol-2-yl)tetrahydro-2H-pyran-4-yl)-2-methylpropane-2-sulfinamide (0.0103 g, 0.017 mmol) in THF (1 mL) was added 6 M aqueous HCl (0.050 mL) and the mixture was stirred at room temperature in a sealed vial for 30 min. The mixture was then diluted with DCM, washed (saturated aqueous NaHCO₃), dried (Na₂SO₄) and evaporated to give a gum. This material was purified by preparative HPLC (Method A) to give a solid which was lyophilized from MeCN-water to give 4-(4-(((6-methoxy-2-(2-methoxyimidazo[2,1-b][1,3,4]thiadiazol-6-yl)benzofuran-4-yl)oxy)methyl)thiazol-2-yl)tetrahydro-2H-pyran-4-amine, TFA (0.005 g, 48.0%) as a white solid. LC (Method A): 1.911 min. HRMS(ESI): calcd for $C_{23}H_{24}N_5O_5S_2$ [M+H]⁺ m/z 514.122; found 514.122. ¹H NMR (400 MHz, DMSO-d₆) δ 8.30 (s, 1H), 7.87 (s, 1H), 6.93 (s, 1H), 6.78 (s, 1H), 6.55 (d, J=1.96 Hz, 1H), 5.25 (s, 2H), 4.14 (s, 3H), 3.74 (s, 3H), 2.26 (m, 4H), 2.20-2.04 (m, 6H).

Method B: To a suspension of (R)—N-(4-(4-(((6-methoxy-2-(2-methoxyimidazo[2,1-b][1,3,4]thiadiazol-6-yl)benzofuran-4-yl)oxy)methyl)thiazol-2-yl)tetrahydro-2H-pyran-4-yl)-2-methylpropane-2-sulfinamide (0.280 g, 0.453 mmol) in THF (12 mL) was added 6 M aqueous HCl (0.755 mL, 4.53 mmol) and the mixture was stirred at room temperature in a sealed vial for 30 min. The mixture was subsequently filtered and the filter-cake was washed with a small amount of THF and then it was dried in vacuo to give 4-(4-(((6-methoxy-2-(2-methoxyimidazo[2,1-b][1,3,4]thiadiazol-6-yl)benzofuran-4-yl)oxy)methyl)thiazol-2-yl)tetrahydro-2H-pyran-4-amine, HCl (0.249 g, 100% yield) as a white solid. A small portion of this solid was partitioned with EtOAc-saturated aqueous NaHCO₃ (a minimum volume of MeOH was added to help solubilize) and the organic phase was separated, dried (Na₂SO₄) and evaporated to give a white solid. Flash chromatography (Isco/0-10% [10% NH₄OH-MeOH]-DCM) afforded 4-(4-(((6-methoxy-2-(2-methoxyimidazo[2,1-b][1,3,4]thiadiazol-6-yl)benzofuran-4-yl)oxy)methyl)thiazol-2-yl)tetrahydro-2H-pyran-4-amine as a white solid. LC (Method A): 2.038 min. HRMS(ESI): calcd for $C_{23}H_{24}N_5O_5S_2$ [M+H]⁺ m/z 514.122; found 514.120. ¹H NMR (400 MHz, DMSO-d₆): δ 8.30 (s, 1H), 7.57 (s, 1H), 6.91 (s, 1H), 6.76 (m, 1H), 6.56 (d, J=1.96 Hz, 1H), 5.18 (s, 2H), 4.14 (s, 3H), 3.74 (s, 3H), 3.70 (dt, J=2.35, 10.96 Hz, 2H), 3.63 (dt, J=4.30, 11.35 Hz, 2H), 2.05 (m, 2H), 1.50 (d, J=12.52 Hz, 2H).

Example 173 tert-Butyl (2-((4-(4-(((6-methoxy-2-(2-methoxyimi-dazo-[2,1-b][1,3,4]thiadiazol-6-yl)benzofuran-4-yl)oxy)methyl)-thiazol-2-yl)tetrahydro-2H-pyran-4-yl)amino)-2-oxoethyl)carbamate

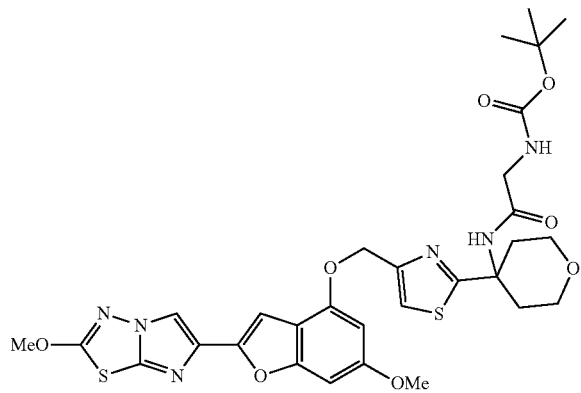 [SMILES: COc1cc(OCc2csc(C3(NC(=O)CNC(=O)OC(C)(C)C)CCOCC3)n2)c2cc(-c3cn4nc(OC)sc4n3)oc2c1]

To a mixture of 4-(4-(((6-methoxy-2-(2-methoxyimidazo[2,1-b][1,3,4]thiadiazol-6-yl)benzofuran-4-yl)oxy)methyl)thiazol-2-yl)tetrahydro-2H-pyran-4-amine (0.035 g, 0.068 mmol) and 2-((tert-butoxycarbonyl)amino)acetic acid (0.013 g, 0.076 mmol) in DMF (2 mL) was added DIEA (0.048 mL, 0.275 mmol), followed by HATU (0.029 g, 0.076 mmol). The resulting pale yellow solution was stirred at room temperature for 16 h and then it was diluted with water (6 mL), the resulting slurry was filtered and the residue was washed with water. The wet residue was then partitioned with DCM-saturated aqueous NaHCO$_3$ and the organic phase was separated, dried (Na$_2$SO$_4$) and evaporated to give a colorless gum. Flash chromatography (Isco/0-10% [10% NH$_4$OH-MeOH]-DCM) gave tert-butyl (2-((4-(4-(((6-methoxy-2-(2-methoxyimidazo[2,1-b][1,3,4]thiadiazol-6-yl)benzofuran-4-yl)oxy)methyl)thiazol-2-yl)tetrahydro-2H-pyran-4-yl)amino)-2-oxoethyl)carbamate (0.029 g, 62.9%) as a colorless gum which was lyophilized from MeCN-water to give a white solid. LC (Method A): 2.292 min. HRMS (ESI): calcd for C$_{30}$H$_{35}$N$_6$O$_8$S$_2$ [M+H]$^+$ m/z 671.196; found 671.195. $^1$H NMR (400 MHz, DMSO-d$_6$): δ 8.38 (s, 1H), 8.34 (s, 1H), 7.69 (s, 1H), 7.01 (s, 1H), 6.93 (t, J=5.87 Hz, 1H), 6.84 (m, 1H), 6.20 (t, J=1.96 Hz, 1H), 5.25 (s, 2H), 4.20 (s, 3H), 3.81 (s, 3H), 3.74 (m, 2H), 3.63-3.57 (m, 4H), 2.32 (m, 2H), 2.12 (m, 2H), 1.38 (s, 9H).

Example 174

2-(Dimethylamino)-N-(4-(4-(((6-methoxy-2-(2-methoxyimidazo[2,1-b][1,3,4]thiadiazol-6-yl)benzofuran-4-yl)oxy)methyl)-thiazol-2-yl)tetrahydro-2H-pyran-4-yl)acetamide

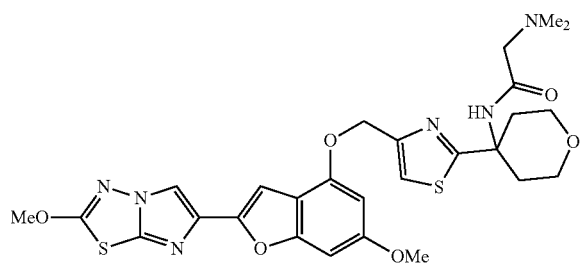 [SMILES: COc1cc(OCc2csc(C3(NC(=O)CN(C)C)CCOCC3)n2)c2cc(-c3cn4nc(OC)sc4n3)oc2c1]

To a suspension of 4-(4-(((6-methoxy-2-(2-methoxyimidazo[2,1-b][1,3,4]thiadiazol-6-yl)benzofuran-4-yl)oxy)methyl)thiazol-2-yl)tetrahydro-2H-pyran-4-amine, HCl (Example 172, 0.035 g, 0.064 mmol) and 2-(dimethylamino)acetic acid (7.44 mg, 0.070 mmol) in DMF (1.5 mL) was added DIEA (0.056 mL, 0.318 mmol), followed by HATU (0.027 g, 0.070 mmol). The resulting pale yellow solution was stirred at room temperature for 1 h and then the mixture was diluted with water (3 mL), the resulting slurry was filtered and the residue was washed with water. The wet residue was then partitioned with DCM-saturated aqueous NaHCO$_3$ and the organic phase was separated, dried (Na$_2$SO$_4$) and evaporated to give a colorless gum. Flash chromatography (Isco/0-10% [10% NH$_4$OH-MeOH]-DCM) gave 2-(dimethylamino)-N-(4-(4-(((6-methoxy-2-(2-methoxyimidazo[2,1-b][1,3,4]thiadiazol-6-yl)benzofuran-4-yl)oxy)methyl)thiazol-2-yl)tetrahydro-2H-pyran-4-yl)acetamide (0.026 g, 68.2%) as a solid. LC (Method A): 2.026 min. HRMS(ESI): calcd for C$_{27}$H$_{31}$NO$_{66}$S$_2$ [M+H]$^+$ m/z 599.175; found 599.176. $^1$H NMR (400 MHz, DMSO-d$_6$): δ 8.31 (s, 1H), 8.13 (s, 1H), 7.62 (s, 1H), 6.93 (s, 1H), 6.77 (s, 1H), 6.55 (d, J=1.96 Hz, 1H), 5.18 (s, 2H), 4.14 (s, 3H), 3.75 (s, 3H), 3.70 (m, 2H), 3.51 (t, J=10.96 Hz, 2H), 2.88 (s, 2H), 2.30 (m, 2H), 2.12 (m, 2H), 2.20 (s, 6H), 2.07 (m, 2H).

Example 175

2-Methoxy-6-(6-methoxy-4-((2-(2-phenylpropan-2-yl)thiazol-4-yl)methoxy)benzofuran-2-yl)imidazo[2,1-b][1,3,4]thiadiazole

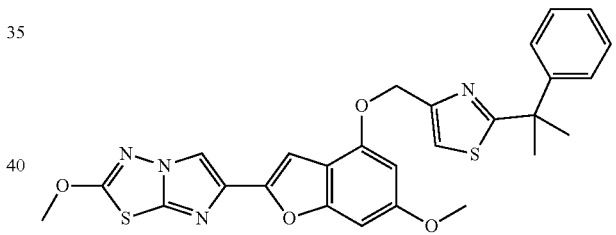

175A. 2-Methyl-2-phenylpropanamide

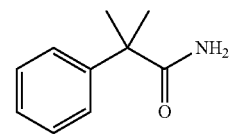

To a stirred solution of 2-methyl-2-phenylpropanoic acid (2.00 g, 12.18 mmol) in DCM (29 mL) was added oxalyl chloride (2.132 mL, 24.36 mmol) and the reaction mixture was stirred for 1 h at room temperature before being evaporated to dryness. The resulting residue was then taken up in THF (6 mL) and was added with stirring to ice-cold concentrated aqueous ammonia (29 mL). After 2 min the cooling bath was removed and the mixture was stirred at room temperature for 30 min. The resulting mixture was diluted with water and then extracted with EtOAc. The organic phase was washed with brine, dried (MgSO$_4$), filtered and concentrated to dryness to give 2-methyl-2- phenylpropanamide (0.763 g, 38.4%) as a white solid. This material was used as such in the next step. LC (Method F): 1.563 min. $^1$H NMR (DMSO-$d_6$, 400 MHz) δ ppm: 7.35-7.29 (m, 4H), 7.20 (m, 1H), 6.86 (br s, 2H), 1.42 (s, 6H).

175B. 2-Methyl-2-phenylpropanethioamide

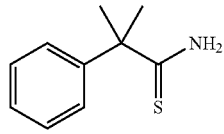

A solution of 2-methyl-2-phenylpropanamide (0.756 g, 4.63 mmol) and Lawesson's reagent (0.937 g, 2.316 mmol) in THF (5 mL) was heated to reflux for 2 h. The cooled reaction mixture was partitioned with EtOAc-saturated aqueous NaHCO$_3$ and the organic phase was separated, dried (MgSO$_4$), filtered and evaporated. The residue was purified by flash chromatography using hexanes-EtOAc as eluent to give 2-methyl-2-phenylpropanethioamide (0.452 g, 54.4%) as a white solid. LC (Method F): 1.784 min. $^1$H NMR (DMSO-$d_6$, 400 MHz) δ ppm: 9.54 (br s, 1H), 8.50 (br s, 1H), 7.38-7.35 (m, 2H), 7.30 (m, 2H), 7.21 (m, 1H), 1.56 (s, 6H).

175C. Ethyl 2-(2-phenylpropan-2-yl)thiazole-4-carboxylate

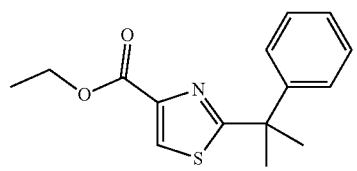 [SMILES: CCOC(=O)c1csc(C(C)(C)c2ccccc2)n1]

To a mixture of 2-methyl-2-phenylpropanethioamide (0.445 g, 2.482 mmol) in i-PrOH (5 mL) was added ethyl bromopyruvate (0.375 mL, 2.98 mmol) and the reaction mixture was heated to reflux for 3 h. The cooled mixture was partitioned with EtOAc-saturated aqueous NaHCO$_3$ and the organic phase was separated, washed with brine, dried (MgSO$_4$), filtered and concentrated to dryness. The residue was purified by column chromatography using a gradient of 0 to 100% EtOAc in hexanes to give ethyl 2-(2-phenylpropan-2-yl)thiazole-4-carboxylate (524 mg, 77% yield) as a clear, colorless oil. LC (Method F): 2.206 min. $^1$H NMR (DMSO-$d_6$, 400 MHz) δ ppm: 8.41 (s, 1H), 7.36-7.31 (m, 4H), 7.28-7.23 (m, 1H), 4.29 (q, J=7.0 Hz, 2H), 1.79 (s, 6H), 1.30 (t, J=7.0 Hz, 3H).

175D. (2-(2-Phenylpropan-2-yl)thiazol-4-yl)methanol

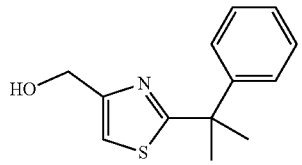 [SMILES: CC(C)(c1ccccc1)c1nc(CO)cs1]

To a solution of ethyl 2-(2-phenylpropan-2-yl)thiazole-4-carboxylate (0.515 g, 1.870 mmol) in THF (9 mL) was added LiBH$_4$ (0.081 g, 3.74 mmol), followed by MeOH (0.151 mL, 3.74 mmol). The reaction mixture was subsequently stirred at room temperature for 16 h and then quenched by dropwise addition of saturated aqueous NH$_4$Cl. The resulting mixture was extracted with ethyl acetate, after which the organic phase was washed with brine, dried (MgSO$_4$), filtered and concentrated to dryness. The residue was purified by flash chromatography using a gradient of 0 to 100% EtOAc in hexanes to give (2-(2-phenylpropan-2-yl)thiazol-4-yl)methanol (0.350 g, 80%) as a clear, colorless oil. LC (Method F): 1.528 min. $^1$H NMR (DMSO-$d_6$, 400 MHz) δ ppm: 7.35-7.26 (m, 5H), 7.22 (m, 1H), 5.26 (t, J=5.7 Hz, 1H), 4.53 (dd, J=0.8, 5.5 Hz, 2H), 1.76 (s, 6H).

Example 175. 2-Methoxy-6-(6-methoxy-4-((2-(2-phenylpropan-2-yl)thiazol-4-yl)methoxy)benzofuran-2-yl)imidazo[2,1-b][1,3,4]thiadiazole

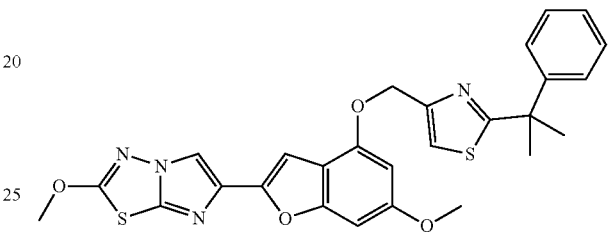

To a suspension of 6-methoxy-2-(2-methoxyimidazo[2,1-b][1,3,4]thiadiazol-6-yl)benzofuran-4-ol (Example 1H, 0.105 g, 0.330 mmol) and (2-(2-phenylpropan-2-yl)thiazol-4-yl)methanol (0.077 g, 0.330 mmol) in dry THF (8 mL) was added tri-n-butylphosphine (0.214 mL, 0.825 mmol), followed by a solution of ADDP (0.208 g, 0.825 mmol) in THF (2 mL) added dropwise over 30 min via syringe pump. After stirring for another 30 min, the reaction mixture was partitioned between EtOAc and saturated aqueous NaHCO$_3$. The organic phase was separated, washed with brine, dried (MgSO$_4$), filtered and concentrated to dryness. The residue was purified by column chromatography using DCM-EtOAc as eluent to give the title compound (0.097 g, 0.182 mmol, 55.2%) as a beige solid. LC (Method A): 2.536 min. HRMS (ESI): calcd for C$_{27}$H$_{25}$N$_4$O$_4$S$_2$ [M+H]$^+$ m/z 533.1317, found 533.1336. $^1$H NMR (DMSO-$d_6$, 400 MHz) δ ppm: 8.37 (s, 1H), 7.69 (s, 1H), 7.37-7.29 (m, 4H), 7.23 (m, 1H), 6.99 (s, 1H), 6.83 (s, 1H), 6.62 (d, J=2.0 Hz, 1H), 5.28 (s, 2H), 4.20 (s, 3H), 3.80 (s, 3H), 1.80 (s, 6H).

Example 176

6-(4-((2-(2-(4-Chlorophenyl)propan-2-yl)thiazol-4-yl)methoxy)-6-methoxybenzofuran-2-yl)-2-methoxyimidazo[2,1-b][1,3,4]thiadiazole

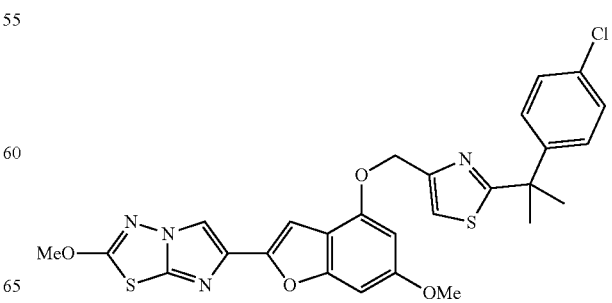

176A. (2-(2-(4-Chlorophenyl)propan-2-yl)thiazol-4-yl)methanol

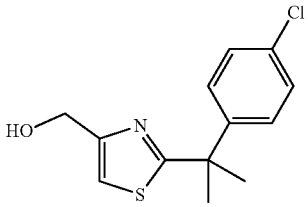 [SMILES: CC(C)(c1ccc(Cl)cc1)c1nc(CO)cs1]

The alcohol was prepared according to the method described in Example 175 above. LC (Method A): 2.032 min. $^1$H NMR (DMSO-d$_6$, 400 MHz) δ ppm: 7.36 (m, 4H), 7.29 (s, 1H), 5.27 (t, J=5.5 Hz, 1H), 4.53 (d, J=4.7 Hz, 2H), 1.75 (s, 6H).

Example 176. 6-(4-((2-(2-(4-Chlorophenyl)propan-2-yl)thiazol-4-yl)methoxy)-6-methoxybenzofuran-2-yl)-2-methoxyimidazo[2,1-b][1,3,4]thiadiazole

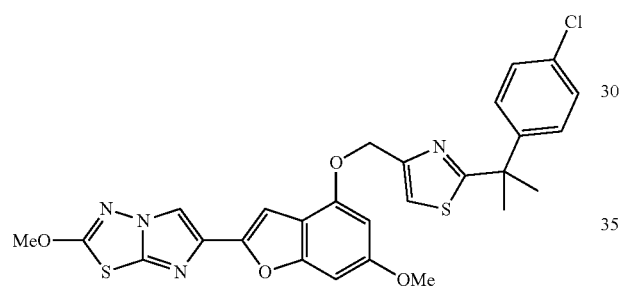

The title compound was prepared according to the method described in Example 175 above and was isolated as a solid. LC (Method A): 2.588 min. HRMS(ESI): calcd for C$_{27}$H$_{24}$ClN$_4$O$_4$S$_2$ [M+H]$^+$ m/z 567.0928, found 567.0937. $^1$H NMR (DMSO-d$_6$, 400 MHz) δ ppm: 8.37 (s, 1H) 7.70 (s, 1H), 7.37 (s, 4H), 6.98 (s, 1H), 6.83 (d, J=0.8 Hz, 1H), 6.61 (d, J=1.6 Hz, 1H), 5.28 (s, 2H), 4.20 (s, 3H), 3.80 (s, 3H), 1.78 (s, 6H).

Example 177

2-Methoxy-6-(6-methoxy-4-((2-(1-(pyridin-3-yl)cyclobutyl)thiazol-4-yl)methoxy)benzofuran-2-yl)imidazo[2,1-b][1,3,4]thiadiazole

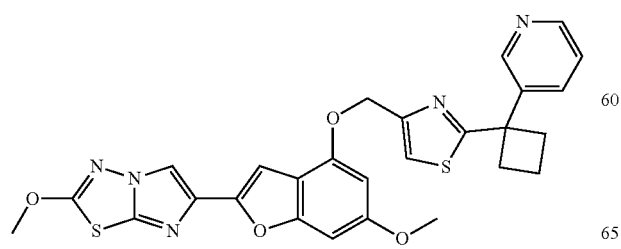

177A. 1-(Pyridin-3-yl)cyclobutanecarbonitrile

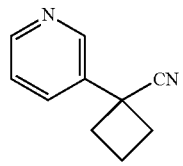 [SMILES: N#CC1(c2cccnc2)CCC1]

To a solution of 2-(pyridin-3-yl)acetonitrile (0.903 mL, 8.46 mmol) in dry THF (10 mL) was added 17 M sodium hydroxide (14.94 mL, 254 mmol) and tetrabutylammonium hydrogen sulfate (0.287 g, 0.846 mmol), followed by dropwise addition of 1,3-dibromopropane (0.902 mL, 8.89 mmol). The resulting mixture was heated to reflux for 4 h and then it was allowed to cool and the aqueous phase was carefully decanted. The organic phase was diluted with EtOAc, washed with water and brine, dried over MgSO$_4$, filtered and concentrated to dryness. The residue was purified by flash column using a gradient of 0 to 10% MeOH:NH$_4$OH (9:1) in DCM to give 1-(pyridin-3-yl)cyclobutanecarbonitrile (0.659 g, 49.2%) as a yellow oil. LC (Method A): 0.746 min. $^1$H NMR (DMSO-d$_6$, 400 MHz) δ ppm: 8.71 (dd, J=0.8, 2.7 Hz, 1H), 8.57 (dd, J=1.6, 4.7 Hz, 1H), 7.92 (m, 1H), 7.48 (ddd, J=0.8, 4.7, 7.8 Hz, 1H), 2.81-2.74 (m, 2H), 2.72-2.64 (m, 2H), 2.30 (m, 1H), 2.04 (m, 1H).

177B. 1-(Pyridin-3-yl)cyclobutanecarboxamide

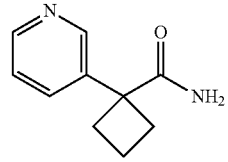 [SMILES: NC(=O)C1(c2cccnc2)CCC1]

A mixture of 1-(pyridin-3-yl)cyclobutanecarbonitrile (0.659 g, 4.17 mmol) and concentrated H$_2$SO$_4$ (4 mL) was stirred at ambient temperature for 16 h. The reaction mixture was then carefully poured onto crushed ice and the mixture was basified with solid NaHCO$_3$ until gas evolution ceased. The mixture was then extracted with EtOAc and the organic phase was separated, dried (MgSO$_4$), filtered and concentrated to dryness. The residue was purified by flash column using 0 to 10% MeOH:NH$_4$OH (9:1) in DCM as eluent to give 1-(pyridin-3-yl)cyclobutanecarboxamide (0.283 g, 34.7% yield) as a beige solid. LCMS (APCI): calcd for C$_{10}$H$_{13}$N$_2$O [M+H]$^+$ m/z 177.10, found 177.20. $^1$H NMR (DMSO-d$_6$, 400 MHz) δ ppm: 8.55 (dd, J=0.8, 2.7 Hz, 1H), 8.43 (m, 1H), 7.70 (m, 1H), 7.35 (ddd, J=0.8, 4.7, 8.2 Hz, 1H), 7.28 (br s, 1H), 6.96 (br s, 1H), 2.75-2.66 (m, 2H), 2.40-2.33 (m, 2H), 1.88-1.72 (m, 2H).

177C. 1-(Pyridin-3-yl)cyclobutanecarbothioamide

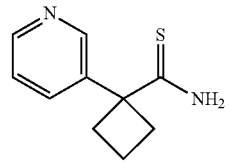 [SMILES: NC(=S)C1(c2cccnc2)CCC1]

To a stirred solution of 1-(pyridin-3-yl)cyclobutanecarboxamide (0.283 g, 1.445 mmol) in THF (5 mL) was added Lawesson's reagent (0.292 g, 0.723 mmol) and the mixture was heated to reflux for 6 h. The cooled mixture was then concentrated to near dryness and the concentrate was partitioned between EtOAc-saturated aqueous NaHCO$_3$. The organic phase was separated, dried (MgSO$_4$), filtered and concentrated to dryness. The residue was purified by column chromatography, using 0 to 10% MeOH:NH$_4$OH (9:1) in DCM as eluent to give 1-(pyridin-3-yl)cyclobutanecarbothioamide (0.208 g, 74.8%) as a white solid. LC (Method A): 0.929 min. $^1$H NMR (DMSO-d$_6$, 400 MHz) δ ppm: 9.54 (br s, 1H), 9.09 (br s, 1H), 8.73 (dd, J=0.8, 2.3 Hz 1H), 8.44 (dd, J=1.6, 4.7 Hz, 1H), 7.90 (m, 1H), 7.36 (ddd, J=0.8, 4.7, 7.8 Hz, 1H), 2.87-2.80 (m, 2H), 2.59-2.52 (m, 2H), 1.73-1.60 (m, 2H).

177D. Ethyl 2-(1-(pyridin-3-yl)cyclobutyl)thiazole-4-carboxylate

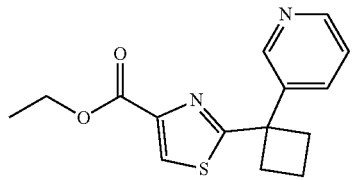 [SMILES: CCOC(=O)c1csc(C2(c3cccnc3)CCC2)n1]

To a suspension of 1-(pyridin-3-yl)cyclobutanecarbothioamide (0.200 g, 1.040 mmol) in ethanol (2 mL) at 0° C. was added dropwise a solution of ethyl 3-bromo-2-oxopropanoate (0.124 mL, 0.988 mmol) in ethanol (2 mL). The ice bath was then removed and the reaction mixture was stirred at ambient temperature for 24 h, before being partitioned between EtOAc and saturated aqueous NaHCO$_3$. The organic phase was separated, dried (MgSO$_4$), filtered and concentrated to dryness. The residue was purified by flash column using 0-10% MeOH:NH$_4$OH (9:1) in DCM to give ethyl 2-(1-(pyridin-3-yl)cyclobutyl)thiazole-4-carboxylate (0.169 g, 53.0% yield) as a light yellow oil. LC (Method A): 1.456 min. LCMS (APCI): calcd for C$_{15}$H$_{17}$N$_2$O$_2$S [M+H]$^+$ m/z 289.10, found 289.20.

177E. (2-(1-(Pyridin-3-yl)cyclobutyl)thiazol-4-yl)methanol

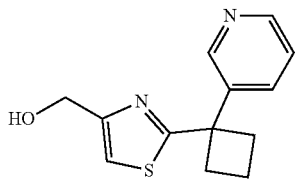 [SMILES: OCc1csc(C2(c3cccnc3)CCC2)n1]

To a stirred solution of ethyl 2-(1-(pyridin-3-yl)cyclobutyl)thiazole-4-carboxylate (0.169 g, 0.586 mmol) in THF (3 mL) at ambient temperature was added LiBH$_4$ (0.027 g, 1.232 mmol) followed by MeOH (0.050 mL, 1.232). The reaction mixture was stirred for 16 h and then it was quenched by the addition of saturated aqueous NH$_4$Cl. The resulting mixture was extracted with ethyl acetate and the organic phase was dried (MgSO$_4$), filtered and concentrated to dryness. The residue was purified by flash column using a gradient of 0-10% MeOH:NH$_4$OH (9:1) in DCM as eluent to give (2-(1-(pyridin-3-yl)cyclobutyl)thiazol-4-yl)methanol (0.053 g, 34.9%) as a clear, colorless oil. LC (Method A): 1.607 min. LCMS (APCI): calcd for C$_{13}$H$_{15}$N$_2$OS [M+H]$^|$ m/z 247.09, found 247.20.

Example 177. 2-Methoxy-6-(6-methoxy-4-((2-(1-(pyridin-3-yl)cyclobutyl)thiazol-4-yl)methoxy)benzofuran-2-yl)imidazo[2,1-b][1,3,4]thiadiazole

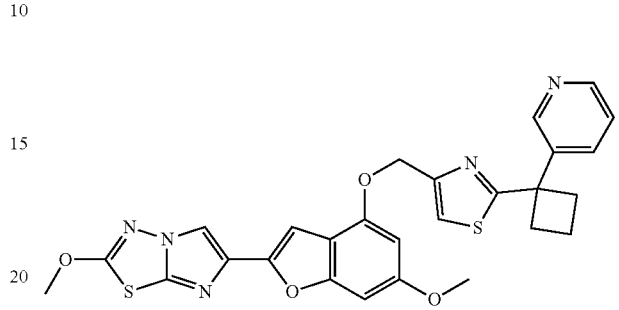

The title compound was prepared according to the method described in Example 175 above and was isolated as a solid. LC (Method A): 2.324 min. HRMS(ESI): calcd for C$_{27}$H$_{24}$N$_5$O$_4$S$_2$ [M+H]$^+$ m/z 546.1270, found 546.1251. $^1$H NMR (DMSO-d$_6$, 400 MHz) δ ppm: 8.51 (d, J=5.5 Hz, 1H), 8.48 (m, 1H), 8.36 (s, 1H), 8.18 (d, J=8.2 Hz, 1H), 7.78 (s, 1H), 7.72 (dd, J=5.7, 8.0 Hz, 1H), 7.18 (br s, 1H), 6.99 (d, J=0.8 Hz, 1H), 6.83 (dd, J=0.8, 1.6 Hz, 1H), 6.60 (d, J=2.0 Hz, 1H), 5.27 (s, 2H), 4.36 (t, J=5.1 Hz, 1H), 4.20 (s, 3H), 3.80 (s, 3H), 3.44 (m, 2H), 2.92-2.81 (m, 4H), 2.20-2.13 (m, 1H), 2.02-1.92 (m, 1H).

Example 178

2-Methoxy-6-(6-methoxy-4-((2-(1-(pyrimidin-5-yl)vinyl)thiazol-4-yl)methoxy)benzofuran-2-yl)imidazo[2,1-b][1,3,4]thiadiazole

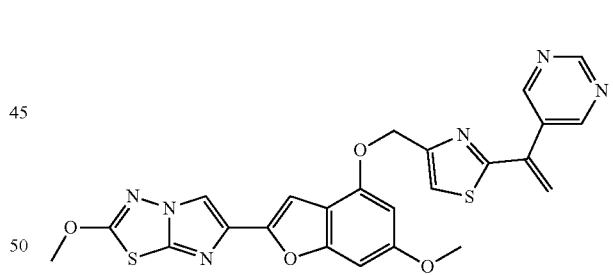

178A. 1-(4-(((tert-Butyldimethylsilyl)oxy)methyl)thiazol-2-yl)ethanone

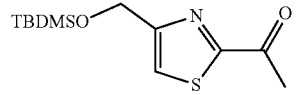 [SMILES: CC(=O)c1nc(CO[Si](C)(C)C(C)(C)C)cs1]

A solution of 2-bromo-4-(((tert-butyldimethylsilyl)oxy)methyl)thiazole (Example 37B, 2.00 g, 6.49 mmol) in dry THF (32 mL) was cooled at −78° C. under N$_2$ and then n-butyllithium (1.45 M in hexanes, 4.92 mL, 7.14 mmol)

was added dropwise. The resulting mixture was stirred for 35 min to give a pale brown solution. To this mixture was slowly added a solution of N,N-dimethylacetamide (0.608 mL, 6.49 mmol) in dry THF (8 mL) and the mixture was stirred at −78° C. for 2 h to give a light brown solution. The reaction was then quenched by the addition of saturated aqueous NH$_4$Cl, the cooling bath was removed and the mixture was partitioned with EtOAc-water. The organic phase was separated, washed (brine), dried (MgSO$_4$) and evaporated to give a pale yellow oil. This oil was purified by column chromatography using a gradient of 0 to 10% ether in hexanes as to give 1-(4-(((tert-butyldimethylsilyl)oxy) methyl)thiazol-2-yl)ethanone (1.07 g, 60.8% yield) as a yellow oil. LC (Method A): 2.368 min. LCMS (APCI): calcd for C$_{12}$H$_{22}$NO$_2$SSi [M+H]$^+$ m/z 272.11, found 272.20.

178B. 1-(4-(((tert-Butyldimethylsilyl)oxy)methyl) thiazol-2-yl)vinyl trifluoromethanesulfonate

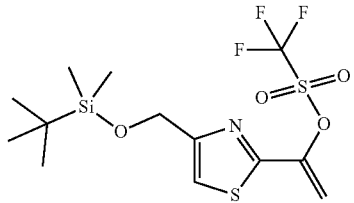 [SMILES: C=C(OS(=O)(=O)C(F)(F)F)c1nc(CO[Si](C)(C)C(C)(C)C)cs1]

To a stirred solution of 1-(4-(((tert-butyldimethylsilyl) oxy)methyl)thiazol-2-yl)ethanone (1.068 g, 3.93 mmol) and 1,1,1-trifluoro-N-phenyl-N-((trifluoromethyl)sulfonyl)-methanesulfonamide (1.546 g, 4.33 mmol) in THF (27 mL) at −78° C. was added KHMDS (1.1 M in THF, 4.32 mL, 3.93 mmol) dropwise over 20 min. The reaction mixture was then allowed to warm to −20° C. and stirred at the same temperature for 2 h, before being quenched with saturated aqueous NH$_4$Cl and extracted with EtOAc. The organic phase was washed with brine, dried (MgSO$_4$), filtered and concentrated to dryness. The residue was purified by flash chromatography using a gradient of 0 to 10% diethyl ether in hexanes to give 1-(4-(((tert-butyldimethylsilyl)oxy) methyl)thiazol-2-yl)vinyl trifluoromethanesulfonate (0.432 g, 27.2% yield) as a clear, colorless oil. LC (Method A): 2.484 min. $^1$H NMR (DMSO-d$_6$, 400 MHz) δ ppm: 7.69 (s, 1H), 6.31 (d, J=5.1 Hz, 1H), 5.84 (d, J=5.1 Hz, 1H), 4.78 (d, J=0.8 Hz, 2H), 0.89 (s, 9H), 0.09 (s, 6H).

178C. 4-(((tert-Butyldimethylsilyl)oxy)methyl)-2-(1-(pyrimidin-5-yl)vinyl)thiazole

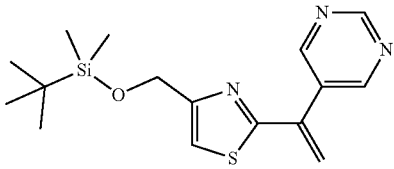 [SMILES: C=C(c1cncnc1)c1nc(CO[Si](C)(C)C(C)(C)C)cs1]

To a mixture of 1-(4-(((tert-butyldimethylsilyl)oxy) methyl)thiazol-2-yl)vinyl trifluoromethanesulfonate (0.272 g, 0.506 mmol) and pyrimidin-5-ylboronic acid (0.094 g, 0.758 mmol) in toluene (8 mL) and ethanol (1.5 mL) was added 2 M sodium carbonate (0.303 mL, 0.607 mmol) and the mixture was degassed with a stream of nitrogen bubbles for 5 min. To this mixture was then added PdCl$_2$(dppf) .CH$_2$Cl$_2$ (0.025 g, 0.030 mmol), the vessel was sealed and the mixture was heated at 90° C. for 3 h. The cooled mixture was partitioned with saturated aqueous NaHCO$_3$-DCM and the organic phase was separated, washed with brine, dried (MgSO$_4$), filtered and concentrated. The residue was purified by flash column using DCM-EtOAc as eluent to give 4-(((tert-butyldimethylsilyl)oxy)methyl)-2-(1-(pyrimidin-5-yl)vinyl)thiazole (0.103 g, 0.309 mmol, 61.1% yield) as a yellow oil. LC (Method A): 2.358 min. LCMS (APCI): calcd for C$_{16}$H$_{24}$N$_3$OSSi [M+H]$^1$ m/z 334.14, found 334.20.

178D. (2-(1-(Pyrimidin-5-yl)vinyl)thiazol-4-yl) methanol

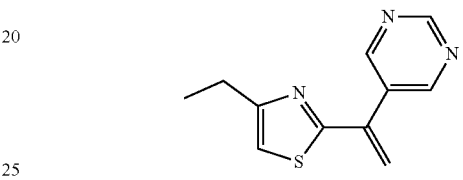

To a stirred solution of 4-(((tert-butyldimethylsilyl)oxy) methyl)-2-(1-(pyrimidin-5-yl)vinyl)thiazole (0.103 g, 0.309 mmol) in THF (2 mL) at ambient temperature was added triethylamine trihydrofluoride (0.251 mL, 1.544 mmol) and the mixture was stirred for 16 h. The resulting mixture was partitioned with EtOAc-saturated aqueous NaHCO$_3$ and the organic phase was separated, dried (MgSO$_4$), filtered and evaporated to dryness. The residue was purified flash column chromatography using hexanes-ethyl acetate as eluent to give (2-(1-(pyrimidin-5-yl)vinyl)thiazol-4-yl)methanol (0.017 g, 0.078 mmol, 25.1%) as a clear, colorless oil. LC (Method A): 1.242 min. LCMS (APCI): calcd for C$_{10}$H$_{10}$N$_3$OS [M+H]$^1$ m/z 220.05, found 220.20.

Example 178. 2-Methoxy-6-(6-methoxy-4-((2-(1-(pyrimidin-5-yl)vinyl)thiazol-4-yl)methoxy)benzo-furan-2-yl)imidazo[2,1-b][1,3,4]thiadiazole

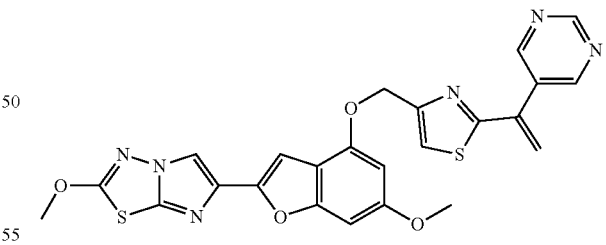

To a suspension of 6-methoxy-2-(2-methoxyimidazo[2,1-b][1,3,4]thiadiazol-6-yl)benzofuran-4-ol (Example 1H, 0.0246 g, 0.078 mmol) and (2-(1-(pyrimidin-5-yl)vinyl) thiazol-4-yl)methanol (0.017 g, 0.078 mmol) in dry THF (8 mL) was added tri-n-butylphosphine (0.050 mL, 0.194 mmol), followed by a solution of ADDP (0.049 g, 0.194 mmol) in THF (2 mL) added dropwise over 30 min via syringe pump. After stirring for another 30 min, the reaction mixture was partitioned with EtOAc-saturated aqueous NaHCO$_3$ and the organic phase was separated, washed with brine, dried (MgSO$_4$), filtered and concentrated to dryness.

The residue was purified by flash column using DCM-EtOAc as eluent to give the impure product. This material was rechromatographed using hexanes-EtOAc as eluent to give the pure product as a white solid which was subsequently lyophilized from acetonitrile-water to give the title compound (0.014 g, 0.024 mmol, 30.6%) as an amorphous white solid. LC (Method A): 2.288 min. HRMS(ESI): calcd for $C_{24}H_{19}N_6O_4S_2$ [M+H]' m/z 519.0904, found 519.0902. $^1$H NMR (DMSO-d$_6$, 400 MHz) δ ppm: 9.21 (s, 1H), 8.99 (s, 2H), 8.36 (s, 1H), 7.92 (s, 1H), 7.00 (d, J=0.8 Hz, 1H), 6.83 (m, 1H), 6.61 (d, J=2.0 Hz, 1H), 6.28 (s, 1H), 6.00 (s, 1H), 5.31 (s, 2H), 4.20 (s, 3H), 3.79 (s, 3H).

Example 179

6-(6-Fluoro-4-((2-phenylthiazol-4-yl)methoxy)benzofuran-2-yl)-2-methoxyimidazo[2,1-b][1,3,4]thiadiazole

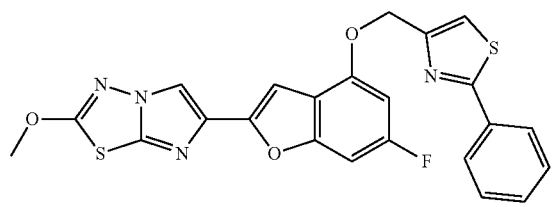 [SMILES: COc1nn2cc(-c3cc4c(OCc5csc(-c6ccccc6)n5)cc(F)cc4o3)nc2s1]

179A. 4-Fluoro-2-hydroxy-6-methoxybenzaldehyde and 2-fluoro-6-hydroxy-4-methoxybenzaldehyde

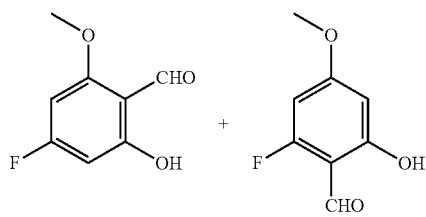

A 1:5 mixture of 4-fluoro-2,6-dimethoxybenzaldehyde and 2-fluoro-4,6-dimethoxybenzaldehyde (*Helvetica Chim. Acta*, 81:1596-1607 (1998), 1 g, 5.43 mmol) in 30 mL of dichloromethane was cooled down to 0-5° C. To this mixture was added dropwise over 25 minutes tribromoborane (7.33 mL, 7.33 mmol) in 10 mL of dichloromethane and the reaction was stirred at 0-5° C. for approx. 5-10 min. The mixture was then poured into ice, diluted down with dichloromethane and extracted twice with dichloromethane. The combined organic layers were dried over MgSO$_4$, filtered and concentrated. The residue was purified on ISCO silica gel column chromatography (40 g gold column using 90% hexanes and 10% dichloromethane up to 80% hexanes with 10% dichloromethane and 10% ethyl acetate). Both isomers were collected at the same time to give the title materials (0.720 g, 78%) as a white crystalline solid. 2-Fluoro-6-hydroxy-4-methoxybenzaldehyde (major isomer, undesired)—$^1$H NMR (400 MHz, CDCl$_3$) δ ppm: 11.91 (s, 1H), 10.05 (s, 1H), 6.17-6.25 (m, 1H), 3.86 (s, 3H). 4-Fluoro-2-hydroxy-6-methoxybenzaldehyde (minor isomer, desired)—$^1$H NMR (400 MHz, CDCl$_3$) δ ppm: 12.23-12.42 (m, 1H), 10.22 (s, 1H), 6.23-6.27 (m, 1H), 6.13 (dd, J=10.96, 2.35 Hz, 1H), 3.90 (s, 3H).

179B.
1-(6-Fluoro-4-methoxybenzofuran-2-yl)ethanone

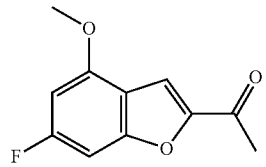

To a solution of a mixture of 4-fluoro-2-hydroxy-6-methoxybenzaldehyde and 2-fluoro-6-hydroxy-4-methoxybenzaldehyde (4.63 g, 27.2 mmol) in acetonitrile (49.7 mL, 952 mmol) was added potassium iodide (0.903 g, 5.44 mmol), cesium carbonate (9.75 g, 29.9 mmol) and 1-chloropropan-2-one (2.395 mL, 28.6 mmol). The mixture was stirred at r.t. for 2 h, was treated with 0.1 eq of cesium carbonate and heated to 60° C. for 1 h and 80° C. for another hour. The reaction was left overnight at r.t., then filtered over a small pad of silica and rinsed with ethyl acetate (approx 500 mL). The residue obtained after concentration was purified by silica gel chromatography (ISCO, 120 g of silica with 100% toluene using UV at 315 nm, then polarity was increased over time up to 10% ethyl acetate). The fractions were evaporated to give a 7:1 mixture of the desired/undesired isomers which was recrystallized overnight with ethyl acetate. The title material was obtained (0.216 g, 3.8%) as colorless crystals. LC (Method B): 1.928 min. LCMS (APCI) calcd for $C_{11}H_{10}FO_3$ [M+H]$^+$ m/z 209.06, found 209.1. $^1$H NMR (CDCl$_3$, 400 MHz) δ ppm: 7.55-7.61 (m, 1H), 6.78-6.99 (m, 1H), 6.46-6.53 (m, 1H), 3.96 (s, 3H), 2.55-2.60 (m, 3H).

179C.
1-(6-Fluoro-4-hydroxybenzofuran-2-yl)ethanone

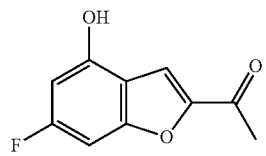

To a stirred solution of 1-(4,6-dimethoxybenzofuran-2-yl)ethanone (0. 216 g, 1.038 mmol) in chlorobenzene (3.69 mL, 36.3 mmol) was added aluminum trichloride (0.277 g, 2.075 mmol). After heating for 3 h at 85° C., the mixture was quenched with ice and 1.0N HCl, and extracted with ethyl acetate (4x). The combined organic layers were dried over anhydrous magnesium sulphate, filtered and concentrated. The residue was purified on silica gel chromatography (BIOTAGE® 24 g, eluting with a gradient of hexanes and ethyl acetate) to give the title material (0.191 g, 95%) as a white solid. LC (Method B): 1.794 min. LCMS (APCI) calcd for $C_{10}H_8FO_3$ [M+H]$^+$ m/z 195.05, found 195.9. $^1$H NMR (CDCl$_3$, 400 MHz) δ ppm: 7.58 (s, 1H), 6.87-6.93 (m, 1H), 6.46-6.53 (m, 1H), 5.62 (s, 1H), 2.60 (s, 3H).

179D. 1-(6-Fluoro-4-((2-phenylthiazol-4-yl)methoxy)benzofuran-2-yl)ethanone

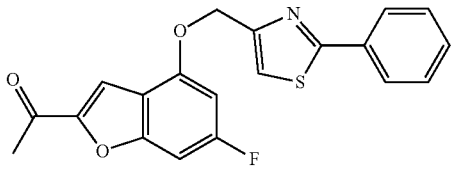 [SMILES: CC(=O)c1cc2c(OCc3csc(-c4ccccc4)n3)cc(F)cc2o1]

Benzene was added to 1-(6-fluoro-4-hydroxybenzofuran-2-yl)ethanone (0.178 g, 0.917 mmol) and the mixture was sonicated for 30 sec. and concentrated in vacuo to remove traces of water in the starting material. Triphenylphosphine (373 mgs, 1.421 mmol) was added and the mixture was dried on high vacuum for 10 min. (2-Phenylthiazol-4-yl)methanol (Example 3B, 0.175 g, 0.917 mmol) and THF (15 mL) were added and the mixture was sonicated/heated for 5 min. Diisopropyl azodicarboxylate (275 µL, 1.412 mmol) in THF (2 mL) was added dropwise over 1 h and the resulting yellow solution was sonicated for 15 min. and stirred overnight at r.t. The mixture was diluted in dichloromethane, washed with saturated. NaHCO$_3$, brine, dried over MgSO$_4$ and concentrated. The residue was purified on silica gel chromatography (ISCO 24 g gold column, using 5% ethyl acetate in hexanes to 40% (10% increments)) to give the title material (0.132 g, 32%) as a white solid. LC (Method B): 2.613 min. LCMS (APCI) calcd for C$_{20}$H$_{15}$FNO$_3$S [M+H]$^+$ m/z 368.07, found 368.2. $^1$H NMR (CDCl$_3$, 400 MHz) δ ppm: 7.94-8.02 (m, 2H), 7.62-7.67 (m, 1H), 7.44-7.51 (m, 3H), 7.38 (s, 1H), 6.91-6.96 (m, 1H), 6.64-6.72 (m, 1H), 5.39 (d, J=0.78 Hz, 2H), 2.58 (s, 3H).

179E. 2-Bromo-1-(6-fluoro-4-((2-phenylthiazol-4-yl)methoxy)benzofuran-2-yl)ethanone

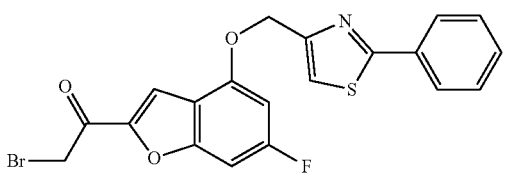 [SMILES: O=C(CBr)c1cc2c(OCc3csc(-c4ccccc4)n3)cc(F)cc2o1]

To a suspension of 1-(6-fluoro-4-((2-phenylthiazol-4-yl)methoxy)benzofuran-2-yl)ethanone (0.132 g, 0.359 mmol) in ethyl acetate (5 mL) was added copper(II) bromide (160 mgs, 0.719 mmol) and the mixture was heated to 80° C. for 48 h. The solid was filtered off and rinsed with cold EtOAc. The solid was purified on silica gel chromatography (ISCO 12 g with dichloromethane and ethyl acetate (95:5)) and provided the title material (0.055 g, 34%) as an off-white solid. LC (Method B): 2.424 min. LCMS (APCI) calcd for C$_{20}$H$_{14}$BrFNO$_3$S [M+H]$^+$ m/z 445.99, found 446.0.

179F. 2-Bromo-6-(6-fluoro-4-((2-phenylthiazol-4-yl)methoxy)benzofuran-2-yl)imidazo[2,1-b][1,3,4]thiadiazole

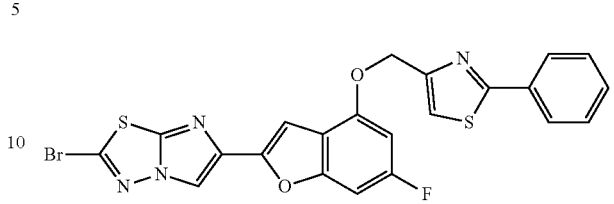

In a 2-5 mL microwave pressure vial was added 2-bromo-1-(6-fluoro-4-((2-phenylthiazol-4-yl)methoxy)benzofuran-2-yl)ethanone (0.035 g, 0.078 mmol) in propan-2-ol (2 mL) followed by 5-bromo-1,3,4-thiadiazol-2-amine (16.2 mgs, 0.09 mmol). The reaction was heated to 80° C. overnight and to 150° C. for 1 h in microwave oven. The reaction mixture was then poured into a mixture of dichloromethane (8 mL) and saturated NaHCO$_3$ (2 mL) and this was extracted twice with dichloromethane. The organic extracts were dried over MgSO$_4$, filtered and concentrated. The residue was purified by silica gel chromatography (ISCO 12 g gold column using 0 to 2% ethyl acetate in dichloromethane) to give the title material (0.018 g, 43%) as a yellowish solid. LC (Method B): 2.754 min. LCMS (APCI) calcd for C$_{22}$H$_{13}$BrFN$_4$O$_2$S$_2$ [M+H]$^+$ m/z 526.96, found 527.0.

Example 179. 6-(6-Fluoro-4-((2-phenylthiazol-4-yl)methoxy)benzofuran-2-yl)-2-methoxyimidazo[2,1-b][1,3,4]thiadiazole

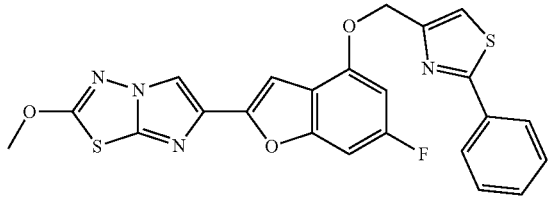 [SMILES: COc1nn2cc(-c3cc4c(OCc5csc(-c6ccccc6)n5)cc(F)cc4o3)nc2s1]

2-Bromo-6-(6-fluoro-4-((2-phenylthiazol-4-yl)methoxy)benzofuran-2-yl)imidazo[2,1-b][1,3,4]thiadiazole (0.017 g, 0.032 mmol) was dissolved in dichloromethane (1.3 mL) (some heat and sonication were required). Methanol was then added (0.3 mL) followed by sodium methoxide (14.74 µL, 0.064 mmol) in one shot. The reaction was stirred at r.t. for 25 min., then quenched with 1.0 N HCl and stirred until the reaction color changes to yellow. Saturated aqueous NaHCO$_3$ was then added and this was extracted with dichloromethane (4×). The combined organic layers were dried over MgSO$_4$, filtered and concentrated. The residue was purified by silica gel column chromatography (BIOTAGE® 12 g column using 0 to 5% ethyl acetate in dichloromethane) to give the title material (0.010 g, 64%) as a yellowish solid. LC (Method A): 2.488 min. HRMS(ESI) calcd for C$_{23}$H$_{15}$FN$_4$O$_3$S$_2$ [M+H]$^+$ m/z 479.0570, found 479.0661. $^1$H NMR (CDCl$_3$, 400 MHz) δ ppm: 7.94-8.03 (m, 2H), 7.89 (s, 1H), 7.43-7.53 (m, 3H), 7.39 (s, 1H), 7.19 (s, 1H), 6.85-6.94 (m, 1H), 6.59-6.68 (m, 1H), 5.40 (s, 2H), 4.23 (s, 3H).

Example 180

N-(2-Cyanoethyl)-N-ethyl-4-(4-(((6-fluoro-2-(2-methoxyimidazo[2,1-b][1,3,4]thiadiazol-6-yl)benzofuran-4-yl)oxy)methyl)thiazol-2-yl)benzamide

180A. 1-(4-(Benzyloxy)-6-fluorobenzofuran-2-yl)ethanone

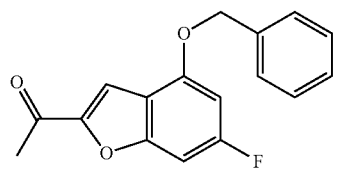

A solution of 1-(6-fluoro-4-hydroxybenzofuran-2-yl)ethanone (Example 179C, 1.00 g, 5.15 mmol) in N,N-dimethylformamide (10 mL) was treated with anhydrous potassium carbonate (0.747 g, 5.41 mmol), followed by benzyl bromide (0.735 mL, 6.18 mmol) added dropwise over 5 min. The resulting heterogeneous mixture was sonicated for 1 h and the resulting suspension was then filtered and the filter-cake washed with N,N-dimethylformamide. The combined filtrate was evaporated to dryness and the residue was partitioned between ethyl acetate and saturated aqueous sodium bicarbonate. The organic phase was separated, washed with brine, dried over anhydrous magnesium sulfate and concentrated in vacuo. The residue obtained was chromatographed on silica gel (ISCO, elution gradient of dichloromethane in hexane) to give 1.33 g (91%) of the title material as a white solid. LC (Method A): 2.334 min. HRMS(ESI): calcd for $C_{17}H_{14}FO_3$ $[M+H]^+$ m/z 285.0927; found 285.0927. $^1$H NMR (400 MHz, CDCl$_3$) δ ppm: 7.59 (s, 1H), 7.33-7.49 (m, 5H), 6.76-6.94 (m, 1H), 6.51-6.58 (m, 1H), 5.16 (s, 2H), 2.54 (s, 3H).

180B. 1-(4-(Benzyloxy)-6-fluorobenzofuran-2-yl)-2-bromoethanone

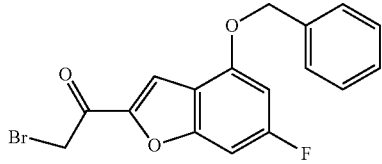 [SMILES: O=C(CBr)c1cc2c(OCc3ccccc3)cc(F)cc2o1]

To a flask equipped with a magnetic stirring bar and purged with a nitrogen atmosphere was added dry THF (35 mL) followed by lithium bis(trimethylsilyl)amide (1 M in THF, 6.30 mL, 6.30 mmol). The mixture was cooled to −78° C. and chlorotrimethylsilane (0.771 mL, 6.04 mmol) was added dropwise over 2 min. After 5 min, a solution of 1-(4-(benzyloxy)-6-fluorobenzofuran-2-yl)ethanone (1.492 g, 5.25 mmol) in dry THF (14 mL) was added dropwise over 10 min and the resulting mixture was stirred at −78° C. for 30 min. The cooling bath was then removed and the mixture was allowed to warm to ca. 10° C. over 20 min. The reaction mixture was then quenched by addition to a cold mixture of ethyl acetate (300 mL), saturated aqueous sodium bicarbonate (40 mL) and ice. The organic phase was rapidly separated, dried over anhydrous magnesium sulfate and evaporated in vacuo to give the silyl enol ether as a clear oil. This oil was co-evaporated with toluene (10 mL, 2 mbar) before being taken up in dry tetrahydrofuran (35 mL). The mixture was cooled to −35° C. under nitrogen and treated with solid sodium bicarbonate (30 mg), followed by N-bromosuccinimide (0.981 g, 5.51 mmol), added in small portions over 10 min. The reaction mixture was allowed to warm to 5° C. over 3.5 h and then it was quenched by addition of ethyl acetate (400 mL) and saturated aqueous sodium bicarbonate (40 mL). The organic phase was separated, washed with brine, dried over anhydrous magnesium sulfate and evaporated to give a white solid. Chromatography on silica gel (ISCO, elution gradient of dichloromethane in hexane) gave 1.509 g (79%) of the title material as a yellow solid. LC (Method A): 2.282 min. HRMS(ESI): calcd for $C_{17}H_{13}BrFO_3$ $[M+H]^+$ m/z 363.0032; found 363.004. $^1$H NMR (400 MHz, CDCl$_3$) δ ppm: 7.75 (d, J=0.78 Hz, 1H), 7.35-7.51 (m, 5H), 6.91 (m, 1H), 6.58 (dd, J=11.35, 1.96 Hz, 1H), 5.19 (s, 2H), 4.37 (s, 2H).

180C. 6-(4-(Benzyloxy)-6-fluorobenzofuran-2-yl)-2-bromoimidazo[2,1-b][1,3,4]thiadiazole

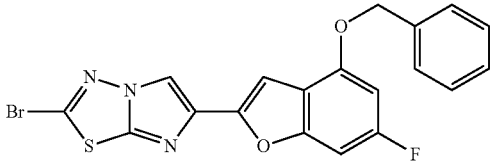 [SMILES: Fc1cc(OCc2ccccc2)c2cc(-c3cn4nc(Br)sc4n3)oc2c1]

A mixture of 1-(4-(benzyloxy)-6-fluorobenzofuran-2-yl)-2-bromoethanone (1.07 g, 2.95 mmol) and 5-bromo-1,3,4-thiadiazol-2-amine (0.610 g, 3.39 mmol) in isopropanol (80 mL) was heated in a sealed pressure flask at 80° C. for 18 h. The resulting heterogeneous mixture was then heated in a microwave reactor at 150° C. for 30 min. The cooled reaction mixture was partitioned with dichloromethane-saturated aqueous sodium bicarbonate and the organic phase was separated, washed with brine, dried over anhydrous magnesium sulfate and concentrated in vacuo. The residue obtained was chromatographed on silica gel (ISCO, elution gradient of ethyl acetate in dichloromethane) to give 0.740 g (57%) of the title material as a solid. LC (Method A): 2.456 min. HRMS(ESI): calcd for $C_{19}H_{12}BrFN_3O_2S$ [M+H]$^+$ m/z 443.9818; found 443.9834. $^1$H NMR (400 MHz, CDCl$_3$) δ ppm: 8.09 (s, 1H), 7.32-7.54 (m, 5H), 7.21 (s, 1H), 6.86-6.91 (m, 1H), 6.52-6.59 (m, 1H), 5.21 (s, 2H).

180D. 6-(4-(Benzyloxy)-6-fluorobenzofuran-2-yl)-2-methoxyimidazo[2,1-b][1,3,4]thiadiazole

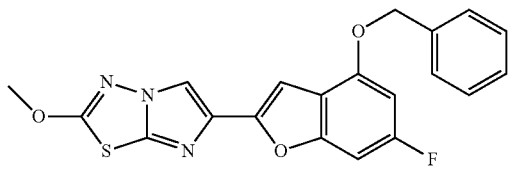 [SMILES: COc1nn2cc(-c3cc4c(OCc5ccccc5)cc(F)cc4o3)nc2s1]

A suspension of 6-(4-(benzyloxy)-6-fluorobenzofuran-2-yl)-2-bromoimidazo[2,1-b][1,3,4]thiadiazole (0.740 g, 1.666 mmol) in a mixture of dichloromethane (30 mL) and methanol (10 mL) was treated at 22° C. with sodium methoxide (25 wt % in MeOH, 1.01 mL, 4.45 mmol), added in one portion. After 30 min, the clear reaction mixture was quenched by the addition of 5 mL of 1 N hydrochloric acid and the solvent was evaporated under reduced pressure. The residue was partitioned between dichloromethane and saturated aqueous sodium bicarbonate, and the organic phase was separated, washed with brine, dried over anhydrous magnesium sulfate and evaporated in vacuo. Chromatography of the residue on silica gel (ISCO, elution gradient of ethyl acetate in dichloromethane) gave 0.480 g (82%) of the title compound as a white solid. LC (Method A): 2.477 min. HRMS(ESI): calcd for $C_{20}H_{15}FN_3O_3S$ [M+H]$^+$ m/z 396.0818; found 396.0862. $^1$H NMR (400 MHz, CDCl$_3$) δ ppm: 7.88 (s, 1H), 7.32-7.55 (m, 5H), 7.13 (s, 1H), 6.88 (m, 1H), 6.54 (m, 1H), 5.20 (s, 2H), 4.22 (s, 3H).

180E. 6-Fluoro-2-(2-methoxyimidazo[2,1-b][1,3,4]thiadiazol-6-yl)benzofuran-4-ol

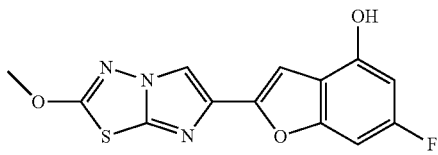 [SMILES: COc1nn2cc(-c3cc4c(O)cc(F)cc4o3)nc2s1]

A mixture of 6-(4-(benzyloxy)-6-fluorobenzofuran-2-yl)-2-methoxyimidazo[2,1-b][1,3,4]thiadiazole (0.480 g, 1.21 mmol) and pentamethylbenzene (1.26 g, 8.50 mmol) in dichloromethane (75 mL) was cooled at −78° C. under nitrogen and then treated with boron trichloride (1 M in DCM, 3.5 mL, 3.5 mmol), added dropwise over 2 min. The resulting mixture was stirred at −78° C. for 40 min and then it was quenched by the addition of saturated aqueous sodium bicarbonate (45 mL). The cooling bath was removed and the resulting mixture was stirred at room temperature for 2 h. The resulting suspension was filtered and the filter-cake was washed successively with water and dichloromethane and then it was dried in vacuo (over phosphorous pentoxide) to give 0.363 g (98%) of title compound as a tan solid. LC (Method A): 2.096 min. HRMS(ESI): calcd for $C_{13}H_9FN_3O_3S$ [M+H]$^+$ m/z 306.0349; found 306.0369. $^1$H NMR (400 MHz, DMSO-d$_6$) δ ppm: 10.51 (br s, 1H), 8.41 (s, 1H), 7.07 (s, 1H), 6.90-6.99 (m, 1H), 6.42-6.52 (m, 1H), 4.21 (s, 3H).

180F. tert-Butyl 4-(4-(((6-fluoro-2-(2-methoxyimidazo[2,1-b][1,3,4]thiadiazol-6-yl)benzofuran-4-yl)oxy)methyl)thiazol-2-yl)benzoate

The title compound was prepared according to the general procedure described in Example 36. LC (Method A): 2.689 min. HRMS(ESI): calcd for $C_{28}H_{24}FN_4O_5S_2$ [M+H]$^+$ m/z 579.1172; found 579.1159. $^1$H NMR (400 MHz, CDCl$_3$) δ ppm: 7.99-8.11 (m, 4H), 7.89 (s, 1H), 7.44 (s, 1H), 7.15 (s, 1H), 6.88-6.94 (m, 1H), 6.63 (dd, J=11.35, 1.96 Hz, 1H), 5.42 (s, 2H), 4.22 (s, 3H), 1.63 (s, 9H).

180G. 4-(4-(((6-Fluoro-2-(2-methoxyimidazo[2,1-b][1,3,4]thiadiazol-6-yl)benzofuran-4-yl)oxy)methyl)thiazol-2-yl)benzoic Acid

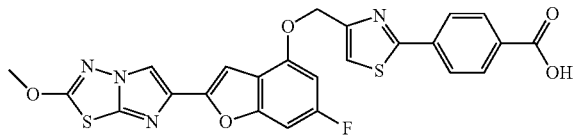

To a solution of tert-butyl 4-(4-(((6-fluoro-2-(2-methoxyimidazo[2,1-b][1,3,4]thiadiazol-6-yl)benzofuran-4-yl)oxy)methyl)thiazol-2-yl)benzoate (0.345 g, 0.596 mmol) in dichloromethane (6 mL) was added trifluoroacetic acid (3 mL) and the homogenous yellowish mixture was stirred at room temperature for 4 h. The volatiles were then evaporated under reduced pressure and the resulting solid residue was triturated with dichloromethane, filtered and dried in vacuo to give 0.272 g (87%) of the title compound as a beige solid. LC (Method A): 2.428 min. HRMS(ESI): calcd. for $C_{24}H_{16}FN_4O_5S_2$ [M+H]$^+$ m/z 523.0546; found 523.0541. $^1$H NMR (400 MHz, DMSO-d$_6$) δ ppm: 8.46 (s, 1H), 8.00-8.13 (m, 5H), 7.18 (d, J=9.00 Hz, 1H), 7.12 (m, 1H), 6.99-7.06 (m, 1H), 5.44 (s, 2H), 4.20 (s, 3H).

Example 180. N-(2-Cyanoethyl)-N-ethyl-4-(4-(((6-fluoro-2-(2-methoxyimidazo[2,1-b][1,3,4]thiadiazol-6-yl)benzofuran-4-yl)oxy)methyl)thiazol-2-yl)benzamide

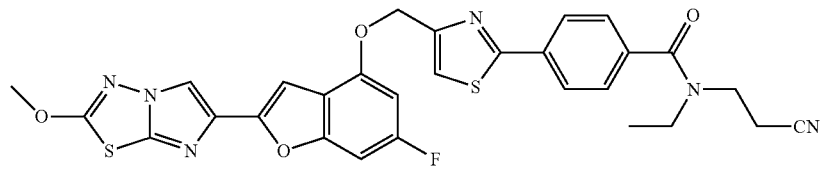 [SMILES: CCN(CCC#N)C(=O)c1ccc(-c2nc(COc3cc(F)cc4oc(-c5cn6nc(OC)sc6n5)cc34)cs2)cc1]

A solution of 4-(4-(((6-fluoro-2-(2-methoxyimidazo[2,1-b][1,3,4]thiadiazol-6-yl)benzofuran-4-yl)oxy)methyl)thiazol-2-yl)benzoic acid (0.040 g, 0.077 mmol) in N,N-dimethylformamide (2 mL) was treated with diisopropylethylamine (0.067 mL, 0.383 mmol), followed by 3-(ethylamino)propanenitrile (0.0083 g, 0.084 mmol). HATU (0.032 g, 0.084 mmol) was then added and the reaction mixture was stirred at room temperature for 3 h. The volatiles were then evaporated in vacuo and the residue was partitioned between chloroform and saturated aqueous sodium bicarbonate. The organic phase was separated, washed with brine, dried over anhydrous sodium sulfate and evaporated in vacuo. Chromatography of the residue on silica gel (ISCO, elution gradient of ethyl acetate in chloroform) gave 0.034 g (74%) of the title compound as a white solid. LC (Method A): 2.374 min. HRMS(ESI): calcd for $C_{29}H_{24}FN_6O_4S_2$ [M+H]$^+$ m/z 603.1285; found 603.1286. $^1$H NMR (400 MHz, CDCl$_3$) δ ppm: 8.05 (m, 2H), 7.89 (s, 1H), 7.52 (m, 2H), 7.43 (d, J=0.78 Hz, 1H), 7.15 (s, 1H), 6.91 (d, J=8.61 Hz, 1H), 6.63 (dd, J=11.54, 1.76 Hz, 1H), 5.41 (s, 2H), 4.22 (s, 3H), 3.74 (br s, 2H), 3.46 (br s, 2H), 2.87 (br s, 2H), 1.21 (br s, 3H).

Example 181

4-(4-(((6-Fluoro-2-(2-methoxyimidazo[2,1-b][1,3,4]thiadiazol-6-yl)benzofuran-4-yl)oxy)methyl)thiazol-2-yl)-N-(2,2,2-trifluoroethyl)benzamide

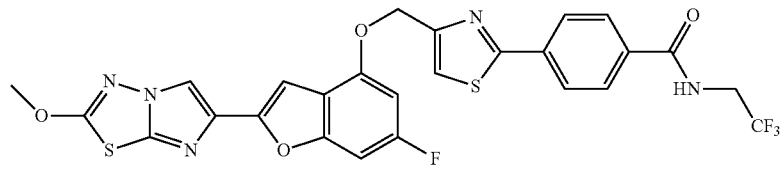 [SMILES: COc1nn2cc(-c3cc4c(OCc5csc(-c6ccc(C(=O)NCC(F)(F)F)cc6)n5)cc(F)cc4o3)nc2s1]

The title compound was prepared according to the method described in Example 180 above. LC (Method A): 2.369 min. HRMS(ESI): calcd for $C_{26}H_{18}F_4N_5O_4S_2$ [M+H]$^+$ m/z 604.0736; found 604.0725. $^1$H NMR (400 MHz, DMSO-d$_6$) δ ppm: 9.24 (t, J=6.26 Hz, 1H), 8.46 (s, 1H), 8.06-8.14 (m, 2H), 7.98-8.06 (m, 3H), 7.18 (d, J=7.83 Hz, 1H), 7.12 (s, 1H), 7.03 (dd, J=12.13, 1.96 Hz, 1H), 5.44 (s, 2H), 4.20 (s, 3H), 4.04-4.17 (m, 2H).

Example 182

N-(tert-Butyl)-4-(4-(((6-fluoro-2-(2-methoxyimidazo[2,1-b][1,3,4]thiadiazol-6-yl)benzofuran-4-yl)oxy)methyl)thiazol-2-yl)-N-methylbenzamide

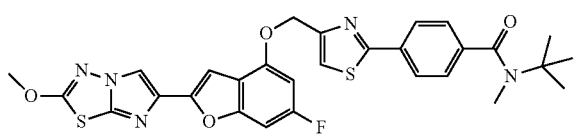 [SMILES: COc1nn2cc(-c3cc4c(OCc5csc(-c6ccc(C(=O)N(C)C(C)(C)C)cc6)n5)cc(F)cc4o3)nc2s1]

The title compound was prepared according to the method described in Example 180 above. LC (Method A): 2.391 min. HRMS(ESI): calcd. for $C_{29}H_{27}FN_5O_4S_2$ [M+H]$^+$ m/z 592.1489; found 592.1500. $^1$H NMR (400 MHz, CDCl$_3$) δ ppm: 7.88-7.94 (m, 2H), 7.81 (s, 1H), 7.41-7.48 (m, 2H), 7.33 (s, 1H), 7.07 (s, 1H), 6.83 (dd, J=8.61, 0.78 Hz, 1H), 6.55 (dd, J=11.35, 1.96 Hz, 1H), 5.32 (s, 2H), 4.14 (s, 3H), 2.82 (s, 3H), 1.46 (s, 9H).

Example 183

(4-(4-(((6-Fluoro-2-(2-methoxyimidazo[2,1-b][1,3,4]thiadiazol-6-yl)benzofuran-4-yl)oxy)methyl)thiazol-2-yl)phenyl)(pyrrolidin-1-yl)methanone

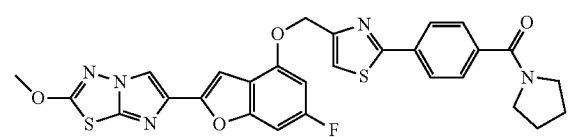 [SMILES: COc1nn2cc(-c3cc4c(OCc5csc(-c6ccc(C(=O)N7CCCC7)cc6)n5)cc(F)cc4o3)nc2s1]

The title compound was prepared according to the method described in Example 180 above. LC (Method A): 2.307 min. HRMS(ESI): calcd for $C_{28}H_{23}FN_5O_4S_2$ [M+H]$^+$ m/z 576.1176; found 576.1159. $^1$H NMR (400 MHz, CDCl$_3$) δ ppm: 8.02 (m, 2H), 7.89 (s, 1H), 7.63 (m, 2H), 7.42 (s, 1H), 7.16 (s, 1H), 6.91 (d, J=8.61 Hz, 1H), 6.63 (dd, J=11.35, 1.96 Hz, 1H), 5.41 (s, 2H), 4.22 (s, 3H), 3.68 (t, J=6.85 Hz, 2H), 3.47 (t, J=6.46 Hz, 2H), 1.84-2.05 (m, 4H).

Example 184

N-(Cyanomethyl)-4-(4-(((6-fluoro-2-(2-methoxyimidazo[2,1-b][1,3,4]thiadiazol-6-yl)benzofuran-4-yl)oxy)methyl)thiazol-2-yl)-N-methylbenzamide

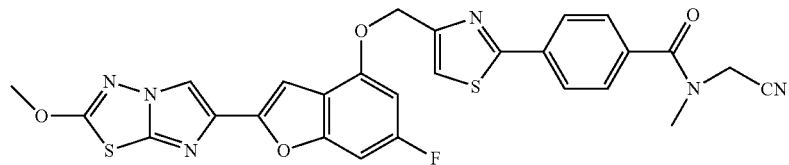 [SMILES: COc1nn2cc(-c3cc4c(OCc5csc(-c6ccc(C(=O)N(C)CC#N)cc6)n5)cc(F)cc4o3)nc2s1]

The title compound was prepared according to the method described in Example 180 above. LC (Method A): 2.274 min. HRMS(ESI): calcd for $C_{27}H_{20}FN_6O_4S_2$ [M+H]$^+$ m/z 575.0972; found 575.0963. $^1$H NMR (400 MHz, CDCl$_3$) δ ppm: 8.07 (m, 2H), 7.89 (s, 1H), 7.58 (m, 2H), 7.45 (s, 1H), 7.15 (s, 1H), 6.91 (dd, J=8.61, 0.78 Hz, 1H), 6.62 (dd, J=11.35, 1.96 Hz, 1H), 5.41 (s, 2H), 4.49 (br s, 2H), 4.22 (s, 3H), 3.20 (s, 3H).

Example 185

4-(4-(((6-Fluoro-2-(2-methoxyimidazo[2,1-b][1,3,4]thiadiazol-6-yl)benzofuran-4-yl)oxy)methyl)thiazol-2-yl)-N,N-dimethylbenzamide

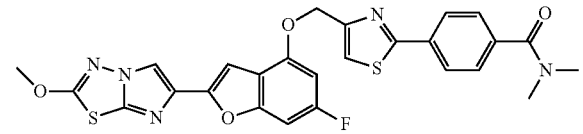

The title compound was prepared from 6-fluoro-2-(2-methoxyimidazo[2,1-b][1,3,4]thiadiazol-6-yl)benzofuran-4-ol (Example 180E) and 4-(4-(hydroxymethyl)thiazol-2-yl)-N,N-dimethylbenzamide (Example 36B) according to the general method described in Example 36. LC (Method A): 2.327 min. HRMS(ESI): calcd for $C_{26}H_{21}FN_5O_4S_2$ [M+H]$^+$ m/z 550.1019; found: 550.0999. $^1$H NMR (400 MHz, CDCl$_3$) δ ppm: 8.02 (m, 2H), 7.89 (s, 1H), 7.53 (m, 2H), 7.42 (s, 1H), 7.15 (s, 1H), 6.91 (d, J=8.61 Hz, 1H), 6.63 (d, J=11.35 Hz, 1H), 5.41 (s, 2H), 4.22 (s, 3H), 3.15 (br s, 3H), 3.02 (br s, 3H).

Example 186

4-(4-(((6-Fluoro-2-(2-methoxyimidazo[2,1-b][1,3,4]thiadiazol-6-yl)benzofuran-4-yl)oxy)methyl)-5-methylthiazol-2-yl)-N-methylbenzamide

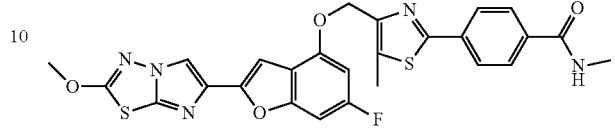

186A. tert-Butyl 4-(4-(((6-fluoro-2-(2-methoxyimidazo[2,1-b][1,3,4]thiadiazol-6-yl)benzofuran-4-yl)oxy)methyl)-5-methylthiazol-2-yl)benzoate

The title compound was prepared from 6-fluoro-2-(2-methoxyimidazo[2,1-b][1,3,4]thiadiazol-6-yl)benzofuran-4-ol (Example 180E) and tert-butyl 4-(4-(hydroxymethyl)-5-methylthiazol-2-yl)benzoate (Example 45D) according to the general method described in Example 180F. LC (Method A): 2.788 min. HRMS(ESI): calcd for $C_{29}H_{26}FN_4O_5S_2$ [M+H]$^+$ m/z 593.1329; found 593.1318. $^1$H NMR (400 MHz, CDCl$_3$) δ ppm: 8.02-8.07 (m, 2H), 7.93-7.99 (m, 2H), 7.87 (s, 1H), 7.08 (s, 1H), 6.89 (dd, J=8.61, 0.78 Hz, 1H), 6.73 (dd, J=11.74, 1.96 Hz, 1H), 5.34 (s, 2H), 4.21 (s, 3H), 2.60 (s, 3H), 1.62 (s, 9H).

186B. 4-(4-(((6-Fluoro-2-(2-methoxyimidazo[2,1-b][1,3,4]thiadiazol-6-yl)benzofuran-4-yl)oxy)methyl)-5-methylthiazol-2-yl)benzoic Acid

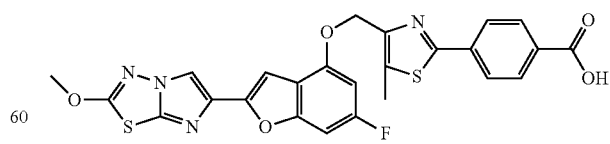

The title compound was prepared according to the general deprotection method described in Example 180G. LC (Method A): 2.436 min. HRMS(ESI): calcd for $C_{25}H_{18}FN_4O_5S_2$ [M+H]$^+$ m/z 537.0703; found 537.0696. $^1$H NMR (400 MHz, DMSO-d$_6$) δ ppm: 13.14 (br s, 1H), 8.46 (s, 1H), 7.99-8.08 (m, 4H), 7.14-7.21 (m, 1H), 6.99-7.09 (m, 2H), 5.37 (s, 2H), 4.20 (s, 3H), 2.60 (s, 3H).

Example 186. 4-(4-(((6-Fluoro-2-(2-methoxyimidazo[2,1-b][1,3,4]thiadiazol-6-yl)benzofuran-4-yl)oxy)methyl)-5-methylthiazol-2-yl)-N-methylbenzamide

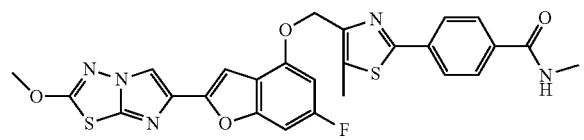

The title compound was prepared according to the general amide coupling method described in Example 180. LC (Method A): 2.389 min. HRMS(ESI): calcd for $C_{26}H_{20}FN_5O_4S_2$ [M+H]$^+$ m/z 549.0941; found 550.1029. $^1$H NMR (400 MHz, CDCl$_3$) δ ppm: 7.98 (d, J=8.0 Hz, 2H), 7.87 (s, 1H), 7.83 (d, J=8.0 Hz, 2H), 7.08 (s, 1H), 6.89 (d, J=8.61 Hz, 1H), 6.72 (dd, J=11.54, 1.76 Hz, 1H), 6.15 (br s, 1H), 5.33 (s, 2H), 4.22 (s, 3H), 3.05 (d, J=5.09 Hz, 3H), 2.59 (s, 3H).

Example 187

6-(6-Chloro-4-((2-phenylthiazol-4-yl)methoxy)benzofuran-2-yl)-2-methoxyimidazo[2,1-b][1,3,4]thiadiazole

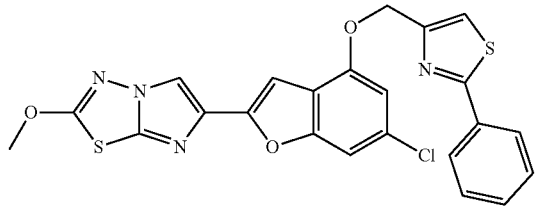 [SMILES: COc1nn2cc(-c3cc4c(OCc5csc(-c6ccccc6)n5)cc(Cl)cc4o3)nc2s1]

187A. 4-Chloro-2,6-dimethoxybenzaldehyde

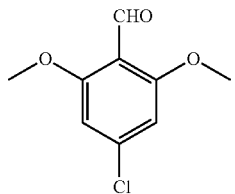

A solution of 1-chloro-3,5-dimethoxybenzene (5 g, 29.0 mmol) and TMEDA (4.37 mL, 29.0 mmol) in diethyl ether (100 mL, 962 mmol) at −78° C. under N$_2$ atmosphere was charged with BuLi (19.91 mL, 31.9 mmol) dropwise over a period of 30 minutes using a syringe pump. After stirring for 4 hours at −78° C., DMF was added and the reaction mixture continued to stir for 1.5 hours after which 1N HCl (~30 mL) was added (all at −78° C.). The reaction mixture was warmed to room temperature and extracted with ethyl acetate. The organic phase was dried (MgSO$_4$), filtered and concentrated to dryness. The residue was purified by ISCO using hexanes/EtOAc as eluent. Fractions containing the desired product were concentrated to dryness to give the title material (1.97 g, 9.82 mmol, 33.9% yield) as a light yellow solid. LC (Method B): 1.924 min. LCMS (APCI) calcd for $C_9H_{10}ClO_3$ [M+H]$^|$ m/z 201.03, found 201.0. $^1$H NMR (CDCl$_3$, 400 MHz) δ ppm: 10.28 (s, 1H), 6.87 (s, 2H), 3.86 (s, 6H).

187B. 4-Chloro-2-hydroxy-6-methoxybenzaldehyde

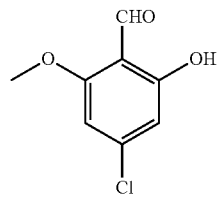

A stirred solution of 4-chloro-2,6-dimethoxybenzaldehyde (1.95 g, 9.72 mmol) in DCM (20 mL, 311 mmol) at −78° C. was slowly added boron tribromide (9.72 mL, 9.72 mmol). The reaction mixture was stirred at −78° C. for 10 minutes then warmed to r.t. and stirred for 1 hour while monitoring reaction progress by LCMS. Once all s.m. had been consumed, the reaction was quenched with water and extracted with DCM. The organic phase was washed with brine, dried (MgSO$_4$), filtered and concentrated to dryness to give the title material (1.79 g, 9.59 mmol, 99% yield) as a purple solid. LC (Method B): 2.199 min. LCMS (APCI) calcd for $C_8H_8ClO_3$ [M+H]$^+$ m/z 187.02, found 187.0. $^1$H NMR (CDCl$_3$, 400 MHz) δ ppm: 11.89 (s, 1H), 10.20 (s, 1H), 6.75 (t, J=2.0 Hz, 1H), 6.66 (m, 1H), 3.91 (s, 1H).

187C. 1-(6-Chloro-4-methoxybenzofuran-2-yl)ethanone

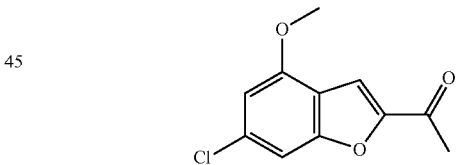

A stirred solution of 4-chloro-2-hydroxy-6-methoxybenzaldehyde (1.79 g, 9.59 mmol) in N,N-dimethylformamide (15 mL, 9.59 mmol) was charged with cesium carbonate (3.75 g, 11.51 mmol) and 1-chloropropan-2-one (0.975 mL, 11.51 mmol). The reaction mixture was heated in a sealable vessel at 65° C. for 7 hours, was filtered over a Whatman filter paper to remove insolubles rinsing with DCM then washed with sat. NaHCO$_3$. The organic phase was dried (MgSO$_4$), filtered and concentrated to dryness. The residue was purified by ISCO using hexanes/EtOAc as eluent. Fractions containing the desired product were concentrated to give the title material (1.43 g, 6.37 mmol, 66% yield) as a light yellow solid. LC (Method A): 1.952 min. LCMS (APCI) calcd for $C_{11}H_{10}ClO_3$ [M+H]$^+$ m/z 225.03, found 225.0. $^1$H NMR (CDCl$_3$, 400 MHz) δ ppm: 7.94 (d, J=0.8 Hz, 1H), 7.49 (dd, J=0.8, 1.6 Hz, 1H), 6.97 (d, J=1.6 Hz, 1H), 3.97 (s, 3H).

187D.
1-(6-Chloro-4-hydroxybenzofuran-2-yl)ethanone

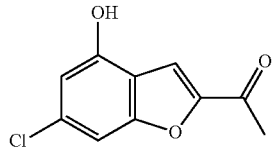

To a stirred solution of 1-(6-chloro-4-methoxybenzofuran-2-yl)ethanone (1.43 g, 6.37 mmol) in chlorobenzene (15 mL, 148 mmol) was added aluminum chloride (3.40 g, 25.5 mmol) in portions over a period of 10 minutes. The reaction vessel was then sealed and heated at 100° C. for 40 minutes, then cool to r.t. and poured onto crushed ice (rinsed stirring bar with EtOAc). This was stirred for 30 minutes, then extracted with ethyl acetate. The organic phase was dried (MgSO$_4$), filtered and concentrated to dryness. The residue was purified by ISCO using hexanes/EtOAc as eluent. Fractions containing the desired product were concentrated to give the title material (1.18 g, 5.60 mmol, 88% yield) as a light brown solid. LC (Method A): 1.783 min. LCMS (APCI) calcd for C$_{10}$H$_8$ClO$_3$ [M+H]$^+$ m/z 211.02, found 211.0. $^1$H NMR (CDCl$_3$, 400 MHz) δ ppm: 11.01 (s, 1H), 7.89 (s, 1H), 6.72 (s, 1H), 2.52 (s, 3H).

187E.
1-(4-(Benzyloxy)-6-chlorobenzofuran-2-yl)ethanone

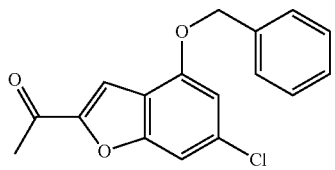 [SMILES: CC(=O)c1cc2c(OCc3ccccc3)cc(Cl)cc2o1]

A stirred solution of 1-(6-chloro-4-hydroxybenzofuran-2-yl)ethanone (1.18 g, 5.60 mmol) in dry DMF (10 mL, 129 mmol) at r.t. was charged with K$_2$CO$_3$ (0.774 g, 5.60 mmol) and DMF. The reaction mixture was stirred for 1.5 hours then partitioned between ethyl acetate and water. The organic phase was washed with brine, dried (MgSO$_4$), filtered and concentrated to dryness. The residue was purified by ISCO using hexanes/EtOAc as eluent. Fractions containing the desired product were concentrated to give the title material (1.57 g, 5.22 mmol, 93% yield) as an amber colored oil. LC (Method B): 2.420 min. LCMS (APCI) calcd for C$_{17}$H$_{14}$ClO$_3$ [M+H]$^|$ m/z 301.06, found 301.0. $^1$H NMR (CDCl$_3$, 400 MHz) δ ppm: 8.00 (d, J=0.8 Hz, 1H), 7.53 (m, 3H), 7.44 (m, 2H), 7.38 (m, 1H), 7.10 (d, J=1.6 Hz, 1H), 5.53 (s, 2H), 2.54 (s, 3H).

187F. 1-(4-(Benzyloxy)-6-chlorobenzofuran-2-yl)-2-bromoethanone

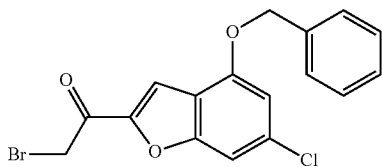 [SMILES: O=C(CBr)c1cc2c(OCc3ccccc3)cc(Cl)cc2o1]

A flame dried 200 ml round-bottom flask equipped with a stirring bar and under nitrogen atmosphere was charged with anhydrous THF (12 mL) followed by lithium bis(trimethylsilyl)amide (6.22 mL, 6.22 mmol). The mixture was cooled to −78° C. and treated with a solution of 1-(4-(benzyloxy)-6-chlorobenzofuran-2-yl)ethanone (1.56 g, 5.19 mmol) in THF (6 ml+2 ml washing) added dropwise over 10 minutes via a syringe pump. The resulting mixture was stirred at −78° C. for 45 minutes and was then charged with trimethylchlorosilane (0.769 mL, 6.02 mmol) added dropwise over 5 minutes by syringe pump then stirred for another 20 minutes. The cooling bath was removed and the mixture was allowed to warm to +10° C. for 30 minutes. The reaction mixture was quenched with a mixture of cold ethyl acetate (80 mL), sat. NaHCO$_3$ (12 mL) and ice. The organic phase was dried (MgSO$_4$), stirring for ~5 minutes to remove all traces of water), filtered and concentrated to dryness to give the silyl enol ether as a yellow oil which was co-evaporated with toluene (4 mL). The silyl enol ether was dissolved in dry THF (20 mL), cooled to −30° C. (employing a cooling bath made from 1:1 CaCl$_2$: water using dry ice, bath stabilizes around −30 to −45° C.) and treated with NaHCO$_3$ (~50 mgs) followed by N-bromosuccinimide (0.923 g, 5.19 mmol) added in small portions over 15 minutes. The reaction mixture was allowed to warm to 0° C. over 2 hours (monitored by LCMS) and then quenched by addition of ethyl acetate (100 mL) and sat. NaHCO$_3$. The organic phase was washed with brine, dried (MgSO$_4$) and evaporated to give an orange solid which was purified by ISCO using hexanes/EtOAc as eluent. Fractions containing the desired product were concentrated to give the title material 1.48 g, 3.51 mmol, 67.6% yield) as a yellow solid. LC (Method B): 2.528 min. LCMS (APCI) calcd for C$_{17}$H$_{13}$BrClO$_3$ [M+H]$^+$ m/z 378.97, found 379.0.

187G. 6-(4-(Benzyloxy)-6-chlorobenzofuran-2-yl)-2-bromoimidazo[2,1-b][1,3,4]thiadiazole

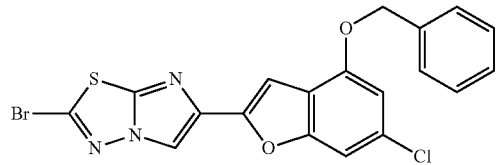 [SMILES: Clc1cc(OCc2ccccc2)c2cc(-c3cn4nc(Br)sc4n3)oc2c1]

A sealable vessel was charged with 1-(4-(benzyloxy)-6-chlorobenzofuran-2-yl)-2-bromoethanone (1.48 g, 3.51 mmol), 5-bromo-1,3,4-thiadiazol-2-amine (0.632 g, 3.51 mmol) and IPA (25 mL, 324 mmol). The reaction mixture was heated in an oil bath at 80° C. for 6 hours then heated in the microwave at 150° C. for 1 hour. The reaction mixture was allowed to stand for 1 hour and the insoluble material was filtered off and rinsed with MeOH to give the desired product as a brown solid (1.19 g, 2.58 mmol, 73.6% yield). LC (Method A): 2.549 min. LCMS (APCI) calcd for C$_{19}$H$_{12}$BrClN$_3$O$_2$S [M+H]$^+$ m/z 459.95, found 460.0. $^1$H NMR (CDCl$_3$, 400 MHz) δ ppm: 8.74 (s, 1H), 7.55-7.50 (m, 2H), 7.45-7.34 (m, 4H), 7.17 (d, J=0.8 Hz, 1H), 7.02 (d, J=1.6 Hz, 1H), 5.32 (s, 2H).

187H. 6-(4-(Benzyloxy)-6-chlorobenzofuran-2-yl)-2-methoxyimidazo[2,1-b][1,3,4]thiadiazole

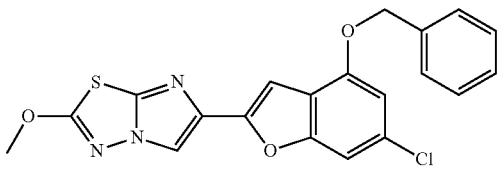 [SMILES: COc1nn2cc(-c3cc4c(OCc5ccccc5)cc(Cl)cc4o3)nc2s1]

To a stirred solution of 6-(4-(benzyloxy)-6-chlorobenzofuran-2-yl)-2-bromoimidazo[2,1-b][1,3,4]thiadiazole (1.18 g, 2.56 mmol) in DCM (40 mL, 622 mmol) and methanol (10 mL, 247 mmol) was added sodium methoxide (1.164 mL, 5.12 mmol). The reaction mixture was stirred at r.t. for 1 h 15 min while monitoring by TLC (7:3 hexanes: EtOAc). The reaction mixture was quenched with 1N HCl and extracted with DCM. The organic phase was washed with brine, dried (MgSO$_4$), filtered and concentrated to dryness. The residue was triturated with MeOH (sonication) and the solid material was filtered off, rinsed with MeOH and sucked dry to give the desired compound as a brown solid (859 mg, 2.086 mmol, 81% yield). LC (Method A): 2.478 min. LCMS (APCI) calcd for $C_{20}H_{15}ClN_3O_3S$ [M+H]$^+$ m/z 412.05, found 412.0. $^1$H NMR (CDCl$_3$, 400 MHz) δ ppm: 8.50 (s, 1H), 7.52 (m, 2H), 7.43 (m, 2H), 7.36 (m, 2H), 7.09 (d, J=0.8 Hz, 1H), 7.00 (d, J=1.6 Hz, 1H), 5.31 (s, 2H), 4.21 (s, 3H).

187I. 6-Chloro-2-(2-methoxyimidazo[2,1-b][1,3,4]thiadiazol-6-yl)benzofuran-4-ol

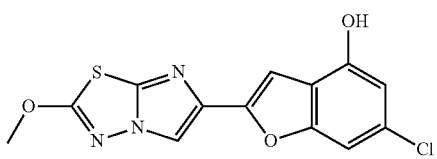 [SMILES: COc1nn2cc(-c3cc4c(O)cc(Cl)cc4o3)nc2s1]

A stirred solution of 6-(4-(benzyloxy)-6-chlorobenzofuran-2-yl)-2-methoxyimidazo[2,1-b][1,3,4]thiadiazole (0.85 g, 2.064 mmol) and pentamethylbenzene (2.142 g, 14.45 mmol) in DCM under N$_2$ atmosphere was cooled to −78° C. after which boron trichloride (5.16 mL, 5.16 mmol) was added dropwise over ~4 minutes. The reaction was monitored by TLC using 1:1 hexanes-EtOAc as eluent. The reaction mixture was stirred at −78° C. for 30 minutes after which a mixture of water (40 mL) and saturated NaHCO$_3$ (5 mL) was added (at −78° C.) and the mixture was stirred until ambient temperature was obtained (removed from cooling bath). The solid precipitate was filtered off and rinsed with diethyl ether then allowed to dry overnight to give the title material (441 mgs, 1.371 mmol, 66.4% yield) as a beige solid. The filtrate was extracted with DCM. The organic phase was washed with brine, dried (MgSO$_4$) and concentrated to dryness. The residue was purified by ISCO using DCM/EtOAc as eluent. Fractions containing the desired product were concentrated to give the title material (25 mgs, 0.078 mmol, 3.77% yield) as a beige solid. LC (Method A): 2.167 min. LCMS (APCI) calcd for $C_{13}H_9ClN_3O_3S$ [M+H]$^+$ m/z 322.00, found 322.0. $^1$H NMR (CDCl$_3$, 400 MHz) δ ppm: 10.50 (br. S, 1H), 8.45 (s, 1H), 7.17 (dd, J=0.8, 1.6 Hz, 1H), 7.09 (d, J=0.8 Hz, 1H), 6.67 (d, J=2.0 Hz, 2H), 4.21 (s, 3H).

Example 187. 6-(6-Chloro-4-((2-phenylthiazol-4-yl)methoxy)benzofuran-2-yl)-2-methoxyimidazo[2,1-b][1,3,4]thiadiazole

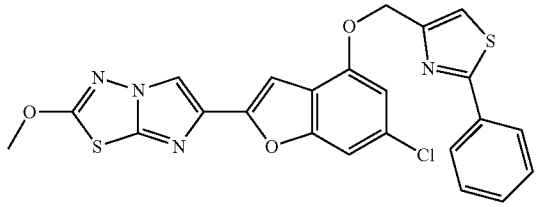 [SMILES: COc1nn2cc(-c3cc4c(OCc5csc(-c6ccccc6)n5)cc(Cl)cc4o3)nc2s1]

A flame-dried 100 mL round-bottom flask containing 6-chloro-2-(2-methoxyimidazo[2,1-b][1,3,4]thiadiazol-6-yl)benzofuran-4-ol (0.025 g, 0.078 mmol) and (2-phenylthiazol-4-yl)methanol (Example 3B, 37.2 mgs, 0.194 mmol) in dry THF (4 mL) was added tributylphosphine (0.050 mL, 0.194 mmol). The resulting solution was charged with a solution of ADDP (0.049 g, 0.194 mmol) in THF (1 mL) added dropwise over 30 minutes via syringe pump. After stirring for 1.5 hours the reaction mixture was diluted with EtOAc then washed with 1N HCl, sat. NaHCO$_3$, water and brine. The organic phase was dried (MgSO$_4$) then concentrated to dryness. The residue was purified by ISCO using 0 to 10% diethyl ether in DCM. Fractions containing the desired product were concentrated to give the title material as a beige solid (0.020 g, 0.040 mmol, 52.0% yield). LC (Method A): 2.534 min. LCMS (APCI) calcd for $C_{23}H_{16}ClN_4O_3S_2$ [M+H]$^+$ m/z 495.03, found 495.0. $^1$H NMR (CDCl$_3$, 400 MHz) δ ppm: 8.49 (s, 1H), 7.99-7.96 (m, 2H), 7.93 (s, 1H), 7.55-7.50 (m, 3H), 7.40 (dd, J=0.8, 1.6 Hz, 1H), 7.15 (dd, J=0.4, 1.6 Hz, 1H), 7.14 (d, J=0.8 Hz, 1H), 5.43 (s, 2H), 4.21 (s, 3H).

Example 188

6-(6-Chloro-4-((2-(4-chlorophenyl)thiazol-4-yl)methoxy)benzofuran-2-yl)-2-methoxyimidazo[2,1-b][1,3,4]thiadiazole

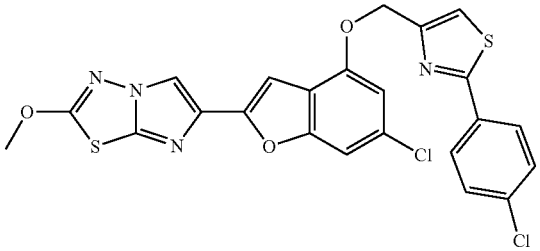 [SMILES: COc1nn2cc(-c3cc4c(OCc5csc(-c6ccc(Cl)cc6)n5)cc(Cl)cc4o3)nc2s1]

A suspension of 6-chloro-2-(2-methoxyimidazo[2,1-b][1,3,4]thiadiazol-6-yl)benzofuran-4-ol (Example 187I, 0.030 g, 0.093 mmol) and 2-(bromomethyl)-4-(4-chlorophenyl)thiazole (0.0404 g, 0.140 mmol) in N,N-dimethylformamide (3 mL) was maintained under vacuum (10 mbar) for 5 min. The flask was then flushed with nitrogen and freshly powdered anhydrous potassium carbonate (0.105 g, 0.756 mmol)

was added all at once. The resulting mixture was stirred at room temperature for 16 h. The heterogeneous mixture was quenched with 1 N hydrochloric acid (1 mL) after which water and MeOH were added. The solid material was filtered off and the filter-cake was rinsed with water, methanol and acetonitrile to give a beige solid. The solid material was dissolved in DCM with a small amount of methanol, then adsorbed onto a silica gel pre-column and purified by flash chromatography (0-100% EtOAc-dichloromethane). The obtained product was lyophilized from acetonitrile-water to give the title compound as an amorphous beige solid (0.031 g, 0.059 mmol, 62.8%). LC (Method F): 2.714 min. HRMS (ESI): calcd for $C_{23}H_{15}Cl_2N_4O_3S_2$ [M+H]$^+$ m/z 528.9963, found 528.9954. $^1$H NMR (DMSO-d$_6$, 400 MHz) δ ppm: 8.47 (s, 1H), 7.98 (m, 2H), 7.94 (s, 1H), 7.58 (m, 2H), 7.38 (s, 1H), 7.12 (d, J=0.8 Hz, 2H), 5.42 (s, 2H), 4.20 (s, 3H).

Example 189

6-(6-Chloro-4-((2-(m-tolyl)thiazol-4-yl)methoxy) benzofuran-2-yl)-2-methoxyimidazo[2,1-b][1,3,4] thiadiazole

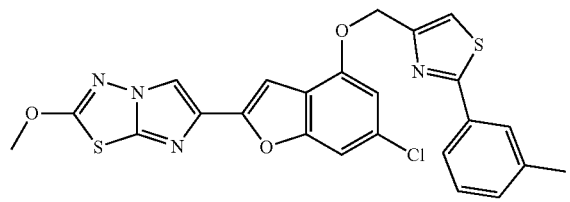

The title compound was prepared according to the method described in Example 188 above to give a solid. LC (Method F): 2.687 min. HRMS(ESI): calcd for $C_{24}H_{18}ClN_4O_3S_2$ [M+H]$^+$ m/z 509.0509, found 509.0512. $^1$H NMR (DMSO-d$_6$, 400 MHz) δ ppm: 8.49 (s, 1H), 7.91 (s, 1H), 7.80 (s, 1H), 7.76 (d, J=7.8 Hz, 1H), 7.40 (t, J=7.6 Hz, 1H), 7.32 (d, J=7.8 Hz, 1H), 7.15 (d, J=1.6 Hz, 1H), 7.14 (d, J=0.8 Hz, 1H), 5.42 (s, 2H), 4.20 (s, 3H), 2.39 (s, 3H).

Example 190

(6-(6-Chloro-4-((2-(4-fluorotetrahydro-2H-pyran-4-yl)thiazol-4-yl)methoxy)benzofuran-2-yl)-2-methoxyimidazo[2,1-b][1,3,4]thiadiazole

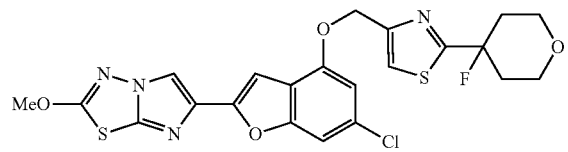 [SMILES: COc1nn2cc(-c3cc4c(OCc5csc(C6(F)CCOCC6)n5)cc(Cl)cc4o3)nc2s1]

To a solution of 4-(bromomethyl)-2-(4-fluorotetrahydro-2H-pyran-4-yl)thiazole (Example 119C, 0.016 g, 0.057 mmol) in DMF (1.5 mL) was added 6-chloro-2-(2-methoxyimidazo[2,1-b][1,3,4]thiadiazol-6-yl)benzofuran-4-ol (Example 187I, 0.017 g, 0.052 mmol), followed by freshly powdered potassium carbonate (0.022 g, 0.156 mmol). The mixture was stirred in a sealed vial at room temperature for 2 h and then it was diluted with water and the resulting mixture was filtered and the filter-cake was washed with saturated aqueous NH$_4$Cl and then with water. The wet residue was taken up in DCM and the solution was washed (saturated aqueous NaHCO$_3$), dried (Na$_2$SO$_4$) and evaporated to give a gum. Flash chromatography (Isco/0-30% EtOAc-DCM) afforded 6-(6-chloro-4-((2-(4-fluorotetrahydro-2H-pyran-4-yl)thiazol-4-yl)methoxy)benzofuran-2-yl)-2-methoxyimidazo[2,1-b][1,3,4]thiadiazole (0.012 g, 44.4%) as a solid. LC (Method A): 2.483 min. HRMS(ESI): calcd for $C_{22}H_{19}ClFN_4O_4S_2$ [M+H]$^+$ m/z 521.052; found 521.053. $^1$H NMR (400 MHz, DMSO-d$_6$): δ 8.46 (s, 1H), 7.94 (s, 1H), 7.36 (br s, 1H), 7.08 (d, J=1.57 Hz, 1H), 7.07 (s, 1H), 5.35 (s, 2H), 4.17 (s, 3H), 3.81 (m, 2H), 3.67 (dt, J=1.96, 10.96 Hz, 2H), 2.33-2.16 (m, 2H), 2.05 (m, 2H).

Example 191

2-Methoxy-6-(4-((2-phenylthiazol-4-yl)methoxy) benzofuran-2-yl)imidazo[2,1-b][1,3,4]thiadiazole

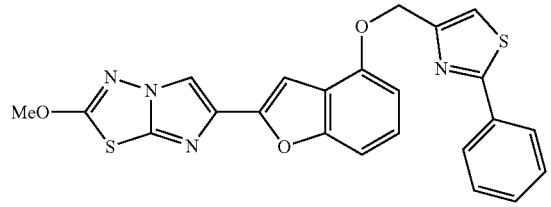 [SMILES: COc1nn2cc(-c3cc4c(OCc5csc(-c6ccccc6)n5)cccc4o3)nc2s1]

191A. 5-(Benzyloxy)-2,2-dimethyl-4H-benzo[d][1,3]dioxin-4-one

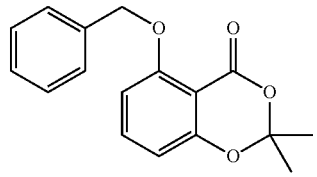 [SMILES: CC1(C)OC(=O)c2c(OCc3ccccc3)cccc2O1]

A solution of 5-hydroxy-2,2-dimethyl-4H-benzo[d][1,3]dioxin-4-one (6.00 g, 30.9 mmol) (Hadfield, A. et al., Synthetic Communications, 24(7):1025-1028 (1994)) in N,N-dimethylformamide (35 mL) was treated with powdered anhydrous potassium carbonate (5.15 g, 37.26 mmol) added all at once. The resulting mixture was stirred in vacuo for 10 min. and then flushed with nitrogen. The reaction flask was placed in a water bath (22° C.) and treated with benzyl bromide (5.55 g, 32.16 mmol) added dropwise over 15 min. The resulting mixture was then stirred at 22° C. for 18 h. The solid formed was filtered and washed with N,N-dimethylformamide. The filtrate was evaporated in vacuo and the residual oil was diluted with ethyl acetate (300 mL), washed with cold 0.1 N hydrochloric acid, saturated sodium bicarbonate and brine. After drying over anhydrous magnesium sulfate, evaporation of the solvent gave a thick syrup. Chromatography on silica gel (4×13 cm, elution toluene-ethyl acetate 0-5%) gave 8.78 g (100% yield) of the title material as a white solid. LC (Method A): 1.982 min. $^1$H NMR (CDCl$_3$, 600 MHz) δ ppm: 1.69 (s, 6H), 5.23 (s, 2H), 6.53 (d, J=8.2 Hz, 1H), 6.62 (d, J=8.4 Hz, 1H), 7.24-7.3 (m, 1H), 7.34-7.4 (m, 3H), 7.52 (broad d, J=7.4 Hz 2H).

191B. 2-(Benzyloxy)-6-hydroxybenzaldehyde

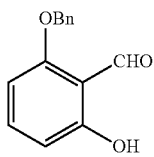

A solution of 5-(benzyloxy)-2,2-dimethyl-4H-benzo[d][1,3]dioxin-4-one (4.00 g, 14.07 mmol) in dichloromethane (80 mL) was cooled to −78° C. and treated with a solution of diisobutylaluminum hydride (6.00 g, 42.2 mmol) in toluene (40 mL) added dropwise over 20 min. The resulting mixture was then stirred at −78° C. for 3 h. The reaction mixture was quenched by the careful addition of methanol (5 mL) added dropwise over 15 min, followed by 4 N hydrochloric acid (20 mL) added dropwise over 15 min. The cooling bath was then removed and an additional 80 mL of 4N hydrochloric acid was added over 10 min and the mixture was stirred vigorously at 22° C. for 4 h. The reaction mixture was diluted with ethyl acetate (200 mL), washed with brine, dried over anhydrous magnesium sulfate and evaporated in vacuo. The resulting oil was chromatographed on silica gel (4×10 cm, elution toluene) to give 2.25 g (70% yield) of the title material as a pale yellow solid. LC (Method A): 2.219 min. HRMS(ESI) calcd for $C_{14}H_{13}O_3$ $[M+H]^+$ m/z 229.0859, found 229.0859. $^1$H NMR (CDCl$_3$, 600 MHz) δ ppm: 5.12 (s, 2H), 6.43 (d, J=8.25 Hz, 1H), 6.52 (d, J=8.46 Hz, 1H), 7.34-7.4 (m, 6H), 10.39 (s, 1H), 11.95 (s, 1H).

191C. 1-(4-(Benzyloxy)benzofuran-2-yl)ethanone

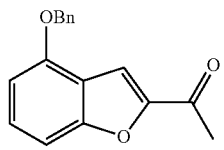

A solution of 2-(benzyloxy)-6-hydroxybenzaldehyde (11.10 g, 48.63 mmole) in N,N-dimethylformamide (120 mL) was treated with powdered anhydrous cesium carbonate (15.8 g, 48.63 mmol) added all at once. The resulting mixture was stirred in vacuo for 10 min and then flushed with nitrogen. The reaction flask was placed in a water bath (22° C.) and treated with chloroacetone (4.65 mL, 58.4 mmol) added dropwise over 10 min. The resulting mixture was then stirred at 22° C. for 18 h (no starting aldehyde left by tlc and formation of the intermediate alkylated aldehyde). The reaction mixture was then maintained under vacuum (10 mbar) for 15 min to remove any un-reacted chloroacetone and then flushed with nitrogen. Then anhydrous cesium carbonate (1.0 g, 3.1 mmol) was added and the mixture was heated at 55° C. and stirred for 40 h (more cesium carbonate, 1 g, was added after 24 h and 32 h) till complete conversion of the intermediate alkylated aldehyde into the benzofuran as monitored by TLC. The solid was filtered and washed with N,N-dimethylformamide. The filtrate was evaporated in vacuo and the residual oil was diluted with ethyl acetate (400 mL), washed with cold 0.1 N hydrochloric acid, saturated sodium bicarbonate and brine. After drying over anhydrous magnesium sulfate, evaporation of the solvent gave a thick syrup. Chromatography on silica gel (4.5×12 cm, elution toluene-ethyl acetate 2-4%) gave 11.67 g (90% yield) of the title benzofuran as a light yellow solid. Recrystallization from a mixture of ethyl acetate (40 mL) and hexane (40 mL) gave colorless prisms (10.50 g). LC (Method A): 2.162 min. HRMS(ESI) calcd for $C_{17}H_{15}O_3$ $[M+H]^+$ m/z 267.1016, found 267.1022. $^1$H NMR (CDCl$_3$, 600 MHz) δ ppm: 2.56 (s, 3H), 5.20 (s, 2H), 6.73 (d, J=8.0 Hz, 1H), 7.17 (d, J=8.4 Hz, 1H), 7.3-7.5 (m, 6H), 7.63 (s, 1H).

191D. 1-(4-(Benzyloxy)benzofuran-2-yl)-2-bromoethanone

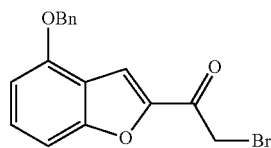 [SMILES: O=C(CBr)c1cc2c(OCc3ccccc3)cccc2o1]

A 250-mL, three-necked flask is equipped with a magnetic stirring bar and purged with a nitrogen atmosphere, was charged with anhydrous tetrahydrofuran (40 mL) followed by 21.6 mL (21.6 mmol) of a 1M solution of lithium bis(trimethylsilyl)amide in tetrahydrofuran. The mixture was cooled to −78° C. and treated with a solution of 1-(4-(benzyloxy)benzofuran-2-yl)ethanone (5.00 g, 18.77 mmole in tetrahydrofuran (20 mL) added dropwise over 10 min. The resulting mixture was then stirred at −78° C. for 45 min. Then chlorotrimethylsilane (2.74 mL, 21.6 mmol) was added dropwise over 5 min and the resulting solution was stirred at −78° C. for another 20 min. The cooling bath was then removed and the mixture is allowed to warm to room temperature over 30 min. The reaction mixture was then quenched by addition to a cold solution of ethyl acetate (300 mL), saturated sodium bicarbonate (40 mL) and ice. The organic phase was rapidly dried over anhydrous magnesium sulfate (magnetic stirring) and evaporated in vacuo to give the silyl enol ether as an oil which is co-evaporated with toluene (20 mL). The silyl enol ether was then dissolved in dry tetrahydrofuran (80 mL), cooled to −25° C. and treated with solid sodium bicarbonate (0.10 g) followed by N-bromosuccinimide (3.34 g, 18.8 mmol) added in small portions over 10 min. The reaction mixture was allowed to warm to 0° C. over 2 h and then quenched by addition of ethyl acetate (350 mL) and saturated sodium bicarbonate. The organic phase was washed with brine, dried over anhydrous magnesium sulfate and evaporated to give an orange oil. Chromatography on silica gel (4.5×12 cm, elution toluene-ethyl acetate 0-1%) gave 6.13 g of the title bromomethylketone as a yellow solid. Recrystallization from ethyl acetate (20 mL) and hexane (40 mL) gave pale yellow prisms (4.93 g, 76% yield). LC (Method A): 2.215 min. HRMS(ESI) calcd for $C_{17}H_{14}BrO$ $[M+H]^+$ m/z 345.0121, found 345.0109. $^1$H NMR (CDCl$_3$, 600 MHz) δ ppm: 4.39 (s, 2H), 5.20 (s, 2H), 6.75 (d, J=7.86 Hz, 1H), 7.17 (d, J=8.25 Hz, 1H), 7.34-7.46 (m, 6H), 7.78 (s, 1H).

191E. 6-(4-(Benzyloxy)benzofuran-2-yl)-2-bromoimidazo[2,1-b][1,3,4]thiadiazole

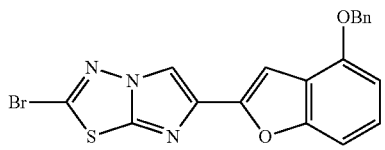 [SMILES: Brc1nn2cc(-c3cc4c(OCc5ccccc5)cccc4o3)nc2s1]

A mixture of 1-(4-(benzyloxy)benzofuran-2-yl)-2-bromoethanone (3.00 g, 8.69 mmol) and 5-bromo-1,3,4-thiadiazol-2-amine (1.80 g, 10.0 mmol) in isopropanol (100 mL) was heated is a pressure flask equipped with a magnetic stirring bar at 80° C. for 20 h (homogeneous after 20 min and then formation of a precipitate after 2 h). The cooled mixture is then transferred into five 20 mL microwave vials and then heated in a microwave apparatus to 150° C. for 30 min. Each vial was then diluted with dichloromethane (250 mL) washed with saturated sodium bicarbonate (25 mL) and brine (25 mL), dried over anhydrous magnesium sulfate. The fractions were combined and concentrated in vacuo. Chromatography of the orange-brown residual solid on silica gel (4×10 cm, slow elution with dichloromethane) gave 2.82 g of the title imidazothiadiazole contaminated with some 1-(4-(benzyloxy)benzofuran-2-yl)ethanone. The solid material was triturated with ethyl acetate (15 mL), filtered, washed with ethyl acetate (10 ml) and dried in vacuo to give 2.37 g (64% yield) of pure title imidazothiadiazole as an off white solid which is used as such for the next step. LC (Method A): 2.425 min. HRMS(ESI) calcd for $C_{19}H_{13}BrN_3O_2S$ [M+H]$^+$ m/z 425.9906, found 425.9893. $^1$H NMR (CDCl$_3$, 600 MHz) δ ppm: 5.21 (s, 2H), 6.72 (d, J=8.07 Hz, 1H), 7.13 (d, J=8.26 Hz, 1H), 7.18 (broad t, 1H), 7.25 (s, 1H), 7.32 (broad t, 1H), 7.38 (broad t, 2H), 7.47 (broad d, 2H), 8.09 (s, 1H).

191F. 6-(4-(Benzyloxy)benzofuran-2-yl)-2-methoxyimidazo[2,1-b][1,3,4]thiadiazole

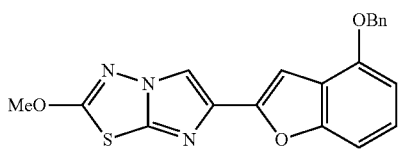 [SMILES: COc1nn2cc(-c3cc4c(OCc5ccccc5)cccc4o3)nc2s1]

A solution of 6-(4-(benzyloxy)benzofuran-2-yl)-2-bromoimidazo[2,1-b][1,3,4]thiadiazole (3.22 g, 7.55 mmol) in a mixture of dichloromethane (400 mL) and methanol (50 mL) was treated at 22° C. with 6.3 mL of a 25 wt. % solution of sodium methoxide in methanol (30.2 mmol) added in one portion. More methanol (45 mL) was added and the mixture was stirred for 40 min. The reaction mixture was quenched by the addition of 40 mL of 1 N hydrochloric acid followed by 10 ml of saturated sodium bicarbonate. The solvent was evaporated under reduced pressure and the residue was diluted with dichloromethane (400 mL), washed with brine, dried over anhydrous magnesium sulfate and evaporated in vacuo. Crystallization of the white solid residue from 1,2-dichloroethane (30 mL) gave 2.19 g of the title material as a white solid. Chromatography of the mother liquors on silica gel (3×10 cm, elution with 0-1% ethyl acetate-dichloromethane) gave another 0.46 g of product (total yield, 2.65 g, 93%). LC (Method A): 2.379 min. HRMS(ESI) calcd for $C_{20}H_{16}N_3O_3S$ [M+H]$^+$ m/z 378.0907, found 378.0911. $^1$H NMR (CDCl$_3$, 600 MHz) δ ppm: 4.18 (s, 3H), 5.21 (s, 2H), 6.71 (dd, J=7.4 Hz and J=0.95 Hz, 1H), 7.12-7.17 (m, 3H), 7.32 (broad t, 1H), 7.38 (broad t, 2H), 7.47 (broad d, 2H), 7.88 (s, 1H).

191G. 2-(2-Methoxyimidazo[2,1-b][1,3,4]thiadiazol-6-yl)benzofuran-4-ol

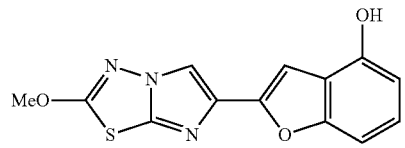 [SMILES: COc1nn2cc(-c3cc4c(O)cccc4o3)nc2s1]

A mixture of 6-(4-(benzyloxy)benzofuran-2-yl)-2-methoxyimidazo[2,1-b][1,3,4]thiadiazole (2.640 g, 6.99 mmol) and pentamethylbenzene (7.25 g, 48.9 mmol) in dichloromethane (400 mL) was cooled to -78° C. under a nitrogen atmosphere and then treated immediately with 18.2 mL (8.2 mmol) of a 1 M solution of boron trichloride in dichloromethane added dropwise over 3 min. The resulting mixture was stirred at -78° C. for 1 h. The reaction mixture was then quenched by the addition of a solution of sodium bicarbonate (10.6 g) in water (50 mL) added in one portion. The cooling bath was removed and the resulting mixture was stirred at room temperature for 1 h. The solid formed was filtered, washed successively with water (50 mL) and dichloromethane (25 mL). The filter cake was allowed to soak with anhydrous ethanol (10 ml) and then sucked dry. The white solid obtained was then dried under vacuum for a few days over phosphorous pentoxide until constant weight to give 1.459 g (72% yield) of title material. The combined filtrate and washings (organic and aqueous phases from the deprotection step) were diluted with dichloromethane (500 mL) and stirred in a warm water bath till the organic phase was clear with no apparent solid in suspension. The organic phase was collected, dried over anhydrous magnesium sulfate and rapidly filtered while still warm. The filtrate was evaporated and the residue (product and pentamethylbenzene) was triturated with toluene (20 mL). The solid was collected by filtration and washed with toluene (20 mL) to give, after drying in vacuo, 0.239 g (12% yield; 84% combined yield) of title material as a tan solid. LC (Method A): 1.908 min. HRMS(ESI) calcd for $C_{13}H_{10}N_3O_3S$ [M+H]$^+$ m/z 288.0437, found 288.0446. $^1$H NMR (DMSO-d$_6$, 600 MHz) δ ppm: 4.46 (s, 3H), 6.58 (d, J=7.8 Hz, 1H), 6.97 (d, J=8.15 Hz, 1H), 7.0-7.07 (m, 3H), 8.40 (s, 1H).

Example 191. 2-Methoxy-6-(4-((2-phenylthiazol-4-yl)methoxy)benzofuran-2-yl)imidazo[2,1-b][1,3,4]thiadiazole

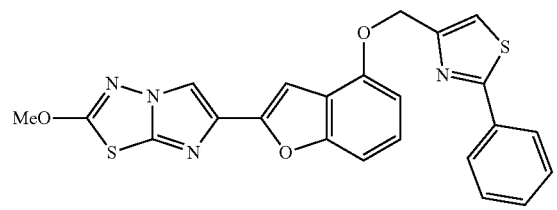 [SMILES: COc1nn2cc(-c3cc4c(OCc5csc(-c6ccccc6)n5)cccc4o3)nc2s1]

A mixture of 2-(2-methoxyimidazo[2,1-b][1,3,4]thiadiazol-6-yl)benzofuran-4-ol (0.100 g, 0.349 mmol), triphenylphosphine (0.165 g, 0.627 mmol) and (2-phenylthiazol-4-yl)methanol (Example 3B, 0.080 g, 0.418 mmol) in a 50 ml flask was maintained under vacuum for 10 min and then purged with nitrogen. Dry tetrahydrofuran (10 mL) was added and the resulting mixture was slightly warmed and maintained in an ultrasonic bath for 5 min. The cooled mixture (still heterogeneous) was treated at 22° C. with a solution of diisopropyl azodicarboxylate (0.113 g, 0.558 mmol) in tetrahydrofuran (2 mL) added dropwise over 1 h. The mixture was then stirred at 2° C. for 4 h. The clear reaction mixture was quenched by the addition of dichloromethane (100 mL) and saturated sodium bicarbonate (10 mL). The organic phase was washed with brine, dried over anhydrous magnesium sulfate and concentrated in vacuo. Chromatography of the residue on silica gel (2.5×12 cm, elution 0-3% ethyl acetate-dichloromethane) followed by crystallization of the desired fraction from ethyl acetate (8 mL) gave 0.028 g (24% yield) of the title material as a white solid. LC (Method A): 2.426 min. HRMS(ESI) calcd for $C_{23}H_{17}N_4O_3S_2$ [M+H]$^+$ m/z 461.0737, found 461.0926. H NMR (CDCl$_3$, 400 MHz) δ ppm: 4.22 (s, 3H), 5.45 (d, J=0.78 Hz, 2H), 6.80 (dd, J=7.04, 1.57 Hz, 1H), 7.15-7.21 (m, 2H), 7.22 (s, 1H), 7.38 (s, 1H), 7.42-7.51 (m, 3H), 7.92 (s, 1H), 7.95-8.03 (m, 2H).

Example 192

(S)-2-(1-Fluoroethyl)-6-(6-methoxy-4-((2-phenylthiazol-4-yl)methoxy)benzofuran-2-yl)imidazo[2,1-b][1,3,4]thiadiazole

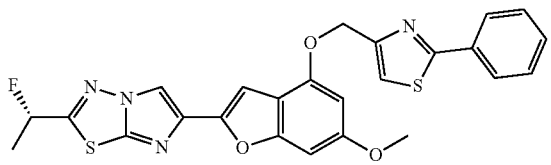 [SMILES: COc1cc(OCc2csc(-c3ccccc3)n2)c2cc(-c3cn4nc([C@H](C)F)sc4n3)oc2c1]

192A. (S)-5-(1-Fluoroethyl)-1,3,4-thiadiazol-2-amine

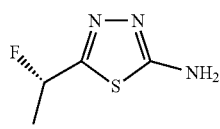

A 350 mL sealable pressure vessel was charged with thiosemicarbazide (11.17 g, 122.5 mmol) and dry dioxane (100 mL), and the mixture was cooled at 0° C. under an N$_2$ atmosphere. To this rapidly stirring mixture was slowly added a solution of (S)-2-fluoropropanoic acid (9.40 g, 102.1 mmol, from Fritz-Langhals, E., *Tetrahedron Asymmetry*, 981 (1994)) in dioxane (10 mL). To the resulting mixture was added POCl$_3$ (11.22 mL, 122.5 mmol) dropwise, then the cooling bath was removed and the thick white slurry was stirred at room temperature for 1 h. The vessel was then sealed and the mixture was heated at 90-95° C. (oil bath temperature) for 5 h. The cooled mixture was stirred at room temperature for 14 h and then the supernatant (two-phase mixture) was decanted and concentrated under reduced pressure. The lower phase was slowly poured into ice water (250 mL) and then the concentrate was also added. This mixture was rapidly stirred until it was essentially a homogeneous (turbid) solution, and then it was basified to pH 9-9.5 using 40% aqueous NaOH. The resulting slurry was filtered and the filter-cake was washed with water (Note: LC of this beige solid showed that it contained only a trace of the desired product, so it was not further investigated). The combined filtrate was then extracted with EtOAc (×3) and the organic phase was dried (Na$_2$SO$_4$) and evaporated to give a cream solid (10.58 g, 70%) which was the essentially pure product according to LC and LCMS. This material was used as such without further purification. An analytical sample was purified by flash chromatography [Isco/0-20% (MeOH—NH$_4$OH, 9:1)-DCM] to give a white solid. LC (Method B): 0.608 min. MS(ESI) calcd. for $C_4H_6FN_3S$ m/z: 147.03; found: 148.05 [M+H]$^+$. $^1$H NMR (600 MHz, DMSO-d$_6$) δ 7.38 (s, 2H), 5.82 (dq, J=6.4, 48.0 Hz, 1H), 1.65 (dd, J=6.4, 24.0 Hz, 3H). Chiral LC: S:R=95:5.

192B. (S)-6-(4-(Benzyloxy)-6-methoxybenzofuran-2-yl)-2-(1-fluoroethyl)imidazo[2,1-b][1,3,4]thiadiazole

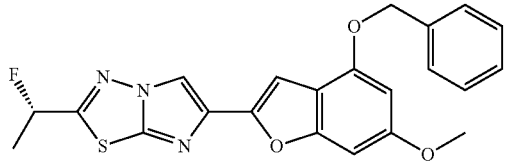 [SMILES: COc1cc(OCc2ccccc2)c2cc(-c3cn4nc([C@H](C)F)sc4n3)oc2c1]

In a 20 mL vial, 1-(4-(benzyloxy)-6-methoxybenzofuran-2-yl)-2-bromoethanone (Example 1E, 1.501 g, 4.000 mmol) and (S)-5-(1-fluoroethyl)-1,3,4-thiadiazol-2-amine (0.589 g, 4.000 mmol) were suspended in 2-propanol (20 mL) and heated at 80° C. for 16 h. The mixture was then heated in a microwave reactor at 150° C. for 30 min. The cooled mixture was evaporated to dryness and the obtained residue was taken up in CH$_2$Cl$_2$ (200 mL), washed (saturated aqueous NaHCO$_3$), dried (Na$_2$SO$_4$) and concentrated. The residue was purified on the ISCO (0-30% acetone-hexanes) to give the title compound (0.922 g, 54.4%) as a pale yellow solid. LC (Method B): 2.403 min. MS(ESI) calcd. for $C_{22}H_{19}FN_3O_3S$ [M+H]$^+$ m/z: 424.1131; found: 424.1146. $^1$H NMR (400 MHz, DMSO-d6) d ppm 8.61 (s, 1H) 7.51 (d, J=7.4 Hz, 2H) 7.42 (t, J=7.6 Hz, 2H) 7.35 (t, J=7.0 Hz, 1H) 7.08 (s, 1H) 6.83-6.85 (m, 1H) 6.54 (d, J=1.2 Hz, 1H) 6.16 (dq, J=47.1, 6.4 Hz, 1H) 5.26 (s, 2H) 3.80 (s, 3H) 1.79 (dd, J=24.5, 6.8 Hz, 3H).

192C. (S)-2-(2-(1-Fluoroethyl)imidazo[2,1-b][1,3,4]thiadiazol-6-yl)-6-methoxybenzofuran-4-ol

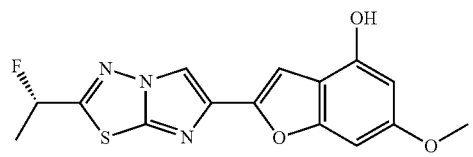 [SMILES: COc1cc(O)c2cc(-c3cn4nc([C@H](C)F)sc4n3)oc2c1]

A mixture of (S)-6-(4-(benzyloxy)-6-methoxybenzofuran-2-yl)-2-(1-fluoroethyl)imidazo[2,1-b][1,3,4]thiadiazole (0.152 g, 0.359 mmol) and pentamethylbenzene (0.374 g, 2.52 mmol) in dichloromethane (24 ml, 373 mmol) was cooled to −78° C. under nitrogen atmosphere and then treated immediately with boron trichloride 1.0M in dichloromethane (1 ml, 1.000 mmol) added dropwise over 3 min. The resulting mixture was stirred at −78° C. for 1 h. The reaction mixture was quenched by addition of a solution of sodium bicarbonate (0.71 g) in water (12 mL) added in one portion. The cooling bath was removed and the resulting mixture was stirred at room temperature for 1 h. The solid formed was filtered, washed successively with water (8 mL) and dichloromethane (8 mL). The filter cake was soaked with anh. ethanol and suck dried. The white solid obtained was dried under vacuum on $P_2O_5$ for 36 h. LC (Method B): 2.038 min. MS(ESI) calcd. for $C_{15}H_{13}FN_3O_3S$ [M+H]$^+$ m/z: 334.0656; found: 334.0680. $^1$H NMR (400 MHz, DMSO-$d_6$) δ ppm 10.06 (s, 1H) 8.56 (s, 1H) 7.09 (s, 1H) 6.67 (s, 1H) 6.26-6.28 (m, 1H) 6.16 (dq, J=46.9, 6.4 Hz, 1H) 3.76 (s, 3H) 1.80 (dd, J=24.7, 6.3 Hz, 3H).

Example 192. (S)-2-(1-Fluoroethyl)-6-(6-methoxy-4-((2-phenylthiazol-4-yl)methoxy)benzofuran-2-yl)imidazo[2,1-b][1,3,4]thiadiazole

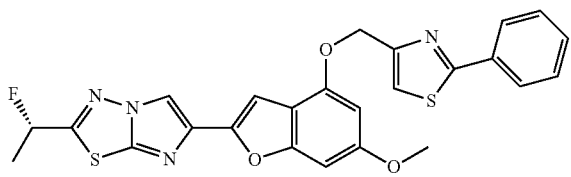 [SMILES: COc1cc(OCc2csc(-c3ccccc3)n2)c2cc(-c3cn4nc([C@H](C)F)sc4n3)oc2c1]

To a mixture of (S)-2-(2-(1-fluoroethyl)imidazo[2,1-b][1,3,4]thiadiazol-6-yl)-6-methoxybenzofuran-4-ol (0.050 g, 0.150 mmol), (2-phenylthiazol-4-yl)methanol (Example 3B, 0.086 g, 0.450 mmol) and triphenylphosphine (0.118 g, 0.450 mmol) under $N_2$ was added dry THF (3 mL). To the resulting light amber solution was added a solution of DIAD (0.087 mL, 0.450 mmol) in dry THF (2 mL) dropwise over 2 h to give light yellow-brown solution. After stirring at room temperature for an additional 30 min, LC showed that no starting material remained. The volatiles were then removed under reduced pressure to give an amber gum. Flash chromatography (Isco/0-20% ether-DCM) afforded the product as a nearly colorless gum. This gum was triturated with a minimum volume of MeOH and the resulting slurry was filtered and the filter-cake was washed with a minimum volume of MeOH and then dried in vacuo to give the title material (0.048 g, 63.2%) as a solid which was further lyophilized from MeCN—H$_2$O to give a cream solid. LC (Method A): 2.453 min. HRMS(ESI) calcd for $C_{25}H_{20}FN_4O_3S_2$ [M+H]$^+$ m/z 507.096, found 506.098. $^1$H NMR (DMSO-$d_6$, 400 MHz) δ ppm: 8.67 (s, 1H), 8.05-8.02 (m, 2H), 7.96 (s, 1H), 7.60-7.56 (m, 3H), 7.20 (d, J=0.8 Hz, 1H), 6.93 (dd, J=0.8, 2.0 Hz, 1H), 6.73 (d, J=1.6 Hz, 1H), 6.23 (dq, J=6.7, 47.0 Hz, 1H), 5.45 (s, 2H), 3.89 (s, 3H), 1.86 (d, J=6.7, 24.6 Hz, 3H).

Example 193

(S)-4-(4-(((2-(2-(1-Fluoroethyl)imidazo[2,1-b][1,3,4]thiadiazol-6-yl)-6-methoxybenzofuran-4-yl)oxy)methyl)thiazol-2-yl)morpholine

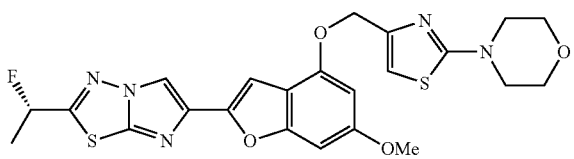 [SMILES: COc1cc(OCc2csc(N3CCOCC3)n2)c2cc(-c3cn4nc([C@H](C)F)sc4n3)oc2c1]

A solution of (S)-2-(2-(1-fluoroethyl)imidazo[2,1-b][1,3,4]thiadiazol-6-yl)-6-methoxybenzofuran-4-ol (Example 192C, 0.050 g, 0.150 mmol) in DMF (2 mL) was stirred under $N_2$ and then 4-(4-(bromomethyl)thiazol-2-yl)morpholine (0.047 g, 0.180 mmol) was added, followed by powdered potassium carbonate (0.062 g, 0.450 mmol), and the mixture was stirred at room temperature for 4 h. The mixture was then diluted with saturated aqueous NH$_4$Cl and extracted with DCM (×2). The organic extract was washed (brine), dried (Na$_2$SO$_4$) and evaporated to give a light amber gum. Flash chromatography (Isco/0-100% EtOAc-hexane) afforded (S)-4-(4-(((2-(2-(1-fluoroethyl)imidazo[2,1-b][1,3,4]thiadiazol-6-yl)-6-methoxybenzofuran-4-yl)oxy)methyl)thiazol-2-yl)morpholine (0.055 g, 71.1%) as a colorless gum, which was lyophilized from MeCN-water as a cream solid. LC (Method A): 2.271 min. HRMS(ESI): calcd for $C_{23}H_{23}FN_5O_4S_2$ [M+H]$^+$ m/z 516.118; found 516.121. $^1$H NMR (400 MHz, DMSO-$d_6$): δ 8.54 (s, 1H), 7.02 (s, 1H), 6.92 (s, 1H), 6.77 (s, 1H), 6.52 (d, J=1.96 Hz, 1H), 6.10 (dq, J=6.26, 46.95 Hz, 1H), 5.01 (s, 2H), 3.74 (s, 3H), 3.64 (t, J=4.89 Hz, 4H), 3.31 (t, J=4.89 Hz, 4H), 1.73 (dd, J=6.26, 24.65 Hz, 3H).

Example 194

(S)-4-(4-(((2-(2-(1-Fluoroethyl)imidazo[2,1-b][1,3,4]thiadiazol-6-yl)-6-methoxybenzofuran-4-yl)oxy)methyl)thiazol-2-yl)-N,N-dimethylbenzamide

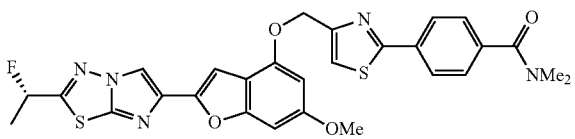 [SMILES: COc1cc(OCc2csc(-c3ccc(C(=O)N(C)C)cc3)n2)c2cc(-c3cn4nc([C@H](C)F)sc4n3)oc2c1]

To a flame-dried flask was added (S)-2-(2-(1-fluoroethyl)imidazo[2,1-b][1,3,4]thiadiazol-6-yl)-6-methoxybenzofuran-4-ol (Example 192C, 0.050 g, 0.150 mmol) and 4-(4-(hydroxymethyl)thiazol-2-yl)-N,N-dimethylbenzamide (Example 36B, 0.047 g, 0.180 mmol), then the flask was flushed with $N_2$ and dry THF (3 mL) was added. To the resulting suspension was added tri-n-butylphosphine (0.097 mL, 0.375 mmol) and then a solution of 1,1'-(azodicarbonyl)dipiperidine (0.096 g, 0.375 mmol) in dry THF (2 mL) was added dropwise (via a syringe pump) over 30 min. The resulting mixture was stirred at room temperature for another 15 min and then the mixture was diluted with EtOAc, washed (saturated aqueous NaHCO$_3$, H$_2$O, brine), dried (Na$_2$SO$_4$) and evaporated to give a yellow semi-solid.

Flash chromatography (Isco/0-100% EtOAc-DCM) afforded a colorless gum which was triturated with MeCN. The resulting slurry was filtered and the filter-cake washed with MeCN and then dried in vacuo to give a pale yellow solid which was lyophilized from MeCN-water to give (S)-4-(4-(((2-(2-(1-fluoroethyl)imidazo[2,1-b][1,3,4]thiadiazol-6-yl)-6-methoxybenzofuran-4-yl)oxy)methyl)thiazol-2-yl)-N,N-dimethylbenzamide (0.066 g, 76%) as a pale yellow solid. LC (Method A): 2.345 min. HRMS(ESI): calcd for $C_{28}H_{25}FN_5O_4S_2$ [M+H]$^+$ m/z 578.133; found 578.133. $^1$H NMR (400 MHz, DMSO-d$_6$): δ 8.54 (s, 1H), 7.96 (d, J=8.61 Hz, 2H), 7.48 (d, J=8.61 Hz, 2H), 7.07 (s, 1H), 6.80 (s, 1H), 6.60 (d, J=1.96 Hz, 1H), 6.10 (dq, J=6.65, 46.95 Hz, 1H), 5.33 (s, 2H), 3.76 (s, 3H), 2.94 (br s, 3H), 2.87 (br s, 3H), 1.73 (dd, J=6.65, 24.65 Hz, 3H).

Example 195

(S)-6-(6-Fluoro-4-((2-phenylthiazol-4-yl)methoxy)benzofuran-2-yl)-2-(1-fluoroethyl)imidazo[2,1-b][1,3,4]thiadiazole

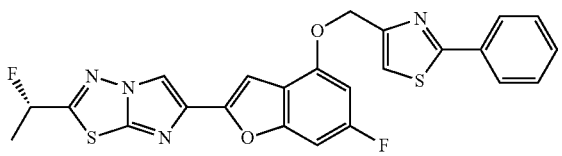 [SMILES: C[C@H](F)c1nn2cc(-c3cc4c(OCc5csc(-c6ccccc6)n5)cc(F)cc4o3)nc2s1]

A solution of 2-bromo-1-(6-fluoro-4-((2-phenylthiazol-4-yl)methoxy)benzofuran-2-yl)ethanone (Example 179E, 0.020 g, 0.045 mmol) and (S)-5-(1-fluoroethyl)-1,3,4-thiadiazol-2-amine (Example 192A, 0.008 g, 0.052 mmol) in propan-2-ol (2 mL) was heated at 70° C. for 16 h. The cooled reaction mixture was then partitioned between dichloromethane and saturated aqueous sodium bicarbonate. The organic phase was separated, washed with brine, dried over anhydrous magnesium sulfate and concentrated in vacuo. The residue obtained was chromatographed on silica gel (ISCO, elution gradient of ethyl acetate in dichloromethane) to give the title compound (0.015 g, 68%) as a white solid. LC (Method A): 2.493 min. HRMS(ESI) calcd for $C_{24}H_{16}F_2N_4O_2S_2$ [M+H]$^+$ m/z: 494.0761; found 495.0776. $^1$H NMR (CDCl$_3$, 400 MHz) δ ppm: 8.07 (s, 1H), 7.93-8.02 (m, 2H), 7.42-7.51 (m, 3H), 7.38 (s, 1H), 7.25 (s, 1H), 6.87-6.94 (m, 1H), 6.64 (dd, J=11.35, 1.96 Hz, 1H), 5.65-6.04 (m, 1H), 5.41 (s, 2H), 1.80-1.95 (m, 3H).

Example 196

(S)-4-(4-(((2-(2-(1-Fluoroethyl)imidazo[2,1-b][1,3,4]thiadiazol-6-yl)-6-methoxybenzofuran-4-yl)oxy)methyl)thiazol-2-yl)tetrahydro-2H-pyran-4-ol

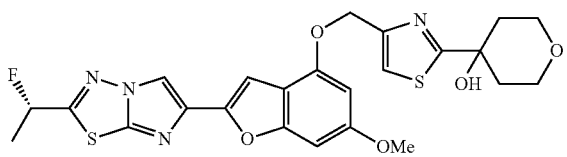 [SMILES: COc1cc(OCc2csc(C3(O)CCOCC3)n2)c2cc(-c3cn4nc([C@H](C)F)sc4n3)oc2c1]

To a flame-dried flask was added (S)-2-(2-(1-fluoroethyl)imidazo[2,1-b][1,3,4]thiadiazol-6-yl)-6-methoxybenzofuran-4-ol (Example 192C, 0.040 g, 0.120 mmol) and 4-(4-(hydroxymethyl)thiazol-2-yl)tetrahydro-2H-pyran-4-ol (Example 118B, 0.032 g, 0.150 mmol), then the flask was flushed with N$_2$ and dry THF (2 mL) was added. To the resulting suspension was added tri-n-butylphosphine (0.078 mL, 0.300 mmol) and then a solution of 1,1'-(azodicarbonyl)dipiperidine (0.076 g, 0.300 mmol) in dry THF (2 mL) was added dropwise (via syringe pump) over 30 min. The resulting mixture was stirred at room temperature for 2 h, at which time more tri-n-butylphosphine (0.078 mL, 0.300 mmol) and 1,1'-(azodicarbonyl)dipiperidine (0.076 g, 0.300 mmol) were added and stirring was continued for 16 h. The mixture was then diluted with EtOAc, washed (saturated aqueous NaHCO$_3$, H$_2$O, brine), dried (Na$_2$SO$_4$) and evaporated to give a golden-yellow gum. Flash chromatography (Isco/0-100% EtOAc-DCM) afforded the title compound (0.047 g, 73.8%) as a colorless gum which was lyophilized from MeCN-water as an off-white solid. LC (Method A): 2.236 min. HRMS(ESI): calcd for $C_{24}H_{24}FN_4O_5S_2$ [M+H]$^+$ m/z 531.117; found 531.120. $^1$H NMR (400 MHz, DMSO-d$_6$): δ 8.54 (s, 1H), 7.64 (s, 1H), 7.02 (s, 1H), 6.78 (s, 1H), 6.57 (d, J=1.96 Hz, 1H), 6.11 (dq, J=6.65, 46.95 Hz, 1H), 6.08 (s, 1H), 5.21 (s, 2H), 3.75 (s, 3H), 3.67 (m, 4H), 2.05 (ddd, J=5.48, 11.35, 13.69 Hz, 2H), 1.73 (dd, J=6.65, 25.04 Hz, 3H), 1.61 (br d, J=12.91 Hz, 3H).

Example 197

(S)-2-(1-Fluoroethyl)-6-(4-((2-(4-fluorotetrahydro-2H-pyran-4-yl)thiazol-4-yl)methoxy)-6-methoxybenzofuran-2-yl)imidazo[2,1-b][1,3,4]thiadiazole

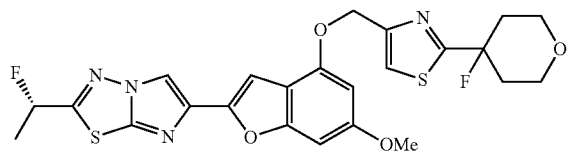 [SMILES: COc1cc(OCc2csc(C3(F)CCOCC3)n2)c2cc(-c3cn4nc([C@H](C)F)sc4n3)oc2c1]

To a solution of 4-(bromomethyl)-2-(4-fluorotetrahydro-2H-pyran-4-yl)thiazole (Example 119C, 0.016 g, 0.057 mmol) in DMF (1.5 mL) was added (S)-2-(2-(1-fluoroethyl)imidazo[2,1-b][1,3,4]thiadiazol-6-yl)-6-methoxybenzofuran-4-ol (Example 192C, 0.017 g, 0.052 mmol), followed by freshly powdered potassium carbonate (0.022 g, 0.156 mmol). The mixture was stirred in a sealed vial at room temperature for 2 h and then it was diluted with saturated aqueous NH$_4$Cl and the resulting mixture was filtered and the filter-cake was washed with water. The wet, gummy residue was taken up in DCM and the solution was washed (saturated aqueous NaHCO$_3$), dried (Na$_2$SO$_4$) and evaporated to give a yellow gum. Flash chromatography (Isco/0-40% EtOAc-DCM) afforded the slightly impure product as a pale yellow gum. This material was repurified by preparative HPLC (Method A) to give pure (S)-2-(1-fluoroethyl)-6-(4-((2-(4-fluorotetrahydro-2H-pyran-4-yl)thiazol-4-yl)methoxy)-6-methoxybenzofuran-2-yl)imidazo[2,1-b][1,3,4]thiadiazole (0.020 g, 72.3%) as a solid. LC (Method A): 2.400 min. HRMS(ESI): calcd for $C_{24}H_{23}F_2N_4O_4S_2$ [M+H]$^+$ m/z 533.113; found 533.115. $^1$H NMR (400 MHz, DMSO-d$_6$): δ 8.57 (s, 1H), 7.91 (s, 1H), 7.07 (s, 1H), 6.83 (m, 1H), 6.61 (d, J=1.57 Hz, 1H), 6.13 (dq, J=6.65, 46.56 Hz, 1H), 5.30 (s, 2H), 3.81 (m, 2H), 3.79 (s, 3H), 3.67 (dt, J=1.57, 10.96 Hz, 2H), 2.33-2.16 (m, 2H), 2.05 (m, 2H), 1.73 (dd, J=6.65, 24.65 Hz, 3H).

Example 198

4-(4-(((2-(2-((S)-1-Fluoroethyl)imidazo[2,1-b][1,3,4]thiadiazol-6-yl)-6-methoxybenzofuran-4-yl)oxy)methyl)thiazol-2-yl)-2,6-dimethyltetrahydro-2H-pyran-4-ol

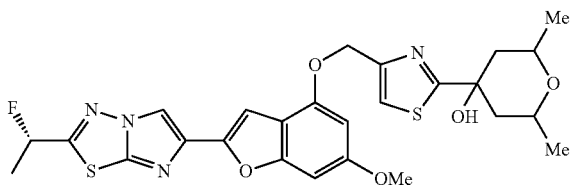 [SMILES: COc1cc(OCc2csc(C3(O)CC(C)OC(C)C3)n2)c2cc(-c3cn4nc([C@H](C)F)sc4n3)oc2c1]

To a flame-dried flask was added (S)-2-(2-(1-fluoroethyl)imidazo[2,1-b][1,3,4]thiadiazol-6-yl)-6-methoxybenzofuran-4-ol (Example 192C, 0.630 g, 1.890 mmol) and 4-(4-(hydroxymethyl)thiazol-2-yl)-2,6-dimethyltetrahydro-2H-pyran-4-ol (Example 121B, 0.552 g, 2.268 mmol), then the flask was flushed with $N_2$ and dry THF (20 mL) was added. To the resulting suspension was added tri-n-butylphosphine (1.227 mL, 4.72 mmol) and then a solution of 1,1'-(azodicarbonyl)dipiperidine (1.204 g, 4.72 mmol) in dry THF (10 mL) was added dropwise (via syringe pump) over 30 min. The resulting mixture was stirred at room temperature for another 2 h and then it was diluted with EtOAc, washed (saturated aqueous $NaHCO_3$, $H_2O$, brine), dried ($Na_2SO_4$) and evaporated to give a yellow semi-solid. Flash chromatography (Isco/0-100% EtOAc-DCM) afforded the product as a solid. This solid was triturated with MeCN and the resulting slurry was filtered and the filter-cake washed with MeCN and then dried in vacuo to give 4-(4-(((2-(2-((S)-1-fluoroethyl)imidazo[2,1-b][1,3,4]thiadiazol-6-yl)-6-methoxybenzofuran-4-yl)oxy)-methyl)thiazol-2-yl)-2,6-dimethyltetrahydro-2H-pyran-4-ol (0.823 g, 78%) as an off-white solid. LC (Method A): 2.324 min. HRMS(ESI): calcd for $C_{26}H_{28}FN_4O_5S_2$ $[M+H]^+$ m/z 559.149; found 559.151. $^1$H NMR (400 MHz, DMSO-$d_6$): δ 8.54 (s, 1H), 7.70 (s, 1H), 7.01 (s, 1H), 6.79 (s, 1H), 6.62 (d, J=1.57 Hz, 1H), 6.11 (dq, J=6.65, 46.95 Hz, 1H), 6.03 (s, 1H), 5.25 (s, 2H), 3.77 (m, 2H), 3.76 (s, 3H), 2.01 (d, J=12.91 Hz, 2H), 1.74 (dd, J=6.65, 25.04 Hz, 3H), 1.39 (t, J=12.91 Hz, 2H), 1.01 (d, J=6.26 Hz, 6H).

Example 199

6-(4-((2-(4-Fluoro-2,6-dimethyltetrahydro-2H-pyran-4-yl)thiazol-4-yl)methoxy)-6-methoxybenzofuran-2-yl)-2-((S)-1-fluoroethyl)imidazo[2,1-b][1,3,4]thiadiazole

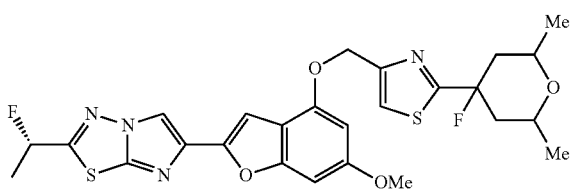 [SMILES: COc1cc(OCc2csc(C3(F)CC(C)OC(C)C3)n2)c2cc(-c3cn4nc([C@H](C)F)sc4n3)oc2c1]

To an ice-cold suspension of 4-(4-(((2-(2-((S)-1-fluoroethyl)imidazo[2,1-b][1,3,4]thia-diazol-6-yl)-6-methoxybenzofuran-4-yl)oxy)methyl)thiazol-2-yl)-2,6-dimethyltetrahydro-2H-pyran-4-ol (Example 198, 0.021 g, 0.038 mmol) in DCM (3 mL) under $N_2$ was added DAST (0.012 mL, 0.094 mmol) dropwise and the resulting mixture was stirred at 0° C. for 20 min. Another aliquot of DAST (0.007 mL, 0.053 mmol) was added, the cooling bath was removed and the resulting pale yellow solution was stirred at room temperature for 16 h. The reaction mixture was then re-cooled at 0° C. and quenched by the dropwise addition of saturated aqueous $NaHCO_3$ (3 mL). The mixture was vigorously stirred at 0° C. for 5 min and then the cooling bath was removed and stirring was continued until no more gas evolution was observed. The organic phase was subsequently separated and applied directly to a silica gel pre-column. Flash chromatography (Isco/0-100% EtOAc-hexane) afforded 6-(4-((2-(4-fluoro-2,6-dimethyltetrahydro-2H-pyran-4-yl)thiazol-4-yl)methoxy)-6-methoxybenzofuran-2-yl)-2-((S)-1-fluoroethyl)imidazo-[2,1-b][1,3,4]thiadiazole (0.014 g, 66.4%) as a colorless gum which was lyophilized from MeCN-water to give a white solid. NMR indicated that this was a 3:2 mixture of isomers. LC (Method A): 2.487 min. HRMS(ESI): calcd for $C_{26}H_{27}F_2N_4O_4S_2$ $[M+H]^+$ m/z 561.144; found 561.146. $^1$H NMR (400 MHz, DMSO-$d_6$): δ 8.54 (s, 0.4H), 8.53 (s, 0.6H), 7.94 (s, 0.6H), 7.85 (s, 0.4H), 7.03 (s, 0.4H), 7.02 (s, 0.6H), 6.79 (m, 1H), 6.59 (d, J=1.57 Hz, 0.6H), 6.57 (d, J=1.96 Hz, 0.4H), 6.10 (dq, J=6.65, 46.56 Hz, 1H), 5.30 (s, 1.2H), 5.25 (s, 0.8H), 3.76 (m, 0.8H), 3.75 (s, 1.2H), 3.74 (s, 1.8H), 3.53 (m, 1.2H), 2.38 (m, 1H), 2.08 (m, 1H), 1.83-1.61 (m, 2H), 1.73 (dd, J=6.65, 25.04 Hz, 3H), 1.10 (d, J=6.26 Hz, 2.4H), 1.01 (d, J=6.26 Hz, 3.6H).

Example 200

(S)-4-(4-(((2-(2-(1-Fluoroethyl)imidazo[2,1-b][1,3,4]thiadiazol-6-yl)-6-methoxybenzofuran-4-yl)oxy)methyl)-5-methylthiazol-2-yl)tetrahydro-2H-pyran-4-ol

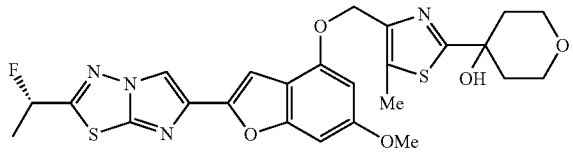

To a flame-dried flask was added (S)-2-(2-(1-fluoroethyl)imidazo[2,1-b][1,3,4]thiadiazol-6-yl)-6-methoxybenzofuran-4-ol (Example 192C, 0.050 g, 0.150 mmol) and 4-(4-(hydroxymethyl)-5-methylthiazol-2-yl)tetrahydro-2H-pyran-4-ol (Example 124D, 0.038 g, 0.165 mmol), then the flask was flushed with $N_2$ and dry THF (3 mL) was added. To the resulting suspension was added tri-n-butylphosphine (0.097 mL, 0.375 mmol) and then a solution of 1,1'-(azodicarbonyl)dipiperidine (0.096 g, 0.375 mmol) in dry THF (2 mL) was added dropwise (via syringe pump) over 30 min. The resulting mixture was stirred at room temperature for another 15 min and then the mixture was diluted with EtOAc, washed (saturated aqueous $NaHCO_3$, $H_2O$, brine), dried ($Na_2SO_4$) and evaporated to give a pale yellow waxy solid. Flash chromatography (Isco/0-100% EtOAc-DCM) afforded the title compound (0.061 g, 74.7%) as a colorless gum which was lyophilized from MeCN-water as a solid.

LC (Method A): 2.256 min. HRMS(ESI): calcd for $C_{25}H_{26}FN_4O_5S_2$ [M+H]$^1$ m/z 545.133; found 545.132. $^1$H NMR (400 MHz, DMSO-d$_6$): δ 8.54 (s, 1H), 6.94 (s, 1H), 6.78 (m, 1H), 6.61 (d, J=1.96 Hz, 1H), 6.09 (dq, J=6.65, 46.95 Hz, 1H), 5.99 (br s, 1H), 5.14 (s, 2H), 3.75 (s, 3H), 3.65 (m, 4H), 2.40 (s, 3H), 2.02 (m, 2H), 1.72 (dd, J=6.65, 24.65 Hz, 3H), 1.58 (d, J=11.74 Hz, 3H).

Example 201

6-Methoxy-2-(2-(methylthio)imidazo[2,1-b][1,3,4]thiadiazol-6-yl)-4-((2-phenylthiazol-4-yl)methoxy)benzo[d]oxazole

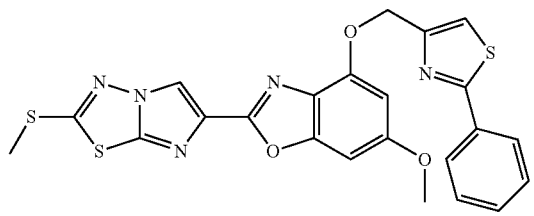 [SMILES: COc1cc(OCc2csc(-c3ccccc3)n2)c2nc(-c3cn4nc(SC)sc4n3)oc2c1]

201A. Ethyl 2-(methylthio)imidazo[2,1-b][1,3,4]thiadiazole-6-carboxylate

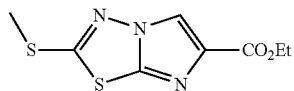

A mixture of 2-amino-5-methylthio-1,3,4-thiadiazole (25.0 g, 0.17 mol), ethyl 3-bromopyruvate (23.7 mL, 0.189 mol) and ethanol (125 mL) in a 350 mL sealable vessel was heated at 150° C. (oil bath temperature) for 20 min. The cooled mixture was then concentrated to dryness and the residue was partitioned with ethyl acetate-saturated aqueous NaHCO$_3$. The organic phase was separated, washed (brine), dried (MgSO$_4$), filtered and concentrated to dryness. The obtained residue was taken up in a minimum volume of dichloromethane and the resulting slurry was filtered and the filter-cake was washed with a little dichloromethane. The solid residue was dried in vacuo to give recovered amino-5-methylthio-1,3,4-thiadiazole (3.7 g, 15%). The obtained filtrate was subsequently evaporated and the residue was crystallized from a minimum volume of hot ethanol to give the title compound as a beige crystalline solid (10.8 g, 26%). LC (Method B): 1.267 min. $^1$H NMR (600 MHz, DMSO-d$_6$) δ ppm: 8.76 (s, 1H), 4.27 (q, J=7.2 Hz, 2H), 2.78 (s, 3H), 1.28 (t, J=7.2 Hz, 3H).

201B. 2-(Methylthio)imidazo[2,1-b][1,3,4]thiadiazole-6-carboxylic Acid

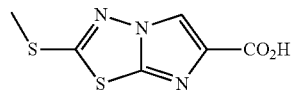

In a sealable microwave vial, a solution of ethyl 2-(methylthio)imidazo[2,1-b][1,3,4]thiadiazole-6-carboxylate (1.22 g, 5.0 mmol) in glacial acetic acid (15 mL) was treated with 48% HBr (1.42 mL, 12.5 mmol) dropwise. The vial was then sealed and the resulting slurry was heated at 150° C. (microwave) for 1.5 h. The cooled mixture was then filtered and the filter-cake was washed with a minimum volume of glacial acetic acid and then DCM. After drying in vacuo, this afforded the essentially pure HBr salt of title compound (1.37 g, 92%) as a white solid. This material was used as such in the next step. LC (Method A): 1.313 min. LCMS (APCI): calcd. for $C_6H_6N_3O_2S_2$ [M+H]$^1$ m/z 215.99; found 216.00. $^1$H NMR (600 MHz, DMSO-d$_6$) δ ppm: 8.63 (s, 1H), 2.75 (s, 3H).

201C. 2-(Methylthio)imidazo[2,1-b][1,3,4]thiadiazole-6-carbonyl chloride

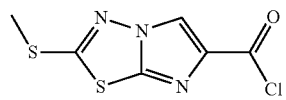

To a stirred suspension of 2-(methylthio)imidazo[2,1-b][1,3,4]thiadiazole-6-carboxylic acid (15.0 g, 0.070 mol) in DCM (350 mL) was added oxalyl chloride (29.5 mL, 0.348 mol) followed by DMF (1 drop). Gas evolution was observed and the reaction mixture was stirred at room temperature for 3.5 h. The suspension was then concentrated to dryness to give the title compound as a light-yellow solid (quantitative yield assumed) which was used as such in the next step. LC (Method A): 1.686 min; 1H NMR (600 MHz, DMSO-d$_6$) δ ppm 8.68 (s, 1H) 2.78 (s, 3H).

201D. N-(2,6-Dihydroxy-4-methoxyphenyl)-2-(methylthio)imidazo[2,1-b][1,3,4]thiadiazole-6-carboxamide

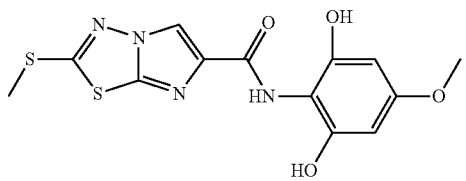

To an ice-cold suspension of 2-(methylthio)imidazo[2,1-b][1,3,4]thiadiazole-6-carbonyl chloride (0.378 g, 1.62 mmol) and 2-amino-5-methoxybenzene-1,3-diol (0.251 g, 1.62 mmol) in DMF (10 mL) was added triethylamine (1.13 mL, 8.10 mmol). The reaction mixture was stirred for 5 min and then the cooling bath was removed and stirring was continued at room temperature for 16 h. The resulting mixture was evaporated to dryness and the residue was partitioned with DCM-brine-water (2:1:1). The organic phase was separated, dried (MgSO$_4$) and evaporated to dryness. The residue was triturated with MeOH and the product was filtered off and dried in vacuo to give the title compound as a beige solid (0.100 g, 0.284 mmol, 17.5%). LC (Method E): 1.828 min. HRMS(ESI): calcd for $C_{13}H_{13}N_4O_4S_2$ [M+H]$^+$ m/z 353.0378, found 353.0603. $^1$H NMR (DMSO-d$_6$, 400 MHz) δ ppm: 10.26 (m, 2H), 9.26 (d, J=9.4 Hz, 1H), 8.76 (s, 1H), 6.01 (d, J=2.3 Hz, 2H), 3.66 (s, 3H), 2.81 (s, 3H).

201E. 6-Methoxy-2-(2-(methylthio)imidazo[2,1-b]
[1,3,4]thiadiazol-6-yl)benzo[d]oxazol-4-ol

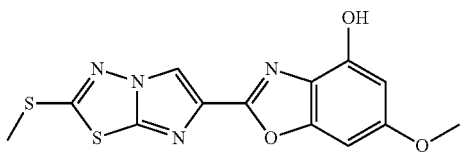

A microwaveable vessel was charged with N-(2,6-dihydroxy-4-methoxyphenyl)-2-(methylthio)imidazo[2,1-b][1,3,4]thiadiazole-6-carboxamide (0.086 g, 0.244 mmol), TFA (1 mL) and acetic acid (1 mL). The vessel was then sealed and heated in a microwave at 200° C. for 10 min. The reaction mixture was allowed to stand at room temperature for 16 h and the resulting brown crystalline solid was filtered off and dried in vacuo to give the title compound (0.044 g, 0.098 mmol, 40%). LC (Method E): 1.961 min. HRMS (ESI): calcd for $C_{13}H_{11}N_4O_3S_2$ [M+H]$^+$ m/z 335.0273, found 335.0505. $^1$H NMR (DMSO-$d_6$, 400 MHz) δ ppm: 8.85 (s, 1H), 6.79 (d, J=1.8 Hz, 1H), 6.36 (d, J=1.8 Hz, 1H), 3.77 (s, 3H), 2.81 (s, 3H).

Example 201. 6-Methoxy-2-(2-(methylthio)imidazo
[2,1-b][1,3,4]thiadiazol-6-yl)-4-((2-phenylthiazol-4-
yl)methoxy)benzo[d]oxazole

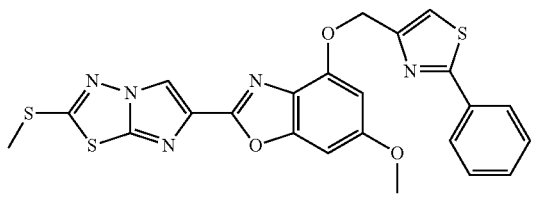 [SMILES: COc1cc(OCc2csc(-c3ccccc3)n2)c2nc(-c3cn4nc(SC)sc4n3)oc2c1]

A suspension of 6-methoxy-2-(2-(methylthio)imidazo[2,1-b][1,3,4]thiadiazol-6-yl)benzo[d]oxazol-4-ol (0.080 g, 0.239 mmol) and 2-(bromomethyl)-4-phenylthiazole (0.122 g, 0.479 mmol) in N,N-dimethylformamide (3 mL) was maintained under vacuum (10 mbar) for 5 min, then the flask was flushed with nitrogen and freshly powdered anhydrous potassium carbonate (0.105 g, 0.756 mmol) was added all at once. The resulting mixture was stirred at room temperature for 16 h, then the reaction was quenched with 1N HCl (2 mL) and finally it was partitioned between dichloromethane (150 mL) and saturated aqueous sodium bicarbonate (20 mL). The organic phase was separated, washed with brine, dried over anhydrous magnesium sulfate and concentrated in vacuo. The residue was triturated with acetonitrile and the desired product was filtered off and dried in vacuo to give 6-methoxy-2-(2-(methylthio)imidazo[2,1-b][1,3,4]thiadiazol-6-yl)-4-((2-phenylthiazol-4-yl)methoxy)benzo[d]oxazole (0.068 g, 0.134 mmol, 56.0%) as a white solid. LC (Method F): 2.653 min. HRMS(ESI): calcd for $C_{23}H_{18}N_5O_3S_3$ [M+H]$^+$ m/z 508.0572, found 508.0607. $^1$H NMR (DMSO-$d_6$, 400 MHz) δ ppm: 8.88 (s, 1H), 7.94 (m, 2H), 7.85 (s, 1H), 7.51-7.46 (m, 3H), 6.96 (d, J=2.0 Hz, 1H), 6.72 (d, J=2.0 Hz, 1H), 5.44 (s, 2H), 3.80 (s, 3H), 2.77 (s, 3H).

Example 202

2-(2-(1,1-Difluoroethyl)imidazo[2,1-b][1,3,4]thiadi-
azol-6-yl)-4-((2-phenylthiazol-4-yl)methoxy)furo[3,
2-c]pyridine

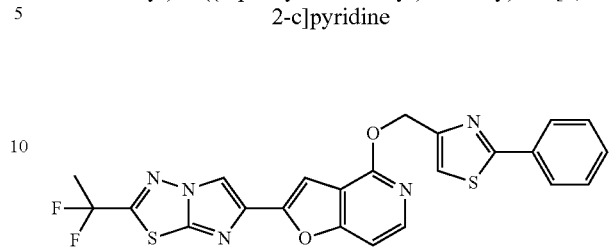

202A. 4-(Benzyloxy)furo[3,2-c]pyridine

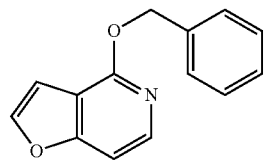 [SMILES: c1ccc(COc2nccc3occc23)cc1]

A microwave vial was charged with furo[3,2-c]pyridin-4(5H)-one (0.676 g, 5.0 mmol, prepared as described in EP 2100895) and benzyl bromide (1.189 mL, 10.0 mmol) and then n-hexane (20 mL) and silver carbonate (50% on CELITE®, 3.31 g, 6.00 mmol) were added. The resulting reaction mixture was then heated at 125° C. in the microwave reactor for 10 min. The crude reaction mixture was filtered, the filter-cake was washed with ethyl acetate and the filtrate was concentrated under reduced pressure. The crude residue obtained was purified by column chromatography (Isco/25 g cartridge) eluting with a gradient of ethyl acetate in hexanes (from 0 to 5%) to give the title compound (0.766 g, 68%). LC (Method A): 2.127 min. LCMS (APCI): calcd for $C_{14}H_{12}NO_2$ [M+H]$^+$ m/z 226.09, found 226.0. $^1$H NMR (CDCl$_3$, 400 MHz) δ ppm: 5.54 (s, 2H), 6.86-6.88 (m, 1H), 7.11-7.13 (m, 1H), 7.30-7.42 (m, 3H), 7.48-7.53 (m, 2H), 7.56 (d, J=2.4 Hz, 1H), 8.02 (d, J=6.3 Hz, 1H).

202B. 1-(4-(Benzyloxy)furo[3,2-c]pyridin-2-yl)etha-
none

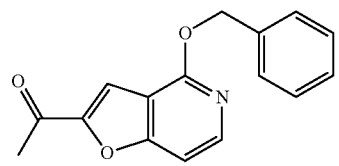 [SMILES: CC(=O)c1cc2c(OCc3ccccc3)nccc2o1]

A solution of 4-(benzyloxy)furo[3,2-c]pyridine (1.532 g, 6.80 mmol) in dry THF (40 mL) was cooled at −78° C. under nitrogen and n-butyllithium (2.5 M in hexanes, 3.40 mL, 8.50 mmol) was added dropwise. After the addition was complete the reaction mixture was stirred for 20 min before N,N-dimethylacetamide (1.265 mL, 13.60 mmol) was added. The reaction mixture was stirred for 1 h at −78° C. and then it was warmed to −30° C. over 4 h. The reaction mixture was subsequently poured onto crushed ice and the mixture was extracted with ethyl acetate (×2). The combined organic extracts were washed with brine, dried over MgSO$_4$, filtered and concentrated. The crude product was purified by column chromatography (Isco, 40 g cartridge) eluting with a gradient of ethyl acetate in hexanes (from 0 to 25%) to give the title compound (1.15 g, 63%). LC (Method A): 2.129 min. LCMS (APCI): calcd for $C_{16}H_{14}NO_3$ [M+H]$^+$ m/z 268.10, found 268.1. $^1$H NMR (CDCl$_3$, 400 MHz) δ ppm: 2.59 (s, 3H), 5.56 (s, 2H), 7.16 (dd, J=1.2, 6.3 Hz, 1H), 7.33-7.43 (m, 3H), 7.48-7.52 (m, 2H), 7.58 (d, J=0.8 Hz, 1H), 8.16 (d, J=6.3 Hz, 1H).

202C. 1-(4-(Benzyloxy)furo[3,2-c]pyridin-2-yl)-2-bromoethanone

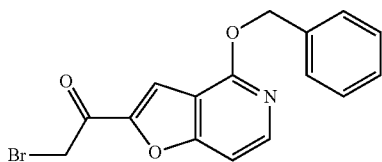 [SMILES: O=C(CBr)c1cc2c(OCc3ccccc3)nccc2o1]

To a solution of LiHMDS (1 M in THF, 5.15 mL, 5.15 mmol) in dry THF (35 mL), stirred at −78° C. under nitrogen, was added a solution of 1-(4-(benzyloxy)furo[3,2-c]pyridin-2-yl)ethanone (1.148 g, 4.30 mmol) in THF (15 mL) dropwise. After 45 min trimethylchlorosilane (0.604 mL, 4.72 mmol) was added and the reaction was stirred at the same temperature for another 30 min. The cooling bath was then removed and the reaction was stirred at room temperature for 30 min before being quenched with saturated aqueous NaHCO$_3$ (15 mL) and diluted with cold ethyl acetate (100 mL). The isolated organic layer was dried over MgSO$_4$, filtered and concentrated. The residue obtained was co-evaporated twice with toluene to remove all traces of water. The silyl enol ether obtained was then dissolved in dry THF (25 mL) and cooled to −30° C. under nitrogen. To the resulting solution was added sodium bicarbonate (0.072 g, 0.859 mmol), followed by NBS (0.726 g, 4.08 mmol) (the latter added in small portions over 15 min). After complete addition, the reaction mixture was allowed to warm to 0° C. over 2 h, while being monitored by LCMS. Upon completion of the reaction, the crude reaction mixture was diluted with EtOAc, washed with saturated aqueous sodium bicarbonate and brine, dried over MgSO$_4$, filtered and concentrated under reduced pressure. The residue obtained was purified by column chromatography (Isco, 40 g cartridge) eluting with hexanes/dichloromethane/ethyl acetate (from 100:0:0 to 0:100:0 to 0:50:50) to give the title compound (0.225 g, 15%). LC (Method A): 2.209 min. LCMS (APCI): calcd for $C_{16}H_{13}BrNO_3$ [M+H]$^+$ m/z 346.01, found 346.0. $^1$H NMR (CDCl$_3$, 400 MHz) δ ppm: 4.38 (s, 2H), 5.56 (s, 2H), 7.17 (dd, J=1.2, 6.3 Hz, 1H), 7.32-7.44 (m, 3H), 7.48-7.52 (m, 2H), 7.73 (d, J=0.8 Hz, 1H), 8.19 (s, 1H).

202D. 5-(1,1-Difluoroethyl)-1,3,4-thiadiazol-2-amine

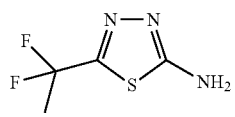

A modification of a reported procedure was used (cf. He, J. et al., *Chinese Chemical Letters*, 19:1281 (2008)). Thus, to an ice-cold suspension of thiosemicarbazide (4.97 g, 54.5 mmol) in dioxane (45 mL) was slowly added a solution of the 2,2-difluoropropanoic acid (4.50 g, 40.9 mmol) in dioxane (5 mL). To the resulting thick off-white slurry was added POCl$_3$ (4.99 mL, 54.5 mmol) dropwise and then the cooling bath was removed and the mixture was stirred at room temperature for 1 h. The vessel was then sealed and the stirred mixture was heated at 90-95° C. (oil bath temperature) for 5 h. The resulting turbid mixture was concentrated under reduced pressure and the concentrate was poured into ice water (150 mL). This mixture was basified to ca. pH 9 using 40% aqueous NaOH and the resulting slurry was filtered and the residue was washed with water, then with ether and finally with hexanes. The residue was dried in vacuo to give the title compound (4.31 g, 64%) as a white solid which was used as such in the next step. LC (Method B): 1.045 min. LCMS (APCI): calcd for $C_4H_6F_2N_3S$ [M+1]$^+$ m/z 165.02; found 166.0. $^1$H NMR (600 MHz, DMSO-d$_6$) δ ppm: 7.69 (s, 2H), 2.06 (t, J=19.0 Hz, 3H).

202E. 2-(2-(1,1-Difluoroethyl)imidazo[2,1-b][1,3,4]thiadiazol-6-yl)furo[3,2-c]pyridin-4-ol

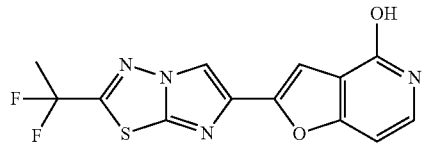 [SMILES: CC(F)(F)c1nn2cc(-c3cc4c(O)nccc4o3)nc2s1]

A microwave vial was charged with 1-(4-(benzyloxy)furo[3,2-c]pyridin-2-yl)-2-bromoethanone (0.100 g, 0.289 mmol), 5-(1,1-difluoroethyl)-1,3,4-thiadiazol-2-amine (0.0573 g, 0.347 mmol) and i-PrOH (2.5 mL). The resulting suspension was heated at 80° C. under microwave radiation for 1 h and then at 150° C. for another 90 min. The crude reaction mixture was diluted with dichloromethane, washed with saturated aqueous sodium bicarbonate, dried over MgSO$_4$, filtered and concentrated. The crude residue obtained was adsorbed on a silica gel pre-column and the product was purified by column chromatography (Isco, 12 g cartridge) eluting with a gradient of a (1% NH$_4$OH-9% MeOH-90% CH$_2$Cl$_2$) in dichloromethane (from 0 to 10%) to give the title compound (0.054 g, 58%). LC (Method A): 2.015 min. HRMS(ESI): calcd for $C_{13}H_9F_2N_4O_2S$ [M+H]$^+$ m/z 323.0414, found 323.0448. $^1$H NMR (DMSO-d$_6$, 400 MHz) δ ppm: 2.24 (t, J=19.6 Hz, 3H), 6.70 (d, J=7.4 Hz, 2H), 7.11 (s, 1H), 7.34 (dd, J=5.9, 7.0 Hz, 1H), 8.76 (s, 1H), 11.55 (br s, 1H).

Example 202. 2-(2-(1,1-Difluoroethyl)imidazo[2,1-b][1,3,4]thiadiazol-6-yl)-4-((2-phenylthiazol-4-yl)methoxy)furo[3,2-c]pyridine

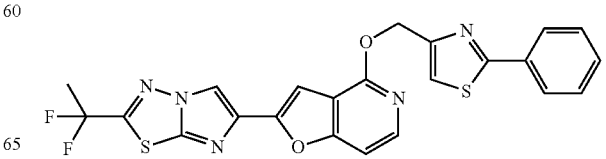

A microwave vial was charged with 2-(2-(1,1-difluoroethyl)imidazo[2,1-b][1,3,4]thiadiazol-6-yl)furo[3,2-c]pyridin-4-ol (0.010 g, 0.031 mmol) and 4-(bromomethyl)-2-phenylthiazole (0.0087 g, 0.034 mmol) before n-hexane (1 mL) and silver carbonate (50% on CELITE®, 0.0107 g, 0.039 mmol) were added. The resulting reaction mixture was then heated at 150° C. under microwave radiation for 1 h. The crude reaction mixture was filtered and the filtrate was concentrated under reduced pressure. The residue obtained was purified by preparative HPLC (Method A) to give the title compound (0.0025 g, 16%). LC (Method A): 2.477 min. HRMS(ESI): calcd for $C_{23}H_{16}F_2N_5O_2S_2$ [M+H]$^+$ m/z 496.0714, found 496.0754. $^1$H NMR (DMSO-$d_6$, 400 MHz) δ ppm: 2.24 (t, J=19.2 Hz, 3H), 5.67 (s, 2H), 7.29 (d, J=1.2 Hz, 1H), 7.41 (dd, J=0.8, 5.9 Hz, 1H), 7.46-7.55 (m, 3H), 7.84-7.85 (m, 1H), 7.94-7.99 (m, 2H), 8.09 (d, J=5.9 Hz, 1H), 8.88 (s, 1H).

Example 203

4-(((6-Methoxy-2-(6-methylimidazo[1,2-b]pyridazin-2-yl)benzofuran-4-yl)oxy)methyl)-2-phenylthiazole

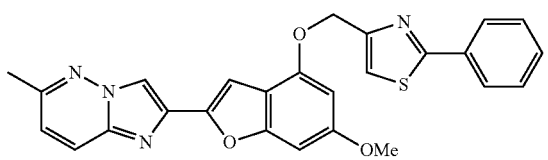 [SMILES: COc1cc(OCc2csc(-c3ccccc3)n2)c2cc(-c3cn4nc(C)ccc4n3)oc2c1]

203A. 2-(4-(Benzyloxy)-6-methoxybenzofuran-2-yl)-6-methylimidazo[1,2-b]pyridazine

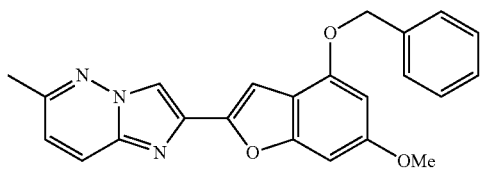 [SMILES: COc1cc(OCc2ccccc2)c2cc(-c3cn4nc(C)ccc4n3)oc2c1]

A mixture of 6-methylpyridazin-3-amine (1.52 g, 13.93 mmol), 1-(4-(benzyloxy)-6-methoxybenzofuran-2-yl)-2-bromoethanone (Example 1E, 5.00 g, 13.33 mmol) and 2-propanol (110 mL) in a 150 mL pressure flask was heated at 65° C. The mixture was almost homogeneous after 30 min of heating and precipitated again after 40 min. The mixture was heated for a total of 48 h. The cooled reaction mixture was diluted with dichloromethane (600 mL), washed with saturated sodium bicarbonate, brine and dried over anhydrous magnesium sulfate. Evaporation gave an orange brown solid which was chromatographed on silica gel (4×9 cm, elution dichloromethane-ethyl acetate 0-5%) to give the title material (3.64 g) as an orange brown solid. The solid was boiled with ethyl acetate (30 mL, partially soluble) and allowed to stand at room temperature for 2 h. The crystals were collected by filtration and dried overnight in vacuo to give the title material (3.440 g, 67%) as pale yellow brown needles. LC (Method A): 2.279 min. HRMS(ESI) calcd for $C_{23}H_{20}N_3O_3$ [M+H]$^+$ m/z 386.1505, found 386.1532. $^1$H NMR (CDCl$_3$, 400 MHz) δ ppm: 2.59 (s, 3H), 3.86 (s, 3H), 5.21 (s, 2H), 6.43 (d, J=1.96 Hz, 1H), 6.75 (broad d, 1H), 6.94 (d, J=9.39 Hz, 1H), 7.31-7.38 (m, 2H), 7.38-7.45 (m, 2H), 7.50 (broad d, J=7.43 Hz, 2H), 7.82 (d, J=9.39 Hz, 1H), 8.19 (s, 1H).

203B. 6-Methoxy-2-(6-methylimidazo[1,2-b]pyridazin-2-yl)benzofuran-4-ol

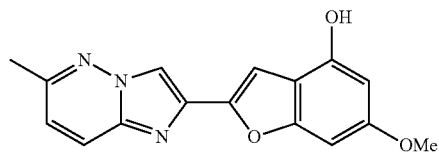 [SMILES: COc1cc(O)c2cc(-c3cn4nc(C)ccc4n3)oc2c1]

A solution of 2-(4-(benzyloxy)-6-methoxybenzofuran-2-yl)-6-methylimidazo[1,2-b]pyridazine (Example 39A, 1.00 g, 2.59 mmol) in a mixture of dichloromethane (420 mL) and methanol (150 mL) in a 1 L flask was hydrogenated over 10% Palladium over carbon (0.30 g, i.e., 30 mg Pd) and under 1 atm of hydrogen for 6 h. The reaction mixture was maintained under vacuum for 2 min and then flushed with nitrogen. The catalyst was filtered and washed with warm dichloromethane-methanol (8:2, 100 mL) and the combined filtrate was concentrated under reduced pressure. The yellow residue was boiled with 1,2-dichloroethane (30 mL) and allowed to stand at room temperature for 18 h. The solid was filtered (contains methanol by NMR) and dried in vacuo at 120° C. for 12 h to give the title material (0.760 g, 99% yield) of a yellow solid. LC (Method A): 1.844 min. $^1$H NMR (DMSO-$d_6$, 400 MHz) δ ppm: 2.54 (s, 3H), 3.77 (s, 3H), 6.28 (d, J=1.96 Hz, 1H), 6.70 (dd, J=1.96, 1.17 Hz, 1H), 7.20 (d, J=9.39 Hz, 1H), 7.24 (d, J=0.78 Hz, 1H), 8.03 (d, J=9.78 Hz, 1H), 8.50 (s, 1H), 10.10 (br s, 1H).

Example 203. 4-(((6-Methoxy-2-(6-methylimidazo[1,2-b]pyridazin-2-yl)benzofuran-4-yl)oxy)methyl)-2-phenylthiazole

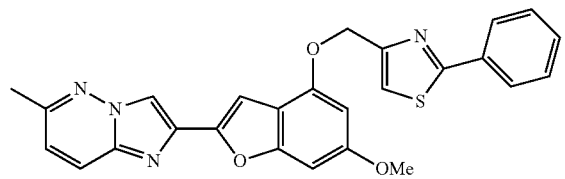 [SMILES: COc1cc(OCc2csc(-c3ccccc3)n2)c2cc(-c3cn4nc(C)ccc4n3)oc2c1]

In a 100 mL round-bottom flask, a suspension of 6-methoxy-2-(6-methylimidazo[1,2-b]pyridazin-2-yl)benzofuran-4-ol (0.190 g, 0.643 mmol) and 4-(bromomethyl)-2-phenylthiazole (0.180 g, 0.708 mmol) in DMF (5 mL) was purged under vacuum and N$_2$ for 10 min. The reaction was treated with potassium carbonate (0.24 g, 1.737 mmol) and stirred at 22° C. for 18 hours, then diluted with DCM and washed with water (1×), brine (1×). The organic layers were dried over anhydrous magnesium sulfate, filtered and concentrated. The residue was purified by silica gel chromatography (2.5×10 cm, 0% to 50% EtOAc in CH$_2$Cl$_2$) to give the impure title material (0.198 g, 66%). The solid was triturated in hot ethyl acetate to provide the pure title material (0.176 g). LC (Method A): 2.414 min. HRMS(ESI) calcd for $C_{26}H_{21}N_4O_3S$ [M+H]$^+$ m/z 469.1334, found 469.1379. $^1$H NMR (CDCl$_3$, 400 MHz) δ ppm: 2.57 (s, 3H), 3.84 (s, 3H), 5.39 (s, 2H), 6.46 (d, J=1.96 Hz, 1H), 6.74 (broad d, 1H), 6.91 (d, J=9.1 Hz, 1H), 7.34 (s, 1H), 7.36 (s, 1H), 7.39-7.46 (m, 3H), 7.80 (d, J=9.1 Hz, 1H), 7.90-8.0 (m, 2H), 8.19 (s, 1H).

Example 204

4-(((6-Methoxy-2-(6-methylimidazo[1,2-b]pyridazin-2-yl)benzofuran-4-yl)oxy)methyl)-2-(tetrahydro-2H-thiopyran-4-yl)thiazole

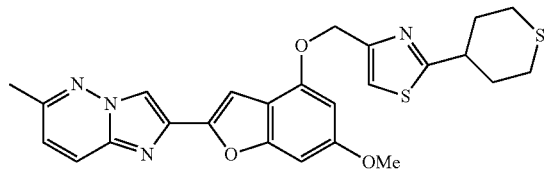 [SMILES: COc1cc(OCc2csc(C3CCSCC3)n2)c2cc(-c3cn4nc(C)ccc4n3)oc2c1]

A mixture of 6-methoxy-2-(6-methylimidazo[1,2-b]pyridazin-2-yl)benzofuran-4-ol (Example 203B, 0.340 g, 1.15 mmol) and (2-(tetrahydro-2H-thiopyran-4-yl)thiazol-4-yl)methanol (0.266 g, 1.24 mmol) in a 100 mL round-bottomed flask fitted with an addition funnel was maintained under vacuum for 5 min. The flask was then flushed with nitrogen and charged with dry tetrahydrofuran (30 mL) followed by tributylphosphine (0.74 mL, 3.0 mmol) added in one portion. The heterogeneous mixture was then treated at 22° C. with a solution of 1,1'-(azodicarbonyl)-dipiperidine (0.43 g, 1.70 mmol) in tetrahydrofuran (20 mL) added dropwise over 1 h (with a few short sonication periods). The reaction mixture was homogeneous at the end of the addition and was stirred for another 2 h. The reaction mixture was then partitioned between dichloromethane (250 mL) and saturated sodium bicarbonate. The organic phase was washed with brine, dried over anhydrous magnesium sulfate and concentrated in vacuo to give a glassy residue. The residue was chromatographed on silica gel (elution 0-30% ethyl acetate-dichloromethane) to give 0.420 g (74% yield) of the title material as light yellow solid. LC (Method A): 2.561 min. HRMS(ESI): calcd for $C_{25}H_{25}N_4O_3S_2$ [M+H]$^+$ m/z 493.1368, found 493.1388. $^1$H NMR (400 MHz, DMSO-d$_6$) δ ppm: 8.53 (s, 1H), 8.01 (d, J=9.4 Hz, 1H), 7.73 (s, 1H), 7.26 (s, 1H), 7.18 (d, J=9.4 Hz, 1H), 6.88 (br d, 1H), 6.63 (d, J=2.0 Hz, 1H), 5.28 (s, 2H), 3.83 (s, 3H), 3.10-3.18 (m, 1H), 2.75-2.85 (m, 2H), 2.65-2.72 (m, 2H), 2.5 (s, 3H), 2.28-2.43 (m, 2H), 1.70-1.90 (m, 2H).

Example 205

2-Bromo-4-(((6-methoxy-2-(6-methylimidazo[1,2-b]pyridazin-2-yl)benzofuran-4-yl)oxy)methyl)thiazole

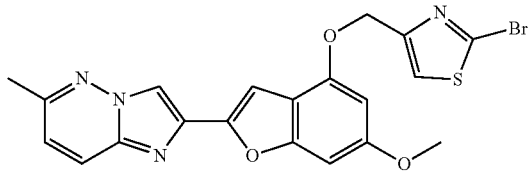 [SMILES: COc1cc(OCc2csc(Br)n2)c2cc(-c3cn4nc(C)ccc4n3)oc2c1]

205A. (2-Bromothiazol-4-yl)methanol

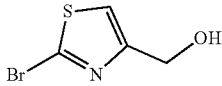

To a solution of methyl 2-bromothiazole-4-carboxylate (1.00 g, 4.50 mmol) in ethanol (15 mL) at 0° C. was added NaBH$_4$ (1.022 g, 27.0 mmol). The cooling bath was removed and the reaction mixture was stirred at ambient temperature for 15 min and then at 90° C. for 1.5 h. The cooled reaction mixture was treated with acetic acid (5 mL) and then the mixture was evaporated to dryness under reduced pressure. The residue obtained was chromatographed on silica gel (ISCO, elution gradient of ethyl acetate in dichloromethane) to give the title material (0.571 g, 65%) as a colorless oil. LC (Method A): 1.101 min. LRMS (APCI): calcd for $C_4H_5BrNOS$ [M+H]$^1$ m/z: 193.93; found 193.90. $^1$H NMR (400 MHz, CDCl$_3$) δ ppm: 7.18 (d, J=0.78 Hz, 1H), 4.76 (d, J=1.00 Hz, 2H), 2.28-2.71 (m, 1H).

205B. 2-Bromo-4-(bromomethyl)thiazole

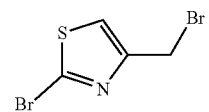

A solution of (2-bromothiazol-4-yl)methanol (0.571 g, 2.94 mmol) in dichloromethane (8 mL) was cooled to 0° C. and treated with PBr$_3$ (0.128 mL, 1.359 mmol) dropwise over 2 min. After 5 min, the ice bath was removed and the solution was stirred at 22° C. for 4 h. The reaction mixture was then poured into a mixture of ethyl acetate and saturated aqueous sodium bicarbonate, the organic phase was separated, washed with brine, dried over anhydrous magnesium sulfate and concentrated in vacuo. The residue obtained was chromatographed on silica gel (ISCO, elution gradient of dichloromethane in hexanes) to give 0.550 g (72%) of the title material as a colorless oil. LC (Method B): 1.813 min. LRMS (APCI): calcd for $C_4H_4Br_2NS$ [M+H]$^+$ m/z: 255.84; found: 255.80. $^1$H NMR (400 MHz, CDCl$_3$) δ ppm: 7.27 (s, 1H, underneath CHCl$_3$), 4.54 (s, 2H).

Example 205. 2-Bromo-4-(((6-methoxy-2-(6-methylimidazo[1,2-b]pyridazin-2-yl)benzofuran-4-yl)oxy)methyl)thiazole

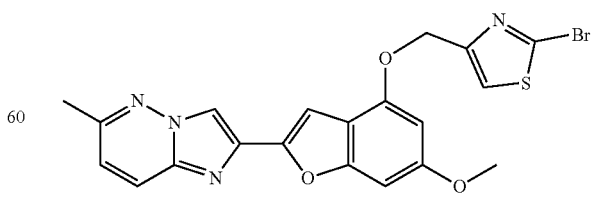

A mixture of 6-methoxy-2-(6-methylimidazo[1,2-b]pyridazin-2-yl)benzofuran-4-ol (Example 203B, 0.208 g, 0.704 mmol) and 2-bromo-4-(bromomethyl)thiazole (0.181 g, 0.704 mmol) in DMF (5 mL) was maintained under vacuum for 5 min, then the flask was flushed with nitrogen and powdered anhydrous potassium carbonate (0.291 g, 2.10 mmol) was added all at once. The resulting mixture was stirred at room temperature for 1.5 h, then it was quenched with 1 N hydrochloric acid (1 mL) and finally partitioned between dichloromethane and saturated aqueous sodium bicarbonate. The organic phase was separated, washed with brine, dried over anhydrous magnesium sulfate and concentrated in vacuo. The residue obtained was chromatographed on silica gel (ISCO, elution gradient of ethyl acetate in dichloromethane) to give 0.220 g (66%) of the title material as a solid. LC (Method A): 2.267 min. HRMS(ESI) calcd. for $C_{20}H_{16}BrN_4O_3S$ [M+H]$^1$ m/z: 471.0126; found 471.0121. $^1$H NMR (400 MHz, CDCl$_3$) δ ppm: 8.18 (s, 1H), 7.82 (d, J=9.39 Hz, 1H), 7.31 (s, 1H), 7.34 (s, 1H), 6.93 (d, J=9.00 Hz, 1H), 6.74-6.79 (m, 1H), 6.40 (d, J=1.96 Hz, 1H), 5.27-5.34 (m, 2H), 3.86 (s, 3H), 2.59 (s, 3H).

Example 206. 2-Chloro-4-(((6-methoxy-2-(6-methylimidazo[1,2-b]pyridazin-2-yl)benzofuran-4-yl)oxy)methyl)thiazole

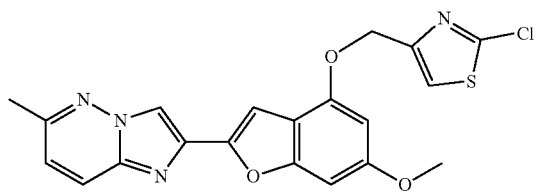 [SMILES: COc1cc(OCc2csc(Cl)n2)c2cc(-c3cn4nc(C)ccc4n3)oc2c1]

The title compound was prepared using 2-chloro-4-(bromomethyl)thiazole, according to the method described in Example 205 above. LC (Method A): 2.314 min. HRMS (ESI) calcd. for $C_{20}H_{16}ClN_4O_3S$ [M+H]$^1$ m/z 427.0632; found 427.0611. $^1$H NMR (400 MHz, CDCl$_3$) δ ppm: 8.19 (s, 1H), 7.82 (d, J=9.39 Hz, 1H), 7.31 (s, 1H), 7.29 (s, 1H), 6.94 (d, J=9.39 Hz, 1H), 6.77 (s, 1H), 6.40 (s, 1H), 5.27 (s, 2H), 3.86 (s, 3H), 2.59 (s, 3H).

Example 207

4-(((6-Methoxy-2-(6-methylimidazo[1,2-b]pyridazin-2-yl)benzofuran-4-yl)oxy)methyl)-2-(4-methylpiperazin-1-yl)thiazole

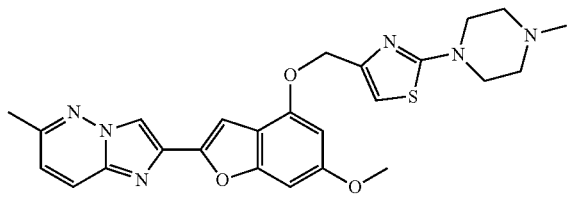

In a sealed tube, 2-bromo-4-(((6-methoxy-2-(6-methylimidazo[1,2-b]pyridazin-2-yl)benzofuran-4-yl)oxy)methyl)thiazole (Example 205, 0.025 g, 0.053 mmol) in tetrahydrofuran (2 mL) was treated with 1-methylpiperazine (8.85 μl, 0.080 mmol) and the resulting mixture was heated at 80° C. for 16 h. The cooled reaction mixture was quenched with 1 N hydrochloric acid (0.5 mL) and then partitioned between dichloromethane and saturated aqueous sodium bicarbonate. The organic phase was separated, washed with brine, dried over anhydrous magnesium sulfate and concentrated in vacuo. The residue obtained was chromatographed on silica gel (ISCO, elution gradient of ethyl acetate in dichloromethane) and the obtained material was triturated with ethyl acetate to give (after filtration and drying in vacuo) 0.016 g (60%) of the title compound as a solid. LC (Method A): 1.955 min. HRMS(ESI) calcd. for $C_{25}H_{27}N_6O_3S$ [M+H]$^+$ m/z: 491.1865; found 491.1876. $^1$H NMR (400 MHz, CDCl$_3$) δ ppm: 8.19 (s, 1H), 7.82 (d, J=9.39 Hz, 1H), 7.34 (s, 1H), 6.94 (d, J=9.39 Hz, 1H), 6.75 (s, 1H), 6.63 (s, 1H), 6.44 (s, 1H), 5.13 (s, 2H), 3.86 (s, 3H), 3.54 (t, J=1.00 Hz, 4H), 2.59 (s, 3H), 2.54 (t, J=4.89 Hz, 4H), 2.36 (s, 3H).

Example 208

4-(((6-Methoxy-2-(6-methylimidazo[1,2-b]pyridazin-2-yl)benzofuran-4-yl)oxy) methyl)-2-(4-(trifluoromethyl)phenyl)thiazole

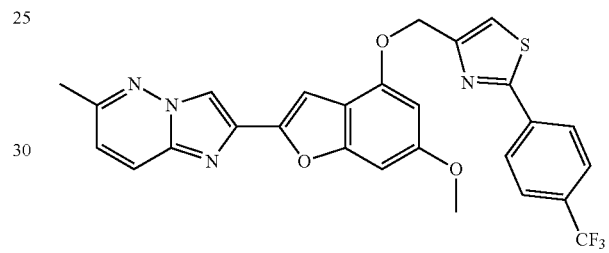

208A. Ethyl 2-(4-(trifluoromethyl)phenyl)thiazole-4-carboxylate

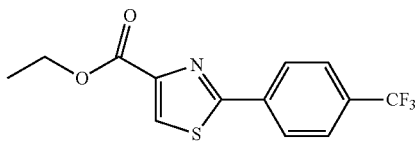 [SMILES: CCOC(=O)c1csc(-c2ccc(C(F)(F)F)cc2)n1]

A solution of 4-(trifluoromethyl)benzothioamide (3.00 g, 14.62 mmol) in THF (45 mL) was treated at 22° C. with a solution of ethyl 3-bromo-2-oxopropanoate (2.202 mL, 17.54 mmol) in THF (5 mL), added dropwise over 5 min. The resulting mixture was stirred at room temperature for 30 min and then it was heated under reflux for 18 h. The cooled mixture was diluted with ethyl acetate (200 mL), washed with saturated sodium bicarbonate and brine, dried over anhydrous magnesium sulfate and evaporated. The residue was purified on the ISCO using a REDISEP® 80 g column (30 to 100% DCM-hexanes) to give the desired product as a yellow solid (2.52 g, 57%). LCMS (APCI): calcd for $C_{13}H_{11}F_3NO_2S$ [M+H]$^+$ m/z 302.05, found 302.0. $^1$H NMR (CDCl$_3$, 400 MHz) δ ppm: 8.23 (s, 1H), 8.14 (d, J=8.4 Hz, 2H), 7.73 (d, J=8.4 Hz, 2H), 4.47 (q, J=7.2 Hz, 2H), 1.45 (t, J=7.2 Hz, 3H).

208B. (2-(4-(Trifluoromethyl)phenyl)thiazol-4-yl)methanol

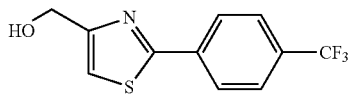

A solution of ethyl 2-(4-(trifluoromethyl)phenyl)thiazole-4-carboxylate (2.00 g, 6.64 mmol) in dry diethyl ether (120 mL) was cooled to −78° C. under nitrogen and then treated with solid LiAlH$_4$ (0.756 g, 19.9 mmol) portion-wise over 5 min. After 3 h at −78° C. the reaction mixture was quenched by the dropwise addition of ethyl acetate (10 mL) over 5 min. After 10 min, water (1 mL) was added dropwise over 10 min, then a 15% aqueous solution of NaOH (1 mL) and finally more water (2.1 mL) was added. The cooling bath was then removed and the heterogeneous mixture was stirred at room temperature for 30 min to give a white suspension. The suspension was then filtered and the filter-cake washed with ether (200 mL). The combined filtrate was washed with brine, dried over anhydrous magnesium sulfate and evaporated to give the desired product as a white solid (1.46 g, 85%). LCMS (APCI): calcd for C$_{11}$H$_9$F$_3$NOS [M+H]$^+$ m/z 260.028, found 260.0. $^1$H NMR (CDCl$_3$, 400 MHz) δ ppm: 8.07 (d, J=8.2 Hz, 2H), 7.71 (d, J=8.2 Hz, 2H), 7.28 (s, 1H), 4.87 (d, J=5.5 Hz, 2H), 2.31 (t, J=5.5 Hz, 1H).

208C. 4-(Bromomethyl)-2-(4-(trifluoromethyl)phenyl)thiazole

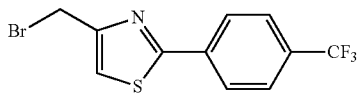 [SMILES: FC(F)(F)c1ccc(-c2nc(CBr)cs2)cc1]

To a stirred solution of (2-(4-(trifluoromethyl)phenyl)thiazol-4-yl)methanol (0.500 g, 1.93 mmol) in dry DCM (20 mL) under nitrogen was added phosphorous tribromide (0.37 mL, 3.86 mmol) and the reaction mixture was stirred at room temperature for 16 h. After completion, the mixture was concentrated and the concentrate partitioned between saturated aqueous sodium bicarbonate and DCM. The organic phase was separated and the aqueous phase was back-extracted twice with DCM. The combined organic layers were washed with brine, dried over MgSO$_4$ and concentrated. The residue was purified on the ISCO using a REDISEP® 40 g column (20 to 100% DCM-hexanes) to give the desired product as a white solid (0.196 g, 32%). LCMS (APCI): calcd for C$_{11}$H$_7$BrF$_3$NS [M+H]$^+$ m/z 321.94, found 321.9. $^1$H NMR (CDCl$_3$, 400 MHz) δ ppm: 8.05-8.11 (m, 2H), 7.68-7.75 (m, 2H), 7.39 (s, 1H), 4.65 (s, 2H).

Example 208. 4-(((6-Methoxy-2-(6-methylimidazo[1,2-b]pyridazin-2-yl) benzofuran-4-yl)oxy)methyl)-2-(4-(trifluoromethyl)phenyl)thiazole

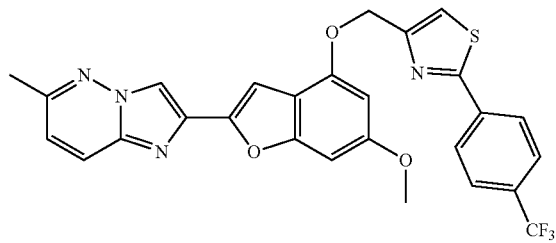 [SMILES: COc1cc(OCc2csc(-c3ccc(C(F)(F)F)cc3)n2)c2cc(-c3cn4nc(C)ccc4n3)oc2c1]

A mixture of 4-methoxy-2-(6-methylimidazo[1,2-b]pyridazin-2-yl)benzofuran-6-ol (Example 203B, 0.060 g, 0.20 mmol) and 4-(bromomethyl)-2-(4-(trifluoromethyl)phenyl)-thiazole (0.072 g, 0.22 mmol) in DMF (8 mL) was treated with K$_2$CO$_3$ (0.076 g, 0.55 mmol) and the resulting homogenous mixture was stirred at 23° C. for 1 h to give a suspension. After another 3 h the reaction mixture was diluted with dichloromethane (100 mL), washed with water and brine, dried over anhydrous magnesium sulfate and evaporated. The resulting off-white powder was suspended in acetonitrile, sonicated, filtered and dried to give the title compound as an off-white solid (0.090 g, 83%). LC (Method F): 2.453 min. LCMS (APCI): calcd for C$_{27}$H$_{20}$F$_3$N$_4$O$_3$S [M+H]$^+$ m/z 537.11, found 537.1. $^1$H NMR (CDCl$_3$, 400 MHz) δ ppm: 8.20 (s, 1H), 8.07-8.13 (m, J=8.2 Hz, 2H), 7.83 (d, J=9.4 Hz, 1H), 7.70-7.75 (m, J=8.2 Hz, 2H), 7.48 (s, 1H), 7.36 (s, 1H), 6.95 (d, J=9.4 Hz, 1H), 6.78 (dd, J=2.0, 0.8 Hz, 1H), 6.49 (d, J=2.0 Hz, 1H), 5.39-5.45 (m, 2H), 3.87 (s, 3H), 2.60 (s, 3H).

Example 209

2-(4-Chlorophenyl)-4-(((6-methoxy-2-(6-methylimidazo[1,2-b]pyridazin-2-yl)benzo furan-4-yl)oxy)methyl)thiazole

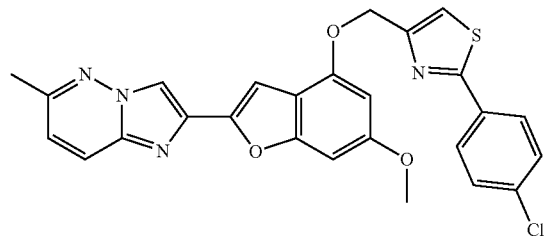 [SMILES: COc1cc(OCc2csc(-c3ccc(Cl)cc3)n2)c2cc(-c3cn4nc(C)ccc4n3)oc2c1]

209A. Ethyl 2-(4-chlorophenyl)thiazole-4-carboxylate

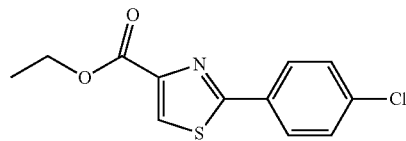 [SMILES: CCOC(=O)c1csc(-c2ccc(Cl)cc2)n1]

The compound was prepared according to the method described in Example 208A. The crude material was purified on the ISCO using a REDISEP® 120 g column (30 to 100% DCM-hexanes) to give the desired product as a yellow solid (3.18 g, 51%). LCMS (APCI): calcd for C$_{12}$H$_{11}$ClNO$_2$S [M+H]$^+$ m/z 268.01, found 268.0. $^1$H NMR (CDCl$_3$, 400 MHz) δ ppm: 8.17 (s, 1H), 7.96 (dd, J=8.8, 4.8 Hz, 2H), 7.44 (dd, J=9.2, 4.8 Hz, 2H), 4.46 (q, J=7.0 Hz, 2H), 1.44 (t, J=7.1 Hz, 3H).

209B. (2-(4-Chlorophenyl)thiazol-4-yl)methanol

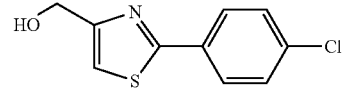

The compound was prepared according to the method described in Example 208B. The desired product was isolated as a yellow solid (2.51 g, 93%). LCMS (APCI): calcd for $C_{10}H_9ClNOS$ [M+H]$^+$ m/z 226.00, found 226.0. $^1$H NMR (CDCl$_3$, 400 MHz) δ ppm: 7.87-7.91 (m, 2H), 7.39-7.45 (m, 2H), 7.21 (t, J=1.0 Hz, 1H), 4.84 (d, J=5.7 Hz, 2H), 2.31 (t, J=5.7 Hz, 1H).

209C. 4-(Bromomethyl)-2-(4-chlorophenyl)thiazole

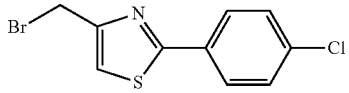

The compound was prepared according to the method described in Example 208C. The desired product was isolated as a white solid (0.320 g, 83%). LCMS (APCI): calcd for $C_{10}H_8BrClNOS$ [M+H]$^+$ m/z 287.92, found 287.9. $^1$H NMR (CDCl$_3$, 400 MHz) δ ppm: 7.90 (d, J=8.0 Hz, 2H), 7.43 (d, J=8.0 Hz, 2H), 7.32 (s, 1H), 4.63 (s, 2H).

Example 209. 2-(4-Chlorophenyl)-4-(((6-methoxy-2-(6-methylimidazo[1,2-b]pyridazin-2-yl) benzofuran-4-yl)oxy)methyl)thiazole

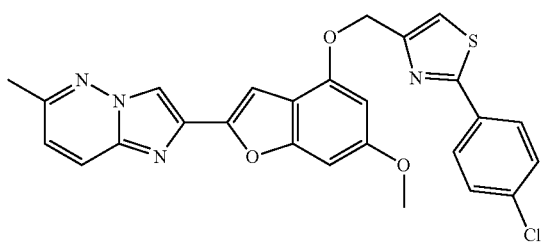 [SMILES: COc1cc(OCc2csc(-c3ccc(Cl)cc3)n2)c2cc(-c3cn4nc(C)ccc4n3)oc2c1]

The compound was prepared according to the method described in Example 208. The crude material was purified on the ISCO using a REDISEP® 12 g column (20 to 100% EtOAc-DCM) and the obtained yellow powder was suspended in acetonitrile, sonicated, filtered and dried to give the title compound as a pale yellow solid (0.087 g, 85%). LC (Method A): 2.569 min. LCMS (APCI): calcd for $C_{26}H_{20}ClN_4O_3S$ [M+H]$^+$ m/z 503.09, found 503.1. $^1$H NMR (CDCl$_3$, 400 MHz) δ ppm: 8.20 (s, 1H), 7.92 (d, J=8.8 Hz, 2H), 7.83 (d, J=9.4 Hz, 1H), 7.44 (d, J=8.8 Hz, 2H), 7.40 (s, 1H), 7.36 (s, 1H), 6.95 (d, J=9.4 Hz, 1H), 6.78 (dd, J=2.0, 0.8 Hz, 1H), 6.48 (d, J=2.0 Hz, 1H), 5.40 (s, 2H), 3.87 (s, 3H), 2.60 (s, 3H).

Example 210

4-(((6-Methoxy-2-(6-methylimidazo[1,2-b]pyridazin-2-yl)benzofuran-4-yl)oxy) methyl)-2-(4-(trifluoromethoxy)phenyl)thiazole

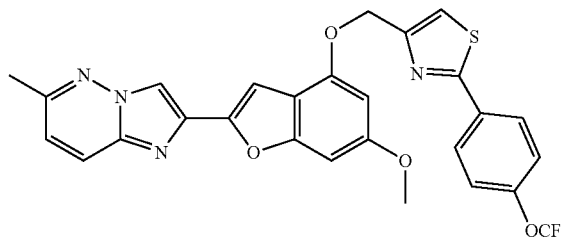

210A. Ethyl 2-(4-(trifluoromethoxy)phenyl)thiazole-4-carboxylate

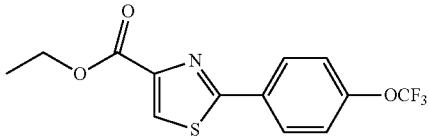 [SMILES: CCOC(=O)c1csc(-c2ccc(OC(F)(F)F)cc2)n1]

The compound was prepared according to the method described in Example 208A. The residue was purified on the ISCO using a REDISEP® 80 g column (30 to 100% DCM-hexanes) to give the desired product as a white solid (3.75 g, 87%). LCMS (APCI): calcd for $C_{13}H_{11}F_3NO_3S$ [M+H]$^+$ m/z 318.03, found 318.0. $^1$H NMR (CDCl$_3$, 400 MHz) δ ppm: 8.18 (s, 1H), 8.06 (d, J=9.0 Hz, 2H), 7.31 (d, J=9.0 Hz, 2H), 4.46 (q, J=7.0 Hz, 2H), 1.44 (t, J=7.0 Hz, 3H).

210B. (2-(4-(Trifluoromethoxy)phenyl)thiazol-4-yl)methanol

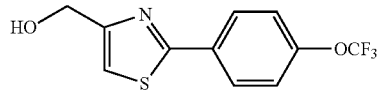 [SMILES: OCc1csc(-c2ccc(OC(F)(F)F)cc2)n1]

The compound was prepared according to the method described in Example 208B. The desired product was isolated as a white solid (2.63 g, 82%). LCMS (APCI): calcd for $C_{11}H_9F_3NO_2S$ [M+H]$^+$ m/z 276.02, found 276.0. $^1$H NMR (CDCl$_3$, 400 MHz) δ ppm: (d, J=8.1, 2H), 7.29 (d, J=8.1 Hz, 2H), 7.22 (s, 1H), 4.84 (d, J=5.5 Hz, 2H), 2.47 (t, J=5.5 Hz, 1H).

210C. 4-(Bromomethyl)-2-(4-(trifluoromethoxy)phenyl)thiazole

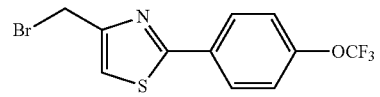 [SMILES: FC(F)(F)Oc1ccc(-c2nc(CBr)cs2)cc1]

The compound was prepared according to the method described in Example 208C. The residue was purified on the ISCO using a REDISEP® 40 g column (50 to 100% DCM-hexanes) to give the title compound as a white solid (0.078 g, 22%). LCMS (APCI): calcd for $C_{11}H_8BrF_3NOS$ [M+H]$^+$ m/z 337.94, found 338.0. $^1$H NMR (CDCl$_3$, 400 MHz) δ ppm: 8.00 (d, J=9.0, 2H), 7.33 (s, 1H), 7.30 (d, J=9.0, 2H), 4.64 (s, 2H).

Example 210. 4-(((6-Methoxy-2-(6-methylimidazo[1,2-b]pyridazin-2-yl) benzofuran-4-yl)oxy)methyl)-2-(4-(trifluoromethoxy)phenyl)thiazole

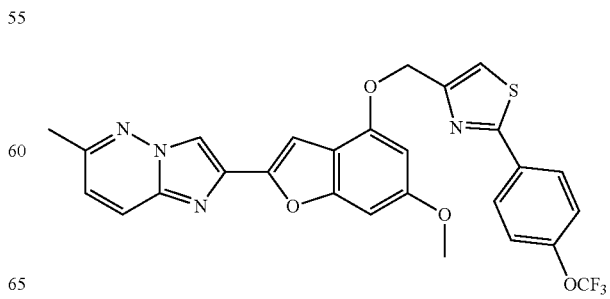

The compound was prepared according to the method described in Example 208. The residue was purified on the ISCO using a REDISEP® 12 g column (10 to 80% EtOAc-DCM) and the obtained yellow powder was suspended in acetonitrile, sonicated, filtered to give the title compound as a yellow solid (0.079 g, 71%). LC (Method A): 2.544 min. LCMS (APCI): calcd for $C_{27}H_{20}F_3N_4O_4S$ [M+H]$^+$ m/z 553.11, found 553.1. $^1$H NMR (CDCl$_3$, 400 MHz) δ ppm: 8.20 (s, 1H), 8.02 (d, J=9.0 Hz, 2H), 7.83 (d, J=9.2 Hz, 1H), 7.42 (s, 1H), 7.36 (s, 1H), 7.31 (d, J=9.0 Hz, 2H), 6.95 (d, J=9.2 Hz, 1H), 6.78 (s, 1H), 6.49 (d, J=2.0 Hz, 1H), 5.41 (s, 2H), 3.87 (s, 3H), 2.60 (s, 3H).

Example 211

4-(((6-Methoxy-2-(6-methylimidazo[1,2-b]pyridazin-2-yl)benzofuran-4-yl)oxy)methyl)-2-(pyridin-4-yl)thiazole

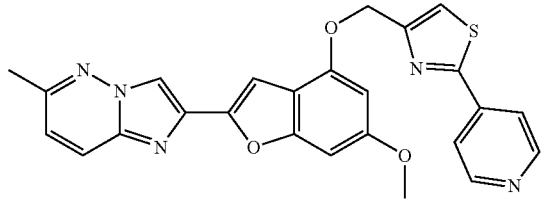 [SMILES: COc1cc(OCc2csc(-c3ccncc3)n2)c2cc(-c3cn4nc(C)ccc4n3)oc2c1]

211A. Ethyl 2-(pyridin-4-yl)thiazole-4-carboxylate

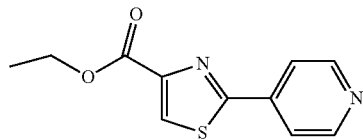 [SMILES: CCOC(=O)c1csc(-c2ccncc2)n1]

A solution of ethyl 2-(pyridin-4-yl)thiazole-4-carboxylate (2.18 g, 9.31 mmol) in EtOH (70 mL) in a 250 mL flask under a nitrogen atmosphere was cooled to 0° C. and treated with NaBH$_4$ (2.11 g, 55.8 mmol) added in small portions over 10 min. After 10 min at 0° C., the cooling bath was removed and the reaction mixture was stirred at 70° C. for 1 h. The cooled mixture was then quenched with saturated aqueous NH$_4$Cl (15 mL) and stirred for another 20 min before being extracted with ethyl acetate (100 mL). The organic phase was washed with brine, dried over MgSO$_4$ and concentrated to give a tan solid which was triturated in Et$_2$O to give the product as a white powder (1.20 g, 67%). LCMS (APCI): calcd for $C_9H_9N_2OS$ [M+H]$^+$ m/z 193.04, found 193.1. $^1$H NMR (DMSO-d$_6$, 400 MHz) δ ppm: 8.69 (d, J=4.4, 2H), 7.85 (d, J=4.4, 2H), 7.66 (d, J=1.1 Hz, 1H), 5.47 (t, J=5.7 Hz, 1H), 4.66 (dd, J=5.7, 1.1 Hz, 2H).

Example 211. 4-(((6-Methoxy-2-(6-methylimidazo[1,2-b]pyridazin-2-yl) benzofuran-4-yl)oxy)methyl)-2-(pyridin-4-yl)thiazole

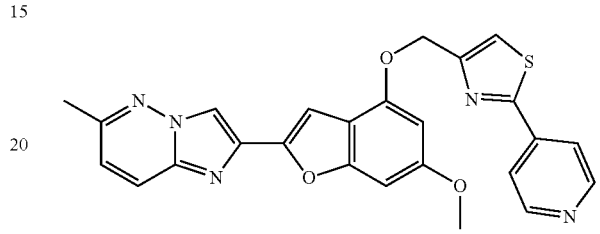

The title compound was prepared according to the general method described in Example 36. The crude product was purified on the ISCO using a REDISEP® 12 g column (0 to 15% MeOH-DCM) and the obtained yellow powder was suspended in CH$_3$CN, sonicated, filtered and dried to give the title compound as a pale yellow solid (0.079 g, 71%). LC (Method A): 2.392 min. LCMS (APCI): calcd for $C_{25}H_{20}N_5O_3S$ [M+H]$^+$ m/z 470.12, found 470.2. $^1$H NMR (CDCl$_3$, 400 MHz) δ ppm: 8.70-8.79 (m, 2H), 8.20 (s, 1H), 7.81-7.87 (m, 3H), 7.54 (s, 1H), 7.36 (s, 1H), 6.95 (d, J=9.4 Hz, 1H), 6.78 (s, 1H), 6.48 (d, J=1.6 Hz, 1H), 5.43 (s, 2H), 3.87 (s, 3H), 2.60 (s, 3H).

Example 212

2-(4-Fluorotetrahydro-2H-pyran-4-yl)-4-(((6-methoxy-2-(6-methylimidazo[1,2-b]pyridazin-2-yl)benzofuran-4-yl)oxy)methyl)thiazole

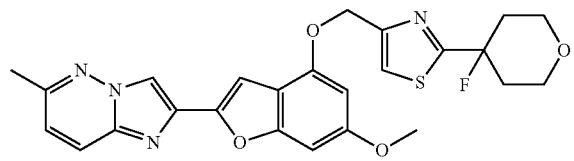

To a solution of 6-methoxy-2-(6-methylimidazo[1,2-b]pyridazin-2-yl)benzofuran-4-ol (Example 203B, 0.0285 g, 0.096 mmol) and 4-(bromomethyl)-2-(4-fluorotetrahydro-2H-pyran-4-yl)thiazole (Example 119C, 0.027 g, 0.096 mmol) in DMF (2 mL) under nitrogen was added potassium carbonate (0.0306 g, 0.222 mmol) and the resulting reaction mixture was stirred at room temperature for 2.5 h. The crude reaction mixture was then diluted with dichloromethane, washed with water and brine, dried over MgSO$_4$, filtered and concentrated. The crude residue obtained was purified by column chromatography (Isco, 12 g cartridge) eluting with a gradient of ethyl acetate in dichloromethane (from 0 to 100%). The product obtained from the column chromatography was triturated in ethanol and the solid was collected by filtration and dried in vacuo to give the pure title compound (0.034 g, 71%). LC (Method A): 2.306 min. HRMS(ESI):

211B. (2-(Pyridin-4-yl)thiazol-4-yl)methanol

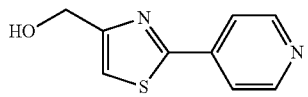 [SMILES: OCc1csc(-c2ccncc2)n1]

calcd for C$_{25}$H$_{24}$FN$_4$O$_4$S [M+H]$^+$ m/z 495.1502, found 495.1797. $^1$H NMR (DMSO-d$_6$, 400 MHz) δ ppm: 2.03-2.15 (m, 2H), 2.18-2.40 (m, 2H), 2.54 (s, 3H), 3.65-3.76 (m, 2H), 3.81-3.89 (m, 2H), 3.83 (s, 3H), 5.34 (s, 2H), 6.65 (d, J=2.0 Hz, 1H), 6.89-6.91 (m, 1H), 7.19 (d, J=9.4 Hz, 1H), 7.28 (s, 1H), 7.97 (s, 1H), 8.01 (d, J=9.0 Hz, 1H), 8.54 (s, 1H).

Examples 213 to 242

The following additional Examples have been prepared, isolated and characterized according to the methods disclosed above.

| Ex. | Structure | Formula | Calc. [M + H]$^-$ m/z | HPLC Retention Time (Min)/ Method | LCMS [M + H]$^+$ m/z | NMR |
|---|---|---|---|---|---|---|
| 213 | 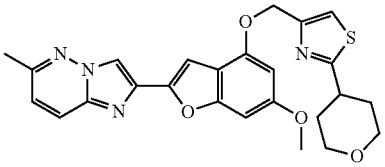 | C$_{25}$H$_{24}$N$_4$O$_4$S | 477.1591 | 2.179/A | 477.1643 | $^1$H NMR (CDCl$_3$) δ ppm: 1.86-2.0 (m, 2 H), 2.04-2.14 (m, 2 H), 2.60 (s, 3 H), 3.28 (tt, J = 11.7, 3.91 Hz, 1 H), 3.57 (tt, J = 11.7, 2.0 Hz, 2 H), 3.87 (s, 3 H), 4.05-4.15 (m, 2 H), 5.32 (d, J = 1.17 Hz, 2 H), 6.45 (d, J = 1.96 Hz, 1 H), 6.76 (dd, J = 1.96, 0.78 Hz, 1 H), 6.94 (d, J = 9.39 Hz, 1 H), 7.29 (br. s, 1 H), 7.33 (d, J = 0.78 Hz, 1 H), 7.82 (d, J = 9.39 Hz, 1 H), 8.19 (s, 1 H). |
| 214 | 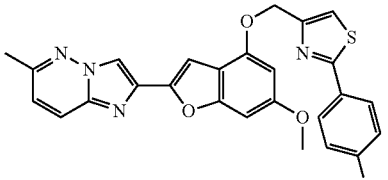 | C$_{24}$H$_{22}$N$_4$O$_4$S | 499.1435 | 2.402/A | 499.1487 | $^1$H NMR (CDCl$_3$) δ ppm: 2.57 (s, 3 H), 3.84 (s, 3 H), 3.85 (s, 3 H), 5.36 (s, 2 H), 6.46 (d, J = 1.92 Hz, 1 H), 6.74 (br. d, 1 H), 6.91 (d, J = 9.3 Hz, 1 H), 6.95 (br. d, J = 8.9 Hz, 2 H), 7.29 (s, 1 H), 7.33 (s, 1 H), 7.80 (d, J = 9.3 Hz, 1 H), 7.89 (br. d, J = 8.9 Hz, 2 H), 8.17 (s, 1 H). |
| 215 | 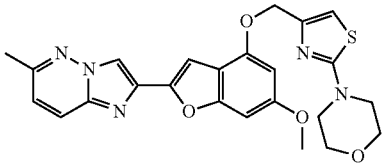 | C$_{24}$H$_{23}$N$_5$O$_4$S | 478.1544 | 2.446/A | 478.1565 | $^1$H NMR (400 MHz, CDCl$_3$) δ ppm: 2.57 (s, 3 H), 3.45-3.49 (m, 4 H), 3.80-3.83 (m, 4 H), 3.83 (s, 3 H), 5.10 (s, 2 H), 6.42 (d, J = 1.6 Hz, 1 H), 6.63 (s, 1H), 6.72 (br. d, 1 H), 6.91 (d, J = 9.46 Hz, 1 H), 7.31 (s, 1 H), 7.80 (d, J = 9.46 Hz, 1 H), 8.16 (s, 1 H). |
| 216 | 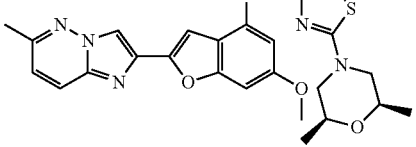 | C$_{26}$H$_{27}$N$_5$O$_4$S | 506.1857 | 2.479/A | 506.1874 | $^1$H NMR (400 MHz, CDCl$_3$) δ 8.19 (s, 1H), 7.82 (d, J = 9.4 Hz, 1H), 7.34 (s, 1H), 6.94 (d, J = 9.4 Hz, 1H), 6.75 (br. d, 1H), 6.64 (s, 1H), 6.44 (d, J = 2.0 Hz, 1H), 5.13 (s, 2H), 3.86 (s, 3H), 3.71-3.83 (m, 4H), 2.76 (dd, J = 12.7, 11.2 Hz, 2H), 2.60 (s, 3H), 1.27 (d, J = 6.2 Hz, 6H) |

| Ex. | Structure | Formula | Calc. [M + H]⁻ m/z | HPLC Retention Time (Min)/ Method | LCMS [M + H]⁺ m/z | NMR |
|---|---|---|---|---|---|---|
| 217 | 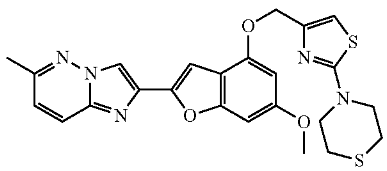 [SMILES: COc1cc(OCc2csc(C3CCOCC3)n2)c2cc(-c3cn4nc(C)ccc4n3)oc2c1] | C₂₄H₂₃FN₅O₃S₂ | 494.1315 | 2.487/A | 494.1451 | ¹H NMR (400 MHz, CDCl₃) δ ppm: 8.18 (s, 1H), 8.06 (d, J = 9.4 Hz, 1H), 7.56 (s, 1H), 7.09 (d, J = 9.4 Hz, 1H), 6.73 (br. d, 1H), 6.66 (s,1H), 6.47 (d, J = 2.0 Hz, 1H), 5.16 (s, 2H), 3.89-3.97 (m, 4H), 3.86 (s, 3H), 2.75-2.80 (m, 4H), 2.64 (s, 3H). |
| 218 | 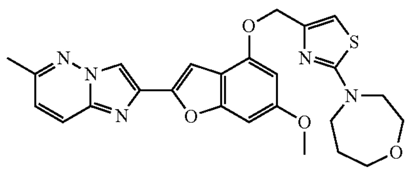 [SMILES: COc1cc(OCc2csc(N3CCCOCC3)n2)c2cc(-c3cn4nc(C)ccc4n3)oc2c1] | C₂₅H₂₅N₅O₄S | 492.17 | 2.386/A | 492.1727 | ¹H NMR (400 MHz, CDCl₃) δ ppm: 8.18 (s, 1H), 7.99 (d, J = 9.2 Hz, 1H), 7.50 (s, 1H), 7.05 (d, J = 9.2 Hz, 1H), 6.74 (br. d, 1H), 6.61 (s, 1H), 6.49 (d, J = 1.2 Hz, 1H), 5.23 (s, 2H), 3.78-3.96 (m, 8H), 3.86 (s, 3H), 2.63 (s, 3H), 2.10-2.15 (m, 2H). |
| 219 | 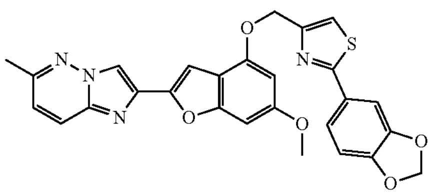 [SMILES: COc1cc(OCc2csc(-c3ccc4c(c3)OCO4)n2)c2cc(-c3cn4nc(C)ccc4n3)oc2c1] | C₂₄H₂₀N₄O₅S | 513.1227 | 2.574/A | 513.1281 | ¹H NMR (400 MHz, DMSO-d₆) δ ppm: 8.54 (s, 1H), 8.01 (d, J = 9.2 Hz, 1H), 7.83 (s, 1H), 7.46-7.55 (m, 2H), 7.31 (d, J = 0.8 Hz, 1H), 7.18 (d, J = 9.2 Hz, 1H), 7.04 (d, J = 8.2 Hz, 1H), 6.89 (br. d, 1H), 6.67 (d, J = 2.0 Hz, 1H), 6.12 (s, 2H), 5.35 (s, 2H), 3.83 (s, 3H), 2.53 (s, 3H). |
| 220 | 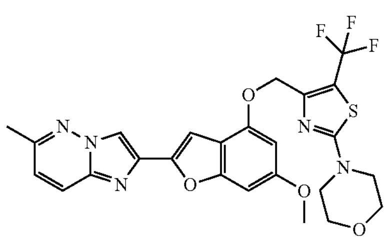 [SMILES: COc1cc(OCc2nc(N3CCOCC3)sc2C(F)(F)F)c2cc(-c3cn4nc(C)ccc4n3)oc2c1] | C₂₅H₂₂F₃N₅O₄S | 546.1417 | 2.521/A | 546.1435 | ¹H NMR (400 MHz, CDCl₃) δ ppm: 8.18 (s, 1H), 7.82 (d, J = 9.4 Hz, 1H), 7.30 (s, 1H), 6.93 (d, J = 9.4 Hz, 1H), 6.76 (s, 1H), 6.49 (s, 1H), 5.14 (s, 2H), 3.87 (s, 3H), 3.80-3.85 (m, 4H), 3.49-3.56 (m, 4H), 2.59 (s, 3H). |
| 221 | 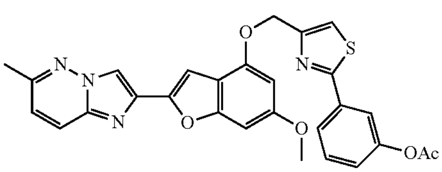 [SMILES: COc1cc(OCc2csc(-c3cccc(OC(C)=O)c3)n2)c2cc(-c3cn4nc(C)ccc4n3)oc2c1] | C₂₈H₂₂N₄O₅S | 527.1384 | 2.513/A | 527.0872 | ¹H NMR (400 MHz, CDCl₃) δ ppm: 8.20 (s, 1H), 7.83 (d, J = 9.0 Hz, 2H), 7.73-7.77 (m, 1H), 7.47 (br. t, J = 7.8 Hz, 1H), 7.41 (s, 1H), 7.36 (s, 1H), 7.15-7.22 (m, 1H), 6.94 (d, J = 9.0 Hz, 1H), 6.77 (br. d, 1H), 6.48 (d, J = 1.6 Hz, 1H), 5.40 (s, 2H), 3.87 (s, 3H), 2.60 (s, 3H), 2.35 (s, 3H). |
| 222 | 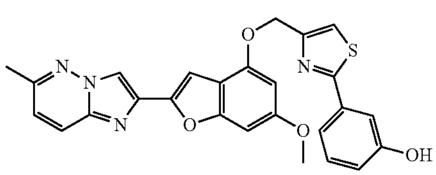 [SMILES: COc1cc(OCc2csc(-c3cccc(O)c3)n2)c2cc(-c3cn4nc(C)ccc4n3)oc2c1] | C₂₆H₂₀N₄O₄S | 485.1278 | 2.441/A | 485.1284 | ¹H NMR (400 MHz, DMSO-d₆) δ ppm: 9.78 (s, 1H), 8.54 (s, 1H), 8.02 (d, J = 9.0 Hz, 1H), 7.89 (s, 1H), 7.35-7.41 (m, 2H), 7.26-7.35 (m, 2H), 7.19 (d, J = 9.0 Hz, 1H), 6.84-6.93 (m, 2H), 6.67 (d, J = 2.0 Hz, 1H), 5.38 (s, 2H), 3.84 (s, 3H), 2.53 (s, 3H). |

| Ex. | Structure | Formula | Calc. [M + H]⁻ m/z | HPLC Retention Time (Min)/ Method | LCMS [M + H]⁺ m/z | NMR |
|---|---|---|---|---|---|---|
| 223 | 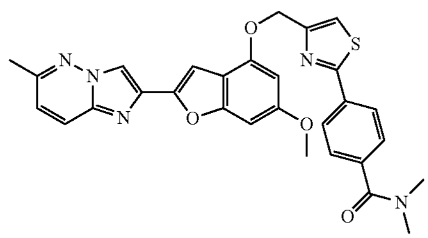 | C₂₉H₂₅N₅O₄S | 540.17 | 2.527/A | 540.1686 | ¹H NMR (400 MHz, CDCl₃) δ ppm: 8.20 (s, 1H), 8.02 (d, J = 8.2 Hz, 2H), 7.83 (d, J = 9.4 Hz, 1H), 7.52 (d, J = 8.2 Hz, 2H), 7.43 (s, 1H), 7.36 (s, 1H), 6.94 (d, J = 9.4 Hz, 1H), 6.77 (br. d, 1H), 6.49 (d, J = 2.0 Hz, 1H), 5.41 (s, 2H), 3.87 (s, 3H), 3.14 (br. s., 3H), 3.02 (br. s., 3H), 2.60 (s, 3H). |
| 224 | 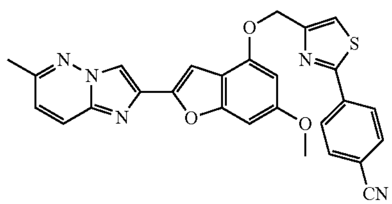 [SMILES: COc1cc(OCc2csc(-c3ccc(C#N)cc3)n2)c2cc(-c3cn4nc(C)ccc4n3)oc2c1] | C₂₇H₁₉N₅O₃S | 494.1281 | 2.556/A | 494.1298 | ¹H NMR (400 MHz, CDCl₃) δ ppm: 8.20 (s, 1H), 8.07-8.13 (m, 2H), 7.83 (d, J = 9.4 Hz, 1H), 7.73-7.79 (m, 2H), 7.51 (s, 1H), 7.36 (d, J = 0.8 Hz, 1H), 6.95 (d, J = 9.4 Hz, 1H), 6.78 (br. d, 1H), 6.48 (d, J = 2.0 Hz, 1H), 5.42 (s, 2H), 3.87 (s, 3H), 2.60 (s, 3H). |
| 225 | 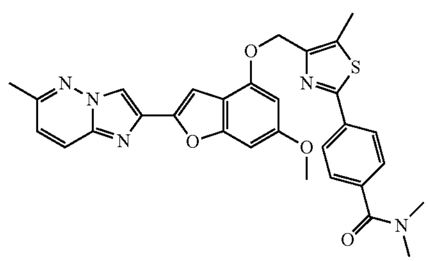 | C₃₀H₂₇N₅O₄S | 554.1857 | 2./A | 554.1865 | ¹H NMR (400 MHz, CDCl₃) δ ppm: 8.18 (s, 1H), 7.96 (d, J = 8.2 Hz, 2H), 7.81 (d, J = 9.2 Hz, 1H), 7.50 (d, J = 8.2 Hz, 2H), 7.29 (s, 1H), 6.93 (d, J = 9.2 Hz, 1H), 6.76 (br. s, 1H), 6.58 (d, J = 1.6 Hz, 1H), 5.34 (s, 2H), 3.87 (s, 3H), 3.14 (br. s., 3H), 3.02 (br. s., 3H), 2.59 (s, 6H). |
| 226 | 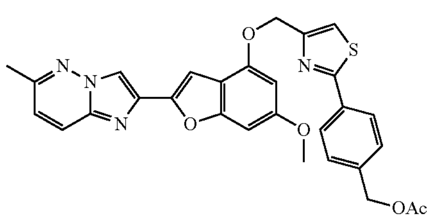 [SMILES: COc1cc(OCc2csc(-c3ccc(COC(C)=O)cc3)n2)c2cc(-c3cn4nc(C)ccc4n3)oc2c1] | C₂₉H₂₄N₄O₅S | 541.154 | 2.585/A | 541.1537 | ¹H NMR (400 MHz, CDCl₃) δ ppm: 8.20 (s, 1H), 7.98 (d, J = 8.2 Hz, 2H), 7.83 (d, J = 9.4 Hz, 1H), 7.45 (d, J = 8.2 Hz, 2H), 7.40 (s, 1H), 7.36 (s, 1H), 6.94 (d, J = 9.4 Hz, 1H), 6.77 (br. d, 1H), 6.49 (d, J = 2.0 Hz, 1H), 5.41 (s, 2H), 5.16 (s, 2H), 3.87 (s, 3H), 2.60 (s, 3H), 2.15 (s, 3H). |
| 227 | 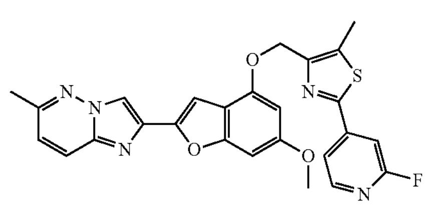 [SMILES: COc1cc(OCc2nc(-c3ccnc(F)c3)sc2C)c2cc(-c3cn4nc(C)ccc4n3)oc2c1] | C₂₆H₂₀FN₅O₃S | 502.1344 | 2.299/A | 502.1344 | ¹H NMR (400 MHz, CDCl₃) δ ppm: 8.29 (d, J = 5.1 Hz, 1H), 8.18 (s, 1H), 7.81 (d, J = 9.2 Hz, 1H), 7.67 (d, J = 5.5 Hz, 1H), 7.45 (br. s, 1H), 7.29 (s, 1H), 6.94 (d, J = 9.2 Hz, 1H), 6.77 (br. s, 1H), 6.56 (d, J = 2.0 Hz, 1H), 5.36 (s, 2H), 3.87 (s, 3H), 2.63 (s, 3H), 2.59 (s, 3H). |

| Ex. | Structure | Formula | Calc. [M + H]⁻ m/z | HPLC Retention Time (Min)/ Method | LCMS [M + H]⁺ m/z | NMR |
|---|---|---|---|---|---|---|
| 228 | 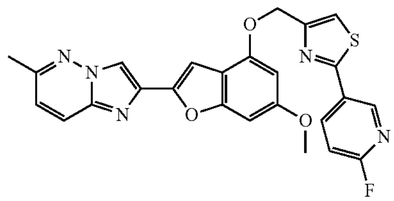 | C₂₅H₁₈FN₅O₃S | 488.1187 | 2.249/A | 488.1189 | ¹H NMR (400 MHz, CDCl₃) δ ppm: 8.81 (d, J = 2.3 Hz, 1H), 8.40 (ddd, J = 8.6, 7.4, 2.3 Hz, 1H), 8.20 (s, 1H), 7.83 (d, J = 9.2 Hz, 1H), 7.46 (s, 1H), 7.36 (br. s, 1H), 7.05 (dd, J = 8.6, 3.1 Hz, 1H), 6.95 (d, J = 9.2 Hz, 1H), 6.78 (br.d, 1H), 6.49 (d, J = 1.6 Hz, 1H), 5.41 (s, 2H), 3.87 (s, 3H), 2.60 (s, 3H) |
| 229 | 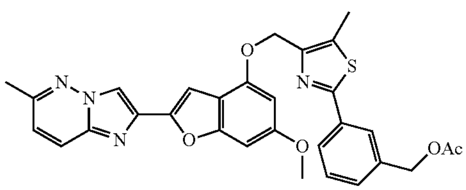 [SMILES: COc1cc(OCc2nc(-c3cccc(COC(C)=O)c3)sc2C)c2cc(-c3cn4nc(C)ccc4n3)oc2c1] | C₃₀H₂₆N₄O₅S | 555.1697 | 2.573/A | 555.1717 | ¹H NMR (400 MHz, CDCl₃) δ ppm: 8.18 (s, 1H), 7.94 (broad s, 1H), 7.82-7.90 (m, 1H), 7.82 (d, J = 9.4 Hz, 1H), 7.38-7.47 (m, 2H), 7.29 (s, 1H), 6.93 (d, J = 9.4 Hz, 1H), 6.76 (broad d, 1H), 6.59 (d, J = 2.0 Hz, 1H), 5.34 (s, 2H), 5.17 (s, 2H), 3.87 (s, 3H), 2.59 (s, 3H), 2.58 (s, 3H), 2.14 (s, 3H). |
| 230 | 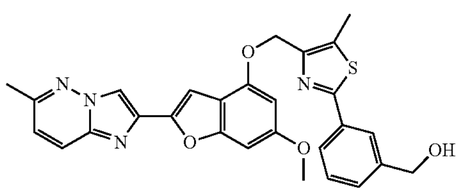 [SMILES: COc1cc(OCc2nc(-c3cccc(CO)c3)sc2C)c2cc(-c3cn4nc(C)ccc4n3)oc2c1] | C₂₈H₂₄N₄O₄S | 513.1591 | 2.472/A | 513.1593 | ¹H NMR (400 MHz, DMSO-d₆) δ ppm: 8.55 (s, 1H), 8.00 (d, J = 9.2 Hz, 1H), 7.89 (s, 1H), 7.76 (broad d, J = 7.4 Hz, 1H), 7.37-7.49 (m, 2H), 7.21 (s, 1H), 7.17 (d, J = 9.2 Hz, 1H), 6.89 (broad s, 1H), 6.71 (d, J = 1.6 Hz, 1H), 5.34 (t, J = 5.5 Hz, 1H), 5.33 (s, 2H), 4.57 (d, J = 5.5 Hz, 2H), 3.84 (s, 3H), 2.57 (s, 3H), 2.52 (s, 3H). |
| 231 | 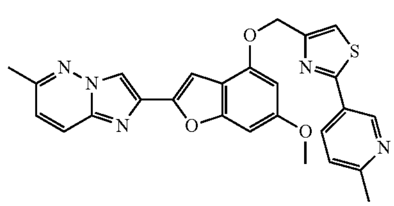 [SMILES: COc1cc(OCc2csc(-c3ccc(C)nc3)n2)c2cc(-c3cn4nc(C)ccc4n3)oc2c1] | C₂₆H₂₁N₅O₃S | 484.1438 | 2.111/A | 484.1446 | ¹H NMR (400 MHz, CDCl₃) δ ppm: 9.07 (d, J = 2.1 Hz, 1H), 8.20 (s, 1H), 8.16 (dd, J = 8.2, 2.1 Hz, 1H), 7.83 (d, J = 9.2 Hz, 1H), 7.43 (br. s, 1H), 7.36 (s, 1H), 7.26 (d, 1H), 6.94 (d, J = 9.2 Hz, 1H), 6.77 (d, J = 0.8 Hz, 1H), 6.49 (d, J = 0.8 Hz, 1H), 5.41 (s, 2H), 3.87 (s, 3H), 2.63 (s, 3H), 2.60 (s, 3H). |
| 232 | 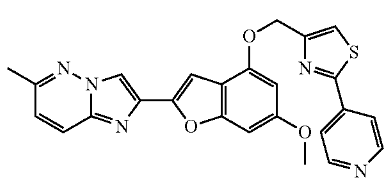 [SMILES: COc1cc(OCc2csc(-c3ccncc3)n2)c2cc(-c3cn4nc(C)ccc4n3)oc2c1] | C₂₅H₁₉N₅O₃S | 470.1281 | 2.127/A | 470.1285 | ¹H NMR (400 MHz, CDCl₃) δ ppm: 8.68-8.80 (m, 2H), 8.20 (s, 1H), 7.82-7.89 (m, 3H), 7.53 (s, 1H), 7.36 (s, 1H), 6.95 (d, J = 9.4 Hz, 1H), 6.78 (br.d, 1H), 6.48 (d, J = 2.0 Hz, 1H), 5.43 (s, 2H), 3.87 (s, 3H), 2.60 (s, 3H). |

| Ex. | Structure | Formula | Calc. [M + H]⁻ m/z | HPLC Retention Time (Min)/ Method | LCMS [M + H]⁺ m/z | NMR |
|---|---|---|---|---|---|---|
| 233 | 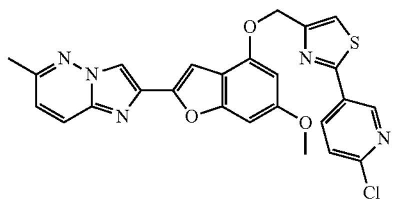 [SMILES: COc1cc(OCc2csc(-c3ccc(Cl)nc3)n2)c2cc(-c3cn4nc(C)ccc4n3)oc2c1] | C₂₅H₁₈ClN₅O₃S | 504.0892 | 2.355/A | 504.0892 | ¹H NMR (400 MHz, CDCl₃) δ ppm: 8.97 (d, J = 2.3 Hz, 1H), 8.25 (dd, J = 8.2, 2.3 Hz, 1H), 8.20 (s, 1H), 7.83 (d, J = 9.4 Hz, 1H), 7.49 (s, 1H), 7.44 (d, J = 8.2 Hz, 1H), 7.35 (s, 1H), 6.95 (d, J = 9.4 Hz, 1H), 6.78 (br. d, 1H), 6.48 (d, J = 2.0 Hz, 1H), 5.41 (s, 2H), 3.87 (s, 3H), 2.60 (s, 3H). |
| 234 | 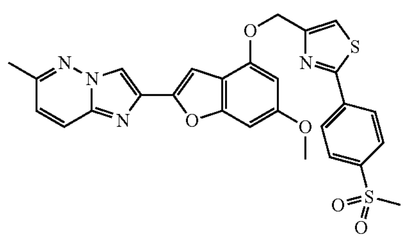 | C₂₇H₂₂N₄O₅S₂ | 547.1104 | 2.250/A | 547.1126 | ¹H NMR (400 MHz, CDCl₃) δ ppm: 8.17-8.21 (m, 3H), 8.04 (d, J = 8.2 Hz, 2H), 7.83 (d, J = 9.4 Hz, 1H), 7.52 (br. s, 1H), 7.36 (s, 1H), 6.95 (d, J = 9.4 Hz, 1H), 6.78 (br. d, 1H), 6.49 (d, J = 1.6 Hz, 1H), 5.43 (s, 2H), 3.88 (s, 3H), 3.11 (s, 3H), 2.60 (s, 3H). |
| 235 | 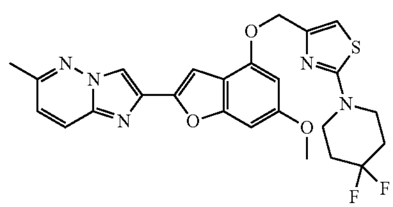 [SMILES: COc1cc(OCc2csc(N3CCC(F)(F)CC3)n2)c2cc(-c3cn4nc(C)ccc4n3)oc2c1] | C₂₅H₂₃F₂N₅O₃S | 512.149 | 2.339/A | 512.2 | ¹H NMR (CDCl₃, 400 MHz) δ ppm: 8.19 (s, 1H), 7.82 (d, J = 9.4 Hz, 1H), 7.34 (s, 1H), 6.94 (d, J = 9.4 Hz, 1H), 6.75 (s, 1H), 6.66 (s, 1H), 6.45 (d, J = 2.0 Hz, 1H), 5.12 (s, 2H), 3.86 (s, 3H), 3.65-3.73 (m, 4H), 2.60 (s, 3H), 2.04-2.19 (m, 4H). |
| 236 | 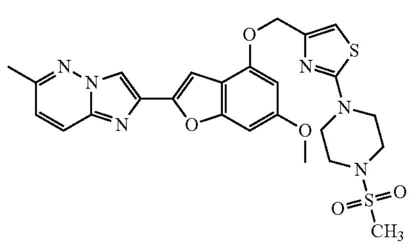 [SMILES: COc1cc(OCc2csc(N3CCN(S(C)(=O)=O)CC3)n2)c2cc(-c3cn4nc(C)ccc4n3)oc2c1] | C₂₅H₂₆N₆O₅S₂ | 555.1484 | 2.205/C | 555.1492 | ¹H NMR (CDCl₃, 400 MHz) δ ppm: 8.54 (s, 1H), 8.01 (d, J = 9.2 Hz, 1H), 7.27 (d, J = 0.8 Hz, 1H), 7.19 (d, J = 9.2 Hz, 1H), 7.03 (s, 1H), 6.87 (s, 1H), 6.59 (d, J = 2.0 Hz, 1H), 5.09 (s, 2H), 3.82 (s, 3H), 3.51-3.59 (m, 4H), 3.22-3.29 (m, 4H), 2.92 (s, 3H), 2.54 (s, 3H). |
| 237 | 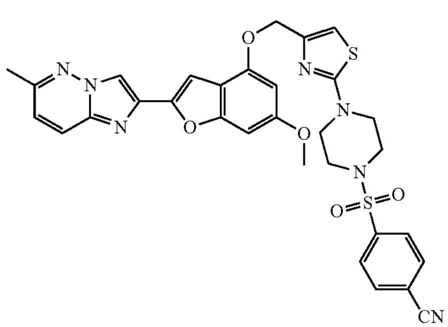 [SMILES: COc1cc(OCc2csc(N3CCN(S(=O)(=O)c4ccc(C#N)cc4)CC3)n2)c2cc(-c3cn4nc(C)ccc4n3)oc2c1] | C₃₁H₂₇N₇O₅S₂ | 642.1593 | 2.344/C | 642.1605 | ¹H NMR (CDCl₃, 400 MHz) δ ppm: 8.17 (s, 1H), 7.85-7.94 (m, 5H), 7.65 (br. s., 1H), 7.18 (d, J = 9.8 Hz, 1H), 6.71 (s, 1H), 6.68 (s, 1H), 6.42 (d, J = 1.6 Hz, 1H), 5.07 (s, 2H), 3.84-3.88 (m, 3H), 3.64-3.70 (m, 4H), 3.20-3.25 (m, 4H), 2.67 (s, 3H). |

| Ex. | Structure | Formula | Calc. [M + H]⁻ m/z | HPLC Retention Time (Min)/ Method | LCMS [M + H]⁺ m/z | NMR |
|---|---|---|---|---|---|---|
| 238 | 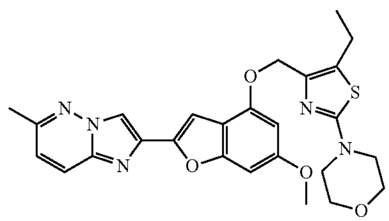 [SMILES: CCc1sc(N2CCOCC2)nc1COc1cc(OC)cc2oc(-c3cn4nc(C)ccc4n3)cc12] | C₂₆H₂₇N₅O₄S | 506.1862 | 2.214/C | 506.1864 | ¹H NMR (CDCl₃, 400 MHz) δ ppm: 8.17 (s, 1H), 7.81 (d, J = 9.2 Hz, 1H), 7.28 (s, 1H), 6.93 (d, J = 9.2 Hz, 1H), 6.74 (s, 1H), 6.53 (d, J = 2.0 Hz, 1H), 5.06 (s, 2H), 3.87 (s, 3H), 3.79-3.85 (m, 4H), 3.42-3.48 (m, 4H), 2.79 (q, J = 7.4 Hz, 2H), 2.59 (s, 3H), 1.23 (t, J = 7.4 Hz, 3H). |
| 239 | 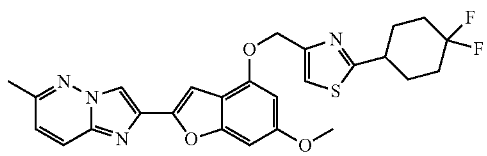 [SMILES: COc1cc(OCc2csc(C3CCC(F)(F)CC3)n2)c2cc(-c3cn4nc(C)ccc4n3)oc2c1] | C₂₆H₂₄F₂N₄O₃S | 511.1615 | 2.509/F | 511.1652 | ¹H NMR (DMSO-d₆, 400 MHz) δ ppm: 8.54 (s, 1H), 8.01 (d, J = 9.4 Hz, 1H), 7.74 (s, 1H), 7.26 (d, J = 0.8 Hz, 1H), 7.19 (d, J = 9.4 Hz, 1H), 6.88 (d, J = 0.8 Hz, 1H), 6.63 (d, J = 1.6 Hz, 1H), 5.29 (s, 2H), 3.83 (s, 3H), 3.25 (m, 1H), 2.54 (s, 3H), 2.19-1.92 (m, 6H), 1.77 (m, 2H). |
| 240 | 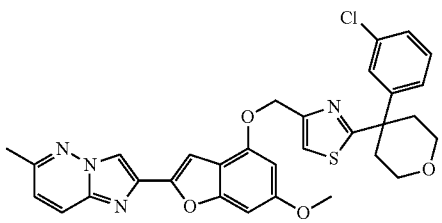 [SMILES: COc1cc(OCc2csc(C3(c4cccc(Cl)c4)CCOCC3)n2)c2cc(-c3cn4nc(C)ccc4n3)oc2c1] | C₃₁H₂₇ClN₄O₄S | 587.1520 | 2.009/F | 587.1564 | ¹H NMR (DMSO-d₆, 400 MHz) δ ppm: 8.53 (s, 1H), 8.01 (d, J = 9.4 Hz, 1H), 7.80 (s, 1H), 7.43-7.35 (m, 3H), 7.30 (dt, J = 2.0, 7.0 Hz, 1H), 7.26 (d, J = 0.8 Hz, 1H), 7.19 (d, J = 9.4 Hz, 1H), 6.88 (m, 1H), 6.65 (d, J = 2.0 Hz, 1H), 5.32 (s, 2H), 3.82 (s, 3H), 3.74 (m, 2H), 3.56 (m, 2H), 2.60 (m, 2H), 2.54 (s, 3H), 2.35 (m, 2H). |
| 241 | 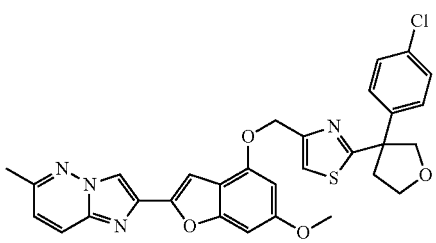 [SMILES: COc1cc(OCc2csc(C3(c4ccc(Cl)cc4)CCOC3)n2)c2cc(-c3cn4nc(C)ccc4n3)oc2c1] | C₃₀H₂₅ClN₄O₄S | 573.1363 | 2.564/F | 573.1397 | ¹H NMR (DMSO-d₆, 400 MHz) δ ppm: 8.54 (s, 1H), 8.01 (d, J = 9.4 Hz, 1H), 7.77 (s, 1H), 7.41 (s, 4H), 7.26 (s, 1H), 7.19 (d, J = 9.4 Hz, 1H), 6.88 (d, J = 0.8 Hz, 1H), 6.63 (d, J = 2.0 Hz, 1H), 5.28 (s, 2H), 4.59 (d, J = 8.6 Hz, 1H), 4.12 (d, J = 8.6 Hz, 1H), 3.97-3.88 (m, 1H), 3.82 (s, 3H), 3.00 (m, 1H), 2.58 (m, 1H), 2.54 (s, 3H). |
| 242 | 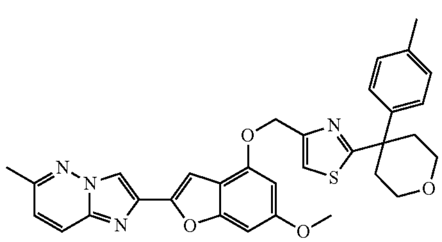 [SMILES: COc1cc(OCc2csc(C3(c4ccc(C)cc4)CCOCC3)n2)c2cc(-c3cn4nc(C)ccc4n3)oc2c1] | C₃₂H₃₀N₄O₄S | 567.2066 | 2.622/F | 567.2117 | ¹H NMR (DMSO-d₆, 400 MHz) δ ppm: 8.54 (s, 1H), 8.01 (d, J = 9.4 Hz, 1H), 7.74 (s, 1H), 7.31 (m, 1H), 7.27 (d, J = 9.4 Hz, 2H), 7.19 (d, J = 9.4 Hz, 1H), 7.14 (d, J = 8.2 Hz, 2H), 6.88 (d, J = 1.2 Hz, 1H), 6.65 (d, J = 2.0 Hz, 1H), 5.30 (s, 2H), 3.82 (s, 3H), 3.74-3.68 (m, 2H), 3.58 (m, 2H), 2.57 (m, 2H), 2.54 (s, 3H), 2.33 (m, 2H), 2.25 (s, 3H). |

Examples 243 to 286 are prepared according to the following procedure:

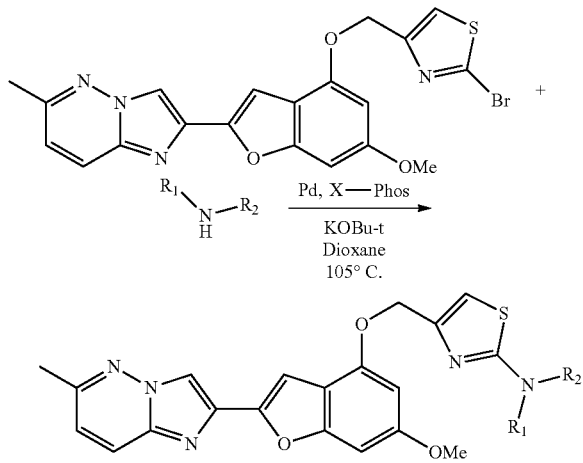

2-Bromo-4-((((6-methoxy-2-(6-methylimidazo[1,2-b]pyridazin-2-yl)benzofuran-4-yl)oxy)methyl)thiazole (Example 205, 15 mg, 0.031 mmol) in dioxane (0.6 mL) was added into a Wheaton tube (16×100 mm) which contains an amine (0.108 mmol) and a stir bar. Then potassium butoxide (8.1 mg, 72 mol) and palladium-chloro(2-dicyclohexylphosphino-2',4',6'-tri-i-propyl-1,1'-biphenyl) [2-(2-aminoethyl)phenyl] palladium(II) methyl-t-butyl ether adduct (2.1 mg, 2.9 μmol) were added into the solution. All tubes were capped and heated at 105° C. in a heating block overnight. All samples were dried by a stream of nitrogen, dissolved in DMF (1.0 mL), filtered with Whatman 0.45 um PVDF filter, and purified by preparative HPLC.

Examples 287 to 317 are prepared according to the following procedure:

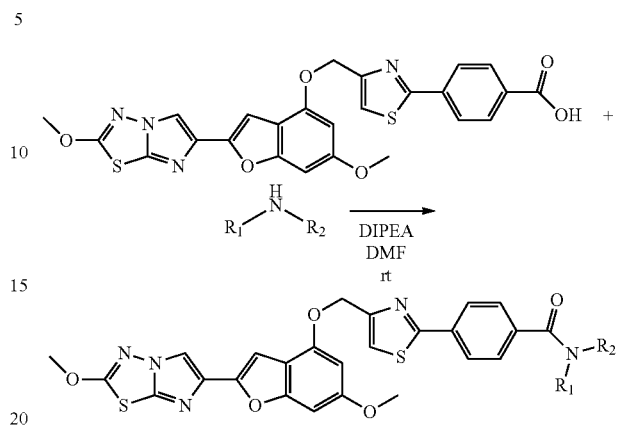

HATU (9.71 mg, 26 μmol) and DIPEA (14 μl, 79 μmol) was added to a solution of 4-(4-(((6-methoxy-2-(2-methoxyimidazo[2,1-b][1,3,4]thiadiazol-6-yl)benzofuran-4-yl)oxy)methyl)thiazol-2-yl)benzoic acid (Example 39D, 10.5 mg, 20 μmol) in DMF (0.6 mL) in a Wheaton tube (16×100 mm). The mixture was stirred at rt for 5 minutes and then the solution of the amine (200 μmol) in DMF was added and the tube was capped and shaken for 2 hours at rt. The crude reaction mixture was purified by preparative HPLC.

In the structures set forth below for Examples 243 to 317, the "—O" attached to a carbon atom is used to denote an "—OH" group. Similarly, in the structures set forth below for Examples 243 to 317, the "N" attached to a carbon atom is used to denote an "NH" moiety.

| Ex. | Structure | Formula Weight | LCMS [M + H]+ m/z | HPLC retention time (min) | HPLC Method |
|---|---|---|---|---|---|
| 243 | 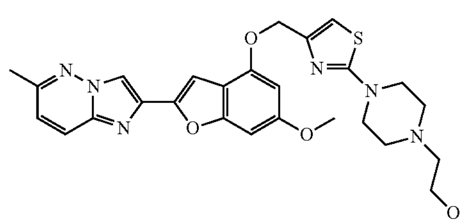 [SMILES: COc1cc(OCc2csc(N3CCN(CCO)CC3)n2)c2cc(-c3cn4nc(C)ccc4n3)oc2c1] | 520.61 | 521.23 | 2.50 | G |
| 244 | 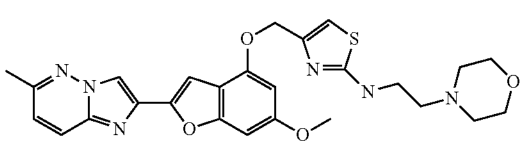 [SMILES: COc1cc(OCc2csc(NCCN3CCOCC3)n2)c2cc(-c3cn4nc(C)ccc4n3)oc2c1] | 520.61 | 521.23 | 4.12 | G |
| 245 | 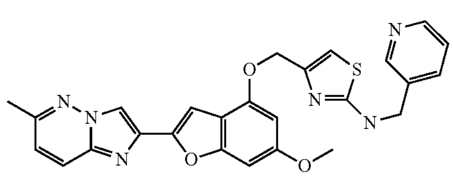 [SMILES: COc1cc(OCc2csc(NCc3cccnc3)n2)c2cc(-c3cn4nc(C)ccc4n3)oc2c1] | 498.57 | 499.19 | 2.64 | H |

| Ex. | Structure | Formula Weight | LCMS [M + H]+ m/z | HPLC retention time (min) | HPLC Method |
|---|---|---|---|---|---|
| 246 | 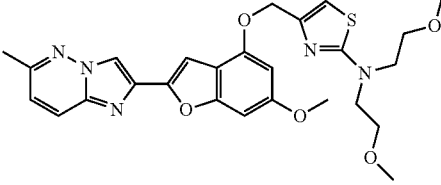 | 523.61 | 524.24 | 3.03 | G |
| 247 | 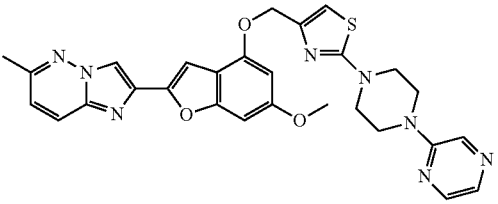 [SMILES: COc1cc(OCc2csc(N3CCN(c4cnccn4)CC3)n2)c2cc(-c3cn4nc(C)ccc4n3)oc2c1] | 554.63 | 553.34 | 4.45 | G |
| 248 | 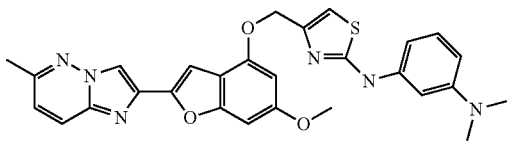 | 526.62 | 527.23 | 4.60 | G |
| 249 | 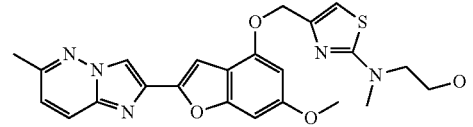 [SMILES: COc1cc(OCc2csc(N(C)CCO)n2)c2cc(-c3cn4nc(C)ccc4n3)oc2c1] | 465.53 | 466.18 | 4.13 | G |
| 250 | 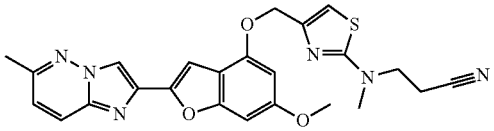 [SMILES: COc1cc(OCc2csc(N(C)CCC#N)n2)c2cc(-c3cn4nc(C)ccc4n3)oc2c1] | 474.54 | 475.17 | 4.12 | G |
| 251 | 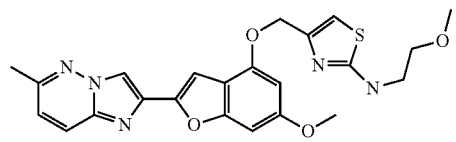 | 465.53 | 466.14 | 4.12 | G |
| 252 | 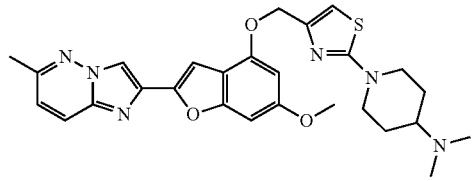 | 518.64 | 519.26 | 2.36 | H |
| 253 | Chiral 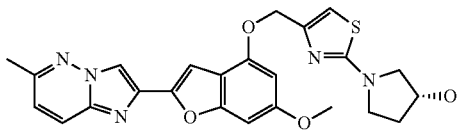 | 477.54 | 478.22 | 4.10 | G |
| 254 | 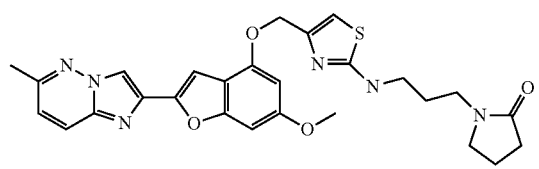 [SMILES: COc1cc(OCc2csc(NCCCN3CCCC3=O)n2)c2cc(-c3cn4nc(C)ccc4n3)oc2c1] | 532.62 | 533.23 | 4.11 | G |

| Ex. | Structure | Formula Weight | LCMS [M + H]+ m/z | HPLC retention time (min) | HPLC Method |
|---|---|---|---|---|---|
| 255 | 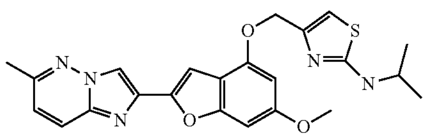 [SMILES: COc1cc(OCc2csc(NC(C)C)n2)c2cc(-c3cn4nc(C)ccc4n3)oc2c1] | 449.53 | 450.19 | 3.08 | H |
| 256 | 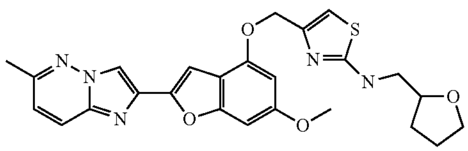 [SMILES: COc1cc(OCc2csc(NCC3CCCO3)n2)c2cc(-c3cn4nc(C)ccc4n3)oc2c1] | 491.57 | 492.20 | 4.26 | G |
| 257 | 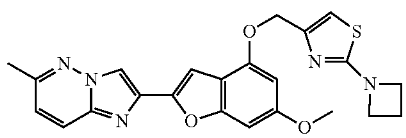 [SMILES: COc1cc(OCc2csc(N3CCC3)n2)c2cc(-c3cn4nc(C)ccc4n3)oc2c1] | 447.52 | 448.02 | 2.96 | H |
| 258 | 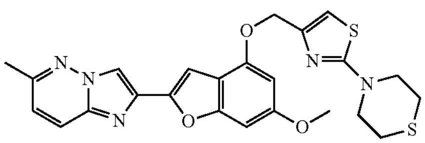 [SMILES: COc1cc(OCc2csc(N3CCSCC3)n2)c2cc(-c3cn4nc(C)ccc4n3)oc2c1] | 493.61 | 494.21 | 3.15 | H |
| 259 | 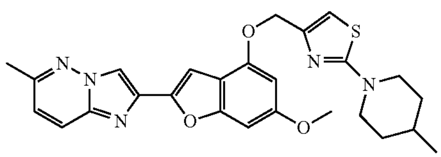 | 489.60 | 490.26 | 4.74 | G |
| 260 | 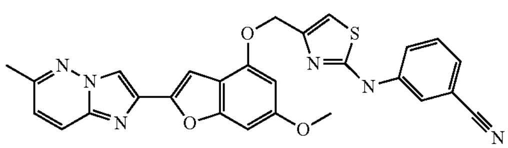 [SMILES: COc1cc(OCc2csc(Nc3cccc(C#N)c3)n2)c2cc(-c3cn4nc(C)ccc4n3)oc2c1] | 508.56 | 509.21 | 3.14 | H |
| 261 | 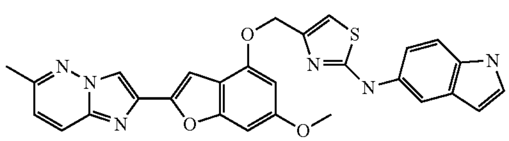 [SMILES: COc1cc(OCc2csc(Nc3ccc4[nH]ccc4c3)n2)c2cc(-c3cn4nc(C)ccc4n3)oc2c1] | 522.59 | 523.20 | 2.96 | H |
| 262 | 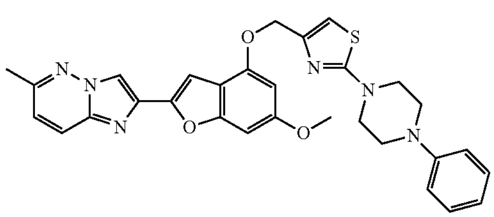 [SMILES: COc1cc(OCc2csc(N3CCN(c4ccccc4)CC3)n2)c2cc(-c3cn4nc(C)ccc4n3)oc2c1] | 552.66 | 553.03 | 3.54 | H |
| 263 | 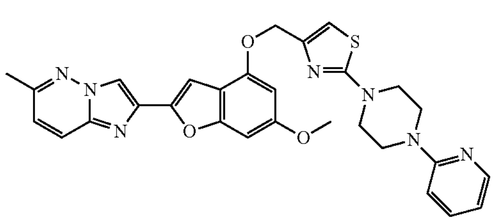 [SMILES: COc1cc(OCc2csc(N3CCN(c4ccccn4)CC3)n2)c2cc(-c3cn4nc(C)ccc4n3)oc2c1] | 553.64 | 554.01 | 3.27 | H |

| Ex. | Structure | Formula Weight | LCMS [M + H]+ m/z | HPLC retention time (min) | HPLC Method |
|---|---|---|---|---|---|
| 264 | 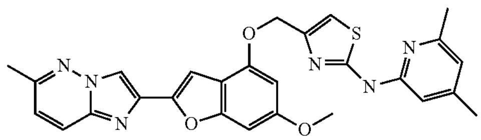 | 512.59 | 513.26 | 4.73 | G |
| 265 | 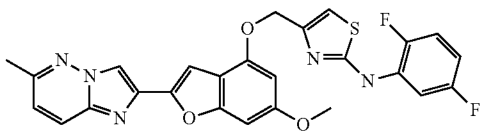 [SMILES: COc1cc(OCc2csc(Nc3cc(F)ccc3F)n2)c2cc(-c3cn4nc(C)ccc4n3)oc2c1] | 519.53 | 520.19 | 3.33 | H |
| 266 | 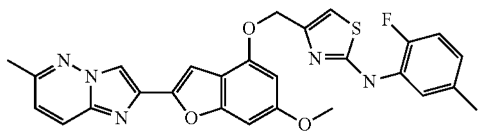 | 515.57 | 516.23 | 3.36 | H |
| 267 | 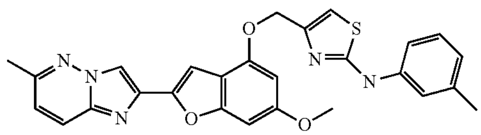 | 497.58 | 498.22 | 4.59 | G |
| 268 | 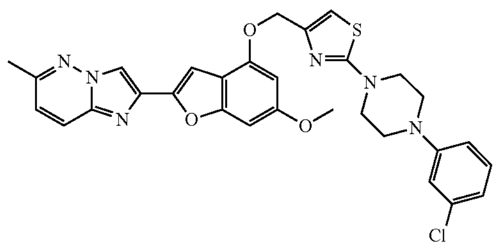 [SMILES: COc1cc(OCc2csc(N3CCN(c4cccc(Cl)c4)CC3)n2)c2cc(-c3cn4nc(C)ccc4n3)oc2c1] | 587.10 | 587.17 | 3.68 | H |
| 269 | 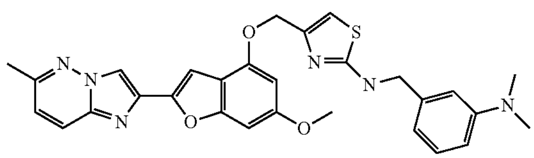 | 540.65 | 541.27 | 3.22 | H |
| 270 | 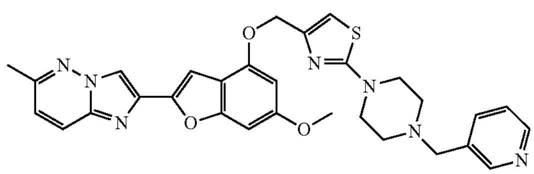 [SMILES: COc1cc(OCc2csc(N3CCN(Cc4cccnc4)CC3)n2)c2cc(-c3cn4nc(C)ccc4n3)oc2c1] | 567.67 | 568.26 | 2.86 | H |
| 271 | 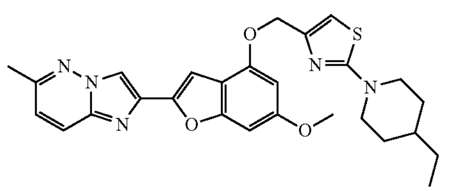 [SMILES: CCC1CCN(c2nc(COc3cc(OC)cc4oc(-c5cn6nc(C)ccc6n5)cc34)cs2)CC1] | 503.63 | 504.05 | 3.74 | H |
| 272 | 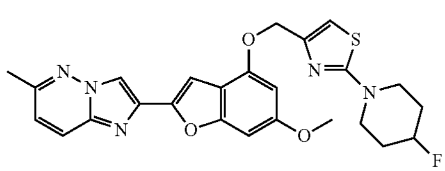 [SMILES: COc1cc(OCc2csc(N3CCC(F)CC3)n2)c2cc(-c3cn4nc(C)ccc4n3)oc2c1] | 493.56 | 494.24 | 3.11 | H |

-continued

| Ex. | Structure | Formula Weight | LCMS [M + H]+ m/z | HPLC retention time (min) | HPLC Method |
|---|---|---|---|---|---|
| 273 | 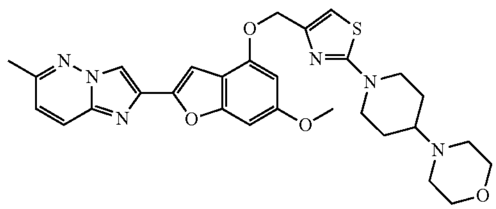 [SMILES: COc1cc(OCc2csc(N3CCC(N4CCOCC4)CC3)n2)c2cc(-c3cn4nc(C)ccc4n3)oc2c1] | 560.68 | 561.02 | 2.77 | H |
| 274 | Chiral | 475.57 | 476.04 | 3.31 | H |
| 275 | Chiral | 475.57 | 476.06 | 3.31 | H |
| 276 | 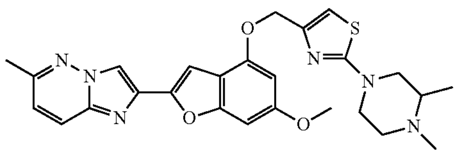 | 504.61 | 505.24 | 4.34 | G |
| 277 | 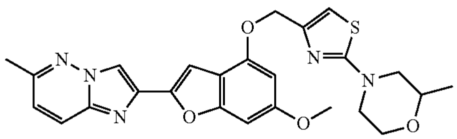 | 491.57 | 492.22 | 4.38 | G |
| 278 | 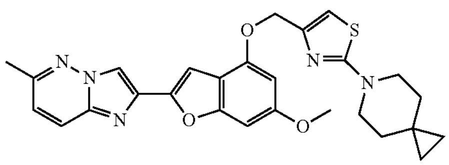 [SMILES: COc1cc(OCc2csc(N3CCC4(CC3)CC4)n2)c2cc(-c3cn4nc(C)ccc4n3)oc2c1] | 501.61 | 502.24 | 3.52 | H |
| 279 | 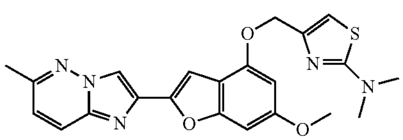 | 435.51 | 436.21 | 2.88 | H |
| 280 | 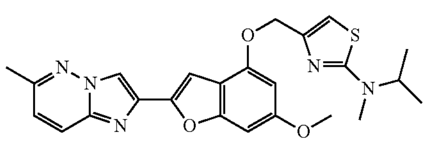 [SMILES: COc1cc(OCc2csc(N(C)C(C)C)n2)c2cc(-c3cn4nc(C)ccc4n3)oc2c1] | 463.56 | 464.06 | 3.30 | H |
| 281 | 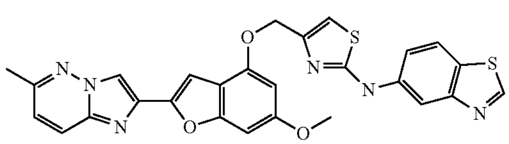 | 540.63 | 541.16 | 4.37 | G |

| Ex. | Structure | Formula Weight | LCMS [M + H]+ m/z | HPLC retention time (min) | HPLC Method |
|---|---|---|---|---|---|
| 282 | 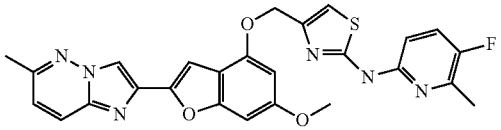 [SMILES: COc1cc(OCc2csc(Nc3ccc(F)c(C)n3)n2)c2cc(-c3cn4nc(C)ccc4n3)oc2c1] | 516.56 | 517.18 | 4.65 | G |
| 283 | 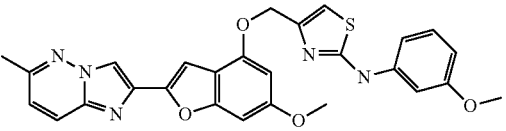 | 513.58 | 514.21 | 3.17 | H |
| 284 | 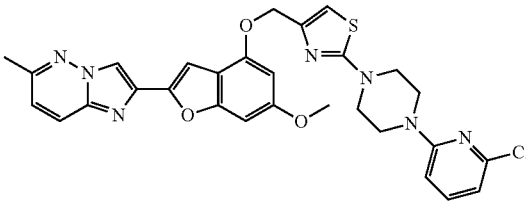 [SMILES: COc1cc(OCc2csc(N3CCN(c4cccc(Cl)n4)CC3)n2)c2cc(-c3cn4nc(C)ccc4n3)oc2c1] | 588.09 | 587.96 | 3.62 | H |
| 285 | 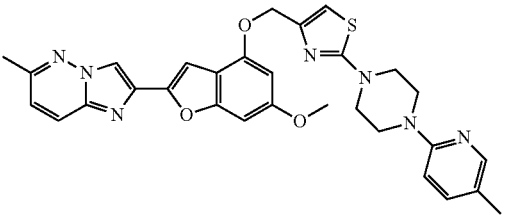 | 567.67 | 568.24 | 4.60 | G |
| 286 | 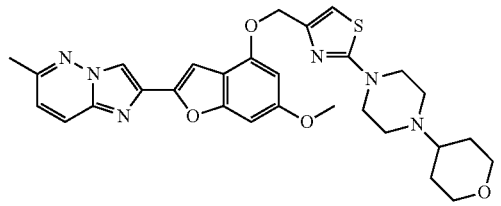 | 560.68 | 561.28 | 2.77 | H |
| 287 | 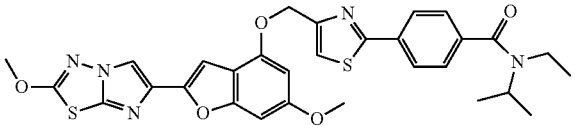 [SMILES: CCN(C(=O)c1ccc(-c2nc(COc3cc(OC)cc4oc(-c5cn6nc(OC)sc6n5)cc34)cs2)cc1)C(C)C] | 603.723 | 604.4 | 3.38 | H |
| 288 | 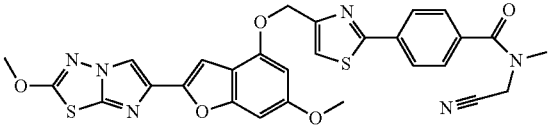 | 586.6521 | 587.4 | 3.04 | H |
| 289 | 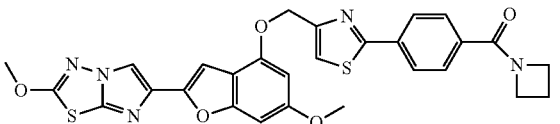 | 573.6533 | 574.4 | 3.00 | H |
| 290 | 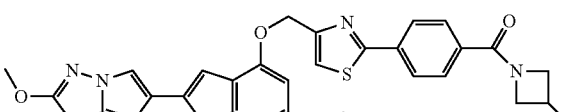 | 589.6527 | 590.4 | 4.06 | G |

-continued
| Ex. | Structure | Formula Weight | LCMS [M + H]+ m/z | HPLC retention time (min) | HPLC Method |
|---|---|---|---|---|---|
| 291 | 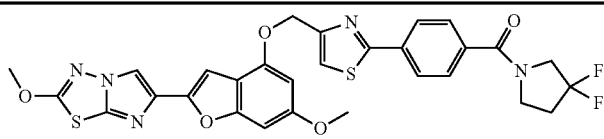 | 623.6611 | 624.5 | 4.31 | G |
| 292 | 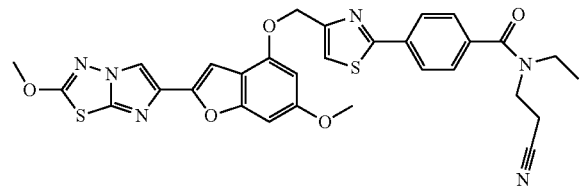 [SMILES: CCN(CCC#N)C(=O)c1ccc(-c2nc(COc3cc(OC)cc4oc(-c5cn6nc(OC)sc6n5)cc34)cs2)cc1] | 614.7059 | 615.5 | 4.17 | G |
| 293 | 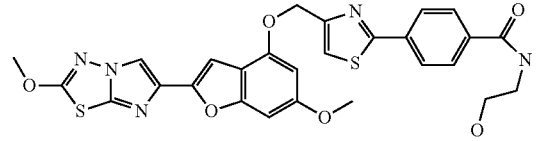 [SMILES: COc1cc(OCc2csc(-c3ccc(C(=O)NCCO)cc3)n2)c2cc(-c3cn4nc(OC)sc4n3)oc2c1] | 577.6417 | 578.4 | 4.05 | G |
| 294 | 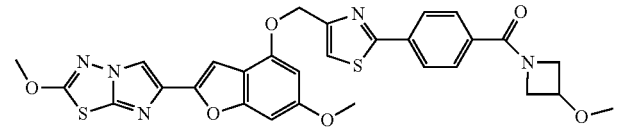 | 603.6796 | 604.4 | 4.24 | G |
| 295 | 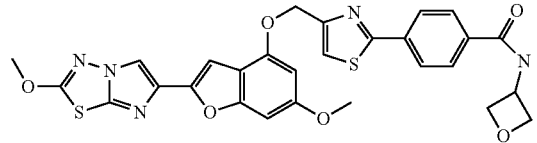 [SMILES: COc1cc(OCc2csc(-c3ccc(C(=O)NC4COC4)cc3)n2)c2cc(-c3cn4nc(OC)sc4n3)oc2c1] | 589.6527 | 590.5 | 3.87 | G |
| 296 | 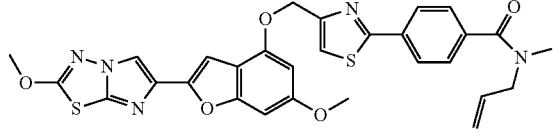 | 587.6802 | 588.4 | 4.36 | G |
| 297 | 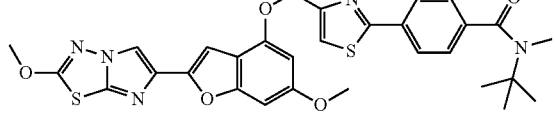 | 603.723 | 604.5 | 4.52 | G |
| 298 | 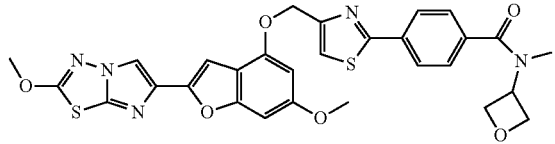 | 603.6796 | 604.4 | 4.13 | G |
| 299 | 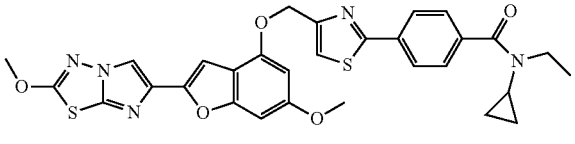 [SMILES: CCN(C(=O)c1ccc(-c2nc(COc3cc(OC)cc4oc(-c5cn6nc(OC)sc6n5)cc34)cs2)cc1)C1CC1] | 601.7071 | 602.5 | 4.43 | G |
| 300 | 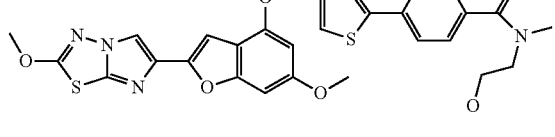 | 591.6686 | 592.5 | 4.09 | G |

-continued

| Ex. | Structure | Formula Weight | LCMS [M + H]+ m/z | HPLC retention time (min) | HPLC Method |
|---|---|---|---|---|---|
| 301 | 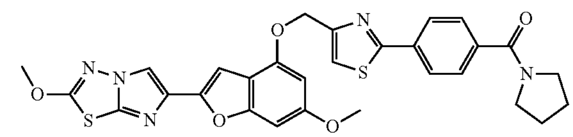 [SMILES: COc1cc(OCc2csc(-c3ccc(C(=O)N4CCCC4)cc3)n2)c2cc(-c3cn4nc(OC)sc4n3)oc2c1] | 587.6802 | 588.7 | 4.42 | G |
| 302 | 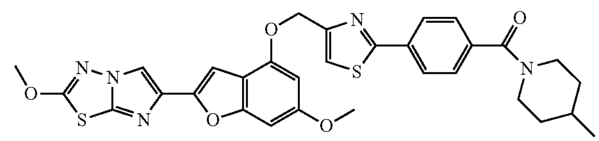 | 615.734 | 616.4 | 4.53 | G |
| 303 | 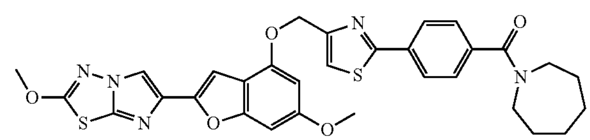 [SMILES: COc1cc(OCc2csc(-c3ccc(C(=O)N4CCCCCC4)cc3)n2)c2cc(-c3cn4nc(OC)sc4n3)oc2c1] | 615.734 | 616.4 | 4.50 | G |
| 304 | 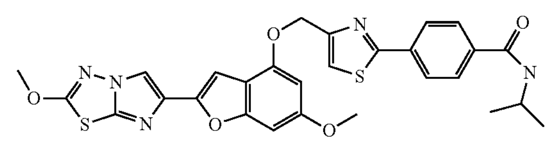 [SMILES: COc1cc(OCc2csc(-c3ccc(C(=O)NC(C)C)cc3)n2)c2cc(-c3cn4nc(OC)sc4n3)oc2c1] | 575.6692 | 576.4 | 4.28 | G |
| 305 | 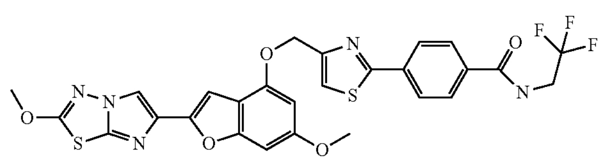 [SMILES: COc1cc(OCc2csc(-c3ccc(C(=O)NCC(F)(F)F)cc3)n2)c2cc(-c3cn4nc(OC)sc4n3)oc2c1] | 615.6137 | 616.5 | 4.35 | G |
| 306 | 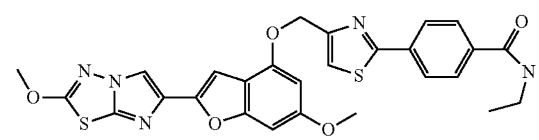 [SMILES: CCNC(=O)c1ccc(-c2nc(COc3cc(OC)cc4oc(-c5cn6nc(OC)sc6n5)cc34)cs2)cc1] | 561.6423 | 562.4 | 4.20 | G |
| 307 | 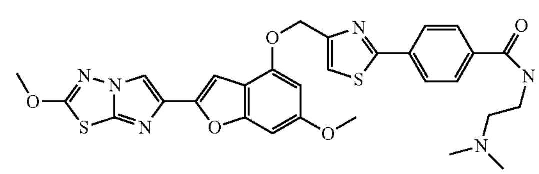 [SMILES: COc1cc(OCc2csc(-c3ccc(C(=O)NCCN(C)C)cc3)n2)c2cc(-c3cn4nc(OC)sc4n3)oc2c1] | 604.7108 | 605.5 | 4.04 | G |
| 308 | 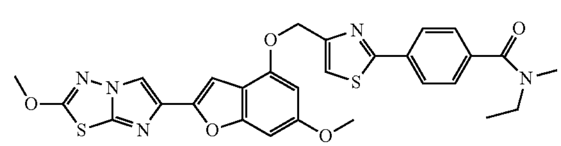 | 575.6692 | 576.4 | 4.27 | G |
| 309 | 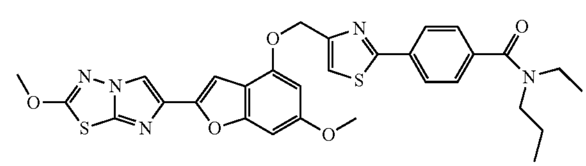 [SMILES: CCCN(CC)C(=O)c1ccc(-c2nc(COc3cc(OC)cc4oc(-c5cn6nc(OC)sc6n5)cc34)cs2)cc1] | 603.723 | 604.5 | 4.54 | G |
| 310 | 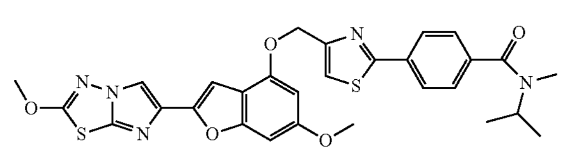 | 589.6961 | 590.5 | 4.37 | G |

| Ex. | Structure | Formula Weight | LCMS [M + H]+ m/z | HPLC retention time (min) | HPLC Method |
|---|---|---|---|---|---|
| 311 | 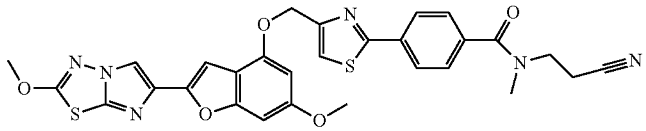 [SMILES: COc1cc(OCc2csc(-c3ccc(C(=O)N(C)CCC#N)cc3)n2)c2cc(-c3cn4nc(OC)sc4n3)oc2c1] | 714.7029 | 601.5 | 4.12 | G |
| 312 | 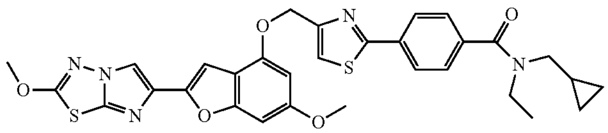 [SMILES: CCN(CC1CC1)C(=O)c1ccc(-c2nc(COc3cc(OC)cc4oc(-c5cn6nc(OC)sc6n5)cc34)cs2)cc1] | 615.734 | 616.4 | 4.53 | G |
| 313 | 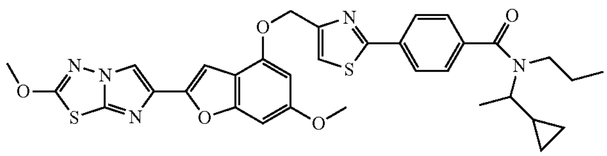 [SMILES: CCCN(C(=O)c1ccc(-c2nc(COc3cc(OC)cc4oc(-c5cn6nc(OC)sc6n5)cc34)cs2)cc1)C(C)C1CC1] | 643.7877 | 644.4 | 4.68 | G |
| 314 | 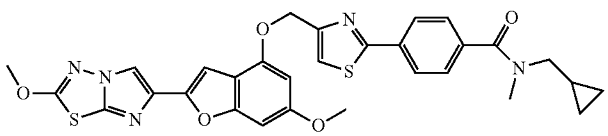 [SMILES: COc1cc(OCc2csc(-c3ccc(C(=O)N(C)CC4CC4)cc3)n2)c2cc(-c3cn4nc(OC)sc4n3)oc2c1] | 601.7071 | 602.3 | 4.45 | G |
| 315 | 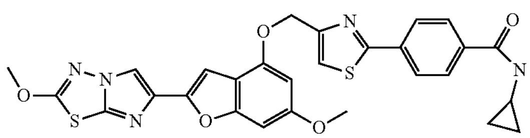 [SMILES: COc1cc(OCc2csc(-c3ccc(C(=O)NC4CC4)cc3)n2)c2cc(-c3cn4nc(OC)sc4n3)oc2c1] | 573.6533 | 574.3 | 4.26 | G |
| 316 | 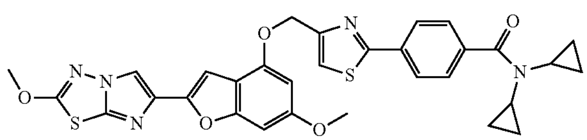 [SMILES: COc1cc(OCc2csc(-c3ccc(C(=O)N(C4CC4)C4CC4)cc3)n2)c2cc(-c3cn4nc(OC)sc4n3)oc2c1] | 613.7181 | 614.4 | 4.45 | G |
| 317 | 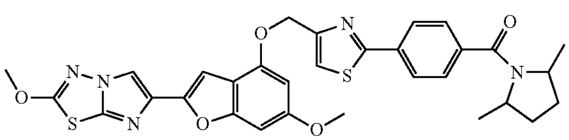 | 615.734 | 616.3 | 4.50 | G |

Example 318

Tritium Labeled 2-Methoxy-6-(6-methoxy-4-((2-phenylthiazol-4-yl)methoxy)benzofuran-2-yl)imidazo[2,1-b][1,3,4]thiadiazole

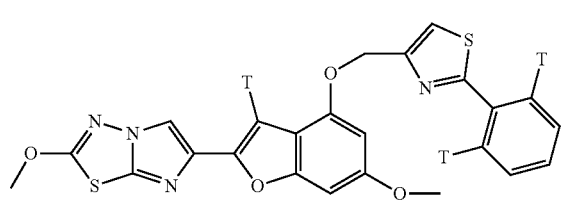

A Trisorber flask with stirbar was charged with 2-methoxy-6-(6-methoxy-4-((2-phenylthiazol-4-yl)methoxy)benzofuran-2-yl)imidazo[2,1-b][1,3,4]thiadiazole (Example 3, 0.50 mg, 1.02 μmol) and Crabtree's catalyst (((SP-4)tris(cyclohexyl)phosphane[(1-2-η:5-6-η)-cyclocta-1,5-diene]pyridineiridium hexafluoridophosphate) (2.3 mg, 2.86 μmol). To this was added $CH_2Cl_2$ (0.50 ml) by syringe. The flask was attached to the Trisorber and submitted to freeze, pump and thaw cycles to remove dissolved gases. To the reaction mixture was added 1.0 Ci of Tritium gas and the mixture was stirred at room temperature. After 18 h, the $CH_2Cl_2$ was removed by rotovap. The crude product was dissolved in ethanol and the labile tritium was exchanged as the ethanol was removed by rotovap. This was repeated two additional times. The crude product was dissolved in 5.0 ml of ethanol. An aliquot of the crude mixture (20 μl) was diluted in 5.0 ml of ethanol. A 20 μl aliquot of this diluted solution was counted by Liquid Scintillation Counting and showed 207 mCi of tritiated material to be present. HPLC analysis (AGILENT® 1100 HPLC with a BetaRam radiochemical detector, column=PHENOMENEX® Luna 5 um C18(2), 250×4.6 mm Mobile Phase A=100 Water: 1 TFA, Mobile Phase B=1000 Acetonitrile: 1 TFA. Gradient=0 min 90% B, 8 min 90% B, 15 min 100% B, flowrate=1.0 ml/min) showed the crude product mixture contained 8.5% of the desired product (retention time=6.4 min). The crude product was purified by Semi-preparative HPLC (AGILENT® 1100 HPLC, Column=PHENOMENEX® Luna, 5 um C18(2), 10×250 mm, Mobile phase A=700 $CH_3CN$: 300 Water with 0.1% TFA, Mobile phase B=MeOH, Gradient=0 min 100% A, 25 min 100% A, 30 min 100% B, Flowrate=4.0 ml/min, UV detection at 305 nm. The fractions containing product were collected with retention times between 20.2 to 23.5 min. Collected fractions were pooled and the solvent removed by rotovap. The resulting product was dissolved in 8.5 ml of 90:10 Ethanol:Water to produce a 1.0 mCi/ml solution, 8.5 mCi total. HPLC/Rad analysis (AGILENT® 1100 HPLC system, column=PHENOMENEX® Luna 5 um C18(2), 4.6×150 mm, Mobile phase A=Water 1000:1 TFA, Mobile phase D=Acetonitrile. Gradient=0 min 65% D, 20 min 65% D, 25 min 100% D, 35 min 100% D, flowrate=1.2 ml/min; UV detection at 305 nm, retention time=11.95 min, 99.74% radiochemically pure. LC/MS analysis (+ ion) showed m/z=491/492/493/494/495/486/497/498/499. The specific activity was determined by LC/MS by comparison to the LC/MS analysis of unlabeled Example 3 and was 42.5 Ci/mmol. $^3$H-NMR (320 MHz, DMSO-$D_6$) δ 8.02 (s, T), 7.09 (s, T).

BIOLOGY

The term "PAR4 antagonist" denotes an inhibitor of platelet aggregation which binds PAR4 and inhibits PAR4 cleavage and/or signaling. Typically, PAR4 activity is reduced in a dose dependent manner by at least 10%, 20%, 30%, 40%, 50%, 60%, 70%, 80%, 90%, or 100% compared to such activity in a control cell. The control cell is a cell that has not been treated with the compound. PAR4 activity is determined by any standard method in the art, including those described herein (for example calcium mobilization in PAR4 expressing cells, platelet aggregation, platelet activation assays measuring e.g., calcium mobilization, p-selectin or CD40 L release, or thrombosis and hemostasis models). The term "PAR4 antagonist" also includes a compound that inhibits both PAR1 and PAR4.

It is desirable to find compounds with advantageous and improved characteristics compared with known anti-platelet agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; (h) improved therapeutic index with less propensity for bleeding; and (h) factors that improve manufacturing costs or feasibility.

The term "compound", as used herein, means a chemical, be it naturally-occurring or artificially-derived. Compounds may include, for example, peptides, polypeptides, synthetic organic molecules, naturally occurring organic molecules, nucleic acid molecules, peptide nucleic acid molecules, and components and derivatives thereof.

As used herein, the term "patient" encompasses all mammalian species.

As used herein, the term "subject" refers to any human or nonhuman organism that could potentially benefit from treatment with a PAR4 antagonist. Exemplary subjects include human beings of any age with risk factors for cardiovascular disease, or patients that have already experienced one episode of cardiovascular disease. Common risk factors include, but are not limited to, age, male sex, hypertension, smoking or smoking history, elevation of triglycerides, elevation of total cholesterol or LDL cholesterol.

In some embodiments, the subject is a species having a dual PAR1/PAR4 platelet receptor repertoire. As used herein, the term "dual PAR1/PAR4 platelet receptor repertoire" means that a subject expresses PAR1 and PAR4 in platelets or their precursors. Exemplary subjects having a dual PAR1/PAR4 platelet receptor repertoire include human beings, non-human primates, and guinea pigs.

In other embodiments, the subject is a species having a dual PAR3/PAR4 platelet receptor repertoire. As used herein, the term "dual PAR3/PAR4 platelet receptor repertoire" means that a subject expresses PAR3 and PAR4 in platelets or their precursors. Exemplary subjects having a dual PAR3/PAR4 platelet receptor repertoire include rodents and rabbits.

As used herein, "treating" or "treatment" cover the treatment of a disease-state in a mammal, particularly in a human, and include: (a) inhibiting the disease-state, i.e., arresting its development; and/or (b) relieving the disease-state, i.e., causing regression of the disease state.

As used herein, "prophylaxis" or "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit and/or antagonize PAR4 and/or to prevent or treat the disorders listed herein. When applied to a combination, the term refers to combined amounts of the active ingredients that result in the preventive or therapeutic effect, whether administered in combination, serially, or simultaneously.

The term "thrombosis", as used herein, refers to formation or presence of a thrombus (pl. thrombi) within a blood vessel that may cause ischemia or infarction of tissues supplied by the vessel. The term "embolism", as used herein, refers to sudden blocking of an artery by a clot or foreign material that has been brought to its site of lodgment by the blood current. The term "thromboembolism", as used herein, refers to obstruction of a blood vessel with thrombotic material carried by the blood stream from the site of origin to plug another vessel. The term "thromboembolic disorders" entails both "thrombotic" and "embolic" disorders (defined above).

The term "thromboembolic disorders" as used herein includes arterial cardiovascular thromboembolic disorders, venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and hemodialysis. In another embodiment, the term "thromboembolic disorders" includes acute coronary syndrome, stroke, deep vein thrombosis, and pulmonary embolism.

In another embodiment, the present invention provides a method for the treatment of a thromboembolic disorder, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the treatment of a thromboembolic disorder, wherein the thromboembolic disorder is selected from acute coronary syndrome, stroke, venous thrombosis, atrial fibrillation, and thrombosis resulting from medical implants and devices.

In another embodiment, the present invention provides a method for the primary prophylaxis of a thromboembolic disorder, wherein the thromboembolic disorder is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the primary prophylaxis of a thromboembolic disorder, wherein the thromboembolic disorder is selected from acute coronary syndrome, stroke, venous thrombosis, and thrombosis resulting from medical implants and devices.

In another embodiment, the present invention provides a method for the secondary prophylaxis of a thromboembolic disorder, wherein the thromboembolic disorder is selected from unstable angina, an acute coronary syndrome, atrial fibrillation, recurrent myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the secondary prophylaxis of a thromboembolic disorder, wherein the thromboembolic disorder is selected from acute coronary syndrome, stroke, atrial fibrillation and venous thrombosis.

The term "stroke", as used herein, refers to embolic stroke or atherothrombotic stroke arising from occlusive thrombosis in the carotid communis, carotid interna, or intracerebral arteries.

It is noted that thrombosis includes vessel occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy.

Thromboembolic disorders are frequently associated with patients with atherosclerosis. Risk factors for atherosclerosis include but are not limited to male gender, age, hypertension, lipid disorders, and diabetes mellitus. Risk factors for atherosclerosis are at the same time risk factors for complications of atherosclerosis, i.e., thromboembolic disorders.

Similarly, arterial fibrillation is frequently associated with thromboembolic disorders. Risk factors for arterial fibrillation and subsequent thromboembolic disorders include cardiovascular disease, rheumatic heart disease, nonrheumatic mitral valve disease, hypertensive cardiovascular disease, chronic lung disease, and a variety of miscellaneous cardiac abnormalities as well as thyrotoxicosis.

Diabetes mellitus is frequently associated with atherosclerosis and thromboembolic disorders. Risk factors for the more common type 2 include but are not limited to family history, obesity, physical inactivity, race/ethnicity, previously impaired fasting glucose or glucose tolerance test, history of gestational diabetes mellitus or delivery of a "big baby", hypertension, low HDL cholesterol, and polycystic ovary syndrome.

Thrombosis has been associated with a variety of tumor types, e.g., pancreatic cancer, breast cancer, brain tumors, lung cancer, ovarian cancer, prostate cancer, gastrointestinal malignancies, and Hodgkins or non-Hodgkins lymphoma. Recent studies suggest that the frequency of cancer in patients with thrombosis reflects the frequency of a particular cancer type in the general population. (Levitan, N. et al., *Medicine* (Baltimore), 78(5):285-291 (1999); Levine M. et al., *N. Engl. J. Med.,* 334(11):677-681 (1996); Blom, J. W. et al., *JAMA,* 293(6):715-722 (2005).) Hence, the most common cancers associated with thrombosis in men are prostate, colorectal, brain, and lung cancer, and in women are breast, ovary, and lung cancer. The observed rate of venous thromboembolism (VTE) in cancer patients is significant. The varying rates of VTE between different tumor types are most likely related to the selection of the patient population. Cancer patients at risk for thrombosis may possess any or all of the following risk factors: (i) the stage of the cancer (i.e., presence of metastases), (ii) the presence of central vein catheters, (iii) surgery and anticancer therapies including chemotherapy, and (iv) hormones and antiangiogenic drugs. Thus, it is common clinical practice to dose patients having advanced tumors with heparin or low molecular heparin to prevent thromboembolic disorders. A number of low molecular weight heparin preparations have been approved by the FDA for these indications.

The term "pharmaceutical composition", as used herein, means any composition, which contains at least one therapeutically or biologically active agent and is suitable for administration to the patient. Any of these formulations can be prepared by well-known and accepted methods of the art. See, for example, Gennaro, A. R., ed., *Remington: The Science and Practice of Pharmacy*, 20th Edition, Mack Publishing Co., Easton, Pa. (2000).

The invention includes administering to a subject a pharmaceutical composition that includes a compound that binds to PAR4 and inhibits PAR4 cleavage and/or signaling (referred to herein as a "PAR4 antagonist" or "therapeutic compound").

The compounds of this disclosure can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The preferred dose of the PAR4 antagonist is a biologically active dose. A biologically active dose is a dose that will inhibit cleavage and/or signaling of PAR4 and have an anti-thrombotic effect. Desirably, the PAR4 antagonist has the ability to reduce the activity of PAR4 by at least 5%, 10%, 20%, 30%, 40%, 50%, 60%, 70%, 80%, 90%, 100%, or more than 100% below untreated control levels. The levels of PAR4 in platelets is measured by any method known in the art, including, for example, receptor binding assay, platelet aggregation, platelet activation assays (e.g., p-selectin expression by FACS), Western blot or ELISA analysis using PAR4 cleavage sensitive antibodies. Alternatively, the biological activity of PAR4 is measured by assessing cellular signaling elicited by PAR4 (e.g., calcium mobilization or other second messenger assays).

In some embodiments, a therapeutically effective amount of a PAR4 compound is preferably from about less than 100 mg/kg, 50 mg/kg, 10 mg/kg, 5 mg/kg, 1 mg/kg, or less than 1 mg/kg. In a more preferred embodiment, the therapeutically effective amount of the PAR4 compound is less than 5 mg/kg. In a most preferred embodiment, the therapeutically effective amount of the PAR4 compound is less than 1 mg/kg. Effective doses vary, as recognized by those skilled in the art, depending on route of administration and excipient usage.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration may contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Dispersion

A spray dried dispersion can be prepared for oral administration by methods know to one skilled in the art.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where two or more of the foregoing second therapeutic agents are administered with the compound of Formula I, IA, IB, IC, ID, IE or IF, preferably, a compound selected from one of the examples, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of the examples and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Additionally, certain compounds disclosed herein may be useful as metabolites of other compounds. Therefore, in one embodiment, compounds may be useful either as a substantially pure compound, which may also then be incorporated into a pharmaceutical composition, or may be useful as metabolite which is generated after administration of the prodrug of that compound. In one embodiment, a compound may be useful as a metabolite by being useful for treating disorders as described herein.

The activity of the PAR4 antagonists of the present invention can be measured in a variety of in vitro assays. Exemplary assays are shown in the Examples below.

The FLIPR assay is an exemplary in vitro assay for measuring the activity of the PAR4 antagonists of the present invention. In this assay, intracellular calcium mobilization is induced in PAR4 expressing cells by a PAR4 agonist and calcium mobilization is monitored. See, e.g., Example A.

AYPGKF is a known PAR4 agonist. An alternative PAR4 agonist is H-Ala-Phe(4-F)-Pro-Gly-Trp-Leu-Val-Lys-Asn-Gly-$NH_2$. As shown in Example B below, H-Ala-Phe(4-F)-Pro-Gly-Trp-Leu-Val-Lys-Asn-Gly-$NH_2$ was validated as a PAR4 agonist in the FLIPR assay. A side-by-side comparison of the $IC_{50}$ values of ~180 compounds were performed using AYPGKF versus H-Ala-Phe(4-F)-Pro-Gly-Trp-Leu-Val-Lys-Asn-Gly-$NH_2$. The results demonstrated a strong correlation between the two assays. Additionally, H-Ala-Phe(4-F)-Pro-Gly-Trp-Leu-Val-Lys-Asn-Gly-$NH_2$ has improved agonist activity as compared to AYPGKF with an $EC_{50}$ that is 10 fold lower than the $EC_{50}$ for AYPGKF in the FLIPR assay. H-Ala-Phe(4-F)-Pro-Gly-Trp-Leu-Val-Lys-Asn-Gly-$NH_2$ can be synthesized using methods well known to those of skill in the art.

The FLIPR assay can also be used as a counterscreen to test agonist activity or PAR1 antagonist activity in a cell line that expresses both PAR1 and PAR4. The PAR1 antagonist activity can be tested by the ability of the compound to inhibit calcium mobilization induced by the PAR1 agonist peptide SFLLRN or other PAR1 agonist peptides.

The compounds of the current invention can be tested in vitro for their ability to inhibit platelet aggregation induced by gamma-thrombin as shown in Example C. Gamma-thrombin, a proteolytic product of alpha-thrombin which no longer interacts with PAR1, selectively cleaves and activates PAR4 (Soslau, G. et al., "Unique pathway of thrombin-induced platelet aggregation mediated by glycoprotein Ib", J. Biol. Chem., 276:21173-21183 (2001)). Platelet aggregation can be monitored in a 96-well microplate aggregation assay format or using standard platelet aggregometer. The aggregation assay can also be employed to test the selectivity of the compound for inhibiting platelet aggregation induced by PAR4 agonist peptides, PAR1 agonist peptide, ADP, or thromboxane analogue U46619.

Example D is an alpha-thrombin-induced platelet aggregation assay. Alpha-thrombin activates both PAR1 and PAR4. The ability of a selective PAR4 antagonist of the present invention, namely, the Example 3 compound to inhibit platelet aggregation was measured using a standard optical aggregometer. Inhibition of alpha-thrombin induced platelet aggregation by the Example 3 compound is shown in FIGS. 1A and 1B. The data shows, for the first time in the art, that a PAR4 antagonist alone can effectively inhibit platelet aggregation. The extent of platelet inhibition by the PAR4 antagonist is at least comparable to what has been previously described for PAR1 antagonists.

Example E is a tissue factor-induced platelet aggregation assay. The conditions in this assay mimic the physiological events during thrombus formation. In this assay, platelet aggregation in human PRP was initiated by the addition of tissue factor and $CaCl_2$. Tissue factor, the initiator of the extrinsic coagulation cascade, is highly elevated in human atherosclerotic plaque. Exposure of blood to tissue factor at the atherosclerotic site triggers a robust generation of thrombin and induces the formation of obstructive thrombi.

The efficacy of the PAR4 antagonists of the present invention in preventing thrombosis can also be measured in a variety of in vivo assays. Exemplary mammals that can provide models of thrombosis and hemostasis to test the effectiveness of the PAR4 antagonists of the present invention as antithrombotic agents include, but are not limited to, guinea pigs and primates. Relevant efficacy models include, but are not limited to, electrolytic injury-induced carotid artery thrombosis, $FeCl_3$-induced carotid artery thrombosis and arteriovenous-shunt thrombosis. Models of kidney bleeding time, renal bleeding time and other bleeding time measurements can be used to assess the bleeding risk of the antithrombotic agents described in the current invention. Example G describes an in vivo model of arterial thrombosis in cynolmolgus monkeys. Compounds of the present invention can be tested in this model for their ability to inhibit thrombus formation induced by electrolytic injury of the carotid artery. Demonstration of efficacy in this model supports the utility of PAR4 antagonists of the present invention for treatment of thromboembolic diseases.

ASSAYS

Materials
1) PAR1 and PAR4 Agonist Peptides

SFFLRR is a known high affinity PAR1 selective agonist peptide. (Reference: Seiler, S. M., "Thrombin receptor antagonists", Seminars in Thrombosis and Hemostasis, 22(3):223-232 (1996).) The PAR4 agonist peptides AYPGKF and H-Ala-Phe(4-F)-Pro-Gly-Trp-Leu-Val-Lys-Asn-Gly-$NH_2$ were synthesized. H-Ala-Phe(4-F)-Pro-Gly-Trp-Leu-Val-Lys-Asn-Gly-$NH_2$ showed improved PAR4 agonist activity over AYPGKF in the FLIPR assay ($EC_{50}$ of 8 µM for H-Ala-Phe(4-F)-Pro-Gly-Trp-Leu-Val-Lys-Asn-Gly-$NH_2$ and 60 µM for AYPGKF) and in washed platelet aggregation assay ($EC_{50}$ of 0.9 µM for H-Ala-Phe(4-F)-Pro-Gly-Trp-Leu-Val-Lys-Asn-Gly-$NH_2$ and 12 µM for AYPGKF).

2) PAR4 Expressing Cells

HEK293 cells stably expressing PAR4 were generated by a standard method of transfection of human F2R23 cDNA expression vector or by RAGE technology from Athersys Inc. (Cleveland, Ohio) and selected based on PAR4 protein expression of mRNA expression. Those cells demonstrated functional responses to PAR4 agonist peptide-induced intracellular calcium elevation using FLIPR (Fluorometric Imaging Plate Reader; Molecular Devices Corp.). These cells express endogenous PAR1 and can elicit calcium signal upon stimulation with PAR1 agonist peptide. Cells were grown in Dulbecco's Modified Eagle's Medium (DMEM) (Invitrogen, Carlsbad, Calif.), 10% FBS, 1% PSG, 3 µg/ml puromycin and 25 nM Methotrexate) at 37° C. with 5% $CO_2$.

3) Preparation of Platelet Rich Plasma (PRP)

Human blood was collected in 3.8% sodium citrate at a ratio of 1 ml per 9 ml blood. The platelet rich plasma was isolated by centrifugation at 170 g for 14 minutes.

4) Preparation of Washed Platelets (WP)

Human blood was collected in ACD (85 mM tri-sodium citrate, 78 mM citric acid, 110 mM D-glucose, pH 4.4) at a ratio of 1.4 ml per 10 ml blood. PRP was isolated by centrifugation at 170 g for 14 minutes and platelets were further pelleted by centrifugation at 1300 g for 6 minutes. Platelets were washed once with 10 ml ACD containing 1 mg/ml bovine serum albumin. Platelets were resuspended at ~$2.5 \times 10^8$/ml in Tyrode's Buffer (137 mM NaCl, 2 mM KCl, 1.0 mM $MgCl_2$, 1 mM $CaCl_2$, 5 mM glucose, 20 mM HEPES pH 7.4).

Example A

FLIPR Assay in PAR4-Expressing HEK293 Cells

The activity of the PAR4 antagonists of the present invention were tested in PAR4 expressing cells by monitoring H-Ala-Phe(4-F)-Pro-Gly-Trp-Leu-Val-Lys-Asn-Gly-$NH_2$-induced intracellular calcium mobilization using FDSS6000 (Hamamatsu Photonics, Japan) by fluo-4. Counter screens for agonist activity and PAR1 antagonist activity were also performed. Briefly, HEK293 EBNA PAR4 clone 20664.1J cells were plated 24 hrs. prior to experiment in 384 well, Poly-D-Lysine coated, black, clear bottom plates (Greiner Bio-One, Monroe, N.C.). Cells were plated at 20,000 cells/well in 20 µl growth medium and incubated at 37° C. with 5% $CO_2$ overnight. At time of assay, media was replaced with 40 µl 1× Hank's Buffered Saline Solution (HBSS) (with 10 mM HEPES) and 20 µl test compound also diluted in 1× HBSS buffer was added at various concentrations and 0.67% DMSO final concentration on the FDSS for agonist measurement. The cells were then incubated for 30 minutes at room temperature followed by addition of 20 µl of agonist peptide for antagonist measurement on the FDSS. The agonist peptide H-Ala-Phe(4-F)-Pro-Gly-Trp-Leu-Val-Lys-Asn-Gly-$NH_2$ for PAR4 antagonist screen or SFFLRR for PAR1 counter screen were routinely tested to ensure a response at $EC_{50}$ in the assay (~2.5 µM for H-Ala-Phe(4-F)-Pro-Gly-Trp-Leu-Val-Lys-Asn-Gly-$NH_2$ and 600 nM for SFFLRR).

Example B

Validation of H-Ala-Phe(4-F)-Pro-Gly-Trp-Leu-Val-Lys-Asn-Gly-NH$_2$ as a PAR4 Agonist To validate H-Ala-Phe(4-F)-Pro-Gly-Trp-Leu-Val-Lys-Asn-Gly-NH$_2$ as a PAR4 agonist in the FLIPR assay, side-by-side comparison of the IC$_{50}$ values of ~180 compounds were performed using AYPGKF versus H-Ala-Phe(4-F)-Pro-Gly-Trp-Leu-Val-Lys-Asn-Gly-NH$_2$. The results demonstrated a strong correlation between the two assays (Spearman's rank correlation coefficient rho=0.7760, p<0.0001). The relevance of the FLIPR assay in the HEK293 cells was confirmed by a direct assay connectivity to the washed platelet assay. The IC$_{50}$ values of ~200 compounds from AYPGKF FLIPR assay was strongly correlated to that from AYPGKF washed platelet aggregation assay (Spearman's rank correlation coefficient rho=0.836, p<0.001). Similar results were obtained comparing FLIPR and washed platelet data using H-Ala-Phe(4-F)-Pro-Gly-Trp-Leu-Val-Lys-Asn-Gly-NH$_2$.

Example C

Gamma Thrombin Induced Platelet Aggregation Assays

The ability of the compounds of the current invention to inhibit platelet aggregation induced by gamma-thrombin was tested in a 96-well microplate aggregation assay format. Briefly, PRP or washed platelet suspension (100 µl) was pre-incubated for 5 minutes at room temperature with varying concentrations of compounds. Aggregation was initiated by ~10-50 nM gamma thrombin (Haematologic Technologies, Essex Junction, Vt.), which was titrated daily to achieve 80% platelet aggregation. Refludan at 1 U/mL (Berlex, Montville, N.J.) was added to the gamma thrombin sample to prevent PAR1 activation induced by residual alpha-thrombin contamination. The plate was then placed into a 37° C. Molecular Devices (Sunnyvale, Calif.) SPECTRAMAX® Plus Plate Reader. The plate was mixed for 10 seconds before the first read and 50 seconds between each read for up to 15 minutes at 405 nM. Data was collected with SOFTMAX® 4.71 software. The plate also included an untreated control sample which served as ODmax, while buffer containing no platelets was the ODmin. Platelet aggregation was determined by subtracting the ODmax from the ODmin for the 100% aggregation value. In experimental samples, the observed transmission was subtracted from the minimum value and then compared to the 100% aggregation value to determine the percentage aggregation. IC$_{50}$ values are determined using Excel Fit software.

The aggregation assays were also employed to test the selectivity of the compound against other platelet receptors by using SFFLRR for PAR1, collagen (Chrono-Log, Havertown, Pa.) for collagen receptors, ADP for P2Y1 and P2Y12 and U46619 (Cayman Chemical, Ann Arbor, Mich.) for thromboxane receptors.

Example D

Alpha-Thrombin Induced Platelet Aggregation Assays

The ability of PAR4 antagonist to inhibit platelet aggregation induced by alpha-thrombin was tested using human washed platelets. Example 3 was pre-incubated with washed platelets for 20 min. Aggregation was initiated by addition of 1.5 nM alpha-thrombin (Haematologic Technologies, Essex Junction, Vt.) to 300 µl of washed platelets at stirring speed of 1000 rpm. Platelet aggregation was monitored using Optical Aggregometer (Chrono-Log, Havertown, Pa.) and the area under the curve (AUC) at 6 min was measured. IC$_{50}$ was calculated using vehicle control as 0% inhibition. The IC$_{50}$ for the inhibition of platelet aggregation by Example 3 was calculated to be 5 nM (n=3) (FIGS. 1A and 1B).

Example E

Tissue Factor-Induced Platelet Aggregation Assay

The ability of PAR1 or PAR4 antagonists to inhibit platelet aggregation induced by endogenous thrombin can be tested in a tissue factor driven aggregation assay. Aggregation is initiated by addition of CaCl$_2$ and recombinant human tissue factor, which results in the generation of thrombin through activation of the coagulation pathway in the plasma. Anticoagulant agents such as corn trypsin inhibitor (Haematologic Technologies, Essex Junction, Vt.) at 50 µg/ml and PEFABLOC® FG (Centerchem, Norwalk, Conn.) are also added to the sample to prevent fibrin clot formation during the time of the study. Platelet aggregation is monitored using standard instrumentation including optical aggregometer or impedance aggregometer.

Example F

The following tables set out results obtained employing various compounds of the invention tested in the FLIPR assay and the platelet aggregation assay (PRP assay). As indicated above, the FLIPR assay, an in vitro assay, measures the PAR4 antagonist activity of compounds tested as described in Example A. The PRP assay, an in vitro assay, measures the PAR4 antagonist assay of the compounds tested in the presence of plasma proteins and thrombin agonist as described in Example C.

TABLE 1

| Example | PAR4 FLIPR assay (EC$_{50}$, nM) |
|---|---|
| 1 | 1.8 |
| 2 | 0.42 |
| 3 | 0.32 |
| 4 | 1.1 |
| 5 | 0.61 |
| 6 | 0.68 |
| 7 | 1.5 |
| 8 | 3.9 |
| 9 | 5.3 |
| 10 | 3.5 |
| 11 | 1.3 |
| 12 | 1.3 |
| 13 | 2.1 |
| 14 | 1.2 |
| 15 | 0.98 |
| 16 | 3.4 |
| 17 | 1.1 |
| 18 | 2.5 |
| 19 | 1.0 |
| 20 | 1.1 |
| 21 | 0.43 |
| 22 | 0.69 |
| 23 | 0.64 |
| 24 | 1.1 |
| 25 | 0.55 |
| 26 | 1.8 |

TABLE 1-continued

| Example | PAR4 FLIPR assay (EC$_{50}$, nM) |
|---|---|
| 27 | 1.6 |
| 28 | 0.51 |
| 29 | 1.4 |
| 30 | 0.65 |
| 31 | 0.59 |
| 32 | 1.3 |
| 33 | 1.7 |
| 34 | 1.2 |
| 35 | 1.3 |
| 36 | 0.45 |
| 37 | 0.45 |
| 38 | 2.5 |
| 39 | 0.46 |
| 40 | 0.26 |
| 41 | 0.90 |
| 42 | 2.5 |
| 43 | 0.34 |
| 44 | 0.90 |
| 45 | 1.3 |
| 46 | 2.4 |
| 47 | 0.77 |
| 48 | 0.51 |
| 49 | 0.82 |
| 50 | 0.21 |
| 51 | 0.26 |
| 52 | 0.51 |
| 53 | 0.52 |
| 54 | 0.36 |
| 55 | 0.79 |
| 56 | 0.24 |
| 57 | 0.67 |
| 58 | 0.33 |
| 59 | 0.47 |
| 60 | 0.38 |
| 61 | 0.64 |
| 62 | 0.48 |
| 63 | 0.63 |
| 64 | 2.3 |
| 65 | 0.81 |
| 66 | 0.75 |
| 67 | 0.34 |
| 68 | 0.49 |
| 69 | 0.23 |
| 70 | 0.89 |
| 71 | 0.46 |
| 72 | 0.26 |
| 73 | 0.35 |
| 74 | 0.56 |
| 75 | 0.32 |
| 76 | 0.42 |
| 77 | 1.0 |
| 78 | 0.40 |
| 79 | 2.6 |
| 80 | 0.74 |
| 81 | 0.85 |
| 82 | 0.67 |
| 83 | 1.1 |
| 84 | 0.97 |
| 85 | 1.1 |
| 86 | 0.30 |
| 87 | 24 |
| 88 | 2.9 |
| 89 | 0.69 |
| 90 | 0.33 |
| 91 | 0.27 |
| 92 | 0.63 |
| 93 | 0.45 |
| 94 | 0.43 |
| 95 | 0.83 |
| 96 | 0.64 |
| 97 | 0.63 |
| 98 | 0.37 |
| 99 | 0.84 |
| 100 | 0.25 |
| 101 | 0.36 |
| 102 | 2.3 |
| 103 | 0.31 |
| 104 | 0.68 |
| 105 | 0.32 |
| 106 | 0.98 |
| 107 | 1.3 |
| 108 | 1.2 |
| 109 | 0.69 |
| 110 | 0.78 |
| 111 | 0.86 |
| 112 | 0.37 |
| 113 | 0.43 |
| 114 | 0.49 |
| 115 | 0.33 |
| 116 | 0.32 |
| 117 | 0.43 |
| 118 | 0.33 |
| 119 | 0.72 |
| 120 | 0.45 |
| 121 | 0.27 |
| 122 | 0.72 |
| 123 | 0.50 |
| 124 | 0.29 |
| 126 | 0.33 |
| 127 | 1.6 |
| 128 | 0.35 |
| 129 | 0.96 |
| 130 | 0.40 |
| 131 | 0.66 |
| 132 | 1.9 |
| 133 | 0.37 |
| 134 | 1.2 |
| 135 | 0.79 |
| 136 | 1.2 |
| 137 | 1.2 |
| 138 | 0.82 |
| 139 | 0.41 |
| 140 | 0.67 |
| 141 | 0.47 |
| 142 | 0.31 |
| 143 | 0.39 |
| 144 | 0.26 |
| 145 | 0.45 |
| 146 | 0.73 |
| 147 | 0.96 |
| 148 | 0.37 |
| 149 | 4.1 |
| 150 | 0.92 |
| 151 | 0.84 |
| 152 | 0.68 |
| 153 | 1.7 |
| 154 | 1.1 |
| 155 | 0.62 |
| 156 | 0.52 |
| 157 | 3.6 |
| 158 | 0.95 |
| 159 | 0.41 |
| 160 | 0.50 |
| 161 | 0.69 |
| 162 | 0.67 |
| 163 | 0.82 |
| 164 | 1.3 |
| 165 | 1.1 |
| 166 | 0.97 |
| 167 | 0.26 |
| 168 | 0.28 |
| 169 | 1.3 |
| 170 | 1.7 |
| 171 | 0.27 |
| 172 | 0.94 |
| 173 | 0.67 |
| 174 | 24 |
| 175 | 1.4 |
| 176 | 1.3 |
| 177 | 0.61 |
| 178 | 0.87 |
| 179 | 1.0 |
| 180 | 0.47 |
| 181 | 0.72 |

TABLE 1-continued

| Example | PAR4 FLIPR assay (EC$_{50}$, nM) |
|---|---|
| 182 | 0.30 |
| 183 | 0.36 |
| 184 | 0.38 |
| 185 | 0.41 |
| 186 | 0.58 |
| 187 | 1.6 |
| 188 | 0.85 |
| 189 | 1.3 |
| 190 | 0.47 |
| 191 | 2.6 |
| 192 | 1.9 |
| 193 | 0.91 |
| 194 | 1.6 |
| 195 | 1.3 |
| 196 | 0.46 |
| 197 | 0.34 |
| 198 | 0.42 |
| 199 | 1.1 |
| 200 | 0.51 |
| 202 | 43 |
| 203 | 0.76 |
| 204 | 0.72 |
| 205 | 3.5 |
| 206 | 12 |
| 207 | 7.7 |
| 208 | 0.82 |
| 209 | 1.2 |
| 210 | 0.86 |
| 211 | 0.72 |
| 212 | 0.29 |
| 213 | 3.6 |
| 214 | 1.2 |
| 215 | 3.3 |
| 216 | 0.99 |
| 217 | 0.61 |
| 218 | 0.56 |
| 219 | 1.0 |
| 220 | 0.72 |
| 221 | 1.2 |
| 222 | 0.65 |
| 223 | 0.62 |
| 224 | 0.75 |
| 225 | 0.54 |
| 226 | 0.81 |
| 227 | 0.31 |
| 228 | 0.18 |
| 229 | 0.76 |
| 230 | 1.3 |
| 231 | 1.8 |
| 232 | 0.99 |
| 233 | 2.8 |
| 234 | 0.66 |
| 235 | 0.44 |
| 236 | 1.9 |
| 237 | 3.5 |
| 238 | 0.73 |
| 239 | 0.58 |
| 240 | 6.9 |
| 241 | 1.2 |
| 242 | 0.59 |
| 243 | 32 |
| 244 | 909 |
| 245 | 5.5 |
| 246 | 1.4 |
| 247 | 0.42 |
| 248 | 3.1 |
| 249 | 15 |
| 250 | 3.6 |
| 251 | 11 |
| 252 | 871 |
| 253 | 9.7 |
| 254 | 19 |
| 255 | 1.7 |
| 256 | 7.8 |
| 257 | 7.5 |
| 258 | 0.81 |
| 259 | 0.58 |
| 260 | 7.0 |
| 261 | 39 |
| 262 | 0.75 |
| 263 | 1.2 |
| 264 | 207 |
| 265 | 48 |
| 266 | 16 |
| 267 | 4.2 |
| 268 | 1.7 |
| 269 | 2.5 |
| 270 | 5.8 |
| 271 | 1.3 |
| 272 | 2.0 |
| 273 | 53 |
| 274 | 3.4 |
| 275 | 4.2 |
| 276 | 24 |
| 277 | 1.1 |
| 278 | 1.4 |
| 279 | 7.3 |
| 280 | 6.2 |
| 281 | 0.60 |
| 282 | 3475 |
| 283 | 2.9 |
| 284 | 1.1 |
| 285 | 2.9 |
| 286 | 110 |
| 287 | 0.48 |
| 288 | 0.36 |
| 289 | 1.2 |
| 290 | 0.60 |
| 291 | 0.65 |
| 292 | 0.27 |
| 293 | 0.72 |
| 294 | 0.40 |
| 295 | 92 |
| 296 | 2.2 |
| 297 | 0.52 |
| 298 | 0.99 |
| 299 | 0.55 |
| 300 | 0.42 |
| 301 | 0.63 |
| 302 | 0.44 |
| 303 | 0.85 |
| 304 | 0.88 |
| 305 | 1.0 |
| 306 | 1.2 |
| 307 | 24 |
| 308 | 0.64 |
| 309 | 0.54 |
| 310 | 0.53 |
| 311 | 0.65 |
| 312 | 0.77 |
| 313 | 0.43 |
| 314 | 0.37 |
| 315 | 1.3 |
| 316 | 0.95 |
| 317 | 1.6 |

TABLE 2

| Example | PRP assay (Gamma Thrombin, IC$_{50}$, nM) |
|---|---|
| 2 | 49 |
| 3 | 4.7 |
| 6 | 2034 |
| 8 | >3000 |
| 9 | >3000 |
| 10 | 2700 |
| 18 | 3.6 |
| 28 | 2.9 |
| 33 | 38 |
| 34 | 2324 |

TABLE 2-continued

| Example | PRP assay (Gamma Thrombin, IC$_{50}$, nM) |
|---|---|
| 36 | 2.1 |
| 39 | 2.1 |
| 44 | 2.0 |
| 48 | 1.2 |
| 56 | 23 |
| 67 | 2.2 |
| 73 | 1.9 |
| 74 | 0.96 |
| 75 | 1.6 |
| 77 | 1.9 |
| 80 | 0.94 |
| 81 | 1.6 |
| 87 | >3000 |
| 93 | 27 |
| 94 | 7.6 |
| 103 | 24 |
| 115 | 28 |
| 118 | 25 |
| 121 | 27 |
| 125 | 5.7 |
| 126 | 1.9 |
| 131 | >3000 |
| 137 | 23 |
| 139 | 26 |
| 141 | 24 |
| 145 | 29 |
| 151 | 26 |
| 152 | 28 |
| 161 | 27 |
| 192 | 28 |
| 201 | 156 |
| 202 | >3000 |
| 205 | 2382 |
| 209 | 23 |
| 219 | 25 |
| 243 | >3000 |
| 244 | >3000 |
| 245 | 3132 |
| 249 | >3000 |
| 254 | >3000 |
| 256 | >3000 |
| 257 | >3000 |
| 261 | >3000 |
| 264 | >3000 |
| 265 | >3000 |
| 266 | >3000 |
| 268 | 2359 |
| 273 | >3000 |
| 274 | >3000 |
| 275 | 2632 |
| 276 | >3000 |
| 279 | >3000 |
| 281 | >3000 |
| 282 | >3000 |
| 285 | 2338 |
| 288 | 1.0 |
| 301 | 1.9 |
| 305 | 2.0 |
| 311 | 2.0 |

Example G

Cynomolgus Monkey Electrolytic Injury-Induced Carotid Artery Thrombosis Model

Healthy cynomolgus monkeys were used in the study. These monkeys were retired from other pharmacokinetic and pharmacodynamic studies and had at least a 4-week washout period.

On the day of the study, compounds or vehicles were administered orally at 1 to 2 hours before the experiment. Monkeys were then sedated by intramuscular administration of 0.2 mg/kg atropine, 5 mg/kg TELAZOL® (tiletamine/ zolazepam) and 0.1 mg/kg hydromorphone to facilitate placement of an endotracheal tube. An intravenous catheter was placed in the left cephalic vein for fluid administration to prevent dehydration. Animals were then administered with an inhalant anesthetic, isoflurane (1-5% to effect) and oxygen, ventilated, and placed on a thermostatically controlled heating pad to maintain the body temperature at 37° C. General anesthesia was maintained at a surgical plane using inhaled isoflurane and oxygen. The left brachial artery was cannulated to record blood pressure and heart rate. Blood pressure and heart rate were monitored to maintain normal vital signs.

The carotid arterial thrombosis model in monkeys was based on a rabbit arterial thrombosis model, as described by Wong et al. (Wong, P. C. et al., "Nonpeptide factor Xa inhibitors: II. Antithrombotic evaluation in a rabbit model of electrically induced carotid artery thrombosis", *J. Pharmacol. Exp. Ther.*, 295:212-218 (2002).) Thrombosis was induced by electrical stimulation of the carotid artery for 5 min at 10 mA using an external stainless-steel bipolar electrode. Carotid blood flow was measured with an appropriately sized TRANSONIC® flow probe and a TRANSONIC® perivascular flowmeter (TS420 Model, Transonic Systems Inc., Ithaca, N.Y.). It was continuously recorded over a 90-min period to monitor thrombosis-induced occlusion. Integrated carotid blood flow was measured by the area under the flow-time curve. It was expressed as percent of total control carotid blood flow, which would result if control blood flow had been maintained continuously for 90 min. In addition, thrombus from the injured artery was removed, blotted twice on a weighing paper to remove residual fluid, and weighed. FIG. 1C shows the results of a dose response experiment with Example 3 in the cynomolgus monkey electrically-induced arterial thrombus model, demonstrating the in vivo antithrombotic efficacy of a PAR4 antagonist.

While it is apparent that the embodiments of the application herein disclosed are well suited to fulfill the objectives stated above, it will be appreciated that numerous modifications and other embodiments may be implemented by those skilled in the art, and it is intended that the appended claims cover all such modifications and embodiments that fall within the true spirit and scope of the present application.

What is claimed is:

1. A compound of Formula I:

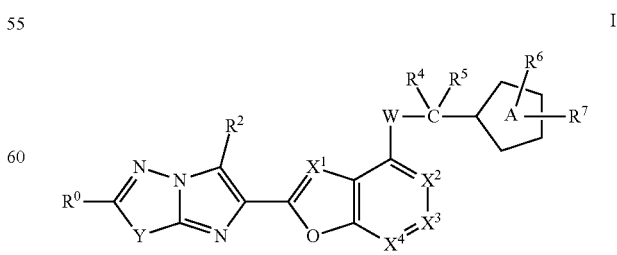

or a stereoisomer, tautomer, pharmaceutically acceptable salt, solvate or prodrug thereof, wherein:

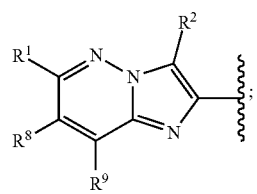 is 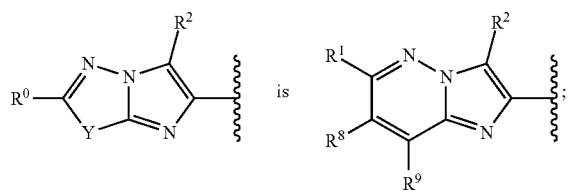;

W is O or S;
R[1] is —CH$_3$;
R[8] and R[9] are H;
R[2] is H;
X[1] is CH;
X[2] and X[4] are each CH;
X[3] is CR[3];
R[3] is OCH$_3$;
R[4] and R[5] are independently selected from H and C$_1$-C$_6$ alkyl, or R[4] and R[5] can be taken together with the carbon to which they are attached to form a C$_3$-C$_7$ cycloalkyl ring;

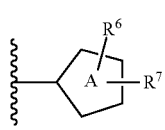 is 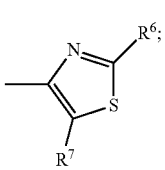;

R[6] is selected from the group consisting of:
  a) phenyl substituted by 0 to 3 groups independently selected from the group consisting of chloro, —CF$_3$, cyano, —OCH$_3$, —OCF$_3$, —SO$_2$CH$_3$ and (C=O)N(CH$_3$)$_2$;
  b) pyridinyl or pyrimidinyl substituted by 0 to 3 groups independently selected from the group consisting of fluoro, chloro, —CH$_3$ and —OCH$_3$; and
  c) piperidinyl, morpholinyl or thiomorpholinyl substituted by 0 to 3 groups independently selected from the group consisting of fluoro, OH, —CH$_3$ and —NH$_2$; and
R[7] is selected from the group consisting of H, and —CH$_3$.

2. The compound as defined in claim 1 wherein:
W is O, and
R[6] is phenyl substituted by 0 to 3 groups independently selected from the group consisting of chloro, —CF$_3$, cyano, —OCH$_3$, —OCF$_3$, —SO$_2$CH$_3$ and (C=O)N(CH$_3$)$_2$.

3. The compound as defined in claim 1 wherein:
W is O; and
R[6] is pyridinyl or pyrimidinyl substituted by 0 or 1 groups independently selected from the group consisting of fluoro, chloro, —CH$_3$ and —OCH$_3$.

4. The compound as defined in claim 1 wherein:
W is O; and
R[6] is piperidinyl, morpholinyl or thiomorpholinyl substituted by 0 to 2 groups independently selected from the group consisting of fluoro, OH, —CH$_3$ and —NH$_2$.

5. The compound as defined in claim 1 wherein:
W is O.

6. The compound as defined in claim 1, wherein the compound is

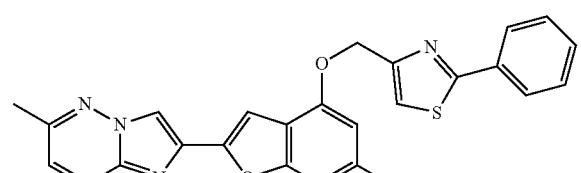,

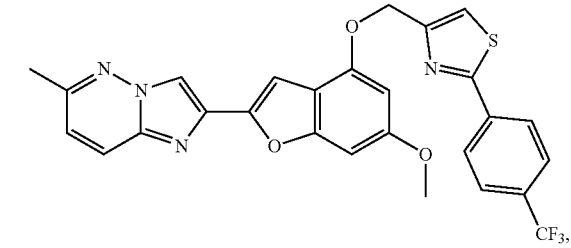,

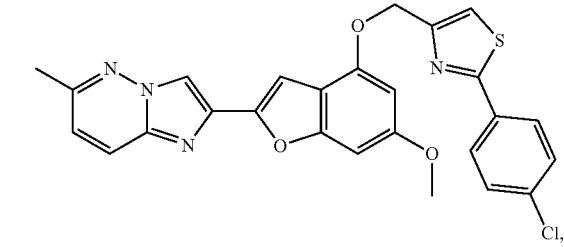,

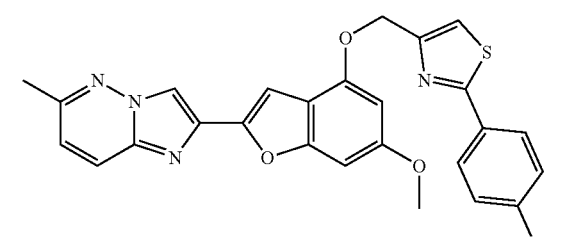,

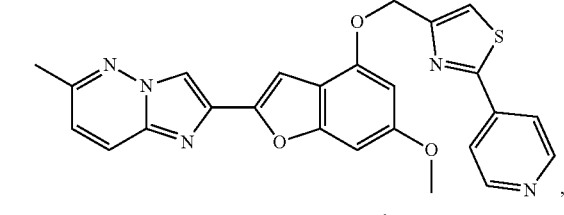,

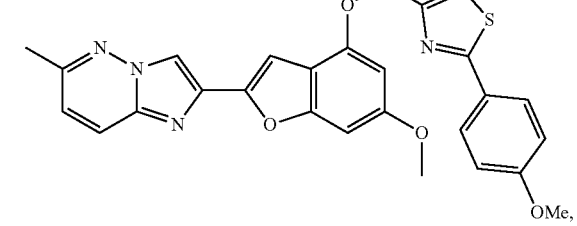,

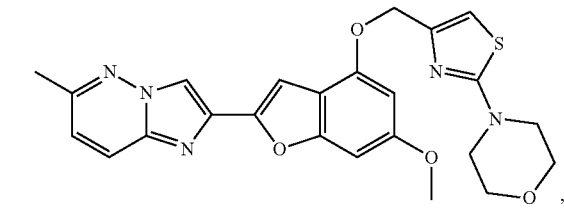,

421
-continued
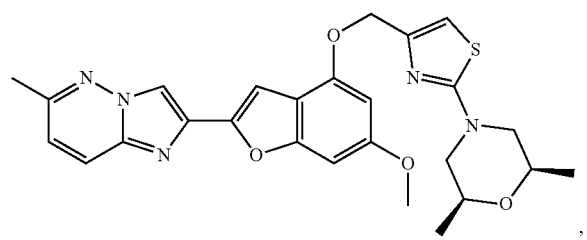
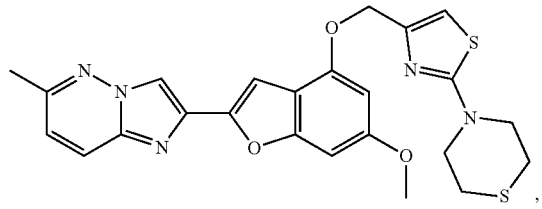
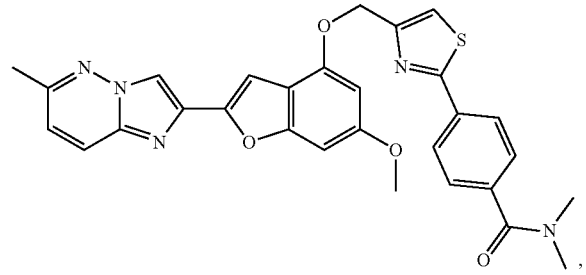
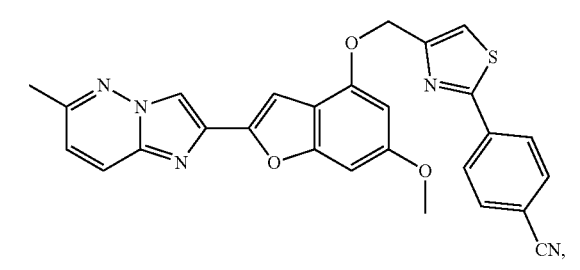
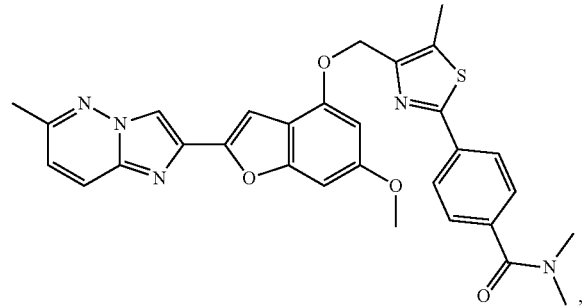
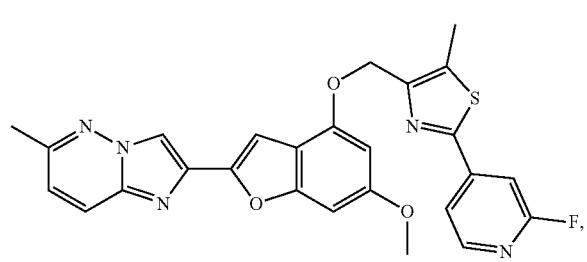
422
-continued
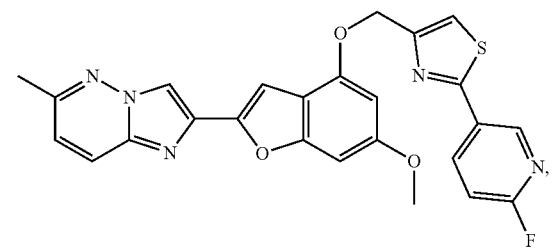
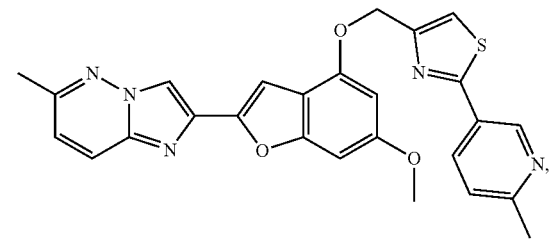
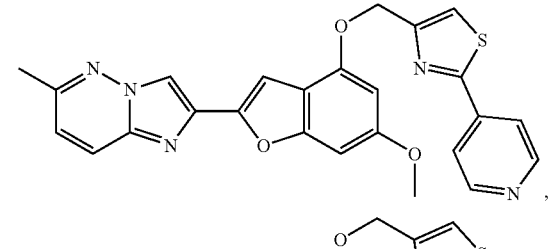
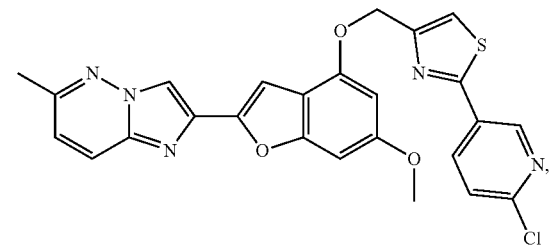
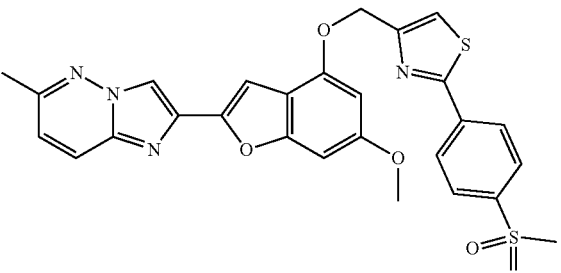
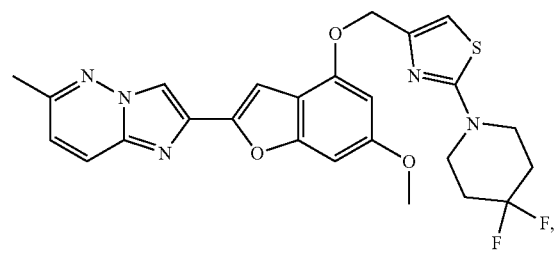
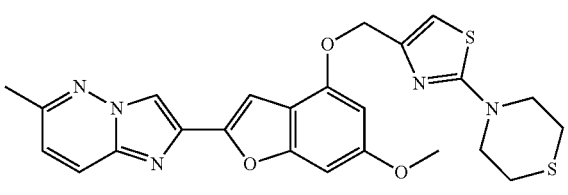

-continued

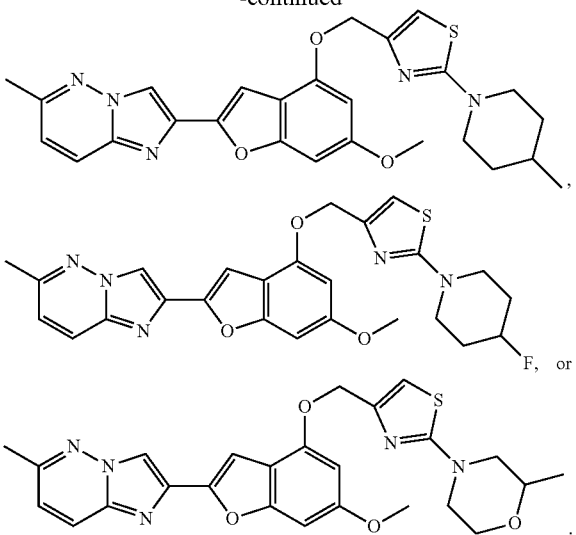

7. A pharmaceutical composition, which comprises a pharmaceutically acceptable carrier and a compound as defined in claim 1, or a stereoisomer, tautomer, pharmaceutically acceptable salt, or solvate thereof, alone or in combination with another therapeutic agent.

8. A method for the treatment of a thromboembolic disorder or the primary or secondary prophylaxis of a thromboembolic disorder, which comprises the step of administering to a patient in need thereof a therapeutically effective amount of a compound as defined in claim 1, or a stereoisomer, tautomer, pharmaceutically acceptable salt, or solvate thereof, wherein the thromboembolic disorder is selected from the group consisting of arterial cardiovascular thromboembolic disorders, venous cardiovascular thromboembolic disorders, cerebrovascular thromboembolic disorders, and thromboembolic disorders in the chambers of the heart or in the peripheral circulation.

9. A method of inhibiting or preventing platelet aggregation, which comprises the step of administering to a subject in need thereof a therapeutically effective amount of a compound as defined in claim 1.

* * * * *